US009550820B2

(12) United States Patent
Mohammadi et al.

(10) Patent No.: US 9,550,820 B2
(45) Date of Patent: Jan. 24, 2017

(54) CHIMERIC FIBROBLAST GROWTH FACTOR 23/FIBROBLAST GROWTH FACTOR 19 PROTEINS AND METHODS OF USE

(71) Applicants: Moosa Mohammadi, Scarsdale, NY (US); Regina Goetz, New York, NY (US)

(72) Inventors: Moosa Mohammadi, Scarsdale, NY (US); Regina Goetz, New York, NY (US)

(73) Assignee: New York University, New York, NY (US)

(*) Notice: Subject to any disclaimer, the term of this patent is extended or adjusted under 35 U.S.C. 154(b) by 0 days.

(21) Appl. No.: 14/185,366

(22) Filed: Feb. 20, 2014

(65) Prior Publication Data

US 2014/0243260 A1 Aug. 28, 2014

Related U.S. Application Data

(60) Provisional application No. 61/768,289, filed on Feb. 22, 2013.

(51) Int. Cl.

| | |
|---|---|
| ***A61K 38/18*** | (2006.01) |
| ***C07K 14/50*** | (2006.01) |
| ***A61K 45/06*** | (2006.01) |
| *A61K 38/00* | (2006.01) |

(52) U.S. Cl.

CPC .......... *C07K 14/50* (2013.01); *A61K 38/1825* (2013.01); *A61K 45/06* (2013.01); *A61K 38/00* (2013.01); *C07K 2319/00* (2013.01)

(58) Field of Classification Search

None

See application file for complete search history.

(56) References Cited

U.S. PATENT DOCUMENTS

| | | | |
|---|---|---|---|
| 5,132,408 | A | 7/1992 | Baird et al. |
| 5,478,804 | A | 12/1995 | Calabresi et al. |
| 5,648,260 | A | 7/1997 | Winter et al. |
| 6,326,484 | B1 | 12/2001 | Gage et al. |
| 6,982,170 | B1 | 1/2006 | Maciag et al. |
| 7,223,563 | B2 | 5/2007 | Econs et al. |
| 7,314,618 | B2 | 1/2008 | Econs et al. |
| 7,491,697 | B2 | 2/2009 | Beals et al. |
| 7,582,607 | B2 | 9/2009 | Frye et al. |
| 7,622,445 | B2 | 11/2009 | Frye et al. |
| 7,655,627 | B2 | 2/2010 | Frye et al. |
| 7,745,406 | B2 | 6/2010 | Econs et al. |
| 7,947,810 | B2 | 5/2011 | Econs et al. |
| 7,956,033 | B2 | 6/2011 | Cheng et al. |
| 8,168,591 | B2 | 5/2012 | Takada et al. |
| 8,642,546 | B2 | 2/2014 | Belouski et al. |
| 8,889,426 | B2 | 11/2014 | Mohammadi et al. |
| 8,889,621 | B2 | 11/2014 | Mohammadi et al. |
| 8,906,854 | B2 | 12/2014 | Jonker et al. |
| 8,951,966 | B2 | 2/2015 | Ling et al. |
| 8,999,929 | B2 | 4/2015 | Mohammadi et al. |
| 9,072,708 | B2 | 7/2015 | Jonker et al. |
| 9,272,017 | B2 | 3/2016 | Mohammadi et al. |
| 2002/0082205 | A1 | 6/2002 | Itoh et al. |
| 2003/0105302 | A1 | 6/2003 | Itoh et al. |
| 2004/0043457 | A1 | 3/2004 | Schumacher et al. |
| 2004/0097414 | A1 | 5/2004 | Itoh et al. |
| 2004/0259780 | A1 | 12/2004 | Glasebrook et al. |
| 2006/0160181 | A1 | 7/2006 | Luethy et al. |
| 2006/0281679 | A1 | 12/2006 | Itoh et al. |
| 2007/0142278 | A1 | 6/2007 | Beals et al. |
| 2007/0237768 | A1 | 10/2007 | Glaesner et al. |
| 2007/0265200 | A1 | 11/2007 | Glaesner et al. |
| 2007/0293430 | A1 | 12/2007 | Frye et al. |

(Continued)

FOREIGN PATENT DOCUMENTS

| | | | |
|---|---|---|---|
| EP | 0 645 451 | B1 | 8/2001 |
| JP | 2008/0117661 | A | 4/2008 |

(Continued)

OTHER PUBLICATIONS

Wu et al. J. Biol. Chem. 283(48): 33304-33309, 2008.*
Wu et al. J. Mol. Biol. 418: 82-89, 2012.*
Goetz et al. J. Biol. Chem. 287(34): 29134-29146, 2012.*
Kurosu et al. Mol. Cell. Endocrinol. 299: 72-78, 2009.*
Yie et al., "FGF21 N- and C-Termini Play Different Roles in Receptor Interaction and Activation," FEBS Lett. 583:19-24 (2009).
Andrukhova et al., "FGF23 Acts Directly on Renal Proximal Tubules to Induce Phosphaturia Through Activation of the ERK1/2-SKG1 Signaling Pathway," Bone 51(3):621-8 (Jun. 12, 2012).

(Continued)

*Primary Examiner* — Christine J Saoud

(74) *Attorney, Agent, or Firm* — LeClairRyan, a Professional Corporation

(57) ABSTRACT

The present invention relates to an isolated chimeric protein. The isolated chimeric protein includes an N-terminus coupled to a C-terminus, where the N-terminus includes an N-terminal portion from a fibroblast growth factor ("FGF") 23 molecule and the C-terminus includes a C-terminal portion from an FGF19 molecule. The present invention also relates to a pharmaceutical composition including an isolated chimeric protein and a pharmaceutically acceptable carrier. The isolated chimeric protein includes an N-terminus coupled to a C-terminus, where the N-terminus includes an N-terminal portion from a fibroblast growth factor ("FGF") 23 molecule and the C-terminus includes a C-terminal portion from an FGF19 molecule, and a pharmaceutically-acceptable carrier. Yet another aspect of the present invention relates to a method for treating a subject suffering from a disorder. This method includes selecting a subject suffering from the disorder and administering to the subject a therapeutically effective amount of a chimeric protein according to the present invention.

16 Claims, 2 Drawing Sheets

(56) References Cited

U.S. PATENT DOCUMENTS

| | | | |
|---|---|---|---|
| 2007/0299007 | A1 | 12/2007 | Frye et al. |
| 2008/0103096 | A1 | 5/2008 | Frye et al. |
| 2008/0255045 | A1 | 10/2008 | Cujec et al. |
| 2008/0261875 | A1 | 10/2008 | Etgen et al. |
| 2009/0111742 | A1 | 4/2009 | Kharitonenkov et al. |
| 2009/0118190 | A1 | 5/2009 | Beals et al. |
| 2009/0305986 | A1 | 12/2009 | Belouski et al. |
| 2010/0062984 | A1 | 3/2010 | Kumar et al. |
| 2010/0158914 | A1 | 6/2010 | Desnoyers |
| 2010/0184665 | A1 | 7/2010 | Suzuki et al. |
| 2010/0216715 | A1 | 8/2010 | Tagmose et al. |
| 2010/0285131 | A1 | 11/2010 | Belouski et al. |
| 2010/0286042 | A1 | 11/2010 | Imamura et al. |
| 2010/0323954 | A1 | 12/2010 | Li et al. |
| 2011/0053841 | A1 | 3/2011 | Yayon et al. |
| 2011/0104152 | A1 | 5/2011 | Sonoda |
| 2011/0150901 | A1 | 6/2011 | Smith et al. |
| 2011/0171218 | A1 | 7/2011 | Seehra et al. |
| 2011/0172401 | A1 | 7/2011 | Cujec et al. |
| 2011/0190207 | A1 | 8/2011 | Mohammadi et al. |
| 2011/0195077 | A1 | 8/2011 | Glass et al. |
| 2012/0052069 | A1 | 3/2012 | Belouski et al. |
| 2012/0288886 | A1 | 11/2012 | Mohammadi et al. |
| 2013/0023474 | A1 | 1/2013 | Ling et al. |
| 2013/0058896 | A1 | 3/2013 | Takada et al. |
| 2013/0116171 | A1 | 5/2013 | Jonker et al. |
| 2013/0172275 | A1 | 7/2013 | Mohammadi et al. |
| 2013/0184211 | A1 | 7/2013 | Mohammadi et al. |
| 2013/0231277 | A1 | 9/2013 | Mohammadi et al. |
| 2013/0331316 | A1 | 12/2013 | Mohammadi et al. |
| 2013/0331317 | A1 | 12/2013 | Mohammadi et al. |
| 2013/0331325 | A1 | 12/2013 | Mohammadi et al. |
| 2014/0094406 | A1 | 4/2014 | Mohammadi et al. |
| 2014/0107022 | A1 | 4/2014 | Mohammadi et al. |
| 2014/0155316 | A1 | 6/2014 | Mohammadi et al. |
| 2014/0171361 | A1 | 6/2014 | Jonker et al. |
| 2015/0111821 | A1 | 4/2015 | Suh et al. |
| 2015/0343022 | A1 | 12/2015 | Jonker et al. |

FOREIGN PATENT DOCUMENTS

| | | | |
|---|---|---|---|
| WO | WO 01/66595 | A2 | 9/2001 |
| WO | WO 01/66596 | A2 | 9/2001 |
| WO | WO 2009/133905 | A1 | 11/2009 |
| WO | 2011/047267 | A1 | 4/2011 |
| WO | 2011/130729 | A2 | 10/2011 |
| WO | WO 2013/027191 | A1 | 2/2013 |
| WO | 2013/184958 | A1 | 12/2013 |
| WO | 2013/184960 | A2 | 12/2013 |
| WO | 2013/184962 | A1 | 12/2013 |
| WO | WO 2015/149069 | | 10/2015 |

OTHER PUBLICATIONS

Beenken et al., "Plasticity in Interactions of Fibroblast Growth Factor 1 (FGF1) N Terminus With FGF Receptors Underlies Promiscuity of FGF1," J. Biol. Chem. 287(5):3067-3078 (Nov. 4, 2011).

Jonker et al., "A PPARgamma-FGF1 Axis is Required for Adaptive Adipose Remodelling and Metabolic Homeostasis," Nature 485(7398):391-394 (Apr. 22, 2012).

Wu et al., "A Unique FGF23 With the Ability to Activate FGFR Signaling Through Both alphaKlotho and betaKlotho," J. Mol. Biol. 418:82-89 (2012).

Beenken & Mohammadi, "The Structural Biology of the FGF19 Subfamily," Adv. Exp. Med. Biol. 728:1-24 (2012).

Wu et al., "C-Terminal Tail of FGF19 Determines Its Specificity Toward Klotho Co-Receptors," J. Biol. Chem. 283(48):33304-33309 (2008).

Goetz et al., "Conversion of a Paracrine Fibroblast Growth Factor Into an Endocrine Fibrobalst Growth Factor," J. Biol. Chem. 287(34):29134-29146 (Jun. 25, 2012).

Goetz et al., "Klotho Coreceptors Inhibit Signaling by Paracrine Fibroblast Growth Factor 8 Subfamily Ligands," Mol. Cell. Biol. 32(10):1944-1954 (Mar. 26, 2012).

Olsen et al., "Insights Into the Molecular Basis for Fibroblast Growth Factor Receptor Autoinhibition and Ligand-Binding Promiscuity," Proc. Nat'l. Acad. Sci. USA 101(4):935-940 (2004).

Wei et al., "Fibroblast Growth Factor 21 Promotes Bone Loss by Potentiating the Effects of Peroxisome Proliferator-Activated Receptor Gamma," Proc. Nat'l. Acad. Sci. USA 109(8):3143-3148 (Feb. 21, 2012).

Wu et al., "Separating Mitogenic and Metabolic Activities of Fibroblast Growth Factor 19 (FGF19)," Proc. Nat'l. Acad. Sci. USA 107(32):14158-14163 (2010).

Wu et al., "FGF19-Induced Hepatocyte Proliferation is Mediated Through FGFR4 Activation," J. Biol. Chem. 285(8):5165-5170 (2009).

Zhang et al., "Receptor Specificity of the Fibroblast Growth Factor Family," J. Biol. Chem. 281(23):15694-15700 (2006).

Presta et al., "Structure-Function Relationship of Basic Fibroblast Growth Factor: Site-Directed Mutagenesis of a Putative Heparin-Binding and Receptor-Binding Region," Biochem. Biophys. Res. Commun. 185(3):1098-1107 (1992).

Zakrzewska et al., "Increased Protein Stability of FGF1 Can Compensate for Its Reduced Affinity for Heparin," J. Biol. Chem. 284(37):25388-403 (2009).

Motomura et al., "An FGF1:FGF2 Chimeric Growth Factor Exhibits Universal FGF Receptor Specificity, Enhanced Stability and Augmented Activity Useful for Epithelial Proliferation and Radioprotection," Biochim. Biophys. Acta 1780 (12):1432-40 (2008).

Nakayama et al., "Post Treatment With an FGF Chimeric Growth Factor Enhances Epithelial Cell Proliferation to Improve Recovery From Radiation-Induced Intestinal Damage," Int. J. Radiat. Oncol. Biol. Phys. 78(3):860-7 (2010).

Kharitonenkov et al., "The Metabolic State of Diabetic Monkeys is Regulated by Fibroblast Growth Factor-21," Endocrinology 148(2):774-81 (2007).

Igarashi et al., "Characterization of Recombinant Human Fibroblast Growth Factor (FGF)-10 Reveals Functional Similarities With Keratinocyte Growth Factor (FGF-7)," J. Biol. Chem. 273(21):13230-5 (1998).

Goetz et al., "Molecular Insights Into the Klotho-Dependent, Endocrine Mode of Action of Fibroblast Growth Factor 19 Subfamily Members," Mol. Cell. Biol. 27(9):3417-3428 (2007).

Beenken, "Structural and Biochemical Studies of FGF-FGFR Complexes," Thesis (Sep. 2011).

Ge et al., "Characterization of a FGF19 Variant With Altered Receptor Specificity Revealed a Central Role for FGFR1c in the Regulation of Glucose Metabolism," PLoS One, 7(3):e33603 (Epub Mar. 23, 2012).

Wu et al., "FGF19 Regulates Cell Proliferation, Glucose and Bile Acid Metabolism Via FGFR4-Dependent and Independent Pathways," PLoS One 6(3):e17868 (Mar. 8, 2011).

Wu et al., "Selective Activation of FGFR4 by an FGF19 Variant Does Not Improve Glucose Metabolism in OB/OB Mice," Proc. Nat'l. Acad Sci U.S.A. 106(34):14379-84 (2009).

Mohammadi et al., "Structural Basis for Fibroblast Growth Factor Receptor Activation," Cytokine & Growth Factor Reviews 16:107-137 (2005).

Hutley et al., "Fibroblast Growth Factor 1: A Key Regulator of Human Adipogenesis," Diabetes 53:3097-3106 (2004).

Imamura et al., "Recovery of Mitogenic Activity of a Growth Factor Mutant with Nuclear Translocation Sequence," Science 249:1567-1570 (Sep. 28, 1990).

Goetz et al., "Isolated C-Terminal tail of FGF23 Alleviates Hypophosphatemia by Inhibiting FGF23-FGFR-Klotho Complex Formation," PNAS 107(1):407-412 (Epub Dec. 4, 2009).

Razzaque, "The FGF23-Klotho Axis: Endocrine Regulation of Phosphate Homeostasis," Nat. Rev. Endocrinol. 5(11):611-19 (2009).

Shalhoub et al. "FGF23 Neutralization Improves Chronic Kidney Disease—Associated Hyperparathyroidism yet Increases Mortality," J. Clin. Invest. 122(7):2543-2553 (2012).

(56) References Cited

OTHER PUBLICATIONS

Nallamsetty et al., "Gateway Vectors for the Production of Combinatorially-Tagged His6-MBP Fusion Proteins in the Cytoplasm and Periplasm of *Escherichia coli*," Protein Sci. 14:2964-2971 (2005).
Isakova et al., "Fibroblast Growth Factor 23 is Elevated Before Parathyroid Hormone and Phosphate in Chronic Kidney Disease," Kidney International 79:1370-1378 (2011).
Faul et al., "FGF23 Induces Left Ventricular Hypertrophy," J. Clin. Invest. 121:4393-4408 (2011).
Andrukhova et al., "FGF23 Drives Progression of Chronic Kidney Disease in Mice," Abstract No. TH-OR105, Kidney Week, Nov. 2015, San Diego, CA.
Fliser et al., "Fibroblast Growth Factor 23 (FGF23) Predicts Progression of Chronic Kidney Disease: The Mild to Moderate Kidney Disease (MMKD) Study," J Am Soc Nephrol 18(9):2600-2608 (2007).
Gutierrez et al., "Fibroblast Growth Factor-23 Mitigates Hyperphosphatemia but Accentuates Calcitriol Deficiency in Chronic Kidney Disease," J Am Soc Nephrol 16(7):2205-2215 (2005).
Gutierrez et al., "Fibroblast Growth Factor 23 and Mortality Among Patients Undergoing Hemodialysis," N Engl J Med 359(6):584-592 (2008).
Gutierrez et al., "Fibroblast Growth Factor 23 and Left Ventricular Hypertrophy in Chronic Kidney Disease," Circulation 119(19):2545-2552 (2009).
Hasegawa et al., "Direct Evidence for a Causative Role of FGF23 in the Abnormal Renal Phosphate Handling and Vitamin D Metabolism in Rats with Early-Stage Chronic Kidney Disease," Kidney International 78:975-980 (2010).
Hsu HJ and Wu MS, "Fibroblast Growth Factor 23: A Possible Cause of Left Ventricular Hypertrophy in Hemodialysis Patients," Am J Med Sci 337(2):116-122 (2009).
Jean et al., "High Levels of Serum Fibroblast Growth Factor (FGF)-23 are Associated with Increased Mortality in Long Haemodialysis Patients," Nephrol Dial Transplant 24(9):2792-2796 (2009).
Larsson et al., "Circulating Concentration of FGF-23 Increases as Renal Function Declines in Patients with Chronic Kidney Disease, but does not Change in Response to Variation in Phosphate Intake in Healthy Volunteers," Kidney Int 64(6):2272-2279 (2003).
Mirza et al., "Circulating Fibroblast Growth Factor-23 is Associated with Vascular Dysfunction in the Community," Atherosclerosis 205(2):385-390 (2009).
Mirza et al., "Serum Intact FGF23 Associate with Left Ventricular Mass, Hypertrophy and Geometry in an Elderly Population," Atherosclerosis 207(2):546-551 (2009).
Mirza et al., "Circulating Fibroblast Growth Factor-23 is Associated with Fat Mass and Dyslipidemia in Two Independent Cohorts of Elderly Individuals," Arterioscler. Thromb. Vasc. Biol. 31:219-227 (2011).
Nakanishi et al., "Serum Fibroblast Growth Factor-23 Levels Predict the Future Refractory Hyperparathyroidism in Dialysis Patients," Kidney Int 67(3):1171-1178 (2005).
Nasrallah et al., "Fibroblast Growth Factor-23 (FGF-23) is Independently Correlated to Aortic Calcification in Haemodialysis Patients," Nephrol Dial Transplant 25(8):2679-2685 (2010).
Shigematsu et al., "Possible Involvement of Circulating Fibroblast Growth Factor 23 in the Development of Secondary Hyperparathyroidism Associated with Renal Insufficiency," Am J Kidney Dis 44(2):250-256 (2004).
Westerberg et al., "Regulation of Fibroblast Growth Factor-23 in Chronic Kidney Disease," Nephrol Dial Transplant 22(11):3202-3207 (2007).
Beenken et al., "The FGF Family. Biology, Pathophysiology and Therapy," Nat Rev Drug Discov. 8(3):235-53 (Mar. 2009).
Perwad et al., "Fibroblast Growth Factor 23 Impairs Phosphorus and Vitamin D Metabolism in Vivo and Suppresses 25-Hydroxyvitamin D-1α-Hydroxylase Expression in Vitro," American J. of Phys. Renal Phys. 293(5):F1577-F1583 (2007).
Aono et al., "Therapeutic Effects of Anti-FGF23 Antibodies in Hypophosphatemic Rickets/Osteomalacia," J. Bone Miner. Res. 24(11):1879-1888 (available online May 4, 2009).
Aono et al., "The Neutralization of FGF-23 Ameliorates Hypophosphatemia and Rickets in Hyp Mice," Abstract, Oral Presentation, No. 1056, 25th American Society for Bone and Mineral Research Meeting, Sep. 19-23, 2003, Minneapolis, Minnesota, J. Bone Miner. Res. 18 (Suppl. S1): S15 (2003).
Shimada et al., "Mutant FGF-23 Responsible for Autosomal Dominant Hypophosphatemic Rickets is Resistant to Proteolytic Cleavage and Causes Hypophosphatemia in Vivo," Endocrinology 143(8):3179-82 (2002).
Shimada et al., "Neutralization of Intrinsic FGF-23 Action by Antibodies Reveals the Essential Role of FGF-23 in Physiological Phosphate and Vitamin D Metabolism," Abstract, Poster Presentation, Nos. SA414 and F414, 25th American Society for Bone and Mineral Research Meeting, Sep. 19-23, 2003, Minneapolis, Minnesota, J. Bone Miner. Res. 18 (Suppl. S1): S93, S164 (2003).
Yamazaki et al., "Anti-FGF23 Neutralizing Antibodies Show the Physiological Role and Structural Features of FGF23," J. Bone Miner. Res. 23(9):1509-1518 (available online Apr. 1, 2008).
Berndt et al., "Biological Activity of FGF-23 Fragments," Eur J Physiol 454:615-623 (2007).
Hu et al., "C-terminal Fragments of Fibroblast Growth Factor (FGF) 23 Inhibit Renal Phosphate (Pi) Excretion as an FGF23 Antagonist by Displacing FGF23 from its Receptor," Abstract SA-FC345, J. Am. Soc. Nephrol. 19:78A (2008).
Hu et al., "C-terminal Fragment of Fibroblast Growth Factor (FGF) 23 Inhibits Renal Phosphate (Pi) Excretion as an FGF23 Antagonist by Displacing FGF23 from its Receptor," Oral Presentation at the 41st Annual Meeting of the American Society of Nephrology (Renal Week 2008) Philadelphia, PA, Nov. 4-9, 2008.
Shimada, "Possible Roles of Fibroblast Growth Factor 23 in Developing X-Linked Hypophosphatemia," Clin. Pediatr. Endocrinol. 14(Suppl 23):33-37 (2005).
Kurosu et al. "Regulation of Fibroblast Growth Factor-23 Signaling by Klotho," J. Biol. Chem. 281(10): 6120-6123 (2006).
Kurosu et al., "Tissue-specific Expression of βKlotho and Fibroblast Growth Factor (FGF) Receptor Isoforms Determines Metabolic Activity of FGF19 and FGF21," J. Biol. Chem. 282(37):26687-26695 (2007).
Micanovic et al., "Different Roles of N- and C- Termini in the Functional Activity of FGF21," J. Cell. Physiol. 219:227-234 (2009).
Kharitonenkov et al.,"FGF-21/FGF-21 Receptor Interaction and Activation is Determined by βKlotho," J. Cell. Physiol. 215:1-7 (2008).
Neyra et al., "Fibroblast Growth Factor 23 and Acute Kidney Injury," Pediatr Nephrol. 30(11):1909-18 (2015).
Hu et al., "Fibroblast Growth Factor 23 and Klotho: Physiology and Pathophysiology of an Endocrine Network of Mineral Metabolism," Annu Rev Physiol. 75:503-33 (2013).
Abraham et al., "Human Basic Fibroblast Growth Factor: Nucleotide Sequence and Genomic Organization," EMBO J. 10:2523-2528 (1986).
Esch et al., "Primary Structure of Bovine Pituitary Basic Fibroblast Growth Factor (FGF) and Comparison with the Amino-Terminal Sequence of Bovine Brain Acidic FGF," PNAS 82:6507-6511 (1985).
Ono et al., "Novel Regulation of Fibroblast Growth Factor 2 (FGF2)-Mediated Cell Growth by Polysialic Acid," J. Biol. Chem. 287(6):3710-3722 (2012).
Schlessinger et al., "Crystal Structure of a Ternary FGF-FGFR-Heparin Complex Reveals a Dual Role for Heparin in FGFR Binding and Dimerization," Molecular Cell 6:743-750 (2000).
Thompson et al., "Energetic Characterization of the Basic Fibroblast Growth Factor-Heparin Interaction: Identification of the Heparin Binding Domains," Biochemistry 33:3831-3840 (1994).
Suh et al., "Endocrinization of FGF1 Produces a Neomorphic and Potent Insulin Sensitizer," Author Manuscript, Nature 513(7518): 436-439 (2014).

(56) References Cited

OTHER PUBLICATIONS

Restriction Requirement in U.S. Appl. No. 14/097,116, 9 pages (mailed Dec. 11, 2014).

Yao et al., "Expression and Pharmacological Evaluation of Fusion Protein FGF21-L-Fc," Acta Pharmaceutica Sinica 46(7):787-92 (2011) (Abstract in English).

* cited by examiner

CHIMERIC FIBROBLAST GROWTH FACTOR 23/FIBROBLAST GROWTH FACTOR 19 PROTEINS AND METHODS OF USE

This application claims priority benefit of U.S. Provisional Patent Application No. 61/768,289, filed Feb. 22, 2013, which is hereby incorporated by reference in its entirety.

This invention was made with government support under grant number DE13686 awarded by the National Institutes of Health. The government has certain rights in this invention.

FIELD OF THE INVENTION

The present invention relates to chimeric fibroblast growth factor ("FGF") proteins and uses thereof.

BACKGROUND OF THE INVENTION

Type 2 diabetes is a chronic progressive disorder, which results from end-organ resistance to the action of insulin in combination with insufficient insulin secretion from the pancreas. The metabolic abnormalities associated with insulin resistance and secretory defects, in particular the hyperglycemia, lead over the course of years to extensive irreversible damage to multiple organs including heart, blood vessels, kidney, and eye. Currently, nearly 200 million or 2.9% of the world population have type 2 diabetes (World Health Organization, Diabetes Fact Sheet N° 312, January 2011; Wild et al., "Global Prevalence of Diabetes: Estimates for the Year 2000 and Projections for 2030," *Diabetes Care* 27(5):1047-1053 (2004)), and its prevalence is rising at an alarmingly fast pace in parallel with the rise in the prevalence of overweight and obesity (World Health Organization, Obesity and Overweight Fact Sheet N° 311, January 2011). Until the end of the 20$^{th}$ century, type 2 diabetes was observed only in adults but what was once known as "adult-onset diabetes" is now also diagnosed in children and adolescents, and this growing incidence can be related to the increase in overweight and obesity among children and adolescents. The prevalence of pre-diabetes, an intermediate metabolic stage between normal glucose homeostasis and diabetes, is even greater than that of type 2 diabetes. Currently, nearly 80 million or 26% of the population in the United States alone have pre-diabetes (Center for Disease Control and Prevention, National Diabetes Fact Sheet 2011), and as such are at high risk for progressing to type 2 diabetes. Type 2 diabetes ranks among the ten leading causes of death worldwide, and the World Health Organization projects that mortality from diabetes (90% of which is type 2) will more than double within the next decade (World Health Organization, Diabetes Fact Sheet N° 312, January 2011). Type 2 diabetes also is a major cause of disability. As a consequence of diabetic retinopathy, about 10% of all patients with diabetes in the world develop severe visual impairment and 2% become blind 15 years into the disease (World Health Organization, Diabetes Fact Sheet N° 312, January 2011). Diabetic neuropathy, which affects up to half of all patients with diabetes worldwide (World Health Organization, Diabetes Fact Sheet N° 312, January 2011), accounts for the majority of nontraumatic lower-limb amputations. Indeed, in its recently published first worldwide report on non-infectious diseases, the World Health Organization considers diabetes, together with other chronic non-infectious diseases like cancer and heart disease, a global economic and social burden, which exceeds that imposed by infectious diseases such as HIV/AIDS.

The current drug therapy for type 2 diabetes is focused on correcting the hyperglycemia in the patients. Although a number of small molecules and biologics with different mechanisms of anti-hyperglycemic action are available for use as mono-therapy or combination therapy, most, if not all of these have limited efficacy, limited tolerability, and significant adverse effects (Moller, "New Drug Targets for Type 2 Diabetes and the Metabolic Syndrome," *Nature* 414 (6865):821-827 (2001)). For example, treatment with sulfonylureas, glinides, thiazolidinediones, or insulin has been associated with weight gain, which is an undesired effect since overweight is considered a driving force in the pathogenesis of type 2 diabetes. Some of these treatments have also been associated with increased risk of hypoglycemia. A limitation specific to the thiazolidinediones is the potential for adverse cardiovascular effects (DeSouza et al., "Therapeutic Targets to Reduce Cardiovascular Disease in Type 2 Diabetes," *Nat Rev Drug Discov* 8(5):361-367 (2009)). A meta-analysis of clinical data on the thiazolidinedione rosiglitazone (Avandia®), which was widely used for the treatment of type 2 diabetes, found that the drug increased the risk of myocardial infarction in patients with type 2 diabetes (Nissen et al., "Effect of Rosiglitazone on the Risk of Myocardial Infarction and Death from Cardiovascular Causes," *N Engl J Med* 356(24):2457-2471 (2007)). Of all diabetic complications, cardiovascular disease is the main cause of morbidity and mortality in patients with diabetes (World Health Organization, Diabetes Fact Sheet N° 312, January 2011; Center for Disease Control and Prevention, National Diabetes Fact Sheet 2011), and hence an aggravation of cardiovascular risk by drug treatment is absolutely unacceptable. In the wake of the debate about the cardiovascular safety of thiazolidinediones, the FDA issued a guidance on evaluating cardiovascular risk in new antidiabetic therapies to treat type 2 diabetes (Opar A, "Diabetes Drugs Pass Cardiovascular Risk Check," *Nat Rev Drug Discov* 8(5):343-344 (2009)). Meanwhile, thiazolidinediones lost their popularity. Even for glucagon-like peptide-1 agonists, one of the latest class of drugs introduced for the treatment of type 2 diabetes, concerns about safety have been raised, namely the potential for carcinogenicity (Opar A, "Diabetes Drugs Pass Cardiovascular Risk Check," *Nat Rev Drug Discov* 8(5):343-344 (2009)). Therefore, novel therapies that are more effective and safer than existing drugs are needed. Since the currently available drugs do not directly target complications of advanced diabetic disease, especially cardiovascular disease, therapies that are not only effective in lowering blood glucose but also reduce cardiovascular risk factors such as dyslipidemia are particularly desired.

There is a need to develop new therapies for the treatment of metabolic disorders such as diabetes, obesity, hyperglycemia, hyperlipidemia, hypercholesterolemia, "metabolic syndrome", and other related metabolic disorders.

A search conducted by Eli Lilly & Co. for potential novel biotherapeutics to treat type 2 diabetes led to the discovery of fibroblast growth factor (FGF) 21 as a protein that stimulates glucose uptake into adipocytes in an insulin-independent fashion (Kharitonenkov et al., "FGF-21 as a Novel Metabolic Regulator," *J Clin Invest* 115(6):1627-1635 (2005)). FGF21 has since emerged as a key endocrine regulator not only of glucose metabolism but also of lipid metabolism, and has become one of the most promising drug candidates for the treatment of type 2 diabetes, obesity, and metabolic syndrome. In mouse models of diabetes and obesity, pharmacologic doses of FGF21 lower plasma glucose and increase insulin sensitivity (Kharitonenkov et al., "FGF-21 as a Novel Metabolic Regulator," *J Clin Invest* 115(6):1627-1635 (2005); Coskun et al., "Fibroblast growth factor 21 corrects obesity in mice," *Endocrinology* 149(12): 6018-6027 (2008)). Concurrently, FGF21 lowers plasma triglyceride and cholesterol, enhances lipolysis and suppresses lipogenesis, and accelerates energy expenditure (Kharitonenkov et al., "FGF-21 as a Novel Metabolic Regulator," *J Clin Invest* 115(6):1627-1635 (2005); Coskun et al., "Fibroblast growth factor 21 corrects obesity in mice," *Endocrinology* 149(12):6018-6027 (2008)). In obese mice, FGF21 causes weight loss, in lean mice, it is weight neutral (Kharitonenkov et al., "FGF-21 as a Novel Metabolic Regulator," *J Clin Invest* 115(6):1627-1635 (2005); Coskun et al., "Fibroblast growth factor 21 corrects obesity in mice," *Endocrinology* 149(12):6018-6027 (2008)). Thus, FGF21 has some of the most desired characteristics of a drug for the treatment of type 2 diabetes; not only does it improve glycemic control, but also directly affects cardiovascular risk factors, such as hypertriglyceridemia, and reduces obesity, which is considered the single most important promoter of type 2 diabetes. Importantly, FGF21 does not induce hypoglycemia (Kharitonenkov et al., "FGF-21 as a Novel Metabolic Regulator," *J Clin Invest* 115(6):1627-1635 (2005)), a side effect that can occur with several of the current anti-diabetic therapies, including insulin. Moreover, FGF21 does not exhibit any mitogenic activity in mice (Kharitonenkov et al., "FGF-21 as a Novel Metabolic Regulator," *J Clin Invest* 115(6):1627-1635 (2005)), ruling out the possibility of a carcinogenic risk. The findings on FGF21 therapy in mouse models of diabetes have been reproduced in diabetic rhesus monkeys (Kharitonenkov et al., "The Metabolic State of Diabetic Monkeys is Regulated by Fibroblast Growth Factor-21," *Endocrinology* 148(2):774-781 (2007)), and are currently followed up with clinical trials in humans (Kharitonenkov et al., "FGF21 Reloaded: Challenges of a Rapidly Growing Field," *Trends Endocrinol Metab* 22(3):81-86 (2011)). However, there is a need for more effective FGF21-like therapeutics.

The present invention is directed to overcoming these and other deficiencies in the art.

SUMMARY OF THE INVENTION

One aspect of the present invention relates to an isolated chimeric protein. The isolated chimeric protein comprises an N-terminus coupled to a C-terminus, where the N-terminus includes an N-terminal portion from a fibroblast growth factor ("FGF") 23 molecule and the C-terminus includes a C-terminal portion from an FGF19 molecule.

Another aspect of the present invention relates to a pharmaceutical composition comprising an isolated chimeric protein and a pharmaceutically acceptable carrier. The isolated chimeric protein includes an N-terminus coupled to a C-terminus, where the N-terminus includes an N-terminal portion from a fibroblast growth factor ("FGF") 23 molecule and the C-terminus includes a C-terminal portion from an FGF19 molecule.

Yet another aspect of the present invention relates to a method for treating a subject suffering from a disorder. This method includes selecting a subject suffering from the disorder and administering to the subject a therapeutically effective amount of a chimeric protein. The chimeric protein includes an N-terminus coupled to a C-terminus, where the N-terminus includes an N-terminal portion from a fibroblast growth factor ("FGF") 23 molecule and the C-terminus includes a C-terminal portion from an FGF19 molecule.

DETAILED DESCRIPTION OF THE INVENTION

Figure 1:
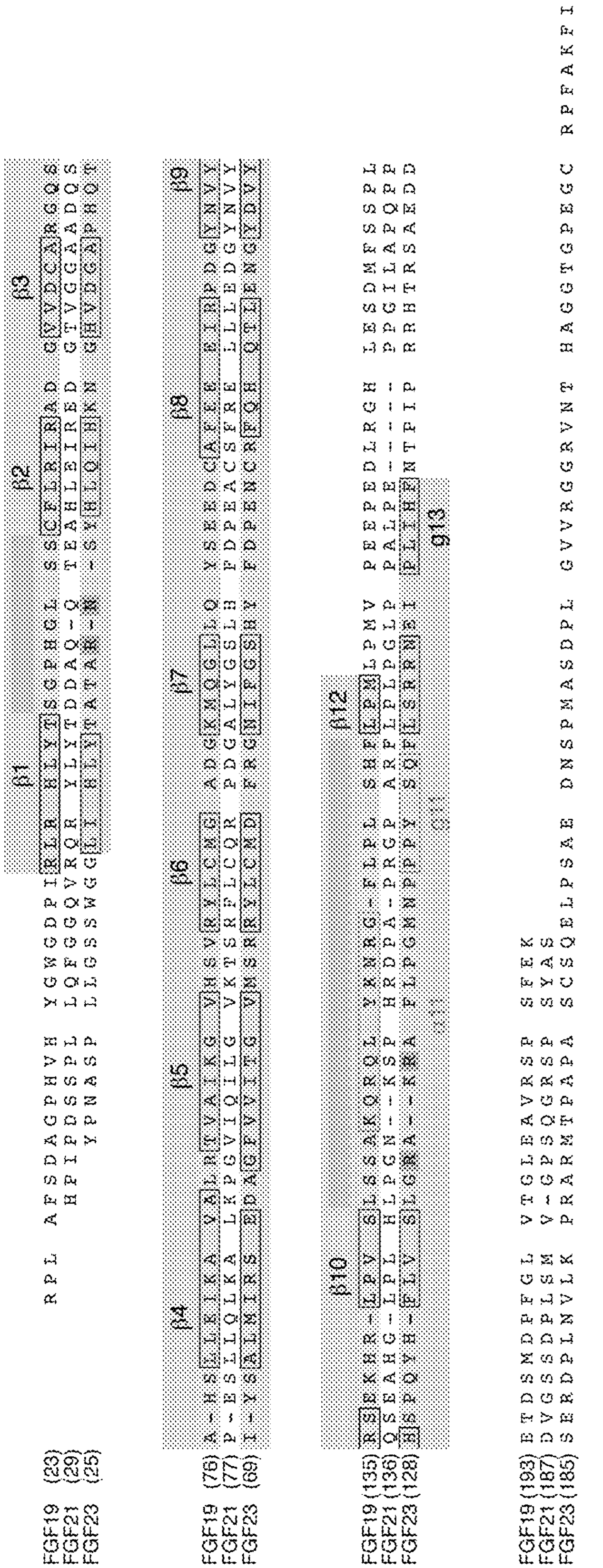
FIG. 1 shows a sequence alignment of the endocrine FGFs. The amino acid sequences of the mature human FGF19, FGF21, and FGF23 ligands are aligned. Residue numbers corresponding to the human sequence of FGF19 (GenBank Accession No. NP_005108, which is hereby incorporated by reference in its entirety) (SEQ ID NO: 89), FGF21 (GenBank Accession No. NP_061986, which is hereby incorporated by reference in its entirety) (SEQ ID NO:176), and FGF23 (GenBank Accession No. AAG09917, which is hereby incorporated by reference in its entirety) (SEQ ID NO:1) are in parenthesis to the left of the alignment. Residues that make up the secondary structure elements known for FGF19 and FGF23 (the 11β strands and the α helix and g helix, respectively) are indicated (black and gray boxes). Gaps (dashes) were introduced to optimize the sequence alignment. The β-trefoil core domain for the known crystal structures of FGF19 and FGF23 is shaded gray. Shaded and starred bars on top of the alignment indicate the location of the HS-binding regions. HS-binding residues in FGF23 selected for mutagenesis are individually shaded.

One aspect of the present invention relates to an isolated chimeric protein. The isolated chimeric protein comprises an N-terminus coupled to a C-terminus, where the N-terminus includes an N-terminal portion from a fibroblast growth factor ("FGF") 23 molecule and the C-terminus includes a C-terminal portion from an FGF19 molecule.

As described by Goetz et al. (Goetz et al., "Molecular Insights into the Klotho-Dependent, Endocrine Mode of Action of Fibroblast Growth Factor 19 Subfamily Members," *Mol Cell Biol* 3417-3428 (2007), which is hereby incorporated by reference in its entirety), the mammalian fibroblast growth factor (FGF) family comprises 18 polypeptides (FGF1 to FGF10 and FGF16 to FGF23), which participate in myriad biological processes during embryogenesis, including but not limited to gastrulation, body plan formation, somitogenesis, and morphogenesis of essentially every tissue/organ such as limb, lung, brain, and kidney (Bottcher et al., "Fibroblast Growth Factor Signaling During Early Vertebrate Development," *Endocr Rev* 26:63-77 (2005), and Thisse et al., "Functions and Regulations of Fibroblast Growth Factor Signaling During Embryonic Development," *Dev Biol* 287:390-402 (2005), which are hereby incorporated by reference in their entirety).

FGF signaling is essential for mammalian development and metabolism (Beenken and Mohammadi, "The FGF Family: Biology, Pathophysiology and Therapy," *Nat. Rev. Drug Discov.* 8:235-253 (2009); Itoh and Ornitz, "Fibroblast Growth Factors: From Molecular Evolution to Roles in Development, Metabolism and Disease," *J. Biochem.* 149:121-130 (2011), which are hereby incorporated by reference in their entirety).

FGFs execute their biological actions by binding to, dimerizing, and activating FGFR tyrosine kinases, which are encoded by four distinct genes (Fgfr1 to Fgfr4). Prototypical FGFRs consist of an extracellular domain composed of three immunoglobulin-like domains, a single-pass transmembrane domain, and an intracellular domain responsible for the tyrosine kinase activity (Mohammadi et al., "Structural Basis for Fibroblast Growth Factor Receptor Activation," *Cytokine Growth Factor Rev* 16:107-137 (2005), which is hereby incorporated by reference in its entirety). The number of principal FGFRs is increased from four to seven due to a major tissue-specific alternative splicing event in the second half of the immunoglobulin-like domain 3 of FGFR1 to FGFR3, which creates epithelial lineage-specific "b" and mesenchymal lineage-specific "c" isoforms (Mohammadi et al., "Structural Basis for Fibroblast Growth Factor Receptor Activation," *Cytokine Growth Factor Rev* 16:107-137 (2005) and Ornitz et al., "Fibroblast Growth Factors," *Genome Biol* 2(3):reviews3005.1-reviews3005.12 (2001), which are hereby incorporated by reference in their entirety). Generally, the receptor-binding specificity of FGFs is divided along this major alternative splicing of receptors whereby FGFRb-interacting FGFs are produced by epithelial cells (Ornitz et al., "Fibroblast Growth Factors," *Genome Biol* 2(3):reviews3005.1-reviews3005.12 (2001), which is hereby incorporated by reference in its entirety). These reciprocal expression patterns of FGFs and FGFRs result in the establishment of a paracrine epithelial-mesenchymal signaling loop which is essential for proper organogenesis and patterning during development as well as tissue homeostasis in the adult organism.

Based on sequence homology and phylogenetic and structural considerations, the eighteen mammalian FGFs are grouped into six subfamilies (Itoh et al., "Fibroblast growth factors: from molecular evolution to roles in development, metabolism, and disease," *J Biochem* 149:121-130 (2011); Mohammadi et al., "Structural basis for fibroblast growth factor receptor activation," *Cytokine Growth Factor Rev* 16:107-137 (2005), which are hereby incorporated by reference in its entirety). The FGF core homology domain (approximately 120 amino acids long) is flanked by N- and C-terminal sequences that are highly variable in both length and primary sequence, particularly among different FGF subfamilies. The core region of FGF19 shares the highest sequence identity with FGF21 (38%) and FGF23 (36%), and therefore, these ligands are considered to form a subfamily.

Based on mode of action, the eighteen mammalian FGFs are grouped into paracrine-acting ligands (five FGF subfamilies) and endocrine-acting ligands (one FGF subfamily) comprising FGF19, FGF21 and FGF23 (Itoh and Ornitz, "Fibroblast Growth Factors: From Molecular Evolution to Roles in Development, Metabolism and Disease," *J. Biochem.* 149:121-130 (2011); Mohammadi et al., "Structural Basis for Fibroblast Growth Factor Receptor Activation," *Cytokine Growth Factor Rev.* 16:107-137 (2005), which are hereby incorporated by reference in their entirety). FGFs mediate their actions by binding and activating FGF receptor tyrosine kinases (FGFRs). There are four FGFR genes in mammals (FGFR1-4) (Itoh and Ornitz, "Evolution of the Fgf and Fgfr Gene Families," *Trends Genet.* 20:563-569 (2004), which is hereby incorporated by reference in its entirety), and tissue-specific alternative splicing of FGFR1-3 generates "b" and "c" splice isoforms with distinct ligand-binding specificity (Chellaiah et al., "Fibroblast Growth Factor Receptor (FGFR) 3," *J. Biol. Chem.* 269:11620-11627 (1994); Johnson et al., "The Human Fibroblast Growth Factor Receptor Genes: A Common Structural Arrangement Underlies the Mechanisms for Generating Receptor Forms that Differ in Their Third Immunoglobulin Domain," *Mol. Cell Biol.* 11:4627-4634 (1991); Miki et al., "Determination of Ligand-binding Specificity by Alternative Splicing: Two Distinct Growth Factor Receptors Encoded by a Single Gene," *Proc. Nat'l. Acad. Sci. U.S.A.* 89:246-250 (1992); Olsen et al., "Structural Basis by Which Alternative Splicing Modulates the Organizer Activity of FGF8 in the Brain," *Genes Dev.* 20:185-198 (2006); Orr-Urtreger et al., "Developmental Localization of the Splicing Alternatives of Fibroblast Growth Factor Receptor-2 (FGFR2)," *Dev. Biol.* 158:475-486 (1993); Yeh et al., "Structural Basis by Which Alternative Splicing Confers Specificity in Fibroblast Growth Factor Receptors," *Proc. Nat'l. Acad. Sci. U.S.A.* 100:2266-2271 (2003), which are hereby incorporated by reference in their entirety).

Paracrine FGFs direct multiple processes during embryogenesis, including gastrulation, somitogenesis, organogenesis, and tissue patterning (Itoh and Ornitz, "Fibroblast Growth Factors: From Molecular Evolution to Roles in Development, Metabolism and Disease," *J. Biochem.* 149:121-130 (2011); Bottcher and Niehrs, "Fibroblast Growth Factor Signaling During Early Vertebrate Development," *Endocr. Rev.* 26:63-77 (2005); Thisse et al., "Functions and Regulations of Fibroblast Growth Factor Signaling During Embryonic Development," *Dev. Biol.* 287:390-402 (2005), which are hereby incorporated by reference in their entirety), and also regulate tissue homeostasis in the adult (Hart et al., "Attenuation of FGF Signalling in Mouse Beta-cells Leads to Diabetes," *Nature* 408:864-868 (2000); Jonker et al., "A PPARγ-FGF1 Axis is Required for Adaptive Adipose Remodelling and Metabolic Homeostasis," *Nature* 485:391-394 (2012), which is hereby incorporated by reference in its entirety).

Endocrine FGFs control major metabolic processes such as bile acid homeostasis (Inagaki et al., "Fibroblast Growth Factor 15 Functions as an Enterohepatic Signal to Regulate Bile Acid Homeostasis," *Cell Metab.* 2:217-225 (2005), which is hereby incorporated by reference in its entirety), and hepatic glucose and protein metabolism (Kir et al., "FGF19 as a Postprandial, Insulin-Independent Activator of Hepatic Protein and Glycogen Synthesis," *Science* 331:1621-1624 (2011); Potthoff et al., "FGF15/19 Regulates Hepatic Glucose Metabolism by Inhibiting the CREB-PGC-1α Pathway," *Cell Metab.* 13:729-738 (2011), which are hereby incorporated by reference in their entirety) (FGF19), glucose and lipid metabolism (Badman et al., "Hepatic Fibroblast Growth Factor 21 Is Regulated by PPARα and Is a Key Mediator of Hepatic Lipid Metabolism in Ketotic States," *Cell Metab.* 5:426-437 (2007); Inagaki et al., "Endocrine Regulation of the Fasting Response by PPARalpha-mediated Induction of Fibroblast Growth Factor 21," *Cell Metab.* 5:415-425 (2007); Kharitonenkov et al., "FGF-21 as a Novel Metabolic Regulator," *J. Clin. Invest.* 115:1627-1635 (2005); Potthoff et al., "FGF21 Induces PGC-1alpha and Regulates Carbohydrate and Fatty Acid Metabolism During the Adaptive Starvation Response," *Proc. Nat'l. Acad. Sci. U.S.A.* 106:10853-10858 (2009), which are hereby incorporated by reference in their entirety) (FGF21), and phosphate and vitamin D homeostasis (White et al., "Autosomal Dominant Hypophosphataemic Rickets is Associated with Mutations in FGF23," *Nat. Genet.* 26:345-348 (2000); Shimada et al., "Targeted Ablation of Fgf23 Demonstrates an Essential Physiological Role of FGF23 in Phosphate and Vitamin D Metabolism," *J. Clin. Invest.* 113:561-568 (2004), which are hereby incorporated by reference in their entirety) (FGF23). Thus, these ligands have attracted much attention as potential drugs for the treatment of various inherited or acquired metabolic disorders (Beenken and Mohammadi, "The FGF Family: Biology, Pathophysiology and Therapy," *Nat. Rev. Drug Discov.* 8:235-253 (2009); Beenken and Mohammadi, "The Structural Biology of the FGF19 Subfamily," in *Endocrine FGFs and Klothos* (Kuro-o, M. ed.), Landes Bioscience. pp 1-24 (2012), which are hereby incorporated by reference in their entirety).

FGFs share a core homology region of about one hundred and twenty amino acids that fold into a β-trefoil (Ago et al., *J. Biochem.* 110:360-363 (1991); Eriksson et al., *Proc. Nat'l. Acad. Sci. U.S.A.* 88:3441-3445 (1991); Zhang et al., *Proc. Nat'l. Acad. Sci. U.S.A.* 88:3446-3450 (1991); Zhu et al., *Science* 251:90-93 (1991), which are hereby incorporated by reference in their entirety) consisting of twelve β strands in paracrine FGFs (β1-β12) and eleven β strands in endocrine FGFs (β1-β10 and β12) (Mohammadi et al., "Structural Basis for Fibroblast Growth Factor Receptor Activation," *Cytokine Growth Factor Rev.* 16:107-137 (2005); Goetz et al., *Mol. Cell Biol.* 27:3417-3428 (2007), which are hereby incorporated by reference in their entirety). The conserved core region is flanked by divergent N- and C-termini, which play a critical role in conferring distinct biological activity on FGFs (Mohammadi et al., "Structural Basis for Fibroblast Growth Factor Receptor Activation," *Cytokine Growth Factor Rev.* 16:107-137 (2005); Olsen et al., *Genes Dev.* 20:185-198 (2006), which are hereby incorporated by reference in their entirety).

All FGFs interact with pericellular heparan sulfate (HS) glycosaminoglycans albeit with different affinities (Asada et al., *Biochim. Biophys. Acta.* 1790:40-48 (2009), which is hereby incorporated by reference in its entirety). The HS-binding site of FGFs is comprised of the β1-β2 loop and the region between β10 and β12 strands (Mohammadi et al., "Structural Basis for Fibroblast Growth Factor Receptor Activation," *Cytokine Growth Factor Rev.* 16:107-137 (2005), which is hereby incorporated by reference in its entirety). HS interacts with both side chain and main chain atoms of the HS-binding site in paracrine FGFs (Schlessinger et al., *Mol. Cell* 6:743-750 (2000), which is hereby incorporated by reference in its entirety). The HS-binding site of endocrine FGFs deviates from the common conformation adopted by paracrine FGFs such that interaction of HS with backbone atoms of the HS-binding site is precluded (Goetz et al., *Mol. Cell Biol.* 27:3417-3428 (2007), which is hereby incorporated by reference in its entirety). As a result, compared to paracrine FGFs, endocrine FGFs exhibit poor affinity for HS (Beenken and Mohammadi, "The FGF Family: Biology, Pathophysiology and Therapy," *Nat. Rev. Drug Discov.* 8:235-253 (2009); Asada et al., *Biochim. Biophys. Acta.* 1790:40-48 (2009), which are hereby incorporated by reference in their entirety). The poor HS affinity enables these ligands to diffuse freely away from the site of their secretion and enter the blood circulation to reach their distant target organs (Goetz et al., *Mol. Cell Biol.* 27:3417-3428 (2007); Asada et al., *Biochim. Biophys. Acta.* 1790:40-48 (2009), which are hereby incorporated by reference in their entirety).

By contrast, owing to their high HS affinity (Asada et al., *Biochim. Biophys. Acta.* 1790:40-48 (2009), which is hereby incorporated by reference in its entirety), paracrine FGFs are mostly immobilized in the vicinity of the cells secreting these ligands, and hence can only act within the same organ.

There is emerging evidence that differences in HS-binding affinity among paracrine FGFs translate into the formation of ligand-specific gradients in the pericellular matrix (Kalinina et al., *Mol. Cell Biol.* 29:4663-4678 (2009); Makarenkova et al., Sci. Signal 2:ra55 (2009), which are hereby incorporated by reference in their entirety), which contribute to the distinct functions of these ligands (Beenken and Mohammadi, "The FGF Family: Biology, Pathophysiology and Therapy," *Nat. Rev. Drug Discov.* 8:235-253 (2009); Itoh and Ornitz, "Fibroblast Growth Factors: From Molecular Evolution to Roles in Development, Metabolism and Disease," *J. Biochem.* 149:121-130 (2011), which are hereby incorporated by reference in their entirety).

Besides controlling ligand diffusion in the extracellular space, HS promotes the formation of the 2:2 paracrine FGF-FGFR signal transduction unit (Schlessinger et al., *Mol. Cell* 6:743-750 (2000); Mohammadi et al., *Curr. Opin. Struct. Biol.* 15:506-516 (2005), which are hereby incorporated by reference in their entirety). HS engages both ligand and receptor to enhance the binding affinity of FGF for receptor and promote dimerization of ligand-bound receptors. Owing to their poor HS-binding affinity, endocrine FGFs rely on Klotho co-receptors to bind their cognate FGFR (Kurosu et al., *J. Biol. Chem.* 282:26687-26695 (2007); Kurosu et al., *J. Biol. Chem.* 281:6120-6123 (2006); Ogawa et al., *Proc. Nat'l. Acad. Sci. U.S.A.* 104:7432-7437 (2007); Urakawa et al., *Nature* 444:770-774 (2006), which are hereby incorporated by reference in their entirety). Klotho co-receptors are single-pass transmembrane proteins with an extracellular domain composed of two type I β-glycosidase domains (Ito et al., *Mech. Dev.* 98:115-119 (2000); Kuro-o et al., *Nature* 390:45-51 (1997), which are hereby incorporated by reference in their entirety). Klotho co-receptors constitutively associate with FGFRs to enhance the binding affinity of endocrine FGFs for their cognate FGFRs in target tissues (Kurosu et al., *J. Biol. Chem.* 282:26687-26695 (2007); Kurosu et al., *J. Biol. Chem.* 281:6120-6123 (2006); Ogawa et al., *Proc. Nat'l. Acad. Sci. U.S.A.* 104:7432-7437 (2007); Urakawa et al., *Nature* 444:770-774 (2006), which are hereby incorporated by reference in their entirety). αKlotho is the co-receptor for FGF23 (Kurosu et al., *J. Biol. Chem.* 281:6120-6123 (2006); Urakawa et al., *Nature* 444:770-774 (2006), which are hereby incorporated by reference in their entirety), and βKlotho is the co-receptor for both FGF19 and FGF21 (Kurosu et al., *J. Biol. Chem.* 282:26687-26695 (2007); Ogawa et al., *Proc. Nat'l. Acad. Sci. U.S.A.* 104:7432-7437 (2007), which are hereby incorporated by reference in their entirety). The C-terminal region of endocrine FGFs mediates binding of these ligands to the FGFR-α/βKlotho co-receptor complex (Goetz et al., *Mol. Cell Biol.* 27:3417-3428 (2007); Goetz et al., *Proc. Nat'l. Acad. Sci. U.S.A* 107:407-412 (2010); Micanovic et al., *J. Cell Physiol.* 219:227-234 (2009); Wu et al., *J. Biol. Chem.* 283:33304-33309 (2008); Yie et al., *FEBS Lett,* 583:19-24 (2009); Goetz et al., *Mol. Cell Biol.* 32:1944-1954 (2012), which are hereby incorporated by reference in their entirety).

Endocrine FGFs still possess residual HS-binding affinity, and moreover, there are differences in this residual binding affinity among the endocrine FGFs (Goetz et al., *Mol. Cell Biol.* 27:3417-3428 (2007), which is hereby incorporated by reference in its entirety). These observations raise the possibility that HS may play a role in endocrine FGF signaling. Indeed, there are several reports showing that HS can promote endocrine FGF signaling in the presence as well as in the absence of Klotho co-receptor. It has been shown that HS augments the mitogenic signal elicited by endocrine FGFs in BaF3 cells over-expressing FGFR and Klotho co-receptor by at least two-fold (Suzuki et al., *Mol. Endocrinol.* 22:1006-1014 (2008), which is hereby incorporated by reference in its entirety). In addition, even in the absence of Klotho co-receptor, HS enables endocrine FGFs to induce proliferation of BaF3 cells over-expressing FGFR (Yu et al., *Endocrinology* 146:4647-4656 (2005); Zhang et al., *J. Biol. Chem.* 281:15694-15700 (2006), which are hereby incorporated by reference in their entirety). Compared to paracrine FGFs, however, significantly higher concentrations of both ligand and HS are needed, and the proliferative response of cells to endocrine FGFs still lags behind that of paracrine FGFs by about one order of magnitude (Zhang et al., *J. Biol. Chem.* 281:15694-15700 (2006), which is hereby incorporated by reference in its entirety).

Fibroblast growth factor (FGF) 23, is an endocrine regulator of phosphate homeostasis, and was originally identified as the mutated gene in patients with the phosphate wasting disorder "autosomal dominant hypophosphatemic rickets" (ADHR) (Anonymous, "Autosomal Dominant Hypophosphataemic Rickets is Associated with Mutations in FGF23," *Nat Genet* 26(3):345-348 (2000), which is hereby incorporated by reference in its entirety). FGF23 inhibits reabsorption of phosphate in the renal proximal tubule by decreasing the abundance of the type II sodium-dependent phosphate transporters $NaP_i$-2A and $NaP_i$-2C in the apical brush border membrane (Baum et al., "Effect of Fibroblast Growth Factor-23 on Phosphate Transport in Proximal Tubules," *Kidney Int* 68(3):1148-1153 (2005); Perwad et al., "Fibroblast Growth Factor 23 Impairs Phosphorus and Vitamin D Metabolism In Vivo and Suppresses 25-hydroxyvitamin D-1alpha-hydroxylase Expression In Vitro," *Am J Physiol Renal Physiol* 293(5):F1577-1583 (2007); Larsson et al., "Transgenic Mice Expressing Fibroblast Growth Factor 23 under the Control of the Alpha1(I) Collagen Promoter Exhibit Growth Retardation, Osteomalacia, and Disturbed Phosphate Homeostasis," *Endocrinology* 145(7):3087-3094 (2004), each of which is hereby incorporated by reference in its entirety). The phosphaturic activity of FGF23 is down-regulated by proteolytic cleavage at the $^{176}$RXXR$^{179}$ (SEQ ID NO: 1) motif, where "XX" is defined as "HT", corresponding to positions 177 and 178, respectively, of the FGF23 amino acid sequence, producing an inactive N-terminal fragment (Y25 to R179) and a C-terminal fragment (S 180 to 1251) (Goetz et al., "Molecular Insights into the Klotho-dependent, Endocrine Mode of Action of Fibroblast Growth Factor 19 Subfamily Members," *Mol Cell Biol* 27(9):3417-3428 (2007), which is hereby incorporated by reference in its entirety). Klotho, a protein first described as an aging suppressor (Kuro-o et al., "Mutation of the Mouse Klotho Gene Leads to a Syndrome Resembling Aging," *Nature* 390(6655):45-51 (1997), which is hereby incorporated by reference in its entirety), is required by FGF23 in its target tissue in order to exert its phosphaturic activity (Kurosu et al., "Regulation of Fibroblast Growth Factor-23 Signaling by Klotho," *J Biol Chem* 281(10):6120-6123 (2006); Urakawa et al., "Klotho Converts Canonical FGF Receptor into a Specific Receptor for FGF23," *Nature* 444(7120):770-774 (2006), each of which is hereby incorporated by reference in its entirety). Klotho constitutively binds the cognate FGFRs of FGF23, and the binary FGFR-Klotho complexes exhibit enhanced binding affinity for FGF23 ((Kurosu et al., "Regulation of Fibroblast Growth Factor-23 Signaling by Klotho," *J Biol Chem* 281(10):6120-6123 (2006); Urakawa et al., "Klotho Converts Canonical FGF Receptor into a Specific Receptor for FGF23," *Nature* 444(7120):770-774 (2006), each of which is hereby incorporated by reference in its entirety). In co-immunoprecipitation studies, it was demonstrated that the mature, full-length form of FGF23 (Y25 to 1251) but not the inactive N-terminal fragment of proteolytic cleavage (Y25 to R179) binds to binary FGFR-Klotho complexes (Goetz et al., "Molecular Insights into the Klotho-dependent, Endocrine Mode of Action of Fibroblast Growth Factor 19 Subfamily Members," *Mol Cell Biol* 27(9):3417-3428 (2007), which is hereby incorporated by reference in its entirety).

FGF23 is an endocrine FGF that was cloned by Itoh et al. at Kyoto University (WO 01/66596 to Itoh et al., which is hereby incorporated by reference in its entirety). FGF23 mRNA is expressed mainly in the brain, preferentially in the ventrolateral thalamic nucleus. It is also expressed in the thymus at low levels (Yamashita et al., "Identification of a Novel Fibroblast Growth Factor, FGF-23, Preferentially Expressed in the Ventrolateral Thalamic Nucleus of the Brain," *Biochem Biophys Res Comm* 277(2):494-498 (2000), which is hereby incorporated by reference in its entirety). The tissue with the highest level of FGF23 expression is bone (osteocytes and osteoblasts), where it is highly expressed during phases of active bone remodeling (Riminucci et al., "FGF-23 in Fibrous Dysplasia of Bone and its Relationship to Renal Phosphate Wasting," *J Clin Invest* 112:683-692 (2003), which is hereby incorporated by reference in its entirety). Expression of FGF23 in dendritic cells has also been reported (Katoh et al., "Comparative Genomics on Mammalian Fgf6-Fgf23 Locus.," *Int J Mol Med* 16(2):355-358 (2005), which is hereby incorporated by reference in its entirety). See also Zhang et al., "Receptor Specificity of the Fibroblast Growth Factor Family," *J Biol Chem* 281(23):15694-15700; Yu et al., "Analysis of the Biochemical Mechanisms for the Endocrine Actions of Fibroblast Growth Factor-23," *Endocrinology* 146(11):4647-4656, which are hereby incorporated by reference in their entirety.

As used herein, the terms "chimeric polypeptide" and "chimeric protein" encompass a polypeptide having a sequence that includes at least a portion of a full-length sequence of first polypeptide sequence and at least a portion of a full-length sequence of a second polypeptide sequence, wherein the first and second polypeptides are different polypeptides. A chimeric polypeptide also encompasses polypeptides that include two or more non-contiguous portions from the same polypeptide. A chimeric polypeptide also encompasses polypeptides having at least one substitution, wherein the chimeric polypeptide includes a first polypeptide sequence in which a portion of the first polypeptide sequence has been substituted by a portion of a second polypeptide sequence.

As used herein, the term "N-terminal portion" of a given polypeptide sequence is a contiguous stretch of amino acids of the given polypeptide sequence that begins at or near the N-terminal residue of the given polypeptide sequence. An N-terminal portion of the given polypeptide can be defined by a contiguous stretch of amino acids (e.g., a number of amino acid residues). Similarly, the term "C-terminal portion" of a given polypeptide sequence is a contiguous length of the given polypeptide sequence that ends at or near the C-terminal residue of the given polypeptide sequence. A C-terminal portion of the given polypeptide can be defined by a contiguous stretch of amino acids (e.g., a number of amino acid residues).

The term "portion," when used herein with respect to a given polypeptide sequence, refers to a contiguous stretch of amino acids of the given polypeptide's sequence that is shorter than the given polypeptide's full-length sequence. A portion of a given polypeptide may be defined by its first position and its final position, in which the first and final positions each correspond to a position in the sequence of the given full-length polypeptide. The sequence position corresponding to the first position is situated N-terminal to the sequence position corresponding to the final position. The sequence of the portion is the contiguous amino acid sequence or stretch of amino acids in the given polypeptide that begins at the sequence position corresponding to the first position and ending at the sequence position corresponding to the final position. A portion may also be defined by reference to a position in the given polypeptide sequence and a length of residues relative to the referenced position, whereby the sequence of the portion is a contiguous amino acid sequence in the given full-length polypeptide that has the defined length and that is located in the given polypeptide in reference to the defined position.

In one embodiment, the N-terminal portion of the chimeric protein according to the present invention is from FGF23. In one embodiment, the FGF23 has the amino acid sequence of SEQ ID NO: 1 (GenBank accession no. AAG09917, which is hereby incorporated by reference in its entirety), as follows:

```
  1 mlgarlrlwv calcsvcsms vlraypnasp llgsswggli
    hlytatarns yhlqihkngh

 61 vdgaphqtiy salmirseda gfvvitgvms rrylcmdfrg
    nifgshyfdp encrfqhqtl

121 engydvyhsp qyhflvslgr akraflpgmn pppysqflsr
    rneiplihfn tpiprrhtrs

181 aeddserdpl nvlkprarmt papascsqel psaednspma
    sdplgvvrgg rvnthaggtg

241 pegcrpfakf i
```

In one embodiment, the N-terminal portion from FGF23 comprises a contiguous sequence of amino acid residues beginning at any of amino acid residues 1 to 28 and ending at any of amino acid residues 162 to 172 of SEQ ID NO: 1. In one embodiment, the N-terminal portion from FGF23 comprises amino acid residues 25-172, 26-172, 27-172, 28-172, 25-170, 26-170, 27-170, 28-170, 25-164, 26-164, 27-164, 28-164, 25-163, 26-163, 27-163, 28-163, 25-162, 26-162, 27-162, or 28-162 of SEQ ID NO: 1.

In one embodiment, the N-terminal portion from FGF23 further comprises one or more substitutions, additions, or deletions. In one embodiment, the portion from the FGF23 molecule comprises a modification to enhance binding affinity for FGF receptor compared to the portion without the modification. In one embodiment, the portion from the FGF23 molecule comprises a modification to enhance stability and extend half-life compared to the portion without the modification. In one embodiment, the portion from the FGF23 molecule comprises a modification to enhance thermal stability.

In one embodiment, the N-terminal portion from FGF23 comprises a modification to decrease binding affinity heparin and/or heparan sulfate compared to the portion without the modification. In one embodiment the modification includes a substitution at amino acid residues R48, N49, R140, and/or R143 of SEQ ID NO: 1. In one embodiment, the modification includes one or more substitutions selected from the group consisting of R48A/G/S/T, N49A/G/S/T, R140A/G/S/T, R143A/G/S/T, and combinations thereof. In one embodiment the modification includes a substitution in the N-terminal portion at amino acid residues corresponding to positions R48, N49, R140, and/or R143 of SEQ ID NO: 1. As noted below, portions corresponding to the above-identified amino acid sequences of human FGF23 may be determined by, for example, sequence analysis and structural analysis.

In one embodiment, the N-terminal region from FGF23 according to the present invention is from a mammal. It will be understood that this includes orthologs of human FGF23, or a polypeptide or protein obtained from one species that is the functional counterpart of a polypeptide or protein from a different species. In one embodiment of the present invention, the N-terminal portion from FGF23 of the chimeric protein according to the present invention is from *Gorilla gorilla, Nomascus leucogenys, Macaca mulatta, Macaca fascicularis, Pan troglodytes, Callithrix jacchus, Loxodonta Africana, Erinaceus telfairi, Erinaceus europaeus, Otolemur garnettii, Oryctolagus cuniculus, Equus caballus, Ailuropoda melanoleuca, Ochotona princeps, Bos taurus, Sus scrofa, Canis lupus familiaris, Cavia porcellus, Cricetulus griseus, Tupaia belangeri, Rattus norvegicus, Mus musculus, Pteropus vampyrus, Myotis lucifugus, Sarcophilus harrisii, Monodelphis domestica, Dasypus novemcinctus, Macropus eugenii, Taeniopygia guttata, Gallus gallus, Meleagris gallopavo, Anolis carolinensis, Latimeria chalumnae, Xenopus silurana tropicalis, Felis catus, Pelodiscus sinensis, Mustela putorius furo, Microcebus murinus, Pongo abelii, Sorex araneus, Tetraodon nigroviridis, Oreochromis niloticus*, or *Danio rerio*.

In one embodiment of the present invention, the N-terminal portion of the chimeric protein of the present invention is from a non-human FGF23 (or an FGF23 ortholog) having an amino acid sequence as shown in Table 1. The portions of an ortholog of human FGF23 of a chimeric protein according to the present invention include portions corresponding to the above-identified amino acid sequences of human FGF23. Corresponding portions may be determined by, for example, sequence analysis and structural analysis.

TABLE 1

Amino acid sequence of *Gorilla gorilla* (gorilla) FGF23 (SEQ ID NO: 2) (Ensembl accession no. ENSGGOP00000002917, which is hereby incorporated by reference in its entirety):

```
  1 MLGARLRLWV CALCSVCSLS VLRAYPNASP LLGSSWGGLI HLYTATARNS YHLQIHKNGH
 61 VDGAPHQTIY SALMIRSEDA GFVVITGVMS RRYLCMDFRG NIFGSHYFDP ENCRFQHQTL
121 ENGYDVYHSP QYHFLVSLGR AKRAFLPGMN PPPYSQFLSR RNEIPLIHFN TPIPRRHTRS
181 AEDDSERDPL NVLKPRARMT PAPASCSQEL PSAEDNSPMA SDPLGVVRGG RVNTYAGGTG
241 PEGCRPFPKF I
```

TABLE 1-continued

| |
|---|
| Amino acid sequence of *Nomascus leucogenys* (Northern white-cheeked gibbon) FGF23 (SEQ ID NO: 3) (GenBank accession no. XP_003273749, which is hereby incorporated by reference in its entirety): |
| 1 mlgarlrlwv calcsvcsms vlraypnasp llgsswggli hlytatarns yhlqihkngh<br>61 vdgaphqtiy salmirseda gfvvitgvms rrylcmdfrg nifgshyfnp encrfqhqtl<br>121 engydvyhsp qhhflvslgr akraflpgmn pppysqflsr rneipllhfn tptprrhtrs<br>181 aeddserdpl nvlkprarmt papascsqel lssednspma sdplgvvrgg rvnthaggtg<br>241 pegcrpfpkf i |
| Amino acid sequence of *Macaca mulatta* (rhesus monkey) FGF23 (SEQ ID NO: 4) (GenBank accession no. NP_001181066, which is hereby incorporated by reference in its entirety): |
| 1 mlgarlrlwv calcsvcsms viraypnasp llgsswggli hlytatarns yhlqihkngh<br>61 vdgaphqtiy salmirseda gfvvitgvms rrylcmdfrg nifgshyfnp encrfrhwtl<br>121 engydvyhsp qhhflvslgr akraflpgmn pppysqflsr rneiplihfn tprprrhtrs<br>181 aeddserdpl nvlkprarmt papascsgel psaednspva sdplgvvrgg rvnthaggtg<br>241 peacrpfpkf i |
| Amino acid sequence of *Macaca fascicularis* (crab-eating macaque) FGF23 (SEQ ID NO: 5) (GenBank accession no. EHH66001, which is hereby incorporated by reference in its entirety): |
| 1 mlgarlrlwv calcsvcsms viraypnasp llgsswggli hlytatarns yhlqihkngh<br>61 vdgaphqtiy salmirseda gfvvitgvms rrylcmdfrg nifgshyfnp encrfrhwtl<br>121 engydvyhsp qhhflvslgr akraflpgmn pppysqflsr rneiplihfn tprprrhtrs<br>181 aeddserdpl nvlkprarmt papascsqel psaednspva sdplgvvrag rvnthaggtg<br>241 peacrpfpkf i |
| Amino acid sequence of *Pan troglodytes* (chimpanzee) FGF23 (SEQ ID NO: 6) (GenBank accession no. XP_001157070, which is hereby incorporated by reference in its entirety): |
| 1 mlgarlrlwv calcsvcsvs vlraypnasp llgsswggli hlytatarns yhlqihkngh<br>61 vdgaphqtiy salmirseda gfvvitgvms rrylcmdfrg nifgshyfnp encrfqhqtl<br>121 engydvyysp qyhflvslgr akraflpsmn pppysqflsr rneiplihfn tpiprrhtrs<br>181 aeddserdpl nvlkprarmt papascsqel psaednspma sdplgvvrgg rvnthaggtg<br>241 pegcrpfpkf i |
| Amino acid sequence of *Callithrix jacchus* (white-tufted-ear marmoset) FGF23 (SEQ ID NO: 7) (GenBank accession no. XP_002752281, which is hereby incorporated by reference in its entirety): |
| 1 mlgarlrlwv calcsvcsms vlraypnasp llasswggli hlytatarns yhlqihkngh<br>61 vdgaphqtiy sallirseda gfvvitgvms rrylcmdfrg nifgshyfnp encrfrpqrl<br>121 engydvyqsp qhhflvslgr akraflpgmn pppysqflsr rneiplihfn tpkprrhtrs<br>181 aeddpeldpl nvlksrvrmt papascsqel lsaednspvg sdplgmvrgg rvnshaegtg<br>241 pegcspfpkl i |
| Amino acid sequence of *Loxodonta africana* (elephant) FGF23 (SEQ ID NO: 8) (GenBank accession no. XP_003410677, which is hereby incorporated by reference in its entirety): |
| 1 mlgarlrlwv ctlcsacsmc svraypnasp llhsswgglt hlytatarns yhlqihkdgh<br>61 vdgtpdqtiy saliirseea gfvvitgvms rrylcmdfrg nifgshyfnp encrfkhwtl<br>121 engydvyhsp qhhflvslgr vkkaflpgmn pppysqflsr rneipliyfn tpkprrhtrs<br>181 aeddserdpl nvlkprprmt papascsqel lsaednsvva ndplgvvrsn rvnthaggig<br>241 vercrpfpkf i |
| Amino acid sequence of *Erinaceus telfairi* (lesser hedgehog tenrec) FGF23 (SEQ ID NO: 9) (Ensembl accession no. ENSETEP00000001298, which is hereby incorporated by reference in its entirety): |
| 1 MLGAHLRLWV CALCSVSAMY HVRAYPNASP LLGTSWAGLT HLYTATARNS FHLQIHKDGH<br>61 VDGTPHQTIY SALMIRSEDS GFVVITGVMS RRYLCMDFRG NIFGSHYFTA DSCRFRQRTL<br>121 ENGYDVYHSP QHHFLISLGR AKRVFLPGMN PPPYSQFLSR RNEIPLIHFN TPRPRRHTRS<br>181 AEEEVEQDPL NVLKPRPRMT PAPASCSQEL PSAEDNSALA SDPLGVVRGK KLNTHAVGMG<br>241 AERCRPFPKF |

TABLE 1-continued

Amino acid sequence of *Erinaceus europaeus* (hedgehog) FGF23 (SEQ ID NO: 10) (Ensembl accession no. ENSEEUP00000007211, which is hereby incorporated by reference in its entirety):

```
  1MLGAHLGLVV CALVSRAYPN ASPLLGFSWG GLTHLYTATA RNSYHLQIHK DGHVDGSPQQ
 61TIY------- --AGFVMITG VMSRRYLCMD FRSNIFGSHH FAPESCRFRH RTLENGYDVY
121HSPQHHFLVS LGRAKRAFLP GTNPPPYSQF LSRRNEVPLI HFNTPRPRRH TRSAEDNSEL
181DPLNVLKPRP RMTPAPASCS QELPSAEDNS MVASDPLGVV RANRVNTHAG GLGVDKCRPF
241PKFI
```

Amino acid sequence of *Otolemur garnettii* (bushbaby) FGF23 (SEQ ID NO: 11) (Ensembl accession no. ENSOGAP00000004657, which is hereby incorporated by reference in its entirety):

```
  1MLGTCLRLWV CALCSVCSVS IVRAYPNASP LLSSSWGGLT HLYTASARNS YHLQIHKDGH
 61VDGTPHQTIY SALMIRSEDA GFVVITGVMS RRYLCMDFKG NIFGSHSFHP ESCRFRHRTL
121ENGYDVYLSP QHHFLVSLGR SKRPFLPGMN PPPFSQFLSR RNDIPLIHFN TPRPRRHTRS
181AEDNDSELDP LNVLKPRPRA TPGPASCSQE LPSAEDNSLV ASDPLGVVRG NRVNAHAGRA
241GLDRCRPFPR YF
```

Amino acid sequence of *Oryctolagus cuniculus* (rabbit) FGF23 (SEQ ID NO: 12) (GenBank accession no. XP_002712872, which is hereby incorporated by reference in its entirety):

```
  1mlgarllrll vcalgsvcsw cvvraypdts pllssswagl thlytatarn syhlqihkdg
 61qvdgtphqti ysalmirsed agfvvitgvm srrylcmdfr gnifgshyfd pqncrfrhrt
121lengydvyhs pehhflvslg rakrpflpgm npppysqfls rrneiplihf ntprprrhtr
181saedaweqdp lnvlkprfrl tpapascsqe apsaednglv asdpfgvlrg nrvnmhgdrm
241gperchhfpk fi
```

Amino acid sequence of *Equus caballus* (horse) FGF23 (SEQ ID NO: 13) (GenBank accession no. XP_001491469, which is hereby incorporated by reference in its entirety):

```
  1msgpclgllv yvlcsavkay pnasplldss wgslthlyta tarnsyhlqi hkdghvdgtp
 61hqtiysalmi rsedagfvvi tgvmsrrylc mdfrgnifgs hhfspescsf rqrtlengyd
121yyhspqhrfl vslgrakraf lpgtnpppys qflsrrneip lvhfntprpr rhtrsaedns
181erdplnvlkp rprmtpapas csqelpsaed nsvlasdplg vvrgnrvnth aggagvercr
241pfpkff
```

Amino acid sequence of *Ailuropoda melanoleuca* (giant panda) FGF23 (SEQ ID NO: 14) (GenBank accession no. XP_002920496, which is hereby incorporated by reference in its entirety):

```
  1msgtrlgllv svlcwvgray pntspllgss wgglthlyta sarnsyhlqi hkdghvdgtp
 61hqtiysalmi rsedagfvvi tgvmsrrylc mdlrgnifgs hlfspescrf rqrtlengyd
121vyhspqhrfl vslgqakrtf lpgtnpppys qflsrrneip lihfntprpr rhtrsaedte
181rdplnvlkpr prmtpapasc sqelpsaedn svvasdplgv lrgnrvnaha ggmgvdrcrp
241fpkfi
```

Amino acid sequence of *Ochotona princeps* (pika) FGF23 (SEQ ID NO: 15) (Ensembl accession no. ENSOPRP00000006546, which is hereby incorporated by reference in its entirety):

```
  1MLGGLGLWVC VLGSVCSWRG VRAYPDTSPL LGSSWTGLTH LYTATARNSF HLQIHKDGHV
 61DGTPQQTIYS ALMIRSEDAG FVVITGVMSR RYLCMDFRGN IFGSHYFEPQ NCRFQQRTLE
121NGYDIYHSPQ HDFLVSLGRA KRPFLPGMNP PPYSQFLSRR NEIPLILFNT PRPRRHTRSA
181EEGWERDPLN VLKSRPRMTP APASCSREAP SAEDDGLLAS DPMGVLRGHR VDVHGGGTGR
241DRCRPFPRFI
```

Amino acid sequence of *Bos taurus* (cattle) FGF23 (SEQ ID NO: 16) (GenBank accession no. XP_002687926, which is hereby incorporated by reference in its entirety):

```
  1mlgarlglwv ctlscvvqay pnsspllgss wgglthlyta tarnsyhlqi hgdghvdgsp
 61qqtvysalmi rsedagfvvi tgvmsrrylc mdftgnifgs hhfspescrf rqrtlengyd
121vyhspqhrfl vslgrakraf lpgtnpppya qflsrrneip lphfaatarp rrhtrsahds
181gdplsvlkpr aratpvpaac sqelpsaeds gpaasdplgv lrghrldvra gsagaercrp
241fpgfa
```

Amino acid sequence of *Sus scrofa* (pig) FGF23 (SEQ ID NO: 17) (GenBank accession no. XP_001926560, which is hereby incorporated by reference in its entirety):

```
  1mlgarlglwv ctlccaaray pdtspllssg wgglthlyta tarnsyhlqi hkdghvdgsp
 61qqtiysalmi rsedagfvvi tgvmsrrylc mdlrgnifgs lhfspescrf rqrtlengyd
121vyhsphyrfl vslgrakraf lpgtnpppya qflsrrneip llhfatarpr rhtrsandgg
181dplsvlkpra ratpapvscs relpsaedgg paasdplgvl rgqrldarag vggaercrpf
241psfa
```

TABLE 1-continued

Amino acid sequence of *Canis lupus familiaris* (dog) FGF23 (SEQ ID NO: 18) (GenBank accession no. XP_854580, which is hereby incorporated by reference in its entirety):

```
  1mwtvefflfd vtgppfkslr ekrresslgl srkiptkkrr krpvrhsrgi keavsgfklq
 61paiqravmsg trlgflvsvl cwvvraysnt spllgsswgs lthlytatar nsyhlqihkd
121ghvdgtphqt iysalmirse dagfvvitgv msrrylcmdf rgnifgshlf spescrfrqr
181tlengydvyh spqhrflvsl gqakraflpg tnpppysqfl srrneiplvh fhtprprrht
241rsaeaperdp lnvlkprprl apapascsqe lpsaedpgap asdplgvlrg hranaraggv
301gvdrcrafpt pi
```

Amino acid sequence of *Cavia porcellus* (domestic guinea pig) FGF23 (SEQ ID NO: 19) (GenBank accession no. XP_003463346, which is hereby incorporated by reference in its entirety):

```
  1mlgtclglla ctvslvgayp dasplltssw gglihlytat arnsyhlqih kdghidgapy
 61ptiysalmir sedagfvvit gvtsrrflcm dfrgnifgsh hfnpqdcrfq hrtlengydv
121ylspehhfli slgrtkkffl pgtnpppysq flsrrnelpl arfvtpgprr htrsaeedqg
181rdplsvlklr pratpapasc sqelpsaeda aqasdplgvl rgarvhahgg prparcrpgp
241gak
```

Amino acid sequence of *Cricetulus griseus* (Chinese hamster) FGF23 (SEQ ID NO: 20) (GenBank accession no. XP_003496132, which is hereby incorporated by reference in its entirety):

```
  1mlgtclrllv gvlcsacslg tvraypdtsp llgsnwgslt hlytatarns yhlqihkdgr
 61vdgtphqtiy salmirseda gfviitgavt rrflcmdlrg nifgshhfsp encrfrqrtl
121engydvylsp qhhylvslgr akrpfepgtn pppfsqflar rnevpllrfh tarprrhtrs
181aedppewdpl nvlkprprat pvpvscsrel psaeegdlaa sdplgvlrrg rgdarggagg
241vdrcrpfprf a
```

Amino acid sequence of *Tupaia belangeri* (tree shrew) FGF23 (SEQ ID NO: 21) (Ensembl accession no. ENSTBEP00000014220, which is hereby incorporated by reference in its entirety):

```
  1ALLIRPEEAG FAVITGVMSR RYLCMDFRGN IFGSHLFSPE SCRFRQRALE NGYDVYHHPQ
 61HHFLVSLGRP KRAFVPGTNP PPYSQFLARK NEIPLIHFNT PKPRRHTRSA EDNSGRDPLN
121VLKPRPRMTP APASCSQELP SAEDNSVVAS DPLGVLRGNR VNTHAGGWGV DRCRPFPRFI
```

Amino acid sequence of *Rattus norvegicus* (Norway rat) FGF23 (SEQ ID NO: 22) (GenBank accession no. NP_570110, which is hereby incorporated by reference in its entirety):

```
  1mlgaclrllv galctvcslg taraysdtsp llgsnwgslt hlytatarns yhlqihrdgh
 61vdgtphqtiy salmitseda gsvviigamt rrflcmdlrg nifgsyhfsp encrfrqwtl
121engydvylsp khhylvslgr skrifqpgtn pppfsqflar rnevpllhfy tarprrhtrs
181aedpperdpl nvlkprprat pipvscsrel psaeeggpaa sdplgvlrrg rgdarrgagg
241tdrcrpfprf v
```

Amino acid sequence of *Mus musculus* (house mouse) FGF23 (SEQ ID NO: 23) (GenBank accession no. AAI20606, which is hereby incorporated by reference in its entirety):

```
  1mlgtclrllv galctvcslg taraypdtsp llgsnwgslt hlytatarts yhlqihrdgh
 61vdgtphqtiy salmitseda gsvvitgamt rrflcmdlhg nifgslhfsp enckfrqwtl
121engydvylsq khhylvslgr akrifqpgtn pppfsqflar rnevpllhfy tvrprrhtrs
181aedpperdpl nvlkprprat pvpvscsrel psaeeggpaa sdplgvlrrg rgdarggagg
241adrcrpfprf v
```

Amino acid sequence of *Pteropus vampyrus* (megabat) FGF23 (SEQ ID NO: 24) (Ensembl accession no. ENSPVAP00000000222, which is hereby incorporated by reference in its entirety):

```
  1MPRGSLGLLV CILCCRAYPD ASPLLSSSLG GLIHLYTATA RNGYHLQIHK DGHVDGTPHQ
 61TIYSALMIRS EDSGFVVIIG VMSRRYLCMD FKGNIFGSHH FSPESCKFRQ RTLENGYDVY
121HSPQHHFFVS LGRAKRAFLP GTNPPPYSQF LSRRNEIPLF QFNTPRPRRH TRSVEDYKDY
181DLDPDPLKVL RPRPRWVPAL PSCSQELPSA EDNSVVANDP LGVLRPSRVN IYRERMGKGR
241CRPHPEFV
```

Amino acid sequence of *Myotis lucifugus* (microbat) FGF23 (SEQ ID NO: 25) (Ensembl accession no. ENSMLUP00000017312, which is hereby incorporated by reference in its entirety):

```
  1MPGARLGLLV CVLALRCVVR AYPNASPLLG SSWGGLTHLY TASARNSYHL QIHKDGHVDG
 61TPHQTIYSAL MIRSEDAGFV VITGVMSRRY LCMDFRGNIF GSLFFSPSNF SFLEWKKESG
121MDHWISRQTH FLVSPGPSQE GLPAGHNPPP YSQFLSRNEI PLFHFNTPAP RRHTRSAEEN
```

TABLE 1-continued

```
181 SAADPLVVLK PVPRLTPPPA SCSRELSSAE DNSVAAHDPL GVLRSSNRVN SHAPPPGPPR
241 TRQGMLLV
```

Amino acid sequence of *Sarcophilus harrisii* (Tasmanian
devil) FGF23 (SEQ ID NO: 26) (Ensembl accession no.
ENSSHAP00000010151, which is hereby incorporated by
reference in its entirety):

```
  1 MSGGCLRLLF CALCSLRAIQ AFPNASPLLS LGWGGLTHLY TATARNSYHL QIHKDGHVDG
 61 SPHQTIYSAL MIRSEDAGLV IITGVMSRRY LCMDIRGNIF GSHFFSPDNC RFKHRTLENG
121 YDIYHSPQNN FLISLGKAKR AFLPGMNPPP YSQFLSRRNE IPIIHFNTPE PHRHTRSAEN
181 SPDLDPMNVL KLRPRITPCS QELHSAEENS VVDDDPLEVL RNSNRLKPYP GRMSLERCLH
241 VPKAA
```

Amino acid sequence of *Monodelphis domestica*
(gray short-tailed opossum) FGF23 (SEQ ID NO: 27)
(GenBank accession no. XP_001372436, which is
hereby incorporated by reference in its entirety):

```
  1 mancrekele myicalmirs edaglviitg vmsrrylcmd irgnifgshf fnpdnckfkh
 61 rtlengydiy hspqnnflis lgkakraflp gmnpppysqf lsrkneipii hfntpephrh
121 trsaenspdl dpmnvlkprp rmtpcsgely saeensvvdd dplevlrnsn rlkpfpgrlg
181 lerchhvpkt d
```

Amino acid sequence of *Dasypus novemcinctus*
(armadillo) FGF23 (SEQ ID NO: 28) (Ensembl accession
no. ENSDNOP00000004491, which is hereby incorporated by
reference in its entirety):

```
  1 ALMISSEDAG FVVITGVMSR RYLCMDFRGN IFGSHDFTPD SCRFRQRTLE NGYDVYHSPQ
 61 HHFLVSLGRA KRAFQPGSNP PPYSQFLSRR NEIPLMRFST PRPRRHTRSA QDHADPDPLR
121 VLKPRLRLTP APASCSQELP SDEDDGAVAS DPLRVVLGRR PHARAAGAGG ERCRPGPQLS
```

Amino acid sequence of *Macropus eugenii* (wallaby) FGF23
(SEQ ID NO: 29) (Ensembl accession no. ENSMEUP00000003725,
which is hereby incorporated by reference in its entirety):

```
  1 ALMIRSEDAG LVIISGVMSR RYLCMDLRGN IFGSHFFSPD NCRFKHRTLE NGYDIYHSPQ
 61 NNLLISLGKA KRAFLPGMNP PPYSQFLSRR NEIPIIHFNT PEPRRHTRSA ENSPDLDPMN
121 VLKPRPRVTP CSQELRSAEE NSVVDDDPLE VLRNSNRLKP YPGRMSLERC LQVPKAA
```

Amino acid sequence of *Taeniopygia guttata* (zebra finch)
FGF23 (SEQ ID NO: 30) (GenBank accession no.
XP_002190520

```
  1 mewratlqgi pcsslllllc slkaslafpn sspllspswg ngdrlmhlyt dterssfhlq
 61 inadgyidga phqtiysalm iksegagsvi itgvksgryl cmdmkgnifg shyfsqedcm
121 fnhrtlengy dvyqspkhhf lvslgrvkqv fspgmnpppy sqflsrknei plfrfntpep
181 hrhtrsadvd pvdphqilvp qrktpvfgsl qqqpadfphm prepmrinqn dvvnpddpha
241 mmearrypsp rfyitr
```

Amino acid sequence of *Gallus gallus* (chicken) FGF23
(SEQ ID NO: 31) (GenBank accession no. XP_425663,
which is hereby incorporated by reference in its entirety):

```
  1 mphtspcscl eymllvlcil kaavafpnss pllnpswgng dqlmhlytst ernsfhlqin
 61 adghingvph qtiysalmik segagcviit gvksgrylcm dmkgdifgsy yfsqedcvfn
121 qrtlengydv yqspkhnflv slgrtkqvff pgmnpppysq flsrrneipl frfntpephr
181 ntrsadvdpl dphqilvpqr kvsalgsqlq lqmdfshvpr epmrvnqndv vnpddphamm
241 darryasprf yitr
```

Amino acid sequence of *Meleagris gallopavo* (turkey) FGF23
(SEQ ID NO: 32) (GenBank accession no. XP_003202623,
which is hereby incorporated by reference in its entirety):

```
  1 mphtspcscl eymllvlcil kaaysfpnss pllnpswgng dqlmhlytst ernsfhlqin
 61 adghisgvpy qtiysalmik segagsviit gvksgrylcm dmkgdifgsh yfsqedcvfn
121 qrtlengydv yqspkhnflv slgrtkqvff pgmnpppysq flsrrneipl frfntpephr
181 ntrsadvdpm dphqilvpqr kvsaiesqlq lqmdfshvpr epmrvnqndv vnpddphamm
241 darryasprf yitr
```

Amino acid sequence of *Anolis carolinensis* (green anole)
FGF23 (SEQ ID NO: 33) (GenBank accession no.
XP_003221411, which is hereby incorporated by
reference in its entirety):

```
  1 mvqatlysfl kymllatcsw kaiaafpnas pllslnwgns dsllhlytst arnsfhlqih
 61 sngyvdgspy qtiysalmik sevagyviin gvksgrflcm dmngnifgsh ffsyedctfk
121 hwvlengydv yqspkynylv slgkakqplf pnmnpppysq flsrrneipl vqfntpkphr
```

TABLE 1-continued

181htrsanadpc gsiissgnia kenlqlqplm yntkmnsnse dedpnsaiin rrflsprtdv
241rs

Amino acid sequence of *Latimeria chalumnae* (coelacanth) FGF23 (SEQ ID NO: 34) (Ensembl accession no. ENSLACP00000020506, which is hereby incorporated by reference in its entirety):

1LESALLAFSM AIFYSFKAVS SFPNSSPLLN PVWGNTDNLI HLYTASETNS FHLQINSDGH
61VDGTPHQTAY SALLIKSEEA GSVVILGVKS GRYLCMDIKG NIIGLHHFSK EDCTFKQEGL
121ENGFDVLRSP KHNILVSLDK TKRSYIPGMN LPPYSQFLSR QNEVALINFI NTPDIHRHSR
181NVDVDPSDPH GMIIQPDVGV SFRKSSSLFS DLPRDSMRTS HNGMDMVDPA DPHGMLDSRR
241RPSPRFFAR

Amino acid sequence of *Xenopus silurana tropicalis* (western clawed frog) FGF23 (SEQ ID NO: 35) (GenBank accession no. XP_002940351, which is hereby incorporated by reference in its entirety):

1mtkqqtrlgl vltvlasikv isafpnsspi isggwgvpdr lmhlytasdw nsfhlqinhd
61gsidgtptqt iysaimikse saghvvitgv ktnrylcmdk sgnifgyhdf nhddcvfkhe
121tlennfdvyh spkhnfvisl kepkhhfrlg mdlppysqfl sleneipitr fnapepemri
181pegnfadpsd iiknprnwdf sqsihnpfqd vwlpfpsgsl piiraslpii hnnvintddp
241eeivkmkryr yfkr Amino acid sequence of *Felis catus* (cat) FGF23 (SEQ ID NO: 36) (Ensembl accession no. ENSFCAP00000000128, which is hereby incorporated by reference in its entirety):

1MSGTRLGLLV SVLCWVVRAY PNTSPLLGSS WGGLTHLYTA TARNSYHLQI HKDGHVDGTP
61HQTIYSALMI RSEDAGFVVI TGVMSQRYLC MDFRGNIFGS HLFSPESCRF RQRTLENGYD
121VYHSPQHRFL VSLGPAKRAF LPGTNRMTPA PASCSQELPS AEDSGVVASD PLGVLRGNRV
181NAHAGGMGVE RCRPFPKFN

Amino acid sequence of *Pelodiscus sinensis* (Chinese softshell turtle) FGF23 (SEQ ID NO: 37) (Ensembl accession no. ENSPSIP00000012755, which is hereby incorporated by reference in its entirety):

1MSQPSQCSCL NFMLFVLCSF KAIAAFPFFS SLLNPSWGET DSLIHLYTAT EKNSFHLQIN
61PDGYVDGTPH QTIYSALMIK SEDAGYVVIS GVKSGRYLCM DIKGNIFGSH YFSQEDCMFK
121HRTLENGYDV YQSPKHNFLV SLGRNKQAFF PGMNLPPYSQ FLPRRNEIPL IRFNTPEPHR
181HTRNADVDPL QILIPRGEAF DTGPQRLQTH FDHLPREPMR INPNDVVSPD DPLAMMDVRR
241NASPRLYITR

Amino acid sequence of *Mustela putorius furo* (Ferret) FGF23 (SEQ ID NO: 38) (Ensembl accession no. ENSMPUP00000009243, which is hereby incorporated by reference in its entirety):

1MSVTRLGLLV SVLCWVVRAY PNASPLLGSS WGGLTHLYTA TARNSYHLQI HKDGHVDGTP
61HQTIYSALMI RSEDAGFVVI TGVMSRRYLC MDFRGNIFGS HLFSPESCRF RQRTLENGYD
121VYHSPQHRFL VSLGQAKRAF LPGTNPPPYS QFLSRRNEIP LIHFNTPRPR RHTRSAEDME
181HDPLNVLKPR PRMTPAPASC SQELPSAEDN SVVASDPLGV LRGNRVNVHA GGMGVDRCRP
241LPKFI

Amino acid sequence of *Microcebus murinus* (Mouse lemur) FGF23 (SEQ ID NO: 39) (Ensembl accession no. ENSMICP00000004444, which is hereby incorporated by reference in its entirety):

1MLGACLRLWV CALCSVCGVS VVRAYPNASP LLASSWGGLI HLYTATARNS YHLQIHKDGH
61VDGTPHQTIY SALMIRSEDA GFVVITGVMS RRYLCMDFRG NIFGSHVFSA ESCRFRQRTL
121ENGFDVYQSP QHHFLVSLGR AKGAFPAGAK PPPFPQFLPR GNEAPGRKTR GPEEKGAPHP
181LRGVESGGRK GGAPPLCLER LSRARE

Amino acid sequence of *Pongo abelii* (Orangutan) FGF23 (SEQ ID NO: 40) (Ensembl accession no. ENSPPYP00000005881, which is hereby incorporated by reference in its entirety) (partial sequence corresponding to human FGF23 residues 23 to 37 and 72 to 251):

1M--------- ---------- --RN--ESLP CLVFSIG--- ---------- ----------
61---------- -ALMIRSEDA GFVVITGVMS RRYLCMDFRG NIFGSHYFNP ENCRFQHQTL
121ENGYDVYHSP QHHFLVSLGR VKRAFLPGM- PPPYSQFLSR RNEIPLIHFN TPVPRRHTRS
181AEDDTERDPL KVLKPRARMT PAPASCSQEL PSSEDNSPMA SDPLGVVRGG RVNTHAGGTG
241PEGCRPFPKF I

TABLE 1-continued

| Amino acid sequence of *Sorex araneus* (Shrew) FGF23 (SEQ ID NO: 41) (Ensembl accession no. ENSSARP00000007042, which is hereby incorporated by reference in its entirety) (partial sequence corresponding to human FGF23 residues 1 to 18, 28 to 70, 106 to 197, and 201 to 235): |
|---|
| 1 MWGLRLGLLV GLLGCVDR-- -------ASP MLASSWGGLT HLYTATARNS YHLQIHKDGL |
| 61 VDGSPQQTVY ---------- ---------- ---------- -----HHFSP ESCRFQQRTL |
| 121 ENGYDVYQSP QHRFLVSLGR PKRAFQPGAN PPPYAQFLAR RNEVPLARFH TPAPRRHTRS |
| 181 AHDNGDADPL NVLAPRA--- AAAASCSHEL PSAEDNSVVA SDPLGVIRSN RFRTH |
| Amino acid sequence of *Tetraodon nigroviridis* (Tetraodon) FGF23 (SEQ ID NO: 42) (Ensembl accession no. ENSTNIP00000014355, which is hereby incorporated by reference in its entirety): |
| 1 MDVNRRIGVK DALLALLLAL LQGCPLGETA PNASPLVGSN WGNPRRYVHL QTSTDMSNFY |
| 61 LEIRLDGTVR KSTARTSYSV ILLKADTRER IAILGVKSNR YLCMDLEGSP FSSPTCIRDD |
| 121 CLFNHSLLEN NRDVYYSSRT GILFNLEGSR QVFVVGQNVP QTSLFLPRTN TVPLERLLLH |
| 181 RDKRNQVVDP SDPHRVAVGR AEEGSDSRAL QEDDADLEVE TEVEVGDDGR NASRERLQAP |
| 241 SDHDPWGVFS SNPGSPRSSG TVG |
| Amino acid sequence of *Oreochromis niloticus* (Tilapia) FGF23 (SEQ ID NO: 43) (Ensembl accession no. ENSONIP00000000020, which is hereby incorporated by reference in its entirety): |
| 1 MDVNRRMGMR DTVLALFLAV LQGFPLGDTV PNPSPLAGSN WGNPRRYVHL QTSTDLNNFY |
| 61 LEIRLDGSVR KTTSRSTYSV ILLKSEARDR VAILGVKSSR YLCMDLEGNP FSSPVCLRDD |
| 121 CLFNHKLLEN NRDVYYSSRT GILFNLEGSR QVYSVGQNLP QTSLFLPRKN TVPLERLLLH |
| 181 REKRNRGQTE EGSDSRAVPE ELEEREVEME TEIETEVGDD GRNVSREKLA APSSHDPWNV |
| 241 HFSNPASPRS TGTVG |
| Amino acid sequence of *Danio rerio* (Zebrafish) FGF23 (SEQ ID NO: 44) (Ensembl accession no. ENSDARP00000067387, which is hereby incorporated by reference in its entirety): |
| 1 MRCALSNLHM LHSSVLALWF TALQGLRPAD AAPNPSPLLG SNWGNPRRYI HLQTTSDLNN |
| 61 YYLEISPSGH VRKTTNRGSY SVILLKTESR DRLAIFGVKS NRFLCMDTGG TLFTSTICNK |
| 121 EDCLFHHKLL ENHRDVYYST KHSILLNLDG DKQAFIAGQN LPQSSLFLSE KNTVPLERLQ |
| 181 HRERRNRQVN PTDPLNALRY AEESDSRAAQ EDDGDMDFEP SEGQNISRET LVSPSDDDPW |
| 241 DLLHDTSPGS PRIAAIVG |

In certain embodiments according to the present invention, the N-terminal portion from FGF23 of the chimeric protein of the present invention includes a polypeptide sequence that has at least 80%, at least 85%, at least 90%, at least 95%, at least 97%, or at least 99% amino acid sequence identity to the amino acid sequence of SEQ ID NO: 1.

Percent (%) amino acid sequence identity with respect to a given polypeptide sequence identified herein is defined as the percentage of amino acid residues in a candidate sequence that are identical to the amino acid residues in the reference sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

It will be understood that the portion from FGF23 of the chimeric protein of the present invention may be from a nucleotide sequence that encodes an FGF23 protein (e.g., those encoding orthologs) from a mammal or even a non-mammalian vertebrate. For example, a nucleotide sequence encoding a mammalian or non-mammalian FGF23 protein according to the present invention may include, but is not limited to, those FGF-encoding nucleotide sequences in Table 2.

TABLE 2

| Human FGF23 gene coding sequence (1-251) (SEQ ID NO: 45) (GenBank accession no. AF263537, which is hereby incorporated by reference in its entirety) |
|---|
| 147 atgt tgggggcccg cctcaggctc tgggtctgtg |
| 181 ccttgtgcag cgtctgcagc atgagcgtcc tcagagccta tcccaatgcc tccccactgc |
| 241 tcggctccag ctggggtggc ctgatccacc tgtacacagc cacagccagg aacagctacc |
| 301 acctgcagat ccacaagaat ggccatgtgg atggcgcacc ccatcagacc atctacagtg |
| 361 ccctgatgat cagatcagag gatgctggct ttgtggtgat tacaggtgtg atgagcagaa |
| 421 gatacctctg catggatttc agaggcaaca tttttggatc acactatttc gacccggaga |
| 481 actgcaggtt ccaacaccag acgctggaaa acgggtacga cgtctaccac tctcctcagt |
| 541 atcacttcct ggtcagtctg ggccgggcga agagagcctt cctgccaggc atgaacccac |
| 601 ccccgtactc ccagttcctg tcccggagga acgagatccc cctaattcac ttcaacaccc |

TABLE 2-continued 661 ccataccacg gcggcacacc cggagcgccg aggacgactc ggagcgggac cccctgaacg
721 tgctgaagcc ccgggcccgg atgaccccgg ccccggcctc ctgttcacag gagctcccga
781 gcgccgagga caacagcccg atggccagtg acccattagg ggtggtcagg ggcggtcgag
841 tgaacacgca cgctggggga acgggcccgg aaggctgccg ccccttcgcc aagttcatct
901 ag

*Gorilla* FGF23 gene coding sequence (1-251) (SEQ ID NO: 46)
(Ensembl accession no. ENSGGOT00000002983, which is hereby
incorporated by reference in its entirety)

1 ATGT TGGGGGCCCG CCTCAGGCTC TGGGTCTGTG
35 CCTTGTGCAG CGTCTGCAGC TTGAGCGTCC TCAGAGCCTA TCCCAATGCC TCCCCACTGC
95 TCGGCTCCAG CTGGGGTGGC CTGATCCACC TGTACACAGC CACAGCCAGG AACAGCTACC
155 ACCTGCAGAT CCACAAGAAT GGCCATGTGG ATGGCGCACC CCATCAGACC ATCTACAGTG
215 CCCTGATGAT CAGATCAGAG GATGCTGGCT TTGTGGTGAT TACAGGTGTG ATGAGCAGAA
275 GATACCTCTG CATGGATTTC AGAGGCAACA TTTTTGGATC ACACTATTTC GACCCGGAGA
335 ACTGCAGGTT CCAACACCAG ACGCTGGAAA ACGGGTACGA CGTCTACCAC TCTCCTCAGT
395 ATCACTTCCT GGTCAGTCTG GGCCGGGCGA AGAGAGCCTT CCTGCCAGGC ATGAACCCAC
455 CCCCGTACTC CCAGTTCCTG TCCCGGAGGA ACGAGATCCC CCTCATTCAC TTCAACACCC
515 CCATACCACG GCGGCACACC CGGAGCGCCG AGGACGACTC GGAGCGGGAC CCCCTGAACG
575 TGCTGAAGCC CCGGGCCCGG ATGACCCCGG CCCCGGCCTC CTGTTCACAG GAGCTCCCGA
635 GCGCCGAGGA CAACAGCCCG ATGGCCAGTG ACCCATTAGG GGTGGTCAGG GGCGGTCGAG
695 TGAACACGTA CGCTGGGGGA ACGGGCCCGG AAGGCTGCCG CCCCTTCCCC AAGTTCATCT
755 AG

Northern white-cheeked gibbon FGF23 gene coding sequence (1-251)
(SEQ ID NO: 47) (GenBank accession no. XM_003273701,
which is hereby incorporated by reference in its entirety)

140 a tgttgggggc ccgcctcagg ctctgggtct gtgccttgtg
181 cagcgtctgc agcatgagcg tcctcagagc ctatcccaat gcctccccac tgctcggctc
241 cagctggggt ggcctgatcc acctgtacac agccacagcc aggaacagct accacctgca
301 gatccacaag aatggccatg tggatggcgc accccatcag accatctaca gtgccctgat
361 gatcagatca gaggatgctg gctttgtggt gattacaggt gtgatgagca gaagatacct
421 ctgcatggat ttcagaggca acatttttgg atcacactat ttcaacccgg agaactgcag
481 gttccaacac cagacgctgg aaaacgggta cgacgtctac cactctcctc agcatcactt
541 cctggtcagt ctgggccggg ccaagagagc cttcctgccg ggcatgaacc caccccgta
601 ctcccagttc ctgtcccgga ggaacgagat ccccctactt cacttcaaca cccccacacc
661 acggcggcac acccggagcg ccgaggacga ctcggagcgg gacccctga acgtgctgaa
721 accccgggcc cggatgaccc cggccccggc ctcctgctca caggagctcc tgagctccga
781 ggacaacagc ccgatggcca gcgacccatt aggggtggtc aggggcggtc gagtgaacac
841 gcacgctggg ggaacgggcc cggaaggctg ccgcccttc cccaagttca tctag Rhesus monkey FGF23 gene coding sequence (1-251) (SEQ ID NO: 48)
(GenBank accession no. NM_001194137, which is hereby
incorporated by reference in its entirety)

69 at gttgggggcc cgcctcaggc tctgggtctg tgccttgtgc agcgtctgca
121 gcatgagcgt catcagagcc tatcccaatg cctccccatt gctcggctcc agctggggtg
181 gcctgatcca cctgtacaca gccacagcca ggaacagcta ccacctgcag atccacaaga
241 atggccacgt ggatggcgca ccccatcaga ccatctacag tgccctgatg atcagatcag
301 aggatgctgg ctttgtggtg attacaggtg tgatgagcag aagatacctc tgcatggatt
361 tcagaggcaa catttttgga tcacactatt tcaacccgga gaactgcagg ttccgacact
421 ggacgctgga gaacggctac gacgtctacc actctcctca gcatcacttt ctggtcagtc
481 tgggccgggc gaagagggcc ttcctgccag gcatgaaccc accccctac tcccagttcc
541 tgtcccggag gaacgagatc cccctcatcc acttcaacac ccccagacca cggcggcaca
601 cccggagcgc cgaggacgac tcggagcggg acccctgaa cgtgctgaag ccccgggccc
661 ggatgacccc ggccccggcc tcctgctcac aggagctccc gagcgccgag gacaacagcc
721 cggtggccag cgacccgtta ggggtggtca ggggcggtcg ggtgaacacg cacgctgggg
781 gaacgggccc ggaagcctgc cgcccttcc ccaagttcat ctag Crab-eating macaque FGF23 gene coding sequence (1-251)
(SEQ ID NO: 49) (GenBank accession no. ENSMMUT00000020999,
which is hereby incorporated by reference in its entirety)

1 ATGTTG GGGGCCCGCC TCAGGCTCTG GGTCTGTGCC TTGTGCAGCG
47 TCTGCAGCAT GAGCGTCATC AGAGCCTATC CCAATGCCTC CCCATTGCTC GGCTCCAGCT
107 GGGGTGGCCT GATCCACCTG TACACAGCCA CAGCCAGGAA CAGCTACCAC CTGCAGATCC
167 ACAAGAATGG CCACGTGGAT GGCGCACCCC ATCAGACCAT CTACAGTGCC CTGATGATCA
227 GATCAGAGGA TGCTGGCTTT GTGGTGATTA CAGGTGTGAT GAGCAGAAGA TACCTCTGCA
287 TGGATTTCAG AGGCAACATT TTTGGATCAC ACTATTTCAA CCCGGAGAAC TGCAGGTTCC
347 GACACTGGAC GCTGGAGAAC GGCTACGACG TCTACCACTC TCCTCAGCAT CACTTTCTGG
407 TCAGTCTGGG CCGGGCGAAG AGGGCCTTCC TGCCAGGCAT GAACCCACCC CCCTACTCCC
467 AGTTCCTGTC CCGGAGGAAC GAGATCCCCC TCATCCACTT CAACACCCCC AGACCACGGC
527 GGCACACCCG GAGCGCCGAG GACGACTCGG AGCGGGACCC CCTGAACGTG CTGAAGCCCC
587 GGGCCCGGAT GACCCCGGCC CCGGCCTCCT GCTCACAGGA GCTCCCGAGC GCCGAGGACA
647 ACAGCCCGGT GGCCAGCGAC CCGTTAGGGG TGGTCAGGGG CGGTCGGGTG AACACGCACG
707 CTGGGGGAAC GGGCCCGGAA GCCTGCCGCC CCTTCCCCAA GTTCATCTAG

TABLE 2-continued

Chimpanzee FGF23 gene coding sequence (1-251) (SEQ ID NO: 50) (GenBank accession no. XM_001157070, which is hereby incorporated by reference in its entirety)

```
141                      atgttggggg cccgcctcag gctctgggtc tgtgccttgt
181 gcagtgtctg cagcgtgagc gtcctcagag cctaccccaa tgcctcccca ctgctcggct
241 ccagctgggg tggcctgatc cacctgtaca cagccacagc caggaacagc taccacctgc
301 agatccacaa gaatggccat gtggatggcg caccccatca gaccatctac agtgccctga
361 tgatcagatc agaggatgct ggctttgtgg tgattacagg tgtgatgagc agaagatacc
421 tctgcatgga tttcagaggc aacatttttg gatcacacta tttcaacccg gagaactgca
481 ggttccaaca ccagacgctg gaaaacgggt acgacgtcta ctactctcct cagtatcact
541 tcctggtcag tctgggccgg gcgaagagag ccttcctgcc aagcatgaac ccacccccgt
601 actcccagtt cctgtcccgg aggaacgaga tcccccctaat tcacttcaac acccccatac
661 cacggcggca cacccggagc gccgaggacg actcggagcg ggacccccctg aacgtgctga
721 agccccgggc ccggatgacc ccggccccgg cctcctgttc acaggagctc ccgagcgccg
781 aggacaacag cccgatggcc agtgacccat taggggtggt caggggcggt cgagtgaaca
841 cgcacgctgg gggaacgggc ccggaaggct gccgcccctt ccccaagttc atctag
```

White-tufted-ear marmoset FGF23 gene coding sequence (1-251) (SEQ ID NO: 51) (GenBank accession no. XM_002752235, which is hereby incorporated by reference in its entirety)

```
  1 atgttggggg cccgcctcag gctctgggtc tgtgccttgt gcagcgtctg cagcatgagc
 61 gtcctcagag cctatcccaa tgcctcccca ctgcttgcct ccagctgggg tggcctgatc
121 cacctgtaca cagccacagc caggaacagc taccacctgc agatccacaa gaatggccat
181 gtggatggcg caccccatca gaccatctac agtgccctgc tgatcagatc agaggatgct
241 ggctttgtgg tgattacagg tgtgatgagc agaagatacc tctgcatgga tttcagaggc
301 aacatttttg gatcacacta tttcaacccg gagaactgca ggttccgacc ccagaggctg
361 gagaacgggt acgacgtcta ccagtctcct cagcatcact tcctggtcag tctgggccgg
421 gcgaagaggg ccttcctgcc aggcatgaac ccacccccgt actcccagtt cctgtcccgg
481 aggaacgaga tcccccctcat tcacttcaac acccccaaac cgcggcggca cacccggagc
541 gccgaggacg acccggagct agacccccctg aacgtgctga agtcccgggt ccggatgacc
601 ccggccccgg cctcctgctc gcaggagctc ctgagcgccg aggacaacag cccggtgggc
661 agcgacccct tagggatggt ccggggtggt cgggtgaaca gccacgctga gggaacaggc
721 ccagaaggct gcagcccctt ccccaagctc atctag
```

Elephant FGF23 gene coding sequence (1-251) (SEQ ID NO: 52) (GenBank accession no. XM_003410629, which is hereby incorporated by reference in its entirety)

```
  1 atgttggggg cccgcctcag gctctgggtc tgcaccctgt gcagtgcctg cagcatgtgc
 61 agtgtcagag cctatcccaa tgcctccccg ctgctccact ccagctgggg tggcctgacc
121 cacctgtaca cagccaccgc caggaacagc taccacctgc agatccacaa ggacggccat
181 gtggatggta cgccggacca gaccatctac agtgccctga taatcagatc agaggaggcc
241 ggcttcgtgg tgattacagg ggtgatgagt aggagatacc tctgtatgga tttcagaggc
301 aacatttttg gatcgcatta cttcaaccca gagaactgca ggttcaaaca ctggacgctg
361 gaaaatggat atgacgtcta tcactctcct cagcatcatt tcctggtcag tctgggtcgc
421 gtgaagaagg ccttcctgcc aggcatgaac ccaccacctt actctcagtt cctgtcccgg
481 aggaatgaga tccccttgat ttacttcaac acccccaagc cccggcggca cacccggagt
541 gccgaggatg actctgaacg ggacccactg aatgtgctga agccccggcc ccgtatgaca
601 cctgctccag cttcttgctc ccaggaactc ctgagtgctg aagacaacag cgtggtggcc
661 aatgaccctt taggagtggt cagaagcaat agggtcaaca cacatgctgg tgggataggt
721 gtggaaaggt gccgcccctt ccccaagttc atctag
```

Lesser hedgehog tenrec FGF23 gene coding sequence (1-250) (SEQ ID NO: 53) (Ensembl accession no. ENSETET00000001609, which is hereby incorporated by reference in its entirety)

```
  1 ATGTTGGGGG CCCACCTCAG ACTCTGGGTC TGTGCCTTGT GCAGTGTGAG CGCCATGTAC
 61 CACGTCAGAG CCTACCCCAA CGCCTCCCCG CTCCTGGGTA CCAGCTGGGC TGGCCTGACC
121 CACCTGTACA CGGCGACAGC CAGGAACAGC TTCCACCTGC AGATCCACAA GGATGGCCAC
181 GTGGACGGCA CCCCCCACCA GACCATCTAC AGTGCCCTGA TGATCCGATC AGAGGACTCT
241 GGCTTCGTGG TGATCACAGG GGTGATGAGC AGGAGATACC TGTGTATGGA TTTCAGAGGC
301 AACATTTTTG GATCGCACTA CTTCACTGCG GACAGCTGCA GGTTCAGACA GCGGACGCTG
361 GAGAACGGCT ATGACGTCTA CCACTCTCCT CAGCATCATT TCCTGATCAG CCTGGGCCGG
421 GCCAAGAGGG TCTTCCTGCC CGGCATGAAC CCGCCGCCTT ACTCCCAGTT CCTGTCCCGA
481 AGGAATGAGA TCCCCCTGAT TCACTTCAAC ACCCCCAGGC CCCGGCGGCA CACACGGAGT
541 GCCGAGGAGG AAGTGGAGCA GGATCCGCTG AACGTGCTGA AGCCCAGGCC CCGGATGACG
601 CCGGCTCCAG CCTCCTGCTC CCAGGAGCTG CCCAGTGCCG AAGACAACAG CGCCCTGGCC
661 AGCGACCCGC TGGGAGTGGT CAGAGGCAAA AAGCTCAACA CCCATGCTGT GGGCATGGGC
721 GCGGAAAGAT GCCGCCCCTT TCCCAAGTTC
```

Hedgehog FGF23 gene coding sequence (1-63 and 73-244) (SEQ ID NO: 54) (Ensembl accession no. ENSEEUT00000007917, which is hereby incorporated by reference in its entirety)

```
  1 ATGTTGGGGG CCCACCTGGG TCTGGTGGTC TGCGCCCTGG TCAGCAGAGC CTATCCCAAT
 61 GCCTCGCCAC TGCTGGGCTT CAGCTGGGGG GGCCTGACAC ATCTGTACAC GGCCACAGCC
121 AGGAACAGCT ACCACCTGCA GATCCACAAG GACGGCCACG TGGACGGCTC GCCTCAGCAG
```

TABLE 2-continued

```
181 ACCATCTACA ---------- ---------- -----TGCTG GTTTCGTGAT GATCACAGGC
241 GTGATGAGTA GGCGCTACCT CTGCATGGAC TTCAGGAGCA ACATCTTTGG ATCGCATCAC
301 TTCGCCCCTG AGAGCTGCAG GTTCAGACAT CGGACACTGG AAAACGGCTA TGACGTCTAC
361 CACTCCCCCC AGCACCATTT CCTGGTCAGC CTGGGCCGGG CCAAGCGGGC CTTCCTGCCG
421 GGCACCAACC CCCCACCATA CTCCCAGTTT TTGTCCCGGA GGAACGAGGT TCCCCTCATC
481 CACTTCAACA CCCCCAGGCC CAGGCGTCAC ACCCGCAGCG CCGAGGACAA CTCAGAGCTG
541 GATCCCCTGA ACGTGCTGAA GCCCAGGCCC CGCATGACCC CCGCCCCAGC CTCCTGCTCC
601 CAGGAGCTTC CGAGCGCTGA GGACAACAGC ATGGTGGCCA GTGACCCACT GGGTGTGGTC
661 AGAGCCAACA GAGTGAACAC ACACGCAGGG GGCCTGGGTG TGGACAAGTG CCGCCCCTTC
721 CCCAAGTTTA TCTAG
```

Bushbaby FGF23 gene coding sequence (1-252) (SEQ ID NO: 55)
(Ensembl accession no. ENSOGAT00000005213, which is hereby incorporated by reference in its entirety)

```
  1 ATGCTGGGGA CCTGCCTCAG GCTCTGGGTC TGTGCCCTGT GCAGTGTTTG CAGCGTGAGC
 61 ATTGTCAGAG CCTATCCCAA CGCCTCCCCA CTGCTCAGCT CCAGCTGGGG TGGCCTGACC
121 CACCTGTACA CGGCCTCGGC CAGAAACAGC TACCACCTGC AGATCCACAA GGATGGCCAT
181 GTGGACGGCA CACCCCACCA GACCATCTAC AGCGCCCTAA TGATCAGGTC AGAGGATGCT
241 GGCTTCGTGG TGATTACAGG CGTGATGAGC AGAAGATACC TCTGTATGGA TTTCAAAGGC
301 AACATTTTTG GATCACACTC CTTCCACCCC GAGAGCTGCA GGTTCAGACA CCGGACTCTG
361 GAGAACGGCT ATGACGTCTA CCTCTCGCCG CAGCATCACT TCTTGGTCAG CCTGGGCCGC
421 TCCAAGAGGC CCTTCCTGCC GGGCATGAAC CCGCCCCCCT TCTCCCAGTT CCTGTCGCGG
481 AGGAACGACA TCCCGCTCAT TCACTTCAAC ACCCCCCGCC CGCGGAGACA CACCCGCAGC
541 GCCGAGGACA ACGACTCGGA GCTCGACCCC CTGAACGTGC TGAAGCCGCG GCCCCGGGCC
601 ACCCCGGGCC CCGCCTCCTG CTCGCAGGAG CTCCCCAGCG CCGAGGACAA CAGCCTGGTG
661 GCCAGCGACC CTTTAGGGGT GGTCCGGGGC AACAGGGTGA ACGCTCACGC CGGGAGGGCC
721 GGCCTGGACA GGTGCCGCCC CTTCCCCAGG TATTTCTAG
```

Rabbit FGF23 gene coding sequence (1-252) (SEQ ID NO: 56)
(GenBank accession no. XM_002712826, which is hereby incorporated by reference in its entirety)

```
  1 atgttagggg cccggctcct ccggctcttg gtctgtgccc tgggcagtgt gtgcagctgg
 61 tgtgtggtcc gagcctaccc tgacacctcc ccgctgctca gctccagctg ggctggcctg
121 acccacctgt acacggccac cgccagaaac agctaccacc tgcagatcca caaggacggc
181 caagtggatg gcacacctca tcagaccatc tacagtgccc tgatgatcag atcggaggat
241 gctggcttcg tggtgataac aggtgtcatg agcaggaggt acctctgtat ggatttcaga
301 ggcaacattt ttggatcgca ttacttcgac ccccagaact gcaggttcag acacaggacg
361 ctggaaaacg ggtacgacgt ctaccactct ccggagcatc acttcctggt cagcctgggc
421 cgggccaaga ggcccttcct gccaggcatg aacccgccac cctattccca gttcctgtcc
481 cggaggaacg agatccccct gatccacttc aacacgccga ggccgcgaag gcacacccgg
541 agcgccgagg acgcctggga gcaggacccg ctgaacgtgc tgaagcccag gttccggctg
601 accccggccc cagcctcctg ctcacaggag gccccaagtg ctgaagacaa tggcctggtg
661 gccagcgacc ccttcggagt gctccggggc aatagggtga acatgcacgg ggacaggatg
721 ggcccggaaa ggtgccacca tttccccaag ttcatctag
```

Horse FGF23 gene coding sequence (1-246) (SEQ ID NO: 57)
(GenBank accession no. XM_001491419, which is hereby incorporated by reference in its entirety)

```
  1 atgtcagggc cctgccttgg gctcctggtc tacgtcctgt gctccgcagt gaaagcctat
 61 cccaacgcct ccccgctgct agactccagc tggggcagcc tgacccacct gtacacggcc
121 acagccagga acagctacca cctgcagatc cacaaggatg gccacgtgga tggcacaccc
181 catcagacca tctacagtgc cctgatgatc agatcagagg atgctggctt tgtggtgata
241 acaggtgtga tgagcaggag atacctctgc atggacttca gaggaaacat tttggatca
301 catcacttca gccccgagag ctgcagcttc cgacagcgga cgctggagaa cggctacgac
361 gtgtaccact cgccgcagca tcgcttcctc gtcagcctgg gccgcgccaa gagggccttc
421 ctgcccggca cgaacccccc gccctactcg cagttcctgt cccggaggaa cgagatcccc
481 ctggtccact tcaacacccc gcggccgcgg cggcacacgc gcagcgccga ggacaactcg
541 gagcgcgacc cgctgaacgt gctgaagccc cggccccgca tgacccccgc gccggcctcc
601 tgctcccagg agctcccgag cgccgaggac aacagcgtgc tggccagcga ccccttaggg
661 gtggtccgtg gcaacagggt gaacacgcac gcgggggcg cgggcgtgga gcgctgccgc
721 cccttcccca agttcttcta g
```

Giant panda FGF23 gene coding sequence (1-245) (SEQ ID NO: 58)
(GenBank accession no. XM_002920450, which is hereby incorporated by reference in its entirety)

```
  1 atgtcaggga cccgccttgg gctgctggtc tctgtcctgt gctgggtagg cagagcctat
 61 cccaacacct ccccactgct cggctccagc tggggtggcc tgacccacct gtacacagcc
121 agcgccagga acagctacca cctgcagatc cacaaggacg gccatgtgga tggcacaccc
181 catcagacca tctacagtgc cctgatgatc aggtcagagg atgccggctt tgtggtgata
241 acaggtgtga tgagtaggcg atacctctgt atggacctca gaggcaacat ctttggatcc
301 cacctcttca gcccggagag ctgcaggttc cgacagcgga cgctggaaaa cggctacgac
361 gtgtaccact cgccgcagca ccgcttcctc gtcagcctgg gccaggccaa gaggaccttc
421 ctgccgggga ccaacccgcc gccctactcc cagttcctgt cccggaggaa cgagatcccc
481 ctcatccact tcaacacccc caggccaagg cggcacacgc gcagcgccga ggacacggag
541 cgcgacccgt tgaacgtgct gaagcccagg ccccgcatga cccccgcccc ggcctcctgc
601 tcccaggagc tcccgagcgc cgaggacaac agtgtggtgg ccagcgaccc gttaggggtg
```

TABLE 2-continued

```
661 ctcagaggca accgggtgaa cgcgcacgcc ggggggatgg gcgtggacag gtgccgcccc
721 ttccccaagt tcatctag
```

Pika FGF23 gene coding sequence (1-250) (SEQ ID NO: 59)
(Ensembl accession no. ENSOPRT00000007149, which is hereby incorporated by reference in its entirety)

```
  1 ATGCTGGGGG GGCTGGGGCT GTGGGTCTGT GTCCTGGGCA GTGTGTGCAG CTGGCGTGGG
 61 GTCCGTGCCT ATCCCGACAC CTCCCCGCTG CTCGGCTCCA GCTGGACTGG CCTGACCCAC
121 CTGTACACGG CCACCGCCAG GAACAGCTTC CACCTGCAGA TCCACAAGGA TGGCCATGTG
181 GATGGCACAC CCCAGCAGAC CATCTATAGT GCCCTGATGA TCAGATCAGA GGATGCCGGC
241 TTCGTGGTGA TAACAGGTGT CATGAGCAGG AGGTACCTCT GTATGGATTT CAGAGGCAAC
301 ATCTTCGGAT CGCATTACTT CGAGCCACAG AACTGCAGGT TCCAGCAGAG GACGCTGGAG
361 AACGGCTACG ACATCTACCA CTCTCCGCAG CACGACTTCC TGGTCAGCCT AGGTCGGGCC
421 AAGAGGCCGT TCCTGCCAGG CATGAACCCG CCACCCTACT CCCAGTTCCT GTCTCGGAGG
481 AACGAGATTC CGCTGATCCT CTTCAACACG CCCAGGCCTC GGAGGCACAC CCGCAGCGCG
541 GAGGAGGGCT GGGAGCGGGA CCCTCTGAAT GTGCTGAAGT CCAGGCCCCG AATGACCCCG
601 GCCCCAGCCT CCTGCTCGCG GGAGGCCCCC AGTGCCGAAG ACGACGGCCT GCTGGCCAGT
661 GACCCCATGG GAGTGCTCAG AGGCCATAGG GTGGATGTGC ACGGGGGTGG GACGGGTAGG
721 GACAGGTGCC GCCCGTTCCC CAGGTTCATC TAG
```

Cattle FGF23 gene coding sequence (1-245) (SEQ ID NO: 60)
(GenBank accession no. XM_002687880, which is hereby incorporated by reference in its entirety)

```
  1 atgctggggg cccgcctggg gctctgggtc tgcaccctga gctgtgtggt ccaagcctat
 61 cccaacagct ccccgctgct gggctccagc tggggcggcc tgacccacct gtacacggcc
121 acggccagga acagctacca cctgcagatc cacggagacg ggcacgtaga tggctccccg
181 cagcagactg tctacagcgc cctgatgatc aggtcggagg atgccggctt cgtggtgata
241 acaggtgtga tgagcaggcg gtacctctgc atggacttca caggcaacat tttggatcc
301 catcacttca gtccggagag ctgccggttc cggcagcgga cactggagaa cggctacgac
361 gtgtaccact cgccgcagca ccgcttcctc gtcagcctgg gccgggccaa gcgcgccttc
421 ctgccgggca ccaacccgcc cccatacgcg cagttcctgt cgcgcaggaa cgagatcccg
481 ctgccgcact tcgccgccac cgcgcggccc cggcgccaca cgcgcagcgc acacgacagc
541 ggggacccgc tcagcgtgct caagccgcgc gcccgcgcca cgcccgtgcc cgccgcctgc
601 tcccaggagc tgcccagcgc cgaggactcc ggccctgccg ccagcgaccc gctcggggtg
661 ctccgcggac accgcctgga cgtgcgcgcc ggctccgcgg gcgccgagcg ctgccggccc
721 ttccccggct tcgcctag
```

Pig FGF23 gene coding sequence (1-244) (SEQ ID NO: 61)
(GenBank accession no. XM_001926525, which is hereby incorporated by reference in its entirety)

```
  1 atgctggggg cccgcctcgg gctctgggtc tgcaccctgt gctgtgcggc cagagcctat
 61 cccgacacct ccccgctgct gagctctggc tggggcggcc tgacccacct gtacacggcc
121 acggccagga acagctacca cctgcagatc cacaaggatg gccacgtgga tggctcaccc
181 caacagacca tctacagtgc cctaatgatc aggtcggagg acgcaggctt cgtggtcata
241 acaggcgtga tgagcaggag atacctctgc atggacttaa ggggcaacat tttggatcg
301 ctgcacttca gccccgagag ctgcaggttc cggcagcgga cgctggagaa cggctacgac
361 gtgtaccact cgccgcacta ccgcttcctc gtcagcctgg gccgggccaa gcgggccttc
421 ctgccgggta ccaacccgcc cccgtacgcg cagttcttgt cgcgcaggaa cgagatcccg
481 ctgctgcact tcgccaccgc gcggccccgg cgccacacgc gcagcgcgca cgacggcggg
541 gacccgctga gcgtcctgaa gccgcgcgcg cgcgccacgc ccgcgcccgt ctcctgctcc
601 cgcgagctgc ccagcgccga ggacggcggc cccgcggcca gcgacccgct cggggtgctc
661 cggggccagc ggctggacgc gcgcgctggg gtgggggcg ccgagcgctg ccggcccttc
721 cccagcttcg cctag
```

Dog FGF23 gene coding sequence (1-312) (SEQ ID NO: 62)
(GenBank accession no. XM_849487, which is hereby incorporated by reference in its entirety)

```
  1 atgtggacag tggagttttt cctgtttgat gtcacagggc cacccttttaa aagtctgagg
 61 gaaaaaagga gggaatctag cctgggactt tcacgcaaga tacccacaaa gaagaggaga
121 aaaaggcctg tgaggcacag ccggggaatc aaggaggcag tgtcaggttt caaactccag
181 ccagccattc agagagctgt gatgtctggc acccgccttg gattcctggt ctctgtcctg
241 tgctgggtag tcagagccta ttccaacacc tccccgctgc tcggctccag ctggggtagc
301 ctaacccacc tgtatacggc cacagccagg aacagctacc acctgcagat ccacaaggac
361 ggccatgtgg atggcacacc tcatcagacc atctacagtg ccttgatgat ccggtcagag
421 gatgccggct ttgtggtgat aacaggtgtg atgagtagga ggtacctctg tatggacttc
481 agaggcaaca tctttggatc acacctcttc agcccggaga gctgccggtt ccgacagcgg
541 acgctggaga acggctacga cgtgtaccac tccccgcagc accgcttcct cgtcagcctg
601 ggccaggcca agagggcctt cctgcccggc accaacccgc cgccctactc gcagttcctg
661 tcccggagga acgagatccc cctcgtgcac ttccacacgc ccaggccgcg gcggcacacg
721 cgcagcgccg aggccccgga gcgcgacccg ctgaacgtgc tgaagcccag gccgcgcttg
781 gcccccgccc cggcctcctg ctcgcaggag ctcccgagcg ccgaggaccc cggcgcgccg
841 gccagcgacc cgctcggggt gctcaggggc cacagggcca acgcgcgcgc cggcggggtg
901 ggcgtggaca ggtgccgcgc cttccccacg cccatctag
```

TABLE 2-continued

Domestic guinea pig FGF23 gene coding sequence (1-243) (SEQ ID NO: 63)
(GenBank accession no. XM_003463298, which is hereby
incorporated by reference in its entirety)

```
  1 atgctgggga cctgccttgg gctcctggcc tgcaccgtga gcttagtagg agcctatcct
 61 gatgcctccc cattgctcac ctccagctgg ggtggcctga tccatctgta cacggccaca
121 gccagaaaca gctaccatct gcagatccac aaagatggcc acatagatgg tgcaccctat
181 ccgaccatct acagtgccct gatgatcaga tcagaagatg ctgggttcgt cgtgataaca
241 ggggtcacaa gcaggagatt cctctgcatg gatttcagag gcaacatttt tggatctcac
301 cacttcaatc cccaagactg ccgattccaa caccgcacgc tggaaaacgg ttacgacgtc
361 tacctctctc ccgagcacca ctttctgatc agcctgggca ggaccaagaa gttcttcctg
421 ccgggcacca acccaccgcc ctactcccag ttcctgtcgc gcaggaacga gctgcccctg
481 gcccgcttcg tcacgcccgg gccgcggcga cacacgcgca gcgcggagga ggaccagggc
541 cgcgacccgc tgagcgtgct caagcttcgg ccccgcgcca cgcccgcgcc cgcctcgtgc
601 tcgcaggagc tgcccagcgc ggaggacgcg gcccaggcca gcgaccccct gggcgtgctg
661 cggggcgcca gggtgcacgc gcacggcggg ccgcgccccg cgaggtgccg cccgggaccc
721 ggggccaagt aa
```

Chinese hamster FGF23 gene coding sequence (1-251) (SEQ ID NO: 64)
(GenBank accession no. XM_003496084, which is hereby
incorporated by reference in its entirety)

```
  1 atgctgggga cctgcctcag actcctggtg ggtgttctgt gtagtgcctg cagcctgggc
 61 actgttagag cctatcctga cacctcccca ctgctcggct ccaattgggg cagcctgacc
121 cacctgtaca cagctacagc caggaacagt tatcacctac agatccacaa ggatggccgt
181 gtagatggca caccccatca gaccatctac agtgccctga tgattagatc agaggatgct
241 ggcttcgtga tcataacagg agctgtgact agaaggttcc tttgtatgga tctcaggggc
301 aacatttttg gatcgcatca cttcagcccg gagaactgca ggttccgcca gcggactctg
361 gagaatggct atgacgtcta cctgtcgcca cagcatcact acctggtgag cctgggccgc
421 gccaagcgcc ccttcgagcc cggcaccaac ccgcctccct tctcgcagtt cctggcgcgc
481 aggaacgagg tcccgctgct gcgcttccat accgcacggc cacggcgcca cacgcgcagc
541 gccgaggacc ctcccgagtg ggacccactg aacgtgctca agccgcggcc ccgtgccacg
601 cccgtgcccg tgtcctgctc gcgggagctg ccgagcgccg aggaaggtga cctcgcggcc
661 agtgacccac tgggcgtcct gcgcagaggc cgcggggatg ctcgcggggg cgcaggaggc
721 gtggaccggt gccgtccctt tcccagattc gcctag
```

Tree shrew FGF23 gene coding sequence (1-180) (SEQ ID NO: 65)
(Ensembl accession no. ENSTBET00000016365, which is hereby
incorporated by reference in its entirety)

```
  1 GCCCTGCTGA TCAGGCCGGA GGAGGCTGGC TTCGCGGTGA TCACGGGCGT GATGAGCAGG
 61 AGATACCTCT GCATGGATTT CAGGGGCAAC ATTTTCGGAT CACACCTCTT CAGCCCGGAG
121 AGCTGCAGGT TCCGGCAGCG CGCCCTGGAG AACGGCTACG ACGTCTACCA CCACCCGCAG
181 CACCACTTCC TGGTCAGCCT GGGCCGGCCC AAGAGGGCCT TCGTGCCAGG CACGAACCCG
241 CCCCCCTACT CCCAGTTCCT GGCCCGGAAG AACGAGATCC CGCTCATCCA CTTCAACACC
301 CCGAAGCCGC GGCGGCACAC CCGCAGCGCA GAGGACAACT CGGGGCGCGA CCCGCTGAAC
361 GTGCTGAAGC CCCGGCCGCG CATGACCCCG GCGCCCGCCT CCTGCTCGCA GGAGCTCCCG
421 AGTGCCGAGG ACAACAGCGT GGTGGCCAGC GACCCCCTGG GAGTGCTCAG GGGCAACAGG
481 GTGAACACGC ACGCGGGGGG CTGGGGCGTG GACCGCTGCC GCCCCTTCCC CAGGTTTATC
541 TAG
```

Norway rat FGF23 gene coding sequence (1-251) (SEQ ID NO: 66)
(GenBank accession no. NM_130754, which is hereby
incorporated by reference in its entirety)

```
  1 atgctagggg cctgcctcag actcctggtg ggcgctctgt gcaccgtctg cagcttgggc
 61 actgctagag cctattcaga cacttcccca ctgcttggct ccaactgggg gagcctgacc
121 cacctgtaca cagctacagc caggaacagc tatcacctac agatccatag ggatggccat
181 gtagacggaa caccccatca gactatctac agtgccctga tgatcacatc agaggatgct
241 ggctccgtag tgataatagg ggccatgacc agaaggttcc tttgtatgga tctccgcggc
301 aacatttttg gatcgtatca cttcagcccg gagaactgca gattccgcca gtggacgcta
361 gagaacggct acgacgtcta cctgtcaccg aagcatcact acctggtgag cttgggccgc
421 tccaagcgca tcttccagcc cggtaccaac ccgccgccct tctcgcagtt cctggcgcgc
481 aggaacgagg tcccgctgct gcacttctac accgcgcgcc cacggcgcca cacgcgcagc
541 gccgaggacc cgcccgagcg cgacccgctg aatgtgctca agccgcggcc ccgcgctact
601 cccataccgg tatcctgctc gcgagagcta ccgagtgcag aggaaggtgg ccccgcggcc
661 agcgaccccc tgggagtgct gcgcagaggc cgcggggatg ctcgccgggg cgcgggaggc
721 acggatcggt gtcgcccctt tcccaggttc gtctag
```

House mouse FGF23 gene coding sequence (1-251) (SEQ ID NO: 67)
(GenBank accession no. BC120605, which is hereby
incorporated by reference in its entirety)

```
 24                          atgctag ggacctgcct tagactcctg gtgggcgcgc
 61 tctgcactgt ctgcagcttg ggcactgcta gagcctatcc agacacttcc ccattgcttg
121 gctccaactg ggaagcctg acccacctgt acacggctac agccaggacc agctatcacc
181 tacagatcca tagggatggt catgtagatg gcacccccca tcagaccatc tacagtgccc
241 tgatgattac atcagaggac gccggctctg tggtgataac aggagccatg actcgaaggt
301 tcctttgtat ggatctccac ggcaacattt ttggatcgct tcacttcagc ccagagaatt
```

TABLE 2-continued

| |
|---|
| 361 gcaagttccg ccagtggacg ctggagaatg gctatgacgt ctacttgtcg cagaagcatc |
| 421 actacctggt gagcctgggc cgcgccaagc gcatcttcca gccgggcacc aacccgccgc |
| 481 ccttctccca gttcctggcg cgcaggaacg aggtcccgct gctgcacttc tacactgttc |
| 541 gcccacggcg ccacacgcgc agcgccgagg acccacccga gcgcgaccca ctgaacgtgc |
| 601 tcaagccgcg gccccgcgcc acgcctgtgc ctgtatcctg ctctcgcgag ctgccgagcg |
| 661 cagaggaagg tggccccgca gccagcgatc ctctgggggt gctgcgcaga ggccgtggag |
| 721 atgctcgcgg gggcgcggga ggcgcggata ggtgtcgccc ctttcccagg ttcgtctag |

| Megabat FGF23 gene coding sequence (1-248) (SEQ ID NO: 68) (Ensembl accession no. ENSPVAT00000000244, which is hereby incorporated by reference in its entirety) |
|---|
| 1 ATGCCGAGGG GCAGCCTAGG GCTCCTGGTC TGCATCCTGT GCTGCAGAGC CTATCCCGAT |
| 61 GCCTCTCCGC TGCTTAGCTC CAGCTTGGGG GGCCTGATCC ACCTCTACAC AGCCACAGCC |
| 121 AGGAACGGCT ACCACCTGCA GATCCACAAG GATGGCCATG TGGATGGCAC ACCCCATCAG |
| 181 ACCATCTACA GTGCCCTGAT GATAAGATCA GAGGACAGTG GCTTTGTGGT GATAATAGGT |
| 241 GTGATGAGTA GAAGATACCT CTGCATGGAC TTCAAAGGCA ACATTTTTGG ATCACATCAC |
| 301 TTCAGCCCCG AGAGCTGCAA GTTCCGCCAG CGAACGCTGG AGAATGGCTA CGACGTGTAT |
| 361 CACTCGCCCC AGCATCACTT CTTCGTCAGC CTGGGCCGAG CTAAGAGGGC CTTCCTGCCG |
| 421 GGCACGAACC CCCCACCTTA CTCCCAGTTC CTGTCCCGAA GGAATGAGAT CCCCCTGTTC |
| 481 CAGTTCAACA CCCCGCGGCC GCGGCGGCAC ACGCGCAGCG TGGAGGACTA CAAAGACTAC |
| 541 GATTTGGACC CCGACCCGCT GAAAGTTCTG AGGCCCCGTC CCCGGTGGGT CCCCGCCCTG |
| 601 CCCTCCTGCT CCCAGGAGCT CCCGAGTGCC GAGGACAACA GCGTGGTAGC CAACGACCCG |
| 661 TTAGGGGTGC TCAGGCCCAG CAGGGTAAAC ATATACCGTG AGAGAATGGG CAAGGGGAGG |
| 721 TGCCGTCCCC ACCCTGAGTT TGTCTAG |

| Microbat FGF23 gene coding sequence (1-248) (SEQ ID NO: 69) (Ensembl accession no. ENSMLUT00000031180, which is hereby incorporated by reference in its entirety) |
|---|
| 1 ATGCCAGGGG CCCGCCTTGG GTTGCTGGTC TGCGTCCTGG CCCTGCGCTG TGTGGTCAGA |
| 61 GCCTATCCCA ACGCCTCCCC ACTGCTCGGC TCCAGCTGGG GTGGCCTGAC CCACCTGTAC |
| 121 ACGGCCTCAG CCAGGAACAG CTACCACCTG CAGATCCACA AGGACGGCCA TGTGGACGGC |
| 181 ACACCCCATC AGACCATCTA CAGTGCCCTG ATGATCAGAT CAGAGGACGC TGGCTTTGTG |
| 241 GTGATAACTG GAGTGATGAG TAGGAGATAC CTCTGCATGG ACTTTAGAGG CAACATTTTT |
| 301 GGATCCCTTT TTTTCAGTCC AAGTAATTTC AGTTTCCTTG AATGGAAAAA GGAAAGTGGG |
| 361 ATGGACCATT GGATAAGCAG ACAGACGCAC TTCCTCGTCA GCCCTGGGCC GAGCCAAGAG |
| 421 GGCCTTCCTG CCGGGCACAA CCCGCCGCCC TACTCGCAGT TCCTGTCGCG AAACGAGATC |
| 481 CCGCTCTTCC ACTTCAACAC GCCCGCGCCG CGCCGGCACA CGCGCAGCGC CGAGGAGAAC |
| 541 TCGGCGGCCG ACCCGCTGGT CGTGCTGAAG CCCGTGCCGC GCCTGACGCC CCCGCCCGCC |
| 601 TCCTGCTCCC GGGAGCTGAG CAGCGCCGAG GACAACAGCG TGGCGGCCCA CGACCCGCTC |
| 661 GGGGTGCTGC GGAGCAGCAA CAGGGTGAAC TCGCACGCGC CGCCCCCAGG TCCACCTAGG |
| 721 ACCCGCCAAG GAATGCTTCT CGTA |

| Tasmanian devil FGF23 gene coding sequence (1-245) (SEQ ID NO: 70) (Ensembl accession no. ENSSHAT00000010240, which is hereby incorporated by reference in its entirety) |
|---|
| 1 ATGTCAGGGG GTTGCCTCAG GCTCCTATTC TGTGCCCTGT GCAGCTTAAG GGCCATCCAA |
| 61 GCCTTCCCCA ATGCTTCCCC CCTGCTCAGC CTTGGCTGGG GGGGTCTGAC TCACCTCTAT |
| 121 ACGGCCACAG CCAGGAACAG CTACCACCTG CAGATCCACA AAGATGGCCA CGTGGATGGG |
| 181 TCTCCTCATC AAACCATCTA TAGTGCCTTG ATGATCAGAT CAGAGGATGC TGGGCTAGTC |
| 241 ATAATAACTG GTGTGATGAG CAGGAGATAT CTCTGTATGG ACATTAGGGG CAACATCTTC |
| 301 GGATCGCATT TCTTCAGCCC AGACAACTGC AGGTTCAAAC ACCGGACATT AGAAAATGGG |
| 361 TATGACATCT ATCACTCTCC CCAGAACAAC TTCCTGATCA GCCTTGGCAA GGCAAAGAGG |
| 421 GCCTTCCTAC CAGGGATGAA CCCACCTCCT TACTCCCAAT TCCTGTCTCG GAGAAATGAA |
| 481 ATCCCCATAA TACACTTCAA TACACCTGAA CCCCACCGGC ATACCAGGAG TGCTGAGAAC |
| 541 AGTCCTGACT TGGACCCAAT GAATGTGCTG AAACTCCGAC CAAGGATAAC TCCCTGCTCC |
| 601 CAGGAACTTC ACAGTGCTGA AGAGAACAGT GTAGTGGATG ATGACCCTTT GGAAGTACTC |
| 661 AGAAATAGCA ATAGATTGAA GCCCTATCCT GGCAGGATGA GTTTGGAAAG ATGCCTCCAT |
| 721 GTCCCCAAGG CAGCTTAA |

| Gray short-tailed opossum FGF23 gene coding sequence (1-191) (SEQ ID NO: 71) (GenBank accession no. XM_001372399, which is hereby incorporated by reference in its entirety) |
|---|
| 1 atggcaaatt gtagagaaaa ggagctggag atgtacattt gtgccttgat gatcagatca |
| 61 gaggatgctg ggctagtcat aataactggt gtgatgagca ggagatatct ctgtatggac |
| 121 atcaggggca acatctttgg ttcgcatttc ttcaacccgg acaactgcaa gttcaagcac |
| 181 cggacactag aaaatgggta tgacatctat cattctcccc agaacaactt cctgatcagc |
| 241 cttggcaagg caaagagggc ctttctgcca ggcatgaatc cacctccgta ctctcaattc |
| 301 ctgtctcgga agaatgagat ccccataatc cacttcaaca cacctgaacc ccaccggcac |
| 361 accaggagtg ctgaaaacag tcctgacttg gacccaatga atgtgctgaa accccgacca |
| 421 aggatgactc cctgctctca ggaactctac agtgctgaag agaacagtgt agtggatgat |
| 481 gaccctttgg aagtacttag aaatagcaat cgactgaagc ccttccctgg taggctgggt |
| 541 ttagaaaggt gccaccatgt tcccaagact gattaa |

TABLE 2-continued

Armadillo FGF23 gene coding sequence (1-180) (SEQ ID NO: 72)
(Ensembl accession no. ENSDNOT00000005805, which is hereby incorporated by reference in its entirety)

```
  1 GCCCTGATGA TCAGCTCTGA AGATGCTGGC TTTGTGGTGA TAACAGGTGT GATGAGCAGG
 61 AGGTACCTCT GTATGGATTT CAGAGGCAAC ATTTTTGGAT CGCACGACTT CACCCCGGAC
121 AGCTGCAGGT TCCGCCAGCG CACGCTGGAG AACGGCTACG ACGTCTACCA CTCGCCGCAG
181 CACCACTTCC TCGTCAGCCT GGGGCGGGCC AAGCGGGCCT TCCAGCCGGG CTCCAACCCG
241 CCGCCCTACT CCCAGTTCCT GTCCCGCAGG AACGAGATCC CGCTGATGCG CTTCAGCACC
301 CCGCGGCCGC GGCGGCACAC GCGCAGCGCC CAGGACCACG CGGACCCCGA CCCGCTGAGG
361 GTGCTCAAGC CCCGGCTCCG GCTGACCCCG GCCCCCGCCT CCTGCTCCCA GGAGCTGCCG
421 AGCGACGAGG ACGACGGCGC GGTGGCCAGC GACCCCCTGC GCGTGGTCCT CGGCCGCCGG
481 CCCCACGCGC GGGCCGCGGG CGCGGGCGGG GAGCGGTGCC GCCCCGGCCC GCAGCTCAGC
541 TAG
```

Wallaby FGF23 gene coding sequence (1-177) (SEQ ID NO: 73)
(Ensembl accession no. ENSMEUT00000004101, which is hereby incorporated by reference in its entirety)

```
  1 GCCTTGATGA TCAGATCAGA GGACGCTGGG CTAGTCATAA TAAGTGGTGT GATGAGCAGG
 61 AGGTATCTCT GTATGGACCT CAGAGGCAAC ATCTTCGGAT CGCATTTCTT CAGCCCAGAC
121 AACTGCAGGT TCAAACACCG GACACTAGAA AATGGGTATG ACATCTATCA CTCTCCACAG
181 AACAACCTCC TGATCAGCCT TGGCAAGGCA AAAAGGGCCT TCCTGCCAGG CATGAACCCA
241 CCTCCTTACT CCCAGTTCCT ATCTCGGAGG AATGAGATCC CCATAATCCA CTTCAATACA
301 CCTGAACCCC GCCGGCACAC CAGGAGCGCA GAGAACAGTC CTGACTTGGA CCCAATGAAT
361 GTGCTGAAAC CCCGACCAAG GGTGACTCCC TGCTCCCAGG AACTCCGCAG TGCTGAAGAG
421 AACAGTGTAG TAGATGATGA CCCTTTGGAA GTACTCAGAA ATAGTAATCG CCTGAAGCCC
481 TACCCTGGTA GAATGAGTTT GGAAAGATGC CTCCAAGTCC CCAAAGCTGC TTAA
```

Zebra finch FGF23 gene coding sequence (1-256) (SEQ ID NO: 74)
(GenBank accession no. XM_002190484, which is hereby incorporated by reference in its entirety)

```
  1 atggagtgga gagccactct ccagggcatt ccctgcagct ccctgctcct gctgctctgc
 61 agcctaaagg cttcccttgc ctttcccaac tcctctccac tgctgagtcc cagctggggc
121 aatggagatc gcctgatgca cctctacacc gacaccgaga ggagcagctt ccacctccag
181 atcaacgctg atggctacat cgatggcgct cctcaccaaa ccatctacag tgccctaatg
241 atcaagtctg agggtgctgg ctcagtaata atcacaggtg tgaagagtgg acgctacctg
301 tgtatggaca tgaaaggaaa tatatttggc tcgcattact tcagccaaga ggactgcatg
361 ttcaaccaca ggacgctgga aaatgggtac gatgtgtacc aatcccccaa acaccacttc
421 ttggtgagct taggcagagt taaacaagtc ttctcccctg gtatgaatcc accaccatac
481 tcccagtttc tgtccaggaa gaatgagatc cctctgttcc gattcaacac ccccgagccc
541 cacaggcaca ccaggagtgc agatgttgat cccgtagatc ctcaccagat cctggtcccg
601 cagaggaaga ccccagtgtt tggctccctg cagcagcagc cagcagactt tccccacatg
661 cccagggagc ccatgaggat caaccagaac gacgtggtga accccgatga tccccacgca
721 atgatggagg ccaggaggta cccaagcccc cgcttctaca tcacgagata a
```

Chicken FGF23 gene coding sequence (1-254) (SEQ ID NO: 75)
(GenBank accession no. XM_425663, which is hereby incorporated by reference in its entirety)

```
  1 atgccacaca ccagtccctg cagctgcctg gagtacatgc tgcttgtgct ctgtatcctg
 61 aaggctgcag tcgccttccc caactcctct ccgctgctga atcccagctg gggaatgga
121 gatcagctga tgcacttgta cacttctaca gagaggaaca gcttccatct ccaaatcaat
181 gctgatggac acatcaatgg tgttcctcac caaaccattt acagtgcctt aatgatcaag
241 tctgagggtg ctggctgtgt aataatcaca ggtgtgaaga gtggacgcta cctatgcatg
301 gacatgaaag gagacatttt tggatcgtat tatttcagcc aagaggactg tgtgttcaac
361 caaaggacac tggaaaatgg atatgatgtg taccaatctc ccaagcacaa ttttctggtt
421 agcttgggca gaactaagca agttttcttc cctggtatga atccaccacc atactcccag
481 tttttgtcca ggagaaacga aatccctttg tttcgattca acacacctga accccacaga
541 aacactagaa gtgcagatgt cgatccactg gatcctcacc aaatcctggt cccacagaga
601 aaggtctctg cattagggtc tcagctgcag ctgcaaatgg acttttccca tgtgcccaga
661 gaacccatga gagtcaatca gaatgatgtg gtcaatccag atgacccaca tgctatgatg
721 gatgctagga ggtatgctag tcctcgcttt tacattacaa gataa
```

Turkey FGF23 gene coding sequence (1-254) (SEQ ID NO: 76)
(GenBank accession no. XM_003202575, which is hereby incorporated by reference in its entirety)

```
  1 atgccgcaca ccagtccctg cagctgcctg gagtacatgc tgcttgtgct ctgtatcctg
 61 aaggctgcag tcagcttccc caactcctct ccactgctga atcccagctg gggaacgga
121 gatcagctga tgcacttgta tacttctaca gagaggaaca gcttccatct tcaaatcaat
181 gctgatggcc acatcagtgg tgttccttac caaaccattt acagtgccct aatgatcaag
241 tctgagggtg ctggcagcgt tataatcaca ggtgtgaaga gtggacgcta cctatgcatg
301 gacatgaaag gagacatttt tggatcgcat tatttcagcc aagaggactg cgtgttcaac
361 caaagaacac tggaaaatgg atatgatgtg tatcaatctc ccaagcacaa ttttctggtt
421 agcttaggca gaactaagca agttttcttc cctggtatga atccaccacc gtactcccag
481 tttttgtcca ggagaaacga aatcccgttg tttcgattca acacacctga accccacaga
541 aacactagaa gtgcagatgt tgatccaatg gatcctcacc agatcctggt cccacagaga
```

TABLE 2-continued

```
601 aaggtctctg caatagagtc tcagctgcaa ctgcaaatgg acttttccca tgtgcccaga
661 gaacccatga gagtcaatca gaacgatgtg gtcaacccag atgacccaca cgctatgatg
721 gatgccagga gatatgctag tcctcgcttt tacattacaa gataa
```

Green anole FGF23 gene coding sequence (1-242) (SEQ ID NO: 77) (GenBank accession no. XM_003221363, which is hereby incorporated by reference in its entirety)

```
  1 atggtccagg ctactctata cagcttcctc aaatatatgc tgcttgcaac atgtagctgg
 61 aaagcaattg ctgctttccc caacgcatca cctttgctca gcctcaactg gggaaattca
121 gacagcctgc tacacttgta cacttccaca gcaagaaaca gcttccacct gcaaatccac
181 tccaatggct acgtggatgg aagtccgtat caaacaattt acagtgcctt gatgatcaaa
241 tctgaagttg ctggttatgt tataataaat ggtgtgaaaa gtggacgttt tctttgtatg
301 gatatgaatg ggaacatctt tggatcgcat ttcttcagtt atgaggactg cactttcaaa
361 cactgggtcc tggaaaatgg ttatgatgtt tatcagtctc ccaaatacaa ctaccttgtc
421 agcttaggaa aagcaaagca accattgttc cccaatatga atccaccacc ttactcccag
481 ttcttgtcca ggagaaatga aattccttta gtccagttca acacaccgaa acctcacaga
541 cataccagaa gtgccaacgc ggatccctgc ggcagcatca tatcatcagg aaatattgcg
601 aaagaaaacc tacagttaca gccactaatg tataacacta aaatgaattc aaacagtgaa
661 gatgaagacc caaacagtgc aataatcaat agaagatttt tgagtcctag aacagatgtc
721 aggagctga
```

Coelacanth FGF23 gene coding sequence (1-249) (SEQ ID NO: 78) (Ensembl accession no. ENSLACT00000020646, which is hereby incorporated by reference in its entirety)

```
  1 CTAGAGTCCG CTCTTCTTGC GTTTTCTATG GCTATATTCT ATAGCTTTAA AGCTGTGAGC
 61 TCTTTTCCAA ATTCTTCGCC ACTGCTTAAC CCAGTCTGGG GAAACACTGA CAACCTGATA
121 CACCTGTATA CAGCTTCTGA GACGAACAGC TTCCACTTGC AGATCAACTC CGATGGACAT
181 GTGGATGGTA CTCCACACCA AACCGCTTAC AGTGCACTGC TGATCAAGTC CGAGGAGGCT
241 GGTTCTGTAG TTATCCTGGG GGTGAAGAGT GGACGTTACC TCTGTATGGA TATCAAGGGC
301 AATATTATTG GACTGCATCA CTTCAGCAAG GAAGACTGTA CATTCAAACA AGAGGGCTTG
361 GAAAATGGAT TTGATGTGCT GCGCTCACCT AAGCACAACA TTTTGGTCAG CCTTGACAAG
421 ACTAAACGCT CCTACATCCC GGGTATGAAC CTGCCACCTT ACTCACAGTT TTTATCCCGA
481 CAGAATGAAG TAGCTCTGAT CAACTTCATT AACACACCTG ACATACACAG ACATAGTCGA
541 AATGTTGATG TTGATCCTTC AGACCCCCAT GGGATGATAA TTCAGCCTGA TGTGGGTGTT
601 TCATTTCGTA AGTCTTCATC TCTGTTTTCA GATCTGCCCA GAGACTCCAT GAGAACTAGC
661 CATAATGGTA TGGATATGGT TGATCCTGCT GACCCACATG GAATGTTAGA TTCCAGGAGA
721 AGACCAAGTC CAAGGTTCTT TGCAAGATAG
```

Western clawed frog FGF23 gene coding sequence (1-254) (SEQ ID NO: 79) (GenBank accession no. XM_002940305, which is hereby incorporated by reference in its entirety)

```
 25                          atgacc aagcagcaaa ctagactagg actggtgctc
 61 actgttcttg ccagtataaa ggttatatct gccttcccca actcttctcc aataatcagt
121 ggcggctggg gggtccctga cagactgatg cacctatata cggccagtga ctggaacagc
181 ttccacctac agatcaacca tgatggaagc attgatggaa cccctaccca aaccatttac
241 agtgcaataa tgatcaaatc agaatccgct gggcacgtgg ttattactgg ggtgaagact
301 aatcggtacc tgtgcatgga taaaagtggg aacatttttg gatatcacga cttcaaccac
361 gacgactgcg tttttaagca cgagactctg gagaacaact ttgacgttta ccattctcca
421 aaacacaact ttgtgatcag cctcaaggag cccaagcatc atttccgcct cggcatggac
481 ctgccccctt actcccaatt cctgtccttg gagaatgaaa tccccataac cagattcaat
541 gctccagagc cggaaatgag aatcccagag ggcaactttg ctgaccccag cgacatcata
601 aagaacccca ggaactggga cttttcgcag tctattcata atccatttca ggatgtgtgg
661 ttgccgttcc ccagcggttc attaccaatc attagagctt ccttgccaat tattcataac
721 aatgtgatta atacagatga ccctgaagaa attgtaaaaa tgaagagata cagatatttc
781 aagaggtag
```

Cat FGF23 gene coding sequence (1-199) (SEQ ID NO: 80) (Ensembl accession no. ENSFCAT00000000141, which is hereby incorporated by reference in its entirety)

```
  1 ATGTCAGGGA CCCGCCTTGG GCTCCTGGTC TCTGTCCTGT GCTGGGTAGT CAGAGCCTAT
 61 CCTAACACCT CCCCGCTGCT GGGCTCCAGC TGGGGTGGCC TGACCCACCT GTACACGGCC
121 ACAGCCAGGA ACAGCTACCA CCTGCAGATA CACAAGGACG GCCATGTGGA TGGCACACCC
181 CATCAGACCA TCTACAGTGC CCTGATGATC AGATCGGAGG ATGCCGGCTT TGTGGTGATA
241 ACAGGTGTGA TGAGTCAGAG GTACCTCTGT ATGGACTTCA GAGGCAATAT CTTCGGATCG
301 CACCTCTTCA GCCCCGAGAG CTGCAGGTTC CGACAGCGGA CGCTGGAAAA CGGCTACGAC
361 GTGTACCACT CCCCGCAGCA CCGCTTCCTA GTCAGCCTGG GCCCGGCCAA GAGGGCCTTC
421 CTGCCGGGCA CCAACCGCAT GACCCCCGCG CCGGCCTCCT GCTCCCAGGA GCTCCCAAGC
481 GCCGAGGACA GCGGCGTGGT GGCCAGCGAC CCGTTAGGGG TGCTCAGGGG CAACAGGGTG
541 AACGCGCACG CCGGGGGGAT GGGCGTGGAG AGGTGCCGCC CCTTCCCCAA GTTCAACTAG
```

Chinese softshell turtle FGF23 gene coding sequence (1-250) (SEQ ID NO: 81) (Ensembl accession no. ENSPSIT00000012816, which is hereby incorporated by reference in its entirety)

```
 98                                    ATG TCACAGCCCA GCCAGTGCAG
121 CTGCCTGAAC TTCATGCTGT TCGTGCTATG TAGCTTCAAA GCTATTGCTG CCTTTCCCTT
```

TABLE 2-continued

```
181 CTTCTCTTCA CTGCTGAATC CCAGCTGGGG GGAAACGGAT AGTTTGATAC ACCTGTACAC
241 AGCTACTGAG AAGAACAGCT TCCATCTGCA GATCAACCCT GATGGTTATG TTGACGGCAC
301 ACCTCACCAA ACCATTTACA GTGCTCTAAT GATCAAATCT GAGGATGCTG GCTATGTGGT
361 GATAAGTGGT GTAAAGAGTG GGCGCTACCT ATGTATGGAC ATTAAAGGAA ATATCTTTGG
421 ATCGCATTAC TTCAGTCAAG AGGACTGCAT GTTTAAACAC AGAACACTGG AAAATGGATA
481 TGATGTGTAC CAGTCTCCCA AGCACAACTT CCTGGTCAGC CTGGGCAGGA ATAAACAAGC
541 TTTCTTCCCT GGTATGAATC TGCCACCATA CTCCCAGTTT TTGCCCAGGA GAAATGAAAT
601 CCCTCTGATC CGATTCAACA CACCCGAACC CCACAGGCAC ACTAGGAATG CAGATGTTGA
661 TCCCCTCCAG ATTTTGATCC CTCGGGGAGA GGCTTTTGAC ACAGGACCTC AGAGGTTGCA
721 GACTCACTTT GATCACCTGC CTAGAGAACC CATGAGAATC AATCCAAATG ATGTAGTCAG
781 CCCGGATGAC CCACTCGCCA TGATGGATGT CAGAAGGAAT GCAAGTCCAC GCCTTTACAT
841 TACAAGA
```

Ferret FGF23 gene coding sequence (1-245) (SEQ ID NO: 82) (Ensembl accession no. ENSMPUT00000009396, which is hereby incorporated by reference in its entirety)

```
186      ATGTC AGTGACCCGT CTTGGGCTCC TGGTCTCTGT CCTGTGCTGG GTAGTCAGAG
241 CCTATCCCAA CGCCTCCCCG CTGCTCGGCT CCAGCTGGGG TGGCCTGACC CACCTGTACA
301 CGGCCACTGC CAGGAACAGC TACCACCTGC AGATCCACAA GGATGGCCAT GTGGATGGCA
361 CACCCCACCA GACCATCTAC AGCGCCCTGA TGATCAGATC AGAGGATGCC GGCTTTGTGG
421 TGATCACAGG TGTGATGAGC AGGCGGTACC TGTGTATGGA CTTCCGAGGC AACATCTTTG
481 GATCCCACCT CTTCAGCCCC GAGAGCTGCA GGTTCCGACA GCGGACACTG GAAAACGGCT
541 ACGACGTGTA CCACTCCCCG CAGCACCGCT TCCTCGTCAG CCTGGGCCAA GCCAAGAGGG
601 CCTTCCTGCC GGGCACCAAC CCGCCGCCCT ACTCCCAGTT TCTGTCCCGG AGGAATGAGA
661 TCCCCCTCAT CCACTTCAAC ACCCCCAGGC CGCGGCGTCA CACGCGCAGC GCCGAGGACA
721 TGGAGCACGA CCCGTTGAAC GTGCTGAAGC CCCGGCCCCG CATGACCCCG GCCCCGGCCT
781 CCTGCTCCCA GGAGCTCCCG AGCGCCGAGG ACAACAGTGT GGTGGCCAGC GACCCGTTAG
841 GGGTGCTCAG AGGCAACCGG GTGAACGTGC ACGCGGGGGG GATGGGCGTG GACAGGTGCC
901 GCCCCCTCCC CAAGTTCATC TAG
```

Mouse lemur FGF23 gene coding sequence (1-206) (SEQ ID NO: 83) (Ensembl accession no. ENSMICT00000004875, which is hereby incorporated by reference in its entirety)

```
  1 ATGCTGGGGG CCTGCCTCAG GCTCTGGGTC TGTGCCCTGT GCAGTGTCTG CGGCGTGAGC
 61 GTCGTCAGAG CCTATCCCAA CGCCTCCCCG CTGCTCGCCT CCAGCTGGGG TGGCCTGATC
121 CACCTGTACA CGGCCACGGC CAGGAACAGC TACCACCTGC AGATCCACAA GGACGGCCAT
181 GTGGACGGCA CACCCCACCA GACCATCTAC AGTGCCTTGA TGATCAGGTC AGAGGATGCT
241 GGCTTTGTGG TGATCACAGG TGTGATGAGC AGAAGATACC TCTGCATGGA TTTCAGAGGC
301 AACATTTTTG GATCACATGT CTTCAGCGCG GAGAGCTGCA GGTTCAGACA GCGGACGCTG
361 GAGAACGGCT TCGACGTGTA CCAGTCCCCT CAGCACCACT TCCTGGTCAG CCTGGGCCGC
421 GCCAAAGGGG CCTTTCCGGC CGGGGCGAAA CCGCCCCCCT TCCCCCAGTT CCTGCCGCGG
481 GGGAACGAGG CTCCCGGGCG CAAAACGCGG GGGCCCGAGG AAAAAGGGGC CCCACACCCT
541 CTCCGCGGGG TGGAAAGCGG GGGCCGGAAA GGCGGGGCCC CGCCTCTCTG TTTGGAGAGG
601 CTCTCCAGAG CCCGAGAG
```

Orangutan FGF23 gene coding sequence (1-251, excluding 2-22 and 38-71) (SEQ ID NO: 84) (Ensembl accession no. ENSPPYT00000006110, which is hereby incorporated by reference in its entirety)

```
  1 ATG------- ---------- ---------- ---------- ---------- ----------
 61 ------CGCA AT------GA GTCTTTGCCC TGCCTGGTTT TCTCCATAGG T---------
121 ---------- ---------- ---------- ---------- ---------- ----------
181 ---------- ---------- ---------- GCCCTGATGA TCAGATCAGA GGATGCTGGC
241 TTTGTGGTGA TTACAGGTGT GATGAGCAGA AGATACCTCT GCATGGATTT CAGAGGCAAC
301 ATTTTTGGAT CACACTATTT CAACCCGGAG AACTGCAGGT TCCAACACCA GACGCTGGAA
361 AACGGGTATG ACGTCTACCA CTCTCCTCAG CATCACTTCC TGGTCAGTCT GGGCCGGGTG
421 AAGAGAGCCT TCCTGCCAGG CATG---CCA CCCCCGTACT CCCAGTTCCT GTCCCGGAGG
481 AACGAGATCC CCCTAATTCA CTTCAACACC CCCGTACCAC GGCGGCACAC CCGGAGCGCC
541 GAGGATGACA CGGAGCGGGA CCCCCTGAAA GTGCTGAAGC CCCGGGCCCG GATGACCCCG
601 GCCCCGGCCT CCTGCTCACA GGAGCTCCCG AGCTCCGAGG ACAACAGCCC GATGGCCAGC
661 GACCCATTAG GGGTGGTCAG GGGCGGTCGA GTGAACACGC ACGCTGGGGG AACGGGCCCG
721 GAAGGCTGCC GCCCCTTCCC CAAGTTCATC
```

Shrew FGF23 gene coding sequence (1-251, excluding 19-27, 71-105, 198-200, and 236-251) (SEQ ID NO: 85) (Ensembl accession no. ENSSART00000007775, which is hereby incorporated by reference in its entirety)

```
  1 ATGTGGGGAC TCCGCCTGGG TCTCTTGGTC GGCCTCCTGG GCTGCGTGGA CAGA------
 61 GCCTCCCCGA TGCTGGCGTC CAGCTGGGGC GGCCTGACGC ACCTGTACAC GGCCACGGCC
121 AGGAACAGCT ACCACCTCCA GATCCACAAG GACGGCCTGG TCGACGGCTC CCCGCAGCAG
181 ACCGTCTAC- ---------- ---------- ---------- ---------- ----------
241 ---------- ---------- ---------- ---------- ---------- ----CACCAT
301 TTCAGCCCGG AGAGCTGCCG CTTCCAGCAG CGCACGCTGG AGAACGGCTA CGACGTGTAC
361 CAGTCCCCGC AGCACCGCTT CCTCGTGAGC CTGGGCCGGC CCAAGCGCGC CTTCCAGCCG
421 GGCGCCAACC CGCCGCCCTA CGCGCAGTTC CTGGCGCGCC GCAACGAGGT GCCCCTGGCG
481 CGCTTCCACA CGCCCGCGCC GCGCCGCCAC ACGCGCAGCG CGCACGACAA CGGCGACGCC
541 GACCCGCTCA ACGTGCTGGC GCCTCGGGCC ---------G CCGCCGCCGC CTCCTGCTCG
```

TABLE 2-continued

601 CACGAGCTGC CCAGCGCCGA GGACAACAGC GTGGTGGCCA GCGACCCGCT GGGCGTCATC
661 CGCAGCAACC GCTTCCGCAC GCAC

Tetraodon FGF23 gene coding sequence (1-263) (SEQ ID NO: 86)
(Ensembl accession no. ENSTNIT00000014553, which is hereby incorporated by reference in its entirety)

1 ATGGACGTAA ACAGAAGGAT CGGGGTGAAG GACGCCTTGC TGGCGCTCCT GCTCGCCCTT
61 CTCCAGGGAT GCCCCCTGGG GGAAACGGCT CCCAACGCGT CACCGCTGGT CGGTTCCAAC
121 TGGGGGAACC CGAGGAGGTA CGTTCACCTT CAGACATCCA CAGACATGAG CAACTTCTAC
181 TTGGAGATCA GACTGGATGG AACCGTGCGC AAAAGCACAG CCCGGACTTC ATACAGTGTG
241 ATTTTACTGA AAGCCGACAC GAGGGAGCGC ATCGCCATCC TGGGCGTCAA GAGCAACCGT
301 TACCTGTGTA TGGACCTCGA GGGGAGCCCA TTTAGCTCTC CCACCTGCAT CAGGGACGAC
361 TGCTTGTTCA ACCACAGTCT TCTGGAGAAC AACCGGGACG TCTACTACTC CAGCCGGACC
421 GGCATTCTCT TCAACCTTGA GGGCTCCCGC CAGGTGTTCG TGGTGGGCCA GAACGTCCCG
481 CAGACCTCCC TCTTCCTGCC CAGGACGAAC ACGGTGCCGC TGGAGCGACT CCTTCTGCAC
541 AGGGACAAGC GGAACCAGGT GGTGGACCCC TCTGACCCGC ACCGCGTCGC CGTGGGTCGC
601 GCCGAGGAGG GCTCGGACTC CCGGGCCTTG CAGGAGGACG ACGCCGACCT GGAGGTGGAG
661 ACAGAGGTTG AGGTCGGGGA CGACGGACGC AACGCGTCCC GGGAGCGGCT GCAGGCTCCG
721 TCCGATCACG ACCCCTGGGG CGTGTTCTCC TCCAACCCCG GGAGCCCCCG CAGCAGCGGC
781 ACGGTGGGCT GA

Tilapia FGF23 gene coding sequence (1-255) (SEQ ID NO: 87)
(Ensembl accession no. ENSONIT00000000020, which is hereby incorporated by reference in its entirety)

472 ATGGACGTC
481 AACAGGCGAA TGGGGATGAG AGACACCGTG CTGGCGCTCT TTCTCGCTGT CTTGCAGGGA
541 TTTCCTCTCG GGGATACGGT CCCGAACCCA TCACCTCTGG CTGGATCCAA CTGGGGGAAC
601 CCAAGGAGAT ACGTCCACCT GCAGACATCC ACAGACCTCA ATAACTTCTA CTTGGAGATC
661 AGATTAGATG GGAGTGTGCG CAAAACTACG TCCAGGAGCA CCTATAGTGT GATTCTACTG
721 AAATCTGAAG CAAGAGATCG CGTCGCCATC CTCGGCGTCA AAAGCAGCCG TTACCTATGC
781 ATGGACCTGG AGGGCAACCC GTTCAGCTCT CCTGTCTGCC TTCGGGATGA CTGTCTGTTC
841 AACCACAAGC TCCTGGAGAA CAACCGGGAC GTGTACTACT CCAGCCGGAC AGGCATCTTG
901 TTCAACCTGG AGGGCTCCCG ACAGGTGTAC TCGGTGGGCC AGAACCTGCC GCAGACCTCC
961 CTCTTCTTGC CCAGGAAAAA CACCGTACCA CTGGAGCGCC TCCTGCTGCA CAGGGAGAAG
1021 AGAAACCGGG GGCAGACAGA AGAGGGTTCG GACTCCCGGG CCGTGCCGGA GGAGCTGGAG
1081 GAAAGGGAGG TGGAAATGGA GACGGAAATA GAAACAGAGG TCGGGGATGA CGGACGCAAC
1141 GTGTCCCGGG AGAAACTCGC GGCTCCATCC AGCCACGACC CCTGGAACGT GCACTTCTCC
1201 AACCCGGCCA GCCCCCGGAG CACCGGGACA GTGGGCTGA

Zebrafish FGF23 gene coding sequence (1-258) (SEQ ID NO: 88)
(Ensembl accession no. ENSDART00000067388, which is hereby incorporated by reference in its entirety)

79 AT GCGTTGCGCA CTTTCCAACC TGCACATGCT GCATTCATCC
121 GTCCTCGCGC TGTGGTTCAC GGCTCTCCAG GGACTCAGAC CTGCAGATGC GGCCCCCAAT
103 CCTTCTCCGC TGCTGGGCTC CAACTGGGGG AACCCGCGGA GATACATCCA CCTTCAGACC
163 ACTTCAGACT TAAACAACTA CTACCTGGAG ATCAGCCCGA GTGGACACGT GCGCAAAACT
223 ACAAATCGGG GCTCATACAG TGTAATCTTA TTGAAAACAG AAAGCAGAGA CCGTCTGGCG
283 ATATTTGGAG TGAAAAGTAA CCGGTTTTTG TGCATGGATA CAGGAGGAAC CCTTTTCACA
343 TCTACGATCT GCAATAAGGA AGACTGTCTT TTCCACCACA AACTGTTGGA AAACCATCGT
403 GATGTGTATT ACTCCACTAA ACACAGCATA CTGCTTAATC TGGACGGGGA CAAACAGGCG
463 TTTATAGCGG GACAAAACCT CCCTCAGTCG TCTCTCTTCT TGTCGGAGAA GAACACGGTT
523 CCGCTGGAGC GCCTGCAGCA TCGGGAGCGC AGGAACCGGC AGGTGAACCC AACAGACCCG
583 CTGAACGCGC TCCGGTACGC GGAGGAGTCT GATTCCAGAG CCGCGCAGGA GGATGATGGA
643 GACATGGATT TTGAGCCCTC AGAAGGTCAA AACATCTCTA GAGAAACCCT TGTTTCCCCT
703 TCCGATGATG ATCCATGGGA TCTTCTGCAC GACACGAGCC CTGGAAGTCC TCGGATTGCA
763 GCAATTGTCG GATAA

As noted above, the chimeric protein includes an N-terminal portion from an FGF23 molecule coupled to a C-terminal portion from an FGF19 molecule. In one embodiment, FGF19 comprises the amino acid sequence of SEQ ID NO: 89 (GenBank Accession No. NP_005108, which is hereby incorporated by reference in its entirety), as follows:

1 mrsgcvvvhv wilaglwlav agrplafsda gphvhygwgd pirlrhlyts gphglsscfl 61 riradgvvdc argqsahsll eikavalrtv aikgvhsvry lcmgadgkmq gllqyseedc -continued 121 afeeeirpdg ynvyrsekhr lpvslssakq rqlyknrgfl plshflpmlp mvpeepedlr 181 ghlesdmfss pletdsmdpf glvtgleavr spsfek In one embodiment, the C-terminal portion from the FGF19 molecule includes a β-Klotho co-receptor binding domain. In one embodiment, the C-terminal portion comprises a domain that selectively binds to β-Klotho co-receptor.

In one embodiment according to the present invention, βKlotho is mammalian βKlotho. In another embodiment, βKlotho is human or mouse βKlotho. In one particular embodiment of the present invention, βKlotho is human or mouse βKlotho (i.e., GenBank Accession No. NP_783864 or GenBank Accession No. NP_112457, respectively, which are hereby incorporated by reference in their entirety).

In one embodiment, the C-terminal portion begins at a residue corresponding to any one of amino acid residues 169 to 204 of SEQ ID NO: 89. In one embodiment, the C-terminal portion begins at a residue corresponding to any one of amino acid residues 169, 174, 197, or 204 of SEQ ID NO: 89. In another embodiment, the C-terminal portion from FGF19 of the chimeric protein of the present invention comprises an amino acid sequence spanning residues corresponding to residues selected from the group consisting of from position 204 to 216 of SEQ ID NO: 89, from position 197 to 216 of SEQ ID NO: 89, from position 174 to 216 of SEQ ID NO: 89, and from position 169 to 216 of SEQ ID NO: 89.

In one embodiment, the C-terminal portion from the FGF19 molecule comprises the amino acid sequence of TGLEAV(R/N)SPSFEK (SEQ ID NO: 131), MDPFGLVTGLEAV(R/N)SPSFEK (SEQ ID NO: 132), or LP(M/I)(V/A)PEEPEDLR(G/R)HLESD(MN)FSSPLETDSMDPFGLVTGLEAV(R/N)SPSFEK (SEQ ID NO: 133).

In one embodiment, the C-terminal region from FGF19 further comprises one or more substitutions, additions, or deletions while retaining the ability to bind β-Klotho. In one embodiment, the C-terminal region from FGF19 further comprises one or more substitutions, additions, or deletions while retaining the ability to selectively bind β-Klotho. In one embodiment, the C-terminal portion further comprises one or more substitutions, additions, or deletions to enhance binding affinity for β-Klotho.

In one embodiment, the C-terminal portion from FGF19 of the chimeric protein of the present invention does not include any of residues 1 to 168 of SEQ ID NO: 89. In certain embodiments of the present invention, the chimeric protein of the present invention does not include residues corresponding to residues spanning residues 1 to 168 of SEQ ID NO: 89.

In other embodiments of the present invention, FGF19 or a portion thereof is or is from a mammalian FGF19. In another embodiment, FGF19 or a portion thereof is or is from a non-human mammalian FGF19. It will be understood that this includes orthologs of human FGF19, or a polypeptide or protein obtained from one species that is the functional counterpart of a polypeptide or protein from a different species. In one embodiment, the C-terminal portion from FGF19 of the chimeric protein of the present invention is from human FGF19. In another embodiment of the present invention, the C-terminal portion from FGF19 is from *Gorilla gorilla, Pan troglodytes, Macaca mulatta, Pongo abelii, Nomascus leucogenys, Callithrix jacchus, Microcebus murinus, Choloepus hoffmanni, Ailuropoda melanoleuca, Sus scrofa, Bos taurus, Canis lupus familiaris, Oryctolagus cuniculus, Pteropus vampyrus, Tursiops truncatus, Myotis lucifugus, Ornithorhynchus anatinus, Monodelphis domestica, Anolis carolinensis, Ochotona princeps, Cavia porcellus, Tupaia belangeri, Rattus norvegicus, Mus musculus, Gallus gallus, Taeniopygia guttata, Danio rerio, Xenopus* (*silurana*) *tropicalis, Otolemur garnetii, Felis catus, Pelodiscus sinensis, Latimeria chalumnae, Mustela putorius furo, Takifugu rubripes, Equus caballus, Oryzias latipes, Xiphophorus maculates, Ictidomys tridecemlineatus, Gasterosteus aculeatus, Oreochromis niloticus*, or *Meleagris gallopavo.*

In other embodiments of the present invention, the portion from FGF19 of the chimeric protein of the present invention is from a non-human having an amino acid sequence as shown in Table 3. The portions of an ortholog of human FGF19 of a chimeric protein according to the present invention include portions corresponding to the above-identified amino acid sequences of human FGF19. Corresponding portions may be determined by, for example, sequence analysis and structural analysis.

TABLE 3

*Gorilla gorilla* (*gorilla*) FGF19 (Ensembl Accession No. ENSGGOP00000021055, which is hereby incorporated by reference in its entirety) (SEQ ID NO: 90)

```
  1 mrsgcvvvhv wilaglwlav agrplafsda gphvhygwgd pirlrhlyts gphglsscfl
 61 riradgvvdc argqsahsll eikavalrtv aikgvhsvry lcmgadgkmq gllqyseedc
121 afeeeirpdg ynvyrsekhr lpvslssakq rqlyknrgfl plshflpmlp mvpeepedlr
181 ghlesdmfss pletdsmdpf glvtgleavr spsfek
```

*Pan troglodytes* (chimpanzee) FGF19 (Ensembl Accession No. ENSPTRP000000068 77, which is hereby incorporated by reference in its entirety) (SEQ ID NO: 91)

```
  1 mrngcvvvhv wilaglwlav agrplafsda grhvhycwgd piplrhlyts gphglsscfl
 61 ripancvmnc argqsahsll eikavalrtv aikgvhsvry lcmgadgkmq gllqyseedc
121 afeeeirpdg ynvyrsekhr lpvslssakq rqlyknrgfl plshflpmlp mvpeepedlr
181 ghlesdmfss pletdsmdpf glvtgleavr spsfek
```

*Macaca mulatta* (Rhesus monkey) FGF19 (GenBank Accession No. XP_001100825, which is hereby incorporated by reference in its entirety) (SEQ ID NO: 92)

```
  1 mrsgcvvvha wilaslwlav agrplafsda gphvhygwgd pirlrhlyts gphglsscfl
 61 rirtdgvvdc argqsahsll eikavalrtv aikgvhsvry lcmgadgkmq gllqyseedc
121 afeeeirpdg ynvyrsekhr lpvslssakq rqlyknrgfl plshflpmlp mapeepedlr
181 ghlesdmfss pletdsmdpf glvtgleavr spsfek
```

*Pongo abelii* (*Sumatran orangutan*) FGF19 (GenBank Accession No. XP_002821459, which is hereby incorporated by reference in its entirety) (SEQ ID NO: 93)

```
  1 mrsgcvvvha wilaglwlav agrplafsds gphvhygwgd pirlrhlyts gphglsscfl
 61 riradgvvdc argqsahsll eikavalrtv aikgvhsvry lcmgadgkmq gllqyseedc
```

TABLE 3-continued

```
121 afeeeirpdg ynvyrsekhr lpvslssakq rqlyknrgfl plshflpmlp mvpeepedlr
181 rhlesdmfss pletdsmdpf glvtgleavr spsfek
```

*Nomascus leucogenys* (Northern white-cheeked gibbon) FGF19 (Genbank Accession No. XP_003278071, which is hereby incorporated by reference in its entirety) (SEQ ID NO: 94)

```
  1 mrsecvvvha wilaglwlav agrplafsda gphvhygwgd pirlrhlyts gphglsscfl
 61 riradgvvdc argqsahsll eikavalrtv aikgvhsvry lcmgadgkmq gllqyseedc
121 afeeeirpdg ynvyrsekhr lpvslssakq rqlyknrgfl plshflpmlp mvpeepedlr
181 ghlesdmfss pletdsmdpf glvtgleavr spsfek
```

*Callithrix jacchus* (white-tufted-ear marmoset) FGF19 (GenBank Accession No. XP_002763730, which is hereby incorporated by reference in its entirety) (SEQ ID NO: 95)

```
  1 mwkataggqq gqseaqmstc phvprplwia qsclfslqlq yseedcafee eirpdgynvy
 61 wsekhrlpvs lssakqrqly kkrgflplsh flpmlpiape epedlrghle sdvfssplet
121 dsmdpfglvt gleavnspsf ek
```

*Microcebus murinus* (mouse lemur) FGF19 (Ensembl Accession No. ENSMICP00000002788, which is hereby incorporated by reference in its entirety) (SEQ ID NO: 96)

```
  1 MPSGQSGCVA ARALILAGLW LTAAGRPLAF SDAGPHVHYG WGEPIRLRHL YTAGPHGLSS
 61 CFLRIRADGS VDCARGQSAH SLLEIRAVAL RTVAIKGVHS VRYLCMGADG RMQGLLRYSE
121 EDCAFEEEIR PDGYNVYRSE KHRLPVSLSS ARQRQLYKGR GFLPLSHFLP MLPVTPAETG
181 DLRDHLESDM FASPLETDSM DPFGIATRLG VVKSPSFQK
```

*Choloepus hoffmanni* (sloth) FGF19 (Ensembl Accession No. ENSCHOP00000002044, which is hereby incorporated by reference in its entirety) (SEQ ID NO: 97) (partial amino acid sequence corresponding to human FGF19 residues 79 to 216)

```
  1 LLEMKAVALR AVAIKGVHSA LYLCMNADGS LHGLPRYSAE DCAFEEEIRP DGYNVYWSRK
 61 HGLPVSLSSA KQRQLYKGRG FLPLSHFLPM LPMTPAEPAD PGDDVESDMF SSPLETDSMD
121 PFGIASRLEL VNSPSFQT
```

*Ailuropoda melanoleuca* (giant panda) FGF19 (GenBank Accession No. XP_002927952, which is hereby incorporated by reference in its entirety) (SEQ ID NO: 98) (partial amino acid sequence corresponding to human FGF19 residues 12 to 216)

```
124    vlaglcl avagrplafs dagphvhygw gepirlrhly tagphglssc flriradggv
181 dcargqsahs lveiravalr tvaikgvhsv rylcmgadgr mqglpqysag dcafeeeirp
241 dgynvyrskk hrlpvslsga kqrqlykdrg flplshflpm lpgspaeprd lqdhaesdgf
301 sapletdsmd pfgiatkmgl vkspsfqk
```

*Sus scrofa* (pig) FGF19 (Ensembl Accession No. ENSSSCP00000013682, which is hereby incorporated by in its entirety) (SEQ ID NO: 99)

```
  1 MRSAPSRCAV VRALVLAGLW LAAAGRPLAF SDAGPHVHYG WGESVRLRHL YTASPHGVSS
 61 CFLRIHSDGP VDCAPGQSAH SLMEIRAVAL STVAIKGERS RYLCMGADGK MQGQTQYSDE
121 DCAFEEEIRP DGYNVYWSKK HHLPVSLSSA RQRQLYKGRG FLPLSHFLPM LSTLPAEPED
181 LQDPFKSDLF SLPLETDSMD PFRIAAKLGA VKSPSFYK
```

*Bos taurus* (bovine) FGF19 (GenBank Accession No. XP_599739, which is hereby incorporated by reference in its entirety) (SEQ ID NO: 100)

```
136                  mrsap srcavaralv laglwlaaag rplafsdagp hvhygwgesv
181 rlrhlytagp qglyscflri hsdgavdcaq vqsahslmei ravalstvai kgersvlylc
241 mdadgkmqgl tqysaedcaf eeeirpdgyn vywsrkhhlp vslsssrqrq lfksrgflpl
301 shflpmlsti paepedlqep lkpdfflplk tdsmdpfgla tklgsvksps fyn
```

*Canis lupus familiaris* (dog) FGF19 (GenBank Accession No. XP_540802, which is hereby incorporated by reference in its entirety) (SEQ ID NO: 101) (partial amino acid sequence corresponding to human FGF19 residues 25 to 216)

```
  1 LAFSDAGPHV HSFWGEPIRL RHLYTAGPHG LSSCFLRIRA DGGVDCARGQ SAHSLMEMRA
 61 VALRTVAIKG VHSGRYLCMG ADGRMQGLPQ YSAGDCTFEE EIRPDGYNVY WSKKHHLPIS
121 LSSAKQRQLY KGRGFLPLSH FLPILPGSPT EPRDLEDHVE SDGFSASLET DSMDPFGIAT
181 KIGLVKSPSF QK
```

TABLE 3-continued

*Oryctolagus cuniculus* (rabbit) FGF19 (GenBank Accession No. XP_002724495, which is hereby incorporated by reference in its entirety) (SEQ ID NO: 102)

```
  1 MRRAPSGGAA ARALVLAGLW LAAAARPLAL SDAGPHLHYG WGEPVRLRHL YATSAHGVSH
 61 CFLRIRADGA VDCERSQSAH SLLEIRAVAL RTVAFKGVHS SRYLCMGADG RMRGQLQYSE
121 EDCAFQEEIS SGYNVYRSTT HHLPVSLSSA KQRHLYKTRG FLPLSHFLPV LPLASEETAA
181 LGDHPEADLF SPPLETDSMD PFGMATKLGP VKSPSFQK
```

*Pteropus vampyrus* (megabat) FGF19 (Ensembl Accession No. ENSPVAP00000009339, which is hereby incorporated by reference in its entirety) (SEQ ID NO: 103)

```
  1 MRSPCAVARA LVLAGLWLAS AAGPLALSDA GPHVHYGWGE AIRLRHLYTA GPHGPSSCFL
 61 RIRADGAVDC ARGQSAHSLV EIRAVALRNV AIKGVHSVRY LCMGADGRML GLLQYSADDC
121 AFEEEIRPDG YNVYHSKKHH LPVSLSSAKQ RQLYKDRGFL PLSHFLPMLP RSPTEPENFE
181 DHLEADTFSS LETDDMDPFG IASKLGLEES PSFQK
```

*Tursiops truncatus* (dolphin) FGF19 (Ensembl Accession No. ENSTTRP00000000061, which is hereby incorporated by reference in its entirety) (SEQ ID NO: 104)

```
  1 MRSAPSRCAV ARALVLAGLW LAAAGRPLAF SDAGPHVHYG WGESVRLRHL YTAGPQGLSS
 61 CFLRIHSDGA VDCAPVQSAH SLMEIRAVAL STVAIKGERS VLYLCMGADG KMQGLSQYSA
121 EDCAFEEEIR PDGYNVYWSK KHHLPVSLSS ARQRQLFKGR GFLPLSHFLP MLSTIPTEPD
181 EIQDHLKPDL FALPLKTDSM DPFGLATKLG VVKSPSFYK
```

*Myotis lucifugus* (microbat) FGF19 (Ensembl Accession No. ENSMLUP00000002279, which is hereby incorporated by reference in its entirety) (SEQ ID NO: 105)

```
  1 MQSAWSRRVV ARALVLASLG LASAGGPLGL SDAGPHVHYG WGESIRLRHL YTSGPHGPSS
 61 CFLRIRADGA VDCARGQSAH SLVEIRAVAL RKVAIKGVHS ALYLCMGGDG RMLGLPQFSP
121 EDCAFEEEIR PDGYNVYRSQ KHQLPVSLSS ARQRQLFKAR GFLPLSHFLP MLPSSPAGPV
181 PRERPSEPDE FSSPLETDSM DPFGIANNLR LVRSPSFQE
```

*Ornithorhynchus anatinus* (platypus) FGF19 (GenBank Accession No. XP_001506714, which is hereby incorporated by reference in its entirety) (SEQ ID NO: 106) (partial amino acid sequence corresponding to human FGF19 residues 79 to 216)

```
  1 MLSCVVLPSL LEIKAVAVRT VAIKGVHISR YLCMEEDGKT PWARLLEIKA VAVRTVAIKG
 61 VHSSRYLCME EDGKLHGQIW YSAEDCAFEE EIRPDGYNVY KSKKYGVPVS LSSAKQRQQF
121 KGRDFLPLSR FLPMINTVPV EPAEFGDYAD YFESDIFSSP LETDSMDPFR IAPKLSPVKS
181 PSFQK
```

*Monodelphis domestica* (opossum) FGF19 (GenBank Accession No. XP_001373690, which is hereby incorporated by reference in its entirety) (SEQ ID NO: 107)

```
  1 MAQLLAPLLT LAALWLAPTA RARPLVDAGP HVYYGWGEPI RLRHLYTANR HGLASFSFLR
 61 IHRDGRVDGS RSQSALSLLE IKAVALRMVA IKGVHSSRYL CMGDAGKLQG SVRFSAEDCT
121 FEEQIRPDGY NVYQSPKYNL PVSLCTDKQR QQAHGKEHLP LSHFLPMINA IPLEAEEPEG
181 PRMLAAPLET DSMDPFGLTS KLLPVKSPSF QK
```

*Anolis carolinensis* (anole lizard) FGF19 (GenBank Accession No. XP_003214715, which is hereby incorporated by reference in its entirety) (SEQ ID NO: 108)

```
  1 MCRRALPLLG ALLGLAAVAS RALPLTDAGP HVSYGWGEPV RLRHLYTAGR QGLFSQFLRI
 61 HADGRVDGAG SQNRQSLLEI RAVSLRAVAL KGVHSSRYLC MEEDGRLRGM LRYSAEDCSF
121 EEEMRPDGYN IYKSKKYGVL VSLSNARQRQ QFKGKDFLPL SHFLPMINTV PVESADFGEY
181 GDTRQHYESD IFSSRLETDS MDPFGLTSEV SSVQSPSFGK
```

*Ochotona princeps* (pika) FGF19 (Ensembl Accession No. ENSOPRP00000009838, which is hereby incorporated by reference in its entirety) (SEQ ID NO: 109) (partial amino acid sequence corresponding to human FGF19 residues 12 to 77 and 113 to 216)

```
  1 VRSRGAMARA LVLATLWLAA TGRPLALSDA GPHLHYGWGE PIRLRHLYAT SAHGLSHCFL
 61 RIRTDGTVDC ERSQSAH--- ---------- ---------- ---------- --LQYSEEDC
121 AFEEEISSGY NVYRSRRYQL PVSLGSARQR QLQRSRGFLP LSHFLPVLPA ASEEVAAPAD
181 HPQADPFSPL ETDSMDPFGM ATKRGLVKSP SFQK
```

TABLE 3-continued

*Cavia porcellus* (guinea pig) FGF19 (Ensembl Accession No. ENSCPOP00000007325, which is hereby incorporated by reference in its entirety) (SEQ ID NO: 110)

```
  1 MWSAPSGCVV IRALVLAGLW LAVAGRPLAR RSLALSDQGP HLYYGWDQPI RLRHLYAAGP
 61 YGRSRCFLRI HTDGAVDCVE EQSEHCLLEI RAVALETVAI KDINSVRYLC MGPDGRMRGL
121 PWYSEEDCAF KEEISYPGYS VYRSQKHHLP IVLSSVKQRQ QYQSKGVVPL SYFLPMLPKA
181 SVEPSDEEES SVFSLPLKTD SMDPFGMASE IGLVKSPSFQ K
```

*Tupaia belangeri* (tree shrew) FGF19 (Ensembl Accession No. ENSTBEP00000000264, which is hereby incorporated by reference in its entirety) (SEQ ID NO: 111) (partial amino acid sequence corresponding to human FGF19 (residues 1 to 112 and 136 to 216)

```
  1 MRRTPSGFAV ARVLFLGSLW LAAAGSPLAL SDAGPHVNYG WDESIRLRHL YTASPHGSTS
 61 CFLRIRDDGS VDCARGQSLH SLLEIKAVAL QTVAIKGVYS VRYLCMDADG RMQGL-----
121 ---------- --------ST KHGLPVSLSS AKQRQLLTVR GFPSLPHFLL MMAKTSAGPG
181 NPRDHPGSNT FSLPLETDSM DPFGMTTRHG LVKSPSFQN
```

*Rattus norvegicus* (Norway rat) FGF15 (GenBank Accession No. NP_570109, which is hereby incorporated by reference in its entirety) (SEQ ID NO: 112)

```
  1 MARKWSGRIV ARALVLATLW LAVSGRPLVQ QSQSVSDEGP LFLYGWGKIT RLQYLYSAGP
 61 YVSNCFLRIR SDGSVDCEED QNERNLLEFR AVALKTIAIK DVSSVRYLCM SADGKIYGLI
121 RYSEEDCTFR EEMDCLGYNQ YRSMKHHLHI IFIKAKPREQ LQGQKPSNFI PIFHRSFFES
181 TDQLRSKMFS LPLESDSMDP FRMVEDVDHL VKSPSFQK
```

*Mus musculus* (house mouse) FGF15 (GenBank Accession No. NP_032029, which is hereby incorporated by reference in its entirety) (SEQ ID NO: 113)

```
  1 MARKWNGRAV ARALVLATLW LAVSGRPLAQ QSQSVSDEDP LFLYGWGKIT RLQYLYSAGP
 61 YVSNCFLRIR SDGSVDCEED QNERNLLEFR AVALKTIAIK DVSSVRYLCM SADGKIYGLI
121 RYSEEDCTFR EEMDCLGYNQ YRSMKHHLHI IFIQAKPREQ LQDQKPSNFI PVFHRSFFET
181 GDQLRSKMFS LPLESDSMDP FRMVEDVDHL VKSPSFQK
```

*Gallus gallus* (chicken) FGF19 (GenBank Accession No. NP_990005, which is hereby incorporated by reference in its entirety) (SEQ ID NO: 114)

```
  1 MGPARPAAPG AALALLGIAA AAAAARSLPL PDVGGPHVNY GWGEPIRLRH LLHRPGKHGL
 61 FSCFLRIGGD GRVDAVGSQS PQSLLEIRAV AVRTVAIKGV QSSRYLCMDE AGRLHGQLSY
121 SIEDCSFEEE IRPDGYNVYK SKKYGISVSL SSAKQRQQFK GKDFLPLSHF LPMINTVPVE
181 VTDFGEYGDY SQAFEPEVYS SPLETDSMDP FGITSKLSPV KSPSFQK
```

*Taeniopygia guttata* (zebra finch) FGF19 (GenBank Accession No. XP_002194493, which is hereby incorporated by reference in its entirety) (SEQ ID NO: 115)

```
  1 MVIISNLYLM QNDVMMNMRR APLRVHAARS SATPASALPL PPPDAGPHLK YGWGEPIRLR
 61 HLYTASKHGL FSCFLRIGAD GRVDAAGSQS PQSLLEIRAV AVRTVAIKGV QSSRYLCMDE
121 AGRLHGQLRN STEDCSFEEE IRPDGYNVYR SKKHGISVSL SSAKQRQQFK GKDFLPLSHF
181 LPMINTVPME SADFGEYGDY SQAFEAEAFS SPLETDSMDP FGIASKLSLV KSPSFQN
```

*Danio rerio* (zebrafish) FGF19 (GenBank Accession No. NP_001012246, which is hereby incorporated by reference in its entirety) (SEQ ID NO: 116)

```
  1 MLLLLFVTVC GSIGVESLPL PDSGPHLAND WSEAVRLRHL YAARHGLHLQ INTDGEIIGS
 61 TCKARTVSLM EIWPVDTGCV AIKGVASSRF LCMERLGNLY GSHIYTKEDC SFLERILPDG
121 YNVYFSSKHG ALVTLSGAKN KLHSNDGTSA SQFLPMINTL SEEHTKQHSG EQHSSVNHGQ
181 DHQLGLEIDS MDPFGKISQI VIQSPSFNKR
```

*Xenopus* (Silurana) *tropicalis* (western clawed frog) FGF19 (GenBank Accession No. NP_001136297, which is hereby incorporated by reference in its entirety) (SEQ ID NO: 117)

```
  1 MWKTLPWILV PMMVAVLYFL GGAESLPLFD AGPHMQNGWG ESIRIRHLYT ARRFGHDSYY
 61 LRIHEDGRVD GDRQQSMHSL LEIRAIAVGI VAIKGYRSSL YLCMGSEGKL YGMHSYSQDD
121 CSFEEELLPD GYNMYKSRKH GVAVSLSKEK QKQQYKGKGY LPLSHFLPVI SWVPMEPTGD
181 VEDDIYRFPF NTDTKSVIDS LDTLGLMDFS SYHKK
```

Amino acid sequence of *Otolemur garnettii* (bushbaby) FGF19 (Ensembl Accession No. ENSOGAP00000017975, which is hereby incorporated by reference in its entirety) (SEQ ID NO: 118)

```
  1 MPSGLRGRVV AGALALASFW LAVAGRPLAF SDAGPHVHYG WGEPIRLRHL YTAGPHGLSS
 61 CFLRVRTDGA VDCARGQSAH SLLEIRAVAL RTVAIKGVHS ARYLCMGADG RMQGLPQYSE
```

TABLE 3-continued

121 EDCAFEEEIR PDGYNVYWSE KHRLPVSLSS ARQRQLYKGR GFLPLSHFLP MLPVTPAEPG
181 DLRDHLESDM FSLPLETDSM DPFGIATRLG VVKSPSFQK

Amino acid sequence of *Felis catus* (cat) FGF19 (Ensembl Accession No. ENSFCAP00000022548, which is hereby incorporated by reference in its entirety) (SEQ ID NO: 119)

1 MRSAPSQCAV TRALVLAGLW LAAAGRPLAF SDAGPHVHYG WGEPIRLRHL YTAGPHGLSS
61 CFLRIRADGG VDCARSQSAH SLVEIRAVAL RTVAIKGVHS VRYLCMGADG RMQGLLQYSA
121 GDCAFQEEIR PDGYNVYRSE KHRLPVSLSS AIQRQLYKGR GFLPLSHFLP MLPGSPAEPR
181 DLQDHVESER FSSPLETDSM DPFGIATKMG LVKSPSFQK

Amino acid sequence of *Pelodiscus sinensis* (Chinese softshell turtle) FGF19 (Ensembl Accession No. ENSPSIP00000010374, which is hereby incorporated by reference in its entirety) (SEQ ID NO: 120)

1 MWRSLCKSHT SLALLGLCFA VVVRSLPFSD AGPHVNYGWG EPIRLRHLYT ASRHGLFNYF
61 LRISSDGKVD GTSIQSPHSL LEIRAVAVRT VAIKGVHSSR YLCMEEDGKL HGLLRYSTED
121 CSFEEEIRPD GYNVYKSKKY GISVSLSSAK QRQQFKGKDF LPLSHFLPMI NTVPVESMDF
181 GEYGDYSHTF ESDLFSSPLE TDSMDPFGIT SKISPVKSPS FQK

Amino acid sequence of *Latimeria chalumnae* (Coelacanth) FGF19 (Ensembl Accession No. ENSLACP00000014596, which is hereby incorporated by reference in its entirety) (SEQ ID NO: 121)

1 MLQALYNLCT ALVLFKLPFA MVGYTLPSAN EGPHLNYDWG ESVRLKHLYT SSKHGLISYF
61 LQINDDGKVD GTTTRSCYSL LEIKSVGPGV LAIKGIQSSR YLCVEKDGKL HGSRTYSADD
121 CSFKEDILPD GYTIYVSKKH GSVVNLSNHK QKRQRNRRTL PPFSQFLPLM DTIRVECMNC
181 GEHCDDNLHD ELETGLSMDP FESTSKKSFQ SPSFHNR

Amino acid sequence of *Mustela putorius* furo (Ferret) FGF19 (Ensembl Accession No. ENSMPUP00000004571, which is hereby incorporated by reference in its entirety) (SEQ ID NO: 122)

1 MRSAASRCAV ARALVLAGLW LAAAGRPLAF SDAGPHVHYG WGEPIRLRHL YTAGPHGLSS
61 CFLRIRADGG VDCARGQSAH SLVEIRAVAL RTVAIKGVYS DRYLCMGADG RMQGLPQYSA
121 GDCAFEEEIR PDGYNVYRSK KHRLPVSLSS AKQRQLYKDR GFLPLSHFLP MLPGSLAEPR
181 DLQDHVEADG FSAPLETDSM DPFGIATKMG LVKSPSFQK

Amino acid sequence of *Takifugu rubripes* (Fugu) FGF19 (Ensembl Accession No. ENSTRUP00000007110, which is hereby incorporated by reference in its entirety) (SEQ ID NO: 123)

1 SSTRISGNMV LLMLPITVAN LFLCAGVLSL PLLDQGSHFP QGWEQVVRFR HLYAASAGLH
61 LLITEEGSIQ GSADPTLYSL MEIRPVDPGC VVIRGAATTR FLCIEGAGRL YSSQTYSKDD
121 CTFREQILAD GYSVYRSVGH GALVSLGNYR QQLRGEDWSV PTLAQFLPRI SSLDQDFKAA
181 LDETEKPEQT APQRSEPVDM VDSFGKLSQI IHSPSFHK

Amino acid sequence of *Equus caballus* (Horse) FGF19 (Ensembl Accession No. ENSECAP00000017705, which is hereby incorporated by reference in its entirety) (SEQ ID NO: 124) (partial sequence corresponding to human FGF19 residues 20 to 113)

1 AAGRPLALSD AGPHVHYGWG EPIRLRHLYT AGPHGLSSCF LRIRADGAVD CARGQSAHSL
61 VEIRAVALRT VAIKGVHSVR YLCMGADGRM QGLV

Amino acid sequence of *Oryzias latipes* (Medaka) FGF19 (Ensembl Accession No. ENSORLP00000000352, which is hereby incorporated by reference in its entirety) (SEQ ID NO: 125)

1 TMLLIVVTIS TMVFSDSGVS SMPLSDHGPH ITHSWSQVVR LRHLYAVKPG QHVQIREDGH
61 IHGSAEQTLN SLLEIRPVAP GRVVFRGVAT SRFLCMESDG RLFSSHTFDK DNCVFREQIL
121 ADGYNIYISD QHGTLLSLGN HRQRQQGLDR DVPALAQFLP RISTLQQGVY PVPDPPHQMR
181 TMQTEKTLDA TDTFGQLSKI IHSPSFNKR

Amino acid sequence of *Xiphophorus maculatus* (Platyfish) FGF19 (Ensembl Accession No. ENSXMAP00000001516, which is hereby incorporated by reference in its entirety) (SEQ ID NO: 126)

1 MFVFILCIAG ELFTLGVFCM PMMDQGPLVT HGWGQVVRHR HLYAAKPGLH LLISEDGQIH
61 GSADQTLYSL LEIQPVGPGR VVIKGVATTR FLCMESDGRL YSTETYSRAD CTFREQIQAD
121 GYNVYTSDSH GALLSLGNNQ QRHSGSDRGV PALARFLPRL NTLQQAVPTE PDVPDQLSPE
181 KVQQTVDMVA SFGKLSHIIH SPSFHKR

Amino acid sequence of *Ictidomys tridecemlineatus* (Squirrel) FGF19 (Ensembl Accession No. ENSSTOP00000021639, which is hereby incorporated by reference in its entirety) (SEQ ID NO: 127)

1 MRSAPSGRAL ARALVLASLW LAVAGRPLAR RSLALSDQGP HLYYGWDQPI RLRHLYAAGP
61 YGFSNCFLRI RTDGAVDCEE KQSERSLMEI RAVALETVAI KDINSVRYLC MGADGRIQGL

TABLE 3-continued

| |
|---|
| 121PRYSEEECTF KEEISYDGYN VYRSQKYHLP VVLSSAKQRQ LYQSKGVVPL SYFLPMLPLA<br>181SAETRDRLES DVFSLPLETD SMDPFGMASE VGLKSPSFQK |
| Amino acid sequence of *Gasterosteus aculeatus* (Stickleback) FGF19 (Ensembl Accession No. ENSGACP00000018732, which is hereby by reference in its entirety) (SEQ ID NO: 128) |
| 1MLLLLVPAYV ASVFLALGVV CLPLTDQGLH MADDWGQSVR LKHLYAASPG LHLLIGEDGR<br>61IQGSAQQSPY SLLEISAVDP GCVVIRGVAT ARFLCIEGDG RLYSSDTYSR DDCTFREQIL<br>121PDGYSVYVSH GHGALLSLGN HRQRLQGRDH GVPALAQFLP RVSTMDQASA PDAPGQTATE<br>181TEEPVDSFGK LSQIIHSPSF HER |
| Amino acid sequence of *Oreochromis niloticus* (Tilapia) FGF19 (Ensembl Accession No. ENSONIP00000022796, which is hereby incorporated by reference in its entirety) (SEQ ID NO: 129) |
| 1MLLLLIVSIV NMLFGVGMVC MPLSDNGPHI AHGWAQVVRL RHLYATRPGM HLLISEGGQI<br>61RGSAVQTLHS LMEIRPVGPG RVVIRGVATA RFLCIEDDGT LYSSHAYSRE DCIFREQILP<br>121DGYNIYISDR HGVLLSLGNH RQRLQGLDRG DPALAQFLPR ISTLNQIPSP GANIGDHMKV<br>181AKTEEPVDTI DSFGKFSQII DSPSFHKR |
| Amino acid sequence of *Meleagris gallopavo* (Turkey) FGF19 (Ensembl Accession No. ENSMGAP00000010265, which is hereby incorporated by reference in its entirety) (SEQ ID NO: 130) (partial sequence corresponding to human FGF19 residues 71 to 216) |
| 1VGNQSPQSIL EITAVDVGIV AIKGLFSGRY LAMNKRGRLY ASLSYSIEDC SFEEEIRPDG<br>61YNVYKSKKYG ISVSLSSAKQ RQQFKGKDFL PLSHFLPMIN TVPVEVTDFG EYGDYSQAFE<br>121PEVYSSPLET DSMDPFGITS KLSPVKSPSF QK |

In one embodiment, a C-terminal portion from FGF19 of the chimeric protein of the present invention comprises the conserved amino acid sequence TGLEAV(R/N)SPSFEK (SEQ ID NO: 131). In another embodiment, a C-terminal portion from FGF19 comprises the conserved amino acid sequence MDPFGLVTGLEAV (R/N)SPSFEK (SEQ ID NO: 132). In yet another embodiment, the C-terminal portion from FGF19 of the chimeric protein of the present invention comprises the conserved amino acid sequence LP(M/I)(V/A)PEEPEDLR(G/R)HLESD(MN)FSS-PLETDSMDPFGLVTGLEAV(R/N)SPSFEK (SEQ ID NO: 133).

In yet another embodiment, the C-terminal portion from FGF19 of the chimeric protein of the present invention consists of an amino acid sequence selected from the group consisting of TGLEAV(R/N)SPSFEK (SEQ ID NO: 131); MDPFGLVTGLEAV(R/N)SPSFEK (SEQ ID NO: 132); and LP(M/I)(V/A)PEEPEDLR(G/R)HLESD(MN)FSS-PLETDSMDPFGLVTGLEAV(R/N)SPSFEK (SEQ ID NO: 133).

In certain embodiments according to the present invention, the C-terminal portion from FGF19 of the chimeric protein of the present invention includes a polypeptide sequence that has at least 80%, at least 85%, at least 90%, at least 95%, at least 97%, or at least 99% amino acid sequence identity to the amino acid sequences of SEQ ID NO: 89, TGLEAV(R/N)SPSFEK (SEQ ID NO: 131); MDP-FGLVTGLEAV (R/N)SPSFEK (SEQ ID NO: 132); and/or LP(M/I)(V/A)PEEPEDLR(G/R)HLESD(MN)FSS-PLETDSMDPFGLVTGLEAV(R/N)SPSFEK (SEQ ID NO: 133). In one embodiment, the C-terminal portion from the FGF19 molecule comprises an amino acid sequence that has at least 80%, at least 85%, at least 90%, at least 95%, at least 97% or at least 99% amino acid sequence identity to an amino acid sequence spanning residues (or those corresponding to residues) selected from the group consisting of from position 204 to 216 of SEQ ID NO: 89, position 197 to 216 of SEQ ID NO: 89, position 174 to 216 of SEQ ID NO: 89, and position 169 to 216 of SEQ ID NO: 89.

It will be understood that the portion from FGF19 of the chimeric protein of the present invention may be from a nucleotide sequence that encodes an FGF19 protein (e.g., those encoding orthologs) from a mammal or even a non-mammalian species. For example, a nucleotide sequence encoding a mammalian or non-mammalian FGF19 protein according to the present invention may include, but is not limited to, those FGF-encoding nucleotide sequences in Table 4.

TABLE 4

| |
|---|
| Human FGF19 gene coding sequence (SEQ ID NO: 134) (GenBank Accession No. NM_005117, which is hereby incorporated by reference in its entirety) |
| 464 atgcgga gcgggtgtgt ggtggtccac gtatggatcc tggccggcct ctggctggcc<br>521 gtggccgggc gcccccctcgc cttctcggac gcggggcccc acgtgcacta cggctggggc<br>581 gaccccatcc gcctgcggca cctgtacacc tccggccccc acgggctctc cagctgcttc<br>641 ctgcgcatcc gtgccgacgg cgtcgtggac tgcgcgcggg gccagagcgc gcacagtttg<br>701 ctggagatca aggcagtcgc tctgcggacc gtggccatca agggcgtgca cagcgtgcgg<br>761 tacctctgca tgggcgccga cggcaagatg caggggctgc ttcagtactc ggaggaagac<br>821 tgtgctttcg aggaggagat ccgcccagat ggctacaatg tgtaccgatc cgagaagcac<br>881 cgcctcccgg tctccctgag cagtgccaaa cagcggcagc tgtacaagaa cagaggcttt<br>941 cttccactct ctcatttcct gcccatgctg cccatggtcc cagaggagcc tgaggacctc<br>1001 aggggccact tggaatctga catgttctct tcgcccctgg agaccgacag catggaccca<br>1061 tttgggcttg tcaccggact ggaggccgtg aggagtccca gctttgagaa gtaa |

TABLE 4-continued

*Gorilla gorilla* (*gorilla*) FGF19 gene coding sequence (SEQ ID NO: 135) (Ensembl Accession No. ENSGGOT00000028361, which is hereby incorporated by reference in its entirety)

463 ATGCGGAG CGGGTGTGTG GTGGTCCACG TCTGGATCCT GGCCGGCCTC TGGCTGGCCG
521 TGGCCGGGCG CCCCCTCGCC TTCTCGGACG CGGGGCCCCA CGTGCACTAC GGCTGGGGCG
581 ACCCCATCCG CCTGCGGCAC CTGTACACCT CCGGCCCCCA CGGGCTCTCC AGCTGCTTCC
641 TGCGCATCCG TGCCGACGGC GTCGTGGACT GCGCGCGGGG CCAGAGCGCG CACAGTTTGC
701 TGGAGATCAA GGCAGTCGCT CTGCGGACCG TGGCCATCAA GGGCGTGCAC AGCGTGCGGT
761 ACCTCTGCAT GGGCGCCGAC GGCAAGATGC AGGGGCTGCT TCAGTACTCG GAGGAAGACT
821 GTGCTTTCGA GGAGGAGATC CGCCCAGATG GCTACAATGT GTACCGATCT GAGAAGCACC
881 GCCTCCCGGT CTCCCTGAGC AGTGCCAAAC AGCGGCAGCT GTACAAGAAC AGAGGCTTTC
941 TTCCGCTCTC TCATTTCCTG CCCATGCTGC CCATGGTCCC AGAGGAGCCT GAGGACCTCA
1001 GGGGCCACTT GGAATCTGAC ATGTTCTCTT CACCCCTGGA GACCGACAGC ATGGACCCAT
1061 TTGGGCTTGT CACCGGACTG GAGGCCGTGA GGAGTCCTAG CTTTGAGAAG TAA

*Pan troglodytes* (chimpanzee) FGF19 gene coding sequence (SEQ ID NO: 136) (Ensembl Accession No. ENSPTRT00000007454, which is hereby incorporated by reference in its entirety)

1 ATGCGGAACG GGTGTGTGGT GGTCCACGTC TGGATCCTGG CCGGCCTCTG GCTGGCCGTG
61 GCCGGGCGCC CCCTCGCCTT CTCGGACGCG GGGCGCCACG TGCACTACTG CTGGGGCGAC
121 CCCATCCCCC TGCGGCACCT GTACACCTCC GGCCCCCATG GGCTCTCCAG CTGCTTCCTG
181 CGCATCCCTG CGAACTGCGT CATGAACTGC GCGCGGGGCC AGAGCGCGCA CAGTTTGCTG
241 GAGATCAAGG CAGTCGCTCT GCGGACCGTG GCCATCAAGG GCGTGCACAG CGTGCGGTAC
301 CTCTGCATGG GCGCCGACGG CAAGATGCAG GGGCTGCTTC AGTACTCGGA GGAAGACTGT
361 GCTTTCGAGG AGGAGATCCG CCCAGATGGC TACAATGTGT ACCGATCCGA GAAGCACCGC
421 CTCCCGGTCT CCCTGAGCAG TGCCAAACAG CGGCAGCTGT ACAAGAACAG AGGCTTTCTT
481 CCACTCTCTC ATTTCCTGCC CATGCTGCCC ATGGTCCCAG AGGAGCCTGA GGACCTCAGG
541 GGCCACTTGG AATCTGACAT GTTCTCTTCG CCCCTGGAGA CCGACAGCAT GGACCCATTT
601 GGGCTTGTCA CCGGACTGGA GGCCGTGAGG AGTCCCAGCT TTGAGAAGTA A

*Macaca mulatta* (Rhesus monkey) FGF19 gene coding sequence (SEQ ID NO: 137) (GenBank Accession No. XM_001100825, which is hereby incorporated by reference in its entirety)

758 atg aggagcgggt gtgtggtggt ccacgcctgg atcctggcca gcctctggct
811 ggccgtggcc gggcgtcccc tcgccttctc ggacgcgggg ccccacgtgc actacggctg
871 gggcgacccc atccgcctgc ggcacctgta cacctccggc ccccatgggc tctccagctg
931 cttcctgcgc atccgcaccg acggcgtcgt ggactgcgcg cggggccaaa gcgcgcacag
991 tttgctggag atcaaggcag tagctctgcg gaccgtggcc atcaagggcg tgcacagcgt
1051 gcggtacctc tgcatgggcg ccgacggcaa gatgcagggg ctgcttcagt actcagagga
1111 agactgtgct ttcgaggagg agatccgccc tgatggctac aatgtatacc gatccgagaa
1171 gcaccgcctc ccggtctctc tgagcagtgc caaacagagg cagctgtaca agaacagagg
1231 ctttcttccg ctctctcatt tcctacccat gctgcccatg gccccagagg agcctgagga
1291 cctcaggggc cacttggaat ctgacatgtt ctcttcgccc ctggagactg acagcatgga
1351 cccatttggg cttgtcaccg gactggaggc ggtgaggagt cccagctttg agaaataa

*Pongo abelii* (*Sumatran orangutan*) FGF19 gene coding sequence (SEQ ID NO: 138) (GenBank Accession No. XM_002821413, which is hereby incorporated by reference in its entirety)

763 atgcggag cgggtgtgtg gtggtccacg cctggatcct ggccggcctc tggctggccg
821 tggccgggcg cccccctcgcc ttctcggact cggggcccca cgtgcactac ggctggggcg
881 accccatccg cctgcggcac ctgtacacct ccggccccca cgggctctcc agctgcttcc
941 tgcgcatccg tgccgacggc gtcgtggact gcgcgcgggg ccagagcgcg cacagtttgc
1001 tggagatcaa ggcagtcgct ctgcggaccg tggccatcaa gggcgtgcac agcgtgcggt
1061 acctctgcat gggcgccgac ggcaagatgc aggggctgct tcagtactcg gaggaagact
1121 gtgctttcga ggaggagatc cgcccagatg gctacaatgt gtaccgatcc gagaagcacc
1181 gcctcccggt ctccctgagc agtgccaaac agcggcagct gtacaagaac aggggctttc
1241 ttccgctctc tcatttcctg cccatgctgc ccatggtccc agaggagcct gaggacctca
1301 ggcgccactt ggaatccgac atgttctctt cgcccctgga gaccgacagc atggacccat
1361 ttgggcttgt caccggactg gaggccgtga ggagtcccag ctttgagaaa taa

*Nomascus leucogenys* (Northern white-cheeked gibbon) FGF19 gene coding sequence (SEQ ID NO: 139) (Genbank Accession No. XM_003278023, which is hereby incorporated by reference in its entirety)

456 atgcg gagcgagtgt gtggtggtcc acgcctggat cctggccggc ctctggctgg
511 cagtggccgg gcgcccctc gccttttcgg acgcggggcc ccacgtgcac tacggctggg
571 gcgaccccat ccgtctgcgg cacctgtaca cctccggccc ccacgggctc tccagctgct
631 tcctgcgcat ccgtgccgac ggcgtcgtgg actgcgcgcg gggccagagc gcgcacagtt
691 tgctggagat caaggcagtc gctctgcgga ccgtggccat aaagggcgtg cacagcgtgc
751 ggtacctctg catgggcgcc gacggcaaga tgcaggggct gcttcagtat tcggaggaag
811 actgtgcttt cgaggaggag atccgcccag atggctacaa tgtgtaccga tccgagaagc
871 accgcctccc cgtctccctg agcagtgcca aacagcggca gctgtataag aacagaggct
931 ttcttccact ctctcatttc ctgcccatgc tgcccatggt cccagaggag cctgaggacc TABLE 4-continued

| | |
|---|---|
| 991 | tcaggggcca cttggaatct gacatgttct cttcgcccct ggagaccgac agcatggacc |
| 1051 | catttgggct tgtcaccgga ctggaggccg tgaggagtcc cagctttgag aaataa |

*Callithrix jacchus* (white-tufted-ear marmoset) FGF19 gene coding sequence (SEQ ID NO: 140) (GenBank Accession No. XM_002763684, which is hereby incorporated by reference in its entirety)

| | |
|---|---|
| 1 | atgtggaagg ccaccgctgg tggccagcag ggacagtccg aagcacaaat gtccacatgt |
| 61 | ccccatgttc ctcgtcctct gtggattgct cagagctgcc tgtttctct gcagctccag |
| 121 | tactcggagg aagactgtgc tttcgaggag gagatccgcc ctgatggcta caatgtgtac |
| 181 | tggtccgaga agcaccgcct cccggtctcc ctgagcagcg ccaaacagcg gcagctgtac |
| 241 | aagaaacgag gctttcttcc actgtcccat ttcctgccca tgctgcccat agccccagaa |
| 301 | gagcctgagg acctcagggg acacctggaa tctgacgtgt tctcttcacc cctggagact |
| 361 | gacagcatgg acccatttgg gcttgtcacg ggactggagg cggtgaacag tcccagcttt |
| 421 | gagaagtaa |

*Microcebus murinus* (mouse lemur) FGF19 gene coding sequence (SEQ ID NO: 141) (Ensembl Accession No. ENSMICT00000003065, which is hereby incorporated by reference in its entirety)

| | |
|---|---|
| 1 | ATGCCGAGCG GGCAAAGCGG TTGTGTGGCG GCCCGCGCCC TGATCCTGGC CGGCCTCTGG |
| 61 | CTGACCGCGG CCGGGCGCCC GCTGGCCTTC TCCGACGCGG GCCCGCACGT GCACTACGGC |
| 121 | TGGGGCGAGC CCATCCGCCT GCGGCACCTG TACACCGCCG GCCCCCACGG CCTCTCCAGC |
| 181 | TGCTTCCTGC GCATCCGCGC AGACGGCTCC GTGGACTGCG CGCGGGGCCA GAGCGCACAC |
| 241 | AGTTTGCTGG AGATCAGGGC GGTCGCTCTT CGGACTGTGG CCATCAAGGG CGTGCACAGC |
| 301 | GTGCGGTACC TCTGCATGGG CGCAGACGGC AGGATGCAGG GGCTGCTCCG GTACTCGGAG |
| 361 | GAAGACTGTG CCTTCGAGGA GGAGATCCGC CCCGATGGCT ACAACGTGTA CCGGTCTGAG |
| 421 | AAGCACCGCC TGCCGGTGTC TCTGAGCAGC GCCAGGCAGA GGCAGCTGTA CAAGGGCAGG |
| 481 | GGCTTCCTGC CGCTCTCTCA CTTCCTGCCC ATGCTGCCCG TGACCCCGGC AGAGACCGGG |
| 541 | GACCTCAGGG ACCACTTGGA GTCCGACATG TTCGCTTCGC CCCTGGAGAC CGACAGCATG |
| 601 | GACCCGTTTG GGATCGCCAC CAGACTTGGG GTGGTGAAGA GTCCCAGCTT TCAGAAATGA |

*Choloepus hoffmanni* (sloth) FGF19 gene coding sequence (SEQ ID NO: 142) (Ensembl Accession No. ENSCHOT00000002324, which is hereby incorporated by reference in its entirety)

| | |
|---|---|
| 1 | TTGCTCGAAA TGAAGGCAGT GGCGCTGCGG GCCGTGGCCA TCAAGGGCGT GCACAGTGCT |
| 61 | CTGTACCTCT GCATGAACGC CGACGGCAGT CTGCACGGGC TGCCTCGGTA CTCTGCAGAA |
| 121 | GACTGTGCTT TTGAGGAGGA AATCCGCCCC GACGGCTACA ATGTGTACTG GTCTAGGAAG |
| 181 | CACGGCCTCC CTGTCTCTTT GAGCAGTGCA AAACAGAGGC AGCTGTACAA AGGCAGAGGC |
| 241 | TTTCTGCCCC TGTCCCACTT CCTGCCCATG CTGCCCATGA CGCCGGCCGA GCCCGCAGAC |
| 301 | CCCGGGGATG ACGTGGAGTC GGACATGTTC TCTTCACCTC TGGAAACCGA CAGCATGGAT |
| 361 | CCTTTTGGAA TTGCCTCCAG ACTTGAGCTT GTGAACAGTC CAGCTTTCAG CATAA |

*Ailuropoda melanoleuca* (giant panda) FGF19 gene coding sequence (SEQ ID NO: 143) (GenBank Accession No. XM_002927906, which is hereby incorporated by reference in its entirety)

| | |
|---|---|
| 69 | gg tcctagccgg cctctgcctg gcggtagccg ggcgcccccct agccttctcg |
| 421 | gacgcggggc cgcacgtgca ctacggctgg ggtgagccca tccgcctacg gcacctgtac |
| 481 | accgccggcc cccacggcct ctccagctgc ttcctgcgca tccgtgccga cggcggggtt |
| 541 | gactgcgcgc ggggccagag cgcgcacagt ttggtggaga tcagggcagt cgctctgcgg |
| 601 | accgtggcca tcaagggtgt gcacagcgtc cggtacctct gcatgggcgc ggacggcagg |
| 661 | atgcaagggc tgcctcagta ctctgcaggg gactgtgctt tcgaggagga gatccgcccc |
| 721 | gacggctaca atgtgtaccg gtccaagaag caccgtctcc ccgtctctct gagcggtgcc |
| 781 | aaacagaggc agctttacaa agacagaggc tttctgcccc tgtcccactt cttgcccatg |
| 841 | ctgcccggga gcccagcaga gcccagggac ctccaggacc atgcggagtc ggacgggttt |
| 901 | tctgcacccc tagaaacaga cagcatggac ccttttggga tcgccaccaa aatgggacta |
| 961 | gtgaagagtc ccagcttcca gaaataa |

*Sus scrofa* (pig) FGF19 gene coding sequence (SEQ ID NO: 144) (Ensembl Accession No. ENSSSCT00000014068, which is hereby incorporated by reference in its entirety)

| | |
|---|---|
| 1 | ATGCGGAGCG CTCCGAGCCG GTGCGCGGTG GTCCGCGCCC TGGTCCTGGC CGGCCTCTGG |
| 61 | CTGGCCGCAG CCGGGCGCCC CCTAGCCTTC TCGGATGCTG GGCCGCACGT GCACTACGGC |
| 121 | TGGGGCGAGT CGGTCCGCCT GCGGCACCTG TACACTGCGA GTCCCCACGG CGTCTCCAGC |
| 181 | TGCTTCCTGC GCATCCACTC AGACGGCCCC GTGGACTGCG CGCCGGGACA GAGCGCGCAC |
| 241 | AGTTTGATGG AGATCAGGGC AGTCGCGCTG AGTACCGTGG CGATCAAGGG CGAGCGCAGC |
| 301 | GGCCGTTACC TCTGCATGGG CGCCGACGGC AAGATGCAAG GGCAGACTCA GTACTCGGAT |
| 361 | GAGGACTGTG CTTTCGAGGA GGAGATCCGC CCTGATGGCT ACAACGTGTA CTGGTCCAAG |
| 421 | AAACACCATC TGCCCGTCTC TCTGAGCAGC GCCAGGCAGA GGCAGCTGTA CAAAGGCAGG |
| 481 | GGCTTCCTGC CGCTGTCCCA CTTTCTGCCC ATGCTGTCCA CTCTCCCAGC CGAGCCGGAG |
| 541 | GACCTCCAGG ACCCCTTCAA GTCCGACCTG TTTTCTTTGC CCCTGGAAAC GGACAGCATG |
| 601 | GACCCTTTCC GGATCGCCGC CAAACTGGGA GCGGTGAAGA GTCCCAGCTT CTATAAATAA |

TABLE 4-continued

*Bos taurus* (bovine) FGF19 gene coding sequence (SEQ ID NO: 145) (GenBank Accession No. XM_599739, which is hereby incorporated by reference in its entirety)

```
406                                                        atgcg gagcgctccg
421 agccggtgcg ccgtggcccg cgccctggtc ctggctggcc tctggctggc cgcagccggg
481 cgccccctgg ccttctcgga tgcggggccg cacgtgcact acggctgggg cgagtcggtt
541 cgcttgcggc acctgtatac cgcgggcccg cagggcctct acagctgctt tctgcgcatc
601 cactccgacg gcgccgtgga ctgcgcgcag gtccagagcg cgcacagttt gatggagatc
661 agggcggtcg ctctgagcac cgtagccatc aagggcgagc gcagcgtgct gtacctctgc
721 atggacgccg acggcaagat gcaaggactg acccagtact cagccgagga ctgtgctttc
781 gaggaggaga tccgtcctga cggctacaac gtgtactggt ccaggaagca ccatctcccg
841 gtctccctga gcagctccag gcagaggcag ctgttcaaaa gcaggggctt cctgccgctg
901 tctcacttcc tgcccatgct gtccaccatc ccagccgaac ctgaagacct ccaggaaccc
961 ctgaagcctg atttctttct gcccctgaaa acagatagca tggacccttt cgggctcgcc
1021 accaaactgg gatcggtgaa gagtcccagc ttctataatt aa
```

*Canis lupus familiaris* (dog) FGF19 gene coding sequence (SEQ ID NO: 146) (GenBank Accession No. XM_540802, which is hereby incorporated by reference in its entirety)

```
  1 ctagccttct ccgacgcggg gccgcacgtg cactccttct ggggggagcc catccgcctg
 61 cggcacctgt acaccgccgg cccccacggc ctctccagct gcttcctgcg catccgcgcc
121 gacggcgggg tggactgcgc gcggggccag agcgcgcaca gtctgatgga gatgagggcg
181 gtcgctctgc ggaccgtggc catcaagggc gtgcacagcg gccggtacct ctgcatgggc
241 gccgacggca ggatgcaagg gctgcctcag tactccgccg gagactgtac tttcgaggag
301 gagatccgtc ccgatggcta caatgtgtac tggtccaaga agcaccatct ccccatctct
361 ctgagtagtg ccaaacagag gcagctctac aagggcaggg gctttttgcc cctgtcccac
421 ttcttaccta tcttgcccgg gagcccaaca gagcccaggg acctggaaga ccatgtggag
481 tctgacgggt tttctgcatc cctggaaaca gacagcatgg acccttttgg gatcgccacc
541 aaaattggac tagtgaagag tcccagtttc caaaaataa
```

*Oryctolagus cuniculus* (rabbit) FGF19 gene coding sequence (SEQ ID NO: 147) (GenBank Accession No. XM_002724449, which is hereby incorporated by reference in its entirety)

```
  1 atgcgccgcg cgccgagcgg aggtgccgcg gcccgcgcct tggtcctggc cggcctctgg
 61 ctggccgcgg ccgcgcgccc cttggccttg tccgacgcgg gcccgcatct gcactacggc
121 tggggcgagc ccgtccgcct gcggcacctg tacgccacca gcgcccacgg cgtctcgcac
181 tgcttcctgc gtatacgcgc cgacggcgcc gtggactgcg agcggagcca gagcgcacac
241 agcttgctgg agatccgagc ggtcgccctg cgcaccgtgg ccttcaaggg cgtgcacagc
301 tcccgctacc tctgcatggg cgccgacggc aggatgcggg ggcagctgca gtactcggag
361 gaggactgtg ccttccagga ggagatcagc tccggctaca acgtgtaccg ctccacgacg
421 caccacctgc ccgtgtctct gagcagtgcc aagcagagac acctgtacaa gaccagaggc
481 ttcctgcccc tctcccactt cctgcccgtg ctgcccctgg cctccgagga gaccgcggcc
541 ctcggcgacc accctgaagc cgacctgttc tccccgcccc tggaaaccga cagcatggac
601 cccttcggca tggccaccaa gctcgggccg gtgaagagcc ccagctttca gaagtag
```

*Pteropus vampyrus* (megabat) FGF19 gene coding sequence (SEQ ID NO: 148) (Ensembl Accession No. ENSPVAT00000009907, which is hereby incorporated by reference in its entirety)

```
  1 ATGCGGAGCC CGTGCGCTGT GGCCCGCGCC TTGGTCCTGG CCGGCCTCTG GCTGGCCTCA
 61 GCTGCGGGCC CCCTCGCCCT CTCGGACGCG GGGCCGCACG TGCACTACGG CTGGGGCGAG
121 GCCATCCGCC TGCGGCACCT GTACACCGCC GGCCCCCACG GCCCCTCCAG CTGCTTCCTG
181 CGCATCCGCG CGGATGGGGC GGTGGACTGC GCGCGGGGCC AGAGCGCGCA CAGTTTGGTG
241 GAAATCCGGG CTGTCGCCCT GCGGAACGTG GCTATCAAGG GCGTGCACAG CGTCCGATAC
301 CTCTGCATGG GAGCCGACGG CAGGATGCTA GGGCTGCTTC AGTACTCCGC TGACGACTGC
361 GCCTTCGAGG AGGAGATCCG CCCGGACGGC TACAACGTGT ACCACTCCAA GAAGCACCAC
421 CTCCCGGTCT CTCTGAGCAG TGCCAAGCAG AGGCAACTGT ACAAGGACAG GGGCTTCCTG
481 CCCCTGTCCC ATTTCCTGCC CATGCTGCCC AGGAGCCCGA CAGAGCCCGA GAACTTCGAA
541 GACCACTTGG AGGCCGACAC GTTTTCCTCG CCCCTGGAGA CAGACGACAT GGACCCTTTT
601 GGGATTGCCA GTAAATTGGG GCTGGAGGAA AGTCCCAGCT TCCAGAAGTA A
```

*Tursiops truncatus* (dolphin) FGF19 gene coding sequence (SEQ ID NO: 149) (Ensembl Accession No. ENSTTRT00000000066, which is hereby incorporated by reference in its entirety)

```
  1 ATGCGGAGCG CTCCGAGCCG GTGCGCCGTG GCCCGCGCCC TGGTCCTGGC CGGCCTCTGG
 61 CTGGCTGCAG CCGGGCGCCC CCTAGCCTTC TCGGATGCCG GGCCGCACGT GCACTACGGC
121 TGGGGCGAGT CCGTCCGCCT GCGGCACCTG TACACCGCGG GTCCCCAGGG CCTCTCCAGC
181 TGCTTCCTGC GCATCCACTC AGACGGCGCC GTGGACTGCG CGCCGGTTCA GAGCGCGCAC
241 AGTTTGATGG AGATCAGGGC AGTCGCTCTG AGTACCGTGG CCATCAAGGG CGAACGCAGC
301 GTCCTGTACC TCTGCATGGG CGCCGACGGC AAAATGCAAG GGCTGAGTCA GTACTCAGCT
361 GAGGACTGTG CCTTTGAGGA GGAAATCCGT CCGGACGGCT ACAACGTGTA CTGGTCCAAG
421 AAACACCACC TCCCGGTGTC CCTGAGCAGC GCCAGGCAGC GGCAGCTGTT CAAAGGCAGG
481 GGTTTCCTGC CGCTGTCTCA CTTCCTTCCC ATGCTGTCCA CCATCCCCAC AGAGCCCGAT
541 GAAATCCAGG ACCACTTGAA GCCCGATTTG TTTGCTTTGC CCCTGAAAAC AGATAGCATG
601 GACCCATTTG GGCTCGCCAC CAAACTGGGA GTGGTGAAGA GTCCCAGCTT CTATAAGTAA
```

TABLE 4-continued

*Myotis lucifugus* (microbat) FGF19 gene coding sequence
(SEQ ID NO: 150) (Ensembl Accession No. ENSMLUT00000002508,
which is hereby incorporated by reference in its entirety)

```
  1 ATGCAAAGCG CGTGGAGCCG ACGCGTTGTG GCCCGAGCCC TGGTCTTGGC CAGCCTCGGG
 61 CTGGCCTCAG CCGGGGGGCC CCTCGGTCTT TCGGACGCTG GGCCGCACGT GCACTACGGC
121 TGGGGGGAGT CCATCCGCCT GCGCCACCTG TACACCTCCG GCCCCCACGG CCCATCCAGC
181 TGCTTCCTGC GCATCCGCGC TGACGGCGCA GTGGACTGCG CGCGGGGCCA GAGCGCGCAC
241 AGTTTGGTGG AGATCAGGGC CGTCGCCTTG CGGAAAGTGG CCATCAAGGG CGTGCACAGC
301 GCCCTGTACC TCTGCATGGG AGGCGACGGC AGGATGCTGG GGCTGCCTCA GTTCTCGCCC
361 GAGGACTGTG CTTTCGAGGA GGAGATCCGC CCGGACGGCT ACAACGTGTA CCGGTCCCAG
421 AAGCACCAGC TGCCCGTCTC GCTGAGCAGT GCCCGGCAGA GGCAGCTGTT CAAGGCCCGG
481 GGCTTCCTGC CGCTGTCCCA CTTCCTGCCC ATGCTGCCCA GCAGCCCCGC GGGACCCGTG
541 CCCCGAGAGC GCCCCTCGGA GCCGGACGAG TTCTCTTCGC CCCTGGAAAC AGACAGCATG
601 GACCCTTTTG GGATTGCCAA CAACCTGAGG CTGGTGAGAA GTCCCAGCTT TCAGGAATAA
```

*Ornithorhynchus anatinus* (platypus) FGF19 gene coding sequence
(SEQ ID NO: 151) (GenBank Accession No. XM_001506664,
which is hereby incorporated by reference in its entirety)

```
  1 atgctttcct gtgtggtttt gcctagtctg ctggagatca aggcggtggc cgtgcgcacg
 61 gtggccatca aaggggtcca catctctcgg tacctctgca tggaagagga tgggaaaact
121 ccatgggcac gtctgctgga gatcaaggcg gtggccgtgc gcacggtggc catcaaaggg
181 gtccacagct ctcggtacct ctgcatggaa gaggatggaa aactccatgg gcagatttgg
241 tattctgcag aagactgtgc ttttgaagag gaaatacgtc cagatggcta caatgtgtat
301 aaatctaaga aatatggtgt tcctgtttct ttaagcagcg ccaaacaaag gcagcaattc
361 aaaggaagag actttctgcc tctttctcgt ttcttgccaa tgatcaacac agtgcctgtg
421 gagccagcag agtttgggga ctatgccgat tactttgaat cagatatatt ttcctcacct
481 ctggaaactg acagcatgga cccatttaga attgccccta aactgtcccc tgtaaagagc
541 cccagctttc agaaataa
```

*Monodelphis domestica* (opossum) FGF19 gene coding sequence
(SEQ ID NO: 152) (GenBank Accession No. XM_001373653,
which is hereby incorporated by reference in its entirety)

```
  1 atggcccagc tcctggcccc gctcctcacc ctggctgctc tctggctggc cccgacggcg
 61 cgtgcccgac cgctggtgga cgccgggcct cacgtctact acggctgggg ggagcccatt
121 cgtctgcggc atctctacac ggccaatcgg cacgggctcg ccagcttctc cttcctccgg
181 atccaccgcg acggccgcgt ggacggcagc cggagtcaga gcgcgctcag tttgctggag
241 atcaaggcgg tagctcttcg gatggtggcg atcaaaggtg tccatagctc tcggtacctg
301 tgtatgggag acgccgggaa actccaggga tcggtgaggt tctcggccga ggactgcacc
361 ttcgaggagc agattcgccc cgacggctac aacgtgtacc agtcccccaa gtacaacctc
421 cccgtctcgc tctgcactga caagcagagg cagcaggccc acggcaagga gcacctgccc
481 ctgtcccact tcctgcccat gatcaatgct attcctttgg aggccgagga gcccgagggc
541 cccaggatgt tggcggcgcc tctggagacg gacagcatgg accccttcgg cctcacctcc
601 aagctgttgc cggtcaagag ccccagcttt cagaaataa
```

*Anolis carolinensis* (anole lizard) FGF19 gene coding sequence
(SEQ ID NO: 153) (GenBank Accession No. XM_003214667,
which is hereby incorporated by reference in its entirety)

```
  1 atgtgtcggc gggcgttgcc tctgctgggg gcccttctgg gcttggcggc cgtggcctcc
 61 cgcgccctcc cgctcaccga cgccgggccc cacgtcagct acggctgggg ggagcccgtc
121 cggctcaggc acctctacac cgcggggcgg cagggcctct tcagccagtt cctccgcatc
181 cacgccgacg ggagagtcga cggcgccggc agccagaacc ggcagagttt gctggagatc
241 cgcgcggtct cgttgcgcgc cgtggccctc aaaggcgtgc acagctcccg ctacctctgc
301 atggaggagg acggccggct ccgcgggatg ctcagatatt ctgcagaaga ctgttccttt
361 gaagaggaga tgcgtccaga tggctacaat atctacaagt caaagaaata cggagttttg
421 gtctccctaa gtaatgccag acaaagacag caattcaaag ggaaagattt tcttcctttg
481 tctcatttct tgccgatgat caacactgtg ccagtggagt ctgcagactt tggagagtat
541 ggtgacacca ggcagcatta tgaatcggat attttcagtt cacgtcttga aactgacagc
601 atggaccctt ttggcctcac ttcagaagtg tcatcagtac aaagtcctag ctttgggaaa
661 taa
```

*Ochotona princeps* (pika) FGF19 gene coding sequence
(SEQ ID NO: 154) (Ensembl Accession No. ENSOPRT00000010769,
which is hereby incorporated by reference in its entirety)

```
  1 GTGCGGAGCA GGGGAGCCAT GGCCCGCGCT CTGGTTCTAG CCACTCTCTG GCTGGCCGCG
 61 ACGGGGCGGC CGCTGGCCTT GTCCGACGCG GGGCCGCACC TGCACTACGG CTGGGGCGAG
121 CCCATCCGCC TGCGGCACCT GTACGCCACC AGCGCCCACG GCCTCTCGCA CTGCTTTTTG
181 CGCATCCGTA CCGACGGCAC CGTGGACTGC GAGCGCAGCC AGAGCGCGCA CA--------
    ---------- ---------- ---------- ---------- ---------- ----------
242 ---------- ---------- ---------- ------CTAC AGTACTCGGA GGAGGACTGC
266 GCCTTCGAAG AGGAGATCAG CTCTGGCTAT AACGTGTACC GCTCCAGGAG GTACCAGCTG
326 CCCGTGTCCC TGGGCAGCGC CAGGCAGAGG CAGCTGCAGC GGAGCCGTGG CTTCCTGCCC
386 CTGTCCCACT TCCTGCCGGT GCTGCCCGCG GCCTCGGAGG AGGTGGCGGC CCCCGCTGAC
446 CACCCGCAAG CAGACCCTTT CTCGCCCCTG GAGACCGACA GCATGGACCC ATTTGGAATG
506 GCCACCAAGC GGGGGCTGGT GAAGAGCCCC AGCTTCCAGA AGTGA
```

TABLE 4-continued

*Cavia porcellus* (guinea pig) FGF19 gene coding sequence (SEQ ID NO: 155) (Ensembl Accession No. ENSCPOT00000008222, which is hereby incorporated by reference in its entirety)

```
  1 ATGTGGAGTG CGCCGAGCGG ATGTGTGGTG ATCCGCGCCC TGGTCCTGGC TGGCCTGTGG
 61 CTGGCGGTGG CGGGGCGCCC CCTGGCCCGG CGGTCTCTCG CGCTATCTGA CCAGGGGCCG
121 CACTTGTACT ACGGCTGGGA CCAGCCGATC CGCCTTCGGC ACCTGTACGC CGCGGGCCCC
181 TACGGCCGCT CGCGCTGCTT CCTGCGCATT CACACGGACG GCGCGGTGGA CTGCGTCGAG
241 GAACAGAGCG AGCACTGTTT GCTGGAGATC AGAGCAGTCG CTCTGGAGAC CGTGGCCATC
301 AAGGACATAA ACAGCGTCCG GTACCTGTGC ATGGGCCCCG ACGGCAGGAT GCGGGGCCTG
361 CCCTGGTATT CGGAGGAGGA CTGTGCCTTC AAGGAAGAGA TCAGCTACCC GGGCTACAGC
421 GTGTACCGCT CCCAGAAGCA CCACCTCCCC ATCGTGCTGA GCAGTGTCAA GCAGAGGCAG
481 CAGTACCAGA GCAAGGGGGT GGTGCCCCTG TCCTACTTCC TGCCCATGCT GCCCAAGGCC
541 TCTGTGGAGC CCAGCGACGA GGAGGAATCC AGCGTGTTCT CGTTGCCCCT GAAGACGGAC
601 AGCATGGACC CCTTTGGGAT GGCCAGTGAG ATCGGGCTGG TGAAGAGTCC CAGCTTTCAG
661 AAGTAA
```

*Tupaia belangeri* (tree shrew) FGF19 gene coding sequence (SEQ ID NO: 156) (from Ensembl Accession No. ENSTBET00000000307, which is hereby incorporated by reference in its entirety)

```
  1 ATGAGGAGAA CACCGAGCGG GTTTGCAGTG GCCCGTGTCC TCTTCCTGGG CAGCCTTTGG
 61 CTGGCCGCAG CCGGGAGCCC CTTGGCCCTG TCCGACGCCG GGCCGCATGT GAACTACGGC
121 TGGGATGAGT CCATACGCCT GCGACACTTG TACACCGCCA GCCCGCACGG CTCCACCAGC
181 TGCTTCTTGC GCATCCGTGA CGACGGCTCA GTGGACTGCG CGCGGGGCCA GAGTTTGCAC
241 AGTTTGCTGG AGATCAAGGC AGTCGCTTTG CAGACCGTGG CCATCAAAGG CGTGTACAGT
301 GTCCGCTACC TCTGCATGGA CGCCGACGGC AGGATGCAGG GGCTG----- ----------
361 ---------- ---------- ---------- ---------- ---------- NNGGTCCACG
369 AAGCACGGCC TCCCAGTCTC CCTGAGCAGT GCCAAGCAGA GGCAGCTGTT AACGGTTAGG
429 GGCTTTCCTT CCCTTCCCCA CTTCCTGCTC ATGATGGCCA AGACTTCAGC AGGGCCTGGA
489 AACCCCAGGG ACCACCCAGG GTCTAACACT TTCTCGTTGC CCCTGGAAAC TGATAGCATG
549 GACCCATTTG GGATGACCAC CAGACATGGG CTGGTGAAGA GTCCCAGCTT TCAAAACTAA
```

*Rattus norvegicus* (Norway rat) FGF15 gene coding sequence (SEQ ID NO: 157) (GenBank Accession No. NM_130753, which is hereby incorporated by reference in its entirety) (SEQ ID NO: 56)

```
  1 atggcgagaa agtggagtgg gcgtattgtg gcccgagctc tggtcctggc cactctgtgg
 61 ctggccgtgt ctgggcgtcc cctggtccag caatcccagt ctgtgtcgga tgaaggtcca
121 ctctttctct atggctgggg caagattacc cgcctgcagt acctgtactc tgctggtccc
181 tacgtctcca actgcttcct gcgtatccgg agtgacggct ctgtggactg cgaggaggac
241 cagaacgaac gaaatctgtt ggagttccgc gcggttgctc tgaagacaat tgccatcaag
301 gacgtcagca gcgtgcggta cctctgcatg agcgccgacg gcaagatata cgggctgatt
361 cgctactcgg aggaagactg taccttcagg gaggaaatgg actgtttggg ctacaaccag
421 tacaggtcca tgaagcacca cctccacatc atcttcatca aggccaagcc cagagagcag
481 ctccagggcc agaaaccttc aaactttatc cccatatttc accggtcttt ctttgaatcc
541 acggaccagc tgaggtctaa aatgttctct ctgcccctgg agagcgacag catggatccg
601 ttcagaatgg tggaggatgt ggaccaccta gtgaagagtc ccagcttcca gaaatga
```

*Mus musculus* (house mouse) FGF15 gene coding sequence (SEQ ID NO: 158) (GenBank Accession No. NM_008003, which is hereby incorporated by reference in its entirety)

```
148                            atg gcgagaaagt ggaacgggcg tgcggtggcc
181 cgagccctgg tcctggccac tctgtggctg gctgtgtctg ggcgtcccct ggctcagcaa
241 tcccagtctg tgtcagatga agatccactc tttctctacg gctggggcaa gattacccgc
301 ctgcagtacc tgtactcccgc tggtccctat gtctccaact gcttcctccg aatccggagc
361 gacggctctg tggactgcga ggaggaccaa aacgaacgaa atttgttgga attccgcgcg
421 gtcgctctga agacgattgc catcaaggac gtcagcagcg tgcggtacct ctgcatgagc
481 gcggacggca agatatacgg gctgattcgc tactcggagg aagactgtac cttcagggag
541 gaaatggact gtttaggcta caaccagtac agatccatga agcaccatct ccatatcatc
601 ttcatccagg ccaagcccag agaacagctc caggaccaga aaccctcaaa ctttatcccc
661 gtgtttcacc gctccttctt tgaaaccggg gaccagctga ggtctaaaat gttctccctg
721 cccctggaga gtgacagcat ggatccgttc aggatggtgg aggatgtaga ccacctagtg
781 aagagtccca gcttccagaa atga
```

*Gallus gallus* (chicken) FGF19 gene coding sequence (SEQ ID NO: 159) (GenBank Accession No. NM_204674, which is hereby incorporated by reference in its entirety)

```
127       atgg ggccggcccg ccccgccgca cccggcgctg ccctggcgct gctggggatc
181 gccgccgccg ccgccgccgc caggtccctg ccgctgcccg acgtcggggg tccgcacgtc
241 aactacggct ggggggaacc catccggctg cggcacctac tacaccgccc aggcaagcac
301 gggctcttca gctgcttcct gcgcatcggc ggcgacggcc gggtggacgc tgtcggtagc
361 cagagcccgc agagtctgtt ggagatccgc gccgtggcgg tgcgcaccgt ggccatcaag
421 ggcgtgcaga gctcccgcta cctctgcatg gacgaggcgg ggcggctgca cgggcagctc
481 agctattcca ttgaggactg ttcctttgaa gaggagattc gtccagacgg ctacaacgtg
541 tataaatcaa agaaatacgg gatatcggtg tctttgagca gtgccaaaca aagacagcaa
```

TABLE 4-continued

```
601 ttcaaaggaa aagattttct cccgctgtct cacttcttac ccatgatcaa cactgtgcca
661 gtggaggtgg cagactttgg tgaatatggt gattacagcc aggcttttga gccagaggtc
721 tactcatcgc ctctcgaaac ggacagcatg gatccctttg ggatcacttc caaactgtct
781 ccagtgaaga gccccagctt tcagaaatga
```

*Taeniopygia guttata* (zebra finch) FGF19 gene coding sequence (SEQ ID NO: 160) (GenBank Accession No. XM_002194457, which is hereby incorporated by reference in its entirety)

```
  1 atggttatca taagcaatct atatctgatg cagaacgatg ttatgatgaa tatgaggcga
 61 gcaccccttc gcgttcacgc tgctcgctct tcggccaccc ctgcctccgc gctgccgctg
121 ccgccgcccg acgccggccc gcacctcaaa tacggctggg gagagcccat ccggctgcgg
181 cacctctaca ccgccagcaa gcacgggctc ttcagctgct tcctgcgtat cggcgctgac
241 ggccgggtgg acgcggccgg cagccagagc ccgcagagcc tgctagagat ccgcgccgtg
301 gccgtgcgca ccgtggccat caagggcgtg cagagctccc ggtacctgtg catggacgag
361 gcggggcggc tgcacgggca gctcaggaat tccactgaag actgctcctt tgaggaggag
421 attcgcccag acggctacaa tgtgtataga tctaaaaaac atggaatatc ggtgtctttg
481 agcagtgcca aacaaagaca gcagttcaag ggaaagatt tccttcccct gtctcacttc
541 ttgcccatga tcaacactgt gcccatggag tcagcagact ttggtgaata tggtgattac
601 agccaggcct ttgaggcaga ggccttctcc tcacctctgg agacggacag catggacccc
661 tttggcatcg cctccaaact gtccctagtg aagagcccta gcttccaaaa ctga
```

*Danio rerio* (zebrafish) FGF19 gene coding sequence (SEQ ID NO: 161) (GenBank Accession No. NM_001012246, which is hereby incorporated by reference in its entirety)

```
  1 atgctcctct tactctttgt cactgtttgt ggaagtatcg gcgtggagag cctcccgttg
 61 cccgactctg gtccacattt ggcaaatgac tggagtgaag ccgtccggct acgacatctg
121 tacgcagcca gacatggctt acatctgcaa ataaacacag acggagaaat cattggatcc
181 acatgcaaag ctcggacagt aagtttgatg gagatatggc cggtggacac aggctgcgta
241 gccattaagg gagttgcaag ctcccgattt ctttgcatgg aaagactggg aaacctgtac
301 ggatcgcaca tttacactaa agaggactgc tcttttttgg aacgcatcct tccagacggc
361 tacaacgtct acttctcgag caaacacgga gctcttgtga ctttaagtgg tgcgaaaaac
421 aagttgcaca gtaacgatgg gacttctgca tcccagttcc tccccatgat caacacactt
481 tcagaggaac acactaaaca gcactcaggg gaacagcact cttctgttaa ccatggacag
541 gaccatcagt tgggccttga aatagacagt atggaccctt tcggaaagat ctctcaaata
601 gtgatccaga gtcccagctt caacaaaaga tga
```

*Xenopus* (Silurana) *tropicalis* (Western clawed frog) FGF19 gene coding sequence (SEQ ID NO: 162) (GenBank Accession No. NM_001142825, which is hereby incorporated by reference in its entirety)

```
  1 atgtggaaga ccctgccttg gattttggtt cccatgatgg tggccgtgct gtatttcctc
 61 ggaggggcgg aaagtctgcc gctttttgat gccgggccgc acatgcagaa cggctggggg
121 gagtcgatca gaattcggca cctgtatacg gccaggaggt tcgggcacga cagctactac
181 ctccggatac acgaggatgg cagagtcgat ggtgacaggc aacaaagcat gcacagttta
241 ttggaaatca gagcaattgc agttggaatt gttgccatta aagggtatcg cagctctctg
301 tacctgtgca tggggtccga gggaaaactc tatggaatgc acagttactc ccaggatgat
361 tgctcttttg aagaggagct tctcccggat ggatacaaca tgtataaatc aaggaaacat
421 ggcgttgctg tctccctaag caaggagaag cagaagcaac aatacaaagg aaagggctac
481 ctcccgttgt cccatttcct acccgtgata agctgggtgc ccatggagcc caccggagat
541 gtagaagatg atatctacag gtttccattc aatacggaca caaaaagtgt cattgacagc
601 cttgataccc tgggactaat ggatttttcg agttatcaca agaaatag
```

*Otolemur garnettii* (bushbaby) FGF19 gene coding sequence (SEQ ID NO: 163) (Ensembl accession no. ENSOGAT00000031686, which is hereby incorporated by reference in its entirety)

```
  1 ATGCCCAGCG GGCTGAGAGG GCGTGTGGTA GCCGGCGCCC TGGCCCTGGC CAGCTTCTGG
 61 CTGGCCGTGG CCGGGCGCCC GCTGGCCTTC TCGGATGCCG GCCCTCACGT GCACTACGGC
121 TGGGGTGAGC CCATCCGCCT GCGACACCTG TACACCGCCG GCCCCCACGG CCTCTCCAGC
181 TGCTTCCTGC GCGTACGCAC CGACGGTGCG GTAGACTGCG CGCGGGGCCA GAGCGCACAC
241 AGTTTGCTGG AAATCAGGGC CGTCGCTCTC CGGACCGTGG CCATCAAAGG CGTGCACAGC
301 GCGCGGTACC TCTGCATGGG CGCCGACGGC AGGATGCAGG GGCTGCCTCA GTACTCGGAG
361 GAAGACTGTG CCTTTGAGGA GGAGATCCGG CCAGACGGCT ACAACGTCTA CTGGTCTGAG
421 AAGCACCGCC TGCCGGTGTC TCTGAGCAGT GCCCGGCAGA GGCAGCTGTA CAAGGGCAGG
481 GGCTTTCTGC CGCTCTCTCA CTTCCTGCCC ATGCTGCCTG TGACCCCAGC CGAGCCCGGG
541 GACCTCAGAG ACCACCTGGA ATCCGACATG TTCTCTTTGC CCCTGGAAAC TGACAGCATG
601 GATCCATTTG GGATCGCCAC CAGACTGGGC GTGGTGAAGA GTCCCAGCTT TCAGAAATGA
```

*Felis catus* (cat) FGF19 gene coding sequence (SEQ ID NO: 164) (Ensembl accession no. ENSFCAT00000026317, which is hereby incorporated by reference in its entirety)

```
  1 ATGCGGAGCG CGCCGAGCCA GTGCGCGGTA ACCCGCGCCC TGGTCCTAGC CGGTCTCTGG
 61 CTGGCAGCAG CCGGGCGCCC CCTAGCCTTC TCGGACGCGG GGCCTCACGT GCACTACGGC
121 TGGGGTGAGC CCATCCGCCT GCGGCACCTG TACACCGCCG GCCCCCACGG CCTCTCCAGC
181 TGCTTCCTGC GCATCCGAGC CGACGGGGGG GTTGACTGCG CGCGGAGCCA GAGCGCGCAC
241 AGTTTGGTGG AGATCAGGGC AGTCGCTCTG CGGACCGTGG CCATCAAGGG CGTGCACAGC
```

TABLE 4-continued

```
 301 GTCCGGTACC TCTGCATGGG CGCCGACGGC AGGATGCAAG GGCTGCTTCA GTACTCTGCT
 361 GGGGACTGTG CCTTCCAAGA GGAGATCCGC CCCGACGGCT ACAATGTGTA CCGGTCCGAG
 421 AAGCACCGTC TCCCCGTCTC TTTGAGTAGT GCCATACAGA GGCAGCTGTA CAAGGGCAGA
 481 GGGTTTTTGC CCCTGTCCCA TTTCTTGCCC ATGCTGCCCG GCAGCCCAGC AGAGCCCAGG
 541 GACCTCCAGG ACCACGTGGA GTCGGAGAGG TTTTCTTCAC CCCTGGAAAC AGACAGCATG
 601 GACCCTTTTG GGATTGCCAC CAAAATGGGG TTAGTGAAGA GTCCCAGCTT CCAAAAGTAA
```

*Pelodiscus sinensis* (Chinese softshell turtle) FGF19 gene coding sequence (SEQ ID NO: 165) (Ensembl accession no. ENSPSIT00000010427, which is hereby incorporated by reference in its entirety)

```
 241                                  ATGTGGAG GAGCCTGTGC AAATCTCACA
 301 CGTCTCTGGC TCTGCTGGGA CTCTGCTTTG CGGTGGTCGT GAGATCTCTG CCTTTCTCGG
 361 ATGCAGGGCC ACATGTGAAC TATGGCTGGG GGGAGCCTAT TCGATTAAGG CACCTATACA
 421 CCGCCAGCAG ACACGGGCTG TTCAATTACT TCCTGAGGAT CAGCAGTGAT GGCAAAGTGG
 481 ATGGCACCAG CATTCAGAGT CCTCACAGTC TGCTGGAAAT CAGGGCTGTG GCAGTTCGCA
 541 CGGTGGCGAT CAAGGGCGTC CACAGTTCCC GGTACCTCTG CATGGAAGAA GACGGGAAGC
 601 TGCATGGACT TCTCAGGTAT TCTACAGAAG ATTGCTCCTT TGAAGAGGAG ATACGCCCAG
 661 ATGGCTACAA TGTATATAAA TCAAAGAAAT ATGGAATCTC TGTGTCCTTA AGTAGTGCCA
 721 AACAAAGACA ACAATTCAAA GGAAAAGACT TTCTTCCATT GTCTCACTTC TTGCCTATGA
 781 TCAATACAGT ACCTGTGGAG TCAATGGATT TTGGAGAATA TGGTGATTAT AGTCATACTT
 841 TTGAATCAGA TCTATTCTCT TCACCTCTCG AAACTGACAG CATGGATCCC TTTGGAATCA
 901 CCTCTAAAAT ATCTCCAGTG AAGAGCCCCA GCTTTCAGAA ATAA
```

*Latimeria chalumnae* (coelacanth) FGF19 gene coding sequence (SEQ ID NO: 166) (Ensembl accession no. ENSLACT00000014697, which is hereby incorporated by reference in its entirety)

```
   1 ATGTTACAGG CACTGTACAA TCTCTGTACA GCTCTAGTTT TGTTTAAGCT TCCTTTTGCA
  61 ATGGTGGGGT ACACCCTGCC TTCTGCCAAT GAAGGGCCCC ATCTGAACTA TGACTGGGGA
 121 GAATCTGTAA GACTCAAACA TCTGTACACA TCTAGCAAGC ATGGATTGAT CAGTTACTTT
 181 TTACAGATCA ATGATGATGG CAAAGTAGAT GGGACCACTA CACGAAGCTG TTATAGTTTG
 241 CTCGAAATAA AATCAGTGGG GCCAGGAGTT TTGGCAATTA AAGGCATACA GAGCTCCAGA
 301 TACCTTTGTG TCGAGAAGGA TGGAAAATTG CATGGATCGC GCACTTATTC AGCAGACGAT
 361 TGCTCCTTCA AAGAGGATAT ACTCCCAGAT GGTTACACTA TCTACGTGTC AAAGAAACAT
 421 GGATCTGTTG TTAATCTGAG CAACCACAAA CAGAAACGTC AGAGAAATCG CAGAACCCTG
 481 CCTCCATTTT CTCAGTTCCT ACCGCTTATG GACACCATTC GTGTGGAGTG CATGAACTGC
 541 GGGGAGCACT GTGACGACAA CCTGCATGAC GAGCTAGAAA CAGGACTGTC CATGGATCCC
 601 TTTGAAAGTA CATCCAAAAA ATCCTTTCAG AGTCCCAGCT TTCACAATAG ATAA
```

*Mustela putorius furo* (ferret) FGF19 gene coding sequence (SEQ ID NO: 167) (Ensembl accession no. ENSMPUT00000004650, which is hereby incorporated by reference in its entirety)

```
 421     ATGCGG AGCGCCGCGA GTCGGTGCGC GGTAGCCCGC GCGCTGGTCC TAGCCGGCCT
 481 TTGGCTGGCC GCAGCCGGGC GCCCCCTAGC CTTCTCGGAC GCGGGGCCGC ACGTGCACTA
 541 TGGCTGGGGT GAGCCCATCC GCCTACGGCA CCTGTACACC GCCGGCCCCC ACGGCCTCTC
 601 CAGCTGCTTC CTGCGCATCC GTGCCGACGG CGGGGTTGAC TGCGCGCGGG GCCAGAGCGC
 661 GCACAGTTTG GTGGAGATCC GGGCAGTCGC TCTGCGGACG GTGGCCATCA AGGGCGTGTA
 721 CAGCGACCGC TATCTCTGCA TGGGTGCGGA CGGCAGGATG CAAGGGCTGC CTCAGTACTC
 781 CGCCGGAGAC TGTGCTTTCG AGGAGGAGAT CCGCCCTGAT GGCTACAACG TGTACCGGTC
 841 CAAGAAGCAC CGTCTCCCCG TCTCCCTGAG CAGTGCGAAA CAAAGGCAGC TGTACAAGGA
 901 CCGGGGCTTT TTGCCTCTGT CCCATTTCTT GCCCATGCTG CCCGGGAGCC TGGCGGAGCC
 961 CAGGGACCTC CAGGACCACG TGGAGGCTGA TGGGTTTTCT GCCCCCCTAG AAACAGACAG
1021 CATGGACCCT TTTGGGATTG CCACCAAAAT GGGACTAGTG AAGAGTCCCA GCTTCCAAAA
1081 ATGA
```

*Takifugu rubripes* (fugu) FGF19 gene coding sequence (SEQ ID NO: 168) (Ensembl accession no. ENSTRUT00000007155, which is hereby incorporated by reference in its entirety)

```
   1 TCATCTACAA GGATTAGTGG AAACATGGTT CTCCTCATGC TCCCCATCAC CGTTGCAAAC
  61 CTCTTCCTCT GTGCTGGAGT TCTCTCCTTG CCTTTGTTGG ATCAAGGGTC TCATTTTCCC
 121 CAAGGCTGGG AACAGGTAGT CCGCTTCAGG CACCTGTATG CTGCCAGTGC AGGGCTGCAC
 181 CTGCTGATCA CTGAAGAGGG CTCGATCCAA GGCTCTGCAG ATCCAACTTT ATACAGCCTG
 241 ATGGAGATCC GTCCGGTGGA CCCAGGCTGT GTTGTCATTA GAGGAGCAGC AACCACACGC
 301 TTCCTCTGCA TAGAAGGTGC TGGAAGACTG TACTCATCAC AGACCTACAG CAAAGACGAC
 361 TGTACCTTCA GAGAGCAAAT CCTAGCAGAC GGCTACAGCG TCTACAGATC TGTCGGACAC
 421 GGAGCTCTGG TCAGTCTGGG AAACTACCGG CAGCAGCTGA GGGGGGAGGA CTGGAGCGTT
 481 CCGACACTGG CTCAGTTCCT CCCCAGAATA AGTTCACTGG ATCAGGACTT TAAAGCTGCT
 541 CTTGACGAGA CTGAGAAGCC AGAACAAACT GCACCTCAAA GATCGGAACC TGTCGACATG
 601 GTGGACTCAT TTGGAAAGCT CTCTCAGATC ATCCACAGTC CCAGTTTTCA CAAG
```

*Equus caballus* (horse) FGF19 gene coding sequence (SEQ ID NO: 169) (Ensembl accession no. ENSECAT00000021494, which is hereby incorporated by reference in its entirety)

```
   1 ---------- ---------- ---------- ---------- ---------- -------GCG
   4 GCCGGGCGCC CCCTAGCCTT GTCCGACGCT GGGCCGCACG TGCACTACGG CTGGGGCGAG
```

TABLE 4-continued

```
 64 CCGATCCGCC TGCGGCACCT GTACACCGCC GGCCCCCACG GCCTCTCCAG CTGCTTCCTG
124 CGCATCCGCG CCGATGGCGC CGTGGACTGC GCGCGGGGCC AGAGCGCGCA CAGTTTGGTG
184 GAGATCAGAG CAGTCGCTCT GCGCACCGTG GCCATCAAGG GCGTGCACAG CGTCCGGTAC
244 CTCTGCATGG GCGCCGACGG CAGGATGCAA GGGCTGGTA
```

*Oryzias latipes* (medaka) FGF19 gene coding sequence (SEQ ID NO: 170) (Ensembl accession no. ENSORLT00000000352, which is hereby incorporated by reference in its entirety)

```
  1 ACCATGCTGC TCATTGTGGT CACCATTTCC ACAATGGTGT TTTCTGACTC TGGAGTTTCC
 61 AGCATGCCGC TCTCTGATCA TGGACCCCAC ATCACTCACA GCTGGAGCCA AGTGGTCCGC
121 CTCCGGCACC TGTACGCGGT CAAGCCTGGA CAACATGTCC AGATCAGAGA GGATGGACAC
181 ATCCACGGCT CAGCAGAACA AACTCTGAAC AGCCTGCTGG AGATCCGTCC GGTTGCTCCG
241 GGACGGGTGG TCTTCAGAGG AGTAGCCACC TCAAGGTTTC TGTGCATGGA GAGCGACGGC
301 AGACTCTTCT CCTCACACAC ATTTGACAAG GACAACTGCG TCTTCAGAGA GCAGATCTTG
361 GCAGACGGCT ACAACATCTA CATTTCAGAT CAGCATGGAA CCCTGCTTAG TTTGGGAAAC
421 CACCGGCAAA GGCAGCAGGG TTTAGACCGG GATGTTCCAG CCCTGGCTCA GTTCCTCCCC
481 AGGATCAGCA CCCTGCAGCA GGGCGTGTAC CCAGTGCCAG ACCCCCCCCA CCAGATGAGA
541 ACAATGCAAA CAGAGAAGAC TCTAGATGCC ACGGACACAT TGGGCAACT CTCTAAAATC
601 ATTCACAGTC CCAGCTTCAA CAAAAGATGA
```

*Xiphophorus maculates* (platyfish) FGF19 gene coding sequence (SEQ ID NO: 171) (Ensembl accession no. ENSXMAT00000001519, which is hereby incorporated by reference in its entirety)

```
  1                                                          ATG
  4 TTTGTGTTCA TTCTATGCAT TGCTGGTGAA CTTTTTACTC TGGGAGTATT TTGCATGCCA
 64 ATGATGGACC AGGGGCCACT TGTCACCCAT GGCTGGGGCC AGGTGGTCCG GCACCGGCAT
124 CTGTATGCAG CCAAGCCAGG ACTGCACCTA CTGATCAGTG AGGATGGACA AATCCACGGT
184 TCCGCAGATC AAACTCTTTA CAGCCTGCTG GAGATCCAAC CTGTTGGCCC CGGACGTGTT
244 GTGATCAAAG GAGTGGCAAC CACACGCTTC CTCTGCATGG AGAGCGACGG CAGATTGTAC
304 TCAACTGAAA CATACAGCAG AGCTGACTGC ACCTTCAGAG AACAGATCCA GGCAGACGGC
364 TACAACGTCT ACACCTCTGA TAGCCATGGA GCCCTCCTCA GTTTGGGAAA CAACCAGCAA
424 AGACACAGCG GCTCAGACCG TGGTGTTCCA GCTCTGGCCC GCTTTCTTCC CAGGTTAAAC
484 ACCCTTCAGC AGGCCGTCCC CACAGAGCCG GATGTTCCTG ATCAGCTCAG TCCAGAGAAA
544 GTACAACAGA CTGTGGACAT GGTGGCCTCC TTTGGCAAGC TCTCTCATAT AATTCACAGT
604 CCCAGCTTCC ATAAGAGATG A
```

*Ictidomys tridecemlineatus* (squirrel) FGF19 gene coding sequence (SEQ ID NO: 172) (Ensembl accession no. ENSSTOT00000026298, which is hereby incorporated by reference in its entirety)

```
  1 ATGCGGAGCG CGCCGAGCGG ACGTGCCTTA GCCCGCGCCC TGGTGCTGGC CAGCCTCTGG
 61 TTGGCAGTGG CCGGACGACC CCTGGCCCGG CGCTCTCTGG CTCTCTCCGA CCAGGGGCCA
121 CACTTGTACT ATGGCTGGGA TCAGCCCATC CGCCTCCGGC ACCTGTACGC CGCGGGCCCC
181 TACGGCTTCT CCAACTGTTT CCTGCGCATC CGCACCGACG GCGCCGTGGA CTGCGAGGAG
241 AAGCAGAGCG AGCGTAGTTT GATGGAGATC AGGGCGGTCG CTCTGGAGAC TGTGGCCATC
301 AAGGACATAA ACAGCGTCCG GTACCTCTGC ATGGGCGCCG ACGGCAGGAT ACAGGGACTG
361 CCTCGGTACT CGGAGGAAGA GTGCACGTTC AAGGAGGAGA TCAGCTATGA CGGCTACAAC
421 GTGTACCGGT CCCAGAAGTA CCACCTTCCC GTGGTGCTCA GCAGTGCCAA GCAGCGGCAG
481 CTGTACCAGA GCAAGGGCGT GGTTCCCCTG TCCTACTTCC TGCCCATGCT GCCCCTGGCC
541 TCTGCGGAGA CCAGGGACCG CTTGGAATCC GATGTGTTCT CTTTACCTCT GGAAACTGAC
601 AGCATGGACC CGTTTGGGAT GGCCAGTGAA GTGGGCCTGA AGAGCCCCAG CTTCCAGAAG
661 TAA
```

*Gasterosteus aculeatus* (stickleback) FGF19 gene coding sequence (SEQ ID NO: 173) (Ensembl accession no. ENSGACT00000018770, which is hereby incorporated by reference in its entirety)

```
  1 ATGCTGCTGC TGCTGGTCCC CGCGTACGTT GCCAGTGTGT TTTTAGCTCT CGGGGTTGTT
 61 TGCTTGCCCC TAACAGATCA GGGTCTCCAC ATGGCCGACG ACTGGGGCCA GTCGGTCCGA
121 CTCAAGCACC TGTACGCCGC CAGCCCGGGA CTCCACCTGC TGATCGGGGA GGATGGTCGG
181 ATCCAAGGCT CGGCGCAGCA AAGCCCCTAC AGCCTGCTGG AGATCAGTGC AGTGGATCCG
241 GGCTGTGTGG TCATCAGAGG AGTAGCAACC GCACGGTTTC TCTGCATCGA AGGCGATGGA
301 AGACTGTACT CATCGGACAC CTACAGCAGA GACGACTGCA CCTTCAGGGA GCAGATCCTC
361 CCGGACGGCT ACAGCGTCTA CGTCTCCCAT GGACACGGGG CCCTGCTCAG CCTGGGGAAC
421 CACAGGCAGA GGCTGCAGGG TCGAGACCAC GGCGTGCCGG CTCTGGCCCA GTTCCTCCCG
481 AGGGTCAGCA CCATGGATCA GGCCTCGGCC CCCGACGCGC CCGGGCAGAC CGCCACCGAG
541 ACGGAAGAGC CCGTGGACTC GTTTGGAAAG CTCTCTCAGA TCATTCACAG TCCCAGCTTC
601 CACGAGAGAT GA
```

*Oreochromis niloticus* (tilapia) FGF19 gene coding sequence (SEQ ID NO: 174) (Ensembl accession no. ENSONIT00000022816, which is hereby incorporated by reference in its entirety)

```
 55                                                       ATGCTG
 61 CTGCTCCTCA TCGTATCCAT TGTCAATATG CTTTTTGGTG TTGGAATGGT TTGCATGCCC
121 CTGTCAGACA ACGGGCCCCA CATCGCCCAC GGCTGGGCCC AGGTGGTCCG GCTCAGGCAC
181 CTTTACGCCA CCAGACCGGG AATGCACCTG CTGATCAGTG AGGGTGGACA GATCCGTGGT
241 TCTGCCGTCC AGACTCTGCA CAGCCTAATG GAGATTCGTC CAGTCGGTCC AGGCCGTGTT
301 GTCATCAGAG GGGTAGCAAC CGCAAGGTTT CTCTGCATAG AAGACGACGG CACACTGTAC
```

TABLE 4-continued

| | |
|---|---|
| 361 | TCATCGCACG CCTACAGCAG AGAGGACTGC ATCTTCAGAG AGCAGATCTT GCCAGATGGG |
| 421 | TACAACATCT ACATCTCTGA CAGACATGGA GTCCTGCTCA GTCTGGGAAA CCACCGGCAA |
| 481 | AGACTGCAGG GCTTAGACCG AGGAGATCCA GCCCTGGCCC AGTTCCTCCC CAGGATCAGC |
| 541 | ACTCTGAATC AAATCCCTTC CCCTGGGGCA AACATCGGTG ACCACATGAA AGTAGCAAAA |
| 601 | ACAGAAGAAC CTGTGGACAC AATAGATTCA TTTGGAAAGT TCTCTCAGAT CATTGACAGT |
| 607 | CCCAGCTTCC ATAAGAGATG A |

*Meleagris gallopavo* (turkey) FGF19 gene coding sequence (SEQ ID NO: 175) (Ensembl accession no. ENSMGAT00000011114, which is hereby incorporated by reference in its entirety)

| | |
|---|---|
| 1 | GTAGGCAATC AATCACCACA GAGCATCCTT GAAATAACTG CTGTTGATGT CGGGATCGTC |
| 61 | GCTATCAAGG GCTTGTTCTC TGGCAGATAC CTGGCCATGA ACAAAAGGGG CAGGCTTTAT |
| 121 | GCATCACTCA GCTATTCCAT TGAGGACTGT TCCTTTGAAG AGGAGATTCG TCCAGATGGC |
| 181 | TATAACGTGT ATAAATCAAA GAAATACGGA ATATCAGTGT CTTTGAGCAG TGCCAAACAA |
| 241 | AGACAACAAT TCAAAGGAAA AGATTTTCTC CCACTGTCTC ACTTCTTACC CATGATCAAC |
| 301 | ACTGTGCCAG TGGAGGTGAC AGACTTTGGT GAATACGGTG ATTACAGCCA GGCTTTTGAG |
| 361 | CCAGAGGTCT ACTCATCGCC TCTCGAAACG GACAGCATGG ATCCCTTTGG GATCACTTCC |
| 421 | AAACTGTCTC CAGTGAAGAG CCCCAGCTTT CAGAAA |

As noted above, the chimeric protein may include one or more substitutions for or additions of amino acids from another FGF molecule. In one embodiment, the N-terminal portion from FGF23 and/or the C-terminal portion from FGF19 includes a modification that includes a substitution for or addition of amino acid residues from an FGF21 molecule.

FGF21 is an endocrine FGF expressed primarily by the pancreas (Fon Tacer et al., "Research Resource: Comprehensive Expression Atlas of the Fibroblast Growth Factor System in Adult Mouse," *Mol Endocrinol* 24(10):2050-2063 (2010), which is hereby incorporated by reference in its entirety) and has metabolic effects similar to that of FGF19, such as increased energy metabolism, weight loss, lowered blood glucose levels, and resistance to obesity and diabetes (Kharitonenkov et al., "FGF-21 as a Novel Metabolic Regulator," *J Clin Invest* 115(6), 1627-1635 (2005); Coskun et al., "Fibroblast growth factor 21 corrects obesity in mice," *Endocrinology* 149(12):6018-6027 (2008), which are hereby incorporated by reference in their entirety). Transgenic mice overexpressing FGF21 are also resistant to diet-induced obesity (Kharitonenkov et al., "FGF-21 as a Novel Metabolic Regulator," *J Clin Invest* 115(6), 1627-1635 (2005), which is hereby incorporated by reference in its entirety). Moreover, in diabetic rodent models, FGF21 administration lowers blood glucose and triglyceride levels (Kharitonenkov et al., "FGF-21 as a Novel Metabolic Regulator," *J Clin Invest* 115(6), 1627-1635 (2005), which is hereby incorporated by reference in its entirety).

In one embodiment, FGF21 has the amino acid sequence of SEQ ID NO: 176 (GenBank Accession No. NP_061986, which is hereby incorporated by reference in its entirety), as follows:

```
  1 mdsdetgfeh sglwvsvlag lllgacqahp ipdsspllqf
    ggqvrqryly tddaqqteah

 61 leiredgtvg gaadqspesl lqlkalkpgv iqilgvktsr
    flcqrpdgal ygslhfdpea

121 csfrellled gynvyqseah glplhlpgnk sphrdpaprg
    parflplpgl ppalpeppgi

181 lapqppdvgs sdplsmvgps qgrspsyas.
```

In one embodiment, the N-terminal portion from FGF23 comprises a modification that includes a substitution of amino acid residues from an FGF21 molecule. In one embodiment, the modification includes a substitution of the FGF23 heparan sulfate binding region for corresponding amino acid residues of another FGF molecule (e.g., FGF21). In one embodiment, the modification includes a substitution of amino acid residues 5137 to Q156 of SEQ ID NO: 1 for amino acid residues H145 to R163 of SEQ ID NO: 176.

In one embodiment, the C-terminal portion from FGF19 comprises a modification that includes a substitution of amino acid residues from an FGF21 molecule. In one embodiment, the modification comprises a substitution for or addition of amino acid residues 168 to 209 of SEQ ID NO: 176. In one embodiment, the modification is a substitution of amino acid residues from SEQ ID NO: 176 for corresponding amino acid residues of SEQ ID NO: 89. As shown in FIG. 1, the corresponding residues of FGF molecules may be identified by sequence analysis and/or structural analysis. In one embodiment, the modification includes a substitution of a contiguous stretch of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 amino acid residues 168 to 209 of SEQ ID NO: 176 for the corresponding contiguous stretch of amino acid residues of SEQ ID NO: 89. In one embodiment, amino acid residues 169 to 173, 169 to 196, or 169 to 203 of SEQ ID NO: 89 are substituted with the corresponding amino acid residues selected from the sequence comprising amino acid residues 168 to 209 of SEQ ID NO: 176.

In one embodiment, the modification includes a substitution of one or more individual amino acid residues from residues 168 to 209 of SEQ ID NO: 176 for the corresponding amino acid residues of SEQ ID NO: 89. In one embodiment, the C-terminal portion includes substitutions of one or more of amino acid residues 169, 170, 171, 172, 174, 175, 183, 184, 185, 186, 187, 188, 189, 190, 192, 193, 194, 195, 197, 200, 201, 202, 206, 207, 208, 209, 214, 215, or 216 of SEQ ID NO: 89 for the corresponding amino acid residues of SEQ ID NO: 176.

In one embodiment of the present invention, the C-terminal portion from FGF19 comprises a modification that includes a deletion of amino acid residues that are absent in the corresponding C-terminal portion from FGF21. In one embodiment, the modification comprises a deletion of amino acid residues selected from the sequence comprising residues 204 to 216, 197 to 216, 174 to 216, or 169 to 216 of SEQ ID NO: 89. In one embodiment, the modification comprises a deletion of amino acid residue 204 of SEQ ID NO: 89. In one embodiment, the modification comprises a deletion of amino acid residues 178, 179, 180, 181, and/or 182 of SEQ ID NO: 89 individually or in combination.

In one embodiment, the portion from FGF21 according to the present invention is from a mammal. It will be understood that this includes orthologs of human FGF21, or a polypeptide or protein obtained from one species that is the functional counterpart of a polypeptide or protein from a different species. In one embodiment of the present invention, the FGF21 portion of the chimeric protein according to the present invention is from *Pongo abelii, Pan troglodytes, Canis lupus familiaris, Bos taurus, Equus caballus, Ailuropoda melanoleuca, Oryctolagus cuniculus, Gorilla gorilla, Nomascus leucogenys, Procavia capensis, Cavia porcellus, Tupaia belangeri, Sorex araneus, Ictidomys tridecemlineatus, Loxodonta africana, Sus scrofa, Felis catus, Otolemur garnetti, Rattus norvegicus, Mus musculus, Vicugna pacos, Anolis carolinensis, Gadus morhua, Latimeria chalumnae, Tursiops truncatus, Mustela putorius furo, Takifugu rubripes, Dipodomys ordii, Echinops telfairi, Macaca mulatta, Microcebus murinus, Ochotona princeps, Xiphophorus maculates, Gasterosteus aculeatus, Sarcophilus harrisii, Macropus eugenii, Xenopus tropicalis*, or *Danio rerio.*

In one embodiment of the present invention, the portion from FGF21 of the chimeric protein of the present invention is from a non-human FGF21 (or an FGF21 ortholog) having an amino acid sequence as shown in Table 5. The portions of an ortholog of human FGF21 of a chimeric protein according to the present invention include portions corresponding to the above-identified amino acid sequences of human FGF21. Corresponding portions may be determined by, for example, analysis and structural analysis.

TABLE 5

*Pongo abelii* (*Sumatran orangutan*) FGF21 (GenBank Accession No. XP_002829565, which is hereby incorporated by reference in its entirety) (SEQ ID NO: 177)

```
  1 mdsdetgfeh sglwvpvlag lllgacqahp ipdsspllqf ggqvrqryly tddaqqteah
 61 leiredgtvg gaadqspesl lqlkalkpgv iqilgvktsr flcqrpdgal ygslhfdpea
121 csfrellled gynvyqseah glplhlpgnk sphrdpaprg parflplpgl ppappeppgi
181 lapqppdvgs sdplsmvgps qgrspsyas
```

*Pan troglodytes* (chimpanzee) FGF21 (GenBank Accession No. XP_524333, which is hereby incorporated by reference in its entirety) (SEQ ID NO: 178)

```
  1 mdsdetgfeh sglwvsvlag lllgacqahp ipdsspllqf ggqvrqryly tddaqqteah
 61 leiredgtvg gaadqspesl lqlkalkpgv iqilgvktsr flcqrpdgal ygslhfdpea
121 csfrellled gynvyqseah glplhlpgnk sphrdpaprg parflplpgl ppappeppgi
181 lapqppdvgs sdplsmvgps qgrspsyts
```

*Canis lupus familiaris* (dog) FGF21 (GenBank Accession No. XP_541510, which is hereby incorporated by reference in its entirety) (SEQ ID NO: 179)

```
  1 mgwaeagfeh lglwvpvlav llleacrahp ipdsspllqf ggqvrqryly tddaqeteah
 61 leiradgtvv gaarqspesl lelkalkpgv iqilgvktsr flcqgpdgtl ygslhfdpva
121 csfrellled gyniyhsetl glplrlrphn sayrdlaprg parflplpgl lpappeppgi
181 lapeppdvgs sdplsmvgps qgrspsyas
```

*Bos taurus* (bovine) FGF21 (GenBank Accession No. XP_001789639, which is hereby incorporated by reference in its entirety) (SEQ ID NO: 180)

```
  1 mgwdeakfkh lglwvpvlav lllgtcrahp ipdsspllqf ggqvrqryly tddaqeteah
 61 leiradgtvv gaarqspesl lelkalkpgv iqilgvktsr flcqgpdgkl ygslhfdpka
121 csfrellled gynvyqsetl glplrlppqr ssnrdpaprg parflplpgl paappdppgi
181 lapeppdvgs sdplsmvgps ygrspsyts
```

*Equus caballus* (horse) FGF21 (GenBank Accession No. XP_001489202, which is hereby incorporated by reference in its entirety) (SEQ ID NO: 181)

```
  1 mdwdktgfky qglwvpvlav lllgacqshp ipdsspllqf ggqvrqrhly tddaqeteah
 61 leiradgtva gavhrspesl lelkalkpgv iqilgvktsr flcqgpdgtl ygslhfdpva
121 csfrellled gynvyqsetl glplrlphhs spyqdpapra parflplpgf ppappeppgi
181 papeppdvgs sdplsmvgps rsrspsyts
```

*Ailuropoda melanoleuca* (giant panda) FGF21 (GenBank Accession No. XP_002917910, which is hereby incorporated by reference in its entirety) (SEQ ID NO: 182)

```
  1 mgwdearseq lglwvpvlav llleacqahp ipdsspllqf ggqvrqryly tddaqeteah
 61 lairadgtvv gaasrspesl lelkalkpgv iqilgvktsr flcqgpdgtl ygsvrfdpva
121 csfrellled gyniyhsetl glplrlpahn spyrdsaprg parflplpgl lpvppdppgi
181 lgpeppdvgs sdplsmvgps qgrspsyas
```

TABLE 5-continued

*Oryctolagus cuniculus* (rabbit) FGF21 (GenBank Accession No. XP_002723745, which is hereby incorporated by reference in its entirety) (SEQ ID NO: 183)

```
  1 mdwgkakcrp pglwvpalaa lllgacqahp ipdsspllqf gdqvrqqhly tddaqeteah
 61 leiradgtvv gaarrspesl lqmkalqpgi iqilgvqtsr flcqrpdgtl ygslhfdrea
121 csfrellred gynvylseal glplrlspgs sprrapaprg parflplpgl ppdlpeppgl
181 laaappdvds pdplsmvqpa ldqspsyts
```

*Gorilla gorilla (gorilla)* FGF21 (Ensembl Accession No. ENSGGOP00000001229, which is hereby incorporated by reference in its entirety) (SEQ ID NO: 184)

```
  1 mdsdetgfeh sglwvsvlag lllgacqahp ipdsspllqf ggqvrqryly tddaqqteah
 61 leiredgtvg gaadqspesl lqlkalkpgv iqilgvktsr flcqrpdgal ygslhfdpea
121 csfrellled gynvyqseah glplhlpgnk sphrdpaprg parflplpgl ppappeppgi
181 lapqppdvgs sdplsmvgps qgrspsyas
```

*Nomascus leucogenys* (Northern white-cheeked gibbon) FGF21 (Ensembl Accession No. ENSNLEP00000005639, which is hereby incorporated by reference in its entirety) (SEQ ID NO: 185)

```
  1 mdsdetgfeh sglwvpvlag lllgacqahp ipdsspllqf ggqvrqryly tddaqqteah
 61 leiredgtvg gaadqspesl lqlkalkpgv iqilgvktsr floqrpdgal ygslhfdpea
121 csfrellled gynvyqseah glplhlpgnk sphrdpaprg parflplpgl ppappeppgi
181 lapqppdvgs sdplsmvgps qgrspsyas
```

*Procavia capensis* (hyrax) FGF21 (Ensembl Accession No. ENSOGAG00000001210, which is hereby incorporated by reference in its entirety) (SEQ ID NO: 186)

```
  1 mdwakfgieh pglwvpvmav lllgacqgyp ipdsspllqf ggqvrqryly tddaqeteah
 61 leiradgtvv gaahrspesl lelkalkpgi iqilgvktsr flcqgpdgvl ygslrfdpva
121 csfrellled gynvyqseah glplrlpshn spqrdlasry parflplpgr ltvlpepsgv
181 lgpeppdvds sdplsmvgps qgrspsyas
```

*Cavia porcellus* (guinea pig) FGF21 (Ensembl Accession No. ENSCPOP00000000237, which is hereby incorporated by reference in its entirety) (SEQ ID NO: 187)

```
  1 mdwartecer prlwvsmlai llvgacqahp ipdsspllqf ggqvrqryly tddaqdtevh
 61 leiradgsvr giahrspesl lelkalkpgv iqilgirtsr flcqrpdgsl ygslhfdpea
121 csfrelllad gynvykseah glplhllrgd slsqepappg parflplpgl patppepprm
181 lppgppdvgs sdplsmvgpl wdrspsyts
```

*Tupaia belangeri* (tree shrew) FGF21 (Ensembl Accession No. ENSTBEP00000013946, which is hereby incorporated by reference in its entirety) (SEQ ID NO: 188)

```
  1 mgwdkarfeh lgawapvlav lllgacqayp ipdsspllqf ggqvrqryly tddtqdteah
 61 leiradgtvv gaahqspesl lelkalkpgv iqilgvktsr flcqrpdgal ygslhfdpea
121 csfrellled gyniyqsear glplrlpphd sphrdrtprg parflplpgl plvppelpgv
181 laleppdvgs sdplsmmgps qgqspsyas
```

*Sorex araneus* (shrew) FGF21 (Ensembl Accession No. ENSSARP00000002784, which is hereby incorporated by reference in its entirety) (SEQ ID NO: 189)

```
  1 mvwdkargqq lglwapmllg lllgacqahp lpdsspllqf ggqvrlrfly tddaqrtgah
 61 leiradgtvq gaahrtpecl lelkalkpgv iqilgvstsr flcqrpdgvl ygslrfdpea
121 csfrelllqd gynvyqseal glplylhpps apvsqepasr gavrflplpg lppasleppr
181 ppapvppdvg ssdplsmvgp perhspsyts
```

*Ictidomys tridecemlineatus* (squirrel) FGF21 (SEQ ID NO: 190)

```
  1 mdwvkaklep lglwvlvlaa ivigacqayp ipdsspllqf ggqvrqryly tddaqeteah
 61 leiradgtvv gaahqspesi lelkalkpgv iqilgvktsr flcqrpdgvl ygslhfdpea
121 csfreqlled gynvyqsesh glpvrlppns pyrdpappgp arflplpglp paaleppgil
181 gpeppdvgss dplsmvgplq grspsyas
```

*Loxodonta africana* (elephant) FGF21 (Ensembl Accession No. ENSLAFP00000016854, which is hereby incorporated by reference in its entirety) (SEQ ID NO: 191)

```
  1 mdwakfgle hpglwvpvma vlllgacqgh pipdsspllq fggqvrqryl ytddqeteah
 60 leiradgtva gaahrssesl lelkalkpgi iqilgvktsr flcqgpdgvl ygslhfdpaa
```

TABLE 5-continued

120csfrellled gynvywseah glpirlpshn spyrdpasry parflplpgl lpmlqeppgv
180lapeppdvds sdplsmvgps qgrspsyas

*Sus scrofa* (pig) FGF21 (GenBank Accession No. NP_001156882, which is hereby incorporated by reference in its entirety) (SEQ ID NO: 192)

1mgwaeakfer lglwvpvlav llgacqarpi pdsspllqfg gqvrqrylyt ddaqeteahl
61eiradgtvag varqspesll elkalkpgvi qilgvqtsrf lcqgpdgrly gslhfdpeac
121sfrellledg ynvyqsealg lplrlpphrs snrdlaprgp arflplpglp pappeppgil
181apeppdvgss dplsmvgpsh grspsyts

*Felis catus* (cat) FGF21 (Ensembl Accession No. ENSFCAP00000006832, which is hereby incorporated by reference in its entirety) (SEQ ID NO: 193)

1 mdwdeagsq rlglwvvlgv llpeacqahp ipdsspllqf ggqvrqrfly tddaqetevh
60leikadgtvv gtarrspesl lelkalkpgv iqilgvktsr flcqgpdgtl ygslrfdpaa
120csfrellled gyniyhsetl glplrlpphn spyrdlapra parflplpgl lpappeppgi
180lapeppdvgs sdplsmvgps qgrspsyas

*Otolemur garnetti* (bushbaby) FGF21 (Ensembl Accession No. ENSOGAG00000003581, which is hereby incorporated by reference in its entirety) (SEQ ID NO: 194)

1 dkartgfkh pgpwfpllav lllgacqahp ipdsspllqf ggqvrqryly tddaqeteah
60leiredgtvv gaaqqspesl lelkalkpgv iqilgvktsr flcqrpdggl ygslyfdpka
120csfrellled gynvywsety glplhlppan spywgpslrs parflplpgp paaspelpgi
180laleppdvgs sdplsmvgps qgrspsyas

*Rattus norvegicus* (Norway rat) FGF21 (GenBank Accession No. NP_570108, which is hereby incorporated by reference in its entirety) (SEQ ID NO: 195)

1mdwmksrvga pglwvclllp vfllgvceay pisdsspllq fggqvrqryl ytdddqdtea
61hleiredgtv vgtahrspes llelkalkpg viqilgvkas rflcqqpdgt lygsphfdpe
121acsfrelllk dgynvyqsea hglplrlpqk dsqdpatrgp vrflpmpglp hepqeqpgvl
181ppeppdvgss dplsmveplq grspsyas

*Mus musculus* (house mouse) FGF21 (GenBank Accession No. NP_064397, which is hereby incorporated by reference in its entirety) (SEQ ID NO: 196)

1mewmrsrvgt lglwvrllla vfllgvyqay pipdsspllq fggqvrqryl ytdddqdtea
61hleiredgtv vgaahrspes llelkalkpg viqilgvkas rflcqqpdga lygsphfdpe
121acsfrellle dgynvyqsea hglplrlpqk dspnqdatsw gpvrflpmpg llhepqdqag
181flppeppdvg ssdplsmvep lqgrspsyas Amino acid sequence of *Vicugna pacos* (alpaca) FGF21 (Ensembl Accession No. ENSVPAP00000005562, which is hereby incorporated by reference in its entirety) (SEQ ID NO: 197) (partial sequence corresponding to human FGF21 residues 1 to 78, 169 to 171, and 183 to 209)

1MDWDEAKFEH RGLWVPVLTV LLLGACQARP IPDSSPLLQF GGQVRQRYLY TDDAQETEAH
61LEIRADGTVV GVARQPE--- ---------- ---------- ---------- ----------
121---------- ---------- ---------- ---------- --------GI P---------
181--PEPPDVGS SDPLSMVGPS YSRSPSYTS

Amino acid sequence of *Anolis carolinensis* (Anole lizard) FGF21 (Ensembl Accession No. ENSACAP00000016895, which is hereby incorporated by reference in its entirety) (SEQ ID NO: 198)

1CKSKGGGKGG ERMWVDLVFW AALLRTAPAL PLRNSNPIYQ FDGQVRLRHL YTADEQTHLH
61LEILPDGTVG GSRFQNPFSL MEIKAVKPGV IRMQAKKTSR FLCMKPNGRL YGSLFYSEEA
121CNFHEKVLSD GYNLYYSENY NIPVSLSSAG NLGQSRQLPP FSQFLPLVNK IPLEPVLEDF
181DFYGHQLDVE SADPLSILGQ NPGFMSPSYV F

Amino acid sequence of *Gadus morhua* (Cod) FGF21 (Ensembl Accession No. ENSGMOP00000013789, which is hereby incorporated by reference in its entirety) (SEQ ID NO: 199)

1LLLATLLHIG LSFYVPDSGP LLWLGDQVRE RHLYTAESHR RGLFLEMSPD GQVTGSAAQT
61PLSVLELRSV RAGDTVIRAR LSSLYLCVDR AGHLTGQRQY TESDCTFREV ILEDGYTHFL
121SVHHGLPISL APRHSPGRQG LRFSRFLPLR SSLSEDRVAE PPDSPLNLDS EDPLGMGLGS
181LLSPAFSM

TABLE 5-continued

| Amino acid sequence of *Latimeria chalumnae* (Coelacanth) FGF21 (Ensembl Accession No. ENSLACP00000003781, which is hereby incorporated by reference in its entirety) (SEQ ID NO: 200) |
|---|
| 1 MLCQSFVILS QKFIFGLFLT GLGLTGLAWT RPFQDSNPIL QYSDSIRLRH LYTASESRHL<br>61 HLQINSDGQV GGTTKQSPYS LLEMKAVKTG FVVIRGKKSA RYLCMERSGR LYGSLQYTEK<br>121 DCTFKEVVLA DGYNLYVSEE HQATVTLSPM RARIAQGKKI PPFSHFLPMV NKVPVEDVAA<br>181 EMEFVQVLRE MTADVDSPDP FGMTWEESVH SPSFFA |
| Amino acid sequence of *Tursiops truncatus* (Dolphin) FGF21 (Ensembl Accession No. ENSTTRP00000013808, which is hereby incorporated by reference in its entirety) (SEQ ID NO: 201) |
| 1 MGWDKTKLEH LGLWVPVLAV LLGPCQAHPI PDSSPLLQFG GQVRQRYLYT DDAQETEAHL<br>61 EIRADGTVVG TARRSPEGVK TSRFLCQGPE GRLYGSLHFN PQACSFRELL LEDGYNVYQS<br>121 EALGIPLRLP PHRSSNWDLA PRGPARFLPL PGFLPPPLEP PGILAPEPPN VGSSDPLSMV<br>181 GPSHGRSPSY TS |
| Amino acid sequence of *Mustela putorius furo* (Ferret) FGF21 (Ensembl Accession No. ENSMPUP00000003687, which is hereby incorporated by reference in its entirety) (SEQ ID NO: 202) |
| 1 MGWEEARSEH LGLWVPVLAV LLLGACQAYP IPDSSPLLQF GGQVRQRYLY TDDAQETEAH<br>61 LEIRADGTVV GAARRSPESL LELKALKPGV IQILGVKTSR FLCQGPNGTL YGSFHFDPVA<br>121 CSFREVLLED GYNIYHSETL GLPLRLPPHN SPHRDLAPRG PARFLPLPGL LPATPESRGI<br>181 PAPEPPNVGS SDPLSMVGPL QGQSPSYTS |
| Amino acid sequence of *Takifugu rubripes* (Fugu) FGF21 (Ensembl Accession No. ENSTRUP00000033950, which is hereby incorporated by reference in its entirety) (SEQ ID NO: 203) |
| 1 FIYLFIQTAL FSPSKWFNFY LPDSNPLLSF DSHGRGIHLY TDNQRRGMYL QMSTDGSVSG<br>61 SDVQTANSVL ELKSVRNGHV VIRGKSSSLF LCMDSRGRLW GQRHPTEADC TFREVLLADG<br>121 YTRFLSLHNG TPVSLAPKQS PDQHTVPFTR FLPLRNTLAE ESMSEPPSNQ QRYFNIDSDD<br>181 LLGMDLNAMV SPQFSGDK |
| Amino acid sequence of *Dipodomys ordii* (Kangaroo rat) FGF21 (Ensembl Accession No. ENSDORP00000001155, which is hereby incorporated by reference in its entirety) (SEQ ID NO: 204) |
| 1 MDQAKTRVGA RGLGGLVLAV IILGACKARP IPDSSPLLQF GGQVRLRHLY TDDTQETEAH<br>61 LEIRADGTVV GTAHRSPESL LELKALKPGV IQILGIKTSR FLCQRPDGTL YGSLHFDPEV<br>121 CSFQELLLED GYNIYRSEAL GLPLRLSPDP APWGPARFLP LPGVPPAPPE PPGILAPEPP<br>181 DVGSSDPLSM VGLLQGRSPS YAS |
| Amino acid sequence of *Echinops telfairi* (Lesser hedgehog tenrec) FGF21 (Ensembl Accession No. ENSETEP00000008707, which is hereby incorporated by reference in its entirety) (SEQ ID NO: 205) |
| 1 MGCTKSGWKS PGLWVPVLAS LLLGGCGAHP IPDSSPLLQF GGQVRQRYLY TDDAQTTEAH<br>61 LEIRADGTVG GVAHQSPEKF LSQWREKPLR SLHFDPAACS FREKLLEDGY NLYHSETHGL<br>121 PLRLPPRGGD PSSQPGARFP PLPGQLPQLQ ETPGVLAPEP PDVGSSDPLS MVGPWRGQSP<br>181 SYAS |
| Amino acid sequence of *Macaca mulatta* (Rhesus monkey) FGF21 (Ensembl Accession No. ENSMMUP00000031540, which is hereby incorporated by reference in its entirety) (SEQ ID NO: 206) |
| 1 MDSDETGFEH SGLWVPVLAG LLLGACQAHP IPDSSPLLQF GGQVRQRYLY TDDAQQTEAH<br>61 LEIREDGTVG GAAHQSPESE CGPEPGSEGG GAVGGAEGPG LLGLREAGLG PGSWLHFDPE<br>121 ACSFRELLLE NGYNVYQSEA HGLPLHLPGN KSPHRDPASQ GPARFLPLPG LPPAPPEPPG<br>181 ILAPQPPDVG SSDPLSMVGP SQARSPSYAS |
| Amino acid sequence of *Microcebus murinus* (Mouse lemur) FGF21 (Ensembl Accession No. ENSMICP00000012089, which is hereby incorporated by reference in its entirety) (SEQ ID NO: 207) |
| 1 MGWDEAGAGF EHPGLWFPML GVLLLGACQA YPIPDSSPLL QFGGQVRQRH LYTDDIQETE<br>61 AHLEIRADGT VVGAARQSPE LELKALKPGV IQILGVKTSR FLCQRPDGAL YGSLHFDPEC<br>121 SFRELLLEDG YNVYCPYLPL HLSPRIELAG SRSALPLPPA PERRILAPEP PDGSSDPLSM<br>181 VGPSQGRSPS YAS |

TABLE 5-continued

Amino acid sequence of *Ochotona princeps* (Pika) FGF21 (Ensembl Accession No. ENSOPRP00000006754, which is hereby incorporated by reference in its entirety) (SEQ ID NO: 208)

1 KDMDGLQPPG LRVPVLAALL LGVGQARPIP DSSPLLQFGG QVRQRHLYTD DAQESEVHLE

61 IRADGTVAGT ARRSPESLLE MKALKPGVIQ ILGVHTSRFL CQRPDGTLYG SLHFDHKACS

121 FREQLLEDGY NVYHSETHGL PLRLSPDRAP RGPARFLPLP GPPPDLLVPP LPPDVLAPEP

181 PDVDSPDPLS MVGPLQGQSP SYTS

Amino acid sequence of *Xiphophorus maculatus* (Platyfish) FGF21 (Ensembl Accession No. ENSXMAP00000001576, which is hereby incorporated by reference in its entirety) (SEQ ID NO: 209)

1 CPFPFLFLIL SLPFFSSSFY IPESNPIFAF RNQLREVHLY TENHRRGLYV EIHLDGRVTG

61 SDAQSPYSVL QIKSVKPGHV VIKGQTSSLF LCMDDSGNLR GQTTYDEADC SFRELLLADG

121 YTRFLNSQHG VPLSLASRNS PDRHSVPFTR FLPLRNTLTV SEESTKTQRD FNLDSDDLLG

181 MG

Amino acid sequence of *Gasterosteus aculeatus* (Stickleback) FGF21 (Ensembl Accession No. ENSGACP00000010703, which is hereby incorporated by reference in its entirety) (SEQ ID NO: 210)

1 SLLLMVPLPF CSSFYLTDSS PLLPFNNQVK EVHLYTAENH RRAMYLQIAL DGSVSGSDAR

61 STYSVLQLKS IQPGHVVIRG KASSMFLCVD SGGRLRGQGP YSEADCSFRE LLLGDGYTRF

121 LSSQHGSPLS LASRPSPDPN SVPFTRFLPI RTAPEAESVI EEPPSNQRYV NVDSEDLLGM

181 GLNTVVSPQF SA

Amino acid sequence of *Sarcophilus harrisii* (Tasmanian devil) FGF21 (Ensembl Accession No. ENSSHAP00000005963, which is hereby incorporated by reference in its entirety) (SEQ ID NO: 211) (partial sequence corresponding to human FGF21 residues 3 to 172)

1 VSAMGLRERA PRYLAPLLSL LLACRASGHP LPDSSPMLLF GGQVRLRHLY TDVGQEAEAH

61 VELASDGTVR AAARRSPNSL LELKAVKPGI VRILAVHSSR FLCMRPNGEL YGAIHYDPSA

121 CNFRERLLGD GYNVYESEAH GRTLRLPPKA APGPAGPSRF LPLPG

Amino acid sequence of *Macropus eugenii* (Wallaby) FGF21 (Ensembl Accession No. ENSMEUP00000013936, which is hereby incorporated by reference in its entirety) (SEQ ID NO: 212)

1 TEEPSTGSRH LGQWAPGLPG PLLSLLLAYR GWGSPIPDSS PMLLFGGQVR LRHLYTDDGQ

61 DTEAHVELGP DGVVRAVAER SPNSLLELKA VKPGVIRILA VQSSRFLCMR PNGELYGAVH

121 YDPSACNFRE HLLGDGYNVY ESETHRRTLR LSPSLGQAGP SRFLPLPGDW LPGPDPPWAQ

181 GPEPPDVGSA DPLSMVGAVQ GLSPSYSS

Amino acid sequence of *Xenopus tropicalis* (Western clawed frog) FGF21 (Ensembl Accession No. ENSXETP00000009917, which is hereby incorporated by reference in its entirety) (SEQ ID NO: 213) (partial sequence corresponding to human FGF21 residues 1 to 169)

1 RGGRTKKKTL LRKWLCLLAI MLSRSRFSLA NPIQNSNPIL SNDNQVRTQY LYTDNNNMHL

61 YLQITHNGVV TGTEEKNDYG VLEIKAVKAG VVVIKGIRSN LYLCMDSRHQ LYASAYDKDD

121 CHFHEKITPD NYNMYSSEKH SEYVSLAPLK GSQMARFLPI

Amino acid sequence of *Danio rerio* (Zebrafish) FGF21 (Ensembl Accession No. ENSDARP00000094287, which is hereby incorporated by reference in its entirety) (SEQ ID NO: 214)

1 MLLACFFIFF ALFPHLRWCM YVPAQNVLLQ FGTQVRERLL YTDGLFLEMN PDGSVKGSPE

61 KNLNCVLELR SVKAGETVIQ SAATSLYLCV DDQDKLKGQH HYSALDCTFQ ELLLDGYSFF

121 LSPHTNLPVS LLSKRQKHGN PLSRFLPVSR AEDSRTQEVK QYIQDINLDS DDPLGMGHRS

181 HLQTVFSPSL HTKK

In certain embodiments according to the present invention, the portion from FGF21 of the chimeric protein of the present invention includes a polypeptide sequence that has at least 80%, at least 85%, at least 90%, at least 95%, at least 97%, or at least 99% amino acid sequence identity to the corresponding amino acid sequences of SEQ ID NO: 176 described herein.

It will be understood that the portion from FGF21 of the chimeric protein of the present invention may be from a nucleotide sequence that encodes an FGF21 protein (e.g., those encoding orthologs) from a mammal or even a non-mammalian species. For example, a nucleotide sequence encoding a mammalian or non-mammalian FGF21 protein according to the present invention may include, but is not limited to, those FGF-encoding nucleotide sequences in Table 6.

TABLE 6

Human FGF21 gene coding sequence (SEQ ID NO: 215) (GenBank Accession No. NM_019113, which is hereby incorporated by reference in its entirety)

```
151 atggactcgg acgagaccgg gttcgagcac tcaggactgt gggtttctgt gctggctggt
211 cttctgctgg gagcctgcca ggcacacccc atccctgact ccagtcctct cctgcaattc
271 gggggccaag tccggcagcg gtacctctac acagatgatg cccagcagac agaagcccac
331 ctggagatca gggaggatgg gacggtgggg ggcgctgctg accagagccc cgaaagtctc
391 ctgcagctga aagccttgaa gccgggagtt attcaaatct tgggagtcaa gacatccagg
451 ttcctgtgcc agcggccaga tggggccctg tatggatcgc tccactttga ccctgaggcc
511 tgcagcttcc gggagctgct tcttgaggac ggatacaatg tttaccagtc cgaagcccac
571 ggcctcccgc tgcacctgcc agggaacaag tccccacacc gggaccctgc accccgagga
631 ccagctcgct tcctgccact accaggcctg ccccccgcac tcccggagcc acccggaatc
691 ctggcccccc agccccccga tgtgggctcc tcggaccctc tgagcatggt gggaccttcc
751 cagggccgaa gccccagcta cgcttcctga
```

*Pongo abelii* (Sumatran orangutan) FGF21 gene coding sequence (SEQ ID NO: 216) (GenBank Accession No. XM_002829519, which is hereby incorporated by reference in its entirety)

```
165     atggac tcggacgaga ccgggttcga gcactcagga ctgtgggttc ctgtgctggc
221 tggtcttctg ctgggagcct gccaggcaca ccccatccct gactccagtc ctctcctgca
281 attcgggggc caagtccggc agcggtacct ctacacagat gatgcccagc agacagaagc
341 ccacctggag atcagggagg atgggacggt gggggcgct gctgaccaga gccccgaaag
401 tctcctgcag ctgaaagcct tgaagccggg agttattcaa atcttgggag tcaagacatc
461 caggttcctg tgccagaggc cagatggggc cctgtatgga tcgctccact ttgaccctga
521 ggcctgcagc ttccgggagc tgcttcttga ggacggatac aatgtttatc agtccgaggc
581 ccatggcctc ccgctgcacc tgccgggaaa caagtcccca caccgggacc ctgcaccccg
641 aggaccagct cgcttcctgc cactaccagg cctgcccccc gcacccccag agccgcccgg
701 aatcctggcc ccccagcccc ccgatgtggg ctcctcggac cctctgagca tggtgggacc
761 ttcccagggc cgaagcccca gctatgcttc ctga
```

*Pan troglodytes* (chimpanzee) FGF21 gene coding sequence (SEQ ID NO: 217) (GenBank Accession No. XM_524333, which is hereby incorporated by reference in its entirety)

```
573   atggactc ggacgagacc gggttcgagc actcaggact gtgggtttct gtgctggctg
631 gtcttctgct aggagcctgc caggcacacc ccatccctga ctccagtcct ctcctgcaat
691 tcgggggcca agtccggcag cggtacctct acacagatga tgcccagcag acagaagccc
751 acctggagat cagggaggat gggacggtgg ggggcgctgc tgaccagagc cccgaaagtc
811 tcctgcagct gaaagccttg aagccgggag ttattcaaat cttgggagtc aagacatcca
871 ggttcctgtg ccagaggcca gatggggccc tgtatggatc gctccacttt gaccctgagg
931 cctgcagctt ccgggagctg cttcttgagg acggatacaa tgtttaccag tccgaggccc
991 acggcctccc gctgcacctg ccggggaaca agtccccaca ccgggaccct gcaccccgag
1051 gaccagctcg cttcctgcca ctaccaggcc tgcccccgc accccggag ccacccggaa
1111 tcctggcccc ccagcccccc gatgtgggct cctcagaccc tctgagcatg gtgggacctt
1171 cccagggccg aagccccagc tacacttcct ga
```

*Canis lupus familiaris* (dog) FGF21 gene coding sequence (SEQ ID NO: 218) (GenBank Accession No. XM_541510, which is hereby incorporated by reference in its entirety)

```
1 atgggctggg ccgaggccgg gttcgagcac ctgggactgt gggtccctgt gctggctgtg
61 cttttgctgg aagcctgccg ggcacatccg atccctgact ccagcccct cctacaattt
121 ggaggtcaag ttcgacagcg gtacctctac accgacgatg cccaggagac agaggcccac
181 ctagagatca gggccgatgg cacagtggtg ggggctgccc gccagagccc tgaaagtctc
241 ctggagctga aagccctaaa gccaggggtc attcaaatct tgggagtcaa aacatccagg
301 ttcctgtgcc agggcccaga tgggacacta tatggctcgc tccatttcga ccctgtggcc
361 tgcagtttcc gagaactgct tcttgaggat gggtacaaca tctaccactc cgagaccctt
421 ggtctcccgc ttcgcctgcg cccccacaac tccgcatacc gggacttggc accccgcggg
481 cctgcccgct tcctgccact gccaggcctg cttccagcac cccagagcc tccagggatc
541 ctggccccgg agcctcctga cgtgggctcc tcggaccctc tgagcatggt ggggccttca
601 cagggccgga gtcccagcta tgcttcctaa
```

*Bos taurus* (bovine) FGF21 gene coding sequence (SEQ ID NO: 219) (GenBank Accession No. XP_001789587, which is hereby incorporated by reference in its entirety)

```
1 atgggctggg acgaggccaa gttcaagcac ttgggactgt gggtccctgt gctggctgtc
61 ctcctgctag gaacctgccg ggcgcatccc attccagact ccagcccct cctccagttt
121 gggggccaag tccgccagcg gtacctctac acggatgatg cccaggagac agaggcccac
181 ctggagatca gggccgatgg cacagtggtg gggcagccc gccagagccc cgaaagtctc
241 ttggagctga aagccctgaa gccaggcgtc attcagatct tgggagttaa aacatccagg
301 tttctctgcc aggggccaga tgggaagctg tacggatcgc tgcactttga ccccaaagcc
361 tgcagctttc gggagctgct tcttgaagat ggatacaacg tctaccagtc ggagaccctg
421 ggccttccac tccgcctgcc cccccagcgc tcgtccaacc gggacccggc cccgcgggga
481 cctgctcgct tccttccact gccgggcctg cccgcggcgc ccccggatcc tccagggatc
541 ttggccccccg agcctcccga cgtgggctcc tcggatcccc tgagtatggt gggaccctcg
601 tatggccgaa gccccagcta cacttcttga
```

TABLE 6-continued

*Equus caballus* (horse) FGF21 gene coding sequence (SEQ ID NO: 220) (GenBank Accession No. XM_001489152, which is hereby incorporated by reference in its entirety)

```
  1 atggactggg acaagacggg gttcaagtac cagggactgt gggtccctgt gctggctgtc
 61 cttctgctgg gagcctgcca gtcacacccc atccctgact ccagtcccct cctccaattc
121 gggggccaag tcaggcagcg ccacctctac acagatgatg cccaggagac agaggcgcac
181 ctggagatca gggctgacgg cactgtggca ggggctgtcc accggagccc agaaagtctc
241 ttggagctga aagccctgaa gccaggggta attcaaatct tgggagtcaa gacatccagg
301 tttctgtgcc aggggccaga cgggacgctg tacggatcgc tccacttcga ccccgtggcc
361 tgcagcttcc gggagctgct tctcgaagac ggctacaacg tttaccagtc tgagaccctt
421 ggcctcccac tccgcctgcc ccaccacagc tccccatacc aggatccggc cctcgggca
481 cccgcccgct tcctgccgct gccaggcttt cccccagcac cccggagcc tccagggatc
541 ccggcccccg agcccccgga cgtgggctcc tcggaccccc tgagcatggt ggggccttca
601 cgcagccgga gccccagcta cacttcctga
```

*Ailuropoda melanoleuca* (giant panda) FGF21 gene coding sequence (SEQ ID NO: 221) (GenBank Accession No. XM_002917864, which is hereby incorporated by reference in its entirety)

```
  1 atgggctggg acgaggccag gtccgagcag ctggggctgt gggtccctgt gctggctgtc
 61 cttttgctgg aagcttgcca ggcacaccct atccctgact ccagcccccct cctccaattc
121 ggaggccaag ttcgacagcg gtacctctac acggacgatg cccaggagac agaggcccac
181 ctagcgatca gggctgatgg cacagtggtg ggggctgcca gccggagccc agaaagtctc
241 ttggagctga aagccctgaa accgggggtc attcaaatcc tgggagtgaa aacatctagg
301 ttcctgtgcc agggcccaga tgggacactg tacggatcgg tccgcttcga ccccgtagcc
361 tgcagcttcc gggaactgct cctggaggat gggtacaaca tctaccactc tgagaccctc
421 ggcctcccac ttcgcctgcc cgcccacaac tctccatacc gggactcggc gccccggggg
481 cctgcccgct tcctgcccct gccaggcctg cttccggtcc ccccggaccc cccagggatc
541 ctgggccccg agcctcccga cgtgggctcc tcggaccccc tgagcatggt ggggccttca
601 cagggccgaa gtcccagcta cgcttcctga
```

*Oryctolagus cuniculus* (rabbit) FGF21 gene coding sequence (SEQ ID NO: 222) (GenBank Accession No. XM_002723699, which is hereby incorporated by reference in its entirety)

```
  1 atggactggg gcaaggccaa gtgccggccc ccggggctgt gggtccccgc gctcgctgcc
 61 ctgctgctgg gggcctgcca ggcacacccc atccctgact ccagcccccct cctccagttt
121 ggggaccaag tgcggcagca gcacctgtac acggacgatg cgcaggaaac agaagcccac
181 ctggagatca gggcggatgg cacggtggtg gggcctgccc ggaggagccc agaaagtctc
241 ttgcagatga aagccttaca accggggatc attcagatct tgggggtcca gacgtccagg
301 ttcctctgcc agaggccgga tggcacgctc tacggctcgc tccacttcga ccgcgaggcc
361 tgcagcttcc gggagctgct gcgtgaggat gggtacaacg tttacctctc ggaggccctg
421 ggcctgcccc tgcgcctgtc cccggcagc tccccacgca gggcgccggc cccccggga
481 ccagcccgct tcctgccgct gcccggcctg ccgccagacc ttccggaacc gccaggcctc
541 ctggccgccg cgcccccga tgtcgactcc ccggaccccc tgagcatggt gcagcctgcg
601 ctggaccaga gccccagcta cacctcctga
```

*Gorilla gorilla* (*gorilla*) FGF21 gene coding sequence (SEQ ID NO: 223) (Ensembl Accession No. ENSGGOT00000001253, which is hereby incorporated by reference in its entirety)

```
151 ATGGACTCGG ACGAGACCGG GTTCGAGCAC TCAGGACTGT GGGTTTCTGT GCTGGCTGGT
211 CTTCTGCTGG GAGCCTGCCA GGCACACCCC ATCCCTGACT CCAGTCCTCT CCTGCAATTC
271 GGGGGCCAAG TCCGGCAGCG GTACCTCTAC ACAGATGATG CCCAGCAGAC AGAAGCCCAC
331 CTGGAGATCA GGGAGGATGG GACGGTGGGG GGTGCTGCTG ACCAGAGCCC TGAAAGTCTC
391 CTGCAGCTGA AAGCCTTGAA GCCGGGAGTT ATTCAAATCT TGGGAGTCAA GACATCCAGG
451 TTCCTGTGCC AGAGGCCAGA TGGGGCCCTG TATGGATCGC TCCACTTTGA CCCTGAGGCC
511 TGCAGCTTCC GGGAGCTGCT TCTTGAGGAC GGATACAATG TTTACCAGTC CGAGGCCCAC
571 GGCCTCCCGC TGCACCTGCC GGGGAACAAG TCCCCACACC GGGACCCTGC ACCCCGAGGA
631 CCAGCTCGCT TCCTGCCACT ACCAGGCCTG CCCCCCGCAC CCCCGGAGCC ACCCGGAATC
691 CTGGCCCCCC AGCCCCCCGA TGTGGGCTCC TCGGACCCTC TGAGCATGGT GGGACCTTCC
751 CAGGGCCGAA GCCCCAGCTA CGCTTCCTG
```

*Nomascus leucogenys* (Northern white-cheeked gibbon) FGF21 gene coding sequence (SEQ ID NO: 224) (Ensembl Accession No. ENSNLET00000005931, which is hereby incorporated by reference in its entirety)

```
 587       ATGG ACTCGGACGA GACCGGGTTC GAGCACTCAG GACTGTGGGT TCCTGTGCTG
 647 GCTGGTCTTC TGCTGGGAGC CTGCCAGGCA CACCCCATCC CTGACTCCAG TCCTCTCCTG
 707 CAATTCGGGG GCCAAGTCCG GCAGCGGTAC CTCTACACAG ATGATGCCCA GCAGACAGAA
 767 GCCCACCTGG AGATCAGGGA GGATGGGACG GTGGGGGGCG CTGCTGACCA GAGCCCTGAA
 831 AGTCTCCTGC AGCTGAAAGC CTTGAAGCCG GGAGTTATTC AAATCTTGGG AGTCAAGACA
 891 TCCAGGTTCC TATGCCAGAG GCCAGATGGG GCCCTGTATG GATCGCTCCA CTTTGACCCT
 951 GAGGCCTGCA GCTTCCGGGA GCTGCTTCTT GAGGACGGAT ACAATGTTTA CCAGTCCGAG
1011 GCCCATGGCC TCCCGCTGCA CCTGCCGGGG AACAAGTCCC CACACCGGGA CCCTGCACCC
1071 CGAGGACCAG CTCGCTTCCT GCCACTACCA GGCCTGCCCC CTGCACCCCC AGAGCCGCCC
```

TABLE 6-continued

```
1131 GGAATCCTGG CCCCCCAGCC CCCCGATGTG GGCTCCTCGG ACCCTCTGAG CATGGTGGGA
1191 CCTTCCCAGG GCCGAAGCCC CAGCTACGCT TCCTGA
```

*Procavia capensis* (hyrax) FGF21 gene coding sequence (SEQ ID NO: 225) (Ensembl Accession No. ENSPCAT00000001288, which is hereby incorporated by reference in its entirety)

```
  1 ATGGACTGGG CCAAGTTTGG GATCGAGCAC CCGGGACTGT GGGTCCCGGT GATGGCAGTA
 61 CTTCTGCTGG GAGCCTGCCA AGGATACCCT ATTCCTGACT CCAGCCCCCT TCTCCAATTC
121 GGAGGCCAGG TCCGGCAACG TTACCTCTAC ACAGATGACG CGCAGGAGAC CGAGGCCCAC
181 CTGGAGATCC GAGCAGACGG CACGGTGGTG GGGGCTGCCC ACCGGAGCCC CGAGAGTCTC
241 TTGGAGCTGA AAGCTTTGAA GCCCGGCATA ATTCAGATCT TGGGAGTCAA GACATCCAGA
301 TTCCTCTGCC AGGGTCCTGA TGGGGTGCTG TATGGATCGC TCCGTTTTGA CCCAGTGGCC
361 TGCAGCTTCC GGGAGCTGCT TCTTGAAGAT GGATACAATG TTTACCAGTC TGAGGCCCAC
421 GGCCTCCCGC TTCGCCTACC ATCCCACAAT TCCCCACAGA GGGACCTGGC GTCCCGGGTG
481 CCAGCCCGCT TCCTGCCACT GCCAGGCCGG CTCACGGTGC TCCCAGAACC TTCGGGGGTC
541 CTGGGCCCTG AGCCCCCCGA TGTGGACTCC TCAGACCCCC TGAGCATGGT GGGGCCTTCG
601 CAGGGCCGAA GCCCCAGTTA CGCCTCCTGA
```

*Cavia porcellus* (guinea pig) FGF21 gene coding sequence (SEQ ID NO: 226) (Ensembl Accession No. ENSCPOT00000000273, which is hereby incorporated by reference in its entirety)

```
  1 ATGGACTGGG CCCGGACTGA GTGTGAGCGC CCAAGGCTGT GGGTCTCCAT GCTGGCCATC
 61 CTTCTGGTGG GAGCCTGCCA GGCACACCCT ATCCCTGACT CCAGCCCCCT CCTCCAGTTT
121 GGGGGCCAGG TCCGGCAGCG GTACCTCTAC ACAGATGATG CTCAGGACAC TGAAGTGCAC
181 CTGGAGATCA GGGCCGATGG CTCAGTACGG GGCATTGCCC ACAGGAGCCC TGAAAGTCTC
241 CTGGAGCTGA AAGCCTTGAA GCCAGGAGTC ATTCAGATCT TGGGAATCAG GACTTCCAGG
301 TTCCTGTGCC AGAGGCCCGA TGGGAGTCTG TATGGATCAC TCCACTTTGA TCCTGAGGCC
361 TGCAGCTTCC GGGAGCTGCT GCTTGCTGAT GGCTACAATG TCTACAAGTC TGAAGCCCAC
421 GGCCTCCCTC TGCACCTGCT GCGCGGTGAC TCTCTATCGC AGGAACCAGC ACCCCCAGGA
481 CCAGCCCGAT TTCTGCCACT ACCAGGCCTG CCCGCAACAC CCCCGGAGCC ACCCAGGATG
541 CTGCCCCCAG GGCCCCCAGA TGTGGGCTCC TCGGACCCTT TGAGCATGGT GGGGCCTTTA
601 TGGGACCGAA GCCCCAGCTA TACTTCCTGA
```

*Tupaia belangeri* (tree shrew) FGF21 gene coding sequence (SEQ ID NO: 227) (Ensembl Accession No. ENSTBET00000016056, which is hereby incorporated by reference in its entirety)

```
  1 ATGGGCTGGG ACAAGGCCCG GTTCGAGCAC CTGGGAGCGT GGGCTCCTGT GCTGGCTGTC
 61 CTCCTCCTGG GAGCCTGCCA GGCATACCCC ATCCCTGACT CCAGCCCCCT CCTACAATTC
121 GGGGGCCAGG TCCGGCAGCG GTACCTCTAC ACGGACGACA CGCAGGACAC AGAAGCCCAC
181 CTTGAGATCA GGGCCGACGG CACCGTGGTG GGGGCCGCCC ACCAAAGCCC GGAAAGTCTC
241 CTGGAGCTGA AAGCCTTGAA GCCGGGGGTC ATTCAAATCC TGGGAGTCAA GACCTCCAGG
301 TTCCTGTGCC AGAGGCCAGA CGGGGCCCTG TACGGGTCGC TTCACTTCGA CCCCGAGGCC
361 TGCAGCTTCC GGGAGCTGCT TCTCGAGGAT GGATACAACA TTTACCAGTC TGAGGCTCGT
421 GGCCTCCCCC TGCGCCTGCC GCCCCACGAC TCCCCACATC GGGACCGGAC CCCTCGGGGA
481 CCAGCTCGTT TCCTGCCGCT GCCTGGCCTG CCCCTGGTTC CTCCAGAGCT GCCAGGGGTC
541 CTGGCCCTTG AGCCCCCCGA CGTGGGCTCC TCAGACCCGC TGA
```

*Sorex araneus* (shrew) FGF21 gene coding sequence (SEQ ID NO: 228) (Ensembl Accession No. ENSSART00000003074, which is hereby incorporated by reference in its entirety)

```
  1 ATGGTCTGGG ACAAGGCCAG GGGGCAGCAG TTGGGACTGT GGGCCCCCAT GCTGCTGGGC
 61 TTGCTGCTGG GTGCCTGCCA GGCACACCCC CTCCCTGACT CCAGCCCCCT CCTCCAATTT
121 GGGGGCCAAG TCCGACTGAG GTTCCTGTAC ACCGACGATG CCCAGAGGAC AGGGGCGCAC
181 CTGGAGATCA GGGCCGACGG CACAGTGCAG GGTGCGGCCC ACAGGACCCC AGAATGTCTC
241 CTGGAGCTGA AAGCCTTGAA GCCAGGCGTA ATTCAAATCC TTGGGGTCAG CACATCCAGA
301 TTCCTGTGCC AGCGGCCCGA TGGGGTCCTG TATGGATCGC TTCGCTTTGA CCCAGAGGCC
361 TGCAGTTTCC GGGAACTTCT TCTCCAGGAT GGATATAACG TTTACCAGTC TGAGGCCCTG
421 GGTCTCCCGC TCTACCTACA CCCGCCCAGT GCCCCAGTGT CCCAGGAACC AGCCTCACGG
481 GGCGCCGTCC GCTTCCTGCC ACTGCCAGGA CTGCCACCTG CCTCCCTGGA GCCCCCCAGG
541 CCCCCCGCCC CGGTGCCTCC AGACGTGGGT TCCTCAGACC CCCTGA
```

*Ictidomys tridecemlineatus* (squirrel) FGF21 gene coding sequence (SEQ ID NO: 229)

```
  1 ATGTACCCCA TCCCTGACTC AAGCCCCCTC CTCCAATTTG GGGGCCAAGT CCGGCAGCGG
 61 TACCTGTACA CAGATGATGC CCAGGAGACT GAGGCCCACC TGGAGATCAG GGCTGATGGC
121 ACCGTGGTGG GGGCTGCCCA TCAAAGCCCG GAAAGTCTCT TGGAACTGAA AGCCTTGAAG
181 CCTGGGGTCA TTCAAATCTT GGGGGTCAAA ACATCCAGGT TCCTGTGCCA GAGGCCAGAT
241 GGAGTGCTGT ATGGATCGCT CCACTTTGAC CCTGAGGCCT GCAGCTTCCG GGAGCAGCTT
301 CTGGAGGACG GGTACAACGT TTACCAGTCA GAATCCCACG GCCTCCCCGT GCGCCTGCCC
361 CCTAACTCAC CATACCGGGA CCCAGCGCCG CCAGGACCAG CCCGCTTCCT TCCACTGCCA
421 GGCCTGCCCC CAGCAGCCCT GGAGCCGCCA GGGATCCTGG GCCCTGAGCC CCCTGATGTG
481 GGCTCCTCCG ACCCACTCAG CATGGTGGGG CCTTTGCAGG GCCGAAGCCC CAGTTACGCT
541 TCCTGA
```

TABLE 6-continued

*Loxodonta africana* (elephant) FGF21 gene coding sequence (SEQ ID NO: 230) (Ensembl Accession No. ENSLAFT00000022429, which is hereby incorporated by reference in its entirety)

```
  1 ATGGACTGGG CCAAGTTTGG GTTGGAGCAC CCAGGACTGT GGGTCCCTGT GATGGCTGTC
 61 CTTCTGCTGG GAGCCTGCCA GGGACACCCC ATCCCTGACT CCAGCCCCCT CCTCCAATTC
121 GGGGGCCAGG TCCGGCAACG TTACCTCTAC ACAGATGATC AGGAGACCGA GGCCCACCTG
181 GAGATCAGAG CAGATGGCAC AGTGGCGGGA GCCGCTCACC GGAGCTCTGA GAGTCTCTTG
241 GAGCTGAAAG CTTTGAAGCC TGGAATAATT CAGATCTTGG GGGTCAAGAC ATCCCGGTTC
301 CTGTGCCAGG GGCCTGATGG GGTGCTGTAC GGATCGCTCC ATTTCGACCC AGCCGCCTGC
361 AGCTTCCGGG AGCTGCTTCT TGAAGATGGA TACAATGTTT ACTGGTCCGA GGCCCATGGA
421 CTCCCAATCC GCCTGCCCTC CCACAACTCC CCATATAGGG ACCCAGCATC CCGGGTACCA
481 GCCCGCTTCC TGCCACTGCC AGGCCTGCTC CCAATGCTCC AAGAACCTCC AGGGGTCCTG
541 GCCCCTGAGC CCCCTGATGT GGACTCCTCA GACCCCCTGA GCATGGTGGG GCCTTCACAG
601 GGCCGAAGCC CCAGCTATGC CTCCTGA
```

*Sus scrofa* (pig) FGF21 gene coding sequence) (SEQ ID NO: 231) (GenBank Accession No. NM_001163410, which is hereby incorporated by reference in its entirety

```
131 atgggctggg ccgaggccaa gttcgagcgc ttgggactgt gggtccctgt gctggctgtc
191 ctgctgggag cctgccaggc acgtcccatt cctgactcca gccccctcct ccaatttggg
251 ggccaagtgc gccaacgata cctctacacg gatgatgccc aggaaactga agcccacctg
311 gagatcagag ctgatggcac cgtggcaggg gtagcccgcc agagccctga aagtctcttg
371 gagctgaaag ccctgaagcc aggggtcatt caaattttgg gagtccagac atcccggttc
431 ctgtgccagg ggccagacgg gagactgtac ggatcgctcc acttcgaccc tgaggcctgc
491 agcttccggg agctgcttct tgaggatggc tacaacgttt accagtctga ggcccttggc
551 ctcccactcc ggctgcctcc gcaccgctcc tccaaccggg acctggcccc ccggggacct
611 gctcgcttcc tgccactgcc aggcctgccc ccggcacccc cggagccgcc agggatcttg
671 gcccctgaac ctcccgacgt gggctcctcg gaccccctga gcatggtggg gccttcacac
731 ggccggagcc ccagctacac ttcttga
```

*Felis catus* (cat) FGF21 gene coding sequence (SEQ ID NO: 232) (Ensembl Accession No. ENSFCAT00000007367, which is hereby incorporated by reference in its entirety)

```
  1 ATGGGCTGGG ACGAGGCCGG GTCCCAGCGC CTGGGACTGT GGGTCGTGCT GGGGGTCCTT
 61 TTGCCGGAAG CCTGCCAGGC ACACCCTATC CCTGACTCCA GCCCCCTCCT CCAATTCGGG
121 GGCCAAGTTC GACAGCGGTT CCTCTACACG GACGACGCCC AGGAGACAGA GGTCCACCTC
181 GAGATCAAGG CTGATGGCAC AGTGGTGGGG ACCGCTCGCC GGAGCCCTGA GAGTCTCTTG
241 GAGCTAAAAG CCCTGAAGCC GGGGGTAATT CAAATCTTGG GGGTCAAAAC GTCCAGGTTC
301 CTGTGCCAGG GCCCAGATGG GACACTGTAT GGATCGCTCC GCTTTGACCC CGCAGCCTGC
361 AGCTTCCGGG AACTGCTCCT GGAGGACGGA TACAACATCT ACCACTCGGA GACCCTCGGG
421 CTCCCACTCC GCCTGCCCCC CCACAACTCC CCATACCGGG ACTTGGCCCC CCGGGCACCT
481 GCCCGCTTCC TGCCGCTGCC AGGCCTGCTT CCGGCACCCC CGGAGCCTCC AGGGATCCTG
541 GCCCCCGAGC CCCCGGACGT GGGCTCCTCG GACCCTCTGA GCATGGTGGG GCCTTCCCAG
601 GGCCGAAGTC CCAGCTACGC TTCCTGA
```

*Otolemur garnetti* (bushbaby) FGF21 gene coding sequence (SEQ ID NO: 233) (Ensembl Accession No. ENSOGAT00000003585, which is hereby incorporated by reference in its entirety)

```
  1 GACAAGGCCA GGACTGGGTT CAAGCACCCA GGACCATGGT TTCCCCTGCT GGCTGTACTT
 61 TTGTTGGGAG CCTGCCAGGC ACACCCTATC CCTGACTCCA GCCCCCTACT CCAGTTTGGT
121 GGCCAAGTCC GGCAGCGGTA CCTCTACACA GATGATGCCC AGGAGACAGA AGCCCACCTG
181 GAGATCAGGG AAGATGGCAC AGTGGTGGGG GCTGCACAAC AGAGCCCTGA AAGTCTCTTG
241 GAGCTGAAAG CTTTAAAGCC AGGGGTCATT CAAATCTTGG GAGTCAAGAC ATCCAGGTTC
301 CTGTGCCAGA GGCCAGATGG GGGCTATAT GGATCGCTCT ACTTTGACCC CAAGGCCTGC
361 AGTTTCCGGG AGCTGCTTCT TGAGGATGGA TACAACGTTT ACTGGTCTGA GACCTATGGC
421 CTCCCACTGC ACCTGCCTCC TGCCAATTCC CCATACTGGG GCCCATCCCT TCGGAGCCCA
481 GCCCGCTTCC TGCCACTGCC AGGCCCTCCT GCAGCATCCC CAGAGCTGCC GGGGATCTTG
541 GCCCTGGAAC CCCCCGATGT GGGCTCCTCG GACCCTCTGA GCATGGTGGG GCCTTCGCAG
601 GGCCGAAGCC CCAGCTATGC TTCCTGA
```

*Rattus norvegicus* (Norway rat) FGF21 gene coding sequence (SEQ ID NO: 234) (GenBank Accession No. NM_130752, which is hereby incorporated by reference in its entirety)

```
  1 atggactgga tgaaatctag agttggggcc ccgggactgt gggtctgtct cctgctgcct
 61 gtcttcctgc tgggggtgtg cgaggcatac cccatctctg actccagccc cctcctccag
121 tttgggggtc aagtccgaca gaggtatctc tacacagatg acgaccagga caccgaagcc
181 cacctggaga tcagggagga cggaacagtg gtgggcacag cacaccgcag tccagaaagt
241 ctcctggagc tcaaagcctt gaagccaggg gtcattcaaa tcctgggtgt caaagcctct
301 aggtttcttt gccaacaacc agatggaact ctctatggat cgcctcactt tgatcctgag
361 gcctgcagtt tcagagagct gctgcttaag gacggataca atgtgtacca gtctgaggcc
421 catggcctgc ccctgcgtct gccccagaag gactcccagg atccagcaac ccggggacct
481 gtgcgcttcc tgcccatgcc aggcctgccc cacgagcccc aagagcaacc aggagtcctt
541 cccccagagc cccagatgt gggttcctcc gaccccctga gcatggtaga gcctttgcaa
601 ggccgaagcc ccagctatgc atcttga
```

TABLE 6-continued

*Mus musculus* (house mouse) FGF21 gene coding sequence (SEQ ID NO: 235) (GenBank Accession No. NM_020013, which is hereby incorporated by reference in its entirety)

```
185     atggaa tggatgagat ctagagttgg gaccctggga ctgtgggtcc gactgctgct
241 ggctgtcttc ctgctggggg tctaccaagc ataccccatc cctgactcca gcccccctcct
301 ccagtttggg ggtcaagtcc ggcagaggta cctctacaca gatgacgacc aagacactga
361 agcccacctg gagatcaggg aggatggaac agtggtaggc gcagcacacc gcagtccaga
421 aagtctcctg gagctcaaag ccttgaagcc aggggtcatt caaatcctgg gtgtcaaagc
481 ctctaggttt ctttgccaac agccagatgg agctctctat ggatcgcctc actttgatcc
541 tgaggcctgc agcttcagag aactgctgct ggaggacggt tacaatgtgt accagtctga
601 agcccatggc ctgcccctgc gtctgcctca gaaggactcc ccaaaccagg atgcaacatc
661 ctggggacct gtgcgcttcc tgcccatgcc aggcctgctc cacgagcccc aagaccaagc
721 aggattcctg cccccagagc cccagatgt gggctcctct gaccccctga gcatggtaga
781 gcctttacag ggccgaagcc ccagctatgc gtcctga
```

*Vicugna pacos* (alpaca) FGF21 gene coding sequence (SEQ ID NO: 236) (Ensembl accession no. ENSVPAT00000005993, which is hereby incorporated by reference in its entirety)

```
  1 ATGGACTGGG ACGAGGCCAA GTTCGAGCAT CGGGGACTGT GGGTCCCAGT GCTCACTGTC
 61 CTTCTGCTGG GAGCCTGCCA GGCACGCCCC ATTCCTGACT CCAGCCCCCT CCTCCAATTC
121 GGGGGCCAAG TCCGGCAGCG GTACCTCTAC ACGGATGACG CCCAGGAGAC AGAAGCCCAC
181 CTGGAGATCA GGGCTGATGG CACAGTGGTG GGGGTGGCCC GCCAG---CC CGAA------
241 ---------- ---------- ---------- ---------- ---------- ----------
301 ---------- ---------- ---------- ---------- ---------- ----------
361 ---------- ---------- ---------- ---------- ---------- ----------
421 ---------- ---------- ---------- ---------- ---------- ----------
481 ---------- ---------- ----GGAATT CCT------- ---------- ----------
541 ------CCCG AGCCTCCTGA CGTGGGCTCC TCAGACCCCC TGAGCATGGT GGGGCCTTCA
601 TACAGCAGAA GCCCCAGCTA CACTTCCTGA
```

*Anolis carolinensis* (anole lizard) FGF21 gene coding sequence (SEQ ID NO: 237) (Ensembl accession no. ENSACAT00000017230, which is hereby incorporated by reference in its entirety)

```
  1 TGTAAAAGCA AGGGAGGAGG GAAGGGGGGA GAGAGGATGT GGGTAGACCT AGTTTTCTGG
 61 GCTGCCTTGC TCCGCACAGC TCCTGCTCTT CCCTTGCGGA ATTCCAACCC CATCTACCAA
121 TTTGATGGGC AGGTCCGGCT TCGGCACCTC TACACAGCAG ATGAACAGAC GCACCTCCAC
181 TTGGAGATCT TGCCAGACGG TACCGTGGGT GGATCCAGGT TTCAGAATCC CTTCAGTTTG
241 ATGGAGATCA AAGCTGTGAA GCCAGGAGTC ATTCGCATGC AGGCCAAGAA GACCTCTAGA
301 TTTCTCTGTA TGAAACCCAA TGGACGACTG TATGGCTCGC TGTTCTACTC TGAGGAGGCA
361 TGCAACTTCC ATGAGAAGGT TCTCAGCGAT GGCTACAACC TCTACTATTC TGAAAACTAC
421 AACATACCTG TCAGCCTCAG CTCGGCAGGG AACCTGGGTC AGAGCCGTCA GTTGCCTCCC
481 TTCTCCCAAT TCCTGCCGTT AGTCAACAAA ATTCCTCTTG AGCCTGTGCT TGAAGACTTT
541 GACTTCTATG GACATCAATT GGATGTTGAA TCAGCTGATC CTTTGAGCAT TTTAGGACAA
601 AACCCTGGTT TCATGAGTCC GAGCTATGTC TTC
```

*Gadus morhua* (cod) FGF21 gene coding sequence (SEQ ID NO: 238) (Ensembl accession no. ENSGMOT00000014151, which is hereby incorporated by reference in its entirety)

```
  1 CTCCTCCTCG CCACCCTCCT CCACATCGGC CTCTCCTTCT ACGTCCCCGA CTCCGGCCCC
 61 CTGCTGTGGC TGGGCGACCA GGTCAGGGAG AGACACCTCT ACACAGCAGA GAGCCACCGG
121 AGGGGGCTGT TCCTGGAGAT GAGCCCGGAC GGTCAGGTGA CAGGAAGTGC TGCTCAGACG
181 CCGCTCAGTG TTCTGGAGCT GAGGTCGGTC AGAGCAGGAG ATACGGTCAT CAGAGCGCGC
241 CTCTCCTCTC TCTACCTGTG TGTGGACAGG GCAGGTCACC TGACAGGACA GAGACAGTAC
301 ACAGAGTCCG ACTGCACCTT CAGAGAGGTC ATCCTTGAGG ACGGCTACAC CCACTTCCTG
361 TCCGTGCACC ACGGACTTCC TATTTCGCTG GCGCCGAGAC ACTCCCCAGG GAGACAGGGG
421 CTGCGCTTCA GCAGGTTCCT CCCGCTGAGG AGCAGTCTGT CAGAGGATAG GGTCGCCGAG
481 CCCCCAGACA GCCCACTGAA CCTGGACTCT GAAGACCCCC TGGGGATGGG TCTGGGTTCG
541 CTCCTCAGCC CGGCCTTCTC CATG
```

*Latimeria chalumnae* (coelacanth) FGF21 gene coding sequence (SEQ ID NO: 239) (Ensembl accession no. ENSLACT00000003815, which is hereby incorporated by reference in its entirety)

```
  1 ATGTTATGCC AGAGTTTTGT GATATTAAGT CAGAAATTCA TTTTTGGGCT CTTTTTGACT
 61 GGATTGGGGC TAACAGGATT GGCTTGGACA AGGCCCTTCC AGGATTCCAA TCCCATCCTG
121 CAGTATTCCG ATTCCATCCG GCTCCGACAT CTGTACACTG CCAGTGAGAG TCGGCACCTT
181 CACCTACAAA TCAACTCGGA TGGACAGGTG GGAGGGACAA CCAAGCAAAG CCCTTACAGT
241 CTGTTGGAGA TGAAGGCGGT GAAGACAGGT TTTGTGGTCA TCAGGGGCAA GAAAAGCGCC
301 CGTTACCTCT GTATGGAACG TAGTGGACGG CTCTATGGAT CGCTGCAGTA TACAGAAAAA
361 GACTGCACCT TCAAAGAGGT TGTGTTGGCA GATGGATACA ACCTGTATGT CTCAGAGGAA
421 CACCAGGCCA CAGTGACGCT GAGCCCCATG AGGGCGAGGA TAGCGCAAGG GAAAAAGATC
481 CCACCCTTTT CCCATTTCCT TCCAATGGTG AACAAGGTGC CTGTGGAGGA TGTTGCCGCT
541 GAGATGGAGT TTGTCCAGGT GCTGCGGGAA ATGACGGCCG ACGTGGACTC TCCGGATCCC
601 TTTGGAATGA CCTGGGAAGA ATCGGTTCAC AGTCCGAGCT TTTTTGCC
```

TABLE 6-continued

| *Tursiops truncatus* (dolphin) FGF21 gene coding sequence (SEQ ID NO: 240) (Ensembl accession no. ENSTTRT00000014561, which is hereby incorporated by reference in its entirety) |
|---|
| 1 ATGGGCTGGG ACAAGACCAA ACTCGAGCAC CTGGGACTGT GGGTCCCTGT GCTAGCTGTC |
| 61 CTGCTGGGAC CCTGCCAGGC ACATCCCATT CCTGACTCCA GCCCCCTCCT CCAATTTGGG |
| 121 GGCCAAGTCC GCCAGCGATA CCTCTACACG GATGACGCCC AGGAGACGGA GGCCCACCTG |
| 181 GAGATCAGGG CTGATGGCAC AGTGGTGGGG ACGGCCCGCC GGAGCCCCGA AGGAGTTAAA |
| 241 ACATCCAGGT TCCTGTGCCA GGGGCCAGAG GGGAGGCTGT ATGGATCGCT CCACTTCAAC |
| 301 CCCCAGGCCT GCAGCTTCCG GGAGCTGCTT CTTGAGGATG GATACAACGT TTACCAGTCT |
| 361 GAGGCTCTTG GCATTCCCCT CCGCCTGCCC CCGCACCGCT CCTCCAACTG GGACCTGGCC |
| 421 CCCCGGGGAC CTGCTCGCTT CCTGCCGCTG CCAGGCTTCC TCCCGCCACC CCTGGAGCCT |
| 481 CCAGGGATCT TGGCCCCCGA GCCTCCCAAC GTAGGTTCCT CGGACCCCTT GAGCATGGTG |
| 541 GGACCTTCAC ATGGCCGAAG CCCCAGCTAC ACTTCCTGA |

| *Mustela putorius furo* (ferret) FGF21 gene coding sequence (SEQ ID NO: 241) (Ensembl accession no. ENSMPUT00000003755, which is hereby incorporated by reference in its entirety) |
|---|
| 188 ATG GGCTGGGAAG AGGCCAGGTC CGAGCACCTG GGGCTGTGGG TCCCTGTGCT |
| 241 GGCGGTCCTT TTGCTGGGAG CCTGCCAGGC ATACCCTATT CCTGACTCCA GCCCCCTCCT |
| 301 CCAATTTGGA GGCCAAGTTC GACAGCGGTA CCTCTACACA GACGACGCTC AGGAGACGGA |
| 361 GGCCCACCTA GAGATCAGGG CTGATGGCAC GGTGGTGGGG GCTGCCCGCC GGAGCCCCGA |
| 421 AAGTCTCTTG GAGCTGAAAG CCCTGAAGCC AGGGGTCATT CAGATCTTGG GAGTGAAAAC |
| 481 ATCCAGGTTC CTGTGCCAGG GCCCGAATGG GACACTGTAC GGATCGTTCC ACTTCGACCC |
| 541 CGTAGCCTGC AGCTTCCGGG AAGTGCTTCT GGAAGATGGA TACAACATCT ACCACTCTGA |
| 601 GACCCTGGGC CTCCCACTGC GCCTGCCCCC CCACAACTCC CCACACAGGG ACCTGGCGCC |
| 661 CCGGGGGCCT GCCCGCTTCC TGCCCCTGCC AGGCCTGCTT CCGGCCACCC CGGAGTCCCG |
| 721 GGGGATCCCA GCCCCCGAGC CTCCCAACGT GGGCTCCTCA GACCCCCTGA GCATGGTGGG |
| 781 GCCTTTGCAG GGTCAAAGTC CCAGCTACAC TTCCTGA |

| *Takifugu rubripes* (fugu) FGF21 gene coding sequence (SEQ ID NO: 242) (Ensembl accession no. ENSTRUT00000034076, which is hereby incorporated by reference in its entirety) |
|---|
| 1 TTTATTTATT TATTTATTCA AACTGCACTT TTTTCCCCTT CCAAATGGTT CAACTTTTAT |
| 61 CTCCCTGACT CCAACCCGCT CTTATCCTTT GACAGTCATG GCAGAGGCAT CCACCTCTAC |
| 121 ACAGATAATC AAAGGCGAGG GATGTATCTG CAGATGAGCA CAGATGGAAG CGTTTCCGGG |
| 181 AGTGATGTCC AGACGGCGAA CAGTGTGCTG GAACTGAAGT CAGTCAGAAA CGGCCACGTC |
| 241 GTCATCCGAG GAAAATCGTC TTCTCTGTTT CTCTGTATGG ACAGCAGAGG CCGTTTATGG |
| 301 GGGCAGAGGC ACCCCACTGA GGCCGACTGC ACTTTCAGGG AAGTGTTGCT GGCAGATGGA |
| 361 TACACTCGCT TCCTGTCCCT GCACAACGGA ACTCCTGTGT CTCTGGCACC TAAACAATCT |
| 421 CCAGACCAGC ACACAGTCCC CTTCACTCGT TTCCTGCCGC TCAGGAATAC ACTGGCAGAG |
| 481 GAGAGCATGT CTGAACCACC ATCAAACCAA CAGAGATATT TTAACATTGA CTCTGATGAT |
| 541 CTTCTTGGAA TGGATTTAAA TGCGATGGTC AGTCCTCAGT TTTCAGGGGA CAAGTGA |

| *Dipodomys ordii* (Kangaroo rat) FGF21 gene coding sequence (SEQ ID NO: 243) (Ensembl accession no. ENSDORT00000001234, which is hereby incorporated by reference in its entirety) |
|---|
| 1 ATGGACCAGG CAAAGACCAG GGTTGGGGCC CGGGGGCTGG GGGGCCTTGT GCTGGCTGTC |
| 61 ATAATTCTGG GAGCATGCAA GGCACGGCCT ATCCCTGACT CCAGCCCCCT CCTCCAATTT |
| 121 GGGGGTCAAG TTCGGCTTCG GCACCTCTAC ACAGATGACA CTCAGGAGAC GGAAGCCCAT |
| 181 CTGGAGATCA GGGCAGATGG CACGGTAGTG GGGACTGCCC ACCGGAGCCC TGAAAGTCTC |
| 241 TTGGAGCTGA AAGCCTTGAA GCCAGGAGTC ATTCAAATCT TAGGGATCAA GACATCCAGA |
| 301 TTCTTATGCC AGAGACCAGA CGGGACACTG TATGGATCAC TCCACTTTGA CCCTGAGGTT |
| 361 TGCAGCTTCC AGGAGCTGCT TCTGGAAGAT GGATACAACA TTTACCGTTC TGAAGCCCTG |
| 421 GGTCTCCCCC TGCGCCTGTC CCCAGATCCA GCACCCTGGG GGCCAGCCCG CTTCCTGCCC |
| 481 CTGCCTGGTG TGCCCCCCGC ACCGCCGGAG CCCCCCGGGA TCCTGGCTCC CGAACCCCCT |
| 541 GATGTCGGCT CCTCCGACCC TCTGAGTATG GTGGGACTGT TGCAGGGCCG AAGCCCCAGC |
| 601 TATGCATCCT GA |

| *Echinops telfairi* (lesser hedgehog tenrec) FGF21 gene coding sequence (SEQ ID NO: 244) (Ensembl accession no. ENSETET00000010721, which is hereby incorporated by reference in its entirety) |
|---|
| 1 ATGGGTTGCA CCAAATCTGG GTGGAAGTCC CCGGGACTGT GGGTCCCTGT GCTGGCCAGC |
| 61 CTTCTGCTGG GAGGCTGCGG AGCACACCCC ATCCCTGACT CCAGCCCCCT CCTCCAATTC |
| 121 GGGGGCCAAG TCCGGCAGCG ATACCTCTAT ACGGATGACG CCCAGACCAC CGAGGCCCAC |
| 181 CTGGAGATCA GAGCGGATGG CACAGTGGGG GGCGTCGCCC ACCAGAGCCC AGAGAAGTTC |
| 241 CTGAGTCAAT GGCGTGAAAA GCCCCTGAGA TCACTCCATT TCGACCCAGC CGCCTGCAGC |
| 301 TTCCGGGAGA AGCTTCTAGA AGACGGATAC AACTTGTACC ACTCTGAGAC CCACGGCCTC |
| 361 CCCCTCCGCC TCCCACCCCG TGGGGGCGAC CCCTCTTCTC AGCCTGGGGC CCGCTTCCCA |
| 421 CCGCTGCCGG GCCAGCTCCC ACAACTCCAA GAGACGCCAG GGGTCCTCGC CCCCGAACCC |
| 481 CCCGACGTGG GCTCTTCAGA CCCCCTGAGC ATGGTGGGGC CTTGGCGAGG GCAAAGTCCC |
| 541 AGTTATGCCT CCTGA |

TABLE 6-continued

*Macaca mulatta* (rhesus monkey) FGF21 gene coding sequence (SEQ ID NO: 245) (Ensembl accession no. ENSMMUT00000038440, which is hereby incorporated by reference in its entirety)

```
  1 ATGGACTCGG ACGAGACCGG GTTCGAGCAC TCAGGACTGT GGGTTCCTGT GCTGGCTGGT
 61 CTTCTGCTGG GAGCCTGCCA GGCACACCCC ATCCCTGACT CCAGTCCTCT CCTGCAATTC
121 GGGGGCCAAG TCCGGCAACG GTACCTCTAC ACAGATGATG CCCAGCAGAC AGAAGCCCAC
181 CTGGAGATCA GGGAGGATGG GACAGTGGGG GGCGCTGCTC ACCAGAGCCC CGAAAGTGAG
241 TGTGGGCCAG AGCCTGGGTC TGAGGGAGGA GGGGCTGTGG GAGGTGCTGA GGGACCTGGA
301 CTCCTGGGTC TGAGGGAGGC AGGGCTGGGG CCTGGATCCT GGCTCCACTT TGACCCTGAG
361 GCCTGCAGCT TCCGGGAGCT GCTTCTTGAG AACGGATACA ATGTTTACCA GTCCGAGGCC
421 CACGGCCTCC CACTGCACCT GCCGGGAAAC AAGTCCCCAC ACCGGGACCC TGCATCCCAA
481 GGACCAGCTC GCTTCCTGCC ACTACCAGGC CTGCCCCCCG CACCCCCGGA GCCGCCAGGA
541 ATCCTCGCCC CCCAGCCCCC CGATGTGGGC TCCTCGGACC CTCTGAGCAT GGTGGGACCT
601 TCCCAGGCCC GAAGCCCCAG CTATGCTTCC TGA
```

*Microcebus murinus* (mouse lemur) FGF21 gene coding sequence (SEQ ID NO: 246) (Ensembl accession no. ENSMICT00000013258, which is hereby incorporated by reference in its entirety)

```
  1 ATGGGCTGGG ACGAGGCCGG CGCCGGGTTC GAGCACCCAG GACTGTGGTT TCCCATGCTG
 61 GGTGTCCTGC TGCTGGGAGC CTGCCAGGCG TACCCCATCC CTGACTCCAG CCCCCTCCTC
121 CAATTTGGCG GCCAAGTCCG GCAGCGGCAC CTCTACACAG ACGATATCCA GGAGACAGAA
181 GCCCACCTGG AGATCAGGGC GGACGGCACA GTGGTGGGGG CCGCCCGACA GAGCCCTGAG
241 TTGGAGCTGA AAGCCTTAAA GCCAGGGGTC ATTCAAATCT TGGGAGTCAA GACCTCCAGG
301 TTCCTGTGCC AGAGGCCAGA CGGGGCCCTG TACGGATCGC TCCACTTTGA CCCCGAGTGC
361 AGCTTCCGGG AGCTGCTTCT TGAGGATGGA TACAACGTCT ACTGTCCCTA CCTCCCGCTG
421 CACCTGTCCC CACGCATCGA ACTGGCCGGA TCACGCTCTG CGCTGCCACT GCCCCCAGCA
481 CCTGAACGCA GGATTTTGGC CCCGGAGCCC CCGGATGGCT CCTCGGACCC TCTGAGCATG
541 GTGGGGCCTT CGCAGGGCCG AAGTCCCAGC TATGCTTCCT GA
```

*Ochotona princeps* (pika) FGF21 gene coding sequence (SEQ ID NO: 247) (Ensembl accession no. ENSOPRT00000007373, which is hereby incorporated by reference in its entirety)

```
  1 AAAGACATGG ACGGGCTCCA GCCTCCGGGG CTGCGGGTTC CTGTGCTGGC TGCCCTGCTT
 61 TTGGGAGTTG GCCAGGCACG CCCCATCCCT GATTCTAGCC CTCTCCTCCA ATTCGGGGGC
121 CAGGTCCGGC AGAGGCACCT CTACACGGAT GACGCCCAGG AATCGGAAGT ACACCTGGAG
181 ATCCGGGCAG ACGGCACCGT GGCAGGGACT GCCCGCCGGA GCCCTGAAAG TCTCTTAGAA
241 ATGAAAGCGT TGAAGCCAGG CGTCATTCAG ATCCTGGGGG TCCACACATC CAGGTTCCTG
301 TGCCAGAGAC CAGACGGGAC GCTGTACGGC TCGCTCCACT TCGACCACAA GGCCTGCAGC
361 TTCCGGGAGC AGCTGCTGGA GGATGGGTAC AACGTGTACC ACTCAGAGAC ACACGGCCTC
421 CCGCTGCGCC TGTCTCCAGA CCGAGCCCCC CGGGGCCCAG CCCGCTTCCT GCCACTGCCA
481 GGCCCTCCTC CTGACCTCCT GGTGCCACCC CTGCCACCGG ACGTCCTAGC CCCTGAGCCC
541 CCCGACGTGG ACTCCCCAGA CCCCCTGAGC ATGGTGGGGC CCTTGCAGGG CCAAAGCCCC
601 AGCTACACTT CCTGA
```

*Xiphophorus maculatus* (platyfish) FGF21 gene coding sequence (SEQ ID NO: 248) (Ensembl accession no. ENSXMAT00000001579, which is hereby incorporated by reference in its entirety)

```
  1 TGCCCGTTCC CCTTCCTTTT CTTAATCCTC TCTCTTCCCT TTTTCTCTTC CTCGTTTTAC
 61 ATCCCAGAAT CCAACCCAAT CTTTGCCTTC AGGAATCAGC TCAGAGAGGT GCATCTCTAC
121 ACAGAAAATC ACAGACGGGG TTTGTATGTG GAGATACATC TGGATGGGAG AGTGACTGGA
181 AGTGATGCTC AGAGTCCTTA TAGTGTGTTG CAGATAAAGT CTGTTAAACC GGGTCATGTG
241 GTCATAAAGG GACAGACATC GTCCCTGTTC CTCTGCATGG ACGACTCCGG GAATCTAAGA
301 GGACAGACAA CCTATGACGA GGCTGACTGC TCCTTCAGGG AACTGCTGCT GGCCGATGGC
361 TACACCCGTT TCCTGAACTC ACAACATGGC GTTCCTTTAT CACTGGCATC CAGAAACTCT
421 CCAGATCGAC ACTCCGTTCC TTTCACAAGA TTTTTACCTC TCAGGAATAC TTTAACGGTT
481 TCAGAAGAAT CAACAAAAAC TCAGAGGGAC TTCAACCTGG ACTCGGACGA CCTTCTCGGG
541 ATGGGA
```

*Gasterosteus aculeatus* (stickleback) FGF21 gene coding sequence (SEQ ID NO: 249) (Ensembl accession no. ENSGACT00000010725, which is hereby incorporated by reference in its entirety)

```
  1 TCTCTCCTCC TCATGGTCCC ACTTCCTTTC TGTTCATCCT TTTATCTCAC TGACTCCAGC
 61 CCACTTCTAC CCTTCAATAA TCAAGTCAAA GAGGTGCACC TCTACACAGC AGAGAATCAC
121 AGAAGAGCGA TGTACCTGCA GATCGCTCTG GACGGGAGCG TGTCGGGAAG CGACGCTCGG
181 TCCACTTACA GTGTGCTGCA GCTGAAATCT ATCCAGCCGG GCCACGTGGT CATCAGAGGG
241 AAGGCCTCCT CCATGTTCCT CTGCGTGGAC AGCGGGGGCC GTTTGAGAGG ACAGGGGCCG
301 TACTCAGAGG CCGACTGCAG CTTCAGGGAG CTGCTGCTGG GGGATGGCTA CACCCGGTTC
361 CTGTCCTCGC AGCACGGGTC CCCGCTGTCT CTGGCGTCGA GGCCTTCCCC GGATCCCAAC
421 TCGGTGCCCT TCACTCGATT CCTACCCATC CGGACCGCCC CCGAGGCTGA GAGCGTGATC
481 GAAGAGCCAC CGAGCAATCA GAGATACGTC AACGTGGACT CCGAGGATCT TCTTGGAATG
541 GGCCTGAACA CTGTGGTCAG TCCTCAGTTC TCGGCG
```

TABLE 6-continued

*Sarcophilus harrisii* (Tasmanian devil) FGF21 gene coding sequence (SEQ ID NO: 250) (Ensembl accession no. ENSSHAT00000006017, which is hereby incorporated by reference in its entirety)

```
132           GTGTCTGCC ATGGGCCTGA GGGAGCGAGC TCCCAGGTAC CTGGCCCCGC
181 TGCTGTCCTT GCTCTTGGCC TGCAGGGCCT CGGGTCACCC CCTCCCGGAT TCCAGCCCCA
241 TGCTCCTGTT TGGGGGGCAG GTCCGCCTCC GGCACCTCTA CACGGATGTG GGCCAGGAGG
301 CCGAGGCCCA CGTGGAACTG GCGTCCGACG GCACAGTCCG GGCGGCAGCG CGGAGGAGTC
361 CCAACAGTCT CCTGGAGCTG AAGGCTGTGA AGCCGGGCAT CGTCCGAATC CTGGCCGTCC
421 ACAGCTCTCG GTTTCTGTGT ATGAGGCCCA ACGGGGAGCT GTACGGAGCG ATACACTACG
481 ACCCTTCCGC CTGCAACTTT CGGGAGCGCC TGCTGGGGGA CGGCTACAAC GTGTACGAGT
541 CCGAGGCTCA CGGGAGGACC CTCCGCCTGC CCCCCAAGGC CGCACCGGGA CCCGCCGGAC
601 CTTCTCGCTT CCTGCCGCTC CCCGGC
```

*Macropus eugenii* (wallaby) FGF21 gene coding sequence (SEQ ID NO: 251) (Ensembl accession no. ENSMEUT00000015309, which is hereby incorporated by reference in its entirety)

```
  1 ACAGAGGAGC CTTCTACTGG GTCCAGGCAC CTGGGACAAT GGGCTCCCGG GCTGCCTGGT
 61 CCTCTGCTGT CCTTGCTCCT GGCCTACAGG GGCTGGGGCT CCCCCATCCC TGATTCCAGC
121 CCCATGCTCC TGTTTGGTGG CCAGGTCCGC CTCCGACACC TGTACACAGA TGATGGCCAG
181 GACACGGAGG CCCATGTGGA GCTGGGGCCA GATGGAGTGG TTCGAGCTGT GGCTGAGAGG
241 AGCCCCAACA GTCTTCTGGA ACTGAAGGCG GTGAAGCCTG GAGTCATCCG AATCCTCGCT
301 GTCCAGAGCT CTCGGTTTCT GTGTATGAGG CCCAACGGGG AACTGTATGG AGCGGTACAC
361 TATGACCCTT CTGCCTGCAA CTTTCGGGAA CATCTGCTGG GGGATGGTTA TAATGTGTAT
421 GAATCAGAGA CTCACAGAAG GACCCTCCGT CTGTCCCCAT CCCTGGGTCA GGCTGGCCCC
481 TCTCGCTTCC TGCCACTTCC AGGCGACTGG CTGCCCGGCC CTGATCCACC TTGGGCACAG
541 GGCCCTGAGC CCCCAGACGT GGGCTCTGCA GACCCCCTGA GCATGGTGGG GGCCGTGCAG
601 GGCCTCAGCC CCAGCTACTC CTCCTGA
```

*Xenopus tropicalis* (Western clawed frog) FGF21 gene coding sequence (SEQ ID NO: 252) (Ensembl accession no. ENSXETT00000009917, which is hereby incorporated by reference in its entirety)

```
  1 AGAGGGGGTA GGACCAAAAA AAAGACGTTA CTCAGGAAAT GGCTTTGCCT TTTAGCCATT
 61 ATGTTGAGTA GGTCAAGGTT TTCTTTAGCA AATCCTATCC AGAATTCGAA CCCAATCTTA
121 TCCAACGACA ACCAAGTACG GACTCAGTAT TTATACACAG ATAACAATAA CATGCACCTG
181 TATCTTCAGA TCACCCACAA TGGAGTAGTA ACTGGTACCG AAGAAAAGAA TGACTATGGT
241 GTGCTGGAAA TAAAGGCAGT AAAAGCTGGG GTTGTAGTTA TAAAAGGAAT TCGAAGCAAT
301 CTCTACCTAT GCATGGATTC TAGACACCAA TTGTATGCGT CGGCATATGA TAAAGATGAC
361 TGCCATTTCC ATGAAAAGAT CACACCAGAT AATTACAACA TGTATAGCTC AGAGAAGCAT
421 TCAGAATACG TGTCCTTAGC TCCATTAAAA GGAAGCCAGA TGGCTCGTTT TCTACCTATA
```

*Danio rerio* (zebrafish) FGF21 gene coding sequence (SEQ ID NO: 253) (Ensembl accession no. ENSDART00000103511, which is hereby incorporated by reference in its entirety)

```
 30                                A TGCTTCTTGC CTGCTTTTTT ATATTTTTTG
 61 CTCTTTTTCC TCATCTTCGG TGGTGTATGT ATGTTCCTGC ACAGAACGTG CTTCTGCAGT
121 TTGGCACACA AGTCAGGGAA CGCCTGCTTT ACACAGATGG GTTGTTTCTT GAAATGAATC
181 CAGATGGCTC CGTCAAAGGC TCTCCTGAAA AGAATCTAAA TTGTGTGCTG GAGCTGCGTT
241 CAGTCAAAGC GGGTGAAACC GTCATCCAGA GTGCAGCTAC ATCTCTCTAC CTCTGCGTCG
301 ATGATCAAGA CAAGCTGAAA GGACAGCATC ATTACTCTGC ACTAGACTGC ACCTTTCAGG
361 AATTGCTACT GGATGGATAT TCGTTTTTCC TTTCTCCACA CACTAATCTT CCCGTATCGC
421 TCCTCTCGAA ACGTCAGAAA CACGGCAATC CTCTTTCTCG CTTCCTCCCT GTTAGCAGAG
481 CAGAGGACAG CCGGACACAG GAGGTGAAAC AGTATATTCA GGATATAAAC CTGGACTCTG
541 ACGACCCACT AGGAATGGGA CATCGGTCAC ACTTACAGAC CGTCTTCAGT CCCAGTCTGC
572 ATACTAAAAA ATGA
```

In one embodiment, the chimeric protein of the present invention comprises the amino acid sequence of SEQ ID NO: 254, SEQ ID NO: 255, SEQ ID NO: 256, SEQ ID NO: 257, SEQ ID NO: 258, SEQ ID NO: 259, SEQ ID NO: 260, or SEQ ID NO: 261, as shown in Table 7.

TABLE 7

| Description of Chimeric Protein | Sequence |
|---|---|
| Amino acid sequence of a FGF23/19 chimera composed of residues Y25 to P172 of human FGF23 and residues E174 to K216 of human FGF19 (bold) | SEQ ID NO: 254<br>MLGARLRLWV CALCSVCSMS VLRAYPNASP<br>LLGSSWGGLI HLYTATARNS YHLQIHKNGH<br>VDGAPHQTIY SALMIRSEDA GFVVITGVMS<br>RRYLCMDFRG NIFGSHYFDP ENCRFQHQTL |

TABLE 7-continued

| Description of Chimeric Protein | Sequence |
|---|---|
| | ENGYDVYHSP QYHFLVSLGR AKRAFLPGMN<br>PPPYSQFLSR RNEIPLIHFN TP**EEPEDLRG**<br>**HLESDMFSSP LETDSMDPFG LVTGLEAVRS PSFEK** |
| Amino acid sequence of a FGF23/19 chimera composed of residues Y25 to N162 of human FGF23 and residues L169 to K216 of human FGF19 (bold) | SEQ ID NO: 255<br>MLGARLRLWV CALCSVCSMS VLRAYPNASP<br>LLGSSWGGLI HLYTATARNS YHLQIHKNGH<br>VDGAPHQTIY SALMIRSEDA GFVVITGVMS<br>RRYLCMDFRG NIFGSHYFDP ENCRFQHQTL<br>ENGYDVYHSP QYHFLVSLGR AKRAFLPGMN<br>PPPYSQFLSR RN**LPMVPEEP EDLRGHLESD**<br>**MFSSPLETDS MDPFGLVTGL EAVRSPSFEK** |
| Amino acid sequence of a FGF23/19 chimera composed of residues Y25 to P172 of human FGF23 harboring R140A/R143A double mutation (bold) and residues E174 to K216 of human FGF19 (bold) | SEQ ID NO: 256<br>MLGARLRLWV CALCSVCSMS VLRAYPNASP<br>LLGSSWGGLI HLYTATARNS YHLQIHKNGH<br>VDGAPHQTIY SALMIRSEDA GFVVITGVMS<br>RRYLCMDFRG NIFGSHYFDP ENCRFQHQTL<br>ENGYDVYHSP QYHFLVSLG**R** AK**R**AFLPGMN<br>PPPYSQFLSR RNEIPLIHFN TP**EEPEDLRG**<br>**HLESDMFSSP LETDSMDPFG LVTGLEAVRS PSFEK** |
| Amino acid sequence of a FGF23/19 chimera composed of residues Y25 to P172 of human FGF23 harboring R48A/N49A double mutation (bold) and residues E174 to K216 of human FGF19 (bold) | SEQ ID NO: 257<br>MLGARLRLWV CALCSVCSMS VLRAYPNASP<br>LLGSSWGGLI HLYTATA**RN**S YHLQIHKNGH<br>VDGAPHQTIY SALMIRSEDA GFVVITGVMS<br>RRYLCMDFRG NIFGSHYFDP ENCRFQHQTL<br>ENGYDVYHSP QYHFLVSLGR AKRAFLPGMN<br>PPPYSQFLSR RNEIPLIHFN TP**EEPEDLRG**<br>**HLESDMFSSP LETDSMDPFG LVTGLEAVRS PSFEK** |
| Amino acid sequence of a FGF23/21/19 chimera composed of residues Y25 to V136 and F157 to P172 of human FGF23, residues H145 to R163 of human FGF21 (bold Italic) and residues E174 to K216 of human FGF19 (bold) | SEQ ID NO: 258<br>MLGARLRLWV CALCSVCSMS VLRAYPNASP<br>LLGSSWGGLI HLYTATARNS YHLQIHKNGH<br>VDGAPHQTIY SALMIRSEDA GFVVITGVMS<br>RRYLCMDFRG NIFGSHYFDP ENCRFQHQTL<br>ENGYDVYHSP QYHFLV***HLPG NKSPHRDPAP***<br>***RGPAR***FLSRR NEIPLIHFNT P**EEPEDLRGH**<br>**LESDMFSSPL ETDSMDPFGL VTGLEAVRSP SFEK** |
| Amino acid sequence of a FGF23/19 chimera composed of residues Y25 to N162 of human FGF23 harboring R140A/R143A double mutation (bold) and residues L169 to K216 of human FGF19 (bold) | SEQ ID NO: 259<br>MLGARLRLWV CALCSVCSMS VLRAYPNASP<br>LLGSSWGGLI HLYTATARNS YHLQIHKNGH<br>VDGAPHQTIY SALMIRSEDA GFVVITGVMS<br>RRYLCMDFRG NIFGSHYFDP ENCRFQHQTL<br>ENGYDVYHSP QYHFLVSLG**R** AK**R**AFLPGMN<br>PPPYSQFLSR RN**LPMVPEEP EDLRGHLESD**<br>**MFSSPLETDS MDPFGLVTGL EAVRSPSFEK** |
| Amino acid sequence of a FGF23/19 chimera composed of residues Y25 to N162 of human FGF23 harboring R48A/N49A double mutation (bold) and residues L169 to K216 of human FGF19 (bold) | SEQ ID NO: 260<br>MLGARLRLWV CALCSVCSMS VLRAYPNASP<br>LLGSSWGGLI HLYTATA**RN**S YHLQIHKNGH<br>VDGAPHQTIY SALMIRSEDA GFVVITGVMS<br>RRYLCMDFRG NIFGSHYFDP ENCRFQHQTL<br>ENGYDVYHSP QYHFLVSLGR AKRAFLPGMN<br>PPPYSQFLSR RN**LPMVPEEP EDLRGHLESD**<br>**MFSSPLETDS MDPFGLVTGL EAVRSPSFEK** |
| Amino acid sequence of a FGF23/21/19 chimera composed of residues Y25 to V136 and F157 to N162 of human FGF23, residues H145 to 8163 of human FGF21 (bold Italic) and residues L169 to K216 of human FGF19 (bold) | SEQ ID NO: 261<br>MLGARLRLWV CALCSVCSMS VLRAYPNASP<br>LLGSSWGGLI HLYTATARNS YHLQIHKNGH<br>VDGAPHQTIY SALMIRSEDA GFVVITGVMS<br>RRYLCMDFRG NIFGSHYFDP ENCRFQHQTL<br>ENGYDVYHSP QYHFLV***HLPG NKSPHRDPAP***<br>***RGPAR***FLSRR N**LPMVPEEPE DLRGHLESDM**<br>**FSSPLETDSM DPFGLVTGLE AVRSPSFEK** |

As noted above, a chimeric protein according to the present invention may have enhanced stability (i.e., thermal stability) compared to a native molecule or portion thereof. In one embodiment, a chimeric protein according to the present invention may have enhanced thermal stability compared to native FGF21. Thermal stability of FGFs is a critical determinant for the ligands' biological activity. It was recently shown that differences in thermal stability among FGFs, including ligands of the same subfamily, account for the differences in the ability of FGFs to support pluripotency of stem cells (Chen et al., "Thermal Stability of FGF Protein is a Determinant Factor in Regulating Self-Renewal, Differentiation and Reprogramming in Human Pluripotent Stem Cells," *Stem Cells* 30(4):623-630 (2012), which is hereby incorporated by reference in its entirety). Mutations were introduced into FGF1 to improve the ligand's thermal stability (Zakrzewska et al., "Highly Stable Mutants of Human Fibroblast Growth Factor-1 Exhibit Prolonged Biological Action," *J Mol Biol* 352:860-875 (2005), which is hereby incorporated by reference in its entirety), and it was shown that the mutant FGF1 exhibits a prolonged half-life and enhanced mitogenic activity compared to the native ligand (Zakrzewska et al., "Highly Stable Mutants of Human Fibroblast Growth Factor-1 Exhibit Prolonged Biological Action," *J Mol Biol* 352:860-875 (2005), which is hereby incorporated by reference in its entirety). Based on extensive analysis of the crystal structures of FGF ligands, including the structures of endocrine-acting FGF19 and FGF23, and comparison of the primary sequences of FGF ligands (Mohammadi et al., "Structural Basis for Fibroblast Growth Factor Receptor Activation," *Cytokine & Growth Factor Rev* 16(2):107-137 (2005); Goetz et al., "Molecular Insights into the Klotho-dependent, Endocrine Mode of Action of Fibroblast Growth Factor 19 Subfamily Members," *Mol Cell Biol* 27:3417-3428 (2007), which are hereby incorporated by reference in their entirety), it was found that the β-trefoil core domain of FGF23 would have a greater thermal stability than the core domain of FGF21.

Accordingly, in one embodiment, the chimeric protein according to the present invention is an FGF21 agonist with enhanced thermal stability compared to native FGF21. In one embodiment, the chimeric protein according to the present invention may include an FGF21 molecule with its core domain replaced with that of FGF23. Accordingly, in one embodiment, a chimeric protein according to the present invention is engineered by replacing the core domain in FGF21 with that of FGF23. This generates an FGF21 ligand with agonistic properties owing to enhanced thermal stability. Receptor-binding specificity would not be affected because the FGF23 core domain has a similar receptor-binding specificity as the FGF21 core domain, with a binding preference for the "c" splice isoform of FGF receptor 1.

Native FGF23 has been shown to have greater binding affinity for FGFR1c than native FGF21. Goetz et al., "Conversion of a Paracrine Fibroblast Growth Factor into an Endocrine Fibroblast Growth Factor," *J Biol Chem.* 287:29134-29146 (2012), which is hereby incorporated by reference in its entirety. In one embodiment, the chimeric protein according to the present invention has enhanced binding affinity for FGFR1c, and hence agonistic properties, compared to native FGF21. In one embodiment, the chimeric protein according to the present invention has enhanced binding affinity for FGFR1c compared to native FGF23.

FGFs 19, 21, and 23 function as hormones that control major metabolic processes, including glucose and lipid metabolism (FGF21) and phosphate and vitamin D homeostasis (FGF23). These FGFs depend on Klotho co-receptors for signaling because compared to paracrine FGFs, these ligands have intrinsically low binding affinity for both heparan sulfate and FGF receptor (FGFR) (Goetz et al., "Molecular Insights into the Klotho-dependent, Endocrine Mode of Action of Fibroblast Growth Factor 19 Subfamily Members," *Mol Cell Biol* 27:3417-3428 (2007); Goetz et al., "Conversion of a Paracrine Fibroblast Growth Factor into an Endocrine Fibroblast Growth Factor," *J Biol Chem* 287:29134-29146 (2012), which are hereby incorporated by reference in their entirety). Their low affinity for heparan sulfate enables these FGFs to signal in an endocrine fashion, whereas their low affinity for FGFR safeguards against nonspecific off-target signaling. FGF21 depends on βKlotho to activate its cognate FGFR (FGFR1c) in its target tissues including white adipose tissue (Ogawa et al., "βKlotho is Required for Metabolic Activity of Fibroblast Growth Factor 21," *Proc Natl Acad Sci USA* 104(18):7432-7437 (2007); Ding et al., "βKlotho is Required for Fibroblast Growth Factor 21 Effects on Growth and Metabolism," *Cell Metab* 16:387-393 (2012), which are hereby incorporated by reference in their entirety). βKlotho promotes binding of FGF21 to its cognate FGFR by engaging ligand and receptor independently through two distinct binding sites (Goetz et al., "Klotho Coreceptors Inhibit Signaling by Paracrine Fibroblast Growth Factor 8 Subfamily Ligands," *Mol Cell Biol* 32:1944-1954 (2012), which is hereby incorporated by reference in its entirety). βKlotho plays the same role in promoting binding of FGF19, a regulator of bile acid homeostasis, to its cognate FGFR (Goetz et al., "Klotho Coreceptors Inhibit Signaling by Paracrine Fibroblast Growth Factor 8 Subfamily Ligands," *Mol Cell Biol* 32:1944-1954 (2012), which is hereby incorporated by reference in its entirety). The binding site for βKlotho was mapped on FGF19 and FGF21 to the C-terminal region of each ligand that follows the β-trefoil core domain (Goetz et al., "Klotho Coreceptors Inhibit Signaling by Paracrine Fibroblast Growth Factor 8 Subfamily Ligands," *Mol Cell Biol* 32:1944-1954 (2012), which is hereby incorporated by reference in its entirety). The C-terminal tail peptides of FGF19 and FGF21 bind to a common site on βKlotho, with the C-terminal tail peptide of FGF19 exhibiting a greater binding affinity for that site than the C-terminal tail peptide of FGF21 (Goetz et al., "Klotho Coreceptors Inhibit Signaling by Paracrine Fibroblast Growth Factor 8 Subfamily Ligands," *Mol Cell Biol* 32:1944-1954 (2012), which is hereby incorporated by reference in its entirety). Thus, replacing the C-terminal region in FGF21 that follows the β-trefoil core domain with that of FGF19 would generate an FGF21 ligand with agonistic properties owing to enhanced binding affinity for βKlotho.

Accordingly, in one embodiment, a chimeric protein according to the present invention includes a β-trefoil core domain of FGF23 and a C-terminal region of FGF19. Such a protein will possess enhanced thermal stability, enhanced binding affinity for FGFR1c, and enhanced binding affinity for βKlotho compared to native FGF21. Such a molecule will therefore be particularly suited for use as a therapeutic.

Chimeric proteins according to the present invention may be isolated proteins or polypeptides. The isolated chimeric proteins of the present invention may be prepared for use in accordance with the methods of the present invention using standard methods of synthesis known in the art, including solid phase peptide synthesis (Fmoc or Boc strategies) or solution phase peptide synthesis. Alternatively, peptides of the present invention may be prepared using recombinant expression systems.

Accordingly, another aspect of the present invention relates to an isolated nucleic acid molecule encoding a chimeric protein according to the present invention. In one embodiment, the nucleic acid molecule comprises the nucleotide sequence of SEQ ID NO: 262, SEQ ID NO: 263, SEQ ID NO: 264, SEQ ID NO: 265, SEQ ID NO: 266, SEQ ID NO: 267, SEQ ID NO: 268, or SEQ ID NO: 269, as shown in Table 8.

TABLE 8

| Description of Chimeric Protein | Sequence |
|---|---|
| Nucleotide sequence of a FGF23/19 chimera composed of residues Y25 to P172 of human FGF23 and residues E174 to K216 of human FGF19 (bold) | SEQ ID NO: 262<br>ta tcccaatgcc tccccactgc<br>tcggctccag ctggggtggc ctgatccacc<br>tgtacacagc cacagccagg aacagctacc<br>acctgcagat ccacaagaat ggccatgtgg<br>atggcgcacc ccatcagacc atctacagtg<br>ccctgatgat cagatcagag gatgctggct<br>ttgtggtgat tacaggtgtg atgagcagaa<br>gatacctctg catggatttc agaggcaaca<br>tttttggatc acactatttc gacccggaga<br>actgcaggtt ccaacaccag acgctggaaa<br>acgggtacga cgtctaccac tctcctcagt<br>atcacttcct ggtcagtctg ggccgggcga<br>agagagcctt cctgccaggc atgaacccac<br>ccccgtactc ccagttcctg tcccggagga<br>acgagatccc cctaattcac ttcaacaccc<br>cc**gaggagcc tgaggacctc aggggccact**<br>**tggaatctga catgttctct tcgcccctgg**<br>**agaccgacag catggaccca tttgggcttg**<br>**tcaccggact ggaggccgtg aggagtccca**<br>**gctttgagaa g** |
| Nucleotide sequence of a FGF23/19 chimera composed of residues Y25 to N162 of human FGF23 and residues L169 to K216 of human FGF19 (bold) | SEQ ID NO: 263<br>ta tcccaatgcc tccccactgc<br>tcggctccag ctggggtggc ctgatccacc<br>tgtacacagc cacagccagg aacagctacc<br>acctgcagat ccacaagaat ggccatgtgg<br>atggcgcacc ccatcagacc atctacagtg<br>ccctgatgat cagatcagag gatgctggct<br>ttgtggtgat tacaggtgtg atgagcagaa<br>gatacctctg catggatttc agaggcaaca<br>tttttggatc acactatttc gacccggaga<br>actgcaggtt ccaacaccag acgctggaaa<br>acgggtacga cgtctaccac tctcctcagt<br>atcacttcct ggtcagtctg ggccgggcga<br>agagagcctt cctgccaggc atgaacccac<br>ccccgtactc ccagttcctg tcccggagga<br>ac**ctgcccat ggtcccagag gagcctgagg**<br>**acctcagggg ccacttggaa tctgacatgt**<br>**tctcttcgcc cctggagacc gacagcatgg**<br>**acccatttgg gcttgtcacc ggactggagg**<br>**ccgtgaggag tcccagcttt gagaag** |
| Nucleotide sequence of a FGF23/19 chimera composed of residues Y25 to P172 of human FGF23 harboring R140A/R143A double mutation (bold) and residues E174 to K216 of human FGF19 (bold) | SEQ ID NO: 264<br>ta tcccaatgcc tccccactgc<br>tcggctccag ctggggtggc ctgatccacc<br>tgtacacagc cacagccagg aacagctacc<br>acctgcagat ccacaagaat ggccatgtgg<br>atggcgcacc ccatcagacc atctacagtg<br>ccctgatgat cagatcagag gatgctggct<br>ttgtggtgat tacaggtgtg atgagcagaa<br>gatacctctg catggatttc agaggcaaca<br>tttttggatc acactatttc gacccggaga<br>actgcaggtt ccaacaccag acgctggaaa<br>acgggtacga cgtctaccac tctcctcagt<br>atcacttcct ggtcagtctg ggc**gcg**gcga<br>ag**gca**gcctt cctgccaggc atgaacccac<br>ccccgtactc ccagttcctg tcccggagga<br>acgagatccc cctaattcac ttcaacaccc<br>**gaggagcctg aggacctcag gggccacttg**<br>**gaatctgaca tgttctcttc gcccctggag**<br>**accgacagca tggacccatt tgggcttgtc**<br>**accggactgg aggccgtgag gagtcccagc**<br>**tttgagaag** |
| Nucleotide sequence of a FGF23/19 chimera composed of residues Y25 to P172 of human FGF23 harboring R48A/N49A double mutation (bold) and residues E174 to K216 of human FGF19 (bold) | SEQ ID NO: 265<br>ta tcccaatgcc tccccactgc<br>tcggctccag ctggggtggc ctgatccacc<br>tgtacacagc cacagcc**gcg gcc**agctacc<br>acctgcagat ccacaagaat ggccatgtgg<br>atggcgcacc ccatcagacc atctacagtg<br>ccctgatgat cagatcagag gatgctggct<br>ttgtggtgat tacaggtgtg atgagcagaa<br>gatacctctg catggatttc agaggcaaca<br>tttttggatc acactatttc gacccggaga<br>actgcaggtt ccaacaccag acgctggaaa<br>acgggtacga cgtctaccac tctcctcagt<br>atcacttcct ggtcagtctg ggccgggcga |

TABLE 8-continued

| Description of Chimeric Protein | Sequence |
|---|---|
| | agagagcctt cctgccaggc atgaacccac<br>ccccgtactc ccagttcctg tcccggagga<br>acgagatccc cctaattcac ttcaacaccc<br>**gaggagcctg aggacctcag gggccacttg**<br>**gaatctgaca tgttctcttc gcccctggag**<br>**accgacagca tggacccatt tgggcttgtc**<br>**accggactgg aggccgtgag gagtcccagc**<br>**tttgagaag** |
| Nucleotide sequence of a FGF23/21/19 chimera composed of residues Y25 to V136 and F157 to P172 of human FGF23, residues H145 to R163 of human FGF21 (bold Italic) and residues E174 to K216 of human FGF19 (bold) | SEQ ID NO: 266<br>ta tcccaatgcc tccccactgc<br>tcggctccag ctggggtggc ctgatccacc<br>tgtacacagc cacagccagg aacagctacc<br>acctgcagat ccacaagaat ggccatgtgg<br>atggcgcacc ccatcagacc atctacagtg<br>ccctgatgat cagatcagag gatgctggct<br>ttgtggtgat tacaggtgtg atgagcagaa<br>gatacctctg catggatttc agaggcaaca<br>tttttggatc acactatttc gacccggaga<br>actgcaggtt ccaacaccag acgctggaaa<br>acgggtacga cgtctaccac tctcctcagt<br>atcacttcct ggtc***cacctg ccagggaaca***<br>***agtccccaca ccgggaccct gcaccccgag***<br>***gaccagctcg c***ttcctgtcc cggaggaacg<br>agatccccct aattcacttc aacaccccc**g**<br>**aggagcctga ggacctcagg ggccacttgg**<br>**aatctgacat gttctcttcg cccctggaga**<br>**ccgacagcat ggacccattt gggcttgtca**<br>**ccggactgga ggccgtgagg agtcccagct**<br>**ttgagaag** |
| Nucleotide sequence of a FGF23/19 chimera composed of residues Y25 to N162 of human FGF23 harboring R140A/R143A double mutation (bold) and residues L169 to K216 of human FGF19 (bold) | SEQ ID NO: 267<br>ta tcccaatgcc tccccactgc<br>tcggctccag ctggggtggc ctgatccacc<br>tgtacacagc cacagccagg aacagctacc<br>acctgcagat ccacaagaat ggccatgtgg<br>atggcgcacc ccatcagacc atctacagtg<br>ccctgatgat cagatcagag gatgctggct<br>ttgtggtgat tacaggtgtg atgagcagaa<br>gatacctctg catggatttc agaggcaaca<br>tttttggatc acactatttc gacccggaga<br>actgcaggtt ccaacaccag acgctggaaa<br>acgggtacga cgtctaccac tctcctcagt<br>atcacttcct ggtcagtctg ggc**gcg**gcga<br>ag**gca**gcctt cctgccaggc atgaacccac<br>ccccgtactc ccagttcctg tcccggagga<br>acgagatccc cctaattcac ttcaacaccc<br>**ctgcccatgg tcccagagga gcctgaggac**<br>**ctcaggggcc acttggaatc tgacatgttc**<br>**tcttcgcccc tggagaccga cagcatggac**<br>**ccatttgggc ttgtcaccgg actggaggcc**<br>**gtgaggagtc ccagctttga gaag** |
| Nucleotide sequence of a FGF23/19 chimera composed of residues Y25 to N162 of human FGF23 harboring R48A/N49A double mutation (bold) and residues L169 to K216 of human FGF19 (bold) | SEQ ID NO: 268<br>ta tcccaatgcc tccccactgc<br>tcggctccag ctggggtggc ctgatccacc<br>tgtacacagc cacagcc**gcg gcc**agctacc<br>acctgcagat ccacaagaat ggccatgtgg<br>atggcgcacc ccatcagacc atctacagtg<br>ccctgatgat cagatcagag gatgctggct<br>ttgtggtgat tacaggtgtg atgagcagaa<br>gatacctctg catggatttc agaggcaaca<br>tttttggatc acactatttc gacccggaga<br>actgcaggtt ccaacaccag acgctggaaa<br>acgggtacga cgtctaccac tctcctcagt<br>atcacttcct ggtcagtctg ggccgggcga<br>agagagcctt cctgccaggc atgaacccac<br>ccccgtactc ccagttcctg tcccggagga<br>acgagatccc cctaattcac ttcaacaccc<br>**ctgcccatgg tcccagagga gcctgaggac**<br>**ctcaggggcc acttggaatc tgacatgttc**<br>**tcttcgcccc tggagaccga cagcatggac**<br>**ccatttgggc ttgtcaccgg actggaggcc**<br>**gtgaggagtc ccagctttga gaag** |
| Nucleotide sequence of a FGF23/21/19 chimera composed of residues Y25 to V136 and | SEQ ID NO: 269<br>ta tcccaatgcc tccccactgc<br>tcggctccag ctggggtggc ctgatccacc |

TABLE 8-continued

| Description of Chimeric Protein | Sequence |
|---|---|
| F157 to N162 of human FGF23, residues H145 to R163 of human FGF21 (bold Italic) and residues L169 to K216 of human FGF19 (bold) | tgtacacagc cacagccagg aacagctacc<br>acctgcagat ccacaagaat ggccatgtgg<br>atggcgcacc ccatcagacc atctacagtg<br>ccctgatgat cagatcagag gatgctggct<br>ttgtggtgat tacaggtgtg atgagcagaa<br>gatacctctg catggatttc agaggcaaca<br>tttttggatc acactatttc gacccggaga<br>actgcaggtt ccaacaccag acgctggaaa<br>acgggtacga cgtctaccac tctcctcagt<br>atcacttcct ggtc***cacctg ccagggaaca***<br>***agtccccaca ccgggaccct gcaccccgag***<br>***gaccagctcg c***ttcctgtcc cggaggaacg<br>agatccccct aattcacttc aacacccccc<br>**tgcccatggt cccagaggag cctgaggacc**<br>**tcaggggcca cttggaatct gacatgttct**<br>**cttcgcccct ggagaccgac agcatggacc**<br>**catttgggct tgtcaccgga ctggaggccg**<br>**tgaggagtcc cagctttgag aag** |

Another aspect of the present invention relates to a nucleic acid construct comprising a nucleic acid molecule encoding a chimeric protein according to the present invention, a 5' DNA promoter sequence, and a 3' terminator sequence. The nucleic acid molecule, the promoter, and the terminator are operatively coupled to permit transcription of the nucleic acid molecule.

Also encompassed are vectors or expression vectors comprising nucleic acid molecules encoding a chimeric protein according to the present invention and host cells comprising such nucleic acid molecules. Nucleic acid molecules according to the present invention can be expressed in a host cell, and the encoded polynucleotides isolated, according to techniques that are known in the art.

Generally, the use of recombinant expression systems involves inserting the nucleic acid molecule encoding the amino acid sequence of the desired peptide into an expression system to which the molecule is heterologous (i.e., not normally present). One or more desired nucleic acid molecules encoding a peptide of the invention may be inserted into the vector. When multiple nucleic acid molecules are inserted, the multiple nucleic acid molecules may encode the same or different peptides. The heterologous nucleic acid molecule is inserted into the expression system or vector in proper sense (5'→3') orientation relative to the promoter and any other 5' regulatory molecules, and correct reading frame.

The preparation of the nucleic acid constructs can be carried out using standard cloning procedures well known in the art as described by Joseph Sambrook et al., MOLECULAR CLONING: A LABORATORY MANUAL (Cold Springs Harbor 1989). U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in a suitable host cell.

A variety of genetic signals and processing events that control many levels of gene expression (e.g., DNA transcription and messenger RNA ("mRNA") translation) can be incorporated into the nucleic acid construct to maximize peptide production. For the purposes of expressing a cloned nucleic acid sequence encoding a desired peptide, it is advantageous to use strong promoters to obtain a high level of transcription. Depending upon the host system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR.

There are other specific initiation signals required for efficient gene transcription and translation in prokaryotic cells that can be included in the nucleic acid construct to maximize peptide production. Depending on the vector system and host utilized, any number of suitable transcription and/or translation elements, including constitutive, inducible, and repressible promoters, as well as minimal 5' promoter elements, enhancers or leader sequences may be used. For a review on maximizing gene expression see Roberts and Lauer, "Maximizing Gene Expression On a Plasmid Using Recombination In Vitro," *Methods in Enzymology* 68:473-82 (1979), which is hereby incorporated by reference in its entirety.

A nucleic acid molecule encoding an isolated peptide of the present invention, a promoter molecule of choice, including, without limitation, enhancers, and leader sequences; a suitable 3' regulatory region to allow transcription in the host, and any additional desired components, such as reporter or marker genes, are cloned into the vector of choice using standard cloning procedures in the art, such as described in Joseph Sambrook et al., MOLECULAR CLONING: A LABORATORY MANUAL (Cold Springs Harbor 1989); Frederick M. Ausubel, SHORT PROTOCOLS IN MOLECULAR BIOLOGY (Wiley 1999); and U.S. Pat. No. 4,237,224 to Cohen and Boyer, which are hereby incorporated by reference in their entirety.

Once the nucleic acid molecule encoding the peptide has been cloned into an expression vector, it is ready to be incorporated into a host. Recombinant molecules can be introduced into cells, without limitation, via transfection (if the host is a eukaryote), transduction, conjugation, mobilization, or electroporation, lipofection, protoplast fusion, mobilization, or particle bombardment, using standard cloning procedures known in the art, as described by JOSEPH SAMBROOK et al., MOLECULAR CLONING: A LABORATORY MANUAL (Cold Springs Harbor 1989), which is hereby incorporated by reference in its entirety.

A variety of suitable host-vector systems may be utilized to express the recombinant protein or polypeptide. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria.

Purified peptides may be obtained by several methods readily known in the art, including ion exchange chromatography, hydrophobic interaction chromatography, affinity chromatography, gel filtration, and reverse phase chromatography. The peptide is preferably produced in purified form (preferably at least about 80% or 85% pure, more preferably at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC.

Another aspect of the present invention relates to a pharmaceutical composition comprising a chimeric protein according to the present invention and a pharmaceutically acceptable carrier.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "pharmaceutically acceptable" means it is, within the scope of sound medical judgment, suitable for use in contact with the cells of humans and lower animals without undue toxicity, irritation, allergic response, and the like, and is commensurate with a reasonable benefit/risk ratio.

In one embodiment, the pharmaceutical composition includes an organotropic targeting agent. In one embodiment, the targeting agent is covalently linked to the chimeric protein via a linker that is cleaved under physiological conditions.

Another aspect of the present invention relates to a method of treating a subject suffering from a disorder and administering to this selected subject a therapeutically effective amount of a chimeric protein according to the present invention.

The chimeric protein of the present invention or pharmaceutical composition thereof can be administered orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes. The most suitable route may depend on the condition and disorder of the recipient. The formulations may conveniently be presented in unit dosage form and may be prepared by any of the methods well known in the art of pharmacy.

In some embodiments, the chimeric protein of the present invention or a pharmaceutical composition thereof is administered in a therapeutically effective amount in combination with a therapeutically effective amount of a second agent. In some embodiments, the chimeric protein of the present invention or pharmaceutical composition thereof is administered in conjunction with the second agent, i.e., the respective periods of administration are part of a single administrative regimen. In some embodiments, the chimeric protein of the present invention or pharmaceutical composition thereof and the second agent are administered concurrently, i.e., the respective periods of administration overlap each other. In some embodiments, the chimeric protein of the present invention or pharmaceutical composition thereof and the second agent are administered non-concurrently, i.e., the respective periods of administration do not overlap each other. In some embodiments, the chimeric protein of the present invention or pharmaceutical composition thereof and the second agent are administered sequentially, i.e., the chimeric protein of the present invention or pharmaceutical composition thereof is administered prior to and/or after the administration of the second agent. In some embodiments, the chimeric protein of the present invention or pharmaceutical composition thereof and the second agent are administered simultaneously as separate compositions. In some embodiments, the chimeric protein of the present invention or pharmaceutical composition thereof and the second agent are administered simultaneously as part of the same compositions.

In some embodiments, the second agent is an anti-inflammatory agent, an antihypertensive agent, an anti-diabetic agent, a triglyceride-lowering agent, and/or cholesterol-lowering drug (such as a drug of the "statin" class). In some embodiments, the second agent is insulin. In some embodiments, the insulin is rapid acting, short acting, regular acting, intermediate acting, or long acting insulin. In some embodiments, the insulin is and/or comprises Humalog, Lispro, Novolog, Apidra, Humulin, Aspart, regular insulin, NPH, Lente, Ultralente, Lantus, Glargine, Levemir, or Detemir. In some embodiments, the second agent is a statin. In some embodiments, the statin is and/or comprises Atorvastatin (e.g., Lipitor or Torvast), Cerivastatin (e.g., Lipobay or Baycol), Fluvastatin (e.g., Lescol or Lescol), Lovastatin (e.g., Mevacor, Altocor, or Altoprev) Mevastatin, Pitavastatin (e.g., Livalo or Pitava), Pravastatin (e.g., Pravachol, Selektine, or Lipostat) Rosuvastatin (e.g., Crestor), Simvastatin (e.g., Zocor or Lipex), Vytorin, Advicor, Besylate Caduet or Simcor.

In one particular embodiment of the present invention, the chimeric protein of the present invention or pharmaceutical composition thereof is administered with one or more agents selected from the group consisting of an anti-inflammatory agent, an antidiabetic agent, a triglyceride-lowering agent, a cholesterol-lowering agent, an antihypertensive agent, and combinations thereof.

In one embodiment, the subject is a mammal. In one particular embodiment, the subject is a human.

In one embodiment the subject suffering from diabetes, obesity, or metabolic syndrome. In one embodiment the subject has diabetes. As used herein, diabetes includes type I diabetes, type II diabetes, and gestational diabetes. In yet another embodiment, the subject has obesity. In yet another embodiment, the subject has metabolic syndrome.

The pharmaceutical compositions comprising a chimeric protein of the present invention provided herein can be used to treat a number of conditions. The condition may be one which the therapeutic outcome includes a decrease in blood glucose, a decrease in blood fructosamine, an increase in energy expenditure, an increase in fat utilization, a decrease in body weight, a decrease in body fat, a decrease in triglycerides, a decrease in free fatty acids, an increase in fat excretion, a preservation of pancreatic β-cell function and mass, a decrease in total blood cholesterol, a decrease in blood low-density lipoprotein cholesterol, an increase in blood high-density lipoprotein cholesterol, an increase in blood adiponectin, an increase in insulin sensitivity, an increase in leptin sensitivity, a decrease in blood insulin, a decrease in blood leptin, a decrease in blood glucagon, an increase in glucose uptake by adipocytes, a decrease in fat accumulation in hepatocytes, and/or an increase in fat oxidation in hepatocytes. Each of these parameters can be measured by standard methods, for example, by measuring oxygen consumption to determine metabolic rate, using scales to determine weight, and measuring lean body mass composition or mass to determine fat. Moreover, the presence and amount of triglycerides, free fatty acids, glucose and leptin can be determined by standard methods (e.g., blood test).

Additional conditions that are treatable in accordance with the present invention include one or more of high blood glucose, metabolic syndrome, lipodystrophy syndrome, dyslipidemia, insulin resistance, leptin resistance, atherosclerosis, vascular disease, hypercholesterolemia, hypertriglyceridemia, non-alcoholic fatty liver disease, overweight, and obesity.

Dosages and desired drug concentrations of pharmaceutical compositions of the present invention may vary depending on the particular use envisioned. The determination of the appropriate dosage or route of administration is well within the skill of an ordinary physician.

When in vivo administration of chimeric protein of the present invention or pharmaceutical composition thereof is employed, normal dosage amounts may vary from, e.g., about 10 ng/kg to up to 100 mg/kg of mammal body weight or more per day, preferably about 1 μg/kg/day to 10 mg/kg/day, depending upon the route of administration. Guidance as to particular dosages and methods of delivery is provided in the literature; see, for example, U.S. Pat. No. 4,657,760; 5,206,344; or 5,225,212, which are hereby incorporated by reference in their entirety. It is anticipated that different formulations will be effective for different treatment compounds and different disorders, that administration targeting one organ or tissue, for example, may necessitate delivery in a manner different from that to another organ or tissue.

Where sustained-release administration of a chimeric protein of the present invention is desired in a formulation with release characteristics suitable for the treatment of any disease or disorder requiring administration of the chimeric protein of the present invention, microencapsulation is contemplated. Microencapsulation of recombinant proteins for sustained release has been successfully performed with human growth hormone (rhGH), interferon-(rhIFN-), interleukin-2, and MN rgp120. Johnson et al., "Preparation and Characterization of Poly(D,L-lactide-co-glycolide) Microspheres for Controlled Release of Human Growth Hormone," *Nat. Med.* 2:795-799 (1996); Yasuda, "Sustained Release Formulation of Interferon," *Biomed. Ther.* 27:1221-1223 (1993); Hora et al., "Controlled Release of Interleukin-2 from Biodegradable Microspheres," *Nat. Biotechnol.* 8:755-758 (1990); Cleland, "Design and Production of Single Immunization Vaccines Using Polylactide Polyglycolide Microsphere Systems," in VACCINE DESIGN: THE SUBUNIT AND ADJUVANT APPROACH 439-462 (Powell and Newman, eds. 1995); WO 97/03692; WO 96/40072; WO 96/07399; and U.S. Pat. No. 5,654,010, which are hereby incorporated by reference in their entirety. The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis. "Controlled release of bioactive agents from lactide/glycolide polymer," in: BIODEGRADABLE POLYMERS AS DRUG DELIVERY SYSTEMS 1-41 (M. Chasin and R. Langer eds. 1990), which is hereby incorporated by reference in its entirety.

The chimeric protein of the present invention or pharmaceutical composition thereof may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. For other patients, it will be necessary to prescribe not more than one or two doses per day.

EXAMPLES

Example 1

Generation of an Expression Construct for a Chimeric FGF23 Protein

Figure 2:
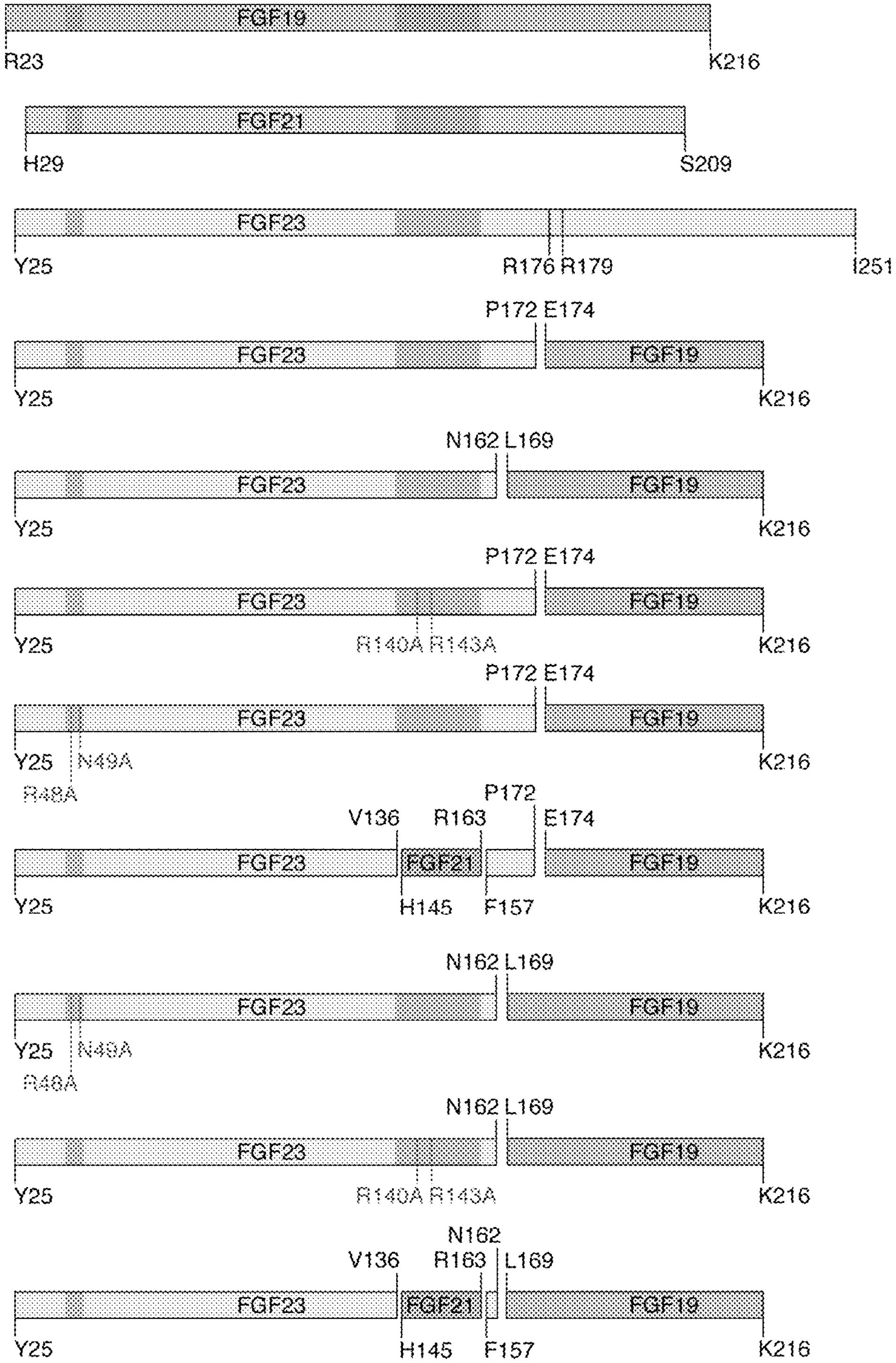
FIG. 2 is a schematic drawing illustrating exemplary chimeric proteins according to the present invention. Amino acid boundaries of each endocrine FGF ligand and of each component of the chimeras are labeled with residue letter and number. Also labeled are the arginine residues of the proteolytic cleavage site in FGF23. The HS-binding regions are shaded. HS-binding residues mutated in the FGF23 portion of the chimeras are labeled with residue letter and number.

To make the expression constructs for the chimeric FGF23 proteins of the present invention (see FIG. 2), a method of gene splicing by overlap extension polymerase chain reaction was employed (Horton et al., Gene 77:61-68 (1989), which is hereby incorporated by reference in its entirety). Specifically, the FGF23$^{Y25\text{-}P172}$-FGF19$^{E174\text{-}K216}$ chimera (SEQ ID NO: 254) was generated as follows: the sequence of the human FGF23 gene encoding residues 25 to 172 was amplified by polymerase chain reaction (PCR) using a 3' primer with an extension by 18 nucleotides that encode residues 174 to 179 of human FGF19. In a separate PCR reaction, the sequence of the human FGF19 gene encoding residues 174 to 216 was amplified using a 5' primer with an extension by 18 nucleotides that encode residues 167 to 172 of human FGF23. Thus, DNA fragments encoding the components of the chimeric FGF23 protein were generated, each containing a small sequence of the other.

The two DNA fragments were mixed and another PCR reaction was carried out to splice them together to generate the DNA encoding the chimeric FGF23 protein. The primers used for this PCR reaction were the flanking primers of the first two PCR reactions, that is, the 5' primer with which the FGF23 DNA fragment had been amplified and the 3' primer with which the FGF19 DNA fragment had been amplified. These primers contained restriction enzyme sites for insertion of the PCR product into a pET30 expression vector to generate an expression construct encoding a $FGF23^{Y25-P172}$ $FGF19^{E174-K216}$ chimera with an N-terminal fusion tag. The fusion tag consisted of a hexahistidine tag, a Thrombin cleavage site, an S-tag, and an Enterokinase cleavage site.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An isolated chimeric protein comprising:

an N-terminus coupled to a C-terminus, wherein the N-terminus comprises an N-terminal portion from an FGF23 molecule and the C-terminus comprises a C-terminal portion from an FGF19 molecule, wherein the isolated chimeric protein has the amino acid sequence of SEQ ID NO: 254.

2. A pharmaceutical composition comprising the chimeric protein according to claim 1 and a pharmaceutically-acceptable carrier.

3. The pharmaceutical composition according to claim 2 further comprising:

one or more agents selected from the group consisting of an anti-inflammatory agent, an antidiabetic agent, a triglyceride-lowering agent, a cholesterol-lowering agent, an antihypertensive agent, and combinations thereof.

4. The pharmaceutical composition according to claim 3 further comprising an organotropic targeting agent.

5. The pharmaceutical composition according to claim 4, wherein the targeting agent is covalently linked to the chimeric protein via a linker that is cleaved under physiological conditions.

6. A method for decreasing blood glucose levels in a subject in need thereof, the method comprising:

administering to the subject the chimeric protein according to claim 1.

7. The method according to claim 6, wherein the subject has diabetes, obesity, or metabolic syndrome.

8. The method according to claim 6, wherein the subject has type II diabetes or gestational diabetes.

9. The method according to claim 6, wherein the subject has type I diabetes.

10. The method according to claim 6, wherein the subject has obesity.

11. The method according to claim 6, wherein the subject has metabolic syndrome.

12. The method according to claim 6, wherein said administering is carried out parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes.

13. The method according to claim 6, wherein the chimeric protein is administered with a pharmaceutically-acceptable carrier.

14. The method according to claim 6, wherein the subject is a mammal.

15. The method according to claim 6, wherein the subject is a human.

16. The method according to claim 6, wherein the chimeric protein is co-administered with one or more of an anti-inflammatory agent, an antidiabetic agent, a triglyceride-lowering agent, a cholesterol-lowering agent, or an antihypertensive agent.

* * * * *

UNITED STATES PATENT AND TRADEMARK OFFICE

CERTIFICATE OF CORRECTION

PATENT NO. : 9,550,820 B2
APPLICATION NO. : 14/185366
DATED : January 24, 2017
INVENTOR(S) : Mohammadi et al.

It is certified that error appears in the above-identified patent and that said Letters Patent is hereby corrected as shown below:

In the Specification

Column 1, Lines 10-13, delete "This invention was made with government support under grant number DE13686 awarded by the National Institutes of Health. The government has certain rights in this invention." and insert in its place --This invention was made with government support under grant number DE013686 awarded by the National Institutes of Health. The government has certain rights in the invention.--

Signed and Sealed this
First Day of April, 2025

Coke Morgan Stewart
*Acting Director of the United States Patent and Trademark Office*

SEQUENCE LISTING

<160> NUMBER OF SEQ ID NOS: 269

<210> SEQ ID NO 1
<211> LENGTH: 251
<212> TYPE: PRT
<213> ORGANISM: Homo sapiens

<400> SEQUENCE: 1

Met Leu Gly Ala Arg Leu Arg Leu Trp Val Cys Ala Leu Cys Ser Val
1 5 10 15

Cys Ser Met Ser Val Leu Arg Ala Tyr Pro Asn Ala Ser Pro Leu Leu
20 25 30

Gly Ser Ser Trp Gly Gly Leu Ile His Leu Tyr Thr Ala Thr Ala Arg
35 40 45

Asn Ser Tyr His Leu Gln Ile His Lys Asn Gly His Val Asp Gly Ala
50 55 60

Pro His Gln Thr Ile Tyr Ser Ala Leu Met Ile Arg Ser Glu Asp Ala
65 70 75 80

Gly Phe Val Val Ile Thr Gly Val Met Ser Arg Arg Tyr Leu Cys Met
85 90 95

Asp Phe Arg Gly Asn Ile Phe Gly Ser His Tyr Phe Asp Pro Glu Asn
100 105 110

Cys Arg Phe Gln His Gln Thr Leu Glu Asn Gly Tyr Asp Val Tyr His
115 120 125

Ser Pro Gln Tyr His Phe Leu Val Ser Leu Gly Arg Ala Lys Arg Ala
130 135 140

Phe Leu Pro Gly Met Asn Pro Pro Pro Tyr Ser Gln Phe Leu Ser Arg
145 150 155 160

Arg Asn Glu Ile Pro Leu Ile His Phe Asn Thr Pro Ile Pro Arg Arg
165 170 175

His Thr Arg Ser Ala Glu Asp Asp Ser Glu Arg Asp Pro Leu Asn Val
180 185 190

Leu Lys Pro Arg Ala Arg Met Thr Pro Ala Pro Ala Ser Cys Ser Gln
195 200 205

Glu Leu Pro Ser Ala Glu Asp Asn Ser Pro Met Ala Ser Asp Pro Leu
210 215 220

Gly Val Val Arg Gly Gly Arg Val Asn Thr His Ala Gly Gly Thr Gly
225 230 235 240

Pro Glu Gly Cys Arg Pro Phe Ala Lys Phe Ile
245 250

<210> SEQ ID NO 2
<211> LENGTH: 251
<212> TYPE: PRT
<213> ORGANISM: Gorilla gorilla

<400> SEQUENCE: 2

Met Leu Gly Ala Arg Leu Arg Leu Trp Val Cys Ala Leu Cys Ser Val

-continued

```
1               5                   10                  15

Cys Ser Leu Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr Tyr Ala Gly Gly Thr Gly
225                 230                 235                 240

Pro Glu Gly Cys Arg Pro Phe Pro Lys Phe Ile
                245                 250


<210> SEQ ID NO 3
<211> LENGTH: 251
<212> TYPE: PRT
<213> ORGANISM: Nomascus leucogenys

<400> SEQUENCE: 3

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asn Pro Glu Asn
            100                 105                 110

Cys Arg Phe Gln His Gln Thr Leu Glu Asn Gly Tyr Asp Val Tyr His
        115                 120                 125
```

Ser Pro Gln His His Phe Leu Val Ser Leu Gly Arg Ala Lys Arg Ala
130 135 140

Phe Leu Pro Gly Met Asn Pro Pro Pro Tyr Ser Gln Phe Leu Ser Arg
145 150 155 160

Arg Asn Glu Ile Pro Leu Leu His Phe Asn Thr Pro Thr Pro Arg Arg
165 170 175

His Thr Arg Ser Ala Glu Asp Asp Ser Glu Arg Asp Pro Leu Asn Val
180 185 190

Leu Lys Pro Arg Ala Arg Met Thr Pro Ala Pro Ala Ser Cys Ser Gln
195 200 205

Glu Leu Leu Ser Ser Glu Asp Asn Ser Pro Met Ala Ser Asp Pro Leu
210 215 220

Gly Val Val Arg Gly Gly Arg Val Asn Thr His Ala Gly Gly Thr Gly
225 230 235 240

Pro Glu Gly Cys Arg Pro Phe Pro Lys Phe Ile
245 250

<210> SEQ ID NO 4
<211> LENGTH: 251
<212> TYPE: PRT
<213> ORGANISM: Macaca mulatta

<400> SEQUENCE: 4

Met Leu Gly Ala Arg Leu Arg Leu Trp Val Cys Ala Leu Cys Ser Val
1 5 10 15

Cys Ser Met Ser Val Ile Arg Ala Tyr Pro Asn Ala Ser Pro Leu Leu
20 25 30

Gly Ser Ser Trp Gly Gly Leu Ile His Leu Tyr Thr Ala Thr Ala Arg
35 40 45

Asn Ser Tyr His Leu Gln Ile His Lys Asn Gly His Val Asp Gly Ala
50 55 60

Pro His Gln Thr Ile Tyr Ser Ala Leu Met Ile Arg Ser Glu Asp Ala
65 70 75 80

Gly Phe Val Val Ile Thr Gly Val Met Ser Arg Arg Tyr Leu Cys Met
85 90 95

Asp Phe Arg Gly Asn Ile Phe Gly Ser His Tyr Phe Asn Pro Glu Asn
100 105 110

Cys Arg Phe Arg His Trp Thr Leu Glu Asn Gly Tyr Asp Val Tyr His
115 120 125

Ser Pro Gln His His Phe Leu Val Ser Leu Gly Arg Ala Lys Arg Ala
130 135 140

Phe Leu Pro Gly Met Asn Pro Pro Pro Tyr Ser Gln Phe Leu Ser Arg
145 150 155 160

Arg Asn Glu Ile Pro Leu Ile His Phe Asn Thr Pro Arg Pro Arg Arg
165 170 175

His Thr Arg Ser Ala Glu Asp Asp Ser Glu Arg Asp Pro Leu Asn Val
180 185 190

Leu Lys Pro Arg Ala Arg Met Thr Pro Ala Pro Ala Ser Cys Ser Gln
195 200 205

Glu Leu Pro Ser Ala Glu Asp Asn Ser Pro Val Ala Ser Asp Pro Leu
210 215 220

Gly Val Val Arg Gly Gly Arg Val Asn Thr His Ala Gly Gly Thr Gly
225 230 235 240

Pro Glu Ala Cys Arg Pro Phe Pro Lys Phe Ile
245 250

<210> SEQ ID NO 5
<211> LENGTH: 251
<212> TYPE: PRT
<213> ORGANISM: Macaca fascicularis

<400> SEQUENCE: 5

```
Met Leu Gly Ala Arg Leu Arg Leu Trp Val Cys Ala Leu Cys Ser Val
1               5                   10                  15

Cys Ser Met Ser Val Ile Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asn Pro Glu Asn
            100                 105                 110

Cys Arg Phe Arg His Trp Thr Leu Glu Asn Gly Tyr Asp Val Tyr His
        115                 120                 125

Ser Pro Gln His His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile His Phe Asn Thr Pro Arg Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Val Ala Ser Asp Pro Leu
    210                 215                 220

Gly Val Val Arg Ala Gly Arg Val Asn Thr His Ala Gly Gly Thr Gly
225                 230                 235                 240

Pro Glu Ala Cys Arg Pro Phe Pro Lys Phe Ile
                245                 250
```

<210> SEQ ID NO 6
<211> LENGTH: 251
<212> TYPE: PRT
<213> ORGANISM: Pan troglodytes

<400> SEQUENCE: 6

```
Met Leu Gly Ala Arg Leu Arg Leu Trp Val Cys Ala Leu Cys Ser Val
1               5                   10                  15

Cys Ser Val Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80
```

```
Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asn Pro Glu Asn
            100                 105                 110

Cys Arg Phe Gln His Gln Thr Leu Glu Asn Gly Tyr Asp Val Tyr Tyr
        115                 120                 125

Ser Pro Gln Tyr His Phe Leu Val Ser Leu Gly Arg Ala Lys Arg Ala
    130                 135                 140

Phe Leu Pro Ser Met Asn Pro Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Pro Lys Phe Ile
                245                 250


<210> SEQ ID NO 7
<211> LENGTH: 251
<212> TYPE: PRT
<213> ORGANISM: Callithrix jacchus

<400> SEQUENCE: 7

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Ala Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Leu Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asn Pro Glu Asn
            100                 105                 110

Cys Arg Phe Arg Pro Gln Arg Leu Glu Asn Gly Tyr Asp Val Tyr Gln
        115                 120                 125

Ser Pro Gln His His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile His Phe Asn Thr Pro Lys Pro Arg Arg
                165                 170                 175

His Thr Arg Ser Ala Glu Asp Asp Pro Glu Leu Asp Pro Leu Asn Val
            180                 185                 190

Leu Lys Ser Arg Val Arg Met Thr Pro Ala Pro Ala Ser Cys Ser Gln
```

-continued

```
        195                 200                 205

Glu Leu Leu Ser Ala Glu Asp Asn Ser Pro Val Gly Ser Asp Pro Leu
    210                 215                 220

Gly Met Val Arg Gly Gly Arg Val Asn Ser His Ala Glu Gly Thr Gly
225                 230                 235                 240

Pro Glu Gly Cys Ser Pro Phe Pro Lys Leu Ile
                245                 250


<210> SEQ ID NO 8
<211> LENGTH: 251
<212> TYPE: PRT
<213> ORGANISM: Loxodonta africana

<400> SEQUENCE: 8

Met Leu Gly Ala Arg Leu Arg Leu Trp Val Cys Thr Leu Cys Ser Ala
1               5                   10                  15

Cys Ser Met Cys Ser Val Arg Ala Tyr Pro Asn Ala Ser Pro Leu Leu
            20                  25                  30

His Ser Ser Trp Gly Gly Leu Thr His Leu Tyr Thr Ala Thr Ala Arg
        35                  40                  45

Asn Ser Tyr His Leu Gln Ile His Lys Asp Gly His Val Asp Gly Thr
    50                  55                  60

Pro Asp Gln Thr Ile Tyr Ser Ala Leu Ile Ile Arg Ser Glu Glu Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asn Pro Glu Asn
            100                 105                 110

Cys Arg Phe Lys His Trp Thr Leu Glu Asn Gly Tyr Asp Val Tyr His
        115                 120                 125

Ser Pro Gln His His Phe Leu Val Ser Leu Gly Arg Val Lys Lys Ala
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile Tyr Phe Asn Thr Pro Lys Pro Arg Arg
                165                 170                 175

His Thr Arg Ser Ala Glu Asp Asp Ser Glu Arg Asp Pro Leu Asn Val
            180                 185                 190

Leu Lys Pro Arg Pro Arg Met Thr Pro Ala Pro Ala Ser Cys Ser Gln
        195                 200                 205

Glu Leu Leu Ser Ala Glu Asp Asn Ser Val Val Ala Asn Asp Pro Leu
    210                 215                 220

Gly Val Val Arg Ser Asn Arg Val Asn Thr His Ala Gly Gly Ile Gly
225                 230                 235                 240

Val Glu Arg Cys Arg Pro Phe Pro Lys Phe Ile
                245                 250


<210> SEQ ID NO 9
<211> LENGTH: 250
<212> TYPE: PRT
<213> ORGANISM: Erinaceus telfairi

<400> SEQUENCE: 9

Met Leu Gly Ala His Leu Arg Leu Trp Val Cys Ala Leu Cys Ser Val
1               5                   10                  15

Ser Ala Met Tyr His Val Arg Ala Tyr Pro Asn Ala Ser Pro Leu Leu
```

```
            20                  25                  30

Gly Thr Ser Trp Ala Gly Leu Thr His Leu Tyr Thr Ala Thr Ala Arg
        35                  40                  45

Asn Ser Phe His Leu Gln Ile His Lys Asp Gly His Val Asp Gly Thr
    50                  55                  60

Pro His Gln Thr Ile Tyr Ser Ala Leu Met Ile Arg Ser Glu Asp Ser
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Thr Ala Asp Ser
            100                 105                 110

Cys Arg Phe Arg Gln Arg Thr Leu Glu Asn Gly Tyr Asp Val Tyr His
        115                 120                 125

Ser Pro Gln His His Phe Leu Ile Ser Leu Gly Arg Ala Lys Arg Val
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile His Phe Asn Thr Pro Arg Pro Arg Arg
                165                 170                 175

His Thr Arg Ser Ala Glu Glu Glu Val Glu Gln Asp Pro Leu Asn Val
            180                 185                 190

Leu Lys Pro Arg Pro Arg Met Thr Pro Ala Pro Ala Ser Cys Ser Gln
        195                 200                 205

Glu Leu Pro Ser Ala Glu Asp Asn Ser Ala Leu Ala Ser Asp Pro Leu
    210                 215                 220

Gly Val Val Arg Gly Lys Lys Leu Asn Thr His Ala Val Gly Met Gly
225                 230                 235                 240

Ala Glu Arg Cys Arg Pro Phe Pro Lys Phe
                245                 250


<210> SEQ ID NO 10
<211> LENGTH: 235
<212> TYPE: PRT
<213> ORGANISM: Erinaceus europaeus

<400> SEQUENCE: 10

Met Leu Gly Ala His Leu Gly Leu Val Val Cys Ala Leu Val Ser Arg
1               5                   10                  15

Ala Tyr Pro Asn Ala Ser Pro Leu Leu Gly Phe Ser Trp Gly Gly Leu
            20                  25                  30

Thr His Leu Tyr Thr Ala Thr Ala Arg Asn Ser Tyr His Leu Gln Ile
        35                  40                  45

His Lys Asp Gly His Val Asp Gly Ser Pro Gln Gln Thr Ile Tyr Ala
    50                  55                  60

Gly Phe Val Met Ile Thr Gly Val Met Ser Arg Arg Tyr Leu Cys Met
65                  70                  75                  80

Asp Phe Arg Ser Asn Ile Phe Gly Ser His His Phe Ala Pro Glu Ser
                85                  90                  95

Cys Arg Phe Arg His Arg Thr Leu Glu Asn Gly Tyr Asp Val Tyr His
            100                 105                 110

Ser Pro Gln His His Phe Leu Val Ser Leu Gly Arg Ala Lys Arg Ala
        115                 120                 125

Phe Leu Pro Gly Thr Asn Pro Pro Pro Tyr Ser Gln Phe Leu Ser Arg
    130                 135                 140
```

```
Arg Asn Glu Val Pro Leu Ile His Phe Asn Thr Pro Arg Pro Arg Arg
145                 150                 155                 160

His Thr Arg Ser Ala Glu Asp Asn Ser Glu Leu Asp Pro Leu Asn Val
                165                 170                 175

Leu Lys Pro Arg Pro Arg Met Thr Pro Ala Pro Ala Ser Cys Ser Gln
            180                 185                 190

Glu Leu Pro Ser Ala Glu Asp Asn Ser Met Val Ala Ser Asp Pro Leu
        195                 200                 205

Gly Val Val Arg Ala Asn Arg Val Asn Thr His Ala Gly Gly Leu Gly
    210                 215                 220

Val Asp Lys Cys Arg Pro Phe Pro Lys Phe Ile
225                 230                 235
```

<210> SEQ ID NO 11
<211> LENGTH: 252
<212> TYPE: PRT
<213> ORGANISM: Otolemur garnettii

<400> SEQUENCE: 11

```
Met Leu Gly Thr Cys Leu Arg Leu Trp Val Cys Ala Leu Cys Ser Val
1               5                   10                  15

Cys Ser Val Ser Ile Val Arg Ala Tyr Pro Asn Ala Ser Pro Leu Leu
            20                  25                  30

Ser Ser Ser Trp Gly Gly Leu Thr His Leu Tyr Thr Ala Ser Ala Arg
        35                  40                  45

Asn Ser Tyr His Leu Gln Ile His Lys Asp Gly His Val Asp Gly Thr
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Lys Gly Asn Ile Phe Gly Ser His Ser Phe His Pro Glu Ser
            100                 105                 110

Cys Arg Phe Arg His Arg Thr Leu Glu Asn Gly Tyr Asp Val Tyr Leu
        115                 120                 125

Ser Pro Gln His His Phe Leu Val Ser Leu Gly Arg Ser Lys Arg Pro
    130                 135                 140

Phe Leu Pro Gly Met Asn Pro Pro Pro Phe Ser Gln Phe Leu Ser Arg
145                 150                 155                 160

Arg Asn Asp Ile Pro Leu Ile His Phe Asn Thr Pro Arg Pro Arg Arg
                165                 170                 175

His Thr Arg Ser Ala Glu Asp Asn Asp Ser Glu Leu Asp Pro Leu Asn
            180                 185                 190

Val Leu Lys Pro Arg Pro Arg Ala Thr Pro Gly Pro Ala Ser Cys Ser
        195                 200                 205

Gln Glu Leu Pro Ser Ala Glu Asp Asn Ser Leu Val Ala Ser Asp Pro
    210                 215                 220

Leu Gly Val Val Arg Gly Asn Arg Val Asn Ala His Ala Gly Arg Ala
225                 230                 235                 240

Gly Leu Asp Arg Cys Arg Pro Phe Pro Arg Tyr Phe
                245                 250
```

<210> SEQ ID NO 12
<211> LENGTH: 252
<212> TYPE: PRT
<213> ORGANISM: Oryctolagus cuniculus

<400> SEQUENCE: 12

```
Met Leu Gly Ala Arg Leu Leu Arg Leu Leu Val Cys Ala Leu Gly Ser
1               5                   10                  15

Val Cys Ser Trp Cys Val Val Arg Ala Tyr Pro Asp Thr Ser Pro Leu
            20                  25                  30

Leu Ser Ser Ser Trp Ala Gly Leu Thr His Leu Tyr Thr Ala Thr Ala
        35                  40                  45

Arg Asn Ser Tyr His Leu Gln Ile His Lys Asp Gly Gln Val Asp Gly
    50                  55                  60

Thr Pro His Gln Thr Ile Tyr Ser Ala Leu Met Ile Arg Ser Glu Asp
65                  70                  75                  80

Ala Gly Phe Val Val Ile Thr Gly Val Met Ser Arg Arg Tyr Leu Cys
                85                  90                  95

Met Asp Phe Arg Gly Asn Ile Phe Gly Ser His Tyr Phe Asp Pro Gln
            100                 105                 110

Asn Cys Arg Phe Arg His Arg Thr Leu Glu Asn Gly Tyr Asp Val Tyr
        115                 120                 125

His Ser Pro Glu His His Phe Leu Val Ser Leu Gly Arg Ala Lys Arg
    130                 135                 140

Pro Phe Leu Pro Gly Met Asn Pro Pro Pro Tyr Ser Gln Phe Leu Ser
145                 150                 155                 160

Arg Arg Asn Glu Ile Pro Leu Ile His Phe Asn Thr Pro Arg Pro Arg
                165                 170                 175

Arg His Thr Arg Ser Ala Glu Asp Ala Trp Glu Gln Asp Pro Leu Asn
            180                 185                 190

Val Leu Lys Pro Arg Phe Arg Leu Thr Pro Ala Pro Ala Ser Cys Ser
        195                 200                 205

Gln Glu Ala Pro Ser Ala Glu Asp Asn Gly Leu Val Ala Ser Asp Pro
    210                 215                 220

Phe Gly Val Leu Arg Gly Asn Arg Val Asn Met His Gly Asp Arg Met
225                 230                 235                 240

Gly Pro Glu Arg Cys His His Phe Pro Lys Phe Ile
                245                 250
```

<210> SEQ ID NO 13
<211> LENGTH: 246
<212> TYPE: PRT
<213> ORGANISM: Equus caballus

<400> SEQUENCE: 13

```
Met Ser Gly Pro Cys Leu Gly Leu Leu Val Tyr Val Leu Cys Ser Ala
1               5                   10                  15

Val Lys Ala Tyr Pro Asn Ala Ser Pro Leu Leu Asp Ser Ser Trp Gly
            20                  25                  30

Ser Leu Thr His Leu Tyr Thr Ala Thr Ala Arg Asn Ser Tyr His Leu
        35                  40                  45

Gln Ile His Lys Asp Gly His Val Asp Gly Thr Pro His Gln Thr Ile
    50                  55                  60

Tyr Ser Ala Leu Met Ile Arg Ser Glu Asp Ala Gly Phe Val Val Ile
65                  70                  75                  80

Thr Gly Val Met Ser Arg Arg Tyr Leu Cys Met Asp Phe Arg Gly Asn
                85                  90                  95

Ile Phe Gly Ser His His Phe Ser Pro Glu Ser Cys Ser Phe Arg Gln
            100                 105                 110
```

-continued

```
Arg Thr Leu Glu Asn Gly Tyr Asp Val Tyr His Ser Pro Gln His Arg
        115                 120                 125

Phe Leu Val Ser Leu Gly Arg Ala Lys Arg Ala Phe Leu Pro Gly Thr
    130                 135                 140

Asn Pro Pro Pro Tyr Ser Gln Phe Leu Ser Arg Arg Asn Glu Ile Pro
145                 150                 155                 160

Leu Val His Phe Asn Thr Pro Arg Pro Arg Arg His Thr Arg Ser Ala
                165                 170                 175

Glu Asp Asn Ser Glu Arg Asp Pro Leu Asn Val Leu Lys Pro Arg Pro
            180                 185                 190

Arg Met Thr Pro Ala Pro Ala Ser Cys Ser Gln Glu Leu Pro Ser Ala
        195                 200                 205

Glu Asp Asn Ser Val Leu Ala Ser Asp Pro Leu Gly Val Val Arg Gly
    210                 215                 220

Asn Arg Val Asn Thr His Ala Gly Gly Ala Gly Val Glu Arg Cys Arg
225                 230                 235                 240

Pro Phe Pro Lys Phe Phe
                245


<210> SEQ ID NO 14
<211> LENGTH: 245
<212> TYPE: PRT
<213> ORGANISM: Ailuropoda melanoleuca

<400> SEQUENCE: 14

Met Ser Gly Thr Arg Leu Gly Leu Leu Val Ser Val Leu Cys Trp Val
1               5                   10                  15

Gly Arg Ala Tyr Pro Asn Thr Ser Pro Leu Leu Gly Ser Ser Trp Gly
            20                  25                  30

Gly Leu Thr His Leu Tyr Thr Ala Ser Ala Arg Asn Ser Tyr His Leu
        35                  40                  45

Gln Ile His Lys Asp Gly His Val Asp Gly Thr Pro His Gln Thr Ile
    50                  55                  60

Tyr Ser Ala Leu Met Ile Arg Ser Glu Asp Ala Gly Phe Val Val Ile
65                  70                  75                  80

Thr Gly Val Met Ser Arg Arg Tyr Leu Cys Met Asp Leu Arg Gly Asn
                85                  90                  95

Ile Phe Gly Ser His Leu Phe Ser Pro Glu Ser Cys Arg Phe Arg Gln
            100                 105                 110

Arg Thr Leu Glu Asn Gly Tyr Asp Val Tyr His Ser Pro Gln His Arg
        115                 120                 125

Phe Leu Val Ser Leu Gly Gln Ala Lys Arg Thr Phe Leu Pro Gly Thr
    130                 135                 140

Asn Pro Pro Pro Tyr Ser Gln Phe Leu Ser Arg Arg Asn Glu Ile Pro
145                 150                 155                 160

Leu Ile His Phe Asn Thr Pro Arg Pro Arg Arg His Thr Arg Ser Ala
                165                 170                 175

Glu Asp Thr Glu Arg Asp Pro Leu Asn Val Leu Lys Pro Arg Pro Arg
            180                 185                 190

Met Thr Pro Ala Pro Ala Ser Cys Ser Gln Glu Leu Pro Ser Ala Glu
        195                 200                 205

Asp Asn Ser Val Val Ala Ser Asp Pro Leu Gly Val Leu Arg Gly Asn
    210                 215                 220

Arg Val Asn Ala His Ala Gly Gly Met Gly Val Asp Arg Cys Arg Pro
```

225 230 235 240

Phe Pro Lys Phe Ile
245

<210> SEQ ID NO 15
<211> LENGTH: 250
<212> TYPE: PRT
<213> ORGANISM: Ochotona princeps

<400> SEQUENCE: 15

Met Leu Gly Gly Leu Gly Leu Trp Val Cys Val Leu Gly Ser Val Cys
1 5 10 15

Ser Trp Arg Gly Val Arg Ala Tyr Pro Asp Thr Ser Pro Leu Leu Gly
20 25 30

Ser Ser Trp Thr Gly Leu Thr His Leu Tyr Thr Ala Thr Ala Arg Asn
35 40 45

Ser Phe His Leu Gln Ile His Lys Asp Gly His Val Asp Gly Thr Pro
50 55 60

Gln Gln Thr Ile Tyr Ser Ala Leu Met Ile Arg Ser Glu Asp Ala Gly
65 70 75 80

Phe Val Val Ile Thr Gly Val Met Ser Arg Arg Tyr Leu Cys Met Asp
85 90 95

Phe Arg Gly Asn Ile Phe Gly Ser His Tyr Phe Glu Pro Gln Asn Cys
100 105 110

Arg Phe Gln Gln Arg Thr Leu Glu Asn Gly Tyr Asp Ile Tyr His Ser
115 120 125

Pro Gln His Asp Phe Leu Val Ser Leu Gly Arg Ala Lys Arg Pro Phe
130 135 140

Leu Pro Gly Met Asn Pro Pro Pro Tyr Ser Gln Phe Leu Ser Arg Arg
145 150 155 160

Asn Glu Ile Pro Leu Ile Leu Phe Asn Thr Pro Arg Pro Arg Arg His
165 170 175

Thr Arg Ser Ala Glu Glu Gly Trp Glu Arg Asp Pro Leu Asn Val Leu
180 185 190

Lys Ser Arg Pro Arg Met Thr Pro Ala Pro Ala Ser Cys Ser Arg Glu
195 200 205

Ala Pro Ser Ala Glu Asp Asp Gly Leu Leu Ala Ser Asp Pro Met Gly
210 215 220

Val Leu Arg Gly His Arg Val Asp Val His Gly Gly Gly Thr Gly Arg
225 230 235 240

Asp Arg Cys Arg Pro Phe Pro Arg Phe Ile
245 250

<210> SEQ ID NO 16
<211> LENGTH: 245
<212> TYPE: PRT
<213> ORGANISM: Bos Taurus

<400> SEQUENCE: 16

Met Leu Gly Ala Arg Leu Gly Leu Trp Val Cys Thr Leu Ser Cys Val
1 5 10 15

Val Gln Ala Tyr Pro Asn Ser Ser Pro Leu Leu Gly Ser Ser Trp Gly
20 25 30

Gly Leu Thr His Leu Tyr Thr Ala Thr Ala Arg Asn Ser Tyr His Leu
35 40 45

Gln Ile His Gly Asp Gly His Val Asp Gly Ser Pro Gln Gln Thr Val

```
    50                  55                  60

Tyr Ser Ala Leu Met Ile Arg Ser Glu Asp Ala Gly Phe Val Val Ile
65                  70                  75                  80

Thr Gly Val Met Ser Arg Arg Tyr Leu Cys Met Asp Phe Thr Gly Asn
                85                  90                  95

Ile Phe Gly Ser His His Phe Ser Pro Glu Ser Cys Arg Phe Arg Gln
            100                 105                 110

Arg Thr Leu Glu Asn Gly Tyr Asp Val Tyr His Ser Pro Gln His Arg
        115                 120                 125

Phe Leu Val Ser Leu Gly Arg Ala Lys Arg Ala Phe Leu Pro Gly Thr
    130                 135                 140

Asn Pro Pro Pro Tyr Ala Gln Phe Leu Ser Arg Arg Asn Glu Ile Pro
145                 150                 155                 160

Leu Pro His Phe Ala Ala Thr Ala Arg Pro Arg Arg His Thr Arg Ser
                165                 170                 175

Ala His Asp Ser Gly Asp Pro Leu Ser Val Leu Lys Pro Arg Ala Arg
            180                 185                 190

Ala Thr Pro Val Pro Ala Ala Cys Ser Gln Glu Leu Pro Ser Ala Glu
        195                 200                 205

Asp Ser Gly Pro Ala Ala Ser Asp Pro Leu Gly Val Leu Arg Gly His
    210                 215                 220

Arg Leu Asp Val Arg Ala Gly Ser Ala Gly Ala Glu Arg Cys Arg Pro
225                 230                 235                 240

Phe Pro Gly Phe Ala
                245


<210> SEQ ID NO 17
<211> LENGTH: 244
<212> TYPE: PRT
<213> ORGANISM: Sus scrofa

<400> SEQUENCE: 17

Met Leu Gly Ala Arg Leu Gly Leu Trp Val Cys Thr Leu Cys Cys Ala
1               5                   10                  15

Ala Arg Ala Tyr Pro Asp Thr Ser Pro Leu Leu Ser Ser Gly Trp Gly
            20                  25                  30

Gly Leu Thr His Leu Tyr Thr Ala Thr Ala Arg Asn Ser Tyr His Leu
        35                  40                  45

Gln Ile His Lys Asp Gly His Val Asp Gly Ser Pro Gln Gln Thr Ile
    50                  55                  60

Tyr Ser Ala Leu Met Ile Arg Ser Glu Asp Ala Gly Phe Val Val Ile
65                  70                  75                  80

Thr Gly Val Met Ser Arg Arg Tyr Leu Cys Met Asp Leu Arg Gly Asn
                85                  90                  95

Ile Phe Gly Ser Leu His Phe Ser Pro Glu Ser Cys Arg Phe Arg Gln
            100                 105                 110

Arg Thr Leu Glu Asn Gly Tyr Asp Val Tyr His Ser Pro His Tyr Arg
        115                 120                 125

Phe Leu Val Ser Leu Gly Arg Ala Lys Arg Ala Phe Leu Pro Gly Thr
    130                 135                 140

Asn Pro Pro Pro Tyr Ala Gln Phe Leu Ser Arg Arg Asn Glu Ile Pro
145                 150                 155                 160

Leu Leu His Phe Ala Thr Ala Arg Pro Arg Arg His Thr Arg Ser Ala
                165                 170                 175
```

-continued

His Asp Gly Gly Asp Pro Leu Ser Val Leu Lys Pro Arg Ala Arg Ala
180 185 190

Thr Pro Ala Pro Val Ser Cys Ser Arg Glu Leu Pro Ser Ala Glu Asp
195 200 205

Gly Gly Pro Ala Ala Ser Asp Pro Leu Gly Val Leu Arg Gly Gln Arg
210 215 220

Leu Asp Ala Arg Ala Gly Val Gly Gly Ala Glu Arg Cys Arg Pro Phe
225 230 235 240

Pro Ser Phe Ala

<210> SEQ ID NO 18
<211> LENGTH: 312
<212> TYPE: PRT
<213> ORGANISM: Canis lupus familiaris

<400> SEQUENCE: 18

Met Trp Thr Val Glu Phe Phe Leu Phe Asp Val Thr Gly Pro Pro Phe
1 5 10 15

Lys Ser Leu Arg Glu Lys Arg Arg Glu Ser Ser Leu Gly Leu Ser Arg
20 25 30

Lys Ile Pro Thr Lys Lys Arg Arg Lys Arg Pro Val Arg His Ser Arg
35 40 45

Gly Ile Lys Glu Ala Val Ser Gly Phe Lys Leu Gln Pro Ala Ile Gln
50 55 60

Arg Ala Val Met Ser Gly Thr Arg Leu Gly Phe Leu Val Ser Val Leu
65 70 75 80

Cys Trp Val Val Arg Ala Tyr Ser Asn Thr Ser Pro Leu Leu Gly Ser
85 90 95

Ser Trp Gly Ser Leu Thr His Leu Tyr Thr Ala Thr Ala Arg Asn Ser
100 105 110

Tyr His Leu Gln Ile His Lys Asp Gly His Val Asp Gly Thr Pro His
115 120 125

Gln Thr Ile Tyr Ser Ala Leu Met Ile Arg Ser Glu Asp Ala Gly Phe
130 135 140

Val Val Ile Thr Gly Val Met Ser Arg Arg Tyr Leu Cys Met Asp Phe
145 150 155 160

Arg Gly Asn Ile Phe Gly Ser His Leu Phe Ser Pro Glu Ser Cys Arg
165 170 175

Phe Arg Gln Arg Thr Leu Glu Asn Gly Tyr Asp Val Tyr His Ser Pro
180 185 190

Gln His Arg Phe Leu Val Ser Leu Gly Gln Ala Lys Arg Ala Phe Leu
195 200 205

Pro Gly Thr Asn Pro Pro Pro Tyr Ser Gln Phe Leu Ser Arg Arg Asn
210 215 220

Glu Ile Pro Leu Val His Phe His Thr Pro Arg Pro Arg Arg His Thr
225 230 235 240

Arg Ser Ala Glu Ala Pro Glu Arg Asp Pro Leu Asn Val Leu Lys Pro
245 250 255

Arg Pro Arg Leu Ala Pro Ala Pro Ala Ser Cys Ser Gln Glu Leu Pro
260 265 270

Ser Ala Glu Asp Pro Gly Ala Pro Ala Ser Asp Pro Leu Gly Val Leu
275 280 285

Arg Gly His Arg Ala Asn Ala Arg Ala Gly Gly Val Gly Val Asp Arg
290 295 300

Cys Arg Ala Phe Pro Thr Pro Ile
305 310

<210> SEQ ID NO 19
<211> LENGTH: 243
<212> TYPE: PRT
<213> ORGANISM: Cavia porcellus

<400> SEQUENCE: 19

Met Leu Gly Thr Cys Leu Gly Leu Leu Ala Cys Thr Val Ser Leu Val
1 5 10 15

Gly Ala Tyr Pro Asp Ala Ser Pro Leu Leu Thr Ser Ser Trp Gly Gly
20 25 30

Leu Ile His Leu Tyr Thr Ala Thr Ala Arg Asn Ser Tyr His Leu Gln
35 40 45

Ile His Lys Asp Gly His Ile Asp Gly Ala Pro Tyr Pro Thr Ile Tyr
50 55 60

Ser Ala Leu Met Ile Arg Ser Glu Asp Ala Gly Phe Val Val Ile Thr
65 70 75 80

Gly Val Thr Ser Arg Arg Phe Leu Cys Met Asp Phe Arg Gly Asn Ile
85 90 95

Phe Gly Ser His His Phe Asn Pro Gln Asp Cys Arg Phe Gln His Arg
100 105 110

Thr Leu Glu Asn Gly Tyr Asp Val Tyr Leu Ser Pro Glu His His Phe
115 120 125

Leu Ile Ser Leu Gly Arg Thr Lys Lys Phe Phe Leu Pro Gly Thr Asn
130 135 140

Pro Pro Pro Tyr Ser Gln Phe Leu Ser Arg Arg Asn Glu Leu Pro Leu
145 150 155 160

Ala Arg Phe Val Thr Pro Gly Pro Arg Arg His Thr Arg Ser Ala Glu
165 170 175

Glu Asp Gln Gly Arg Asp Pro Leu Ser Val Leu Lys Leu Arg Pro Arg
180 185 190

Ala Thr Pro Ala Pro Ala Ser Cys Ser Gln Glu Leu Pro Ser Ala Glu
195 200 205

Asp Ala Ala Gln Ala Ser Asp Pro Leu Gly Val Leu Arg Gly Ala Arg
210 215 220

Val His Ala His Gly Gly Pro Arg Pro Ala Arg Cys Arg Pro Gly Pro
225 230 235 240

Gly Ala Lys

<210> SEQ ID NO 20
<211> LENGTH: 251
<212> TYPE: PRT
<213> ORGANISM: Cricetulus griseus

<400> SEQUENCE: 20

Met Leu Gly Thr Cys Leu Arg Leu Leu Val Gly Val Leu Cys Ser Ala
1 5 10 15

Cys Ser Leu Gly Thr Val Arg Ala Tyr Pro Asp Thr Ser Pro Leu Leu
20 25 30

Gly Ser Asn Trp Gly Ser Leu Thr His Leu Tyr Thr Ala Thr Ala Arg
35 40 45

Asn Ser Tyr His Leu Gln Ile His Lys Asp Gly Arg Val Asp Gly Thr
50 55 60

Pro His Gln Thr Ile Tyr Ser Ala Leu Met Ile Arg Ser Glu Asp Ala

-continued

```
65                  70                  75                  80

Gly Phe Val Ile Ile Thr Gly Ala Val Thr Arg Arg Phe Leu Cys Met
                85                  90                  95

Asp Leu Arg Gly Asn Ile Phe Gly Ser His His Phe Ser Pro Glu Asn
            100                 105                 110

Cys Arg Phe Arg Gln Arg Thr Leu Glu Asn Gly Tyr Asp Val Tyr Leu
        115                 120                 125

Ser Pro Gln His His Tyr Leu Val Ser Leu Gly Arg Ala Lys Arg Pro
    130                 135                 140

Phe Glu Pro Gly Thr Asn Pro Pro Pro Phe Ser Gln Phe Leu Ala Arg
145                 150                 155                 160

Arg Asn Glu Val Pro Leu Leu Arg Phe His Thr Ala Arg Pro Arg Arg
                165                 170                 175

His Thr Arg Ser Ala Glu Asp Pro Pro Glu Trp Asp Pro Leu Asn Val
            180                 185                 190

Leu Lys Pro Arg Pro Arg Ala Thr Pro Val Pro Val Ser Cys Ser Arg
        195                 200                 205

Glu Leu Pro Ser Ala Glu Glu Gly Asp Leu Ala Ala Ser Asp Pro Leu
    210                 215                 220

Gly Val Leu Arg Arg Gly Arg Gly Asp Ala Arg Gly Gly Ala Gly Gly
225                 230                 235                 240

Val Asp Arg Cys Arg Pro Phe Pro Arg Phe Ala
                245                 250
```

<210> SEQ ID NO 21
<211> LENGTH: 180
<212> TYPE: PRT
<213> ORGANISM: Tupaia belangeri

<400> SEQUENCE: 21

```
Ala Leu Leu Ile Arg Pro Glu Glu Ala Gly Phe Ala Val Ile Thr Gly
1               5                   10                  15

Val Met Ser Arg Arg Tyr Leu Cys Met Asp Phe Arg Gly Asn Ile Phe
            20                  25                  30

Gly Ser His Leu Phe Ser Pro Glu Ser Cys Arg Phe Arg Gln Arg Ala
        35                  40                  45

Leu Glu Asn Gly Tyr Asp Val Tyr His His Pro Gln His His Phe Leu
    50                  55                  60

Val Ser Leu Gly Arg Pro Lys Arg Ala Phe Val Pro Gly Thr Asn Pro
65                  70                  75                  80

Pro Pro Tyr Ser Gln Phe Leu Ala Arg Lys Asn Glu Ile Pro Leu Ile
                85                  90                  95

His Phe Asn Thr Pro Lys Pro Arg Arg His Thr Arg Ser Ala Glu Asp
            100                 105                 110

Asn Ser Gly Arg Asp Pro Leu Asn Val Leu Lys Pro Arg Pro Arg Met
        115                 120                 125

Thr Pro Ala Pro Ala Ser Cys Ser Gln Glu Leu Pro Ser Ala Glu Asp
    130                 135                 140

Asn Ser Val Val Ala Ser Asp Pro Leu Gly Val Leu Arg Gly Asn Arg
145                 150                 155                 160

Val Asn Thr His Ala Gly Gly Trp Gly Val Asp Arg Cys Arg Pro Phe
                165                 170                 175

Pro Arg Phe Ile
            180
```

<210> SEQ ID NO 22
<211> LENGTH: 251
<212> TYPE: PRT
<213> ORGANISM: Rattus norvegicus

<400> SEQUENCE: 22

```
Met Leu Gly Ala Cys Leu Arg Leu Leu Val Gly Ala Leu Cys Thr Val
1               5                   10                  15

Cys Ser Leu Gly Thr Ala Arg Ala Tyr Ser Asp Thr Ser Pro Leu Leu
            20                  25                  30

Gly Ser Asn Trp Gly Ser Leu Thr His Leu Tyr Thr Ala Thr Ala Arg
        35                  40                  45

Asn Ser Tyr His Leu Gln Ile His Arg Asp Gly His Val Asp Gly Thr
    50                  55                  60

Pro His Gln Thr Ile Tyr Ser Ala Leu Met Ile Thr Ser Glu Asp Ala
65                  70                  75                  80

Gly Ser Val Val Ile Ile Gly Ala Met Thr Arg Arg Phe Leu Cys Met
                85                  90                  95

Asp Leu Arg Gly Asn Ile Phe Gly Ser Tyr His Phe Ser Pro Glu Asn
            100                 105                 110

Cys Arg Phe Arg Gln Trp Thr Leu Glu Asn Gly Tyr Asp Val Tyr Leu
        115                 120                 125

Ser Pro Lys His His Tyr Leu Val Ser Leu Gly Arg Ser Lys Arg Ile
    130                 135                 140

Phe Gln Pro Gly Thr Asn Pro Pro Pro Phe Ser Gln Phe Leu Ala Arg
145                 150                 155                 160

Arg Asn Glu Val Pro Leu Leu His Phe Tyr Thr Ala Arg Pro Arg Arg
                165                 170                 175

His Thr Arg Ser Ala Glu Asp Pro Pro Glu Arg Asp Pro Leu Asn Val
            180                 185                 190

Leu Lys Pro Arg Pro Arg Ala Thr Pro Ile Pro Val Ser Cys Ser Arg
        195                 200                 205

Glu Leu Pro Ser Ala Glu Glu Gly Gly Pro Ala Ala Ser Asp Pro Leu
    210                 215                 220

Gly Val Leu Arg Arg Gly Arg Gly Asp Ala Arg Arg Gly Ala Gly Gly
225                 230                 235                 240

Thr Asp Arg Cys Arg Pro Phe Pro Arg Phe Val
                245                 250
```

<210> SEQ ID NO 23
<211> LENGTH: 251
<212> TYPE: PRT
<213> ORGANISM: Mus musculus

<400> SEQUENCE: 23

```
Met Leu Gly Thr Cys Leu Arg Leu Leu Val Gly Ala Leu Cys Thr Val
1               5                   10                  15

Cys Ser Leu Gly Thr Ala Arg Ala Tyr Pro Asp Thr Ser Pro Leu Leu
            20                  25                  30

Gly Ser Asn Trp Gly Ser Leu Thr His Leu Tyr Thr Ala Thr Ala Arg
        35                  40                  45

Thr Ser Tyr His Leu Gln Ile His Arg Asp Gly His Val Asp Gly Thr
    50                  55                  60

Pro His Gln Thr Ile Tyr Ser Ala Leu Met Ile Thr Ser Glu Asp Ala
65                  70                  75                  80
```

-continued

```
Gly Ser Val Val Ile Thr Gly Ala Met Thr Arg Arg Phe Leu Cys Met
                85                  90                  95

Asp Leu His Gly Asn Ile Phe Gly Ser Leu His Phe Ser Pro Glu Asn
            100                 105                 110

Cys Lys Phe Arg Gln Trp Thr Leu Glu Asn Gly Tyr Asp Val Tyr Leu
        115                 120                 125

Ser Gln Lys His His Tyr Leu Val Ser Leu Gly Arg Ala Lys Arg Ile
    130                 135                 140

Phe Gln Pro Gly Thr Asn Pro Pro Pro Phe Ser Gln Phe Leu Ala Arg
145                 150                 155                 160

Arg Asn Glu Val Pro Leu Leu His Phe Tyr Thr Val Arg Pro Arg Arg
                165                 170                 175

His Thr Arg Ser Ala Glu Asp Pro Pro Glu Arg Asp Pro Leu Asn Val
            180                 185                 190

Leu Lys Pro Arg Pro Arg Ala Thr Pro Val Pro Val Ser Cys Ser Arg
        195                 200                 205

Glu Leu Pro Ser Ala Glu Glu Gly Gly Pro Ala Ala Ser Asp Pro Leu
    210                 215                 220

Gly Val Leu Arg Arg Gly Arg Gly Asp Ala Arg Gly Gly Ala Gly Gly
225                 230                 235                 240

Ala Asp Arg Cys Arg Pro Phe Pro Arg Phe Val
                245                 250


<210> SEQ ID NO 24
<211> LENGTH: 248
<212> TYPE: PRT
<213> ORGANISM: Pteropus vampyrus

<400> SEQUENCE: 24

Met Pro Arg Gly Ser Leu Gly Leu Leu Val Cys Ile Leu Cys Cys Arg
1               5                   10                  15

Ala Tyr Pro Asp Ala Ser Pro Leu Leu Ser Ser Ser Leu Gly Gly Leu
            20                  25                  30

Ile His Leu Tyr Thr Ala Thr Ala Arg Asn Gly Tyr His Leu Gln Ile
        35                  40                  45

His Lys Asp Gly His Val Asp Gly Thr Pro His Gln Thr Ile Tyr Ser
    50                  55                  60

Ala Leu Met Ile Arg Ser Glu Asp Ser Gly Phe Val Val Ile Ile Gly
65                  70                  75                  80

Val Met Ser Arg Arg Tyr Leu Cys Met Asp Phe Lys Gly Asn Ile Phe
                85                  90                  95

Gly Ser His His Phe Ser Pro Glu Ser Cys Lys Phe Arg Gln Arg Thr
            100                 105                 110

Leu Glu Asn Gly Tyr Asp Val Tyr His Ser Pro Gln His His Phe Phe
        115                 120                 125

Val Ser Leu Gly Arg Ala Lys Arg Ala Phe Leu Pro Gly Thr Asn Pro
    130                 135                 140

Pro Pro Tyr Ser Gln Phe Leu Ser Arg Arg Asn Glu Ile Pro Leu Phe
145                 150                 155                 160

Gln Phe Asn Thr Pro Arg Pro Arg Arg His Thr Arg Ser Val Glu Asp
                165                 170                 175

Tyr Lys Asp Tyr Asp Leu Asp Pro Asp Pro Leu Lys Val Leu Arg Pro
            180                 185                 190

Arg Pro Arg Trp Val Pro Ala Leu Pro Ser Cys Ser Gln Glu Leu Pro
        195                 200                 205
```

-continued

```
Ser Ala Glu Asp Asn Ser Val Val Ala Asn Asp Pro Leu Gly Val Leu
    210                 215                 220

Arg Pro Ser Arg Val Asn Ile Tyr Arg Glu Arg Met Gly Lys Gly Arg
225                 230                 235                 240

Cys Arg Pro His Pro Glu Phe Val
                245


<210> SEQ ID NO 25
<211> LENGTH: 248
<212> TYPE: PRT
<213> ORGANISM: Myotis lucifugus

<400> SEQUENCE: 25

Met Pro Gly Ala Arg Leu Gly Leu Leu Val Cys Val Leu Ala Leu Arg
1               5                   10                  15

Cys Val Val Arg Ala Tyr Pro Asn Ala Ser Pro Leu Leu Gly Ser Ser
            20                  25                  30

Trp Gly Gly Leu Thr His Leu Tyr Thr Ala Ser Ala Arg Asn Ser Tyr
        35                  40                  45

His Leu Gln Ile His Lys Asp Gly His Val Asp Gly Thr Pro His Gln
    50                  55                  60

Thr Ile Tyr Ser Ala Leu Met Ile Arg Ser Glu Asp Ala Gly Phe Val
65                  70                  75                  80

Val Ile Thr Gly Val Met Ser Arg Arg Tyr Leu Cys Met Asp Phe Arg
                85                  90                  95

Gly Asn Ile Phe Gly Ser Leu Phe Phe Ser Pro Ser Asn Phe Ser Phe
            100                 105                 110

Leu Glu Trp Lys Lys Glu Ser Gly Met Asp His Trp Ile Ser Arg Gln
        115                 120                 125

Thr His Phe Leu Val Ser Pro Gly Pro Ser Gln Glu Gly Leu Pro Ala
    130                 135                 140

Gly His Asn Pro Pro Pro Tyr Ser Gln Phe Leu Ser Arg Asn Glu Ile
145                 150                 155                 160

Pro Leu Phe His Phe Asn Thr Pro Ala Pro Arg Arg His Thr Arg Ser
                165                 170                 175

Ala Glu Glu Asn Ser Ala Ala Asp Pro Leu Val Val Leu Lys Pro Val
            180                 185                 190

Pro Arg Leu Thr Pro Pro Pro Ala Ser Cys Ser Arg Glu Leu Ser Ser
        195                 200                 205

Ala Glu Asp Asn Ser Val Ala Ala His Asp Pro Leu Gly Val Leu Arg
    210                 215                 220

Ser Ser Asn Arg Val Asn Ser His Ala Pro Pro Pro Gly Pro Pro Arg
225                 230                 235                 240

Thr Arg Gln Gly Met Leu Leu Val
                245


<210> SEQ ID NO 26
<211> LENGTH: 245
<212> TYPE: PRT
<213> ORGANISM: Sarcophilus harrisii

<400> SEQUENCE: 26

Met Ser Gly Gly Cys Leu Arg Leu Leu Phe Cys Ala Leu Cys Ser Leu
1               5                   10                  15

Arg Ala Ile Gln Ala Phe Pro Asn Ala Ser Pro Leu Leu Ser Leu Gly
            20                  25                  30
```

```
Trp Gly Gly Leu Thr His Leu Tyr Thr Ala Thr Ala Arg Asn Ser Tyr
        35                  40                  45

His Leu Gln Ile His Lys Asp Gly His Val Asp Gly Ser Pro His Gln
    50                  55                  60

Thr Ile Tyr Ser Ala Leu Met Ile Arg Ser Glu Asp Ala Gly Leu Val
65                  70                  75                  80

Ile Ile Thr Gly Val Met Ser Arg Arg Tyr Leu Cys Met Asp Ile Arg
                85                  90                  95

Gly Asn Ile Phe Gly Ser His Phe Phe Ser Pro Asp Asn Cys Arg Phe
            100                 105                 110

Lys His Arg Thr Leu Glu Asn Gly Tyr Asp Ile Tyr His Ser Pro Gln
        115                 120                 125

Asn Asn Phe Leu Ile Ser Leu Gly Lys Ala Lys Arg Ala Phe Leu Pro
    130                 135                 140

Gly Met Asn Pro Pro Pro Tyr Ser Gln Phe Leu Ser Arg Arg Asn Glu
145                 150                 155                 160

Ile Pro Ile Ile His Phe Asn Thr Pro Glu Pro His Arg His Thr Arg
                165                 170                 175

Ser Ala Glu Asn Ser Pro Asp Leu Asp Pro Met Asn Val Leu Lys Leu
            180                 185                 190

Arg Pro Arg Ile Thr Pro Cys Ser Gln Glu Leu His Ser Ala Glu Glu
        195                 200                 205

Asn Ser Val Val Asp Asp Asp Pro Leu Glu Val Leu Arg Asn Ser Asn
    210                 215                 220

Arg Leu Lys Pro Tyr Pro Gly Arg Met Ser Leu Glu Arg Cys Leu His
225                 230                 235                 240

Val Pro Lys Ala Ala
                245


<210> SEQ ID NO 27
<211> LENGTH: 191
<212> TYPE: PRT
<213> ORGANISM: Monodelphis domestica

<400> SEQUENCE: 27

Met Ala Asn Cys Arg Glu Lys Glu Leu Glu Met Tyr Ile Cys Ala Leu
1               5                   10                  15

Met Ile Arg Ser Glu Asp Ala Gly Leu Val Ile Ile Thr Gly Val Met
            20                  25                  30

Ser Arg Arg Tyr Leu Cys Met Asp Ile Arg Gly Asn Ile Phe Gly Ser
        35                  40                  45

His Phe Phe Asn Pro Asp Asn Cys Lys Phe Lys His Arg Thr Leu Glu
    50                  55                  60

Asn Gly Tyr Asp Ile Tyr His Ser Pro Gln Asn Asn Phe Leu Ile Ser
65                  70                  75                  80

Leu Gly Lys Ala Lys Arg Ala Phe Leu Pro Gly Met Asn Pro Pro Pro
                85                  90                  95

Tyr Ser Gln Phe Leu Ser Arg Lys Asn Glu Ile Pro Ile Ile His Phe
            100                 105                 110

Asn Thr Pro Glu Pro His Arg His Thr Arg Ser Ala Glu Asn Ser Pro
        115                 120                 125

Asp Leu Asp Pro Met Asn Val Leu Lys Pro Arg Pro Arg Met Thr Pro
    130                 135                 140

Cys Ser Gln Glu Leu Tyr Ser Ala Glu Glu Asn Ser Val Val Asp Asp
```

```
145                 150                 155                 160

Asp Pro Leu Glu Val Leu Arg Asn Ser Asn Arg Leu Lys Pro Phe Pro
                165                 170                 175

Gly Arg Leu Gly Leu Glu Arg Cys His His Val Pro Lys Thr Asp
            180                 185                 190


<210> SEQ ID NO 28
<211> LENGTH: 180
<212> TYPE: PRT
<213> ORGANISM: Dasypus novemcinctus

<400> SEQUENCE: 28

Ala Leu Met Ile Ser Ser Glu Asp Ala Gly Phe Val Val Ile Thr Gly
1               5                   10                  15

Val Met Ser Arg Arg Tyr Leu Cys Met Asp Phe Arg Gly Asn Ile Phe
            20                  25                  30

Gly Ser His Asp Phe Thr Pro Asp Ser Cys Arg Phe Arg Gln Arg Thr
        35                  40                  45

Leu Glu Asn Gly Tyr Asp Val Tyr His Ser Pro Gln His His Phe Leu
    50                  55                  60

Val Ser Leu Gly Arg Ala Lys Arg Ala Phe Gln Pro Gly Ser Asn Pro
65                  70                  75                  80

Pro Pro Tyr Ser Gln Phe Leu Ser Arg Arg Asn Glu Ile Pro Leu Met
                85                  90                  95

Arg Phe Ser Thr Pro Arg Pro Arg Arg His Thr Arg Ser Ala Gln Asp
            100                 105                 110

His Ala Asp Pro Asp Pro Leu Arg Val Leu Lys Pro Arg Leu Arg Leu
        115                 120                 125

Thr Pro Ala Pro Ala Ser Cys Ser Gln Glu Leu Pro Ser Asp Glu Asp
    130                 135                 140

Asp Gly Ala Val Ala Ser Asp Pro Leu Arg Val Val Leu Gly Arg Arg
145                 150                 155                 160

Pro His Ala Arg Ala Ala Gly Ala Gly Gly Glu Arg Cys Arg Pro Gly
                165                 170                 175

Pro Gln Leu Ser
            180


<210> SEQ ID NO 29
<211> LENGTH: 177
<212> TYPE: PRT
<213> ORGANISM: Macropus eugenii

<400> SEQUENCE: 29

Ala Leu Met Ile Arg Ser Glu Asp Ala Gly Leu Val Ile Ile Ser Gly
1               5                   10                  15

Val Met Ser Arg Arg Tyr Leu Cys Met Asp Leu Arg Gly Asn Ile Phe
            20                  25                  30

Gly Ser His Phe Phe Ser Pro Asp Asn Cys Arg Phe Lys His Arg Thr
        35                  40                  45

Leu Glu Asn Gly Tyr Asp Ile Tyr His Ser Pro Gln Asn Asn Leu Leu
    50                  55                  60

Ile Ser Leu Gly Lys Ala Lys Arg Ala Phe Leu Pro Gly Met Asn Pro
65                  70                  75                  80

Pro Pro Tyr Ser Gln Phe Leu Ser Arg Arg Asn Glu Ile Pro Ile Ile
                85                  90                  95

His Phe Asn Thr Pro Glu Pro Arg Arg His Thr Arg Ser Ala Glu Asn
```

100 105 110

Ser Pro Asp Leu Asp Pro Met Asn Val Leu Lys Pro Arg Pro Arg Val
115 120 125

Thr Pro Cys Ser Gln Glu Leu Arg Ser Ala Glu Glu Asn Ser Val Val
130 135 140

Asp Asp Asp Pro Leu Glu Val Leu Arg Asn Ser Asn Arg Leu Lys Pro
145 150 155 160

Tyr Pro Gly Arg Met Ser Leu Glu Arg Cys Leu Gln Val Pro Lys Ala
165 170 175

Ala

<210> SEQ ID NO 30
<211> LENGTH: 256
<212> TYPE: PRT
<213> ORGANISM: Taeniopygia guttata

<400> SEQUENCE: 30

Met Glu Trp Arg Ala Thr Leu Gln Gly Ile Pro Cys Ser Ser Leu Leu
1 5 10 15

Leu Leu Leu Cys Ser Leu Lys Ala Ser Leu Ala Phe Pro Asn Ser Ser
20 25 30

Pro Leu Leu Ser Pro Ser Trp Gly Asn Gly Asp Arg Leu Met His Leu
35 40 45

Tyr Thr Asp Thr Glu Arg Ser Ser Phe His Leu Gln Ile Asn Ala Asp
50 55 60

Gly Tyr Ile Asp Gly Ala Pro His Gln Thr Ile Tyr Ser Ala Leu Met
65 70 75 80

Ile Lys Ser Glu Gly Ala Gly Ser Val Ile Ile Thr Gly Val Lys Ser
85 90 95

Gly Arg Tyr Leu Cys Met Asp Met Lys Gly Asn Ile Phe Gly Ser His
100 105 110

Tyr Phe Ser Gln Glu Asp Cys Met Phe Asn His Arg Thr Leu Glu Asn
115 120 125

Gly Tyr Asp Val Tyr Gln Ser Pro Lys His His Phe Leu Val Ser Leu
130 135 140

Gly Arg Val Lys Gln Val Phe Ser Pro Gly Met Asn Pro Pro Pro Tyr
145 150 155 160

Ser Gln Phe Leu Ser Arg Lys Asn Glu Ile Pro Leu Phe Arg Phe Asn
165 170 175

Thr Pro Glu Pro His Arg His Thr Arg Ser Ala Asp Val Asp Pro Val
180 185 190

Asp Pro His Gln Ile Leu Val Pro Gln Arg Lys Thr Pro Val Phe Gly
195 200 205

Ser Leu Gln Gln Gln Pro Ala Asp Phe Pro His Met Pro Arg Glu Pro
210 215 220

Met Arg Ile Asn Gln Asn Asp Val Val Asn Pro Asp Asp Pro His Ala
225 230 235 240

Met Met Glu Ala Arg Arg Tyr Pro Ser Pro Arg Phe Tyr Ile Thr Arg
245 250 255

<210> SEQ ID NO 31
<211> LENGTH: 254
<212> TYPE: PRT
<213> ORGANISM: Gallus gallus

<400> SEQUENCE: 31

```
Met Pro His Thr Ser Pro Cys Ser Cys Leu Glu Tyr Met Leu Leu Val
1               5                   10                  15

Leu Cys Ile Leu Lys Ala Ala Val Ala Phe Pro Asn Ser Ser Pro Leu
            20                  25                  30

Leu Asn Pro Ser Trp Gly Asn Gly Asp Gln Leu Met His Leu Tyr Thr
        35                  40                  45

Ser Thr Glu Arg Asn Ser Phe His Leu Gln Ile Asn Ala Asp Gly His
    50                  55                  60

Ile Asn Gly Val Pro His Gln Thr Ile Tyr Ser Ala Leu Met Ile Lys
65                  70                  75                  80

Ser Glu Gly Ala Gly Cys Val Ile Ile Thr Gly Val Lys Ser Gly Arg
                85                  90                  95

Tyr Leu Cys Met Asp Met Lys Gly Asp Ile Phe Gly Ser Tyr Tyr Phe
            100                 105                 110

Ser Gln Glu Asp Cys Val Phe Asn Gln Arg Thr Leu Glu Asn Gly Tyr
        115                 120                 125

Asp Val Tyr Gln Ser Pro Lys His Asn Phe Leu Val Ser Leu Gly Arg
    130                 135                 140

Thr Lys Gln Val Phe Phe Pro Gly Met Asn Pro Pro Pro Tyr Ser Gln
145                 150                 155                 160

Phe Leu Ser Arg Arg Asn Glu Ile Pro Leu Phe Arg Phe Asn Thr Pro
                165                 170                 175

Glu Pro His Arg Asn Thr Arg Ser Ala Asp Val Asp Pro Leu Asp Pro
            180                 185                 190

His Gln Ile Leu Val Pro Gln Arg Lys Val Ser Ala Leu Gly Ser Gln
        195                 200                 205

Leu Gln Leu Gln Met Asp Phe Ser His Val Pro Arg Glu Pro Met Arg
    210                 215                 220

Val Asn Gln Asn Asp Val Val Asn Pro Asp Asp Pro His Ala Met Met
225                 230                 235                 240

Asp Ala Arg Arg Tyr Ala Ser Pro Arg Phe Tyr Ile Thr Arg
                245                 250


<210> SEQ ID NO 32
<211> LENGTH: 254
<212> TYPE: PRT
<213> ORGANISM: Meleagris gallopavo

<400> SEQUENCE: 32

Met Pro His Thr Ser Pro Cys Ser Cys Leu Glu Tyr Met Leu Leu Val
1               5                   10                  15

Leu Cys Ile Leu Lys Ala Ala Val Ser Phe Pro Asn Ser Ser Pro Leu
            20                  25                  30

Leu Asn Pro Ser Trp Gly Asn Gly Asp Gln Leu Met His Leu Tyr Thr
        35                  40                  45

Ser Thr Glu Arg Asn Ser Phe His Leu Gln Ile Asn Ala Asp Gly His
    50                  55                  60

Ile Ser Gly Val Pro Tyr Gln Thr Ile Tyr Ser Ala Leu Met Ile Lys
65                  70                  75                  80

Ser Glu Gly Ala Gly Ser Val Ile Ile Thr Gly Val Lys Ser Gly Arg
                85                  90                  95

Tyr Leu Cys Met Asp Met Lys Gly Asp Ile Phe Gly Ser His Tyr Phe
            100                 105                 110

Ser Gln Glu Asp Cys Val Phe Asn Gln Arg Thr Leu Glu Asn Gly Tyr
```

```
        115                 120                 125

Asp Val Tyr Gln Ser Pro Lys His Asn Phe Leu Val Ser Leu Gly Arg
    130                 135                 140

Thr Lys Gln Val Phe Phe Pro Gly Met Asn Pro Pro Pro Tyr Ser Gln
145                 150                 155                 160

Phe Leu Ser Arg Arg Asn Glu Ile Pro Leu Phe Arg Phe Asn Thr Pro
                165                 170                 175

Glu Pro His Arg Asn Thr Arg Ser Ala Asp Val Asp Pro Met Asp Pro
            180                 185                 190

His Gln Ile Leu Val Pro Gln Arg Lys Val Ser Ala Ile Glu Ser Gln
        195                 200                 205

Leu Gln Leu Gln Met Asp Phe Ser His Val Pro Arg Glu Pro Met Arg
    210                 215                 220

Val Asn Gln Asn Asp Val Val Asn Pro Asp Asp Pro His Ala Met Met
225                 230                 235                 240

Asp Ala Arg Arg Tyr Ala Ser Pro Arg Phe Tyr Ile Thr Arg
                245                 250


<210> SEQ ID NO 33
<211> LENGTH: 242
<212> TYPE: PRT
<213> ORGANISM: Anolis carolinensis

<400> SEQUENCE: 33

Met Val Gln Ala Thr Leu Tyr Ser Phe Leu Lys Tyr Met Leu Leu Ala
1               5                   10                  15

Thr Cys Ser Trp Lys Ala Ile Ala Ala Phe Pro Asn Ala Ser Pro Leu
            20                  25                  30

Leu Ser Leu Asn Trp Gly Asn Ser Asp Ser Leu Leu His Leu Tyr Thr
        35                  40                  45

Ser Thr Ala Arg Asn Ser Phe His Leu Gln Ile His Ser Asn Gly Tyr
    50                  55                  60

Val Asp Gly Ser Pro Tyr Gln Thr Ile Tyr Ser Ala Leu Met Ile Lys
65                  70                  75                  80

Ser Glu Val Ala Gly Tyr Val Ile Ile Asn Gly Val Lys Ser Gly Arg
                85                  90                  95

Phe Leu Cys Met Asp Met Asn Gly Asn Ile Phe Gly Ser His Phe Phe
            100                 105                 110

Ser Tyr Glu Asp Cys Thr Phe Lys His Trp Val Leu Glu Asn Gly Tyr
        115                 120                 125

Asp Val Tyr Gln Ser Pro Lys Tyr Asn Tyr Leu Val Ser Leu Gly Lys
    130                 135                 140

Ala Lys Gln Pro Leu Phe Pro Asn Met Asn Pro Pro Pro Tyr Ser Gln
145                 150                 155                 160

Phe Leu Ser Arg Arg Asn Glu Ile Pro Leu Val Gln Phe Asn Thr Pro
                165                 170                 175

Lys Pro His Arg His Thr Arg Ser Ala Asn Ala Asp Pro Cys Gly Ser
            180                 185                 190

Ile Ile Ser Ser Gly Asn Ile Ala Lys Glu Asn Leu Gln Leu Gln Pro
        195                 200                 205

Leu Met Tyr Asn Thr Lys Met Asn Ser Asn Ser Glu Asp Glu Asp Pro
    210                 215                 220

Asn Ser Ala Ile Ile Asn Arg Arg Phe Leu Ser Pro Arg Thr Asp Val
225                 230                 235                 240
```

Arg Ser

<210> SEQ ID NO 34
<211> LENGTH: 249
<212> TYPE: PRT
<213> ORGANISM: Latimeria chalumnae

<400> SEQUENCE: 34

Leu Glu Ser Ala Leu Leu Ala Phe Ser Met Ala Ile Phe Tyr Ser Phe
1               5                   10                  15

Lys Ala Val Ser Ser Phe Pro Asn Ser Ser Pro Leu Leu Asn Pro Val
            20                  25                  30

Trp Gly Asn Thr Asp Asn Leu Ile His Leu Tyr Thr Ala Ser Glu Thr
        35                  40                  45

Asn Ser Phe His Leu Gln Ile Asn Ser Asp Gly His Val Asp Gly Thr
    50                  55                  60

Pro His Gln Thr Ala Tyr Ser Ala Leu Leu Ile Lys Ser Glu Glu Ala
65                  70                  75                  80

Gly Ser Val Val Ile Leu Gly Val Lys Ser Gly Arg Tyr Leu Cys Met
                85                  90                  95

Asp Ile Lys Gly Asn Ile Ile Gly Leu His His Phe Ser Lys Glu Asp
            100                 105                 110

Cys Thr Phe Lys Gln Glu Gly Leu Glu Asn Gly Phe Asp Val Leu Arg
        115                 120                 125

Ser Pro Lys His Asn Ile Leu Val Ser Leu Asp Lys Thr Lys Arg Ser
    130                 135                 140

Tyr Ile Pro Gly Met Asn Leu Pro Pro Tyr Ser Gln Phe Leu Ser Arg
145                 150                 155                 160

Gln Asn Glu Val Ala Leu Ile Asn Phe Ile Asn Thr Pro Asp Ile His
                165                 170                 175

Arg His Ser Arg Asn Val Asp Val Asp Pro Ser Asp Pro His Gly Met
            180                 185                 190

Ile Ile Gln Pro Asp Val Gly Val Ser Phe Arg Lys Ser Ser Ser Leu
        195                 200                 205

Phe Ser Asp Leu Pro Arg Asp Ser Met Arg Thr Ser His Asn Gly Met
    210                 215                 220

Asp Met Val Asp Pro Ala Asp Pro His Gly Met Leu Asp Ser Arg Arg
225                 230                 235                 240

Arg Pro Ser Pro Arg Phe Phe Ala Arg
                245

<210> SEQ ID NO 35
<211> LENGTH: 254
<212> TYPE: PRT
<213> ORGANISM: Xenopus silurana tropicalis

<400> SEQUENCE: 35

Met Thr Lys Gln Gln Thr Arg Leu Gly Leu Val Leu Thr Val Leu Ala
1               5                   10                  15

Ser Ile Lys Val Ile Ser Ala Phe Pro Asn Ser Ser Pro Ile Ile Ser
            20                  25                  30

Gly Gly Trp Gly Val Pro Asp Arg Leu Met His Leu Tyr Thr Ala Ser
        35                  40                  45

Asp Trp Asn Ser Phe His Leu Gln Ile Asn His Asp Gly Ser Ile Asp
    50                  55                  60

Gly Thr Pro Thr Gln Thr Ile Tyr Ser Ala Ile Met Ile Lys Ser Glu

```
65                  70                  75                  80

Ser Ala Gly His Val Val Ile Thr Gly Val Lys Thr Asn Arg Tyr Leu
                85                  90                  95

Cys Met Asp Lys Ser Gly Asn Ile Phe Gly Tyr His Asp Phe Asn His
            100                 105                 110

Asp Asp Cys Val Phe Lys His Glu Thr Leu Glu Asn Asn Phe Asp Val
        115                 120                 125

Tyr His Ser Pro Lys His Asn Phe Val Ile Ser Leu Lys Glu Pro Lys
    130                 135                 140

His His Phe Arg Leu Gly Met Asp Leu Pro Pro Tyr Ser Gln Phe Leu
145                 150                 155                 160

Ser Leu Glu Asn Glu Ile Pro Ile Thr Arg Phe Asn Ala Pro Glu Pro
                165                 170                 175

Glu Met Arg Ile Pro Glu Gly Asn Phe Ala Asp Pro Ser Asp Ile Ile
            180                 185                 190

Lys Asn Pro Arg Asn Trp Asp Phe Ser Gln Ser Ile His Asn Pro Phe
        195                 200                 205

Gln Asp Val Trp Leu Pro Phe Pro Ser Gly Ser Leu Pro Ile Ile Arg
    210                 215                 220

Ala Ser Leu Pro Ile Ile His Asn Asn Val Ile Asn Thr Asp Asp Pro
225                 230                 235                 240

Glu Glu Ile Val Lys Met Lys Arg Tyr Arg Tyr Phe Lys Arg
                245                 250


<210> SEQ ID NO 36
<211> LENGTH: 199
<212> TYPE: PRT
<213> ORGANISM: Felis catus

<400> SEQUENCE: 36

Met Ser Gly Thr Arg Leu Gly Leu Leu Val Ser Val Leu Cys Trp Val
1               5                   10                  15

Val Arg Ala Tyr Pro Asn Thr Ser Pro Leu Leu Gly Ser Ser Trp Gly
            20                  25                  30

Gly Leu Thr His Leu Tyr Thr Ala Thr Ala Arg Asn Ser Tyr His Leu
        35                  40                  45

Gln Ile His Lys Asp Gly His Val Asp Gly Thr Pro His Gln Thr Ile
    50                  55                  60

Tyr Ser Ala Leu Met Ile Arg Ser Glu Asp Ala Gly Phe Val Val Ile
65                  70                  75                  80

Thr Gly Val Met Ser Gln Arg Tyr Leu Cys Met Asp Phe Arg Gly Asn
                85                  90                  95

Ile Phe Gly Ser His Leu Phe Ser Pro Glu Ser Cys Arg Phe Arg Gln
            100                 105                 110

Arg Thr Leu Glu Asn Gly Tyr Asp Val Tyr His Ser Pro Gln His Arg
        115                 120                 125

Phe Leu Val Ser Leu Gly Pro Ala Lys Arg Ala Phe Leu Pro Gly Thr
    130                 135                 140

Asn Arg Met Thr Pro Ala Pro Ala Ser Cys Ser Gln Glu Leu Pro Ser
145                 150                 155                 160

Ala Glu Asp Ser Gly Val Val Ala Ser Asp Pro Leu Gly Val Leu Arg
                165                 170                 175

Gly Asn Arg Val Asn Ala His Ala Gly Gly Met Gly Val Glu Arg Cys
            180                 185                 190
```

Arg Pro Phe Pro Lys Phe Asn
195

<210> SEQ ID NO 37
<211> LENGTH: 250
<212> TYPE: PRT
<213> ORGANISM: Pelodiscus sinensis

<400> SEQUENCE: 37

Met Ser Gln Pro Ser Gln Cys Ser Cys Leu Asn Phe Met Leu Phe Val
1 5 10 15

Leu Cys Ser Phe Lys Ala Ile Ala Ala Phe Pro Phe Phe Ser Ser Leu
20 25 30

Leu Asn Pro Ser Trp Gly Glu Thr Asp Ser Leu Ile His Leu Tyr Thr
35 40 45

Ala Thr Glu Lys Asn Ser Phe His Leu Gln Ile Asn Pro Asp Gly Tyr
50 55 60

Val Asp Gly Thr Pro His Gln Thr Ile Tyr Ser Ala Leu Met Ile Lys
65 70 75 80

Ser Glu Asp Ala Gly Tyr Val Val Ile Ser Gly Val Lys Ser Gly Arg
85 90 95

Tyr Leu Cys Met Asp Ile Lys Gly Asn Ile Phe Gly Ser His Tyr Phe
100 105 110

Ser Gln Glu Asp Cys Met Phe Lys His Arg Thr Leu Glu Asn Gly Tyr
115 120 125

Asp Val Tyr Gln Ser Pro Lys His Asn Phe Leu Val Ser Leu Gly Arg
130 135 140

Asn Lys Gln Ala Phe Phe Pro Gly Met Asn Leu Pro Pro Tyr Ser Gln
145 150 155 160

Phe Leu Pro Arg Arg Asn Glu Ile Pro Leu Ile Arg Phe Asn Thr Pro
165 170 175

Glu Pro His Arg His Thr Arg Asn Ala Asp Val Asp Pro Leu Gln Ile
180 185 190

Leu Ile Pro Arg Gly Glu Ala Phe Asp Thr Gly Pro Gln Arg Leu Gln
195 200 205

Thr His Phe Asp His Leu Pro Arg Glu Pro Met Arg Ile Asn Pro Asn
210 215 220

Asp Val Val Ser Pro Asp Asp Pro Leu Ala Met Met Asp Val Arg Arg
225 230 235 240

Asn Ala Ser Pro Arg Leu Tyr Ile Thr Arg
245 250

<210> SEQ ID NO 38
<211> LENGTH: 245
<212> TYPE: PRT
<213> ORGANISM: Mustela putorius furo

<400> SEQUENCE: 38

Met Ser Val Thr Arg Leu Gly Leu Leu Val Ser Val Leu Cys Trp Val
1 5 10 15

Val Arg Ala Tyr Pro Asn Ala Ser Pro Leu Leu Gly Ser Ser Trp Gly
20 25 30

Gly Leu Thr His Leu Tyr Thr Ala Thr Ala Arg Asn Ser Tyr His Leu
35 40 45

Gln Ile His Lys Asp Gly His Val Asp Gly Thr Pro His Gln Thr Ile
50 55 60

-continued

```
Tyr Ser Ala Leu Met Ile Arg Ser Glu Asp Ala Gly Phe Val Val Ile
65                  70                  75                  80

Thr Gly Val Met Ser Arg Arg Tyr Leu Cys Met Asp Phe Arg Gly Asn
                85                  90                  95

Ile Phe Gly Ser His Leu Phe Ser Pro Glu Ser Cys Arg Phe Arg Gln
            100                 105                 110

Arg Thr Leu Glu Asn Gly Tyr Asp Val Tyr His Ser Pro Gln His Arg
        115                 120                 125

Phe Leu Val Ser Leu Gly Gln Ala Lys Arg Ala Phe Leu Pro Gly Thr
    130                 135                 140

Asn Pro Pro Pro Tyr Ser Gln Phe Leu Ser Arg Arg Asn Glu Ile Pro
145                 150                 155                 160

Leu Ile His Phe Asn Thr Pro Arg Pro Arg Arg His Thr Arg Ser Ala
                165                 170                 175

Glu Asp Met Glu His Asp Pro Leu Asn Val Leu Lys Pro Arg Pro Arg
            180                 185                 190

Met Thr Pro Ala Pro Ala Ser Cys Ser Gln Glu Leu Pro Ser Ala Glu
        195                 200                 205

Asp Asn Ser Val Val Ala Ser Asp Pro Leu Gly Val Leu Arg Gly Asn
    210                 215                 220

Arg Val Asn Val His Ala Gly Gly Met Gly Val Asp Arg Cys Arg Pro
225                 230                 235                 240

Leu Pro Lys Phe Ile
                245


<210> SEQ ID NO 39
<211> LENGTH: 206
<212> TYPE: PRT
<213> ORGANISM: Microcebus marinus

<400> SEQUENCE: 39

Met Leu Gly Ala Cys Leu Arg Leu Trp Val Cys Ala Leu Cys Ser Val
1               5                   10                  15

Cys Gly Val Ser Val Val Arg Ala Tyr Pro Asn Ala Ser Pro Leu Leu
            20                  25                  30

Ala Ser Ser Trp Gly Gly Leu Ile His Leu Tyr Thr Ala Thr Ala Arg
        35                  40                  45

Asn Ser Tyr His Leu Gln Ile His Lys Asp Gly His Val Asp Gly Thr
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Val Phe Ser Ala Glu Ser
            100                 105                 110

Cys Arg Phe Arg Gln Arg Thr Leu Glu Asn Gly Phe Asp Val Tyr Gln
        115                 120                 125

Ser Pro Gln His His Phe Leu Val Ser Leu Gly Arg Ala Lys Gly Ala
    130                 135                 140

Phe Pro Ala Gly Ala Lys Pro Pro Pro Phe Pro Gln Phe Leu Pro Arg
145                 150                 155                 160

Gly Asn Glu Ala Pro Gly Arg Lys Thr Arg Gly Pro Glu Glu Lys Gly
                165                 170                 175

Ala Pro His Pro Leu Arg Gly Val Glu Ser Gly Gly Arg Lys Gly Gly
            180                 185                 190
```

```
Ala Pro Pro Leu Cys Leu Glu Arg Leu Ser Arg Ala Arg Glu
        195                 200                 205


<210> SEQ ID NO 40
<211> LENGTH: 193
<212> TYPE: PRT
<213> ORGANISM: Pongo abelii

<400> SEQUENCE: 40

Met Arg Asn Glu Ser Leu Pro Cys Leu Val Phe Ser Ile Gly Ala Leu
1               5                   10                  15

Met Ile Arg Ser Glu Asp Ala Gly Phe Val Val Ile Thr Gly Val Met
            20                  25                  30

Ser Arg Arg Tyr Leu Cys Met Asp Phe Arg Gly Asn Ile Phe Gly Ser
        35                  40                  45

His Tyr Phe Asn Pro Glu Asn Cys Arg Phe Gln His Gln Thr Leu Glu
    50                  55                  60

Asn Gly Tyr Asp Val Tyr His Ser Pro Gln His His Phe Leu Val Ser
65                  70                  75                  80

Leu Gly Arg Val Lys Arg Ala Phe Leu Pro Gly Met Pro Pro Pro Tyr
                85                  90                  95

Ser Gln Phe Leu Ser Arg Arg Asn Glu Ile Pro Leu Ile His Phe Asn
            100                 105                 110

Thr Pro Val Pro Arg Arg His Thr Arg Ser Ala Glu Asp Asp Thr Glu
        115                 120                 125

Arg Asp Pro Leu Lys Val Leu Lys Pro Arg Ala Arg Met Thr Pro Ala
    130                 135                 140

Pro Ala Ser Cys Ser Gln Glu Leu Pro Ser Ser Glu Asp Asn Ser Pro
145                 150                 155                 160

Met Ala Ser Asp Pro Leu Gly Val Val Arg Gly Gly Arg Val Asn Thr
                165                 170                 175

His Ala Gly Gly Thr Gly Pro Glu Gly Cys Arg Pro Phe Pro Lys Phe
            180                 185                 190

Ile


<210> SEQ ID NO 41
<211> LENGTH: 188
<212> TYPE: PRT
<213> ORGANISM: Sorex araneus

<400> SEQUENCE: 41

Met Trp Gly Leu Arg Leu Gly Leu Leu Val Gly Leu Leu Gly Cys Val
1               5                   10                  15

Asp Arg Ala Ser Pro Met Leu Ala Ser Ser Trp Gly Gly Leu Thr His
            20                  25                  30

Leu Tyr Thr Ala Thr Ala Arg Asn Ser Tyr His Leu Gln Ile His Lys
        35                  40                  45

Asp Gly Leu Val Asp Gly Ser Pro Gln Gln Thr Val Tyr His His Phe
    50                  55                  60

Ser Pro Glu Ser Cys Arg Phe Gln Gln Arg Thr Leu Glu Asn Gly Tyr
65                  70                  75                  80

Asp Val Tyr Gln Ser Pro Gln His Arg Phe Leu Val Ser Leu Gly Arg
                85                  90                  95

Pro Lys Arg Ala Phe Gln Pro Gly Ala Asn Pro Pro Pro Tyr Ala Gln
            100                 105                 110
```

-continued

Phe Leu Ala Arg Arg Asn Glu Val Pro Leu Ala Arg Phe His Thr Pro
        115                 120                 125

Ala Pro Arg Arg His Thr Arg Ser Ala His Asp Asn Gly Asp Ala Asp
    130                 135                 140

Pro Leu Asn Val Leu Ala Pro Arg Ala Ala Ala Ala Ala Ser Cys Ser
145                 150                 155                 160

His Glu Leu Pro Ser Ala Glu Asp Asn Ser Val Val Ala Ser Asp Pro
                165                 170                 175

Leu Gly Val Ile Arg Ser Asn Arg Phe Arg Thr His
            180                 185

<210> SEQ ID NO 42
<211> LENGTH: 263
<212> TYPE: PRT
<213> ORGANISM: Tetraodon nigroviridis

<400> SEQUENCE: 42

Met Asp Val Asn Arg Arg Ile Gly Val Lys Asp Ala Leu Leu Ala Leu
1               5                   10                  15

Leu Leu Ala Leu Leu Gln Gly Cys Pro Leu Gly Glu Thr Ala Pro Asn
            20                  25                  30

Ala Ser Pro Leu Val Gly Ser Asn Trp Gly Asn Pro Arg Arg Tyr Val
        35                  40                  45

His Leu Gln Thr Ser Thr Asp Met Ser Asn Phe Tyr Leu Glu Ile Arg
    50                  55                  60

Leu Asp Gly Thr Val Arg Lys Ser Thr Ala Arg Thr Ser Tyr Ser Val
65                  70                  75                  80

Ile Leu Leu Lys Ala Asp Thr Arg Glu Arg Ile Ala Ile Leu Gly Val
                85                  90                  95

Lys Ser Asn Arg Tyr Leu Cys Met Asp Leu Glu Gly Ser Pro Phe Ser
            100                 105                 110

Ser Pro Thr Cys Ile Arg Asp Asp Cys Leu Phe Asn His Ser Leu Leu
        115                 120                 125

Glu Asn Asn Arg Asp Val Tyr Tyr Ser Ser Arg Thr Gly Ile Leu Phe
    130                 135                 140

Asn Leu Glu Gly Ser Arg Gln Val Phe Val Val Gly Gln Asn Val Pro
145                 150                 155                 160

Gln Thr Ser Leu Phe Leu Pro Arg Thr Asn Thr Val Pro Leu Glu Arg
                165                 170                 175

Leu Leu Leu His Arg Asp Lys Arg Asn Gln Val Val Asp Pro Ser Asp
            180                 185                 190

Pro His Arg Val Ala Val Gly Arg Ala Glu Glu Gly Ser Asp Ser Arg
        195                 200                 205

Ala Leu Gln Glu Asp Asp Ala Asp Leu Glu Val Glu Thr Glu Val Glu
    210                 215                 220

Val Gly Asp Asp Gly Arg Asn Ala Ser Arg Glu Arg Leu Gln Ala Pro
225                 230                 235                 240

Ser Asp His Asp Pro Trp Gly Val Phe Ser Ser Asn Pro Gly Ser Pro
                245                 250                 255

Arg Ser Ser Gly Thr Val Gly
            260

<210> SEQ ID NO 43
<211> LENGTH: 255
<212> TYPE: PRT
<213> ORGANISM: Oreochromis niloticus

<400> SEQUENCE: 43

Met Asp Val Asn Arg Arg Met Gly Met Arg Asp Thr Val Leu Ala Leu
1 5 10 15

Phe Leu Ala Val Leu Gln Gly Phe Pro Leu Gly Asp Thr Val Pro Asn
20 25 30

Pro Ser Pro Leu Ala Gly Ser Asn Trp Gly Asn Pro Arg Arg Tyr Val
35 40 45

His Leu Gln Thr Ser Thr Asp Leu Asn Asn Phe Tyr Leu Glu Ile Arg
50 55 60

Leu Asp Gly Ser Val Arg Lys Thr Thr Ser Arg Ser Thr Tyr Ser Val
65 70 75 80

Ile Leu Leu Lys Ser Glu Ala Arg Asp Arg Val Ala Ile Leu Gly Val
85 90 95

Lys Ser Ser Arg Tyr Leu Cys Met Asp Leu Glu Gly Asn Pro Phe Ser
100 105 110

Ser Pro Val Cys Leu Arg Asp Asp Cys Leu Phe Asn His Lys Leu Leu
115 120 125

Glu Asn Asn Arg Asp Val Tyr Tyr Ser Ser Arg Thr Gly Ile Leu Phe
130 135 140

Asn Leu Glu Gly Ser Arg Gln Val Tyr Ser Val Gly Gln Asn Leu Pro
145 150 155 160

Gln Thr Ser Leu Phe Leu Pro Arg Lys Asn Thr Val Pro Leu Glu Arg
165 170 175

Leu Leu Leu His Arg Glu Lys Arg Asn Arg Gly Gln Thr Glu Glu Gly
180 185 190

Ser Asp Ser Arg Ala Val Pro Glu Glu Leu Glu Glu Arg Glu Val Glu
195 200 205

Met Glu Thr Glu Ile Glu Thr Glu Val Gly Asp Asp Gly Arg Asn Val
210 215 220

Ser Arg Glu Lys Leu Ala Ala Pro Ser Ser His Asp Pro Trp Asn Val
225 230 235 240

His Phe Ser Asn Pro Ala Ser Pro Arg Ser Thr Gly Thr Val Gly
245 250 255

<210> SEQ ID NO 44
<211> LENGTH: 258
<212> TYPE: PRT
<213> ORGANISM: Danio rerio

<400> SEQUENCE: 44

Met Arg Cys Ala Leu Ser Asn Leu His Met Leu His Ser Ser Val Leu
1 5 10 15

Ala Leu Trp Phe Thr Ala Leu Gln Gly Leu Arg Pro Ala Asp Ala Ala
20 25 30

Pro Asn Pro Ser Pro Leu Leu Gly Ser Asn Trp Gly Asn Pro Arg Arg
35 40 45

Tyr Ile His Leu Gln Thr Thr Ser Asp Leu Asn Asn Tyr Tyr Leu Glu
50 55 60

Ile Ser Pro Ser Gly His Val Arg Lys Thr Thr Asn Arg Gly Ser Tyr
65 70 75 80

Ser Val Ile Leu Leu Lys Thr Glu Ser Arg Asp Arg Leu Ala Ile Phe
85 90 95

Gly Val Lys Ser Asn Arg Phe Leu Cys Met Asp Thr Gly Gly Thr Leu
100 105 110

```
Phe Thr Ser Thr Ile Cys Asn Lys Glu Asp Cys Leu Phe His His Lys
        115                 120                 125

Leu Leu Glu Asn His Arg Asp Val Tyr Tyr Ser Thr Lys His Ser Ile
    130                 135                 140

Leu Leu Asn Leu Asp Gly Asp Lys Gln Ala Phe Ile Ala Gly Gln Asn
145                 150                 155                 160

Leu Pro Gln Ser Ser Leu Phe Leu Ser Glu Lys Asn Thr Val Pro Leu
                165                 170                 175

Glu Arg Leu Gln His Arg Glu Arg Arg Asn Arg Gln Val Asn Pro Thr
            180                 185                 190

Asp Pro Leu Asn Ala Leu Arg Tyr Ala Glu Glu Ser Asp Ser Arg Ala
        195                 200                 205

Ala Gln Glu Asp Asp Gly Asp Met Asp Phe Glu Pro Ser Glu Gly Gln
    210                 215                 220

Asn Ile Ser Arg Glu Thr Leu Val Ser Pro Ser Asp Asp Asp Pro Trp
225                 230                 235                 240

Asp Leu Leu His Asp Thr Ser Pro Gly Ser Pro Arg Ile Ala Ala Ile
                245                 250                 255

Val Gly
```

<210> SEQ ID NO 45
<211> LENGTH: 756
<212> TYPE: DNA
<213> ORGANISM: Homo sapiens

<400> SEQUENCE: 45

```
atgttggggg cccgcctcag gctctgggtc tgtgccttgt gcagcgtctg cagcatgagc     60

gtcctcagag cctatcccaa tgcctcccca ctgctcggct ccagctgggg tggcctgatc    120

cacctgtaca cagccacagc caggaacagc taccacctgc agatccacaa gaatggccat    180

gtggatggcg caccccatca gaccatctac agtgccctga tgatcagatc agaggatgct    240

ggctttgtgg tgattacagg tgtgatgagc agaagatacc tctgcatgga tttcagaggc    300

aacatttttg gatcacacta tttcgacccg gagaactgca ggttccaaca ccagacgctg    360

gaaaacgggt acgacgtcta ccactctcct cagtatcact tcctggtcag tctgggccgg    420

gcgaagagag ccttcctgcc aggcatgaac ccacccccgt actcccagtt cctgtcccgg    480

aggaacgaga tcccccctaat tcacttcaac acccccatac cacggcggca cacccggagc    540

gccgaggacg actcggagcg ggacccccctg aacgtgctga agccccgggc ccggatgacc    600

ccggccccgg cctcctgttc acaggagctc ccgagcgccg aggacaacag cccgatggcc    660

agtgacccat taggggtggt caggggcggt cgagtgaaca cgcacgctgg gggaacgggc    720

ccggaaggct gccgcccctt cgccaagttc atctag                               756
```

<210> SEQ ID NO 46
<211> LENGTH: 756
<212> TYPE: DNA
<213> ORGANISM: Gorilla

<400> SEQUENCE: 46

```
atgttggggg cccgcctcag gctctgggtc tgtgccttgt gcagcgtctg cagcttgagc     60

gtcctcagag cctatcccaa tgcctcccca ctgctcggct ccagctgggg tggcctgatc    120

cacctgtaca cagccacagc caggaacagc taccacctgc agatccacaa gaatggccat    180

gtggatggcg caccccatca gaccatctac agtgccctga tgatcagatc agaggatgct    240
```

-continued

```
ggctttgtgg tgattacagg tgtgatgagc agaagatacc tctgcatgga tttcagaggc    300

aacatttttg gatcacacta tttcgacccg gagaactgca ggttccaaca ccagacgctg    360

gaaaacgggt acgacgtcta ccactctcct cagtatcact tcctggtcag tctgggccgg    420

gcgaagagag ccttcctgcc aggcatgaac ccaccccgt actcccagtt cctgtcccgg    480

aggaacgaga tccccctcat tcacttcaac acccccatac cacggcggca cacccggagc    540

gccgaggacg actcggagcg ggacccccctg aacgtgctga agccccgggc ccggatgacc    600

ccggccccgg cctcctgttc acaggagctc ccgagcgccg aggacaacag cccgatggcc    660

agtgacccat taggggtggt caggggcggt cgagtgaaca cgtacgctgg gggaacgggc    720

ccggaaggct gccgcccctt ccccaagttc atctag                              756
```

<210> SEQ ID NO 47
<211> LENGTH: 756
<212> TYPE: DNA
<213> ORGANISM: Northern white-cheeked gibbon

<400> SEQUENCE: 47

```
atgttggggg cccgcctcag gctctgggtc tgtgccttgt gcagcgtctg cagcatgagc     60

gtcctcagag cctatcccaa tgcctcccca ctgctcggct ccagctgggg tggcctgatc    120

cacctgtaca cagccacagc caggaacagc taccacctgc agatccacaa gaatggccat    180

gtggatggcg caccccatca gaccatctac agtgccctga tgatcagatc agaggatgct    240

ggctttgtgg tgattacagg tgtgatgagc agaagatacc tctgcatgga tttcagaggc    300

aacatttttg gatcacacta tttcaacccg gagaactgca ggttccaaca ccagacgctg    360

gaaaacgggt acgacgtcta ccactctcct cagcatcact tcctggtcag tctgggccgg    420

gccaagagag ccttcctgcc gggcatgaac ccaccccgt actcccagtt cctgtcccgg    480

aggaacgaga tccccctact tcacttcaac acccccacac cacggcggca cacccggagc    540

gccgaggacg actcggagcg ggacccccctg aacgtgctga aaccccgggc ccggatgacc    600

ccggccccgg cctcctgctc acaggagctc ctgagctccg aggacaacag cccgatggcc    660

agcgacccat taggggtggt caggggcggt cgagtgaaca cgcacgctgg gggaacgggc    720

ccggaaggct gccgcccctt ccccaagttc atctag                              756
```

<210> SEQ ID NO 48
<211> LENGTH: 756
<212> TYPE: DNA
<213> ORGANISM: Rhesus monkey

<400> SEQUENCE: 48

```
atgttggggg cccgcctcag gctctgggtc tgtgccttgt gcagcgtctg cagcatgagc     60

gtcatcagag cctatcccaa tgcctcccca ttgctcggct ccagctgggg tggcctgatc    120

cacctgtaca cagccacagc caggaacagc taccacctgc agatccacaa gaatggccac    180

gtggatggcg caccccatca gaccatctac agtgccctga tgatcagatc agaggatgct    240

ggctttgtgg tgattacagg tgtgatgagc agaagatacc tctgcatgga tttcagaggc    300

aacatttttg gatcacacta tttcaacccg gagaactgca ggttccgaca ctggacgctg    360

gagaacggct acgacgtcta ccactctcct cagcatcact ttctggtcag tctgggccgg    420

gcgaagaggg ccttcctgcc aggcatgaac ccacccccct actcccagtt cctgtcccgg    480

aggaacgaga tccccctcat ccacttcaac acccccagac cacggcggca cacccggagc    540
```

-continued

```
gccgaggacg actcggagcg ggaccccctg aacgtgctga agccccgggc ccggatgacc    600

ccggccccgg cctcctgctc acaggagctc ccgagcgccg aggacaacag cccggtggcc    660

agcgacccgt taggggtggt caggggcggt cgggtgaaca cgcacgctgg gggaacgggc    720

ccggaagcct gccgcccctt ccccaagttc atctag                              756
```

<210> SEQ ID NO 49
<211> LENGTH: 756
<212> TYPE: DNA
<213> ORGANISM: Crab-eating macaque

<400> SEQUENCE: 49

```
atgttggggg cccgcctcag gctctgggtc tgtgccttgt gcagcgtctg cagcatgagc     60

gtcatcagag cctatcccaa tgcctcccca ttgctcggct ccagctgggg tggcctgatc    120

cacctgtaca cagccacagc caggaacagc taccacctgc agatccacaa gaatggccac    180

gtggatggcg caccccatca gaccatctac agtgccctga tgatcagatc agaggatgct    240

ggctttgtgg tgattacagg tgtgatgagc agaagatacc tctgcatgga tttcagaggc    300

aacatttttg gatcacacta tttcaacccg gagaactgca ggttccgaca ctggacgctg    360

gagaacggct acgacgtcta ccactctcct cagcatcact ttctggtcag tctgggccgg    420

gcgaagaggg ccttcctgcc aggcatgaac ccaccccct actcccagtt cctgtcccgg     480

aggaacgaga tcccccctcat ccacttcaac acccccagac cacggcggca cacccggagc   540

gccgaggacg actcggagcg ggaccccctg aacgtgctga agccccgggc ccggatgacc    600

ccggccccgg cctcctgctc acaggagctc ccgagcgccg aggacaacag cccggtggcc    660

agcgacccgt taggggtggt caggggcggt cgggtgaaca cgcacgctgg gggaacgggc    720

ccggaagcct gccgcccctt ccccaagttc atctag                              756
```

<210> SEQ ID NO 50
<211> LENGTH: 756
<212> TYPE: DNA
<213> ORGANISM: Chimpanzee

<400> SEQUENCE: 50

```
atgttggggg cccgcctcag gctctgggtc tgtgccttgt gcagtgtctg cagcgtgagc     60

gtcctcagag cctaccccaa tgcctcccca ctgctcggct ccagctgggg tggcctgatc    120

cacctgtaca cagccacagc caggaacagc taccacctgc agatccacaa gaatggccat    180

gtggatggcg caccccatca gaccatctac agtgccctga tgatcagatc agaggatgct    240

ggctttgtgg tgattacagg tgtgatgagc agaagatacc tctgcatgga tttcagaggc    300

aacatttttg gatcacacta tttcaacccg gagaactgca ggttccaaca ccagacgctg    360

gaaaacgggt acgacgtcta ctactctcct cagtatcact tcctggtcag tctgggccgg    420

gcgaagagag ccttcctgcc aagcatgaac ccacccccgt actcccagtt cctgtcccgg    480

aggaacgaga tcccccctaat tcacttcaac acccccatac cacggcggca cacccggagc   540

gccgaggacg actcggagcg ggaccccctg aacgtgctga agccccgggc ccggatgacc    600

ccggccccgg cctcctgttc acaggagctc ccgagcgccg aggacaacag cccgatggcc    660

agtgacccat taggggtggt caggggcggt cgagtgaaca cgcacgctgg gggaacgggc    720

ccggaaggct gccgcccctt ccccaagttc atctag                              756
```

<210> SEQ ID NO 51
<211> LENGTH: 756

<212> TYPE: DNA
<213> ORGANISM: White-tufted-ear marmoset

<400> SEQUENCE: 51
atgttggggg cccgcctcag gctctgggtc tgtgccttgt gcagcgtctg cagcatgagc 60
gtcctcagag cctatcccaa tgcctcccca ctgcttgcct ccagctgggg tggcctgatc 120
cacctgtaca cagccacagc caggaacagc taccacctgc agatccacaa gaatggccat 180
gtggatggcg caccccatca gaccatctac agtgccctgc tgatcagatc agaggatgct 240
ggctttgtgg tgattacagg tgtgatgagc agaagatacc tctgcatgga tttcagaggc 300
aacatttttg gatcacacta tttcaacccg gagaactgca ggttccgacc ccagaggctg 360
gagaacgggt acgacgtcta ccagtctcct cagcatcact tcctggtcag tctgggccgg 420
gcgaagaggg ccttcctgcc aggcatgaac ccaccccgt actcccagtt cctgtcccgg 480
aggaacgaga tccccctcat tcacttcaac acccccaaac cgcggcggca cacccggagc 540
gccgaggacg acccggagct agacccccctg aacgtgctga agtcccgggt ccggatgacc 600
ccggccccgg cctcctgctc gcaggagctc ctgagcgccg aggacaacag cccggtgggc 660
agcgacccct tagggatggt ccggggtggt cgggtgaaca gccacgctga gggaacaggc 720
ccagaaggct gcagcccctt ccccaagctc atctag 756

<210> SEQ ID NO 52
<211> LENGTH: 756
<212> TYPE: DNA
<213> ORGANISM: Elephant

<400> SEQUENCE: 52
atgttggggg cccgcctcag gctctgggtc tgcaccctgt gcagtgcctg cagcatgtgc 60
agtgtcagag cctatcccaa tgcctccccg ctgctccact ccagctgggg tggcctgacc 120
cacctgtaca cagccaccgc caggaacagc taccacctgc agatccacaa ggacggccat 180
gtggatggta cgccggacca gaccatctac agtgccctga taatcagatc agaggaggcc 240
ggcttcgtgg tgattacagg ggtgatgagt aggagatacc tctgtatgga tttcagaggc 300
aacatttttg gatcgcatta cttcaaccca gagaactgca ggttcaaaca ctggacgctg 360
gaaaatggat atgacgtcta tcactctcct cagcatcatt tcctggtcag tctgggtcgc 420
gtgaagaagg ccttcctgcc aggcatgaac ccaccacctt actctcagtt cctgtcccgg 480
aggaatgaga tccccttgat ttacttcaac acccccaagc ccggcggca cacccggagt 540 gccgaggatg actctgaacg ggacccactg aatgtgctga agccccggcc ccgtatgaca 600
cctgctccag cttcttgctc ccaggaactc ctgagtgctg aagacaacag cgtggtggcc 660
aatgaccctt taggagtggt cagaagcaat agggtcaaca cacatgctgg tgggataggt 720
gtggaaaggt gccgcccctt ccccaagttc atctag 756

<210> SEQ ID NO 53
<211> LENGTH: 750
<212> TYPE: DNA
<213> ORGANISM: Lesser hedgehog tenrec

<400> SEQUENCE: 53
atgttggggg cccacctcag actctgggtc tgtgccttgt gcagtgtgag cgccatgtac 60
cacgtcagag cctaccccaa cgcctccccg ctcctgggta ccagctgggc tggcctgacc 120
cacctgtaca cggcgacagc caggaacagc ttccacctgc agatccacaa ggatggccac 180
gtggacggca ccccccacca gaccatctac agtgccctga tgatccgatc agaggactct 240
ggcttcgtgg tgatcacagg ggtgatgagc aggagatacc tgtgtatgga tttcagaggc 300
aacatttttg gatcgcacta cttcactgcg gacagctgca ggttcagaca gcggacgctg 360
gagaacggct atgacgtcta ccactctcct cagcatcatt tcctgatcag cctgggccgg 420
gccaagaggg tcttcctgcc cggcatgaac ccgccgcctt actcccagtt cctgtcccga 480
aggaatgaga tccccctgat tcacttcaac acccccaggc cccggcggca cacacggagt 540
gccgaggagg aagtggagca ggatccgctg aacgtgctga agcccaggcc ccggatgacg 600
ccggctccag cctcctgctc ccaggagctg cccagtgccg aagacaacag cgccctggcc 660
agcgacccgc tgggagtggt cagaggcaaa aagctcaaca cccatgctgt gggcatgggc 720
gcggaaagat gccgcccctt tcccaagttc 750

<210> SEQ ID NO 54
<211> LENGTH: 710
<212> TYPE: DNA
<213> ORGANISM: Hedgehog

<400> SEQUENCE: 54
atgttggggg cccacctggg tctggtggtc tgcgccctgg tcagcagagc ctatcccaat 60
gcctcgccac tgctgggctt cagctggggg ggcctgacac atctgtacac ggccacagcc 120
aggaacagct accacctgca gatccacaag gacggccacg tggacggctc gcctcagcag 180
accatctaca tgctggtttc gtgatgatca caggcgtgat gagtaggcgc tacctctgca 240
tggacttcag gagcaacatc tttggatcgc atcacttcgc ccctgagagc tgcaggttca 300
gacatcggac actggaaaac ggctatgacg tctaccactc cccccagcac catttcctgg 360
tcagcctggg ccgggccaag cgggccttcc tgccgggcac caaccccccca ccatactccc 420 agtttttgtc ccggaggaac gaggttcccc tcatccactt caacaccccc aggcccaggc 480
gtcacacccg cagcgccgag gacaactcag agctggatcc cctgaacgtg ctgaagccca 540
ggccccgcat gacccccgcc ccagcctcct gctcccagga gcttccgagc gctgaggaca 600
acagcatggt ggccagtgac ccactgggtg tggtcagagc caacagagtg aacacacacg 660
cagggggcct gggtgtggac aagtgccgcc ccttccccaa gtttatctag 710

<210> SEQ ID NO 55
<211> LENGTH: 759
<212> TYPE: DNA
<213> ORGANISM: Bushbaby

<400> SEQUENCE: 55
atgctgggga cctgcctcag gctctgggtc tgtgccctgt gcagtgtttg cagcgtgagc 60
attgtcagag cctatcccaa cgcctcccca ctgctcagct ccagctgggg tggcctgacc 120
cacctgtaca cggcctcggc cagaaacagc taccacctgc agatccacaa ggatggccat 180
gtggacggca caccccacca gaccatctac agcgccctaa tgatcaggtc agaggatgct 240
ggcttcgtgg tgattacagg cgtgatgagc agaagatacc tctgtatgga tttcaaaggc 300
aacatttttg gatcacactc cttccacccc gagagctgca ggttcagaca ccggactctg 360
gagaacggct atgacgtcta cctctcgccg cagcatcact tcttggtcag cctgggccgc 420
tccaagaggc ccttcctgcc gggcatgaac ccgccccccct tctcccagtt cctgtcgcgg 480
aggaacgaca tcccgctcat tcacttcaac acccccccgcc cgcggagaca cacccgcagc 540
gccgaggaca acgactcgga gctcgacccc ctgaacgtgc tgaagccgcg gccccgggcc 600
accccgggcc ccgcctcctg ctcgcaggag ctccccagcg ccgaggacaa cagcctggtg 660
gccagcgacc ctttaggggt ggtccggggc aacagggtga acgctcacgc cgggagggcc 720
ggcctggaca ggtgccgccc cttccccagg tatttctag 759

<210> SEQ ID NO 56
<211> LENGTH: 759
<212> TYPE: DNA
<213> ORGANISM: Rabbit

<400> SEQUENCE: 56
atgttagggg cccggctcct ccggctcttg gtctgtgccc tgggcagtgt gtgcagctgg 60
tgtgtggtcc gagcctaccc tgacacctcc ccgctgctca gctccagctg ggctggcctg 120
acccacctgt acacggccac cgccagaaac agctaccacc tgcagatcca caaggacggc 180
caagtggatg gcacacctca tcagaccatc tacagtgccc tgatgatcag atcggaggat 240
gctggcttcg tggtgataac aggtgtcatg agcaggaggt acctctgtat ggatttcaga 300
ggcaacattt ttggatcgca ttacttcgac ccccagaact gcaggttcag acacaggacg 360
ctggaaaacg ggtacgacgt ctaccactct ccggagcatc acttcctggt cagcctgggc 420
cgggccaaga ggcccttcct gccaggcatg aacccgccac cctattccca gttcctgtcc 480
cggaggaacg agatccccct gatccacttc aacacgccga ggccgcgaag gcacacccgg 540
agcgccgagg acgcctggga gcaggacccg ctgaacgtgc tgaagcccag gttccggctg 600
accccggccc cagcctcctg ctcacaggag gccccaagtg ctgaagacaa tggcctggtg 660
gccagcgacc ccttcggagt gctccggggc aatagggtga acatgcacgg ggacaggatg 720
ggcccggaaa ggtgccacca tttccccaag ttcatctag 759

<210> SEQ ID NO 57
<211> LENGTH: 741
<212> TYPE: DNA
<213> ORGANISM: Horse

<400> SEQUENCE: 57
atgtcagggc cctgccttgg gctcctggtc tacgtcctgt gctccgcagt gaaagcctat 60
cccaacgcct ccccgctgct agactccagc tggggcagcc tgacccacct gtacacggcc 120
acagccagga acagctacca cctgcagatc cacaaggatg gccacgtgga tggcacaccc 180
catcagacca tctacagtgc cctgatgatc agatcagagg atgctggctt tgtggtgata 240
acaggtgtga tgagcaggag atacctctgc atggacttca gaggaaacat tttggatca 300 catcacttca gccccgagag ctgcagcttc cgacagcgga cgctggagaa cggctacgac 360
gtgtaccact cgccgcagca tcgcttcctc gtcagcctgg gccgcgccaa gagggccttc 420
ctgcccggca cgaacccccc gccctactcg cagttcctgt cccggaggaa cgagatcccc 480
ctggtccact tcaacacccc gcggccgcgg cggcacacgc gcagcgccga ggacaactcg 540
gagcgcgacc cgctgaacgt gctgaagccc cggccccgca tgacccccgc gccggcctcc 600
tgctcccagg agctcccgag cgccgaggac aacagcgtgc tggccagcga ccccttaggg 660
gtggtccgtg gcaacagggt gaacacgcac gcggggggcg cgggcgtgga gcgctgccgc 720
cccttcccca agttcttcta g 741

<210> SEQ ID NO 58
<211> LENGTH: 738
<212> TYPE: DNA

<213> ORGANISM: Giant panda

<400> SEQUENCE: 58

```
atgtcaggga cccgccttgg gctgctggtc tctgtcctgt gctgggtagg cagagcctat     60
cccaacacct ccccactgct cggctccagc tggggtggcc tgacccacct gtacacagcc    120
agcgccagga acagctacca cctgcagatc cacaaggacg gccatgtgga tggcacaccc    180
catcagacca tctacagtgc cctgatgatc aggtcagagg atgccggctt tgtggtgata    240
acaggtgtga tgagtaggcg atacctctgt atggacctca gaggcaacat ctttggatcc    300
cacctcttca gcccggagag ctgcaggttc cgacagcgga cgctggaaaa cggctacgac    360
gtgtaccact cgccgcagca ccgcttcctc gtcagcctgg gccaggccaa gaggaccttc    420
ctgccgggga ccaacccgcc gccctactcc cagttcctgt cccggaggaa cgagatcccc    480
ctcatccact tcaacacccc caggccaagg cggcacacgc gcagcgccga ggacacggag    540
cgcgacccgt tgaacgtgct gaagcccagg ccccgcatga cccccgcccc ggcctcctgc    600
tcccaggagc tcccgagcgc cgaggacaac agtgtggtgg ccagcgaccc gttaggggtg    660
ctcagaggca accgggtgaa cgcgcacgcc ggggggatgg gcgtggacag gtgccgcccc    720
ttccccaagt tcatctag                                                  738
```

<210> SEQ ID NO 59
<211> LENGTH: 753
<212> TYPE: DNA
<213> ORGANISM: Pika

<400> SEQUENCE: 59

```
atgctggggg ggctggggct gtgggtctgt gtcctgggca gtgtgtgcag ctggcgtggg     60
gtccgtgcct atcccgacac ctccccgctg ctcggctcca gctggactgg cctgacccac    120
ctgtacacgg ccaccgccag gaacagcttc cacctgcaga tccacaagga tggccatgtg    180
gatggcacac cccagcagac catctatagt gccctgatga tcagatcaga ggatgccggc    240
ttcgtggtga taacaggtgt catgagcagg aggtacctct gtatggattt cagaggcaac    300
atcttcggat cgcattactt cgagccacag aactgcaggt tccagcagag gacgctggag    360
aacggctacg acatctacca ctctccgcag cacgacttcc tggtcagcct aggtcgggcc    420
aagaggccgt tcctgccagg catgaacccg ccaccctact cccagttcct gtctcggagg    480
aacgagattc cgctgatcct cttcaacacg cccaggcctc ggaggcacac ccgcagcgcg    540
gaggagggct gggagcggga ccctctgaat gtgctgaagt ccaggccccg aatgaccccg    600
gccccagcct cctgctcgcg ggaggccccc agtgccgaag acgacggcct gctggccagt    660
gaccccatgg gagtgctcag aggccatagg gtggatgtgc acgggggtgg gacgggtagg    720
gacaggtgcc gcccgttccc caggttcatc tag                                 753
```

<210> SEQ ID NO 60
<211> LENGTH: 738
<212> TYPE: DNA
<213> ORGANISM: Cattle

<400> SEQUENCE: 60

```
atgctggggg cccgcctggg gctctgggtc tgcaccctga gctgtgtggt ccaagcctat     60
cccaacagct ccccgctgct gggctccagc tggggcggcc tgacccacct gtacacggcc    120
acggccagga acagctacca cctgcagatc cacggagacg ggcacgtaga tggctccccg    180
cagcagactg tctacagcgc cctgatgatc aggtcggagg atgccggctt cgtggtgata    240
```

acaggtgtga tgagcaggcg gtacctctgc atggacttca caggcaacat ttttggatcc 300
catcacttca gtccggagag ctgccggttc cggcagcgga cactggagaa cggctacgac 360
gtgtaccact cgccgcagca ccgcttcctc gtcagcctgg gccgggccaa gcgcgccttc 420
ctgccgggca ccaacccgcc cccatacgcg cagttcctgt cgcgcaggaa cgagatcccg 480
ctgccgcact tcgccgccac cgcgcggccc cggcgccaca cgcgcagcgc acacgacagc 540
ggggacccgc tcagcgtgct caagccgcgc gcccgcgcca cgcccgtgcc cgccgcctgc 600
tcccaggagc tgcccagcgc cgaggactcc ggccctgccg ccagcgaccc gctcggggtg 660
ctccgcggac accgcctgga cgtgcgcgcc ggctccgcgg gcgccgagcg ctgccggccc 720
ttccccggct tcgcctag 738

<210> SEQ ID NO 61
<211> LENGTH: 735
<212> TYPE: DNA
<213> ORGANISM: Pig

<400> SEQUENCE: 61
atgctggggg cccgcctcgg gctctgggtc tgcaccctgt gctgtgcggc cagagcctat 60
cccgacacct ccccgctgct gagctctggc tggggcggcc tgacccacct gtacacggcc 120
acggccagga acagctacca cctgcagatc cacaaggatg gccacgtgga tggctcaccc 180
caacagacca tctacagtgc cctaatgatc aggtcggagg acgcaggctt cgtggtcata 240
acaggcgtga tgagcaggag atacctctgc atggacttaa ggggcaacat ttttggatcg 300
ctgcacttca gccccgagag ctgcaggttc cggcagcgga cgctggagaa cggctacgac 360
gtgtaccact cgccgcacta ccgcttcctc gtcagcctgg gccgggccaa gcgggccttc 420
ctgccgggta ccaacccgcc cccgtacgcg cagttcttgt cgcgcaggaa cgagatcccg 480
ctgctgcact tcgccaccgc gcggccccgg cgccacacgc gcagcgcgca cgacggcggg 540
gacccgctga gcgtcctgaa gccgcgcgcg cgcgccacgc ccgcgcccgt ctcctgctcc 600
cgcgagctgc ccagcgccga ggacggcggc cccgcggcca gcgacccgct cggggtgctc 660
cggggccagc ggctggacgc gcgcgctggg gtgggggcgg ccgagcgctg ccggcccttc 720
cccagcttcg cctag 735

<210> SEQ ID NO 62
<211> LENGTH: 939
<212> TYPE: DNA
<213> ORGANISM: Dog

<400> SEQUENCE: 62
atgtggacag tggagttttt cctgtttgat gtcacagggc caccctttaa aagtctgagg 60
gaaaaaagga gggaatctag cctgggactt tcacgcaaga tacccacaaa gaagaggaga 120
aaaaggcctg tgaggcacag ccggggaatc aaggaggcag tgtcaggttt caaactccag 180
ccagccattc agagagctgt gatgtctggc acccgccttg gattcctggt ctctgtcctg 240
tgctgggtag tcagagccta ttccaacacc tccccgctgc tcggctccag ctggggtagc 300
ctaacccacc tgtatacggc cacagccagg aacagctacc acctgcagat ccacaaggac 360
ggccatgtgg atggcacacc tcatcagacc atctacagtg ccttgatgat ccggtcagag 420
gatgccggct ttgtggtgat aacaggtgtg atgagtagga ggtacctctg tatggacttc 480
agaggcaaca tctttggatc acacctcttc agcccggaga gctgccggtt ccgacagcgg 540
acgctggaga acggctacga cgtgtaccac tccccgcagc accgcttcct cgtcagcctg 600
ggccaggcca agagggcctt cctgcccggc accaacccgc cgccctactc gcagttcctg 660
tcccggagga acgagatccc cctcgtgcac ttccacacgc ccaggccgcg gcggcacacg 720
cgcagcgccg aggccccgga gcgcgacccg ctgaacgtgc tgaagcccag gccgcgcttg 780
gcccccgccc cggcctcctg ctcgcaggag ctcccgagcg ccgaggaccc cggcgcgccg 840
gccagcgacc cgctcggggt gctcaggggc cacagggcca acgcgcgcgc cggcggggtg 900
ggcgtggaca ggtgccgcgc cttccccacg cccatctag 939

<210> SEQ ID NO 63
<211> LENGTH: 732
<212> TYPE: DNA
<213> ORGANISM: Domestic guinea pig

<400> SEQUENCE: 63
atgctgggga cctgccttgg gctcctggcc tgcaccgtga gcttagtagg agcctatcct 60
gatgcctccc cattgctcac ctccagctgg ggtggcctga tccatctgta cacggccaca 120
gccagaaaca gctaccatct gcagatccac aaagatggcc acatagatgg tgcaccctat 180
ccgaccatct acagtgccct gatgatcaga tcagaagatg ctgggttcgt cgtgataaca 240
ggggtcacaa gcaggagatt cctctgcatg gatttcagag gcaacatttt tggatctcac 300
cacttcaatc cccaagactg ccgattccaa caccgcacgc tggaaaacgg ttacgacgtc 360
tacctctctc ccgagcacca ctttctgatc agcctgggca ggaccaagaa gttcttcctg 420
ccgggcacca acccaccgcc ctactcccag ttcctgtcgc gcaggaacga gctgcccctg 480
gcccgcttcg tcacgcccgg gccgcggcga cacacgcgca gcgcggagga ggaccagggc 540
cgcgacccgc tgagcgtgct caagcttcgg ccccgcgcca cgcccgcgcc cgcctcgtgc 600
tcgcaggagc tgcccagcgc ggaggacgcg gcccaggcca gcgacccccct gggcgtgctg 660 cggggcgcca gggtgcacgc gcacggcggg ccgcgccccg cgaggtgccg cccgggaccc 720
ggggccaagt aa 732

<210> SEQ ID NO 64
<211> LENGTH: 756
<212> TYPE: DNA
<213> ORGANISM: Chinese hamster

<400> SEQUENCE: 64
atgctgggga cctgcctcag actcctggtg ggtgttctgt gtagtgcctg cagcctgggc 60
actgttagag cctatcctga cacctcccca ctgctcggct ccaattgggg cagcctgacc 120
cacctgtaca cagctacagc caggaacagt tatcacctac agatccacaa ggatggccgt 180
gtagatggca caccccatca gaccatctac agtgccctga tgattagatc agaggatgct 240
ggcttcgtga tcataacagg agctgtgact agaaggttcc tttgtatgga tctcaggggc 300
aacatttttg gatcgcatca cttcagcccg gagaactgca ggttccgcca gcggactctg 360
gagaatggct atgacgtcta cctgtcgcca cagcatcact acctggtgag cctgggccgc 420
gccaagcgcc ccttcgagcc cggcaccaac ccgcctccct tctcgcagtt cctggcgcgc 480
aggaacgagg tcccgctgct gcgcttccat accgcacggc cacggcgcca cacgcgcagc 540
gccgaggacc ctcccgagtg ggacccactg aacgtgctca agccgcggcc ccgtgccacg 600
cccgtgcccg tgtcctgctc gcgggagctg ccgagcgccg aggaaggtga cctcgcggcc 660
agtgacccac tgggcgtcct gcgcagaggc cgcggggatg ctcgcggggg cgcaggaggc 720
gtggaccggt gccgtccctt tcccagattc gcctag 756

<210> SEQ ID NO 65
<211> LENGTH: 543
<212> TYPE: DNA
<213> ORGANISM: Tree shrew

<400> SEQUENCE: 65
gccctgctga tcaggccgga ggaggctggc ttcgcggtga tcacgggcgt gatgagcagg 60
agatacctct gcatggattt caggggcaac attttcggat cacacctctt cagcccggag 120
agctgcaggt tccggcagcg cgccctggag aacggctacg acgtctacca ccacccgcag 180
caccacttcc tggtcagcct gggccggccc aagagggcct tcgtgccagg cacgaacccg 240 ccccccctact cccagttcct ggcccggaag aacgagatcc cgctcatcca cttcaacacc 300
ccgaagccgc ggcggcacac ccgcagcgca gaggacaact cggggcgcga cccgctgaac 360
gtgctgaagc cccggccgcg catgaccccg gcgcccgcct cctgctcgca ggagctcccg 420
agtgccgagg acaacagcgt ggtggccagc gaccccctgg gagtgctcag gggcaacagg 480
gtgaacacgc acgcgggggg ctggggcgtg gaccgctgcc gccccttccc caggtttatc 540
tag 543

<210> SEQ ID NO 66
<211> LENGTH: 756
<212> TYPE: DNA
<213> ORGANISM: Norway rat

<400> SEQUENCE: 66
atgctggggg cctgcctcag actcctggtg ggcgctctgt gcaccgtctg cagcttgggc 60
actgctagag cctattcaga cacttcccca ctgcttggct ccaactgggg gagcctgacc 120
cacctgtaca cagctacagc caggaacagc tatcacctac agatccatag ggatggccat 180
gtagacggaa caccccatca gactatctac agtgccctga tgatcacatc agaggatgct 240
ggctccgtag tgataatagg ggccatgacc agaaggttcc tttgtatgga tctccgcggc 300
aacatttttg gatcgtatca cttcagcccg gagaactgca gattccgcca gtggacgcta 360
gagaacggct acgacgtcta cctgtcaccg aagcatcact acctggtgag cttgggccgc 420
tccaagcgca tcttccagcc cggtaccaac ccgccgccct tctcgcagtt cctggcgcgc 480
aggaacgagg tcccgctgct gcacttctac accgcgcgcc cacggcgcca cacgcgcagc 540
gccgaggacc cgcccgagcg cgacccgctg aatgtgctca agccgcggcc ccgcgctact 600
cccataccgg tatcctgctc gcgagagcta ccgagtgcag aggaaggtgg ccccgcggcc 660
agcgaccccc tgggagtgct gcgcagaggc cgcggggatg ctcgccgggg cgcgggaggc 720
acggatcggt gtcgcccctt tcccaggttc gtctag 756

<210> SEQ ID NO 67
<211> LENGTH: 756
<212> TYPE: DNA
<213> ORGANISM: House mouse

<400> SEQUENCE: 67
atgctaggga cctgccttag actcctggtg ggcgcgctct gcactgtctg cagcttgggc 60
actgctagag cctatccaga cacttcccca ttgcttggct ccaactgggg aagcctgacc 120
cacctgtaca cggctacagc caggaccagc tatcacctac agatccatag ggatggtcat 180

-continued gtagatggca ccccccatca gaccatctac agtgccctga tgattacatc agaggacgcc 240
ggctctgtgg tgataacagg agccatgact cgaaggttcc tttgtatgga tctccacggc 300
aacatttttg gatcgcttca cttcagccca gagaattgca agttccgcca gtggacgctg 360
gagaatggct atgacgtcta cttgtcgcag aagcatcact acctggtgag cctgggccgc 420
gccaagcgca tcttccagcc gggcaccaac ccgccgccct tctcccagtt cctggcgcgc 480
aggaacgagg tcccgctgct gcacttctac actgttcgcc cacggcgcca cacgcgcagc 540
gccgaggacc cacccgagcg cgacccactg aacgtgctca agccgcggcc ccgcgccacg 600
cctgtgcctg tatcctgctc tcgcgagctg ccgagcgcag aggaaggtgg ccccgcagcc 660
agcgatcctc tgggggtgct gcgcagaggc cgtggagatg ctcgcggggg cgcgggaggc 720
gcggataggt gtcgcccctt tcccaggttc gtctag 756

<210> SEQ ID NO 68
<211> LENGTH: 747
<212> TYPE: DNA
<213> ORGANISM: Megabat

<400> SEQUENCE: 68
atgccgaggg gcagcctagg gctcctggtc tgcatcctgt gctgcagagc ctatcccgat 60
gcctctccgc tgcttagctc cagcttgggg ggcctgatcc acctctacac agccacagcc 120
aggaacggct accacctgca gatccacaag gatggccatg tggatggcac accccatcag 180
accatctaca gtgccctgat gataagatca gaggacagtg gctttgtggt gataataggt 240
gtgatgagta gaagatacct ctgcatggac ttcaaaggca acatttttgg atcacatcac 300
ttcagccccg agagctgcaa gttccgccag cgaacgctgg agaatggcta cgacgtgtat 360
cactcgcccc agcatcactt cttcgtcagc ctgggccgag ctaagagggc cttcctgccg 420
ggcacgaacc ccccacctta ctcccagttc ctgtcccgaa ggaatgagat ccccctgttc 480
cagttcaaca ccccgcggcc gcggcggcac acgcgcagcg tggaggacta caaagactac 540
gatttggacc ccgacccgct gaaagttctg aggccccgtc cccggtgggt ccccgccctg 600
ccctcctgct cccaggagct cccgagtgcc gaggacaaca gcgtggtagc caacgacccg 660
ttaggggtgc tcaggcccag cagggtaaac atataccgtg agagaatggg caaggggagg 720
tgccgtcccc accctgagtt tgtctag 747

<210> SEQ ID NO 69
<211> LENGTH: 744
<212> TYPE: DNA
<213> ORGANISM: Microbat

<400> SEQUENCE: 69
atgccagggg cccgccttgg gttgctggtc tgcgtcctgg ccctgcgctg tgtggtcaga 60
gcctatccca acgcctcccc actgctcggc tccagctggg gtggcctgac ccacctgtac 120
acggcctcag ccaggaacag ctaccacctg cagatccaca aggacggcca tgtggacggc 180
acaccccatc agaccatcta cagtgccctg atgatcagat cagaggacgc tggctttgtg 240
gtgataactg gagtgatgag taggagatac ctctgcatgg actttagagg caacattttt 300
ggatcccttt ttttcagtcc aagtaatttc agtttccttg aatggaaaaa ggaaagtggg 360
atggaccatt ggataagcag acagacgcac ttcctcgtca gccctgggcc gagccaagag 420
ggccttcctg ccgggcacaa cccgccgccc tactcgcagt tcctgtcgcg aaacgagatc 480
ccgctcttcc acttcaacac gcccgcgccg cgccggcaca cgcgcagcgc cgaggagaac 540
tcggcggccg acccgctggt cgtgctgaag cccgtgccgc gcctgacgcc cccgcccgcc 600
tcctgctccc gggagctgag cagcgccgag gacaacagcg tggcggccca cgacccgctc 660
ggggtgctgc ggagcagcaa cagggtgaac tcgcacgcgc cgcccccagg tccacctagg 720
acccgccaag gaatgcttct cgta 744

<210> SEQ ID NO 70
<211> LENGTH: 738
<212> TYPE: DNA
<213> ORGANISM: Tasmanian devil

<400> SEQUENCE: 70
atgtcagggg gttgcctcag gctcctattc tgtgccctgt gcagcttaag ggccatccaa 60
gccttcccca atgcttcccc cctgctcagc cttggctggg ggggtctgac tcacctctat 120
acggccacag ccaggaacag ctaccacctg cagatccaca aagatggcca cgtggatggg 180
tctcctcatc aaaccatcta tagtgccttg atgatcagat cagaggatgc tgggctagtc 240
ataataactg gtgtgatgag caggagatat ctctgtatgg acattagggg caacatcttc 300
ggatcgcatt tcttcagccc agacaactgc aggttcaaac accggacatt agaaaatggg 360
tatgacatct atcactctcc ccagaacaac ttcctgatca gccttggcaa ggcaaagagg 420
gccttcctac cagggatgaa cccacctcct tactcccaat tcctgtctcg gagaaatgaa 480
atccccataa tacacttcaa tacacctgaa ccccaccggc ataccaggag tgctgagaac 540
agtcctgact tggacccaat gaatgtgctg aaactccgac caaggataac tccctgctcc 600
caggaacttc acagtgctga agagaacagt gtagtggatg atgacccttt ggaagtactc 660
agaaatagca atagattgaa gccctatcct ggcaggatga gtttggaaag atgcctccat 720
gtccccaagg cagcttaa 738

<210> SEQ ID NO 71
<211> LENGTH: 576
<212> TYPE: DNA
<213> ORGANISM: Gray short-tailed opossum

<400> SEQUENCE: 71
atggcaaatt gtagagaaaa ggagctggag atgtacattt gtgccttgat gatcagatca 60
gaggatgctg ggctagtcat aataactggt gtgatgagca ggagatatct ctgtatggac 120
atcaggggca acatctttgg ttcgcatttc ttcaacccgg acaactgcaa gttcaagcac 180
cggacactag aaaatgggta tgacatctat cattctcccc agaacaactt cctgatcagc 240
cttggcaagg caaagagggc ctttctgcca ggcatgaatc cacctccgta ctctcaattc 300
ctgtctcgga agaatgagat ccccataatc cacttcaaca cacctgaacc ccaccggcac 360
accaggagtg ctgaaaacag tcctgacttg gacccaatga atgtgctgaa accccgacca 420
aggatgactc cctgctctca ggaactctac agtgctgaag agaacagtgt agtggatgat 480
gaccctttgg aagtacttag aaatagcaat cgactgaagc ccttccctgg taggctgggt 540
ttagaaaggt gccaccatgt tcccaagact gattaa 576

<210> SEQ ID NO 72
<211> LENGTH: 543
<212> TYPE: DNA
<213> ORGANISM: Armadillo

<400> SEQUENCE: 72

```
gccctgatga tcagctctga agatgctggc tttgtggtga taacaggtgt gatgagcagg      60
aggtacctct gtatggattt cagaggcaac atttttggat cgcacgactt caccccggac     120
agctgcaggt tccgccagcg cacgctggag aacggctacg acgtctacca ctcgccgcag     180
caccacttcc tcgtcagcct ggggcgggcc aagcgggcct tccagccggg ctccaacccg     240
ccgccctact cccagttcct gtcccgcagg aacgagatcc cgctgatgcg cttcagcacc     300
ccgcggccgc ggcggcacac gcgcagcgcc caggaccacg cggaccccga cccgctgagg     360
gtgctcaagc cccggctccg gctgaccccg gcccccgcct cctgctccca ggagctgccg     420
agcgacgagg acgacggcgc ggtggccagc gaccccctgc gcgtggtcct cggccgccgg     480
ccccacgcgc gggccgcggg cgcgggcggg gagcggtgcc gccccggccc gcagctcagc     540
tag                                                                   543
```

<210> SEQ ID NO 73
<211> LENGTH: 534
<212> TYPE: DNA
<213> ORGANISM: Wallaby

<400> SEQUENCE: 73

```
gccttgatga tcagatcaga ggacgctggg ctagtcataa taagtggtgt gatgagcagg      60
aggtatctct gtatggacct cagaggcaac atcttcggat cgcatttctt cagcccagac     120
aactgcaggt tcaaacaccg gacactagaa aatgggtatg acatctatca ctctccacag     180
aacaacctcc tgatcagcct tggcaaggca aaaagggcct tcctgccagg catgaaccca     240
cctccttact cccagttcct atctcggagg aatgagatcc ccataatcca cttcaataca     300
cctgaacccc gccggcacac caggagcgca gagaacagtc ctgacttgga cccaatgaat     360
gtgctgaaac cccgaccaag ggtgactccc tgctcccagg aactccgcag tgctgaagag     420
aacagtgtag tagatgatga ccctttggaa gtactcagaa atagtaatcg cctgaagccc     480
taccctggta gaatgagttt ggaaagatgc ctccaagtcc ccaaagctgc ttaa           534
```

<210> SEQ ID NO 74
<211> LENGTH: 771
<212> TYPE: DNA
<213> ORGANISM: Zebra finch

<400> SEQUENCE: 74

```
atggagtgga gagccactct ccagggcatt ccctgcagct ccctgctcct gctgctctgc      60
agcctaaagg cttcccttgc ctttcccaac tcctctccac tgctgagtcc cagctggggc     120
aatggagatc gcctgatgca cctctacacc gacaccgaga ggagcagctt ccacctccag     180
atcaacgctg atggctacat cgatggcgct cctcaccaaa ccatctacag tgccctaatg     240
atcaagtctg agggtgctgg ctcagtaata atcacaggtg tgaagagtgg acgctacctg     300
tgtatggaca tgaaaggaaa tatatttggc tcgcattact tcagccaaga ggactgcatg     360
ttcaaccaca ggacgctgga aaatgggtac gatgtgtacc aatcccccaa acaccacttc     420
ttggtgagct taggcagagt taaacaagtc ttctcccctg gtatgaatcc accaccatac     480
tcccagtttc tgtccaggaa gaatgagatc cctctgttcc gattcaacac ccccgagccc     540
cacaggcaca ccaggagtgc agatgttgat cccgtagatc ctcaccagat cctggtcccg     600
cagaggaaga ccccagtgtt tggctccctg cagcagcagc cagcagactt tccccacatg     660
cccagggagc ccatgaggat caaccagaac gacgtggtga accccgatga tccccacgca     720
atgatggagg ccaggaggta cccaagcccc cgcttctaca tcacgagata a              771
```

<210> SEQ ID NO 75
<211> LENGTH: 765
<212> TYPE: DNA
<213> ORGANISM: Chicken

<400> SEQUENCE: 75

| | | | | | | |
|---|---|---|---|---|---|---|
| atgccacaca | ccagtccctg | cagctgcctg | gagtacatgc | tgcttgtgct | ctgtatcctg | 60 |
| aaggctgcag | tcgccttccc | caactcctct | ccgctgctga | atcccagctg | ggggaatgga | 120 |
| gatcagctga | tgcacttgta | cacttctaca | gagaggaaca | gcttccatct | ccaaatcaat | 180 |
| gctgatggac | acatcaatgg | tgttcctcac | caaaccattt | acagtgcctt | aatgatcaag | 240 |
| tctgagggtg | ctggctgtgt | aataatcaca | ggtgtgaaga | gtggacgcta | cctatgcatg | 300 |
| gacatgaaag | gagacatttt | tggatcgtat | tatttcagcc | aagaggactg | tgtgttcaac | 360 |
| caaaggacac | tggaaaatgg | atatgatgtg | taccaatctc | ccaagcacaa | ttttctggtt | 420 |
| agcttgggca | gaactaagca | agttttcttc | cctggtatga | atccaccacc | atactcccag | 480 |
| tttttgtcca | ggagaaacga | aatccctttg | tttcgattca | acacacctga | accccacaga | 540 |
| aacactagaa | gtgcagatgt | cgatccactg | gatcctcacc | aaatcctggt | cccacagaga | 600 |
| aaggtctctg | cattagggtc | tcagctgcag | ctgcaaatgg | acttttccca | tgtgcccaga | 660 |
| gaacccatga | gagtcaatca | gaatgatgtg | gtcaatccag | atgacccaca | tgctatgatg | 720 |
| gatgctagga | ggtatgctag | tcctcgcttt | tacattacaa | gataa | | 765 |

<210> SEQ ID NO 76
<211> LENGTH: 765
<212> TYPE: DNA
<213> ORGANISM: Turkey

<400> SEQUENCE: 76

| | | | | | | |
|---|---|---|---|---|---|---|
| atgccgcaca | ccagtccctg | cagctgcctg | gagtacatgc | tgcttgtgct | ctgtatcctg | 60 |
| aaggctgcag | tcagcttccc | caactcctct | ccactgctga | atcccagctg | ggggaacgga | 120 |
| gatcagctga | tgcacttgta | tacttctaca | gagaggaaca | gcttccatct | tcaaatcaat | 180 |
| gctgatggcc | acatcagtgg | tgttccttac | caaaccattt | acagtgccct | aatgatcaag | 240 |
| tctgagggtg | ctggcagcgt | tataatcaca | ggtgtgaaga | gtggacgcta | cctatgcatg | 300 |
| gacatgaaag | gagacatttt | tggatcgcat | tatttcagcc | aagaggactg | cgtgttcaac | 360 |
| caaagaacac | tggaaaatgg | atatgatgtg | tatcaatctc | ccaagcacaa | ttttctggtt | 420 |
| agcttaggca | gaactaagca | agttttcttc | cctggtatga | atccaccacc | gtactcccag | 480 |
| tttttgtcca | ggagaaacga | aatcccgttg | tttcgattca | acacacctga | accccacaga | 540 |
| aacactagaa | gtgcagatgt | tgatccaatg | gatcctcacc | agatcctggt | cccacagaga | 600 |
| aaggtctctg | caatagagtc | tcagctgcaa | ctgcaaatgg | acttttccca | tgtgcccaga | 660 |
| gaacccatga | gagtcaatca | gaacgatgtg | gtcaacccag | atgacccaca | cgctatgatg | 720 |
| gatgccagga | gatatgctag | tcctcgcttt | tacattacaa | gataa | | 765 |

<210> SEQ ID NO 77
<211> LENGTH: 729
<212> TYPE: DNA
<213> ORGANISM: Green anole

<400> SEQUENCE: 77

| | | | | | | |
|---|---|---|---|---|---|---|
| atggtccagg | ctactctata | cagcttcctc | aaatatatgc | tgcttgcaac | atgtagctgg | 60 |

aaagcaattg ctgctttccc caacgcatca cctttgctca gcctcaactg gggaaattca 120
gacagcctgc tacacttgta cacttccaca gcaagaaaca gcttccacct gcaaatccac 180
tccaatggct acgtggatgg aagtccgtat caaacaattt acagtgcctt gatgatcaaa 240
tctgaagttg ctggttatgt tataataaat ggtgtgaaaa gtggacgttt tctttgtatg 300
gatatgaatg ggaacatctt tggatcgcat ttcttcagtt atgaggactg cactttcaaa 360
cactgggtcc tggaaaatgg ttatgatgtt tatcagtctc ccaaatacaa ctaccttgtc 420
agcttaggaa aagcaaagca accattgttc cccaatatga atccaccacc ttactcccag 480
ttcttgtcca ggagaaatga aattccttta gtccagttca acacaccgaa acctcacaga 540
cataccagaa gtgccaacgc ggatccctgc ggcagcatca tatcatcagg aaatattgcg 600
aaagaaaacc tacagttaca gccactaatg tataacacta aaatgaattc aaacagtgaa 660
gatgaagacc caaacagtgc aataatcaat agaagatttt tgagtcctag aacagatgtc 720
aggagctga 729

<210> SEQ ID NO 78
<211> LENGTH: 750
<212> TYPE: DNA
<213> ORGANISM: Coelacanth

<400> SEQUENCE: 78
ctagagtccg ctcttcttgc gttttctatg gctatattct atagctttaa agctgtgagc 60
tcttttccaa attcttcgcc actgcttaac ccagtctggg gaaacactga caacctgata 120
cacctgtata cagcttctga gacgaacagc ttccacttgc agatcaactc cgatggacat 180
gtggatggta ctccacacca aaccgcttac agtgcactgc tgatcaagtc cgaggaggct 240
ggttctgtag ttatcctggg ggtgaagagt ggacgttacc tctgtatgga tatcaagggc 300
aatattattg gactgcatca cttcagcaag gaagactgta cattcaaaca agagggcttg 360
gaaaatggat ttgatgtgct gcgctcacct aagcacaaca ttttggtcag ccttgacaag 420
actaaacgct cctacatccc gggtatgaac ctgccacctt actcacagtt tttatcccga 480
cagaatgaag tagctctgat caacttcatt aacacacctg acatacacag acatagtcga 540
aatgttgatg ttgatccttc agacccccat gggatgataa ttcagcctga tgtgggtgtt 600
tcatttcgta agtcttcatc tctgttttca gatctgccca gagactccat gagaactagc 660
cataatggta tggatatggt tgatcctgct gacccacatg gaatgttaga ttccaggaga 720
agaccaagtc caaggttctt tgcaagatag 750

<210> SEQ ID NO 79
<211> LENGTH: 765
<212> TYPE: DNA
<213> ORGANISM: Western clawed frog

<400> SEQUENCE: 79
atgaccaagc agcaaactag actaggactg gtgctcactg ttcttgccag tataaaggtt 60
atatctgcct tccccaactc ttctccaata atcagtggcg gctggggggt ccctgacaga 120
ctgatgcacc tatatacggc cagtgactgg aacagcttcc acctacagat caaccatgat 180
ggaagcattg atggaacccc tacccaaacc atttacagtg caataatgat caaatcagaa 240
tccgctgggc acgtggttat tactggggtg aagactaatc ggtacctgtg catggataaa 300
agtgggaaca tttttggata tcacgacttc aaccacgacg actgcgtttt taagcacgag 360
actctggaga acaactttga cgtttaccat tctccaaaac acaactttgt gatcagcctc 420
aaggagccca agcatcattt ccgcctcggc atggacctgc ccccttactc ccaattcctg 480
tccttggaga atgaaatccc cataaccaga ttcaatgctc cagagccgga aatgagaatc 540
ccagagggca actttgctga ccccagcgac atcataaaga accccaggaa ctgggacttt 600
tcgcagtcta ttcataatcc atttcaggat gtgtggttgc cgttccccag cggttcatta 660
ccaatcatta gagcttcctt gccaattatt cataacaatg tgattaatac agatgaccct 720
gaagaaattg taaaaatgaa gagatacaga tatttcaaga ggtag 765

<210> SEQ ID NO 80
<211> LENGTH: 600
<212> TYPE: DNA
<213> ORGANISM: Cat

<400> SEQUENCE: 80
atgtcaggga cccgccttgg gctcctggtc tctgtcctgt gctgggtagt cagagcctat 60
cctaacacct ccccgctgct gggctccagc tggggtggcc tgacccacct gtacacggcc 120
acagccagga acagctacca cctgcagata cacaaggacg gccatgtgga tggcacaccc 180
catcagacca tctacagtgc cctgatgatc agatcggagg atgccggctt tgtggtgata 240
acaggtgtga tgagtcagag gtacctctgt atggacttca gaggcaatat cttcggatcg 300
cacctcttca gccccgagag ctgcaggttc cgacagcgga cgctggaaaa cggctacgac 360
gtgtaccact ccccgcagca ccgcttccta gtcagcctgg gcccggccaa gagggccttc 420
ctgccgggca ccaaccgcat gacccccgcg ccggcctcct gctcccagga gctcccaagc 480
gccgaggaca gcggcgtggt ggccagcgac ccgttagggg tgctcagggg caacagggtg 540
aacgcgcacg ccggggggat gggcgtggag aggtgccgcc ccttccccaa gttcaactag 600

<210> SEQ ID NO 81
<211> LENGTH: 750
<212> TYPE: DNA
<213> ORGANISM: Chinese softshell turtle

<400> SEQUENCE: 81
atgtcacagc ccagccagtg cagctgcctg aacttcatgc tgttcgtgct atgtagcttc 60
aaagctattg ctgcctttcc cttcttctct tcactgctga atcccagctg gggggaaacg 120
gatagtttga tacacctgta cacagctact gagaagaaca gcttccatct gcagatcaac 180
cctgatggtt atgttgacgg cacacctcac caaaccattt acagtgctct aatgatcaaa 240
tctgaggatg ctggctatgt ggtgataagt ggtgtaaaga gtgggcgcta cctatgtatg 300
gacattaaag gaaatatctt tggatcgcat tacttcagtc aagaggactg catgtttaaa 360
cacagaacac tggaaaatgg atatgatgtg taccagtctc ccaagcacaa cttcctggtc 420
agcctgggca ggaataaaca agctttcttc cctggtatga atctgccacc atactcccag 480
tttttgccca ggagaaatga aatccctctg atccgattca acacacccga accccacagg 540
cacactagga atgcagatgt tgatcccctc cagattttga tccctcgggg agaggctttt 600
gacacaggac ctcagaggtt gcagactcac tttgatcacc tgcctagaga acccatgaga 660
atcaatccaa atgatgtagt cagcccggat gacccactcg ccatgatgga tgtcagaagg 720
aatgcaagtc cacgccttta cattacaaga 750

<210> SEQ ID NO 82
<211> LENGTH: 738
<212> TYPE: DNA

<213> ORGANISM: Ferret

<400> SEQUENCE: 82
atgtcagtga cccgtcttgg gctcctggtc tctgtcctgt gctgggtagt cagagcctat 60
cccaacgcct ccccgctgct cggctccagc tggggtggcc tgacccacct gtacacggcc 120
actgccagga acagctacca cctgcagatc cacaaggatg gccatgtgga tggcacaccc 180
caccagacca tctacagcgc cctgatgatc agatcagagg atgccggctt tgtggtgatc 240
acaggtgtga tgagcaggcg gtacctgtgt atggacttcc gaggcaacat ctttggatcc 300
cacctcttca gccccgagag ctgcaggttc cgacagcgga cactggaaaa cggctacgac 360
gtgtaccact ccccgcagca ccgcttcctc gtcagcctgg gccaagccaa gagggccttc 420
ctgccgggca ccaacccgcc gccctactcc cagtttctgt cccggaggaa tgagatcccc 480
ctcatccact tcaacacccc caggccgcgg cgtcacacgc gcagcgccga ggacatggag 540
cacgacccgt tgaacgtgct gaagccccgg ccccgcatga ccccggcccc ggcctcctgc 600
tcccaggagc tcccgagcgc cgaggacaac agtgtggtgg ccagcgaccc gttaggggtg 660
ctcagaggca accgggtgaa cgtgcacgcg ggggggatgg gcgtggacag gtgccgcccc 720
ctccccaagt tcatctag 738

<210> SEQ ID NO 83
<211> LENGTH: 618
<212> TYPE: DNA
<213> ORGANISM: Mouse lemur

<400> SEQUENCE: 83
atgctggggg cctgcctcag gctctgggtc tgtgccctgt gcagtgtctg cggcgtgagc 60
gtcgtcagag cctatcccaa cgcctccccg ctgctcgcct ccagctgggg tggcctgatc 120
cacctgtaca cggccacggc caggaacagc taccacctgc agatccacaa ggacggccat 180
gtggacggca caccccacca gaccatctac agtgccttga tgatcaggtc agaggatgct 240
ggctttgtgg tgatcacagg tgtgatgagc agaagatacc tctgcatgga tttcagaggc 300
aacatttttg gatcacatgt cttcagcgcg gagagctgca ggttcagaca gcggacgctg 360
gagaacggct tcgacgtgta ccagtcccct cagcaccact tcctggtcag cctgggccgc 420
gccaaagggg cctttccggc cggggcgaaa ccgcccccct tcccccagtt cctgccgcgg 480
gggaacgagg ctcccgggcg caaaacgcgg gggcccgagg aaaaaggggc cccacaccct 540
ctccgcgggg tggaaagcgg gggccggaaa ggcggggccc cgcctctctg tttggagagg 600
ctctccagag cccgagag 618

<210> SEQ ID NO 84
<211> LENGTH: 579
<212> TYPE: DNA
<213> ORGANISM: Orangutan

<400> SEQUENCE: 84
atgcgcaatg agtctttgcc ctgcctggtt ttctccatag gtgccctgat gatcagatca 60
gaggatgctg gctttgtggt gattacaggt gtgatgagca gaagatacct ctgcatggat 120
ttcagaggca acatttttgg atcacactat ttcaacccgg agaactgcag gttccaacac 180
cagacgctgg aaaacgggta tgacgtctac cactctcctc agcatcactt cctggtcagt 240
ctgggccggg tgaagagagc cttcctgcca ggcatgccac ccccgtactc ccagttcctg 300
tcccggagga acgagatccc cctaattcac ttcaacaccc ccgtaccacg gcggcacacc 360
cggagcgccg aggatgacac ggagcgggac cccctgaaag tgctgaagcc ccgggcccgg 420
atgaccccgg ccccggcctc ctgctcacag gagctcccga gctccgagga caacagcccg 480
atggccagcg acccattagg ggtggtcagg ggcggtcgag tgaacacgca cgctggggga 540
acgggcccgg aaggctgccg ccccttcccc aagttcatc 579

<210> SEQ ID NO 85
<211> LENGTH: 564
<212> TYPE: DNA
<213> ORGANISM: Shrew

<400> SEQUENCE: 85
atgtggggac tccgcctggg tctcttggtc ggcctcctgg gctgcgtgga cagagcctcc 60
ccgatgctgg cgtccagctg gggcggcctg acgcacctgt acacggccac ggccaggaac 120
agctaccacc tccagatcca caaggacggc ctggtcgacg gctccccgca gcagaccgtc 180
taccaccatt tcagcccgga gagctgccgc ttccagcagc gcacgctgga gaacggctac 240
gacgtgtacc agtccccgca gcaccgcttc ctcgtgagcc tgggccggcc caagcgcgcc 300
ttccagccgg gcgccaaccc gccgccctac gcgcagttcc tggcgcgccg caacgaggtg 360
cccctggcgc gcttccacac gcccgcgccg cgccgccaca cgcgcagcgc gcacgacaac 420
ggcgacgccg acccgctcaa cgtgctggcg cctcgggccg ccgccgccgc ctcctgctcg 480
cacgagctgc ccagcgccga ggacaacagc gtggtggcca gcgacccgct gggcgtcatc 540
cgcagcaacc gcttccgcac gcac 564

<210> SEQ ID NO 86
<211> LENGTH: 792
<212> TYPE: DNA
<213> ORGANISM: Tetraodon

<400> SEQUENCE: 86
atggacgtaa acagaaggat cggggtgaag gacgccttgc tggcgctcct gctcgccctt 60
ctccagggat gccccctggg ggaaacggct cccaacgcgt caccgctggt cggttccaac 120
tgggggaacc cgaggaggta cgttcacctt cagacatcca cagacatgag caacttctac 180
ttggagatca gactggatgg aaccgtgcgc aaaagcacag cccggacttc atacagtgtg 240
attttactga aagccgacac gagggagcgc atcgccatcc tgggcgtcaa gagcaaccgt 300
tacctgtgta tggacctcga ggggagccca tttagctctc ccacctgcat cagggacgac 360
tgcttgttca accacagtct tctggagaac aaccgggacg tctactactc cagccggacc 420
ggcattctct tcaaccttga gggctcccgc caggtgttcg tggtgggcca gaacgtcccg 480
cagacctccc tcttcctgcc caggacgaac acggtgccgc tggagcgact ccttctgcac 540
agggacaagc ggaaccaggt ggtggacccc tctgacccgc accgcgtcgc cgtgggtcgc 600
gccgaggagg gctcggactc ccgggccttg caggaggacg acgccgacct ggaggtggag 660
acagaggttg aggtcgggga cgacggacgc aacgcgtccc gggagcggct gcaggctccg 720
tccgatcacg acccctgggg cgtgttctcc tccaaccccg ggagcccccg cagcagcggc 780
acggtgggct ga 792

<210> SEQ ID NO 87
<211> LENGTH: 768
<212> TYPE: DNA
<213> ORGANISM: Tilapia

<400> SEQUENCE: 87

```
atggacgtca acaggcgaat ggggatgaga gacaccgtgc tggcgctctt tctcgctgtc      60
ttgcagggat ttcctctcgg ggatacggtc ccgaacccat cacctctggc tggatccaac     120
tgggggaacc caaggagata cgtccacctg cagacatcca cagacctcaa taacttctac     180
ttggagatca gattagatgg gagtgtgcgc aaaactacgt ccaggagcac ctatagtgtg     240
attctactga aatctgaagc aagagatcgc gtcgccatcc tcggcgtcaa aagcagccgt     300
tacctatgca tggacctgga gggcaacccg ttcagctctc ctgtctgcct tcgggatgac     360
tgtctgttca accacaagct cctggagaac aaccgggacg tgtactactc cagccggaca     420
ggcatcttgt tcaacctgga gggctcccga caggtgtact cggtgggcca gaacctgccg     480
cagacctccc tcttcttgcc caggaaaaac accgtaccac tggagcgcct cctgctgcac     540
agggagaaga gaaaccgggg gcagacagaa gagggttcgg actcccgggc cgtgccggag     600
gagctggagg aaagggaggt ggaaatggag acggaaatag aaacagaggt cggggatgac     660
ggacgcaacg tgtcccggga gaaactcgcg gctccatcca gccacgaccc ctggaacgtg     720
cacttctcca acccggccag cccccggagc accgggacag tgggctga                  768
```

<210> SEQ ID NO 88
<211> LENGTH: 777
<212> TYPE: DNA
<213> ORGANISM: Zebrafish

<400> SEQUENCE: 88

```
atgcgttgcg cactttccaa cctgcacatg ctgcattcat ccgtcctcgc gctgtggttc      60
acggctctcc agggactcag acctgcagat gcggccccca atccttctcc gctgctgggc     120
tccaactggg ggaacccgcg gagatacatc caccttcaga ccacttcaga cttaaacaac     180
tactacctgg agatcagccc gagtggacac gtgcgcaaaa ctacaaatcg ggctcatac      240
agtgtaatct tattgaaaac agaaagcaga gaccgtctgg cgatatttgg agtgaaaagt     300
aaccggtttt tgtgcatgga tacaggagga accctttca catctacgat ctgcaataag      360
gaagactgtc ttttccacca caaactgttg gaaaaccatc gtgatgtgta ttactccact     420
aaacacagca tactgcttaa tctggacggg gacaaacagg cgtttatagc gggacaaaac     480
ctccctcagt cgtctctctt cttgtcggag aagaacacgg ttccgctgga gcgcctgcag     540
catcgggagc gcaggaaccg gcaggtgaac ccaacagacc cgctgaacgc gctccggtac     600
gcggaggagt ctgattccag agccgcgcag gaggatgatg gagacatgga ttttgagccc     660
tcagaaggtc aaaacatctc tagagaaacc cttgtttccc cttccgatga tgatccatgg     720
gatcttctgc acgacacgag ccctggaagt cctcggattg cagcaattgt cggataa        777
```

<210> SEQ ID NO 89
<211> LENGTH: 216
<212> TYPE: PRT
<213> ORGANISM: Homo sapiens

<400> SEQUENCE: 89

```
Met Arg Ser Gly Cys Val Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45
```

```
Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215


<210> SEQ ID NO 90
<211> LENGTH: 216
<212> TYPE: PRT
<213> ORGANISM: Gorilla gorilla

<400> SEQUENCE: 90

Met Arg Ser Gly Cys Val Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205
```

```
Val Arg Ser Pro Ser Phe Glu Lys
    210                 215


<210> SEQ ID NO 91
<211> LENGTH: 216
<212> TYPE: PRT
<213> ORGANISM: Pan troglodytes

<400> SEQUENCE: 91

Met Arg Asn Gly Cys Val Val Val His Val Trp Ile Leu Ala Gly Leu
1               5                   10                  15

Trp Leu Ala Val Ala Gly Arg Pro Leu Ala Phe Ser Asp Ala Gly Arg
            20                  25                  30

His Val His Tyr Cys Trp Gly Asp Pro Ile Pro Leu Arg His Leu Tyr
        35                  40                  45

Thr Ser Gly Pro His Gly Leu Ser Ser Cys Phe Leu Arg Ile Pro Ala
    50                  55                  60

Asn Cys Val Met Asn Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215


<210> SEQ ID NO 92
<211> LENGTH: 216
<212> TYPE: PRT
<213> ORGANISM: Macaca mulatta

<400> SEQUENCE: 92

Met Arg Ser Gly Cys Val Val Val His Ala Trp Ile Leu Ala Ser Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Thr
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95
```

```
Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Ala Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215


<210> SEQ ID NO 93
<211> LENGTH: 216
<212> TYPE: PRT
<213> ORGANISM: Pongo abelii

<400> SEQUENCE: 93

Met Arg Ser Gly Cys Val Val Val His Ala Trp Ile Leu Ala Gly Leu
1               5                   10                  15

Trp Leu Ala Val Ala Gly Arg Pro Leu Ala Phe Ser Asp Ser Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Arg His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215


<210> SEQ ID NO 94
<211> LENGTH: 216
<212> TYPE: PRT
```

<213> ORGANISM: Nomascus leucogenys

<400> SEQUENCE: 94

Met Arg Ser Glu Cys Val Val Val His Ala Trp Ile Leu Ala Gly Leu
1 5 10 15

Trp Leu Ala Val Ala Gly Arg Pro Leu Ala Phe Ser Asp Ala Gly Pro
20 25 30

His Val His Tyr Gly Trp Gly Asp Pro Ile Arg Leu Arg His Leu Tyr
35 40 45

Thr Ser Gly Pro His Gly Leu Ser Ser Cys Phe Leu Arg Ile Arg Ala
50 55 60

Asp Gly Val Val Asp Cys Ala Arg Gly Gln Ser Ala His Ser Leu Leu
65 70 75 80

Glu Ile Lys Ala Val Ala Leu Arg Thr Val Ala Ile Lys Gly Val His
85 90 95

Ser Val Arg Tyr Leu Cys Met Gly Ala Asp Gly Lys Met Gln Gly Leu
100 105 110

Leu Gln Tyr Ser Glu Glu Asp Cys Ala Phe Glu Glu Glu Ile Arg Pro
115 120 125

Asp Gly Tyr Asn Val Tyr Arg Ser Glu Lys His Arg Leu Pro Val Ser
130 135 140

Leu Ser Ser Ala Lys Gln Arg Gln Leu Tyr Lys Asn Arg Gly Phe Leu
145 150 155 160

Pro Leu Ser His Phe Leu Pro Met Leu Pro Met Val Pro Glu Glu Pro
165 170 175

Glu Asp Leu Arg Gly His Leu Glu Ser Asp Met Phe Ser Ser Pro Leu
180 185 190

Glu Thr Asp Ser Met Asp Pro Phe Gly Leu Val Thr Gly Leu Glu Ala
195 200 205

Val Arg Ser Pro Ser Phe Glu Lys
210 215

<210> SEQ ID NO 95
<211> LENGTH: 142
<212> TYPE: PRT
<213> ORGANISM: Callithrix jacchus

<400> SEQUENCE: 95

Met Trp Lys Ala Thr Ala Gly Gly Gln Gln Gly Gln Ser Glu Ala Gln
1 5 10 15

Met Ser Thr Cys Pro His Val Pro Arg Pro Leu Trp Ile Ala Gln Ser
20 25 30

Cys Leu Phe Ser Leu Gln Leu Gln Tyr Ser Glu Glu Asp Cys Ala Phe
35 40 45

Glu Glu Glu Ile Arg Pro Asp Gly Tyr Asn Val Tyr Trp Ser Glu Lys
50 55 60

His Arg Leu Pro Val Ser Leu Ser Ser Ala Lys Gln Arg Gln Leu Tyr
65 70 75 80

Lys Lys Arg Gly Phe Leu Pro Leu Ser His Phe Leu Pro Met Leu Pro
85 90 95

Ile Ala Pro Glu Glu Pro Glu Asp Leu Arg Gly His Leu Glu Ser Asp
100 105 110

Val Phe Ser Ser Pro Leu Glu Thr Asp Ser Met Asp Pro Phe Gly Leu
115 120 125

Val Thr Gly Leu Glu Ala Val Asn Ser Pro Ser Phe Glu Lys 130 135 140

<210> SEQ ID NO 96
<211> LENGTH: 219
<212> TYPE: PRT
<213> ORGANISM: Microcebus marinus

<400> SEQUENCE: 96

Met Pro Ser Gly Gln Ser Gly Cys Val Ala Ala Arg Ala Leu Ile Leu
1 5 10 15

Ala Gly Leu Trp Leu Thr Ala Ala Gly Arg Pro Leu Ala Phe Ser Asp
20 25 30

Ala Gly Pro His Val His Tyr Gly Trp Gly Glu Pro Ile Arg Leu Arg
35 40 45

His Leu Tyr Thr Ala Gly Pro His Gly Leu Ser Ser Cys Phe Leu Arg
50 55 60

Ile Arg Ala Asp Gly Ser Val Asp Cys Ala Arg Gly Gln Ser Ala His
65 70 75 80

Ser Leu Leu Glu Ile Arg Ala Val Ala Leu Arg Thr Val Ala Ile Lys
85 90 95

Gly Val His Ser Val Arg Tyr Leu Cys Met Gly Ala Asp Gly Arg Met
100 105 110

Gln Gly Leu Leu Arg Tyr Ser Glu Glu Asp Cys Ala Phe Glu Glu Glu
115 120 125

Ile Arg Pro Asp Gly Tyr Asn Val Tyr Arg Ser Glu Lys His Arg Leu
130 135 140

Pro Val Ser Leu Ser Ser Ala Arg Gln Arg Gln Leu Tyr Lys Gly Arg
145 150 155 160

Gly Phe Leu Pro Leu Ser His Phe Leu Pro Met Leu Pro Val Thr Pro
165 170 175

Ala Glu Thr Gly Asp Leu Arg Asp His Leu Glu Ser Asp Met Phe Ala
180 185 190

Ser Pro Leu Glu Thr Asp Ser Met Asp Pro Phe Gly Ile Ala Thr Arg
195 200 205

Leu Gly Val Val Lys Ser Pro Ser Phe Gln Lys
210 215

<210> SEQ ID NO 97
<211> LENGTH: 138
<212> TYPE: PRT
<213> ORGANISM: Choloepus hoffmanni

<400> SEQUENCE: 97

Leu Leu Glu Met Lys Ala Val Ala Leu Arg Ala Val Ala Ile Lys Gly
1 5 10 15

Val His Ser Ala Leu Tyr Leu Cys Met Asn Ala Asp Gly Ser Leu His
20 25 30

Gly Leu Pro Arg Tyr Ser Ala Glu Asp Cys Ala Phe Glu Glu Glu Ile
35 40 45

Arg Pro Asp Gly Tyr Asn Val Tyr Trp Ser Arg Lys His Gly Leu Pro
50 55 60

Val Ser Leu Ser Ser Ala Lys Gln Arg Gln Leu Tyr Lys Gly Arg Gly
65 70 75 80

Phe Leu Pro Leu Ser His Phe Leu Pro Met Leu Pro Met Thr Pro Ala
85 90 95

Glu Pro Ala Asp Pro Gly Asp Asp Val Glu Ser Asp Met Phe Ser Ser

```
            100                 105                 110

Pro Leu Glu Thr Asp Ser Met Asp Pro Phe Gly Ile Ala Ser Arg Leu
        115                 120                 125

Glu Leu Val Asn Ser Pro Ser Phe Gln Thr
    130                 135


<210> SEQ ID NO 98
<211> LENGTH: 205
<212> TYPE: PRT
<213> ORGANISM: Ailuropoda melanoleuca

<400> SEQUENCE: 98

Val Leu Ala Gly Leu Cys Leu Ala Val Ala Gly Arg Pro Leu Ala Phe
1               5                   10                  15

Ser Asp Ala Gly Pro His Val His Tyr Gly Trp Gly Glu Pro Ile Arg
            20                  25                  30

Leu Arg His Leu Tyr Thr Ala Gly Pro His Gly Leu Ser Ser Cys Phe
        35                  40                  45

Leu Arg Ile Arg Ala Asp Gly Gly Val Asp Cys Ala Arg Gly Gln Ser
    50                  55                  60

Ala His Ser Leu Val Glu Ile Arg Ala Val Ala Leu Arg Thr Val Ala
65                  70                  75                  80

Ile Lys Gly Val His Ser Val Arg Tyr Leu Cys Met Gly Ala Asp Gly
                85                  90                  95

Arg Met Gln Gly Leu Pro Gln Tyr Ser Ala Gly Asp Cys Ala Phe Glu
            100                 105                 110

Glu Glu Ile Arg Pro Asp Gly Tyr Asn Val Tyr Arg Ser Lys Lys His
        115                 120                 125

Arg Leu Pro Val Ser Leu Ser Gly Ala Lys Gln Arg Gln Leu Tyr Lys
    130                 135                 140

Asp Arg Gly Phe Leu Pro Leu Ser His Phe Leu Pro Met Leu Pro Gly
145                 150                 155                 160

Ser Pro Ala Glu Pro Arg Asp Leu Gln Asp His Ala Glu Ser Asp Gly
                165                 170                 175

Phe Ser Ala Pro Leu Glu Thr Asp Ser Met Asp Pro Phe Gly Ile Ala
            180                 185                 190

Thr Lys Met Gly Leu Val Lys Ser Pro Ser Phe Gln Lys
        195                 200                 205


<210> SEQ ID NO 99
<211> LENGTH: 218
<212> TYPE: PRT
<213> ORGANISM: Sus scrofa

<400> SEQUENCE: 99

Met Arg Ser Ala Pro Ser Arg Cys Ala Val Val Arg Ala Leu Val Leu
1               5                   10                  15

Ala Gly Leu Trp Leu Ala Ala Ala Gly Arg Pro Leu Ala Phe Ser Asp
            20                  25                  30

Ala Gly Pro His Val His Tyr Gly Trp Gly Glu Ser Val Arg Leu Arg
        35                  40                  45

His Leu Tyr Thr Ala Ser Pro His Gly Val Ser Ser Cys Phe Leu Arg
    50                  55                  60

Ile His Ser Asp Gly Pro Val Asp Cys Ala Pro Gly Gln Ser Ala His
65                  70                  75                  80

Ser Leu Met Glu Ile Arg Ala Val Ala Leu Ser Thr Val Ala Ile Lys
```

```
                85                  90                  95

Gly Glu Arg Ser Arg Tyr Leu Cys Met Gly Ala Asp Gly Lys Met Gln
            100                 105                 110

Gly Gln Thr Gln Tyr Ser Asp Glu Asp Cys Ala Phe Glu Glu Glu Ile
        115                 120                 125

Arg Pro Asp Gly Tyr Asn Val Tyr Trp Ser Lys Lys His His Leu Pro
    130                 135                 140

Val Ser Leu Ser Ser Ala Arg Gln Arg Gln Leu Tyr Lys Gly Arg Gly
145                 150                 155                 160

Phe Leu Pro Leu Ser His Phe Leu Pro Met Leu Ser Thr Leu Pro Ala
                165                 170                 175

Glu Pro Glu Asp Leu Gln Asp Pro Phe Lys Ser Asp Leu Phe Ser Leu
            180                 185                 190

Pro Leu Glu Thr Asp Ser Met Asp Pro Phe Arg Ile Ala Ala Lys Leu
        195                 200                 205

Gly Ala Val Lys Ser Pro Ser Phe Tyr Lys
    210                 215


<210> SEQ ID NO 100
<211> LENGTH: 218
<212> TYPE: PRT
<213> ORGANISM: Bos Taurus

<400> SEQUENCE: 100

Met Arg Ser Ala Pro Ser Arg Cys Ala Val Ala Arg Ala Leu Val Leu
1               5                   10                  15

Ala Gly Leu Trp Leu Ala Ala Ala Gly Arg Pro Leu Ala Phe Ser Asp
            20                  25                  30

Ala Gly Pro His Val His Tyr Gly Trp Gly Glu Ser Val Arg Leu Arg
        35                  40                  45

His Leu Tyr Thr Ala Gly Pro Gln Gly Leu Tyr Ser Cys Phe Leu Arg
    50                  55                  60

Ile His Ser Asp Gly Ala Val Asp Cys Ala Gln Val Gln Ser Ala His
65                  70                  75                  80

Ser Leu Met Glu Ile Arg Ala Val Ala Leu Ser Thr Val Ala Ile Lys
                85                  90                  95

Gly Glu Arg Ser Val Leu Tyr Leu Cys Met Asp Ala Asp Gly Lys Met
            100                 105                 110

Gln Gly Leu Thr Gln Tyr Ser Ala Glu Asp Cys Ala Phe Glu Glu Glu
        115                 120                 125

Ile Arg Pro Asp Gly Tyr Asn Val Tyr Trp Ser Arg Lys His His Leu
    130                 135                 140

Pro Val Ser Leu Ser Ser Ser Arg Gln Arg Gln Leu Phe Lys Ser Arg
145                 150                 155                 160

Gly Phe Leu Pro Leu Ser His Phe Leu Pro Met Leu Ser Thr Ile Pro
                165                 170                 175

Ala Glu Pro Glu Asp Leu Gln Glu Pro Leu Lys Pro Asp Phe Phe Leu
            180                 185                 190

Pro Leu Lys Thr Asp Ser Met Asp Pro Phe Gly Leu Ala Thr Lys Leu
        195                 200                 205

Gly Ser Val Lys Ser Pro Ser Phe Tyr Asn
    210                 215


<210> SEQ ID NO 101
<211> LENGTH: 192
```

<212> TYPE: PRT
<213> ORGANISM: Canis lupus familiaris

<400> SEQUENCE: 101

```
Leu Ala Phe Ser Asp Ala Gly Pro His Val His Ser Phe Trp Gly Glu
1               5                   10                  15

Pro Ile Arg Leu Arg His Leu Tyr Thr Ala Gly Pro His Gly Leu Ser
            20                  25                  30

Ser Cys Phe Leu Arg Ile Arg Ala Asp Gly Gly Val Asp Cys Ala Arg
        35                  40                  45

Gly Gln Ser Ala His Ser Leu Met Glu Met Arg Ala Val Ala Leu Arg
    50                  55                  60

Thr Val Ala Ile Lys Gly Val His Ser Gly Arg Tyr Leu Cys Met Gly
65                  70                  75                  80

Ala Asp Gly Arg Met Gln Gly Leu Pro Gln Tyr Ser Ala Gly Asp Cys
                85                  90                  95

Thr Phe Glu Glu Glu Ile Arg Pro Asp Gly Tyr Asn Val Tyr Trp Ser
            100                 105                 110

Lys Lys His His Leu Pro Ile Ser Leu Ser Ser Ala Lys Gln Arg Gln
        115                 120                 125

Leu Tyr Lys Gly Arg Gly Phe Leu Pro Leu Ser His Phe Leu Pro Ile
    130                 135                 140

Leu Pro Gly Ser Pro Thr Glu Pro Arg Asp Leu Glu Asp His Val Glu
145                 150                 155                 160

Ser Asp Gly Phe Ser Ala Ser Leu Glu Thr Asp Ser Met Asp Pro Phe
                165                 170                 175

Gly Ile Ala Thr Lys Ile Gly Leu Val Lys Ser Pro Ser Phe Gln Lys
            180                 185                 190
```

<210> SEQ ID NO 102
<211> LENGTH: 218
<212> TYPE: PRT
<213> ORGANISM: Oryctolagus cuniculus

<400> SEQUENCE: 102

```
Met Arg Arg Ala Pro Ser Gly Gly Ala Ala Ala Arg Ala Leu Val Leu
1               5                   10                  15

Ala Gly Leu Trp Leu Ala Ala Ala Ala Arg Pro Leu Ala Leu Ser Asp
            20                  25                  30

Ala Gly Pro His Leu His Tyr Gly Trp Gly Glu Pro Val Arg Leu Arg
        35                  40                  45

His Leu Tyr Ala Thr Ser Ala His Gly Val Ser His Cys Phe Leu Arg
    50                  55                  60

Ile Arg Ala Asp Gly Ala Val Asp Cys Glu Arg Ser Gln Ser Ala His
65                  70                  75                  80

Ser Leu Leu Glu Ile Arg Ala Val Ala Leu Arg Thr Val Ala Phe Lys
                85                  90                  95

Gly Val His Ser Ser Arg Tyr Leu Cys Met Gly Ala Asp Gly Arg Met
            100                 105                 110

Arg Gly Gln Leu Gln Tyr Ser Glu Glu Asp Cys Ala Phe Gln Glu Glu
        115                 120                 125

Ile Ser Ser Gly Tyr Asn Val Tyr Arg Ser Thr Thr His His Leu Pro
    130                 135                 140

Val Ser Leu Ser Ser Ala Lys Gln Arg His Leu Tyr Lys Thr Arg Gly
145                 150                 155                 160
```

```
Phe Leu Pro Leu Ser His Phe Leu Pro Val Leu Pro Leu Ala Ser Glu
                165                 170                 175

Glu Thr Ala Ala Leu Gly Asp His Pro Glu Ala Asp Leu Phe Ser Pro
            180                 185                 190

Pro Leu Glu Thr Asp Ser Met Asp Pro Phe Gly Met Ala Thr Lys Leu
        195                 200                 205

Gly Pro Val Lys Ser Pro Ser Phe Gln Lys
    210                 215


<210> SEQ ID NO 103
<211> LENGTH: 215
<212> TYPE: PRT
<213> ORGANISM: Pteropus vampyrus

<400> SEQUENCE: 103

Met Arg Ser Pro Cys Ala Val Ala Arg Ala Leu Val Leu Ala Gly Leu
1               5                   10                  15

Trp Leu Ala Ser Ala Ala Gly Pro Leu Ala Leu Ser Asp Ala Gly Pro
            20                  25                  30

His Val His Tyr Gly Trp Gly Glu Ala Ile Arg Leu Arg His Leu Tyr
        35                  40                  45

Thr Ala Gly Pro His Gly Pro Ser Ser Cys Phe Leu Arg Ile Arg Ala
    50                  55                  60

Asp Gly Ala Val Asp Cys Ala Arg Gly Gln Ser Ala His Ser Leu Val
65                  70                  75                  80

Glu Ile Arg Ala Val Ala Leu Arg Asn Val Ala Ile Lys Gly Val His
                85                  90                  95

Ser Val Arg Tyr Leu Cys Met Gly Ala Asp Gly Arg Met Leu Gly Leu
            100                 105                 110

Leu Gln Tyr Ser Ala Asp Asp Cys Ala Phe Glu Glu Glu Ile Arg Pro
        115                 120                 125

Asp Gly Tyr Asn Val Tyr His Ser Lys Lys His His Leu Pro Val Ser
    130                 135                 140

Leu Ser Ser Ala Lys Gln Arg Gln Leu Tyr Lys Asp Arg Gly Phe Leu
145                 150                 155                 160

Pro Leu Ser His Phe Leu Pro Met Leu Pro Arg Ser Pro Thr Glu Pro
                165                 170                 175

Glu Asn Phe Glu Asp His Leu Glu Ala Asp Thr Phe Ser Ser Leu Glu
            180                 185                 190

Thr Asp Asp Met Asp Pro Phe Gly Ile Ala Ser Lys Leu Gly Leu Glu
        195                 200                 205

Glu Ser Pro Ser Phe Gln Lys
    210                 215


<210> SEQ ID NO 104
<211> LENGTH: 219
<212> TYPE: PRT
<213> ORGANISM: Tursiops truncatus

<400> SEQUENCE: 104

Met Arg Ser Ala Pro Ser Arg Cys Ala Val Ala Arg Ala Leu Val Leu
1               5                   10                  15

Ala Gly Leu Trp Leu Ala Ala Ala Gly Arg Pro Leu Ala Phe Ser Asp
            20                  25                  30

Ala Gly Pro His Val His Tyr Gly Trp Gly Glu Ser Val Arg Leu Arg
        35                  40                  45
```

-continued

```
His Leu Tyr Thr Ala Gly Pro Gln Gly Leu Ser Ser Cys Phe Leu Arg
    50                  55                  60

Ile His Ser Asp Gly Ala Val Asp Cys Ala Pro Val Gln Ser Ala His
65                  70                  75                  80

Ser Leu Met Glu Ile Arg Ala Val Ala Leu Ser Thr Val Ala Ile Lys
                85                  90                  95

Gly Glu Arg Ser Val Leu Tyr Leu Cys Met Gly Ala Asp Gly Lys Met
            100                 105                 110

Gln Gly Leu Ser Gln Tyr Ser Ala Glu Asp Cys Ala Phe Glu Glu Glu
        115                 120                 125

Ile Arg Pro Asp Gly Tyr Asn Val Tyr Trp Ser Lys Lys His His Leu
    130                 135                 140

Pro Val Ser Leu Ser Ser Ala Arg Gln Arg Gln Leu Phe Lys Gly Arg
145                 150                 155                 160

Gly Phe Leu Pro Leu Ser His Phe Leu Pro Met Leu Ser Thr Ile Pro
                165                 170                 175

Thr Glu Pro Asp Glu Ile Gln Asp His Leu Lys Pro Asp Leu Phe Ala
            180                 185                 190

Leu Pro Leu Lys Thr Asp Ser Met Asp Pro Phe Gly Leu Ala Thr Lys
        195                 200                 205

Leu Gly Val Val Lys Ser Pro Ser Phe Tyr Lys
    210                 215


<210> SEQ ID NO 105
<211> LENGTH: 219
<212> TYPE: PRT
<213> ORGANISM: Myotis lucifugus

<400> SEQUENCE: 105

Met Gln Ser Ala Trp Ser Arg Arg Val Val Ala Arg Ala Leu Val Leu
1               5                   10                  15

Ala Ser Leu Gly Leu Ala Ser Ala Gly Gly Pro Leu Gly Leu Ser Asp
            20                  25                  30

Ala Gly Pro His Val His Tyr Gly Trp Gly Glu Ser Ile Arg Leu Arg
        35                  40                  45

His Leu Tyr Thr Ser Gly Pro His Gly Pro Ser Ser Cys Phe Leu Arg
    50                  55                  60

Ile Arg Ala Asp Gly Ala Val Asp Cys Ala Arg Gly Gln Ser Ala His
65                  70                  75                  80

Ser Leu Val Glu Ile Arg Ala Val Ala Leu Arg Lys Val Ala Ile Lys
                85                  90                  95

Gly Val His Ser Ala Leu Tyr Leu Cys Met Gly Gly Asp Gly Arg Met
            100                 105                 110

Leu Gly Leu Pro Gln Phe Ser Pro Glu Asp Cys Ala Phe Glu Glu Glu
        115                 120                 125

Ile Arg Pro Asp Gly Tyr Asn Val Tyr Arg Ser Gln Lys His Gln Leu
    130                 135                 140

Pro Val Ser Leu Ser Ser Ala Arg Gln Arg Gln Leu Phe Lys Ala Arg
145                 150                 155                 160

Gly Phe Leu Pro Leu Ser His Phe Leu Pro Met Leu Pro Ser Ser Pro
                165                 170                 175

Ala Gly Pro Val Pro Arg Glu Arg Pro Ser Glu Pro Asp Glu Phe Ser
            180                 185                 190

Ser Pro Leu Glu Thr Asp Ser Met Asp Pro Phe Gly Ile Ala Asn Asn
        195                 200                 205
```

```
Leu Arg Leu Val Arg Ser Pro Ser Phe Gln Glu
    210                 215


<210> SEQ ID NO 106
<211> LENGTH: 185
<212> TYPE: PRT
<213> ORGANISM: Ornithorhynchus anatinus

<400> SEQUENCE: 106

Met Leu Ser Cys Val Val Leu Pro Ser Leu Leu Glu Ile Lys Ala Val
1               5                   10                  15

Ala Val Arg Thr Val Ala Ile Lys Gly Val His Ile Ser Arg Tyr Leu
            20                  25                  30

Cys Met Glu Glu Asp Gly Lys Thr Pro Trp Ala Arg Leu Leu Glu Ile
        35                  40                  45

Lys Ala Val Ala Val Arg Thr Val Ala Ile Lys Gly Val His Ser Ser
    50                  55                  60

Arg Tyr Leu Cys Met Glu Glu Asp Gly Lys Leu His Gly Gln Ile Trp
65                  70                  75                  80

Tyr Ser Ala Glu Asp Cys Ala Phe Glu Glu Glu Ile Arg Pro Asp Gly
                85                  90                  95

Tyr Asn Val Tyr Lys Ser Lys Lys Tyr Gly Val Pro Val Ser Leu Ser
            100                 105                 110

Ser Ala Lys Gln Arg Gln Gln Phe Lys Gly Arg Asp Phe Leu Pro Leu
        115                 120                 125

Ser Arg Phe Leu Pro Met Ile Asn Thr Val Pro Val Glu Pro Ala Glu
    130                 135                 140

Phe Gly Asp Tyr Ala Asp Tyr Phe Glu Ser Asp Ile Phe Ser Ser Pro
145                 150                 155                 160

Leu Glu Thr Asp Ser Met Asp Pro Phe Arg Ile Ala Pro Lys Leu Ser
                165                 170                 175

Pro Val Lys Ser Pro Ser Phe Gln Lys
            180                 185


<210> SEQ ID NO 107
<211> LENGTH: 212
<212> TYPE: PRT
<213> ORGANISM: Monodelphis domestica

<400> SEQUENCE: 107

Met Ala Gln Leu Leu Ala Pro Leu Leu Thr Leu Ala Ala Leu Trp Leu
1               5                   10                  15

Ala Pro Thr Ala Arg Ala Arg Pro Leu Val Asp Ala Gly Pro His Val
            20                  25                  30

Tyr Tyr Gly Trp Gly Glu Pro Ile Arg Leu Arg His Leu Tyr Thr Ala
        35                  40                  45

Asn Arg His Gly Leu Ala Ser Phe Ser Phe Leu Arg Ile His Arg Asp
    50                  55                  60

Gly Arg Val Asp Gly Ser Arg Ser Gln Ser Ala Leu Ser Leu Leu Glu
65                  70                  75                  80

Ile Lys Ala Val Ala Leu Arg Met Val Ala Ile Lys Gly Val His Ser
                85                  90                  95

Ser Arg Tyr Leu Cys Met Gly Asp Ala Gly Lys Leu Gln Gly Ser Val
            100                 105                 110

Arg Phe Ser Ala Glu Asp Cys Thr Phe Glu Glu Gln Ile Arg Pro Asp
        115                 120                 125
```

Gly Tyr Asn Val Tyr Gln Ser Pro Lys Tyr Asn Leu Pro Val Ser Leu
    130                 135                 140

Cys Thr Asp Lys Gln Arg Gln Gln Ala His Gly Lys Glu His Leu Pro
145                 150                 155                 160

Leu Ser His Phe Leu Pro Met Ile Asn Ala Ile Pro Leu Glu Ala Glu
                165                 170                 175

Glu Pro Glu Gly Pro Arg Met Leu Ala Ala Pro Leu Glu Thr Asp Ser
            180                 185                 190

Met Asp Pro Phe Gly Leu Thr Ser Lys Leu Leu Pro Val Lys Ser Pro
        195                 200                 205

Ser Phe Gln Lys
    210

<210> SEQ ID NO 108
<211> LENGTH: 220
<212> TYPE: PRT
<213> ORGANISM: Anolis carolinensis

<400> SEQUENCE: 108

Met Cys Arg Arg Ala Leu Pro Leu Leu Gly Ala Leu Leu Gly Leu Ala
1               5                   10                  15

Ala Val Ala Ser Arg Ala Leu Pro Leu Thr Asp Ala Gly Pro His Val
            20                  25                  30

Ser Tyr Gly Trp Gly Glu Pro Val Arg Leu Arg His Leu Tyr Thr Ala
        35                  40                  45

Gly Arg Gln Gly Leu Phe Ser Gln Phe Leu Arg Ile His Ala Asp Gly
    50                  55                  60

Arg Val Asp Gly Ala Gly Ser Gln Asn Arg Gln Ser Leu Leu Glu Ile
65                  70                  75                  80

Arg Ala Val Ser Leu Arg Ala Val Ala Leu Lys Gly Val His Ser Ser
                85                  90                  95

Arg Tyr Leu Cys Met Glu Glu Asp Gly Arg Leu Arg Gly Met Leu Arg
            100                 105                 110

Tyr Ser Ala Glu Asp Cys Ser Phe Glu Glu Glu Met Arg Pro Asp Gly
        115                 120                 125

Tyr Asn Ile Tyr Lys Ser Lys Lys Tyr Gly Val Leu Val Ser Leu Ser
    130                 135                 140

Asn Ala Arg Gln Arg Gln Gln Phe Lys Gly Lys Asp Phe Leu Pro Leu
145                 150                 155                 160

Ser His Phe Leu Pro Met Ile Asn Thr Val Pro Val Glu Ser Ala Asp
                165                 170                 175

Phe Gly Glu Tyr Gly Asp Thr Arg Gln His Tyr Glu Ser Asp Ile Phe
            180                 185                 190

Ser Ser Arg Leu Glu Thr Asp Ser Met Asp Pro Phe Gly Leu Thr Ser
        195                 200                 205

Glu Val Ser Ser Val Gln Ser Pro Ser Phe Gly Lys
    210                 215                 220

<210> SEQ ID NO 109
<211> LENGTH: 179
<212> TYPE: PRT
<213> ORGANISM: Ochotona princeps

<400> SEQUENCE: 109

Val Arg Ser Arg Gly Ala Met Ala Arg Ala Leu Val Leu Ala Thr Leu
1               5                   10                  15

```
Trp Leu Ala Ala Thr Gly Arg Pro Leu Ala Leu Ser Asp Ala Gly Pro
            20                  25                  30

His Leu His Tyr Gly Trp Gly Glu Pro Ile Arg Leu Arg His Leu Tyr
        35                  40                  45

Ala Thr Ser Ala His Gly Leu Ser His Cys Phe Leu Arg Ile Arg Thr
    50                  55                  60

Asp Gly Thr Val Asp Cys Glu Arg Ser Gln Ser Ala His Leu Gln Tyr
65                  70                  75                  80

Ser Glu Glu Asp Cys Ala Phe Glu Glu Glu Ile Ser Ser Gly Tyr Asn
                85                  90                  95

Val Tyr Arg Ser Arg Arg Tyr Gln Leu Pro Val Ser Leu Gly Ser Ala
            100                 105                 110

Arg Gln Arg Gln Leu Gln Arg Ser Arg Gly Phe Leu Pro Leu Ser His
        115                 120                 125

Phe Leu Pro Val Leu Pro Ala Ala Ser Glu Glu Val Ala Ala Pro Ala
    130                 135                 140

Asp His Pro Gln Ala Asp Pro Phe Ser Pro Leu Glu Thr Asp Ser Met
145                 150                 155                 160

Asp Pro Phe Gly Met Ala Thr Lys Arg Gly Leu Val Lys Ser Pro Ser
                165                 170                 175

Phe Gln Lys


<210> SEQ ID NO 110
<211> LENGTH: 221
<212> TYPE: PRT
<213> ORGANISM: Cavia porcellus

<400> SEQUENCE: 110

Met Trp Ser Ala Pro Ser Gly Cys Val Val Ile Arg Ala Leu Val Leu
1               5                   10                  15

Ala Gly Leu Trp Leu Ala Val Ala Gly Arg Pro Leu Ala Arg Arg Ser
            20                  25                  30

Leu Ala Leu Ser Asp Gln Gly Pro His Leu Tyr Tyr Gly Trp Asp Gln
        35                  40                  45

Pro Ile Arg Leu Arg His Leu Tyr Ala Ala Gly Pro Tyr Gly Arg Ser
    50                  55                  60

Arg Cys Phe Leu Arg Ile His Thr Asp Gly Ala Val Asp Cys Val Glu
65                  70                  75                  80

Glu Gln Ser Glu His Cys Leu Leu Glu Ile Arg Ala Val Ala Leu Glu
                85                  90                  95

Thr Val Ala Ile Lys Asp Ile Asn Ser Val Arg Tyr Leu Cys Met Gly
            100                 105                 110

Pro Asp Gly Arg Met Arg Gly Leu Pro Trp Tyr Ser Glu Glu Asp Cys
        115                 120                 125

Ala Phe Lys Glu Glu Ile Ser Tyr Pro Gly Tyr Ser Val Tyr Arg Ser
    130                 135                 140

Gln Lys His His Leu Pro Ile Val Leu Ser Ser Val Lys Gln Arg Gln
145                 150                 155                 160

Gln Tyr Gln Ser Lys Gly Val Val Pro Leu Ser Tyr Phe Leu Pro Met
                165                 170                 175

Leu Pro Lys Ala Ser Val Glu Pro Ser Asp Glu Glu Glu Ser Ser Val
            180                 185                 190

Phe Ser Leu Pro Leu Lys Thr Asp Ser Met Asp Pro Phe Gly Met Ala
        195                 200                 205
```

```
Ser Glu Ile Gly Leu Val Lys Ser Pro Ser Phe Gln Lys
    210                 215                 220


<210> SEQ ID NO 111
<211> LENGTH: 196
<212> TYPE: PRT
<213> ORGANISM: Tupaia belangeri

<400> SEQUENCE: 111

Met Arg Arg Thr Pro Ser Gly Phe Ala Val Ala Arg Val Leu Phe Leu
1               5                   10                  15

Gly Ser Leu Trp Leu Ala Ala Ala Gly Ser Pro Leu Ala Leu Ser Asp
            20                  25                  30

Ala Gly Pro His Val Asn Tyr Gly Trp Asp Glu Ser Ile Arg Leu Arg
        35                  40                  45

His Leu Tyr Thr Ala Ser Pro His Gly Ser Thr Ser Cys Phe Leu Arg
    50                  55                  60

Ile Arg Asp Asp Gly Ser Val Asp Cys Ala Arg Gly Gln Ser Leu His
65                  70                  75                  80

Ser Leu Leu Glu Ile Lys Ala Val Ala Leu Gln Thr Val Ala Ile Lys
                85                  90                  95

Gly Val Tyr Ser Val Arg Tyr Leu Cys Met Asp Ala Asp Gly Arg Met
            100                 105                 110

Gln Gly Leu Ser Thr Lys His Gly Leu Pro Val Ser Leu Ser Ser Ala
        115                 120                 125

Lys Gln Arg Gln Leu Leu Thr Val Arg Gly Phe Pro Ser Leu Pro His
    130                 135                 140

Phe Leu Leu Met Met Ala Lys Thr Ser Ala Gly Pro Gly Asn Pro Arg
145                 150                 155                 160

Asp His Pro Gly Ser Asn Thr Phe Ser Leu Pro Leu Glu Thr Asp Ser
                165                 170                 175

Met Asp Pro Phe Gly Met Thr Thr Arg His Gly Leu Val Lys Ser Pro
            180                 185                 190

Ser Phe Gln Asn
        195


<210> SEQ ID NO 112
<211> LENGTH: 218
<212> TYPE: PRT
<213> ORGANISM: Rattus norvegicus

<400> SEQUENCE: 112

Met Ala Arg Lys Trp Ser Gly Arg Ile Val Ala Arg Ala Leu Val Leu
1               5                   10                  15

Ala Thr Leu Trp Leu Ala Val Ser Gly Arg Pro Leu Val Gln Gln Ser
            20                  25                  30

Gln Ser Val Ser Asp Glu Gly Pro Leu Phe Leu Tyr Gly Trp Gly Lys
        35                  40                  45

Ile Thr Arg Leu Gln Tyr Leu Tyr Ser Ala Gly Pro Tyr Val Ser Asn
    50                  55                  60

Cys Phe Leu Arg Ile Arg Ser Asp Gly Ser Val Asp Cys Glu Glu Asp
65                  70                  75                  80

Gln Asn Glu Arg Asn Leu Leu Glu Phe Arg Ala Val Ala Leu Lys Thr
                85                  90                  95

Ile Ala Ile Lys Asp Val Ser Ser Val Arg Tyr Leu Cys Met Ser Ala
            100                 105                 110
```

```
Asp Gly Lys Ile Tyr Gly Leu Ile Arg Tyr Ser Glu Glu Asp Cys Thr
        115                 120                 125

Phe Arg Glu Glu Met Asp Cys Leu Gly Tyr Asn Gln Tyr Arg Ser Met
    130                 135                 140

Lys His His Leu His Ile Ile Phe Ile Lys Ala Lys Pro Arg Glu Gln
145                 150                 155                 160

Leu Gln Gly Gln Lys Pro Ser Asn Phe Ile Pro Ile Phe His Arg Ser
                165                 170                 175

Phe Phe Glu Ser Thr Asp Gln Leu Arg Ser Lys Met Phe Ser Leu Pro
            180                 185                 190

Leu Glu Ser Asp Ser Met Asp Pro Phe Arg Met Val Glu Asp Val Asp
        195                 200                 205

His Leu Val Lys Ser Pro Ser Phe Gln Lys
    210                 215


<210> SEQ ID NO 113
<211> LENGTH: 218
<212> TYPE: PRT
<213> ORGANISM: Mus musculus

<400> SEQUENCE: 113

Met Ala Arg Lys Trp Asn Gly Arg Ala Val Ala Arg Ala Leu Val Leu
1               5                   10                  15

Ala Thr Leu Trp Leu Ala Val Ser Gly Arg Pro Leu Ala Gln Gln Ser
            20                  25                  30

Gln Ser Val Ser Asp Glu Asp Pro Leu Phe Leu Tyr Gly Trp Gly Lys
        35                  40                  45

Ile Thr Arg Leu Gln Tyr Leu Tyr Ser Ala Gly Pro Tyr Val Ser Asn
    50                  55                  60

Cys Phe Leu Arg Ile Arg Ser Asp Gly Ser Val Asp Cys Glu Glu Asp
65                  70                  75                  80

Gln Asn Glu Arg Asn Leu Leu Glu Phe Arg Ala Val Ala Leu Lys Thr
                85                  90                  95

Ile Ala Ile Lys Asp Val Ser Ser Val Arg Tyr Leu Cys Met Ser Ala
            100                 105                 110

Asp Gly Lys Ile Tyr Gly Leu Ile Arg Tyr Ser Glu Glu Asp Cys Thr
        115                 120                 125

Phe Arg Glu Glu Met Asp Cys Leu Gly Tyr Asn Gln Tyr Arg Ser Met
    130                 135                 140

Lys His His Leu His Ile Ile Phe Ile Gln Ala Lys Pro Arg Glu Gln
145                 150                 155                 160

Leu Gln Asp Gln Lys Pro Ser Asn Phe Ile Pro Val Phe His Arg Ser
                165                 170                 175

Phe Phe Glu Thr Gly Asp Gln Leu Arg Ser Lys Met Phe Ser Leu Pro
            180                 185                 190

Leu Glu Ser Asp Ser Met Asp Pro Phe Arg Met Val Glu Asp Val Asp
        195                 200                 205

His Leu Val Lys Ser Pro Ser Phe Gln Lys
    210                 215


<210> SEQ ID NO 114
<211> LENGTH: 227
<212> TYPE: PRT
<213> ORGANISM: Gallus gallus

<400> SEQUENCE: 114
```

Met Gly Pro Ala Arg Pro Ala Ala Pro Gly Ala Ala Leu Ala Leu Leu
1 5 10 15

Gly Ile Ala Ala Ala Ala Ala Ala Ala Arg Ser Leu Pro Leu Pro Asp
20 25 30

Val Gly Gly Pro His Val Asn Tyr Gly Trp Gly Glu Pro Ile Arg Leu
35 40 45

Arg His Leu Leu His Arg Pro Gly Lys His Gly Leu Phe Ser Cys Phe
50 55 60

Leu Arg Ile Gly Gly Asp Gly Arg Val Asp Ala Val Gly Ser Gln Ser
65 70 75 80

Pro Gln Ser Leu Leu Glu Ile Arg Ala Val Ala Val Arg Thr Val Ala
85 90 95

Ile Lys Gly Val Gln Ser Ser Arg Tyr Leu Cys Met Asp Glu Ala Gly
100 105 110

Arg Leu His Gly Gln Leu Ser Tyr Ser Ile Glu Asp Cys Ser Phe Glu
115 120 125

Glu Glu Ile Arg Pro Asp Gly Tyr Asn Val Tyr Lys Ser Lys Lys Tyr
130 135 140

Gly Ile Ser Val Ser Leu Ser Ser Ala Lys Gln Arg Gln Gln Phe Lys
145 150 155 160

Gly Lys Asp Phe Leu Pro Leu Ser His Phe Leu Pro Met Ile Asn Thr
165 170 175

Val Pro Val Glu Val Thr Asp Phe Gly Glu Tyr Gly Asp Tyr Ser Gln
180 185 190

Ala Phe Glu Pro Glu Val Tyr Ser Ser Pro Leu Glu Thr Asp Ser Met
195 200 205

Asp Pro Phe Gly Ile Thr Ser Lys Leu Ser Pro Val Lys Ser Pro Ser
210 215 220

Phe Gln Lys
225

<210> SEQ ID NO 115
<211> LENGTH: 237
<212> TYPE: PRT
<213> ORGANISM: Taeniopygia guttata

<400> SEQUENCE: 115

Met Val Ile Ile Ser Asn Leu Tyr Leu Met Gln Asn Asp Val Met Met
1 5 10 15

Asn Met Arg Arg Ala Pro Leu Arg Val His Ala Ala Arg Ser Ser Ala
20 25 30

Thr Pro Ala Ser Ala Leu Pro Leu Pro Pro Pro Asp Ala Gly Pro His
35 40 45

Leu Lys Tyr Gly Trp Gly Glu Pro Ile Arg Leu Arg His Leu Tyr Thr
50 55 60

Ala Ser Lys His Gly Leu Phe Ser Cys Phe Leu Arg Ile Gly Ala Asp
65 70 75 80

Gly Arg Val Asp Ala Ala Gly Ser Gln Ser Pro Gln Ser Leu Leu Glu
85 90 95

Ile Arg Ala Val Ala Val Arg Thr Val Ala Ile Lys Gly Val Gln Ser
100 105 110

Ser Arg Tyr Leu Cys Met Asp Glu Ala Gly Arg Leu His Gly Gln Leu
115 120 125

Arg Asn Ser Thr Glu Asp Cys Ser Phe Glu Glu Glu Ile Arg Pro Asp

```
    130                 135                 140

Gly Tyr Asn Val Tyr Arg Ser Lys Lys His Gly Ile Ser Val Ser Leu
145                 150                 155                 160

Ser Ser Ala Lys Gln Arg Gln Gln Phe Lys Gly Lys Asp Phe Leu Pro
                165                 170                 175

Leu Ser His Phe Leu Pro Met Ile Asn Thr Val Pro Met Glu Ser Ala
            180                 185                 190

Asp Phe Gly Glu Tyr Gly Asp Tyr Ser Gln Ala Phe Glu Ala Glu Ala
        195                 200                 205

Phe Ser Ser Pro Leu Glu Thr Asp Ser Met Asp Pro Phe Gly Ile Ala
    210                 215                 220

Ser Lys Leu Ser Leu Val Lys Ser Pro Ser Phe Gln Asn
225                 230                 235


<210> SEQ ID NO 116
<211> LENGTH: 210
<212> TYPE: PRT
<213> ORGANISM: Danio rerio

<400> SEQUENCE: 116

Met Leu Leu Leu Leu Phe Val Thr Val Cys Gly Ser Ile Gly Val Glu
1               5                   10                  15

Ser Leu Pro Leu Pro Asp Ser Gly Pro His Leu Ala Asn Asp Trp Ser
            20                  25                  30

Glu Ala Val Arg Leu Arg His Leu Tyr Ala Ala Arg His Gly Leu His
        35                  40                  45

Leu Gln Ile Asn Thr Asp Gly Glu Ile Ile Gly Ser Thr Cys Lys Ala
    50                  55                  60

Arg Thr Val Ser Leu Met Glu Ile Trp Pro Val Asp Thr Gly Cys Val
65                  70                  75                  80

Ala Ile Lys Gly Val Ala Ser Ser Arg Phe Leu Cys Met Glu Arg Leu
                85                  90                  95

Gly Asn Leu Tyr Gly Ser His Ile Tyr Thr Lys Glu Asp Cys Ser Phe
            100                 105                 110

Leu Glu Arg Ile Leu Pro Asp Gly Tyr Asn Val Tyr Phe Ser Ser Lys
        115                 120                 125

His Gly Ala Leu Val Thr Leu Ser Gly Ala Lys Asn Lys Leu His Ser
    130                 135                 140

Asn Asp Gly Thr Ser Ala Ser Gln Phe Leu Pro Met Ile Asn Thr Leu
145                 150                 155                 160

Ser Glu Glu His Thr Lys Gln His Ser Gly Glu Gln His Ser Ser Val
                165                 170                 175

Asn His Gly Gln Asp His Gln Leu Gly Leu Glu Ile Asp Ser Met Asp
            180                 185                 190

Pro Phe Gly Lys Ile Ser Gln Ile Val Ile Gln Ser Pro Ser Phe Asn
        195                 200                 205

Lys Arg
    210


<210> SEQ ID NO 117
<211> LENGTH: 215
<212> TYPE: PRT
<213> ORGANISM: Xenopus (Silurana) tropicalis

<400> SEQUENCE: 117

Met Trp Lys Thr Leu Pro Trp Ile Leu Val Pro Met Met Val Ala Val
```

```
1               5                   10                  15

Leu Tyr Phe Leu Gly Gly Ala Glu Ser Leu Pro Leu Phe Asp Ala Gly
            20                  25                  30

Pro His Met Gln Asn Gly Trp Gly Glu Ser Ile Arg Ile Arg His Leu
        35                  40                  45

Tyr Thr Ala Arg Arg Phe Gly His Asp Ser Tyr Tyr Leu Arg Ile His
    50                  55                  60

Glu Asp Gly Arg Val Asp Gly Asp Arg Gln Gln Ser Met His Ser Leu
65                  70                  75                  80

Leu Glu Ile Arg Ala Ile Ala Val Gly Ile Val Ala Ile Lys Gly Tyr
                85                  90                  95

Arg Ser Ser Leu Tyr Leu Cys Met Gly Ser Glu Gly Lys Leu Tyr Gly
            100                 105                 110

Met His Ser Tyr Ser Gln Asp Asp Cys Ser Phe Glu Glu Glu Leu Leu
        115                 120                 125

Pro Asp Gly Tyr Asn Met Tyr Lys Ser Arg Lys His Gly Val Ala Val
    130                 135                 140

Ser Leu Ser Lys Glu Lys Gln Lys Gln Gln Tyr Lys Gly Lys Gly Tyr
145                 150                 155                 160

Leu Pro Leu Ser His Phe Leu Pro Val Ile Ser Trp Val Pro Met Glu
                165                 170                 175

Pro Thr Gly Asp Val Glu Asp Asp Ile Tyr Arg Phe Pro Phe Asn Thr
            180                 185                 190

Asp Thr Lys Ser Val Ile Asp Ser Leu Asp Thr Leu Gly Leu Met Asp
        195                 200                 205

Phe Ser Ser Tyr His Lys Lys
    210                 215


<210> SEQ ID NO 118
<211> LENGTH: 219
<212> TYPE: PRT
<213> ORGANISM: Otolemur garnettii

<400> SEQUENCE: 118

Met Pro Ser Gly Leu Arg Gly Arg Val Val Ala Gly Ala Leu Ala Leu
1               5                   10                  15

Ala Ser Phe Trp Leu Ala Val Ala Gly Arg Pro Leu Ala Phe Ser Asp
            20                  25                  30

Ala Gly Pro His Val His Tyr Gly Trp Gly Glu Pro Ile Arg Leu Arg
        35                  40                  45

His Leu Tyr Thr Ala Gly Pro His Gly Leu Ser Ser Cys Phe Leu Arg
    50                  55                  60

Val Arg Thr Asp Gly Ala Val Asp Cys Ala Arg Gly Gln Ser Ala His
65                  70                  75                  80

Ser Leu Leu Glu Ile Arg Ala Val Ala Leu Arg Thr Val Ala Ile Lys
                85                  90                  95

Gly Val His Ser Ala Arg Tyr Leu Cys Met Gly Ala Asp Gly Arg Met
            100                 105                 110

Gln Gly Leu Pro Gln Tyr Ser Glu Glu Asp Cys Ala Phe Glu Glu Glu
        115                 120                 125

Ile Arg Pro Asp Gly Tyr Asn Val Tyr Trp Ser Glu Lys His Arg Leu
    130                 135                 140

Pro Val Ser Leu Ser Ser Ala Arg Gln Arg Gln Leu Tyr Lys Gly Arg
145                 150                 155                 160
```

```
Gly Phe Leu Pro Leu Ser His Phe Leu Pro Met Leu Pro Val Thr Pro
                165                 170                 175

Ala Glu Pro Gly Asp Leu Arg Asp His Leu Glu Ser Asp Met Phe Ser
            180                 185                 190

Leu Pro Leu Glu Thr Asp Ser Met Asp Pro Phe Gly Ile Ala Thr Arg
        195                 200                 205

Leu Gly Val Val Lys Ser Pro Ser Phe Gln Lys
    210                 215
```

<210> SEQ ID NO 119
<211> LENGTH: 219
<212> TYPE: PRT
<213> ORGANISM: Felis catus

<400> SEQUENCE: 119

```
Met Arg Ser Ala Pro Ser Gln Cys Ala Val Thr Arg Ala Leu Val Leu
1               5                   10                  15

Ala Gly Leu Trp Leu Ala Ala Ala Gly Arg Pro Leu Ala Phe Ser Asp
            20                  25                  30

Ala Gly Pro His Val His Tyr Gly Trp Gly Glu Pro Ile Arg Leu Arg
        35                  40                  45

His Leu Tyr Thr Ala Gly Pro His Gly Leu Ser Ser Cys Phe Leu Arg
    50                  55                  60

Ile Arg Ala Asp Gly Gly Val Asp Cys Ala Arg Ser Gln Ser Ala His
65                  70                  75                  80

Ser Leu Val Glu Ile Arg Ala Val Ala Leu Arg Thr Val Ala Ile Lys
                85                  90                  95

Gly Val His Ser Val Arg Tyr Leu Cys Met Gly Ala Asp Gly Arg Met
            100                 105                 110

Gln Gly Leu Leu Gln Tyr Ser Ala Gly Asp Cys Ala Phe Gln Glu Glu
        115                 120                 125

Ile Arg Pro Asp Gly Tyr Asn Val Tyr Arg Ser Glu Lys His Arg Leu
    130                 135                 140

Pro Val Ser Leu Ser Ser Ala Ile Gln Arg Gln Leu Tyr Lys Gly Arg
145                 150                 155                 160

Gly Phe Leu Pro Leu Ser His Phe Leu Pro Met Leu Pro Gly Ser Pro
                165                 170                 175

Ala Glu Pro Arg Asp Leu Gln Asp His Val Glu Ser Glu Arg Phe Ser
            180                 185                 190

Ser Pro Leu Glu Thr Asp Ser Met Asp Pro Phe Gly Ile Ala Thr Lys
        195                 200                 205

Met Gly Leu Val Lys Ser Pro Ser Phe Gln Lys
    210                 215
```

<210> SEQ ID NO 120
<211> LENGTH: 223
<212> TYPE: PRT
<213> ORGANISM: Pelodiscus sinensis

<400> SEQUENCE: 120

```
Met Trp Arg Ser Leu Cys Lys Ser His Thr Ser Leu Ala Leu Leu Gly
1               5                   10                  15

Leu Cys Phe Ala Val Val Val Arg Ser Leu Pro Phe Ser Asp Ala Gly
            20                  25                  30

Pro His Val Asn Tyr Gly Trp Gly Glu Pro Ile Arg Leu Arg His Leu
        35                  40                  45
```

-continued

```
Tyr Thr Ala Ser Arg His Gly Leu Phe Asn Tyr Phe Leu Arg Ile Ser
    50                  55                  60

Ser Asp Gly Lys Val Asp Gly Thr Ser Ile Gln Ser Pro His Ser Leu
65                  70                  75                  80

Leu Glu Ile Arg Ala Val Ala Val Arg Thr Val Ala Ile Lys Gly Val
                85                  90                  95

His Ser Ser Arg Tyr Leu Cys Met Glu Glu Asp Gly Lys Leu His Gly
            100                 105                 110

Leu Leu Arg Tyr Ser Thr Glu Asp Cys Ser Phe Glu Glu Glu Ile Arg
        115                 120                 125

Pro Asp Gly Tyr Asn Val Tyr Lys Ser Lys Lys Tyr Gly Ile Ser Val
    130                 135                 140

Ser Leu Ser Ser Ala Lys Gln Arg Gln Gln Phe Lys Gly Lys Asp Phe
145                 150                 155                 160

Leu Pro Leu Ser His Phe Leu Pro Met Ile Asn Thr Val Pro Val Glu
                165                 170                 175

Ser Met Asp Phe Gly Glu Tyr Gly Asp Tyr Ser His Thr Phe Glu Ser
            180                 185                 190

Asp Leu Phe Ser Ser Pro Leu Glu Thr Asp Ser Met Asp Pro Phe Gly
        195                 200                 205

Ile Thr Ser Lys Ile Ser Pro Val Lys Ser Pro Ser Phe Gln Lys
    210                 215                 220


<210> SEQ ID NO 121
<211> LENGTH: 217
<212> TYPE: PRT
<213> ORGANISM: Latimeria chalumnae

<400> SEQUENCE: 121

Met Leu Gln Ala Leu Tyr Asn Leu Cys Thr Ala Leu Val Leu Phe Lys
1               5                   10                  15

Leu Pro Phe Ala Met Val Gly Tyr Thr Leu Pro Ser Ala Asn Glu Gly
            20                  25                  30

Pro His Leu Asn Tyr Asp Trp Gly Glu Ser Val Arg Leu Lys His Leu
        35                  40                  45

Tyr Thr Ser Ser Lys His Gly Leu Ile Ser Tyr Phe Leu Gln Ile Asn
    50                  55                  60

Asp Asp Gly Lys Val Asp Gly Thr Thr Thr Arg Ser Cys Tyr Ser Leu
65                  70                  75                  80

Leu Glu Ile Lys Ser Val Gly Pro Gly Val Leu Ala Ile Lys Gly Ile
                85                  90                  95

Gln Ser Ser Arg Tyr Leu Cys Val Glu Lys Asp Gly Lys Leu His Gly
            100                 105                 110

Ser Arg Thr Tyr Ser Ala Asp Asp Cys Ser Phe Lys Glu Asp Ile Leu
        115                 120                 125

Pro Asp Gly Tyr Thr Ile Tyr Val Ser Lys Lys His Gly Ser Val Val
    130                 135                 140

Asn Leu Ser Asn His Lys Gln Lys Arg Gln Arg Asn Arg Arg Thr Leu
145                 150                 155                 160

Pro Pro Phe Ser Gln Phe Leu Pro Leu Met Asp Thr Ile Arg Val Glu
                165                 170                 175

Cys Met Asn Cys Gly Glu His Cys Asp Asp Asn Leu His Asp Glu Leu
            180                 185                 190

Glu Thr Gly Leu Ser Met Asp Pro Phe Glu Ser Thr Ser Lys Lys Ser
        195                 200                 205
```

Phe Gln Ser Pro Ser Phe His Asn Arg
    210                 215

<210> SEQ ID NO 122
<211> LENGTH: 219
<212> TYPE: PRT
<213> ORGANISM: Mustela putorius furo

<400> SEQUENCE: 122

Met Arg Ser Ala Ala Ser Arg Cys Ala Val Ala Arg Ala Leu Val Leu
1               5                   10                  15

Ala Gly Leu Trp Leu Ala Ala Ala Gly Arg Pro Leu Ala Phe Ser Asp
            20                  25                  30

Ala Gly Pro His Val His Tyr Gly Trp Gly Glu Pro Ile Arg Leu Arg
        35                  40                  45

His Leu Tyr Thr Ala Gly Pro His Gly Leu Ser Ser Cys Phe Leu Arg
    50                  55                  60

Ile Arg Ala Asp Gly Gly Val Asp Cys Ala Arg Gly Gln Ser Ala His
65                  70                  75                  80

Ser Leu Val Glu Ile Arg Ala Val Ala Leu Arg Thr Val Ala Ile Lys
                85                  90                  95

Gly Val Tyr Ser Asp Arg Tyr Leu Cys Met Gly Ala Asp Gly Arg Met
            100                 105                 110

Gln Gly Leu Pro Gln Tyr Ser Ala Gly Asp Cys Ala Phe Glu Glu Glu
        115                 120                 125

Ile Arg Pro Asp Gly Tyr Asn Val Tyr Arg Ser Lys Lys His Arg Leu
    130                 135                 140

Pro Val Ser Leu Ser Ser Ala Lys Gln Arg Gln Leu Tyr Lys Asp Arg
145                 150                 155                 160

Gly Phe Leu Pro Leu Ser His Phe Leu Pro Met Leu Pro Gly Ser Leu
                165                 170                 175

Ala Glu Pro Arg Asp Leu Gln Asp His Val Glu Ala Asp Gly Phe Ser
            180                 185                 190

Ala Pro Leu Glu Thr Asp Ser Met Asp Pro Phe Gly Ile Ala Thr Lys
        195                 200                 205

Met Gly Leu Val Lys Ser Pro Ser Phe Gln Lys
    210                 215

<210> SEQ ID NO 123
<211> LENGTH: 218
<212> TYPE: PRT
<213> ORGANISM: Takifugu rubripes

<400> SEQUENCE: 123

Ser Ser Thr Arg Ile Ser Gly Asn Met Val Leu Leu Met Leu Pro Ile
1               5                   10                  15

Thr Val Ala Asn Leu Phe Leu Cys Ala Gly Val Leu Ser Leu Pro Leu
            20                  25                  30

Leu Asp Gln Gly Ser His Phe Pro Gln Gly Trp Glu Gln Val Val Arg
        35                  40                  45

Phe Arg His Leu Tyr Ala Ala Ser Ala Gly Leu His Leu Leu Ile Thr
    50                  55                  60

Glu Glu Gly Ser Ile Gln Gly Ser Ala Asp Pro Thr Leu Tyr Ser Leu
65                  70                  75                  80

Met Glu Ile Arg Pro Val Asp Pro Gly Cys Val Val Ile Arg Gly Ala
                85                  90                  95

```
Ala Thr Thr Arg Phe Leu Cys Ile Glu Gly Ala Gly Arg Leu Tyr Ser
            100                 105                 110

Ser Gln Thr Tyr Ser Lys Asp Asp Cys Thr Phe Arg Glu Gln Ile Leu
        115                 120                 125

Ala Asp Gly Tyr Ser Val Tyr Arg Ser Val Gly His Gly Ala Leu Val
    130                 135                 140

Ser Leu Gly Asn Tyr Arg Gln Gln Leu Arg Gly Glu Asp Trp Ser Val
145                 150                 155                 160

Pro Thr Leu Ala Gln Phe Leu Pro Arg Ile Ser Ser Leu Asp Gln Asp
                165                 170                 175

Phe Lys Ala Ala Leu Asp Glu Thr Glu Lys Pro Glu Gln Thr Ala Pro
            180                 185                 190

Gln Arg Ser Glu Pro Val Asp Met Val Asp Ser Phe Gly Lys Leu Ser
        195                 200                 205

Gln Ile Ile His Ser Pro Ser Phe His Lys
    210                 215


<210> SEQ ID NO 124
<211> LENGTH: 94
<212> TYPE: PRT
<213> ORGANISM: Equus caballus

<400> SEQUENCE: 124

Ala Ala Gly Arg Pro Leu Ala Leu Ser Asp Ala Gly Pro His Val His
1               5                   10                  15

Tyr Gly Trp Gly Glu Pro Ile Arg Leu Arg His Leu Tyr Thr Ala Gly
            20                  25                  30

Pro His Gly Leu Ser Ser Cys Phe Leu Arg Ile Arg Ala Asp Gly Ala
        35                  40                  45

Val Asp Cys Ala Arg Gly Gln Ser Ala His Ser Leu Val Glu Ile Arg
    50                  55                  60

Ala Val Ala Leu Arg Thr Val Ala Ile Lys Gly Val His Ser Val Arg
65                  70                  75                  80

Tyr Leu Cys Met Gly Ala Asp Gly Arg Met Gln Gly Leu Val
                85                  90


<210> SEQ ID NO 125
<211> LENGTH: 209
<212> TYPE: PRT
<213> ORGANISM: Oryzias latipes

<400> SEQUENCE: 125

Thr Met Leu Leu Ile Val Val Thr Ile Ser Thr Met Val Phe Ser Asp
1               5                   10                  15

Ser Gly Val Ser Ser Met Pro Leu Ser Asp His Gly Pro His Ile Thr
            20                  25                  30

His Ser Trp Ser Gln Val Val Arg Leu Arg His Leu Tyr Ala Val Lys
        35                  40                  45

Pro Gly Gln His Val Gln Ile Arg Glu Asp Gly His Ile His Gly Ser
    50                  55                  60

Ala Glu Gln Thr Leu Asn Ser Leu Leu Glu Ile Arg Pro Val Ala Pro
65                  70                  75                  80

Gly Arg Val Val Phe Arg Gly Val Ala Thr Ser Arg Phe Leu Cys Met
                85                  90                  95

Glu Ser Asp Gly Arg Leu Phe Ser Ser His Thr Phe Asp Lys Asp Asn
            100                 105                 110
```

```
Cys Val Phe Arg Glu Gln Ile Leu Ala Asp Gly Tyr Asn Ile Tyr Ile
        115                 120                 125

Ser Asp Gln His Gly Thr Leu Leu Ser Leu Gly Asn His Arg Gln Arg
    130                 135                 140

Gln Gln Gly Leu Asp Arg Asp Val Pro Ala Leu Ala Gln Phe Leu Pro
145                 150                 155                 160

Arg Ile Ser Thr Leu Gln Gln Gly Val Tyr Pro Val Pro Asp Pro Pro
                165                 170                 175

His Gln Met Arg Thr Met Gln Thr Glu Lys Thr Leu Asp Ala Thr Asp
            180                 185                 190

Thr Phe Gly Gln Leu Ser Lys Ile Ile His Ser Pro Ser Phe Asn Lys
        195                 200                 205

Arg


<210> SEQ ID NO 126
<211> LENGTH: 207
<212> TYPE: PRT
<213> ORGANISM: Xiphophorus maculatus

<400> SEQUENCE: 126

Met Phe Val Phe Ile Leu Cys Ile Ala Gly Glu Leu Phe Thr Leu Gly
1               5                   10                  15

Val Phe Cys Met Pro Met Met Asp Gln Gly Pro Leu Val Thr His Gly
            20                  25                  30

Trp Gly Gln Val Val Arg His Arg His Leu Tyr Ala Ala Lys Pro Gly
        35                  40                  45

Leu His Leu Leu Ile Ser Glu Asp Gly Gln Ile His Gly Ser Ala Asp
    50                  55                  60

Gln Thr Leu Tyr Ser Leu Leu Glu Ile Gln Pro Val Gly Pro Gly Arg
65                  70                  75                  80

Val Val Ile Lys Gly Val Ala Thr Thr Arg Phe Leu Cys Met Glu Ser
                85                  90                  95

Asp Gly Arg Leu Tyr Ser Thr Glu Thr Tyr Ser Arg Ala Asp Cys Thr
            100                 105                 110

Phe Arg Glu Gln Ile Gln Ala Asp Gly Tyr Asn Val Tyr Thr Ser Asp
        115                 120                 125

Ser His Gly Ala Leu Leu Ser Leu Gly Asn Asn Gln Gln Arg His Ser
    130                 135                 140

Gly Ser Asp Arg Gly Val Pro Ala Leu Ala Arg Phe Leu Pro Arg Leu
145                 150                 155                 160

Asn Thr Leu Gln Gln Ala Val Pro Thr Glu Pro Asp Val Pro Asp Gln
                165                 170                 175

Leu Ser Pro Glu Lys Val Gln Gln Thr Val Asp Met Val Ala Ser Phe
            180                 185                 190

Gly Lys Leu Ser His Ile Ile His Ser Pro Ser Phe His Lys Arg
        195                 200                 205


<210> SEQ ID NO 127
<211> LENGTH: 220
<212> TYPE: PRT
<213> ORGANISM: Ictidomys tridecemlineatus

<400> SEQUENCE: 127

Met Arg Ser Ala Pro Ser Gly Arg Ala Leu Ala Arg Ala Leu Val Leu
1               5                   10                  15
```

```
Ala Ser Leu Trp Leu Ala Val Ala Gly Arg Pro Leu Ala Arg Arg Ser
            20                  25                  30

Leu Ala Leu Ser Asp Gln Gly Pro His Leu Tyr Tyr Gly Trp Asp Gln
        35                  40                  45

Pro Ile Arg Leu Arg His Leu Tyr Ala Ala Gly Pro Tyr Gly Phe Ser
    50                  55                  60

Asn Cys Phe Leu Arg Ile Arg Thr Asp Gly Ala Val Asp Cys Glu Glu
65                  70                  75                  80

Lys Gln Ser Glu Arg Ser Leu Met Glu Ile Arg Ala Val Ala Leu Glu
                85                  90                  95

Thr Val Ala Ile Lys Asp Ile Asn Ser Val Arg Tyr Leu Cys Met Gly
            100                 105                 110

Ala Asp Gly Arg Ile Gln Gly Leu Pro Arg Tyr Ser Glu Glu Glu Cys
        115                 120                 125

Thr Phe Lys Glu Glu Ile Ser Tyr Asp Gly Tyr Asn Val Tyr Arg Ser
    130                 135                 140

Gln Lys Tyr His Leu Pro Val Val Leu Ser Ser Ala Lys Gln Arg Gln
145                 150                 155                 160

Leu Tyr Gln Ser Lys Gly Val Val Pro Leu Ser Tyr Phe Leu Pro Met
                165                 170                 175

Leu Pro Leu Ala Ser Ala Glu Thr Arg Asp Arg Leu Glu Ser Asp Val
            180                 185                 190

Phe Ser Leu Pro Leu Glu Thr Asp Ser Met Asp Pro Phe Gly Met Ala
        195                 200                 205

Ser Glu Val Gly Leu Lys Ser Pro Ser Phe Gln Lys
    210                 215                 220


<210> SEQ ID NO 128
<211> LENGTH: 203
<212> TYPE: PRT
<213> ORGANISM: Gasterosteus aculeatus

<400> SEQUENCE: 128

Met Leu Leu Leu Leu Val Pro Ala Tyr Val Ala Ser Val Phe Leu Ala
1               5                   10                  15

Leu Gly Val Val Cys Leu Pro Leu Thr Asp Gln Gly Leu His Met Ala
            20                  25                  30

Asp Asp Trp Gly Gln Ser Val Arg Leu Lys His Leu Tyr Ala Ala Ser
        35                  40                  45

Pro Gly Leu His Leu Leu Ile Gly Glu Asp Gly Arg Ile Gln Gly Ser
    50                  55                  60

Ala Gln Gln Ser Pro Tyr Ser Leu Leu Glu Ile Ser Ala Val Asp Pro
65                  70                  75                  80

Gly Cys Val Val Ile Arg Gly Val Ala Thr Ala Arg Phe Leu Cys Ile
                85                  90                  95

Glu Gly Asp Gly Arg Leu Tyr Ser Ser Asp Thr Tyr Ser Arg Asp Asp
            100                 105                 110

Cys Thr Phe Arg Glu Gln Ile Leu Pro Asp Gly Tyr Ser Val Tyr Val
        115                 120                 125

Ser His Gly His Gly Ala Leu Leu Ser Leu Gly Asn His Arg Gln Arg
    130                 135                 140

Leu Gln Gly Arg Asp His Gly Val Pro Ala Leu Ala Gln Phe Leu Pro
145                 150                 155                 160

Arg Val Ser Thr Met Asp Gln Ala Ser Ala Pro Asp Ala Pro Gly Gln
                165                 170                 175
```

Thr Ala Thr Glu Thr Glu Glu Pro Val Asp Ser Phe Gly Lys Leu Ser
180 185 190

Gln Ile Ile His Ser Pro Ser Phe His Glu Arg
195 200

<210> SEQ ID NO 129
<211> LENGTH: 208
<212> TYPE: PRT
<213> ORGANISM: Oreochromis niloticus

<400> SEQUENCE: 129

Met Leu Leu Leu Leu Ile Val Ser Ile Val Asn Met Leu Phe Gly Val
1 5 10 15

Gly Met Val Cys Met Pro Leu Ser Asp Asn Gly Pro His Ile Ala His
20 25 30

Gly Trp Ala Gln Val Val Arg Leu Arg His Leu Tyr Ala Thr Arg Pro
35 40 45

Gly Met His Leu Leu Ile Ser Glu Gly Gly Gln Ile Arg Gly Ser Ala
50 55 60

Val Gln Thr Leu His Ser Leu Met Glu Ile Arg Pro Val Gly Pro Gly
65 70 75 80

Arg Val Val Ile Arg Gly Val Ala Thr Ala Arg Phe Leu Cys Ile Glu
85 90 95

Asp Asp Gly Thr Leu Tyr Ser Ser His Ala Tyr Ser Arg Glu Asp Cys
100 105 110

Ile Phe Arg Glu Gln Ile Leu Pro Asp Gly Tyr Asn Ile Tyr Ile Ser
115 120 125

Asp Arg His Gly Val Leu Leu Ser Leu Gly Asn His Arg Gln Arg Leu
130 135 140

Gln Gly Leu Asp Arg Gly Asp Pro Ala Leu Ala Gln Phe Leu Pro Arg
145 150 155 160

Ile Ser Thr Leu Asn Gln Ile Pro Ser Pro Gly Ala Asn Ile Gly Asp
165 170 175

His Met Lys Val Ala Lys Thr Glu Glu Pro Val Asp Thr Ile Asp Ser
180 185 190

Phe Gly Lys Phe Ser Gln Ile Ile Asp Ser Pro Ser Phe His Lys Arg
195 200 205

<210> SEQ ID NO 130
<211> LENGTH: 152
<212> TYPE: PRT
<213> ORGANISM: Meleagris gallopavo

<400> SEQUENCE: 130

Val Gly Asn Gln Ser Pro Gln Ser Ile Leu Glu Ile Thr Ala Val Asp
1 5 10 15

Val Gly Ile Val Ala Ile Lys Gly Leu Phe Ser Gly Arg Tyr Leu Ala
20 25 30

Met Asn Lys Arg Gly Arg Leu Tyr Ala Ser Leu Ser Tyr Ser Ile Glu
35 40 45

Asp Cys Ser Phe Glu Glu Glu Ile Arg Pro Asp Gly Tyr Asn Val Tyr
50 55 60

Lys Ser Lys Lys Tyr Gly Ile Ser Val Ser Leu Ser Ser Ala Lys Gln
65 70 75 80

Arg Gln Gln Phe Lys Gly Lys Asp Phe Leu Pro Leu Ser His Phe Leu
85 90 95

```
Pro Met Ile Asn Thr Val Pro Val Glu Val Thr Asp Phe Gly Glu Tyr
            100                 105                 110

Gly Asp Tyr Ser Gln Ala Phe Glu Pro Glu Val Tyr Ser Ser Pro Leu
        115                 120                 125

Glu Thr Asp Ser Met Asp Pro Phe Gly Ile Thr Ser Lys Leu Ser Pro
    130                 135                 140

Val Lys Ser Pro Ser Phe Gln Lys
145                 150


<210> SEQ ID NO 131
<211> LENGTH: 13
<212> TYPE: PRT
<213> ORGANISM: Artificial
<220> FEATURE:
<223> OTHER INFORMATION: C-terminal portion of FGF19 of the chimeric
      protein
<220> FEATURE:
<221> NAME/KEY: MISC_FEATURE
<222> LOCATION: (7)..(7)
<223> OTHER INFORMATION: Xaa at position 7 is r or n

<400> SEQUENCE: 131

Thr Gly Leu Glu Ala Val Xaa Ser Pro Ser Phe Glu Lys
1               5                   10


<210> SEQ ID NO 132
<211> LENGTH: 20
<212> TYPE: PRT
<213> ORGANISM: Artificial
<220> FEATURE:
<223> OTHER INFORMATION: C-terminal portion of FGF19 of the chimeric
      protein
<220> FEATURE:
<221> NAME/KEY: MISC_FEATURE
<222> LOCATION: (14)..(14)
<223> OTHER INFORMATION: Xaa at position 14 is r or n

<400> SEQUENCE: 132

Met Asp Pro Phe Gly Leu Val Thr Gly Leu Glu Ala Val Xaa Ser Pro
1               5                   10                  15

Ser Phe Glu Lys
            20


<210> SEQ ID NO 133
<211> LENGTH: 48
<212> TYPE: PRT
<213> ORGANISM: Artificial
<220> FEATURE:
<223> OTHER INFORMATION: C-terminal portion of FGF19 of the chimeric
      protein
<220> FEATURE:
<221> NAME/KEY: MISC_FEATURE
<222> LOCATION: (3)..(3)
<223> OTHER INFORMATION: Xaa at position 3 is m or i
<220> FEATURE:
<221> NAME/KEY: MISC_FEATURE
<222> LOCATION: (4)..(4)
<223> OTHER INFORMATION: Xaa at position 4 is v or a
<220> FEATURE:
<221> NAME/KEY: MISC_FEATURE
<222> LOCATION: (13)..(13)
<223> OTHER INFORMATION: Xaa at position 13 is g or r
<220> FEATURE:
<221> NAME/KEY: MISC_FEATURE
<222> LOCATION: (19)..(19)
<223> OTHER INFORMATION: Xaa at position 19 is m or v
<220> FEATURE:
<221> NAME/KEY: MISC_FEATURE
<222> LOCATION: (42)..(42)
```

<223> OTHER INFORMATION: Xaa at position 42 is r or n

<400> SEQUENCE: 133

Leu Pro Xaa Xaa Pro Glu Glu Pro Glu Asp Leu Arg Xaa His Leu Glu
1 5 10 15

Ser Asp Xaa Phe Ser Ser Pro Leu Glu Thr Asp Ser Met Asp Pro Phe
20 25 30

Gly Leu Val Thr Gly Leu Glu Ala Val Xaa Ser Pro Ser Phe Glu Lys
35 40 45

<210> SEQ ID NO 134
<211> LENGTH: 651
<212> TYPE: DNA
<213> ORGANISM: Homo sapiens

<400> SEQUENCE: 134
atgcggagcg ggtgtgtggt ggtccacgta tggatcctgg ccggcctctg gctggccgtg 60
gccgggcgcc ccctcgcctt ctcggacgcg gggccccacg tgcactacgg ctggggcgac 120
cccatccgcc tgcggcacct gtacacctcc ggcccccacg ggctctccag ctgcttcctg 180
cgcatccgtg ccgacggcgt cgtggactgc gcgcggggcc agagcgcgca cagtttgctg 240
gagatcaagg cagtcgctct gcggaccgtg gccatcaagg gcgtgcacag cgtgcggtac 300
ctctgcatgg gcgccgacgg caagatgcag gggctgcttc agtactcgga ggaagactgt 360
gctttcgagg aggagatccg cccagatggc tacaatgtgt accgatccga gaagcaccgc 420
ctcccggtct ccctgagcag tgccaaacag cggcagctgt acaagaacag aggctttctt 480
ccactctctc atttcctgcc catgctgccc atggtcccag aggagcctga ggacctcagg 540
ggccacttgg aatctgacat gttctcttcg cccctggaga ccgacagcat ggacccattt 600
gggcttgtca ccggactgga ggccgtgagg agtcccagct ttgagaagta a 651

<210> SEQ ID NO 135
<211> LENGTH: 651
<212> TYPE: DNA
<213> ORGANISM: Gorilla gorilla

<400> SEQUENCE: 135
atgcggagcg ggtgtgtggt ggtccacgtc tggatcctgg ccggcctctg gctggccgtg 60
gccgggcgcc ccctcgcctt ctcggacgcg gggccccacg tgcactacgg ctggggcgac 120
cccatccgcc tgcggcacct gtacacctcc ggcccccacg ggctctccag ctgcttcctg 180
cgcatccgtg ccgacggcgt cgtggactgc gcgcggggcc agagcgcgca cagtttgctg 240
gagatcaagg cagtcgctct gcggaccgtg gccatcaagg gcgtgcacag cgtgcggtac 300
ctctgcatgg gcgccgacgg caagatgcag gggctgcttc agtactcgga ggaagactgt 360
gctttcgagg aggagatccg cccagatggc tacaatgtgt accgatctga gaagcaccgc 420
ctcccggtct ccctgagcag tgccaaacag cggcagctgt acaagaacag aggctttctt 480
ccgctctctc atttcctgcc catgctgccc atggtcccag aggagcctga ggacctcagg 540
ggccacttgg aatctgacat gttctcttca cccctggaga ccgacagcat ggacccattt 600
gggcttgtca ccggactgga ggccgtgagg agtcctagct ttgagaagta a 651

<210> SEQ ID NO 136
<211> LENGTH: 651
<212> TYPE: DNA
<213> ORGANISM: Pan troglodytes

<400> SEQUENCE: 136
atgcggaacg ggtgtgtggt ggtccacgtc tggatcctgg ccggcctctg gctggccgtg 60
gccgggcgcc ccctcgcctt ctcggacgcg gggcgccacg tgcactactg ctggggcgac 120
cccatccccc tgcggcacct gtacacctcc ggcccccatg ggctctccag ctgcttcctg 180
cgcatccctg cgaactgcgt catgaactgc gcgcggggcc agagcgcgca cagtttgctg 240
gagatcaagg cagtcgctct gcggaccgtg gccatcaagg gcgtgcacag cgtgcggtac 300
ctctgcatgg gcgccgacgg caagatgcag gggctgcttc agtactcgga ggaagactgt 360
gctttcgagg aggagatccg cccagatggc tacaatgtgt accgatccga gaagcaccgc 420
ctcccggtct ccctgagcag tgccaaacag cggcagctgt acaagaacag aggctttctt 480
ccactctctc atttcctgcc catgctgccc atggtcccag aggagcctga ggacctcagg 540
ggccacttgg aatctgacat gttctcttcg cccctggaga ccgacagcat ggacccattt 600
gggcttgtca ccggactgga ggccgtgagg agtcccagct ttgagaagta a 651

<210> SEQ ID NO 137
<211> LENGTH: 651
<212> TYPE: DNA
<213> ORGANISM: Macaca mulatta

<400> SEQUENCE: 137
atgaggagcg ggtgtgtggt ggtccacgcc tggatcctgg ccagcctctg gctggccgtg 60
gccgggcgtc ccctcgcctt ctcggacgcg gggccccacg tgcactacgg ctggggcgac 120
cccatccgcc tgcggcacct gtacacctcc ggcccccatg ggctctccag ctgcttcctg 180
cgcatccgca ccgacggcgt cgtggactgc gcgcggggcc aaagcgcgca cagtttgctg 240
gagatcaagg cagtagctct gcggaccgtg gccatcaagg gcgtgcacag cgtgcggtac 300
ctctgcatgg gcgccgacgg caagatgcag gggctgcttc agtactcaga ggaagactgt 360
gctttcgagg aggagatccg ccctgatggc tacaatgtat accgatccga gaagcaccgc 420
ctcccggtct ctctgagcag tgccaaacag aggcagctgt acaagaacag aggctttctt 480
ccgctctctc atttcctacc catgctgccc atggccccag aggagcctga ggacctcagg 540
ggccacttgg aatctgacat gttctcttcg cccctggaga ctgacagcat ggacccattt 600
gggcttgtca ccggactgga ggcggtgagg agtcccagct ttgagaaata a 651

<210> SEQ ID NO 138
<211> LENGTH: 651
<212> TYPE: DNA
<213> ORGANISM: Pongo abelii

<400> SEQUENCE: 138
atgcggagcg ggtgtgtggt ggtccacgcc tggatcctgg ccggcctctg gctggccgtg 60
gccgggcgcc ccctcgcctt ctcggactcg gggccccacg tgcactacgg ctggggcgac 120
cccatccgcc tgcggcacct gtacacctcc ggcccccacg ggctctccag ctgcttcctg 180
cgcatccgtg ccgacggcgt cgtggactgc gcgcggggcc agagcgcgca cagtttgctg 240
gagatcaagg cagtcgctct gcggaccgtg gccatcaagg gcgtgcacag cgtgcggtac 300
ctctgcatgg gcgccgacgg caagatgcag gggctgcttc agtactcgga ggaagactgt 360
gctttcgagg aggagatccg cccagatggc tacaatgtgt accgatccga gaagcaccgc 420
ctcccggtct ccctgagcag tgccaaacag cggcagctgt acaagaacag ggggctttctt 480 ccgctctctc atttcctgcc catgctgccc atggtcccag aggagcctga ggacctcagg 540
cgccacttgg aatccgacat gttctcttcg cccctggaga ccgacagcat ggacccattt 600
gggcttgtca ccggactgga ggccgtgagg agtcccagct ttgagaaata a 651

<210> SEQ ID NO 139
<211> LENGTH: 651
<212> TYPE: DNA
<213> ORGANISM: Nomascus leucogenys

<400> SEQUENCE: 139
atgcggagcg agtgtgtggt ggtccacgcc tggatcctgg ccggcctctg gctggcagtg 60
gccgggcgcc ccctcgcctt ttcggacgcg gggccccacg tgcactacgg ctggggcgac 120
cccatccgtc tgcggcacct gtacacctcc ggcccccacg ggctctccag ctgcttcctg 180
cgcatccgtg ccgacggcgt cgtggactgc gcgcggggcc agagcgcgca cagtttgctg 240
gagatcaagg cagtcgctct gcggaccgtg gccataaagg gcgtgcacag cgtgcggtac 300
ctctgcatgg gcgccgacgg caagatgcag gggctgcttc agtattcgga ggaagactgt 360
gctttcgagg aggagatccg cccagatggc tacaatgtgt accgatccga gaagcaccgc 420
ctccccgtct ccctgagcag tgccaaacag cggcagctgt ataagaacag aggctttctt 480
ccactctctc atttcctgcc catgctgccc atggtcccag aggagcctga ggacctcagg 540
ggccacttgg aatctgacat gttctcttcg cccctggaga ccgacagcat ggacccattt 600
gggcttgtca ccggactgga ggccgtgagg agtcccagct ttgagaaata a 651

<210> SEQ ID NO 140
<211> LENGTH: 429
<212> TYPE: DNA
<213> ORGANISM: Callithrix jacchus

<400> SEQUENCE: 140
atgtggaagg ccaccgctgg tggccagcag ggacagtccg aagcacaaat gtccacatgt 60
ccccatgttc ctcgtcctct gtggattgct cagagctgcc tgttttctct gcagctccag 120
tactcggagg aagactgtgc tttcgaggag gagatccgcc ctgatggcta caatgtgtac 180
tggtccgaga agcaccgcct cccggtctcc ctgagcagcg ccaaacagcg gcagctgtac 240
aagaaacgag gctttcttcc actgtcccat ttcctgccca tgctgcccat agccccagaa 300
gagcctgagg acctcagggg acacctggaa tctgacgtgt tctcttcacc cctggagact 360
gacagcatgg acccatttgg gcttgtcacg ggactggagg cggtgaacag tcccagcttt 420
gagaagtaa 429

<210> SEQ ID NO 141
<211> LENGTH: 660
<212> TYPE: DNA
<213> ORGANISM: Microcebus marinus

<400> SEQUENCE: 141
atgccgagcg ggcaaagcgg ttgtgtggcg gcccgcgccc tgatcctggc cggcctctgg 60
ctgaccgcgg ccgggcgccc gctggccttc tccgacgcgg gcccgcacgt gcactacggc 120
tggggcgagc ccatccgcct gcggcacctg tacaccgccg gcccccacgg cctctccagc 180
tgcttcctgc gcatccgcgc agacggctcc gtggactgcg cgcggggcca gagcgcacac 240
agtttgctgg agatcagggc ggtcgctctt cggactgtgg ccatcaaggg cgtgcacagc 300
gtgcggtacc tctgcatggg cgcagacggc aggatgcagg ggctgctccg gtactcggag 360
gaagactgtg ccttcgagga ggagatccgc cccgatggct acaacgtgta ccggtctgag 420
aagcaccgcc tgccggtgtc tctgagcagc gccaggcaga ggcagctgta caagggcagg 480
ggcttcctgc cgctctctca cttcctgccc atgctgcccg tgaccccggc agagaccggg 540
gacctcaggg accacttgga gtccgacatg ttcgcttcgc ccctggagac cgacagcatg 600
gacccgtttg ggatcgccac cagacttggg gtggtgaaga gtcccagctt tcagaaatga 660

<210> SEQ ID NO 142
<211> LENGTH: 415
<212> TYPE: DNA
<213> ORGANISM: Choloepus hoffmanni

<400> SEQUENCE: 142
ttgctcgaaa tgaaggcagt ggcgctgcgg gccgtggcca tcaagggcgt gcacagtgct 60
ctgtacctct gcatgaacgc cgacggcagt ctgcacgggc tgcctcggta ctctgcagaa 120
gactgtgctt ttgaggagga aatccgcccc gacggctaca atgtgtactg gtctaggaag 180
cacggcctcc ctgtctcttt gagcagtgca aaacagaggc agctgtacaa aggcagaggc 240
tttctgcccc tgtcccactt cctgcccatg ctgcccatga cgccggccga gcccgcagac 300
cccggggatg acgtggagtc ggacatgttc tcttcacctc tggaaaccga cagcatggat 360
ccttttggaa ttgcctccag acttgagctt gtgaacagtc cagctttcag cataa 415

<210> SEQ ID NO 143
<211> LENGTH: 619
<212> TYPE: DNA
<213> ORGANISM: Ailuropoda melanoleuca

<400> SEQUENCE: 143
ggtcctagcc ggcctctgcc tggcggtagc cgggcgcccc ctagccttct cggacgcggg 60
gccgcacgtg cactacggct ggggtgagcc catccgccta cggcacctgt acaccgccgg 120
cccccacggc ctctccagct gcttcctgcg catccgtgcc gacggcgggg ttgactgcgc 180
gcggggccag agcgcgcaca gtttggtgga gatcagggca gtcgctctgc ggaccgtggc 240
catcaagggt gtgcacagcg tccggtacct ctgcatgggc gcggacggca ggatgcaagg 300
gctgcctcag tactctgcag ggactgtgc tttcgaggag gagatccgcc ccgacggcta 360
caatgtgtac cggtccaaga agcaccgtct ccccgtctct ctgagcggtg ccaaacagag 420
gcagctttac aaagacagag gctttctgcc cctgtcccac ttcttgccca tgctgcccgg 480
gagcccagca gagcccaggg acctccagga ccatgcggag tcggacgggt tttctgcacc 540
cctagaaaca gacagcatgg acccttttgg gatcgccacc aaaatgggac tagtgaagag 600
tcccagcttc cagaaataa 619

<210> SEQ ID NO 144
<211> LENGTH: 660
<212> TYPE: DNA
<213> ORGANISM: Sus scrofa

<400> SEQUENCE: 144
atgcggagcg ctccgagccg gtgcgcggtg gtccgcgccc tggtcctggc cggcctctgg 60
ctggccgcag ccgggcgccc cctagccttc tcggatgctg ggccgcacgt gcactacggc 120
tggggcgagt cggtccgcct gcggcacctg tacactgcga gtccccacgg cgtctccagc 180
tgcttcctgc gcatccactc agacggcccc gtggactgcg cgccgggaca gagcgcgcac 240
agtttgatgg agatcagggc agtcgcgctg agtaccgtgg cgatcaaggg cgagcgcagc 300
ggccgttacc tctgcatggg cgccgacggc aagatgcaag ggcagactca gtactcggat 360
gaggactgtg ctttcgagga ggagatccgc cctgatggct acaacgtgta ctggtccaag 420
aaacaccatc tgcccgtctc tctgagcagc gccaggcaga ggcagctgta caaaggcagg 480
ggcttcctgc cgctgtccca ctttctgccc atgctgtcca ctctcccagc cgagccggag 540
gacctccagg acccccttcaa gtccgacctg ttttctttgc ccctggaaac ggacagcatg 600
gaccctttcc ggatcgccgc caaactggga gcggtgaaga gtcccagctt ctataaataa 660

<210> SEQ ID NO 145
<211> LENGTH: 657
<212> TYPE: DNA
<213> ORGANISM: Bos Taurus

<400> SEQUENCE: 145
atgcggagcg ctccgagccg gtgcgccgtg gcccgcgccc tggtcctggc tggcctctgg 60
ctggccgcag ccgggcgccc cctggccttc tcggatgcgg ggccgcacgt gcactacggc 120
tggggcgagt cggttcgctt gcggcacctg tataccgcgg gcccgcaggg cctctacagc 180
tgctttctgc gcatccactc cgacggcgcc gtggactgcg cgcaggtcca gagcgcgcac 240
agtttgatgg agatcagggc ggtcgctctg agcaccgtag ccatcaaggg cgagcgcagc 300
gtgctgtacc tctgcatgga cgccgacggc aagatgcaag gactgaccca gtactcagcc 360
gaggactgtg ctttcgagga ggagatccgt cctgacggct acaacgtgta ctggtccagg 420
aagcaccatc tcccggtctc cctgagcagc tccaggcaga ggcagctgtt caaaagcagg 480
ggcttcctgc cgctgtctca cttcctgccc atgctgtcca ccatcccagc cgaacctgaa 540
gacctccagg aacccctgaa gcctgatttc tttctgcccc tgaaaacaga tagcatggac 600
cctttcgggc tcgccaccaa actgggatcg gtgaagagtc ccagcttcta taattaa 657

<210> SEQ ID NO 146
<211> LENGTH: 579
<212> TYPE: DNA
<213> ORGANISM: Canis lupus familiaris

<400> SEQUENCE: 146
ctagccttct ccgacgcggg gccgcacgtg cactccttct ggggggagcc catccgcctg 60
cggcacctgt acaccgccgg cccccacggc ctctccagct gcttcctgcg catccgcgcc 120
gacggcgggg tggactgcgc gcggggccag agcgcgcaca gtctgatgga gatgagggcg 180
gtcgctctgc ggaccgtggc catcaagggc gtgcacagcg gccggtacct ctgcatgggc 240
gccgacggca ggatgcaagg gctgcctcag tactccgccg gagactgtac tttcgaggag 300
gagatccgtc ccgatggcta caatgtgtac tggtccaaga agcaccatct ccccatctct 360
ctgagtagtg ccaaacagag gcagctctac aagggcaggg gctttttgcc cctgtcccac 420
ttcttaccta tcttgcccgg gagcccaaca gagcccaggg acctggaaga ccatgtggag 480
tctgacgggt tttctgcatc cctggaaaca gacagcatgg acccttttgg gatcgccacc 540
aaaattggac tagtgaagag tcccagtttc caaaaataa 579

<210> SEQ ID NO 147
<211> LENGTH: 657
<212> TYPE: DNA
<213> ORGANISM: Oryctolagus cuniculus

<400> SEQUENCE: 147
atgcgccgcg cgccgagcgg aggtgccgcg gcccgcgcct tggtcctggc cggcctctgg 60
ctggccgcgg ccgcgcgccc cttggccttg tccgacgcgg gcccgcatct gcactacggc 120
tggggcgagc ccgtccgcct gcggcacctg tacgccacca gcgcccacgg cgtctcgcac 180
tgcttcctgc gtatacgcgc cgacggcgcc gtggactgcg agcggagcca gagcgcacac 240
agcttgctgg agatccgagc ggtcgccctg cgcaccgtgg ccttcaaggg cgtgcacagc 300
tcccgctacc tctgcatggg cgccgacggc aggatgcggg ggcagctgca gtactcggag 360
gaggactgtg ccttccagga ggagatcagc tccggctaca acgtgtaccg ctccacgacg 420
caccacctgc ccgtgtctct gagcagtgcc aagcagagac acctgtacaa gaccagaggc 480
ttcctgcccc tctcccactt cctgcccgtg ctgcccctgg cctccgagga gaccgcggcc 540
ctcggcgacc accctgaagc cgacctgttc tccccgcccc tggaaaccga cagcatggac 600
cccttcggca tggccaccaa gctcgggccg gtgaagagcc ccagctttca gaagtag 657

<210> SEQ ID NO 148
<211> LENGTH: 651
<212> TYPE: DNA
<213> ORGANISM: Pteropus vampyrus

<400> SEQUENCE: 148
atgcggagcc cgtgcgctgt ggcccgcgcc ttggtcctgg ccggcctctg gctggcctca 60
gctgcgggcc ccctcgccct ctcggacgcg gggccgcacg tgcactacgg ctggggcgag 120
gccatccgcc tgcggcacct gtacaccgcc ggcccccacg gcccctccag ctgcttcctg 180
cgcatccgcg cggatggggc ggtggactgc gcgcggggcc agagcgcgca cagtttggtg 240
gaaatccggg ctgtcgccct gcggaacgtg gctatcaagg gcgtgcacag cgtccgatac 300
ctctgcatgg gagccgacgg caggatgcta gggctgcttc agtactccgc tgacgactgc 360
gccttcgagg aggagatccg cccggacggc tacaacgtgt accactccaa gaagcaccac 420
ctcccggtct ctctgagcag tgccaagcag aggcaactgt acaaggacag ggcttcctg 480 cccctgtccc atttcctgcc catgctgccc aggagcccga cagagcccga gaacttcgaa 540
gaccacttgg aggccgacac gttttcctcg cccctggaga cagacgacat ggaccctttt 600
gggattgcca gtaaattggg gctggaggaa agtcccagct tccagaagta a 651

<210> SEQ ID NO 149
<211> LENGTH: 660
<212> TYPE: DNA
<213> ORGANISM: Tursiops truncatus

<400> SEQUENCE: 149
atgcggagcg ctccgagccg gtgcgccgtg gcccgcgccc tggtcctggc cggcctctgg 60
ctggctgcag ccgggcgccc cctagccttc tcggatgccg ggccgcacgt gcactacggc 120
tggggcgagt ccgtccgcct gcggcacctg tacaccgcgg gtccccaggg cctctccagc 180
tgcttcctgc gcatccactc agacggcgcc gtggactgcg cgccggttca gagcgcgcac 240
agtttgatgg agatcagggc agtcgctctg agtaccgtgg ccatcaaggg cgaacgcagc 300
gtcctgtacc tctgcatggg cgccgacggc aaaatgcaag ggctgagtca gtactcagct 360
gaggactgtg cctttgagga ggaaatccgt ccggacggct acaacgtgta ctggtccaag 420
aaacaccacc tcccggtgtc cctgagcagc gccaggcagc ggcagctgtt caaaggcagg 480
ggtttcctgc cgctgtctca cttccttccc atgctgtcca ccatccccac agagcccgat 540
gaaatccagg accacttgaa gcccgatttg tttgctttgc ccctgaaaac agatagcatg 600
gacccatttg ggctcgccac caaactggga gtggtgaaga gtcccagctt ctataagtaa 660

<210> SEQ ID NO 150
<211> LENGTH: 660
<212> TYPE: DNA
<213> ORGANISM: Myotis lucifugus

<400> SEQUENCE: 150
atgcaaagcg cgtggagccg acgcgttgtg gcccgagccc tggtcttggc cagcctcggg 60
ctggcctcag ccggggggcc cctcggtctt tcggacgctg ggccgcacgt gcactacggc 120
tggggggagt ccatccgcct gcgccacctg tacacctccg gcccccacgg cccatccagc 180
tgcttcctgc gcatccgcgc tgacggcgca gtggactgcg cgcggggcca gagcgcgcac 240
agtttggtgg agatcagggc cgtcgccttg cggaaagtgg ccatcaaggg cgtgcacagc 300
gccctgtacc tctgcatggg aggcgacggc aggatgctgg ggctgcctca gttctcgccc 360
gaggactgtg ctttcgagga ggagatccgc ccggacggct acaacgtgta ccggtcccag 420
aagcaccagc tgcccgtctc gctgagcagt gcccggcaga ggcagctgtt caaggcccgg 480
ggcttcctgc cgctgtccca cttcctgccc atgctgccca gcagccccgc gggacccgtg 540
ccccgagagc gcccctcgga gccggacgag ttctcttcgc ccctggaaac agacagcatg 600 gaccctttttg ggattgccaa caacctgagg ctggtgagaa gtcccagctt tcaggaataa 660

<210> SEQ ID NO 151
<211> LENGTH: 558
<212> TYPE: DNA
<213> ORGANISM: Ornithorhynchus anatinus

<400> SEQUENCE: 151
atgctttcct gtgtggtttt gcctagtctg ctggagatca aggcggtggc cgtgcgcacg 60
gtggccatca aaggggtcca catctctcgg tacctctgca tggaagagga tgggaaaact 120
ccatgggcac gtctgctgga gatcaaggcg gtggccgtgc gcacggtggc catcaaaggg 180
gtccacagct ctcggtacct ctgcatggaa gaggatggaa aactccatgg gcagatttgg 240
tattctgcag aagactgtgc ttttgaagag gaaatacgtc cagatggcta caatgtgtat 300
aaatctaaga aatatggtgt tcctgtttct ttaagcagcg ccaaacaaag gcagcaattc 360
aaaggaagag actttctgcc tctttctcgt ttcttgccaa tgatcaacac agtgcctgtg 420
gagccagcag agtttgggga ctatgccgat tactttgaat cagatatatt ttcctcacct 480
ctggaaactg acagcatgga cccatttaga attgccccta aactgtcccc tgtaaagagc 540
cccagctttc agaaataa 558

<210> SEQ ID NO 152
<211> LENGTH: 639
<212> TYPE: DNA
<213> ORGANISM: Monodelphis domestica

<400> SEQUENCE: 152
atggcccagc tcctggcccc gctcctcacc ctggctgctc tctggctggc cccgacggcg 60
cgtgcccgac cgctggtgga cgccgggcct cacgtctact acggctgggg ggagcccatt 120
cgtctgcggc atctctacac ggccaatcgg cacgggctcg ccagcttctc cttcctccgg 180
atccaccgcg acggccgcgt ggacggcagc cggagtcaga gcgcgctcag tttgctggag 240
atcaaggcgg tagctcttcg gatggtggcg atcaaaggtg tccatagctc tcggtacctg 300

```
tgtatgggag acgccgggaa actccaggga tcggtgaggt tctcggccga ggactgcacc    360

ttcgaggagc agattcgccc cgacggctac aacgtgtacc agtcccccaa gtacaacctc    420

cccgtctcgc tctgcactga caagcagagg cagcaggccc acggcaagga gcacctgccc    480

ctgtcccact tcctgcccat gatcaatgct attcctttgg aggccgagga gcccgagggc    540

cccaggatgt tggcggcgcc tctggagacg gacagcatgg accccttcgg cctcacctcc    600

aagctgttgc cggtcaagag ccccagcttt cagaaataa                           639
```

<210> SEQ ID NO 153
<211> LENGTH: 663
<212> TYPE: DNA
<213> ORGANISM: Anolis carolinensis

<400> SEQUENCE: 153

```
atgtgtcggc gggcgttgcc tctgctgggg gcccttctgg gcttggcggc cgtggcctcc     60

cgcgccctcc cgctcaccga cgccgggccc cacgtcagct acggctgggg ggagcccgtc    120

cggctcaggc acctctacac cgcggggcgg cagggcctct tcagccagtt cctccgcatc    180

cacgccgacg ggagagtcga cggcgccggc agccagaacc ggcagagttt gctggagatc    240

cgcgcggtct cgttgcgcgc cgtggccctc aaaggcgtgc acagctcccg ctacctctgc    300

atggaggagg acggccggct ccgcgggatg ctcagatatt ctgcagaaga ctgttccttt    360

gaagaggaga tgcgtccaga tggctacaat atctacaagt caaagaaata cggagttttg    420

gtctccctaa gtaatgccag acaaagacag caattcaaag ggaaagattt tcttcctttg    480

tctcatttct tgccgatgat caacactgtg ccagtggagt ctgcagactt tggagagtat    540

ggtgacacca ggcagcatta tgaatcggat attttcagtt cacgtcttga aactgacagc    600

atggaccctt ttggcctcac ttcagaagtg tcatcagtac aaagtcctag ctttgggaaa    660

taa                                                                  663
```

<210> SEQ ID NO 154
<211> LENGTH: 541
<212> TYPE: DNA
<213> ORGANISM: Ochotona princeps

<400> SEQUENCE: 154

```
gtgcggagca ggggagccat ggcccgcgct ctggttctag ccactctctg gctggccgcg     60

acggggcggc cgctggcctt gtccgacgcg gggccgcacc tgcactacgg ctggggcgag    120

cccatccgcc tgcggcacct gtacgccacc agcgcccacg gcctctcgca ctgctttttg    180

cgcatccgta ccgacggcac cgtggactgc gagcgcagcc agagcgcgca cactacagta    240

ctcggaggag gactgcgcct tcgaagagga gatcagctct ggctataacg tgtaccgctc    300

caggaggtac cagctgcccg tgtccctggg cagcgccagg cagaggcagc tgcagcggag    360

ccgtggcttc ctgcccctgt cccacttcct gccggtgctg cccgcggcct cggaggaggt    420

ggcggccccc gctgaccacc cgcaagcaga ccctttctcg cccctggaga ccgacagcat    480

ggacccattt ggaatggcca ccaagcgggg gctggtgaag agccccagct tccagaagtg    540

a                                                                    541
```

<210> SEQ ID NO 155
<211> LENGTH: 666
<212> TYPE: DNA
<213> ORGANISM: Cavia porcellus

<400> SEQUENCE: 155

```
atgtggagtg cgccgagcgg atgtgtggtg atccgcgccc tggtcctggc tggcctgtgg     60
ctggcggtgg cggggcgccc cctggcccgg cggtctctcg cgctatctga ccaggggccg    120
cacttgtact acggctggga ccagccgatc cgccttcggc acctgtacgc cgcgggcccc    180
tacggccgct cgcgctgctt cctgcgcatt cacacggacg gcgcggtgga ctgcgtcgag    240
gaacagagcg agcactgttt gctggagatc agagcagtcg ctctggagac cgtggccatc    300
aaggacataa acagcgtccg gtacctgtgc atgggccccg acggcaggat gcggggcctg    360
ccctggtatt cggaggagga ctgtgccttc aaggaagaga tcagctaccc gggctacagc    420
gtgtaccgct cccagaagca ccacctcccc atcgtgctga gcagtgtcaa gcagaggcag    480
cagtaccaga gcaagggggt ggtgcccctg tcctacttcc tgcccatgct gcccaaggcc    540
tctgtggagc ccagcgacga ggaggaatcc agcgtgttct cgttgcccct gaagacggac    600
agcatggacc cctttgggat ggccagtgag atcgggctgg tgaagagtcc cagctttcag    660
aagtaa                                                               666
```

```
<210> SEQ ID NO 156
<211> LENGTH: 595
<212> TYPE: DNA
<213> ORGANISM: Tupaia belangeri
<220> FEATURE:
<221> NAME/KEY: misc_feature
<222> LOCATION: (346)..(347)
<223> OTHER INFORMATION: N at positions 346 and 347 is a, c, g, or t

<400> SEQUENCE: 156

atgaggagaa caccgagcgg gtttgcagtg gcccgtgtcc tcttcctggg cagcctttgg     60
ctggccgcag ccgggagccc cttggccctg tccgacgccg ggccgcatgt gaactacggc    120
tgggatgagt ccatacgcct gcgacacttg tacaccgcca gcccgcacgg ctccaccagc    180
tgcttcttgc gcatccgtga cgacggctca gtggactgcg cgcggggcca gagtttgcac    240
agtttgctgg agatcaaggc agtcgctttg cagaccgtgg ccatcaaagg cgtgtacagt    300
gtccgctacc tctgcatgga cgccgacggc aggatgcagg ggctgnnggt ccacgaagca    360
cggcctccca gtctccctga gcagtgccaa gcagaggcag ctgttaacgg ttaggggctt    420
tccttccctt ccccacttcc tgctcatgat ggccaagact tcagcagggc ctggaaaccc    480
cagggaccac ccagggtcta acactttctc gttgcccctg gaaactgata gcatggaccc    540
atttgggatg accaccagac atgggctggt gaagagtccc agctttcaaa actaa         595
```

```
<210> SEQ ID NO 157
<211> LENGTH: 657
<212> TYPE: DNA
<213> ORGANISM: Rattus norvegicus

<400> SEQUENCE: 157

atggcgagaa agtggagtgg gcgtattgtg gcccgagctc tggtcctggc cactctgtgg     60
ctggccgtgt ctgggcgtcc cctggtccag caatcccagt ctgtgtcgga tgaaggtcca    120
ctctttctct atggctgggg caagattacc cgcctgcagt acctgtactc tgctggtccc    180
tacgtctcca actgcttcct gcgtatccgg agtgacggct ctgtggactg cgaggaggac    240
cagaacgaac gaaatctgtt ggagttccgc gcggttgctc tgaagacaat tgccatcaag    300
gacgtcagca gcgtgcggta cctctgcatg agcgccgacg gcaagatata cgggctgatt    360
cgctactcgg aggaagactg taccttcagg gaggaaatgg actgtttggg ctacaaccag    420
```

tacaggtcca tgaagcacca cctccacatc atcttcatca aggccaagcc cagagagcag 480
ctccagggcc agaaaccttc aaactttatc cccatatttc accggtcttt ctttgaatcc 540
acggaccagc tgaggtctaa aatgttctct ctgcccctgg agagcgacag catggatccg 600
ttcagaatgg tggaggatgt ggaccaccta gtgaagagtc ccagcttcca gaaatga 657

<210> SEQ ID NO 158
<211> LENGTH: 657
<212> TYPE: DNA
<213> ORGANISM: Mus musculus

<400> SEQUENCE: 158
atggcgagaa agtggaacgg gcgtgcggtg gcccgagccc tggtcctggc cactctgtgg 60
ctggctgtgt ctgggcgtcc cctggctcag caatcccagt ctgtgtcaga tgaagatcca 120
ctctttctct acggctgggg caagattacc cgcctgcagt acctgtactc cgctggtccc 180
tatgtctcca actgcttcct ccgaatccgg agcgacggct ctgtggactg cgaggaggac 240
caaaacgaac gaaatttgtt ggaattccgc gcggtcgctc tgaagacgat tgccatcaag 300
gacgtcagca gcgtgcggta cctctgcatg agcgcggacg gcaagatata cgggctgatt 360
cgctactcgg aggaagactg taccttcagg gaggaaatgg actgtttagg ctacaaccag 420
tacagatcca tgaagcacca tctccatatc atcttcatcc aggccaagcc cagagaacag 480
ctccaggacc agaaaccctc aaactttatc cccgtgtttc accgctcctt ctttgaaacc 540
ggggaccagc tgaggtctaa aatgttctcc ctgcccctgg agagtgacag catggatccg 600
ttcaggatgg tggaggatgt agaccaccta gtgaagagtc ccagcttcca gaaatga 657

<210> SEQ ID NO 159
<211> LENGTH: 684
<212> TYPE: DNA
<213> ORGANISM: Gallus gallus

<400> SEQUENCE: 159
atggggccgg cccgccccgc cgcacccggc gctgccctgg cgctgctggg gatcgccgcc 60
gccgccgccg ccgccaggtc cctgccgctg cccgacgtcg gggtccgca cgtcaactac 120 ggctgggggg aacccatccg gctgcggcac ctactacacc gcccaggcaa gcacgggctc 180
ttcagctgct tcctgcgcat cggcggcgac ggccgggtgg acgctgtcgg tagccagagc 240
ccgcagagtc tgttggagat ccgcgccgtg gcggtgcgca ccgtggccat caagggcgtg 300
cagagctccc gctacctctg catggacgag gcggggcggc tgcacgggca gctcagctat 360
tccattgagg actgttcctt tgaagaggag attcgtccag acggctacaa cgtgtataaa 420
tcaaagaaat acgggatatc ggtgtctttg agcagtgcca aacaaagaca gcaattcaaa 480
ggaaaagatt ttctcccgct gtctcacttc ttacccatga tcaacactgt gccagtggag 540
gtgacagact ttggtgaata tggtgattac agccaggctt ttgagccaga ggtctactca 600
tcgcctctcg aaacggacag catggatccc tttgggatca cttccaaact gtctccagtg 660
aagagcccca gctttcagaa atga 684

<210> SEQ ID NO 160
<211> LENGTH: 714
<212> TYPE: DNA
<213> ORGANISM: Taeniopygia guttata

<400> SEQUENCE: 160
atggttatca taagcaatct atatctgatg cagaacgatg ttatgatgaa tatgaggcga 60

```
gcaccccttc gcgttcacgc tgctcgctct tcggccaccc ctgcctccgc gctgccgctg    120

ccgccgcccg acgccggccc gcacctcaaa tacggctggg gagagcccat ccggctgcgg    180

cacctctaca ccgccagcaa gcacgggctc ttcagctgct tcctgcgtat cggcgctgac    240

ggccgggtgg acgcggccgg cagccagagc ccgcagagcc tgctagagat ccgcgccgtg    300

gccgtgcgca ccgtggccat caagggcgtg cagagctccc ggtacctgtg catggacgag    360

gcggggcggc tgcacgggca gctcaggaat tccactgaag actgctcctt tgaggaggag    420

attcgcccag acggctacaa tgtgtataga tctaaaaaac atggaatatc ggtgtctttg    480

agcagtgcca aacaaagaca gcagttcaag ggaaagatt tccttcccct gtctcacttc    540

ttgcccatga tcaacactgt gcccatggag tcagcagact ttggtgaata tggtgattac    600

agccaggcct ttgaggcaga ggccttctcc tcacctctgg agacggacag catggacccc    660

tttggcatcg cctccaaact gtccctagtg aagagcccta gcttccaaaa ctga          714
```

<210> SEQ ID NO 161
<211> LENGTH: 633
<212> TYPE: DNA
<213> ORGANISM: Danio rerio

<400> SEQUENCE: 161

```
atgctcctct tactctttgt cactgtttgt ggaagtatcg gcgtggagag cctcccgttg     60

cccgactctg gtccacattt ggcaaatgac tggagtgaag ccgtccggct acgacatctg    120

tacgcagcca gacatggctt acatctgcaa ataaacacag acggagaaat cattggatcc    180

acatgcaaag ctcggacagt aagtttgatg gagatatggc cggtggacac aggctgcgta    240

gccattaagg gagttgcaag ctcccgattt ctttgcatgg aaagactggg aaacctgtac    300

ggatcgcaca tttacactaa agaggactgc tctttttgg aacgcatcct tccagacggc    360

tacaacgtct acttctcgag caaacacgga gctcttgtga ctttaagtgg tgcgaaaaac    420

aagttgcaca gtaacgatgg gacttctgca tcccagttcc tccccatgat caacacactt    480

tcagaggaac acactaaaca gcactcaggg gaacagcact cttctgttaa ccatggacag    540

gaccatcagt tgggccttga aatagacagt atggaccctt tcggaaagat ctctcaaata    600

gtgatccaga gtcccagctt caacaaaaga tga                                  633
```

<210> SEQ ID NO 162
<211> LENGTH: 648
<212> TYPE: DNA
<213> ORGANISM: Xenopus (Silurana) tropicalis

<400> SEQUENCE: 162

```
atgtggaaga ccctgccttg gattttggtt cccatgatgg tggccgtgct gtatttcctc     60

ggaggggcgg aaagtctgcc gctttttgat gccgggccgc acatgcagaa cggctggggg    120

gagtcgatca gaattcggca cctgtatacg gccaggaggt tcgggcacga cagctactac    180

ctccggatac acgaggatgg cagagtcgat ggtgacaggc aacaaagcat gcacagttta    240

ttggaaatca gagcaattgc agttggaatt gttgccatta aagggtatcg cagctctctg    300

tacctgtgca tggggtccga gggaaaactc tatggaatgc acagttactc ccaggatgat    360

tgctcttttg aagaggagct tctcccggat ggatacaaca tgtataaatc aaggaaacat    420

ggcgttgctg tctccctaag caaggagaag cagaagcaac aatacaaagg aaagggctac    480

ctcccgttgt cccatttcct acccgtgata agctgggtgc ccatggagcc caccggagat    540
```

-continued gtagaagatg atatctacag gtttccattc aatacggaca caaaaagtgt cattgacagc 600
cttgataccc tgggactaat ggatttttcg agttatcaca agaaatag 648

<210> SEQ ID NO 163
<211> LENGTH: 660
<212> TYPE: DNA
<213> ORGANISM: Otolemur garnettii

<400> SEQUENCE: 163
atgcccagcg ggctgagagg gcgtgtggta gccggcgccc tggccctggc cagcttctgg 60
ctggccgtgg ccgggcgccc gctggccttc tcggatgccg gccctcacgt gcactacggc 120
tggggtgagc ccatccgcct gcgacacctg tacaccgccg gcccccacgg cctctccagc 180
tgcttcctgc gcgtacgcac cgacggtgcg gtagactgcg cgcggggcca gagcgcacac 240
agtttgctgg aaatcagggc cgtcgctctc cggaccgtgg ccatcaaagg cgtgcacagc 300
gcgcggtacc tctgcatggg cgccgacggc aggatgcagg ggctgcctca gtactcggag 360
gaagactgtg cctttgagga ggagatccgg ccagacggct acaacgtcta ctggtctgag 420
aagcaccgcc tgccggtgtc tctgagcagt gcccggcaga ggcagctgta caagggcagg 480
ggctttctgc cgctctctca cttcctgccc atgctgcctg tgaccccagc cgagcccggg 540
gacctcagag accacctgga atccgacatg ttctctttgc ccctggaaac tgacagcatg 600
gatccatttg ggatcgccac cagactgggc gtggtgaaga gtcccagctt tcagaaatga 660

<210> SEQ ID NO 164
<211> LENGTH: 660
<212> TYPE: DNA
<213> ORGANISM: Felis catus

<400> SEQUENCE: 164
atgcggagcg cgccgagcca gtgcgcggta acccgcgccc tggtcctagc cggtctctgg 60
ctggcagcag ccgggcgccc cctagccttc tcggacgcgg ggcctcacgt gcactacggc 120
tggggtgagc ccatccgcct gcggcacctg tacaccgccg gcccccacgg cctctccagc 180
tgcttcctgc gcatccgagc cgacgggggg gttgactgcg cgcggagcca gagcgcgcac 240
agtttggtgg agatcagggc agtcgctctg cggaccgtgg ccatcaaggg cgtgcacagc 300
gtccggtacc tctgcatggg cgccgacggc aggatgcaag ggctgcttca gtactctgct 360
ggggactgtg ccttccaaga ggagatccgc cccgacggct acaatgtgta ccggtccgag 420
aagcaccgtc tccccgtctc tttgagtagt gccatacaga ggcagctgta caagggcaga 480
gggtttttgc ccctgtccca tttcttgccc atgctgcccg gcagcccagc agagcccagg 540
gacctccagg accacgtgga gtcggagagg ttttcttcac ccctggaaac agacagcatg 600
gacccttttg ggattgccac caaaatgggg ttagtgaaga gtcccagctt ccaaaagtaa 660

<210> SEQ ID NO 165
<211> LENGTH: 672
<212> TYPE: DNA
<213> ORGANISM: Pelodiscus sinensis

<400> SEQUENCE: 165
atgtggagga gcctgtgcaa atctcacacg tctctggctc tgctgggact ctgctttgcg 60
gtggtcgtga gatctctgcc tttctcggat gcagggccac atgtgaacta tggctggggg 120
gagcctattc gattaaggca cctatacacc gccagcagac acgggctgtt caattacttc 180
ctgaggatca gcagtgatgg caaagtggat ggcaccagca ttcagagtcc tcacagtctg 240
ctggaaatca gggctgtggc agttcgcacg gtggcgatca agggcgtcca cagttcccgg 300
tacctctgca tggaagaaga cgggaagctg catggacttc tcaggtattc tacagaagat 360
tgctcctttg aagaggagat acgcccagat ggctacaatg tatataaatc aaagaaatat 420
ggaatctctg tgtccttaag tagtgccaaa caaagacaac aattcaaagg aaaagacttt 480
cttccattgt ctcacttctt gcctatgatc aatacagtac ctgtggagtc aatggatttt 540
ggagaatatg gtgattatag tcatactttt gaatcagatc tattctcttc acctctcgaa 600
actgacagca tggatccctt tggaatcacc tctaaaatat ctccagtgaa gagccccagc 660
tttcagaaat aa 672

<210> SEQ ID NO 166
<211> LENGTH: 654
<212> TYPE: DNA
<213> ORGANISM: Latimeria chalumnae

<400> SEQUENCE: 166
atgttacagg cactgtacaa tctctgtaca gctctagttt tgtttaagct tccttttgca 60
atggtggggt acaccctgcc ttctgccaat gaagggcccc atctgaacta tgactgggga 120
gaatctgtaa gactcaaaca tctgtacaca tctagcaagc atggattgat cagttacttt 180
ttacagatca atgatgatgg caaagtagat gggaccacta cacgaagctg ttatagtttg 240
ctcgaaataa aatcagtggg gccaggagtt ttggcaatta aaggcataca gagctccaga 300
tacctttgtg tcgagaagga tggaaaattg catggatcgc gcacttattc agcagacgat 360
tgctccttca aagaggatat actcccagat ggttacacta tctacgtgtc aaagaaacat 420
ggatctgttg ttaatctgag caaccacaaa cagaaacgtc agagaaatcg cagaaccctg 480
cctccatttt ctcagttcct accgcttatg gacaccattc gtgtggagtg catgaactgc 540
ggggagcact gtgacgacaa cctgcatgac gagctagaaa caggactgtc catggatccc 600
tttgaaagta catccaaaaa atcctttcag agtcccagct ttcacaatag ataa 654

<210> SEQ ID NO 167
<211> LENGTH: 660
<212> TYPE: DNA
<213> ORGANISM: Mustela putorius furo

<400> SEQUENCE: 167
atgcggagcg ccgcgagtcg gtgcgcggta gcccgcgcgc tggtcctagc cggcctttgg 60
ctggccgcag ccgggcgccc cctagccttc tcggacgcgg ggccgcacgt gcactatggc 120
tggggtgagc ccatccgcct acggcacctg tacaccgccg gcccccacgg cctctccagc 180
tgcttcctgc gcatccgtgc cgacggcggg gttgactgcg cgcggggcca gagcgcgcac 240
agtttggtgg agatccgggc agtcgctctg cggacggtgg ccatcaaggg cgtgtacagc 300
gaccgctatc tctgcatggg tgcggacggc aggatgcaag ggctgcctca gtactccgcc 360
ggagactgtg ctttcgagga ggagatccgc cctgatggct acaacgtgta ccggtccaag 420
aagcaccgtc tccccgtctc cctgagcagt gcgaaacaaa ggcagctgta caaggaccgg 480
ggctttttgc ctctgtccca tttcttgccc atgctgcccg ggagcctggc ggagcccagg 540
gacctccagg accacgtgga ggctgatggg ttttctgccc ccctagaaac agacagcatg 600 gaccctttg ggattgccac caaaatggga ctagtgaaga gtcccagctt ccaaaaatga 660

<210> SEQ ID NO 168

<211> LENGTH: 654
<212> TYPE: DNA
<213> ORGANISM: Takifugu rubripes

<400> SEQUENCE: 168
tcatctacaa ggattagtgg aaacatggtt ctcctcatgc tccccatcac cgttgcaaac 60
ctcttcctct gtgctggagt tctctccttg cctttgttgg atcaagggtc tcattttccc 120
caaggctggg aacaggtagt ccgcttcagg cacctgtatg ctgccagtgc agggctgcac 180
ctgctgatca ctgaagaggg ctcgatccaa ggctctgcag atccaacttt atacagcctg 240
atggagatcc gtccggtgga cccaggctgt gttgtcatta gaggagcagc aaccacacgc 300
ttcctctgca tagaaggtgc tggaagactg tactcatcac agacctacag caaagacgac 360
tgtaccttca gagagcaaat cctagcagac ggctacagcg tctacagatc tgtcggacac 420
ggagctctgg tcagtctggg aaactaccgg cagcagctga ggggggagga ctggagcgtt 480
ccgacactgg ctcagttcct ccccagaata agttcactgg atcaggactt taaagctgct 540
cttgacgaga ctgagaagcc agaacaaact gcacctcaaa gatcggaacc tgtcgacatg 600
gtggactcat ttggaaagct ctctcagatc atccacagtc ccagttttca caag 654

<210> SEQ ID NO 169
<211> LENGTH: 282
<212> TYPE: DNA
<213> ORGANISM: Equus caballus

<400> SEQUENCE: 169
gcggccgggc gccccctagc cttgtccgac gctgggccgc acgtgcacta cggctggggc 60
gagccgatcc gcctgcggca cctgtacacc gccggccccc acggcctctc cagctgcttc 120
ctgcgcatcc gcgccgatgg cgccgtggac tgcgcgcggg gccagagcgc gcacagtttg 180
gtggagatca gagcagtcgc tctgcgcacc gtggccatca agggcgtgca cagcgtccgg 240
tacctctgca tgggcgccga cggcaggatg caagggctgg ta 282

<210> SEQ ID NO 170
<211> LENGTH: 630
<212> TYPE: DNA
<213> ORGANISM: Oryzias latipes

<400> SEQUENCE: 170
accatgctgc tcattgtggt caccatttcc acaatggtgt tttctgactc tggagtttcc 60
agcatgccgc tctctgatca tggaccccac atcactcaca gctggagcca agtggtccgc 120
ctccggcacc tgtacgcggt caagcctgga caacatgtcc agatcagaga ggatggacac 180
atccacggct cagcagaaca aactctgaac agcctgctgg agatccgtcc ggttgctccg 240
ggacgggtgg tcttcagagg agtagccacc tcaaggtttc tgtgcatgga gagcgacggc 300
agactcttct cctcacacac atttgacaag gacaactgcg tcttcagaga gcagatcttg 360
gcagacggct acaacatcta catttcagat cagcatggaa ccctgcttag tttgggaaac 420
caccggcaaa ggcagcaggg tttagaccgg gatgttccag ccctggctca gttcctcccc 480
aggatcagca ccctgcagca gggcgtgtac ccagtgccag acccccccca ccagatgaga 540
acaatgcaaa cagagaagac tctagatgcc acggacacat ttgggcaact ctctaaaatc 600
attcacagtc ccagcttcaa caaaagatga 630

<210> SEQ ID NO 171
<211> LENGTH: 624

<212> TYPE: DNA
<213> ORGANISM: Xiphophorus maculates

<400> SEQUENCE: 171
atgtttgtgt tcattctatg cattgctggt gaacttttta ctctgggagt attttgcatg 60
ccaatgatgg accaggggcc acttgtcacc catggctggg gccaggtggt ccggcaccgg 120
catctgtatg cagccaagcc aggactgcac ctactgatca gtgaggatgg acaaatccac 180
ggttccgcag atcaaactct ttacagcctg ctggagatcc aacctgttgg ccccggacgt 240
gttgtgatca aaggagtggc aaccacacgc ttcctctgca tggagagcga cggcagattg 300
tactcaactg aaacatacag cagagctgac tgcaccttca gagaacagat ccaggcagac 360
ggctacaacg tctacacctc tgatagccat ggagccctcc tcagtttggg aaacaaccag 420
caaagacaca gcggctcaga ccgtggtgtt ccagctctgg cccgctttct tcccaggtta 480
aacacccttc agcaggccgt ccccacagag ccggatgttc ctgatcagct cagtccagag 540
aaagtacaac agactgtgga catggtggcc tcctttggca agctctctca tataattcac 600
agtcccagct tccataagag atga 624

<210> SEQ ID NO 172
<211> LENGTH: 663
<212> TYPE: DNA
<213> ORGANISM: Ictidomys tridecemlineatus

<400> SEQUENCE: 172
atgcggagcg cgccgagcgg acgtgcctta gcccgcgccc tggtgctggc cagcctctgg 60
ttggcagtgg ccggacgacc cctggcccgg cgctctctgg ctctctccga ccaggggcca 120
cacttgtact atggctggga tcagcccatc cgcctccggc acctgtacgc cgcgggcccc 180
tacggcttct ccaactgttt cctgcgcatc cgcaccgacg gcgccgtgga ctgcgaggag 240
aagcagagcg agcgtagttt gatggagatc agggcggtcg ctctggagac tgtggccatc 300
aaggacataa acagcgtccg gtacctctgc atgggcgccg acggcaggat acagggactg 360
cctcggtact cggaggaaga gtgcacgttc aaggaggaga tcagctatga cggctacaac 420
gtgtaccggt cccagaagta ccaccttccc gtggtgctca gcagtgccaa gcagcggcag 480
ctgtaccaga gcaagggcgt ggttcccctg tcctacttcc tgcccatgct gcccctggcc 540
tctgcggaga ccagggaccg cttggaatcc gatgtgttct ctttacctct ggaaactgac 600
agcatggacc cgtttgggat ggccagtgaa gtgggcctga agagccccag cttccagaag 660
taa 663

<210> SEQ ID NO 173
<211> LENGTH: 612
<212> TYPE: DNA
<213> ORGANISM: Gasterosteus aculeatus

<400> SEQUENCE: 173
atgctgctgc tgctggtccc cgcgtacgtt gccagtgtgt ttttagctct cggggttgtt 60
tgcttgcccc taacagatca gggtctccac atggccgacg actggggcca gtcggtccga 120
ctcaagcacc tgtacgccgc cagcccggga ctccacctgc tgatcgggga ggatggtcgg 180
atccaaggct cggcgcagca aagcccctac agcctgctgg agatcagtgc agtggatccg 240
ggctgtgtgg tcatcagagg agtagcaacc gcacggtttc tctgcatcga aggcgatgga 300
agactgtact catcggacac ctacagcaga gacgactgca ccttcaggga gcagatcctc 360

```
ccggacggct acagcgtcta cgtctcccat ggacacgggg ccctgctcag cctggggaac    420

cacaggcaga ggctgcaggg tcgagaccac ggcgtgccgg ctctggccca gttcctcccg    480

agggtcagca ccatggatca ggcctcggcc cccgacgcgc ccgggcagac cgccaccgag    540

acggaagagc ccgtggactc gtttggaaag ctctctcaga tcattcacag tcccagcttc    600

cacgagagat ga                                                        612
```

<210> SEQ ID NO 174
<211> LENGTH: 627
<212> TYPE: DNA
<213> ORGANISM: Oreochromis niloticus

<400> SEQUENCE: 174

```
atgctgctgc tcctcatcgt atccattgtc aatatgcttt ttggtgttgg aatggtttgc     60

atgcccctgt cagacaacgg gccccacatc gcccacggct gggcccaggt ggtccggctc    120

aggcaccttt acgccaccag accgggaatg cacctgctga tcagtgaggg tggacagatc    180

cgtggttctg ccgtccagac tctgcacagc ctaatggaga ttcgtccagt cggtccaggc    240

cgtgttgtca tcagaggggt agcaaccgca aggtttctct gcatagaaga cgacggcaca    300

ctgtactcat cgcacgccta cagcagagag gactgcatct tcagagagca gatcttgcca    360

gatgggtaca acatctacat ctctgacaga catggagtcc tgctcagtct gggaaaccac    420

cggcaaagac tgcagggctt agaccgagga gatccagccc tggcccagtt cctccccagg    480

atcagcactc tgaatcaaat cccttcccct ggggcaaaca tcggtgacca catgaaagta    540

gcaaaaacag aagaacctgt ggacacaata gattcatttg gaaagttctc tcagatcatt    600

gacagtccca gcttccataa gagatga                                        627
```

<210> SEQ ID NO 175
<211> LENGTH: 456
<212> TYPE: DNA
<213> ORGANISM: Meleagris gallopavo

<400> SEQUENCE: 175

```
gtaggcaatc aatcaccaca gagcatcctt gaaataactg ctgttgatgt cgggatcgtc     60

gctatcaagg gcttgttctc tggcagatac ctggccatga acaaaagggg caggctttat    120

gcatcactca gctattccat tgaggactgt tcctttgaag aggagattcg tccagatggc    180

tataacgtgt ataaatcaaa gaaatacgga atatcagtgt ctttgagcag tgccaaacaa    240

agacaacaat tcaaaggaaa agattttctc ccactgtctc acttcttacc catgatcaac    300

actgtgccag tggaggtgac agactttggt gaatacggtg attacagcca ggcttttgag    360

ccagaggtct actcatcgcc tctcgaaacg gacagcatgg atccctttgg gatcacttcc    420

aaactgtctc cagtgaagag ccccagcttt cagaaa                              456
```

<210> SEQ ID NO 176
<211> LENGTH: 209
<212> TYPE: PRT
<213> ORGANISM: Homo sapiens

<400> SEQUENCE: 176

```
Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
```

```
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser


<210> SEQ ID NO 177
<211> LENGTH: 209
<212> TYPE: PRT
<213> ORGANISM: Pongo abelii

<400> SEQUENCE: 177

Met Asp Ser Asp Glu Thr Gly Phe Glu His Ser Gly Leu Trp Val Pro
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
```

195 200 205

Ser

<210> SEQ ID NO 178
<211> LENGTH: 209
<212> TYPE: PRT
<213> ORGANISM: Pan troglodytes

<400> SEQUENCE: 178

Met Asp Ser Asp Glu Thr Gly Phe Glu His Ser Gly Leu Trp Val Ser
1 5 10 15

Val Leu Ala Gly Leu Leu Leu Gly Ala Cys Gln Ala His Pro Ile Pro
20 25 30

Asp Ser Ser Pro Leu Leu Gln Phe Gly Gly Gln Val Arg Gln Arg Tyr
35 40 45

Leu Tyr Thr Asp Asp Ala Gln Gln Thr Glu Ala His Leu Glu Ile Arg
50 55 60

Glu Asp Gly Thr Val Gly Gly Ala Ala Asp Gln Ser Pro Glu Ser Leu
65 70 75 80

Leu Gln Leu Lys Ala Leu Lys Pro Gly Val Ile Gln Ile Leu Gly Val
85 90 95

Lys Thr Ser Arg Phe Leu Cys Gln Arg Pro Asp Gly Ala Leu Tyr Gly
100 105 110

Ser Leu His Phe Asp Pro Glu Ala Cys Ser Phe Arg Glu Leu Leu Leu
115 120 125

Glu Asp Gly Tyr Asn Val Tyr Gln Ser Glu Ala His Gly Leu Pro Leu
130 135 140

His Leu Pro Gly Asn Lys Ser Pro His Arg Asp Pro Ala Pro Arg Gly
145 150 155 160

Pro Ala Arg Phe Leu Pro Leu Pro Gly Leu Pro Pro Ala Pro Pro Glu
165 170 175

Pro Pro Gly Ile Leu Ala Pro Gln Pro Pro Asp Val Gly Ser Ser Asp
180 185 190

Pro Leu Ser Met Val Gly Pro Ser Gln Gly Arg Ser Pro Ser Tyr Thr
195 200 205

Ser

<210> SEQ ID NO 179
<211> LENGTH: 209
<212> TYPE: PRT
<213> ORGANISM: Canis lupus familiaris

<400> SEQUENCE: 179

Met Gly Trp Ala Glu Ala Gly Phe Glu His Leu Gly Leu Trp Val Pro
1 5 10 15

Val Leu Ala Val Leu Leu Leu Glu Ala Cys Arg Ala His Pro Ile Pro
20 25 30

Asp Ser Ser Pro Leu Leu Gln Phe Gly Gly Gln Val Arg Gln Arg Tyr
35 40 45

Leu Tyr Thr Asp Asp Ala Gln Glu Thr Glu Ala His Leu Glu Ile Arg
50 55 60

Ala Asp Gly Thr Val Val Gly Ala Ala Arg Gln Ser Pro Glu Ser Leu
65 70 75 80

Leu Glu Leu Lys Ala Leu Lys Pro Gly Val Ile Gln Ile Leu Gly Val
85 90 95

```
Lys Thr Ser Arg Phe Leu Cys Gln Gly Pro Asp Gly Thr Leu Tyr Gly
            100                 105                 110

Ser Leu His Phe Asp Pro Val Ala Cys Ser Phe Arg Glu Leu Leu Leu
        115                 120                 125

Glu Asp Gly Tyr Asn Ile Tyr His Ser Glu Thr Leu Gly Leu Pro Leu
    130                 135                 140

Arg Leu Arg Pro His Asn Ser Ala Tyr Arg Asp Leu Ala Pro Arg Gly
145                 150                 155                 160

Pro Ala Arg Phe Leu Pro Leu Pro Gly Leu Leu Pro Ala Pro Pro Glu
                165                 170                 175

Pro Pro Gly Ile Leu Ala Pro Glu Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser


<210> SEQ ID NO 180
<211> LENGTH: 209
<212> TYPE: PRT
<213> ORGANISM: Bos Taurus

<400> SEQUENCE: 180

Met Gly Trp Asp Glu Ala Lys Phe Lys His Leu Gly Leu Trp Val Pro
1               5                   10                  15

Val Leu Ala Val Leu Leu Leu Gly Thr Cys Arg Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Glu Thr Glu Ala His Leu Glu Ile Arg
    50                  55                  60

Ala Asp Gly Thr Val Val Gly Ala Ala Arg Gln Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Gly Pro Asp Gly Lys Leu Tyr Gly
            100                 105                 110

Ser Leu His Phe Asp Pro Lys Ala Cys Ser Phe Arg Glu Leu Leu Leu
        115                 120                 125

Glu Asp Gly Tyr Asn Val Tyr Gln Ser Glu Thr Leu Gly Leu Pro Leu
    130                 135                 140

Arg Leu Pro Pro Gln Arg Ser Ser Asn Arg Asp Pro Ala Pro Arg Gly
145                 150                 155                 160

Pro Ala Arg Phe Leu Pro Leu Pro Gly Leu Pro Ala Ala Pro Pro Asp
                165                 170                 175

Pro Pro Gly Ile Leu Ala Pro Glu Pro Pro Asp Val Gly Ser Ser Asp
            180                 185                 190

Pro Leu Ser Met Val Gly Pro Ser Tyr Gly Arg Ser Pro Ser Tyr Thr
        195                 200                 205

Ser


<210> SEQ ID NO 181
<211> LENGTH: 209
<212> TYPE: PRT
<213> ORGANISM: Equus caballus

<400> SEQUENCE: 181
```

```
Met Asp Trp Asp Lys Thr Gly Phe Lys Tyr Gln Gly Leu Trp Val Pro
1               5                   10                  15

Val Leu Ala Val Leu Leu Leu Gly Ala Cys Gln Ser His Pro Ile Pro
            20                  25                  30

Asp Ser Ser Pro Leu Leu Gln Phe Gly Gly Gln Val Arg Gln Arg His
        35                  40                  45

Leu Tyr Thr Asp Asp Ala Gln Glu Thr Glu Ala His Leu Glu Ile Arg
    50                  55                  60

Ala Asp Gly Thr Val Ala Gly Ala Val His Arg Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Gly Pro Asp Gly Thr Leu Tyr Gly
            100                 105                 110

Ser Leu His Phe Asp Pro Val Ala Cys Ser Phe Arg Glu Leu Leu Leu
        115                 120                 125

Glu Asp Gly Tyr Asn Val Tyr Gln Ser Glu Thr Leu Gly Leu Pro Leu
    130                 135                 140

Arg Leu Pro His His Ser Ser Pro Tyr Gln Asp Pro Ala Pro Arg Ala
145                 150                 155                 160

Pro Ala Arg Phe Leu Pro Leu Pro Gly Phe Pro Pro Ala Pro Pro Glu
                165                 170                 175

Pro Pro Gly Ile Pro Ala Pro Glu Pro Pro Asp Val Gly Ser Ser Asp
            180                 185                 190

Pro Leu Ser Met Val Gly Pro Ser Arg Ser Arg Ser Pro Ser Tyr Thr
        195                 200                 205

Ser


<210> SEQ ID NO 182
<211> LENGTH: 209
<212> TYPE: PRT
<213> ORGANISM: Ailuropoda melanoleuca

<400> SEQUENCE: 182

Met Gly Trp Asp Glu Ala Arg Ser Glu Gln Leu Gly Leu Trp Val Pro
1               5                   10                  15

Val Leu Ala Val Leu Leu Leu Glu Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Glu Thr Glu Ala His Leu Ala Ile Arg
    50                  55                  60

Ala Asp Gly Thr Val Val Gly Ala Ala Ser Arg Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Gly Pro Asp Gly Thr Leu Tyr Gly
            100                 105                 110

Ser Val Arg Phe Asp Pro Val Ala Cys Ser Phe Arg Glu Leu Leu Leu
        115                 120                 125

Glu Asp Gly Tyr Asn Ile Tyr His Ser Glu Thr Leu Gly Leu Pro Leu
    130                 135                 140

Arg Leu Pro Ala His Asn Ser Pro Tyr Arg Asp Ser Ala Pro Arg Gly
145                 150                 155                 160
```

```
Pro Ala Arg Phe Leu Pro Leu Pro Gly Leu Leu Pro Val Pro Pro Asp
                165                 170                 175

Pro Pro Gly Ile Leu Gly Pro Glu Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser
```

<210> SEQ ID NO 183
<211> LENGTH: 209
<212> TYPE: PRT
<213> ORGANISM: Oryctolagus cuniculus

<400> SEQUENCE: 183

```
Met Asp Trp Gly Lys Ala Lys Cys Arg Pro Pro Gly Leu Trp Val Pro
1               5                   10                  15

Ala Leu Ala Ala Leu Leu Leu Gly Ala Cys Gln Ala His Pro Ile Pro
            20                  25                  30

Asp Ser Ser Pro Leu Leu Gln Phe Gly Asp Gln Val Arg Gln Gln His
        35                  40                  45

Leu Tyr Thr Asp Asp Ala Gln Glu Thr Glu Ala His Leu Glu Ile Arg
    50                  55                  60

Ala Asp Gly Thr Val Val Gly Ala Ala Arg Arg Ser Pro Glu Ser Leu
65                  70                  75                  80

Leu Gln Met Lys Ala Leu Gln Pro Gly Ile Ile Gln Ile Leu Gly Val
                85                  90                  95

Gln Thr Ser Arg Phe Leu Cys Gln Arg Pro Asp Gly Thr Leu Tyr Gly
            100                 105                 110

Ser Leu His Phe Asp Arg Glu Ala Cys Ser Phe Arg Glu Leu Leu Arg
        115                 120                 125

Glu Asp Gly Tyr Asn Val Tyr Leu Ser Glu Ala Leu Gly Leu Pro Leu
    130                 135                 140

Arg Leu Ser Pro Gly Ser Ser Pro Arg Arg Ala Pro Ala Pro Arg Gly
145                 150                 155                 160

Pro Ala Arg Phe Leu Pro Leu Pro Gly Leu Pro Pro Asp Leu Pro Glu
                165                 170                 175

Pro Pro Gly Leu Leu Ala Ala Ala Pro Pro Asp Val Asp Ser Pro Asp
            180                 185                 190

Pro Leu Ser Met Val Gln Pro Ala Leu Asp Gln Ser Pro Ser Tyr Thr
        195                 200                 205

Ser
```

<210> SEQ ID NO 184
<211> LENGTH: 209
<212> TYPE: PRT
<213> ORGANISM: Gorilla gorilla

<400> SEQUENCE: 184

```
Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
```

```
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser


<210> SEQ ID NO 185
<211> LENGTH: 209
<212> TYPE: PRT
<213> ORGANISM: Nomascus leucogenys

<400> SEQUENCE: 185

Met Asp Ser Asp Glu Thr Gly Phe Glu His Ser Gly Leu Trp Val Pro
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser
```

<210> SEQ ID NO 186
<211> LENGTH: 209
<212> TYPE: PRT
<213> ORGANISM: Procavia capensis

<400> SEQUENCE: 186

```
Met Asp Trp Ala Lys Phe Gly Ile Glu His Pro Gly Leu Trp Val Pro
1               5                   10                  15

Val Met Ala Val Leu Leu Leu Gly Ala Cys Gln Gly Tyr Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Glu Thr Glu Ala His Leu Glu Ile Arg
    50                  55                  60

Ala Asp Gly Thr Val Val Gly Ala Ala His Arg Ser Pro Glu Ser Leu
65                  70                  75                  80

Leu Glu Leu Lys Ala Leu Lys Pro Gly Ile Ile Gln Ile Leu Gly Val
                85                  90                  95

Lys Thr Ser Arg Phe Leu Cys Gln Gly Pro Asp Gly Val Leu Tyr Gly
            100                 105                 110

Ser Leu Arg Phe Asp Pro Val Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

Arg Leu Pro Ser His Asn Ser Pro Gln Arg Asp Leu Ala Ser Arg Val
145                 150                 155                 160

Pro Ala Arg Phe Leu Pro Leu Pro Gly Arg Leu Thr Val Leu Pro Glu
                165                 170                 175

Pro Ser Gly Val Leu Gly Pro Glu Pro Pro Asp Val Asp Ser Ser Asp
            180                 185                 190

Pro Leu Ser Met Val Gly Pro Ser Gln Gly Arg Ser Pro Ser Tyr Ala
        195                 200                 205

Ser
```

<210> SEQ ID NO 187
<211> LENGTH: 209
<212> TYPE: PRT
<213> ORGANISM: Cavia porcellus

<400> SEQUENCE: 187

```
Met Asp Trp Ala Arg Thr Glu Cys Glu Arg Pro Arg Leu Trp Val Ser
1               5                   10                  15

Met Leu Ala Ile Leu Leu Val Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Asp Thr Glu Val His Leu Glu Ile Arg
    50                  55                  60

Ala Asp Gly Ser Val Arg Gly Ile Ala His Arg Ser Pro Glu Ser Leu
65                  70                  75                  80

Leu Glu Leu Lys Ala Leu Lys Pro Gly Val Ile Gln Ile Leu Gly Ile
                85                  90                  95

Arg Thr Ser Arg Phe Leu Cys Gln Arg Pro Asp Gly Ser Leu Tyr Gly
            100                 105                 110
```

Ser Leu His Phe Asp Pro Glu Ala Cys Ser Phe Arg Glu Leu Leu Leu
        115                 120                 125

Ala Asp Gly Tyr Asn Val Tyr Lys Ser Glu Ala His Gly Leu Pro Leu
    130                 135                 140

His Leu Leu Arg Gly Asp Ser Leu Ser Gln Glu Pro Ala Pro Pro Gly
145                 150                 155                 160

Pro Ala Arg Phe Leu Pro Leu Pro Gly Leu Pro Ala Thr Pro Pro Glu
                165                 170                 175

Pro Pro Arg Met Leu Pro Pro Gly Pro Pro Asp Val Gly Ser Ser Asp
            180                 185                 190

Pro Leu Ser Met Val Gly Pro Leu Trp Asp Arg Ser Pro Ser Tyr Thr
        195                 200                 205

Ser

<210> SEQ ID NO 188
<211> LENGTH: 209
<212> TYPE: PRT
<213> ORGANISM: Tupaia belangeri

<400> SEQUENCE: 188

Met Gly Trp Asp Lys Ala Arg Phe Glu His Leu Gly Ala Trp Ala Pro
1               5                   10                  15

Val Leu Ala Val Leu Leu Leu Gly Ala Cys Gln Ala Tyr Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Thr Gln Asp Thr Glu Ala His Leu Glu Ile Arg
    50                  55                  60

Ala Asp Gly Thr Val Val Gly Ala Ala His Gln Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Ile Tyr Gln Ser Glu Ala Arg Gly Leu Pro Leu
    130                 135                 140

Arg Leu Pro Pro His Asp Ser Pro His Arg Asp Arg Thr Pro Arg Gly
145                 150                 155                 160

Pro Ala Arg Phe Leu Pro Leu Pro Gly Leu Pro Leu Val Pro Pro Glu
                165                 170                 175

Leu Pro Gly Val Leu Ala Leu Glu Pro Pro Asp Val Gly Ser Ser Asp
            180                 185                 190

Pro Leu Ser Met Met Gly Pro Ser Gln Gly Gln Ser Pro Ser Tyr Ala
        195                 200                 205

Ser

<210> SEQ ID NO 189
<211> LENGTH: 210
<212> TYPE: PRT
<213> ORGANISM: Sorex araneus

<400> SEQUENCE: 189

Met Val Trp Asp Lys Ala Arg Gly Gln Gln Leu Gly Leu Trp Ala Pro
1               5                   10                  15

```
Met Leu Leu Gly Leu Leu Leu Gly Ala Cys Gln Ala His Pro Leu Pro
            20                  25                  30

Asp Ser Ser Pro Leu Leu Gln Phe Gly Gly Gln Val Arg Leu Arg Phe
        35                  40                  45

Leu Tyr Thr Asp Asp Ala Gln Arg Thr Gly Ala His Leu Glu Ile Arg
    50                  55                  60

Ala Asp Gly Thr Val Gln Gly Ala Ala His Arg Thr Pro Glu Cys Leu
65                  70                  75                  80

Leu Glu Leu Lys Ala Leu Lys Pro Gly Val Ile Gln Ile Leu Gly Val
                85                  90                  95

Ser Thr Ser Arg Phe Leu Cys Gln Arg Pro Asp Gly Val Leu Tyr Gly
            100                 105                 110

Ser Leu Arg Phe Asp Pro Glu Ala Cys Ser Phe Arg Glu Leu Leu Leu
        115                 120                 125

Gln Asp Gly Tyr Asn Val Tyr Gln Ser Glu Ala Leu Gly Leu Pro Leu
    130                 135                 140

Tyr Leu His Pro Pro Ser Ala Pro Val Ser Gln Glu Pro Ala Ser Arg
145                 150                 155                 160

Gly Ala Val Arg Phe Leu Pro Leu Pro Gly Leu Pro Pro Ala Ser Leu
                165                 170                 175

Glu Pro Pro Arg Pro Pro Ala Pro Val Pro Pro Asp Val Gly Ser Ser
            180                 185                 190

Asp Pro Leu Ser Met Val Gly Pro Pro Glu Arg His Ser Pro Ser Tyr
        195                 200                 205

Thr Ser
    210


<210> SEQ ID NO 190
<211> LENGTH: 208
<212> TYPE: PRT
<213> ORGANISM: Ictidomys tridecemlineatus

<400> SEQUENCE: 190

Met Asp Trp Val Lys Ala Lys Leu Glu Pro Leu Gly Leu Trp Val Leu
1               5                   10                  15

Val Leu Ala Ala Leu Val Leu Gly Ala Cys Gln Ala Tyr Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Glu Thr Glu Ala His Leu Glu Ile Arg
    50                  55                  60

Ala Asp Gly Thr Val Val Gly Ala Ala His Gln Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Arg Pro Asp Gly Val Leu Tyr Gly
            100                 105                 110

Ser Leu His Phe Asp Pro Glu Ala Cys Ser Phe Arg Glu Gln Leu Leu
        115                 120                 125

Glu Asp Gly Tyr Asn Val Tyr Gln Ser Glu Ser His Gly Leu Pro Val
    130                 135                 140

Arg Leu Pro Pro Asn Ser Pro Tyr Arg Asp Pro Ala Pro Pro Gly Pro
145                 150                 155                 160

Ala Arg Phe Leu Pro Leu Pro Gly Leu Pro Pro Ala Ala Leu Glu Pro
```

```
                165                 170                 175

Pro Gly Ile Leu Gly Pro Glu Pro Pro Asp Val Gly Ser Ser Asp Pro
            180                 185                 190

Leu Ser Met Val Gly Pro Leu Gln Gly Arg Ser Pro Ser Tyr Ala Ser
        195                 200                 205


<210> SEQ ID NO 191
<211> LENGTH: 208
<212> TYPE: PRT
<213> ORGANISM: Loxodonta africana

<400> SEQUENCE: 191

Met Asp Trp Ala Lys Phe Gly Leu Glu His Pro Gly Leu Trp Val Pro
1               5                   10                  15

Val Met Ala Val Leu Leu Leu Gly Ala Cys Gln Gly His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Gln Glu Thr Glu Ala His Leu Glu Ile Arg Ala
    50                  55                  60

Asp Gly Thr Val Ala Gly Ala Ala His Arg Ser Ser Glu Ser Leu Leu
65                  70                  75                  80

Glu Leu Lys Ala Leu Lys Pro Gly Ile Ile Gln Ile Leu Gly Val Lys
                85                  90                  95

Thr Ser Arg Phe Leu Cys Gln Gly Pro Asp Gly Val Leu Tyr Gly Ser
            100                 105                 110

Leu His Phe Asp Pro Ala Ala Cys Ser Phe Arg Glu Leu Leu Leu Glu
        115                 120                 125

Asp Gly Tyr Asn Val Tyr Trp Ser Glu Ala His Gly Leu Pro Ile Arg
    130                 135                 140

Leu Pro Ser His Asn Ser Pro Tyr Arg Asp Pro Ala Ser Arg Val Pro
145                 150                 155                 160

Ala Arg Phe Leu Pro Leu Pro Gly Leu Leu Pro Met Leu Gln Glu Pro
                165                 170                 175

Pro Gly Val Leu Ala Pro Glu Pro Pro Asp Val Asp Ser Ser Asp Pro
            180                 185                 190

Leu Ser Met Val Gly Pro Ser Gln Gly Arg Ser Pro Ser Tyr Ala Ser
        195                 200                 205


<210> SEQ ID NO 192
<211> LENGTH: 208
<212> TYPE: PRT
<213> ORGANISM: Sus scrofa

<400> SEQUENCE: 192

Met Gly Trp Ala Glu Ala Lys Phe Glu Arg Leu Gly Leu Trp Val Pro
1               5                   10                  15

Val Leu Ala Val Leu Leu Gly Ala Cys Gln Ala Arg Pro Ile Pro Asp
            20                  25                  30

Ser Ser Pro Leu Leu Gln Phe Gly Gly Gln Val Arg Gln Arg Tyr Leu
        35                  40                  45

Tyr Thr Asp Asp Ala Gln Glu Thr Glu Ala His Leu Glu Ile Arg Ala
    50                  55                  60

Asp Gly Thr Val Ala Gly Val Ala Arg Gln Ser Pro Glu Ser Leu Leu
65                  70                  75                  80

Glu Leu Lys Ala Leu Lys Pro Gly Val Ile Gln Ile Leu Gly Val Gln
```

```
                85                  90                  95

Thr Ser Arg Phe Leu Cys Gln Gly Pro Asp Gly Arg Leu Tyr Gly Ser
            100                 105                 110

Leu His Phe Asp Pro Glu Ala Cys Ser Phe Arg Glu Leu Leu Leu Glu
        115                 120                 125

Asp Gly Tyr Asn Val Tyr Gln Ser Glu Ala Leu Gly Leu Pro Leu Arg
    130                 135                 140

Leu Pro Pro His Arg Ser Ser Asn Arg Asp Leu Ala Pro Arg Gly Pro
145                 150                 155                 160

Ala Arg Phe Leu Pro Leu Pro Gly Leu Pro Pro Ala Pro Pro Glu Pro
                165                 170                 175

Pro Gly Ile Leu Ala Pro Glu Pro Pro Asp Val Gly Ser Ser Asp Pro
            180                 185                 190

Leu Ser Met Val Gly Pro Ser His Gly Arg Ser Pro Ser Tyr Thr Ser
        195                 200                 205


<210> SEQ ID NO 193
<211> LENGTH: 208
<212> TYPE: PRT
<213> ORGANISM: Felis catus

<400> SEQUENCE: 193

Met Asp Trp Asp Glu Ala Gly Ser Gln Arg Leu Gly Leu Trp Val Val
1               5                   10                  15

Leu Gly Val Leu Leu Pro Glu Ala Cys Gln Ala His Pro Ile Pro Asp
            20                  25                  30

Ser Ser Pro Leu Leu Gln Phe Gly Gly Gln Val Arg Gln Arg Phe Leu
        35                  40                  45

Tyr Thr Asp Asp Ala Gln Glu Thr Glu Val His Leu Glu Ile Lys Ala
    50                  55                  60

Asp Gly Thr Val Val Gly Thr Ala Arg Arg Ser Pro Glu Ser Leu Leu
65                  70                  75                  80

Glu Leu Lys Ala Leu Lys Pro Gly Val Ile Gln Ile Leu Gly Val Lys
                85                  90                  95

Thr Ser Arg Phe Leu Cys Gln Gly Pro Asp Gly Thr Leu Tyr Gly Ser
            100                 105                 110

Leu Arg Phe Asp Pro Ala Ala Cys Ser Phe Arg Glu Leu Leu Leu Glu
        115                 120                 125

Asp Gly Tyr Asn Ile Tyr His Ser Glu Thr Leu Gly Leu Pro Leu Arg
    130                 135                 140

Leu Pro Pro His Asn Ser Pro Tyr Arg Asp Leu Ala Pro Arg Ala Pro
145                 150                 155                 160

Ala Arg Phe Leu Pro Leu Pro Gly Leu Leu Pro Ala Pro Pro Glu Pro
                165                 170                 175

Pro Gly Ile Leu Ala Pro Glu Pro Pro Asp Val Gly Ser Ser Asp Pro
            180                 185                 190

Leu Ser Met Val Gly Pro Ser Gln Gly Arg Ser Pro Ser Tyr Ala Ser
        195                 200                 205


<210> SEQ ID NO 194
<211> LENGTH: 208
<212> TYPE: PRT
<213> ORGANISM: Otolemur garnetti

<400> SEQUENCE: 194

Asp Lys Ala Arg Thr Gly Phe Lys His Pro Gly Pro Trp Phe Pro Leu
```

```
1               5                   10                  15

Leu Ala Val Leu Leu Leu Gly Ala Cys Gln Ala His Pro Ile Pro Asp
            20                  25                  30

Ser Ser Pro Leu Leu Gln Phe Gly Gly Gln Val Arg Gln Arg Tyr Leu
        35                  40                  45

Tyr Thr Asp Asp Ala Gln Glu Thr Glu Ala His Leu Glu Ile Arg Glu
    50                  55                  60

Asp Gly Thr Val Val Gly Ala Ala Gln Gln Ser Pro Glu Ser Leu Leu
65                  70                  75                  80

Glu Leu Lys Ala Leu Lys Pro Gly Val Ile Gln Ile Leu Gly Val Lys
                85                  90                  95

Thr Ser Arg Phe Leu Cys Gln Arg Pro Asp Gly Gly Leu Tyr Gly Ser
            100                 105                 110

Leu Tyr Phe Asp Pro Lys Ala Cys Ser Phe Arg Glu Leu Leu Leu Glu
        115                 120                 125

Asp Gly Tyr Asn Val Tyr Trp Ser Glu Thr Tyr Gly Leu Pro Leu His
    130                 135                 140

Leu Pro Pro Ala Asn Ser Pro Tyr Trp Gly Pro Ser Leu Arg Ser Pro
145                 150                 155                 160

Ala Arg Phe Leu Pro Leu Pro Gly Pro Pro Ala Ala Ser Pro Glu Leu
                165                 170                 175

Pro Gly Ile Leu Ala Leu Glu Pro Pro Asp Val Gly Ser Ser Asp Pro
            180                 185                 190

Leu Ser Met Val Gly Pro Ser Gln Gly Arg Ser Pro Ser Tyr Ala Ser
        195                 200                 205


<210> SEQ ID NO 195
<211> LENGTH: 208
<212> TYPE: PRT
<213> ORGANISM: Rattus norvegicus

<400> SEQUENCE: 195

Met Asp Trp Met Lys Ser Arg Val Gly Ala Pro Gly Leu Trp Val Cys
1               5                   10                  15

Leu Leu Leu Pro Val Phe Leu Leu Gly Val Cys Glu Ala Tyr Pro Ile
            20                  25                  30

Ser Asp Ser Ser Pro Leu Leu Gln Phe Gly Gly Gln Val Arg Gln Arg
        35                  40                  45

Tyr Leu Tyr Thr Asp Asp Asp Gln Asp Thr Glu Ala His Leu Glu Ile
    50                  55                  60

Arg Glu Asp Gly Thr Val Val Gly Thr Ala His Arg Ser Pro Glu Ser
65                  70                  75                  80

Leu Leu Glu Leu Lys Ala Leu Lys Pro Gly Val Ile Gln Ile Leu Gly
                85                  90                  95

Val Lys Ala Ser Arg Phe Leu Cys Gln Gln Pro Asp Gly Thr Leu Tyr
            100                 105                 110

Gly Ser Pro His Phe Asp Pro Glu Ala Cys Ser Phe Arg Glu Leu Leu
        115                 120                 125

Leu Lys Asp Gly Tyr Asn Val Tyr Gln Ser Glu Ala His Gly Leu Pro
    130                 135                 140

Leu Arg Leu Pro Gln Lys Asp Ser Gln Asp Pro Ala Thr Arg Gly Pro
145                 150                 155                 160

Val Arg Phe Leu Pro Met Pro Gly Leu Pro His Glu Pro Gln Glu Gln
                165                 170                 175
```

```
Pro Gly Val Leu Pro Pro Glu Pro Pro Asp Val Gly Ser Ser Asp Pro
            180                 185                 190

Leu Ser Met Val Glu Pro Leu Gln Gly Arg Ser Pro Ser Tyr Ala Ser
        195                 200                 205


<210> SEQ ID NO 196
<211> LENGTH: 210
<212> TYPE: PRT
<213> ORGANISM: Mus musculus

<400> SEQUENCE: 196

Met Glu Trp Met Arg Ser Arg Val Gly Thr Leu Gly Leu Trp Val Arg
1               5                   10                  15

Leu Leu Leu Ala Val Phe Leu Leu Gly Val Tyr Gln Ala Tyr Pro Ile
            20                  25                  30

Pro Asp Ser Ser Pro Leu Leu Gln Phe Gly Gly Gln Val Arg Gln Arg
        35                  40                  45

Tyr Leu Tyr Thr Asp Asp Asp Gln Asp Thr Glu Ala His Leu Glu Ile
    50                  55                  60

Arg Glu Asp Gly Thr Val Val Gly Ala Ala His Arg Ser Pro Glu Ser
65                  70                  75                  80

Leu Leu Glu Leu Lys Ala Leu Lys Pro Gly Val Ile Gln Ile Leu Gly
                85                  90                  95

Val Lys Ala Ser Arg Phe Leu Cys Gln Gln Pro Asp Gly Ala Leu Tyr
            100                 105                 110

Gly Ser Pro His Phe Asp Pro Glu Ala Cys Ser Phe Arg Glu Leu Leu
        115                 120                 125

Leu Glu Asp Gly Tyr Asn Val Tyr Gln Ser Glu Ala His Gly Leu Pro
    130                 135                 140

Leu Arg Leu Pro Gln Lys Asp Ser Pro Asn Gln Asp Ala Thr Ser Trp
145                 150                 155                 160

Gly Pro Val Arg Phe Leu Pro Met Pro Gly Leu Leu His Glu Pro Gln
                165                 170                 175

Asp Gln Ala Gly Phe Leu Pro Pro Glu Pro Pro Asp Val Gly Ser Ser
            180                 185                 190

Asp Pro Leu Ser Met Val Glu Pro Leu Gln Gly Arg Ser Pro Ser Tyr
        195                 200                 205

Ala Ser
    210


<210> SEQ ID NO 197
<211> LENGTH: 107
<212> TYPE: PRT
<213> ORGANISM: Vicugna pacos

<400> SEQUENCE: 197

Met Asp Trp Asp Glu Ala Lys Phe Glu His Arg Gly Leu Trp Val Pro
1               5                   10                  15

Val Leu Thr Val Leu Leu Leu Gly Ala Cys Gln Ala Arg Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Glu Thr Glu Ala His Leu Glu Ile Arg
    50                  55                  60

Ala Asp Gly Thr Val Val Gly Val Ala Arg Gln Pro Glu Gly Ile Pro
65                  70                  75                  80
```

```
Pro Glu Pro Pro Asp Val Gly Ser Ser Asp Pro Leu Ser Met Val Gly
                85                  90                  95

Pro Ser Tyr Ser Arg Ser Pro Ser Tyr Thr Ser
            100                 105
```

<210> SEQ ID NO 198
<211> LENGTH: 211
<212> TYPE: PRT
<213> ORGANISM: Anolis carolinensis

<400> SEQUENCE: 198

```
Cys Lys Ser Lys Gly Gly Gly Lys Gly Gly Glu Arg Met Trp Val Asp
1               5                   10                  15

Leu Val Phe Trp Ala Ala Leu Leu Arg Thr Ala Pro Ala Leu Pro Leu
            20                  25                  30

Arg Asn Ser Asn Pro Ile Tyr Gln Phe Asp Gly Gln Val Arg Leu Arg
        35                  40                  45

His Leu Tyr Thr Ala Asp Glu Gln Thr His Leu His Leu Glu Ile Leu
    50                  55                  60

Pro Asp Gly Thr Val Gly Gly Ser Arg Phe Gln Asn Pro Phe Ser Leu
65                  70                  75                  80

Met Glu Ile Lys Ala Val Lys Pro Gly Val Ile Arg Met Gln Ala Lys
                85                  90                  95

Lys Thr Ser Arg Phe Leu Cys Met Lys Pro Asn Gly Arg Leu Tyr Gly
            100                 105                 110

Ser Leu Phe Tyr Ser Glu Glu Ala Cys Asn Phe His Glu Lys Val Leu
        115                 120                 125

Ser Asp Gly Tyr Asn Leu Tyr Tyr Ser Glu Asn Tyr Asn Ile Pro Val
    130                 135                 140

Ser Leu Ser Ser Ala Gly Asn Leu Gly Gln Ser Arg Gln Leu Pro Pro
145                 150                 155                 160

Phe Ser Gln Phe Leu Pro Leu Val Asn Lys Ile Pro Leu Glu Pro Val
                165                 170                 175

Leu Glu Asp Phe Asp Phe Tyr Gly His Gln Leu Asp Val Glu Ser Ala
            180                 185                 190

Asp Pro Leu Ser Ile Leu Gly Gln Asn Pro Gly Phe Met Ser Pro Ser
        195                 200                 205

Tyr Val Phe
    210
```

<210> SEQ ID NO 199
<211> LENGTH: 188
<212> TYPE: PRT
<213> ORGANISM: Gadus morrhua

<400> SEQUENCE: 199

```
Leu Leu Leu Ala Thr Leu Leu His Ile Gly Leu Ser Phe Tyr Val Pro
1               5                   10                  15

Asp Ser Gly Pro Leu Leu Trp Leu Gly Asp Gln Val Arg Glu Arg His
            20                  25                  30

Leu Tyr Thr Ala Glu Ser His Arg Arg Gly Leu Phe Leu Glu Met Ser
        35                  40                  45

Pro Asp Gly Gln Val Thr Gly Ser Ala Ala Gln Thr Pro Leu Ser Val
    50                  55                  60

Leu Glu Leu Arg Ser Val Arg Ala Gly Asp Thr Val Ile Arg Ala Arg
65                  70                  75                  80
```

-continued

```
Leu Ser Ser Leu Tyr Leu Cys Val Asp Arg Ala Gly His Leu Thr Gly
                85                  90                  95

Gln Arg Gln Tyr Thr Glu Ser Asp Cys Thr Phe Arg Glu Val Ile Leu
            100                 105                 110

Glu Asp Gly Tyr Thr His Phe Leu Ser Val His His Gly Leu Pro Ile
        115                 120                 125

Ser Leu Ala Pro Arg His Ser Pro Gly Arg Gln Gly Leu Arg Phe Ser
    130                 135                 140

Arg Phe Leu Pro Leu Arg Ser Ser Leu Ser Glu Asp Arg Val Ala Glu
145                 150                 155                 160

Pro Pro Asp Ser Pro Leu Asn Leu Asp Ser Glu Asp Pro Leu Gly Met
                165                 170                 175

Gly Leu Gly Ser Leu Leu Ser Pro Ala Phe Ser Met
            180                 185


<210> SEQ ID NO 200
<211> LENGTH: 216
<212> TYPE: PRT
<213> ORGANISM: Latimeria chalumnae

<400> SEQUENCE: 200

Met Leu Cys Gln Ser Phe Val Ile Leu Ser Gln Lys Phe Ile Phe Gly
1               5                   10                  15

Leu Phe Leu Thr Gly Leu Gly Leu Thr Gly Leu Ala Trp Thr Arg Pro
            20                  25                  30

Phe Gln Asp Ser Asn Pro Ile Leu Gln Tyr Ser Asp Ser Ile Arg Leu
        35                  40                  45

Arg His Leu Tyr Thr Ala Ser Glu Ser Arg His Leu His Leu Gln Ile
    50                  55                  60

Asn Ser Asp Gly Gln Val Gly Gly Thr Thr Lys Gln Ser Pro Tyr Ser
65                  70                  75                  80

Leu Leu Glu Met Lys Ala Val Lys Thr Gly Phe Val Val Ile Arg Gly
                85                  90                  95

Lys Lys Ser Ala Arg Tyr Leu Cys Met Glu Arg Ser Gly Arg Leu Tyr
            100                 105                 110

Gly Ser Leu Gln Tyr Thr Glu Lys Asp Cys Thr Phe Lys Glu Val Val
        115                 120                 125

Leu Ala Asp Gly Tyr Asn Leu Tyr Val Ser Glu Glu His Gln Ala Thr
    130                 135                 140

Val Thr Leu Ser Pro Met Arg Ala Arg Ile Ala Gln Gly Lys Lys Ile
145                 150                 155                 160

Pro Pro Phe Ser His Phe Leu Pro Met Val Asn Lys Val Pro Val Glu
                165                 170                 175

Asp Val Ala Ala Glu Met Glu Phe Val Gln Val Leu Arg Glu Met Thr
            180                 185                 190

Ala Asp Val Asp Ser Pro Asp Pro Phe Gly Met Thr Trp Glu Glu Ser
        195                 200                 205

Val His Ser Pro Ser Phe Phe Ala
    210                 215


<210> SEQ ID NO 201
<211> LENGTH: 192
<212> TYPE: PRT
<213> ORGANISM: Tursiops truncatus

<400> SEQUENCE: 201
```

Met Gly Trp Asp Lys Thr Lys Leu Glu His Leu Gly Leu Trp Val Pro
1               5                   10                  15

Val Leu Ala Val Leu Leu Gly Pro Cys Gln Ala His Pro Ile Pro Asp
            20                  25                  30

Ser Ser Pro Leu Leu Gln Phe Gly Gly Gln Val Arg Gln Arg Tyr Leu
        35                  40                  45

Tyr Thr Asp Asp Ala Gln Glu Thr Glu Ala His Leu Glu Ile Arg Ala
    50                  55                  60

Asp Gly Thr Val Val Gly Thr Ala Arg Arg Ser Pro Glu Gly Val Lys
65                  70                  75                  80

Thr Ser Arg Phe Leu Cys Gln Gly Pro Glu Gly Arg Leu Tyr Gly Ser
                85                  90                  95

Leu His Phe Asn Pro Gln Ala Cys Ser Phe Arg Glu Leu Leu Leu Glu
            100                 105                 110

Asp Gly Tyr Asn Val Tyr Gln Ser Glu Ala Leu Gly Ile Pro Leu Arg
        115                 120                 125

Leu Pro Pro His Arg Ser Ser Asn Trp Asp Leu Ala Pro Arg Gly Pro
    130                 135                 140

Ala Arg Phe Leu Pro Leu Pro Gly Phe Leu Pro Pro Pro Leu Glu Pro
145                 150                 155                 160

Pro Gly Ile Leu Ala Pro Glu Pro Pro Asn Val Gly Ser Ser Asp Pro
                165                 170                 175

Leu Ser Met Val Gly Pro Ser His Gly Arg Ser Pro Ser Tyr Thr Ser
            180                 185                 190

<210> SEQ ID NO 202
<211> LENGTH: 209
<212> TYPE: PRT
<213> ORGANISM: Mustela putorius furo

<400> SEQUENCE: 202

Met Gly Trp Glu Glu Ala Arg Ser Glu His Leu Gly Leu Trp Val Pro
1               5                   10                  15

Val Leu Ala Val Leu Leu Leu Gly Ala Cys Gln Ala Tyr Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Glu Thr Glu Ala His Leu Glu Ile Arg
    50                  55                  60

Ala Asp Gly Thr Val Val Gly Ala Ala Arg Arg Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Gly Pro Asn Gly Thr Leu Tyr Gly
            100                 105                 110

Ser Phe His Phe Asp Pro Val Ala Cys Ser Phe Arg Glu Val Leu Leu
        115                 120                 125

Glu Asp Gly Tyr Asn Ile Tyr His Ser Glu Thr Leu Gly Leu Pro Leu
    130                 135                 140

Arg Leu Pro Pro His Asn Ser Pro His Arg Asp Leu Ala Pro Arg Gly
145                 150                 155                 160

Pro Ala Arg Phe Leu Pro Leu Pro Gly Leu Leu Pro Ala Thr Pro Glu
                165                 170                 175

Ser Arg Gly Ile Pro Ala Pro Glu Pro Pro Asn Val Gly Ser Ser Asp
            180                 185                 190

Pro Leu Ser Met Val Gly Pro Leu Gln Gly Gln Ser Pro Ser Tyr Thr
195 200 205

Ser

<210> SEQ ID NO 203
<211> LENGTH: 198
<212> TYPE: PRT
<213> ORGANISM: Takifugu rubripes

<400> SEQUENCE: 203

Phe Ile Tyr Leu Phe Ile Gln Thr Ala Leu Phe Ser Pro Ser Lys Trp
1 5 10 15

Phe Asn Phe Tyr Leu Pro Asp Ser Asn Pro Leu Leu Ser Phe Asp Ser
20 25 30

His Gly Arg Gly Ile His Leu Tyr Thr Asp Asn Gln Arg Arg Gly Met
35 40 45

Tyr Leu Gln Met Ser Thr Asp Gly Ser Val Ser Gly Ser Asp Val Gln
50 55 60

Thr Ala Asn Ser Val Leu Glu Leu Lys Ser Val Arg Asn Gly His Val
65 70 75 80

Val Ile Arg Gly Lys Ser Ser Ser Leu Phe Leu Cys Met Asp Ser Arg
85 90 95

Gly Arg Leu Trp Gly Gln Arg His Pro Thr Glu Ala Asp Cys Thr Phe
100 105 110

Arg Glu Val Leu Leu Ala Asp Gly Tyr Thr Arg Phe Leu Ser Leu His
115 120 125

Asn Gly Thr Pro Val Ser Leu Ala Pro Lys Gln Ser Pro Asp Gln His
130 135 140

Thr Val Pro Phe Thr Arg Phe Leu Pro Leu Arg Asn Thr Leu Ala Glu
145 150 155 160

Glu Ser Met Ser Glu Pro Pro Ser Asn Gln Gln Arg Tyr Phe Asn Ile
165 170 175

Asp Ser Asp Asp Leu Leu Gly Met Asp Leu Asn Ala Met Val Ser Pro
180 185 190

Gln Phe Ser Gly Asp Lys
195

<210> SEQ ID NO 204
<211> LENGTH: 203
<212> TYPE: PRT
<213> ORGANISM: Dipodomys ordii

<400> SEQUENCE: 204

Met Asp Gln Ala Lys Thr Arg Val Gly Ala Arg Gly Leu Gly Gly Leu
1 5 10 15

Val Leu Ala Val Ile Ile Leu Gly Ala Cys Lys Ala Arg Pro Ile Pro
20 25 30

Asp Ser Ser Pro Leu Leu Gln Phe Gly Gly Gln Val Arg Leu Arg His
35 40 45

Leu Tyr Thr Asp Asp Thr Gln Glu Thr Glu Ala His Leu Glu Ile Arg
50 55 60

Ala Asp Gly Thr Val Val Gly Thr Ala His Arg Ser Pro Glu Ser Leu
65 70 75 80

Leu Glu Leu Lys Ala Leu Lys Pro Gly Val Ile Gln Ile Leu Gly Ile
85 90 95

```
Lys Thr Ser Arg Phe Leu Cys Gln Arg Pro Asp Gly Thr Leu Tyr Gly
            100                 105                 110

Ser Leu His Phe Asp Pro Glu Val Cys Ser Phe Gln Glu Leu Leu Leu
        115                 120                 125

Glu Asp Gly Tyr Asn Ile Tyr Arg Ser Glu Ala Leu Gly Leu Pro Leu
    130                 135                 140

Arg Leu Ser Pro Asp Pro Ala Pro Trp Gly Pro Ala Arg Phe Leu Pro
145                 150                 155                 160

Leu Pro Gly Val Pro Pro Ala Pro Pro Glu Pro Pro Gly Ile Leu Ala
                165                 170                 175

Pro Glu Pro Pro Asp Val Gly Ser Ser Asp Pro Leu Ser Met Val Gly
            180                 185                 190

Leu Leu Gln Gly Arg Ser Pro Ser Tyr Ala Ser
        195                 200


<210> SEQ ID NO 205
<211> LENGTH: 184
<212> TYPE: PRT
<213> ORGANISM: Echinops telfairi

<400> SEQUENCE: 205

Met Gly Cys Thr Lys Ser Gly Trp Lys Ser Pro Gly Leu Trp Val Pro
1               5                   10                  15

Val Leu Ala Ser Leu Leu Leu Gly Gly Cys Gly Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Thr Thr Glu Ala His Leu Glu Ile Arg
    50                  55                  60

Ala Asp Gly Thr Val Gly Gly Val Ala His Gln Ser Pro Glu Lys Phe
65                  70                  75                  80

Leu Ser Gln Trp Arg Glu Lys Pro Leu Arg Ser Leu His Phe Asp Pro
                85                  90                  95

Ala Ala Cys Ser Phe Arg Glu Lys Leu Leu Glu Asp Gly Tyr Asn Leu
            100                 105                 110

Tyr His Ser Glu Thr His Gly Leu Pro Leu Arg Leu Pro Pro Arg Gly
        115                 120                 125

Gly Asp Pro Ser Ser Gln Pro Gly Ala Arg Phe Pro Pro Leu Pro Gly
    130                 135                 140

Gln Leu Pro Gln Leu Gln Glu Thr Pro Gly Val Leu Ala Pro Glu Pro
145                 150                 155                 160

Pro Asp Val Gly Ser Ser Asp Pro Leu Ser Met Val Gly Pro Trp Arg
                165                 170                 175

Gly Gln Ser Pro Ser Tyr Ala Ser
            180


<210> SEQ ID NO 206
<211> LENGTH: 210
<212> TYPE: PRT
<213> ORGANISM: Macaca mulatta

<400> SEQUENCE: 206

Met Asp Ser Asp Glu Thr Gly Phe Glu His Ser Gly Leu Trp Val Pro
1               5                   10                  15

Val Leu Ala Gly Leu Leu Leu Gly Ala Cys Gln Ala His Pro Ile Pro
            20                  25                  30
```

Asp Ser Ser Pro Leu Leu Gln Phe Gly Gly Gln Val Arg Gln Arg Tyr
35 40 45

Leu Tyr Thr Asp Asp Ala Gln Gln Thr Glu Ala His Leu Glu Ile Arg
50 55 60

Glu Asp Gly Thr Val Gly Gly Ala Ala His Gln Ser Pro Glu Ser Glu
65 70 75 80

Cys Gly Pro Glu Pro Gly Ser Glu Gly Gly Gly Ala Val Gly Gly Ala
85 90 95

Glu Gly Pro Gly Leu Leu Gly Leu Arg Glu Ala Gly Leu Gly Pro Gly
100 105 110

Ser Trp Leu His Phe Asp Pro Glu Ala Cys Ser Phe Arg Glu Leu Leu
115 120 125

Leu Glu Asn Gly Tyr Asn Val Tyr Gln Ser Glu Ala His Gly Leu Pro
130 135 140

Leu His Leu Pro Gly Asn Lys Ser Pro His Arg Asp Pro Ala Ser Gln
145 150 155 160

Gly Pro Ala Arg Phe Leu Pro Leu Pro Gly Leu Pro Pro Ala Pro Pro
165 170 175

Glu Pro Pro Gly Ile Leu Ala Pro Gln Pro Pro Asp Val Gly Ser Ser
180 185 190

Asp Pro Leu Ser Met Val Gly Pro Ser Gln Ala Arg Ser Pro Ser Tyr
195 200 205

Ala Ser
210

<210> SEQ ID NO 207
<211> LENGTH: 193
<212> TYPE: PRT
<213> ORGANISM: Microcebus marinus

<400> SEQUENCE: 207

Met Gly Trp Asp Glu Ala Gly Ala Gly Phe Glu His Pro Gly Leu Trp
1 5 10 15

Phe Pro Met Leu Gly Val Leu Leu Leu Gly Ala Cys Gln Ala Tyr Pro
20 25 30

Ile Pro Asp Ser Ser Pro Leu Leu Gln Phe Gly Gly Gln Val Arg Gln
35 40 45

Arg His Leu Tyr Thr Asp Asp Ile Gln Glu Thr Glu Ala His Leu Glu
50 55 60

Ile Arg Ala Asp Gly Thr Val Val Gly Ala Ala Arg Gln Ser Pro Glu
65 70 75 80

Leu Glu Leu Lys Ala Leu Lys Pro Gly Val Ile Gln Ile Leu Gly Val
85 90 95

Lys Thr Ser Arg Phe Leu Cys Gln Arg Pro Asp Gly Ala Leu Tyr Gly
100 105 110

Ser Leu His Phe Asp Pro Glu Cys Ser Phe Arg Glu Leu Leu Leu Glu
115 120 125

Asp Gly Tyr Asn Val Tyr Cys Pro Tyr Leu Pro Leu His Leu Ser Pro
130 135 140

Arg Ile Glu Leu Ala Gly Ser Arg Ser Ala Leu Pro Leu Pro Pro Ala
145 150 155 160

Pro Glu Arg Arg Ile Leu Ala Pro Glu Pro Pro Asp Gly Ser Ser Asp
165 170 175

Pro Leu Ser Met Val Gly Pro Ser Gln Gly Arg Ser Pro Ser Tyr Ala
180 185 190

Ser

<210> SEQ ID NO 208
<211> LENGTH: 204
<212> TYPE: PRT
<213> ORGANISM: Ochotona princeps

<400> SEQUENCE: 208

Lys Asp Met Asp Gly Leu Gln Pro Pro Gly Leu Arg Val Pro Val Leu
1 5 10 15

Ala Ala Leu Leu Leu Gly Val Gly Gln Ala Arg Pro Ile Pro Asp Ser
20 25 30

Ser Pro Leu Leu Gln Phe Gly Gly Gln Val Arg Gln Arg His Leu Tyr
35 40 45

Thr Asp Asp Ala Gln Glu Ser Glu Val His Leu Glu Ile Arg Ala Asp
50 55 60

Gly Thr Val Ala Gly Thr Ala Arg Arg Ser Pro Glu Ser Leu Leu Glu
65 70 75 80

Met Lys Ala Leu Lys Pro Gly Val Ile Gln Ile Leu Gly Val His Thr
85 90 95

Ser Arg Phe Leu Cys Gln Arg Pro Asp Gly Thr Leu Tyr Gly Ser Leu
100 105 110

His Phe Asp His Lys Ala Cys Ser Phe Arg Glu Gln Leu Leu Glu Asp
115 120 125

Gly Tyr Asn Val Tyr His Ser Glu Thr His Gly Leu Pro Leu Arg Leu
130 135 140

Ser Pro Asp Arg Ala Pro Arg Gly Pro Ala Arg Phe Leu Pro Leu Pro
145 150 155 160

Gly Pro Pro Pro Asp Leu Leu Val Pro Pro Leu Pro Pro Asp Val Leu
165 170 175

Ala Pro Glu Pro Pro Asp Val Asp Ser Pro Asp Pro Leu Ser Met Val
180 185 190

Gly Pro Leu Gln Gly Gln Ser Pro Ser Tyr Thr Ser
195 200

<210> SEQ ID NO 209
<211> LENGTH: 182
<212> TYPE: PRT
<213> ORGANISM: Xiphophorus maculatus

<400> SEQUENCE: 209

Cys Pro Phe Pro Phe Leu Phe Leu Ile Leu Ser Leu Pro Phe Phe Ser
1 5 10 15

Ser Ser Phe Tyr Ile Pro Glu Ser Asn Pro Ile Phe Ala Phe Arg Asn
20 25 30

Gln Leu Arg Glu Val His Leu Tyr Thr Glu Asn His Arg Arg Gly Leu
35 40 45

Tyr Val Glu Ile His Leu Asp Gly Arg Val Thr Gly Ser Asp Ala Gln
50 55 60

Ser Pro Tyr Ser Val Leu Gln Ile Lys Ser Val Lys Pro Gly His Val
65 70 75 80

Val Ile Lys Gly Gln Thr Ser Ser Leu Phe Leu Cys Met Asp Asp Ser
85 90 95

Gly Asn Leu Arg Gly Gln Thr Thr Tyr Asp Glu Ala Asp Cys Ser Phe
100 105 110

```
Arg Glu Leu Leu Leu Ala Asp Gly Tyr Thr Arg Phe Leu Asn Ser Gln
        115                 120                 125

His Gly Val Pro Leu Ser Leu Ala Ser Arg Asn Ser Pro Asp Arg His
    130                 135                 140

Ser Val Pro Phe Thr Arg Phe Leu Pro Leu Arg Asn Thr Leu Thr Val
145                 150                 155                 160

Ser Glu Glu Ser Thr Lys Thr Gln Arg Asp Phe Asn Leu Asp Ser Asp
                165                 170                 175

Asp Leu Leu Gly Met Gly
            180


<210> SEQ ID NO 210
<211> LENGTH: 192
<212> TYPE: PRT
<213> ORGANISM: Gasterosteus aculeatus

<400> SEQUENCE: 210

Ser Leu Leu Leu Met Val Pro Leu Pro Phe Cys Ser Ser Phe Tyr Leu
1               5                   10                  15

Thr Asp Ser Ser Pro Leu Leu Pro Phe Asn Asn Gln Val Lys Glu Val
            20                  25                  30

His Leu Tyr Thr Ala Glu Asn His Arg Arg Ala Met Tyr Leu Gln Ile
        35                  40                  45

Ala Leu Asp Gly Ser Val Ser Gly Ser Asp Ala Arg Ser Thr Tyr Ser
    50                  55                  60

Val Leu Gln Leu Lys Ser Ile Gln Pro Gly His Val Val Ile Arg Gly
65                  70                  75                  80

Lys Ala Ser Ser Met Phe Leu Cys Val Asp Ser Gly Gly Arg Leu Arg
                85                  90                  95

Gly Gln Gly Pro Tyr Ser Glu Ala Asp Cys Ser Phe Arg Glu Leu Leu
            100                 105                 110

Leu Gly Asp Gly Tyr Thr Arg Phe Leu Ser Ser Gln His Gly Ser Pro
        115                 120                 125

Leu Ser Leu Ala Ser Arg Pro Ser Pro Asp Pro Asn Ser Val Pro Phe
    130                 135                 140

Thr Arg Phe Leu Pro Ile Arg Thr Ala Pro Glu Ala Glu Ser Val Ile
145                 150                 155                 160

Glu Glu Pro Pro Ser Asn Gln Arg Tyr Val Asn Val Asp Ser Glu Asp
                165                 170                 175

Leu Leu Gly Met Gly Leu Asn Thr Val Val Ser Pro Gln Phe Ser Ala
            180                 185                 190


<210> SEQ ID NO 211
<211> LENGTH: 165
<212> TYPE: PRT
<213> ORGANISM: Sarcophilus harrisii

<400> SEQUENCE: 211

Val Ser Ala Met Gly Leu Arg Glu Arg Ala Pro Arg Tyr Leu Ala Pro
1               5                   10                  15

Leu Leu Ser Leu Leu Leu Ala Cys Arg Ala Ser Gly His Pro Leu Pro
            20                  25                  30

Asp Ser Ser Pro Met Leu Leu Phe Gly Gly Gln Val Arg Leu Arg His
        35                  40                  45

Leu Tyr Thr Asp Val Gly Gln Glu Ala Glu Ala His Val Glu Leu Ala
    50                  55                  60
```

```
Ser Asp Gly Thr Val Arg Ala Ala Ala Arg Arg Ser Pro Asn Ser Leu
65                  70                  75                  80

Leu Glu Leu Lys Ala Val Lys Pro Gly Ile Val Arg Ile Leu Ala Val
                85                  90                  95

His Ser Ser Arg Phe Leu Cys Met Arg Pro Asn Gly Glu Leu Tyr Gly
            100                 105                 110

Ala Ile His Tyr Asp Pro Ser Ala Cys Asn Phe Arg Glu Arg Leu Leu
        115                 120                 125

Gly Asp Gly Tyr Asn Val Tyr Glu Ser Glu Ala His Gly Arg Thr Leu
    130                 135                 140

Arg Leu Pro Pro Lys Ala Ala Pro Gly Pro Ala Gly Pro Ser Arg Phe
145                 150                 155                 160

Leu Pro Leu Pro Gly
                165


<210> SEQ ID NO 212
<211> LENGTH: 208
<212> TYPE: PRT
<213> ORGANISM: Macropus eugenii

<400> SEQUENCE: 212

Thr Glu Glu Pro Ser Thr Gly Ser Arg His Leu Gly Gln Trp Ala Pro
1               5                   10                  15

Gly Leu Pro Gly Pro Leu Leu Ser Leu Leu Leu Ala Tyr Arg Gly Trp
            20                  25                  30

Gly Ser Pro Ile Pro Asp Ser Ser Pro Met Leu Leu Phe Gly Gly Gln
        35                  40                  45

Val Arg Leu Arg His Leu Tyr Thr Asp Asp Gly Gln Asp Thr Glu Ala
    50                  55                  60

His Val Glu Leu Gly Pro Asp Gly Val Val Arg Ala Val Ala Glu Arg
65                  70                  75                  80

Ser Pro Asn Ser Leu Leu Glu Leu Lys Ala Val Lys Pro Gly Val Ile
                85                  90                  95

Arg Ile Leu Ala Val Gln Ser Ser Arg Phe Leu Cys Met Arg Pro Asn
            100                 105                 110

Gly Glu Leu Tyr Gly Ala Val His Tyr Asp Pro Ser Ala Cys Asn Phe
        115                 120                 125

Arg Glu His Leu Leu Gly Asp Gly Tyr Asn Val Tyr Glu Ser Glu Thr
    130                 135                 140

His Arg Arg Thr Leu Arg Leu Ser Pro Ser Leu Gly Gln Ala Gly Pro
145                 150                 155                 160

Ser Arg Phe Leu Pro Leu Pro Gly Asp Trp Leu Pro Gly Pro Asp Pro
                165                 170                 175

Pro Trp Ala Gln Gly Pro Glu Pro Pro Asp Val Gly Ser Ala Asp Pro
            180                 185                 190

Leu Ser Met Val Gly Ala Val Gln Gly Leu Ser Pro Ser Tyr Ser Ser
        195                 200                 205


<210> SEQ ID NO 213
<211> LENGTH: 160
<212> TYPE: PRT
<213> ORGANISM: Xenopus tropicalis

<400> SEQUENCE: 213

Arg Gly Gly Arg Thr Lys Lys Lys Thr Leu Leu Arg Lys Trp Leu Cys
1               5                   10                  15
```

```
Leu Leu Ala Ile Met Leu Ser Arg Ser Arg Phe Ser Leu Ala Asn Pro
            20                  25                  30

Ile Gln Asn Ser Asn Pro Ile Leu Ser Asn Asp Asn Gln Val Arg Thr
        35                  40                  45

Gln Tyr Leu Tyr Thr Asp Asn Asn Asn Met His Leu Tyr Leu Gln Ile
    50                  55                  60

Thr His Asn Gly Val Val Thr Gly Thr Glu Glu Lys Asn Asp Tyr Gly
65                  70                  75                  80

Val Leu Glu Ile Lys Ala Val Lys Ala Gly Val Val Val Ile Lys Gly
                85                  90                  95

Ile Arg Ser Asn Leu Tyr Leu Cys Met Asp Ser Arg His Gln Leu Tyr
            100                 105                 110

Ala Ser Ala Tyr Asp Lys Asp Asp Cys His Phe His Glu Lys Ile Thr
        115                 120                 125

Pro Asp Asn Tyr Asn Met Tyr Ser Ser Glu Lys His Ser Glu Tyr Val
    130                 135                 140

Ser Leu Ala Pro Leu Lys Gly Ser Gln Met Ala Arg Phe Leu Pro Ile
145                 150                 155                 160


<210> SEQ ID NO 214
<211> LENGTH: 194
<212> TYPE: PRT
<213> ORGANISM: Danio rerio

<400> SEQUENCE: 214

Met Leu Leu Ala Cys Phe Phe Ile Phe Phe Ala Leu Phe Pro His Leu
1               5                   10                  15

Arg Trp Cys Met Tyr Val Pro Ala Gln Asn Val Leu Leu Gln Phe Gly
            20                  25                  30

Thr Gln Val Arg Glu Arg Leu Leu Tyr Thr Asp Gly Leu Phe Leu Glu
        35                  40                  45

Met Asn Pro Asp Gly Ser Val Lys Gly Ser Pro Glu Lys Asn Leu Asn
    50                  55                  60

Cys Val Leu Glu Leu Arg Ser Val Lys Ala Gly Glu Thr Val Ile Gln
65                  70                  75                  80

Ser Ala Ala Thr Ser Leu Tyr Leu Cys Val Asp Asp Gln Asp Lys Leu
                85                  90                  95

Lys Gly Gln His His Tyr Ser Ala Leu Asp Cys Thr Phe Gln Glu Leu
            100                 105                 110

Leu Leu Asp Gly Tyr Ser Phe Phe Leu Ser Pro His Thr Asn Leu Pro
        115                 120                 125

Val Ser Leu Leu Ser Lys Arg Gln Lys His Gly Asn Pro Leu Ser Arg
    130                 135                 140

Phe Leu Pro Val Ser Arg Ala Glu Asp Ser Arg Thr Gln Glu Val Lys
145                 150                 155                 160

Gln Tyr Ile Gln Asp Ile Asn Leu Asp Ser Asp Asp Pro Leu Gly Met
                165                 170                 175

Gly His Arg Ser His Leu Gln Thr Val Phe Ser Pro Ser Leu His Thr
            180                 185                 190

Lys Lys


<210> SEQ ID NO 215
<211> LENGTH: 630
<212> TYPE: DNA
<213> ORGANISM: Homo sapiens
```

<400> SEQUENCE: 215
atggactcgg acgagaccgg gttcgagcac tcaggactgt gggtttctgt gctggctggt 60
cttctgctgg gagcctgcca ggcacacccc atccctgact ccagtcctct cctgcaattc 120
gggggccaag tccggcagcg gtacctctac acagatgatg cccagcagac agaagcccac 180
ctggagatca gggaggatgg gacggtgggg ggcgctgctg accagagccc cgaaagtctc 240
ctgcagctga aagccttgaa gccgggagtt attcaaatct tgggagtcaa gacatccagg 300
ttcctgtgcc agcggccaga tggggccctg tatggatcgc tccactttga ccctgaggcc 360
tgcagcttcc gggagctgct tcttgaggac ggatacaatg tttaccagtc cgaagcccac 420
ggcctcccgc tgcacctgcc agggaacaag tccccacacc gggaccctgc accccgagga 480
ccagctcgct tcctgccact accaggcctg ccccccgcac tcccggagcc acccggaatc 540
ctggcccccc agccccccga tgtgggctcc tcggaccctc tgagcatggt gggaccttcc 600
cagggccgaa gccccagcta cgcttcctga 630

<210> SEQ ID NO 216
<211> LENGTH: 630
<212> TYPE: DNA
<213> ORGANISM: Pongo abelii

<400> SEQUENCE: 216
atggactcgg acgagaccgg gttcgagcac tcaggactgt gggttcctgt gctggctggt 60
cttctgctgg gagcctgcca ggcacacccc atccctgact ccagtcctct cctgcaattc 120
gggggccaag tccggcagcg gtacctctac acagatgatg cccagcagac agaagcccac 180
ctggagatca gggaggatgg gacggtgggg ggcgctgctg accagagccc cgaaagtctc 240
ctgcagctga aagccttgaa gccgggagtt attcaaatct tgggagtcaa gacatccagg 300
ttcctgtgcc agaggccaga tggggccctg tatggatcgc tccactttga ccctgaggcc 360
tgcagcttcc gggagctgct tcttgaggac ggatacaatg tttatcagtc cgaggcccat 420
ggcctcccgc tgcacctgcc gggaaacaag tccccacacc gggaccctgc accccgagga 480
ccagctcgct tcctgccact accaggcctg ccccccgcac cccagagcc gcccggaatc 540 ctggcccccc agccccccga tgtgggctcc tcggaccctc tgagcatggt gggaccttcc 600
cagggccgaa gccccagcta tgcttcctga 630

<210> SEQ ID NO 217
<211> LENGTH: 630
<212> TYPE: DNA
<213> ORGANISM: Pan troglodytes

<400> SEQUENCE: 217
atggactcgg acgagaccgg gttcgagcac tcaggactgt gggtttctgt gctggctggt 60
cttctgctag gagcctgcca ggcacacccc atccctgact ccagtcctct cctgcaattc 120
gggggccaag tccggcagcg gtacctctac acagatgatg cccagcagac agaagcccac 180
ctggagatca gggaggatgg gacggtgggg ggcgctgctg accagagccc cgaaagtctc 240
ctgcagctga aagccttgaa gccgggagtt attcaaatct tgggagtcaa gacatccagg 300
ttcctgtgcc agaggccaga tggggccctg tatggatcgc tccactttga ccctgaggcc 360
tgcagcttcc gggagctgct tcttgaggac ggatacaatg tttaccagtc cgaggcccac 420
ggcctcccgc tgcacctgcc ggggaacaag tccccacacc gggaccctgc accccgagga 480
ccagctcgct tcctgccact accaggcctg ccccccgcac cccggagcc acccggaatc 540 ctggcccccc agccccccga tgtgggctcc tcagaccctc tgagcatggt gggaccttcc 600
cagggccgaa gccccagcta cacttcctga 630

<210> SEQ ID NO 218
<211> LENGTH: 630
<212> TYPE: DNA
<213> ORGANISM: Canis lupus familiaris

<400> SEQUENCE: 218
atgggctggg ccgaggccgg gttcgagcac ctgggactgt gggtccctgt gctggctgtg 60
cttttgctgg aagcctgccg ggcacatccg atccctgact ccagcccccct cctacaattt 120 ggaggtcaag ttcgacagcg gtacctctac accgacgatg cccaggagac agaggcccac 180
ctagagatca gggccgatgg cacagtggtg gggggctgccc gccagagccc tgaaagtctc 240
ctggagctga aagccctaaa gccaggggtc attcaaatct tgggagtcaa aacatccagg 300
ttcctgtgcc agggcccaga tggacacta tatggctcgc tccatttcga ccctgtggcc 360
tgcagtttcc gagaactgct tcttgaggat gggtacaaca tctaccactc cgagaccctt 420
ggtctcccgc ttcgcctgcg cccccacaac tccgcatacc gggacttggc accccgcggg 480
cctgcccgct tcctgccact gccaggcctg cttccagcac ccccagagcc tccagggatc 540
ctggccccgg agcctcctga cgtgggctcc tcggaccctc tgagcatggt ggggccttca 600
cagggccgga gtcccagcta tgcttcctaa 630

<210> SEQ ID NO 219
<211> LENGTH: 630
<212> TYPE: DNA
<213> ORGANISM: Bos Taurus

<400> SEQUENCE: 219
atgggctggg acgaggccaa gttcaagcac ttgggactgt gggtccctgt gctggctgtc 60
ctcctgctag gaacctgccg ggcgcatccc attccagact ccagcccccct cctccagttt 120 gggggccaag tccgccagcg gtacctctac acggatgatg cccaggagac agaggcccac 180
ctggagatca gggccgatgg cacagtggtg ggggcagccc gccagagccc cgaaagtctc 240
ttggagctga aagccctgaa gccaggcgtc attcagatct tgggagttaa aacatccagg 300
tttctctgcc aggggccaga tgggaagctg tacggatcgc tgcactttga ccccaaagcc 360
tgcagctttc gggagctgct tcttgaagat ggatacaacg tctaccagtc ggagaccctg 420
ggccttccac tccgcctgcc cccccagcgc tcgtccaacc gggacccggc cccgcgggga 480
cctgctcgct tccttccact gccgggcctg cccgcggcgc ccccggatcc tccagggatc 540
ttggcccccg agcctcccga cgtgggctcc tcggatcccc tgagtatggt gggaccctcg 600
tatggccgaa gccccagcta cacttcttga 630

<210> SEQ ID NO 220
<211> LENGTH: 630
<212> TYPE: DNA
<213> ORGANISM: Equus caballus

<400> SEQUENCE: 220
atggactggg acaagacggg gttcaagtac cagggactgt gggtccctgt gctggctgtc 60
cttctgctgg gagcctgcca gtcacacccc atccctgact ccagtcccct cctccaattc 120
gggggccaag tcaggcagcg ccacctctac acagatgatg cccaggagac agaggcgcac 180
ctggagatca gggctgacgg cactgtggca ggggctgtcc accggagccc agaaagtctc 240
ttggagctga aagccctgaa gccaggggta attcaaatct tgggagtcaa gacatccagg 300
tttctgtgcc aggggccaga cgggacgctg tacggatcgc tccacttcga ccccgtggcc 360
tgcagcttcc gggagctgct tctcgaagac ggctacaacg tttaccagtc tgagaccctt 420
ggcctcccac tccgcctgcc ccaccacagc tccccatacc aggatccggc ccctcgggca 480
cccgcccgct tcctgccgct gccaggcttt cccccagcac ccccggagcc tccagggatc 540
ccggcccccg agcccccgga cgtgggctcc tcggaccccc tgagcatggt ggggccttca 600
cgcagccgga gccccagcta cacttcctga 630

<210> SEQ ID NO 221
<211> LENGTH: 630
<212> TYPE: DNA
<213> ORGANISM: Ailuropoda melanoleuca

<400> SEQUENCE: 221
atgggctggg acgaggccag gtccgagcag ctggggctgt gggtccctgt gctggctgtc 60
cttttgctgg aagcttgcca ggcacaccct atccctgact ccagcccccct cctccaattc 120 ggaggccaag ttcgacagcg gtacctctac acggacgatg cccaggagac agaggcccac 180
ctagcgatca gggctgatgg cacagtggtg gggctgcca gccggagccc agaaagtctc 240
ttggagctga aagccctgaa accgggggtc attcaaatcc tgggagtgaa aacatctagg 300
ttcctgtgcc agggcccaga tgggacactg tacggatcgg tccgcttcga ccccgtagcc 360
tgcagcttcc gggaactgct cctggaggat gggtacaaca tctaccactc tgagaccctc 420
ggcctcccac ttcgcctgcc cgcccacaac tctccatacc gggactcggc gccccggggg 480
cctgcccgct tcctgcccct gccaggcctg cttccggtcc ccccggaccc cccagggatc 540
ctgggccccg agcctcccga cgtgggctcc tcggaccccc tgagcatggt ggggccttca 600
cagggccgaa gtcccagcta cgcttcctga 630

<210> SEQ ID NO 222
<211> LENGTH: 630
<212> TYPE: DNA
<213> ORGANISM: Oryctolagus cuniculus

<400> SEQUENCE: 222
atggactggg gcaaggccaa gtgccggccc ccggggctgt gggtccccgc gctcgctgcc 60
ctgctgctgg gggcctgcca ggcacacccc atccccgact ccagccccct cctccagttt 120
ggggaccaag tgcggcagca gcacctgtac acggacgatg cgcaggaaac agaagcccac 180
ctggagatca gggcggatgg cacggtggtg ggggctgccc ggaggagccc agaaagtctc 240
ttgcagatga aagccttaca accggggatc attcagatct tgggggtcca gacgtccagg 300
ttcctctgcc agaggccgga tggcacgctc tacggctcgc tccacttcga ccgcgaggcc 360
tgcagcttcc gggagctgct gcgtgaggat gggtacaacg tttacctctc ggaggccctg 420
ggcctgcccc tgcgcctgtc ccccggcagc tccccacgca gggcgccggc cccccgggga 480
ccagcccgct tcctgccgct gcccggcctg ccgccagacc ttccggaacc gccaggcctc 540
ctggccgccg cgccccccga tgtcgactcc ccggaccccc tgagcatggt gcagcctgcg 600
ctggaccaga gccccagcta cacctcctga 630

<210> SEQ ID NO 223
<211> LENGTH: 630

<212> TYPE: DNA
<213> ORGANISM: Gorilla gorilla

<400> SEQUENCE: 223
atggactcgg acgagaccgg gttcgagcac tcaggactgt gggtttctgt gctggctggt 60
cttctgctgg gagcctgcca ggcacacccc atccctgact ccagtcctct cctgcaattc 120
gggggccaag tccggcagcg gtacctctac acagatgatg cccagcagac agaagcccac 180
ctggagatca gggaggatgg gacggtgggg ggtgctgctg accagagccc tgaaagtctc 240
ctgcagctga aagccttgaa gccgggagtt attcaaatct tgggagtcaa gacatccagg 300
ttcctgtgcc agaggccaga tggggccctg tatggatcgc tccactttga ccctgaggcc 360
tgcagcttcc gggagctgct tcttgaggac ggatacaatg tttaccagtc cgaggcccac 420
ggcctcccgc tgcacctgcc ggggaacaag tccccacacc gggaccctgc accccgagga 480
ccagctcgct tcctgccact accaggcctg ccccccgcac ccccggagcc acccggaatc 540
ctggcccccc agccccccga tgtgggctcc tcggaccctc tgagcatggt gggaccttcc 600
cagggccgaa gccccagcta cgcttcctga 630

<210> SEQ ID NO 224
<211> LENGTH: 630
<212> TYPE: DNA
<213> ORGANISM: Nomascus leucogenys

<400> SEQUENCE: 224
atggactcgg acgagaccgg gttcgagcac tcaggactgt gggttcctgt gctggctggt 60
cttctgctgg gagcctgcca ggcacacccc atccctgact ccagtcctct cctgcaattc 120
gggggccaag tccggcagcg gtacctctac acagatgatg cccagcagac agaagcccac 180
ctggagatca gggaggatgg gacggtgggg ggcgctgctg accagagccc tgaaagtctc 240
ctgcagctga aagccttgaa gccgggagtt attcaaatct tgggagtcaa gacatccagg 300
ttcctatgcc agaggccaga tggggccctg tatggatcgc tccactttga ccctgaggcc 360
tgcagcttcc gggagctgct tcttgaggac ggatacaatg tttaccagtc cgaggcccat 420
ggcctcccgc tgcacctgcc ggggaacaag tccccacacc gggaccctgc accccgagga 480
ccagctcgct tcctgccact accaggcctg ccccctgcac ccccagagcc gcccggaatc 540
ctggcccccc agccccccga tgtgggctcc tcggaccctc tgagcatggt gggaccttcc 600
cagggccgaa gccccagcta cgcttcctga 630

<210> SEQ ID NO 225
<211> LENGTH: 630
<212> TYPE: DNA
<213> ORGANISM: Procavia capensis

<400> SEQUENCE: 225
atggactggg ccaagtttgg gatcgagcac ccgggactgt gggtcccggt gatggcagta 60
cttctgctgg gagcctgcca aggataccct attcctgact ccagccccct tctccaattc 120
ggaggccagg tccggcaacg ttacctctac acagatgacg cgcaggagac cgaggcccac 180
ctggagatcc gagcagacgg cacggtggtg ggggctgccc accggagccc cgagagtctc 240
ttggagctga aagctttgaa gcccggcata attcagatct tgggagtcaa gacatccaga 300
ttcctctgcc agggtcctga tggggtgctg tatggatcgc tccgttttga cccagtggcc 360
tgcagcttcc gggagctgct tcttgaagat ggatacaatg tttaccagtc tgaggcccac 420

-continued

```
ggcctcccgc ttcgcctacc atcccacaat tccccacaga gggacctggc gtcccgggtg    480

ccagcccgct tcctgccact gccaggccgg ctcacggtgc tcccagaacc ttcgggggtc    540

ctgggccctg agccccccga tgtggactcc tcagacccc tgagcatggt ggggccttcg    600

cagggccgaa gccccagtta cgcctcctga                                    630
```

<210> SEQ ID NO 226
<211> LENGTH: 630
<212> TYPE: DNA
<213> ORGANISM: Cavia porcellus

<400> SEQUENCE: 226

```
atggactggg cccggactga gtgtgagcgc ccaaggctgt gggtctccat gctggccatc     60

cttctggtgg gagcctgcca ggcacaccct atccctgact ccagcccccct cctccagttt    120

gggggccagg tccggcagcg gtacctctac acagatgatg ctcaggacac tgaagtgcac    180

ctggagatca gggccgatgg ctcagtacgg ggcattgccc acaggagccc tgaaagtctc    240

ctggagctga aagccttgaa gccaggagtc attcagatct tgggaatcag gacttccagg    300

ttcctgtgcc agaggcccga tgggagtctg tatggatcac tccactttga tcctgaggcc    360

tgcagcttcc gggagctgct gcttgctgat ggctacaatg tctacaagtc tgaagcccac    420

ggcctccctc tgcacctgct gcgcggtgac tctctatcgc aggaaccagc acccccagga    480

ccagcccgat ttctgccact accaggcctg cccgcaacac cccggagcc acccaggatg    540

ctgcccccag ggcccccaga tgtgggctcc tcggaccctt tgagcatggt ggggccttta    600

tgggaccgaa gccccagcta tacttcctga                                    630
```

<210> SEQ ID NO 227
<211> LENGTH: 583
<212> TYPE: DNA
<213> ORGANISM: Tupaia belangeri

<400> SEQUENCE: 227

```
atgggctggg acaaggcccg gttcgagcac ctgggagcgt gggctcctgt gctggctgtc     60

ctcctcctgg gagcctgcca ggcatacccc atccctgact ccagcccccct cctacaattc    120

gggggccagg tccggcagcg gtacctctac acggacgaca cgcaggacac agaagcccac    180

cttgagatca gggccgacgg caccgtggtg gggggccgccc accaaagccc ggaaagtctc    240

ctggagctga aagccttgaa gccgggggtc attcaaatcc tgggagtcaa gacctccagg    300

ttcctgtgcc agaggccaga cggggccctg tacgggtcgc ttcacttcga ccccgaggcc    360

tgcagcttcc gggagctgct tctcgaggat ggatacaaca tttaccagtc tgaggctcgt    420

ggcctccccc tgcgcctgcc gccccacgac tccccacatc gggaccggac cctcgggga    480

ccagctcgtt tcctgccgct gcctggcctg cccctggttc ctccagagct gccaggggtc    540

ctggcccttg agccccccga cgtgggctcc tcagacccgc tga                      583
```

<210> SEQ ID NO 228
<211> LENGTH: 586
<212> TYPE: DNA
<213> ORGANISM: Sorex araneus

<400> SEQUENCE: 228

```
atggtctggg acaaggccag ggggcagcag ttgggactgt gggcccccat gctgctgggc     60

ttgctgctgg gtgcctgcca ggcacacccc ctccctgact ccagcccccct cctccaattt    120

gggggccaag tccgactgag gttcctgtac accgacgatg cccagaggac aggggcgcac    180
```

ctggagatca gggccgacgg cacagtgcag ggtgcggccc acaggacccc agaatgtctc 240
ctggagctga aagccttgaa gccaggcgta attcaaatcc ttggggtcag cacatccaga 300
ttcctgtgcc agcggcccga tggggtcctg tatggatcgc ttcgctttga cccagaggcc 360
tgcagtttcc gggaacttct tctccaggat ggatataacg tttaccagtc tgaggccctg 420
ggtctcccgc tctacctaca cccgcccagt gccccagtgt cccaggaacc agcctcacgg 480
ggcgccgtcc gcttcctgcc actgccagga ctgccacctg cctccctgga gcccccccagg 540 ccccccgccc cggtgcctcc agacgtgggt tcctcagacc ccctga 586

<210> SEQ ID NO 229
<211> LENGTH: 546
<212> TYPE: DNA
<213> ORGANISM: Ictidomys tridecemlineatus

<400> SEQUENCE: 229
atgtacccca tccctgactc aagccccctc ctccaatttg gggggccaagt ccggcagcgg 60 tacctgtaca cagatgatgc ccaggagact gaggcccacc tggagatcag ggctgatggc 120
accgtggtgg gggctgccca tcaaagcccg gaaagtctct tggaactgaa agccttgaag 180
cctggggtca ttcaaatctt gggggtcaaa acatccaggt tcctgtgcca gaggccagat 240
ggagtgctgt atggatcgct ccactttgac cctgaggcct gcagcttccg ggagcagctt 300
ctggaggacg ggtacaacgt ttaccagtca gaatcccacg gcctccccgt gcgcctgccc 360
cctaactcac cataccggga cccagcgccg ccaggaccag cccgcttcct tccactgcca 420
ggcctgcccc cagcagccct ggagccgcca gggatcctgg gccctgagcc ccctgatgtg 480
ggctcctccg acccactcag catggtgggg cctttgcagg gccgaagccc cagttacgct 540
tcctga 546

<210> SEQ ID NO 230
<211> LENGTH: 627
<212> TYPE: DNA
<213> ORGANISM: Loxodonta africana

<400> SEQUENCE: 230
atggactggg ccaagtttgg gttggagcac ccaggactgt gggtccctgt gatggctgtc 60
cttctgctgg gagcctgcca gggacacccc atccctgact ccagcccccct cctccaattc 120 gggggccagg tccggcaacg ttacctctac acagatgatc aggagaccga ggcccacctg 180
gagatcagag cagatggcac agtggcggga gccgctcacc ggagctctga gagtctcttg 240
gagctgaaag ctttgaagcc tggaataatt cagatcttgg gggtcaagac atcccggttc 300
ctgtgccagg ggcctgatgg ggtgctgtac ggatcgctcc atttcgaccc agccgcctgc 360
agcttccggg agctgcttct tgaagatgga tacaatgttt actggtccga ggcccatgga 420
ctcccaatcc gcctgccctc ccacaactcc ccatataggg acccagcatc ccgggtacca 480
gcccgcttcc tgccactgcc aggcctgctc ccaatgctcc aagaacctcc aggggtcctg 540
gcccctgagc cccctgatgt ggactcctca gaccccctga gcatggtggg gccttcacag 600
ggccgaagcc ccagctatgc ctcctga 627

<210> SEQ ID NO 231
<211> LENGTH: 627
<212> TYPE: DNA
<213> ORGANISM: Sus scrofa

<400> SEQUENCE: 231
atgggctggg ccgaggccaa gttcgagcgc ttgggactgt gggtccctgt gctggctgtc 60
ctgctgggag cctgccaggc acgtcccatt cctgactcca gccccctcct ccaatttggg 120
ggccaagtgc gccaacgata cctctacacg gatgatgccc aggaaactga agcccacctg 180
gagatcagag ctgatggcac cgtggcaggg gtagcccgcc agagccctga aagtctcttg 240
gagctgaaag ccctgaagcc aggggtcatt caaattttgg gagtccagac atcccggttc 300
ctgtgccagg ggccagacgg gagactgtac ggatcgctcc acttcgaccc tgaggcctgc 360
agcttccggg agctgcttct tgaggatggc tacaacgttt accagtctga ggcccttggc 420
ctcccactcc ggctgcctcc gcaccgctcc tccaaccggg acctggcccc ccggggacct 480
gctcgcttcc tgccactgcc aggcctgccc ccggcacccc cggagccgcc agggatcttg 540
gcccctgaac ctcccgacgt gggctcctcg gacccccctga gcatggtggg gccttcacac 600
ggccggagcc ccagctacac ttcttga 627

<210> SEQ ID NO 232
<211> LENGTH: 627
<212> TYPE: DNA
<213> ORGANISM: Felis catus

<400> SEQUENCE: 232
atgggctggg acgaggccgg gtcccagcgc ctgggactgt gggtcgtgct gggggtcctt 60
ttgccggaag cctgccaggc acaccctatc cctgactcca gccccctcct ccaattcggg 120
ggccaagttc gacagcggtt cctctacacg gacgacgccc aggagacaga ggtccacctc 180
gagatcaagg ctgatggcac agtggtgggg accgctcgcc ggagccctga gagtctcttg 240
gagctaaaag ccctgaagcc gggggtaatt caaatcttgg gggtcaaaac gtccaggttc 300
ctgtgccagg gcccagatgg gacactgtat ggatcgctcc gctttgaccc cgcagcctgc 360
agcttccggg aactgctcct ggaggacgga tacaacatct accactcgga gaccctcggg 420
ctcccactcc gcctgccccc ccacaactcc ccataccggg acttggcccc ccgggcacct 480
gcccgcttcc tgccgctgcc aggcctgctt ccggcacccc cggagcctcc agggatcctg 540
gcccccgagc cccggacgt gggctcctcg gaccctctga gcatggtggg gccttcccag 600
ggccgaagtc ccagctacgc ttcctga 627

<210> SEQ ID NO 233
<211> LENGTH: 627
<212> TYPE: DNA
<213> ORGANISM: Otolemur garnetti

<400> SEQUENCE: 233
gacaaggcca ggactgggtt caagcaccca ggaccatggt ttcccctgct ggctgtactt 60
ttgttgggag cctgccaggc acaccctatc cctgactcca gcccccctact ccagtttggt 120 ggccaagtcc ggcagcggta cctctacaca gatgatgccc aggagacaga agcccacctg 180
gagatcaggg aagatggcac agtggtgggg gctgcacaac agagccctga aagtctcttg 240
gagctgaaag ctttaaagcc aggggtcatt caaatcttgg gagtcaagac atccaggttc 300
ctgtgccaga ggccagatgg gggcctatat ggatcgctct actttgaccc caaggcctgc 360
agtttccggg agctgcttct tgaggatgga tacaacgttt actggtctga gacctatggc 420
ctcccactgc acctgcctcc tgccaattcc ccatactggg gcccatccct tcggagccca 480
gcccgcttcc tgccactgcc aggccctcct gcagcatccc cagagctgcc ggggatcttg 540
gccctggaac cccccgatgt gggctcctcg gaccctctga gcatggtggg gccttcgcag 600
ggccgaagcc ccagctatgc ttcctga 627

<210> SEQ ID NO 234
<211> LENGTH: 627
<212> TYPE: DNA
<213> ORGANISM: Rattus norvegicus

<400> SEQUENCE: 234
atggactgga tgaaatctag agttggggcc ccgggactgt gggtctgtct cctgctgcct 60
gtcttcctgc tgggggtgtg cgaggcatac cccatctctg actccagccc cctcctccag 120
tttgggggtc aagtccgaca gaggtatctc tacacagatg acgaccagga caccgaagcc 180
cacctggaga tcagggagga cggaacagtg gtgggcacag cacaccgcag tccagaaagt 240
ctcctggagc tcaaagcctt gaagccaggg gtcattcaaa tcctgggtgt caaagcctct 300
aggtttcttt gccaacaacc agatggaact ctctatggat cgcctcactt tgatcctgag 360
gcctgcagtt tcagagagct gctgcttaag gacggataca atgtgtacca gtctgaggcc 420
catggcctgc ccctgcgtct gccccagaag gactcccagg atccagcaac ccggggacct 480
gtgcgcttcc tgcccatgcc aggcctgccc cacgagcccc aagagcaacc aggagtcctt 540
cccccagagc cccagatgt gggttcctcc gaccccctga gcatggtaga gcctttgcaa 600
ggccgaagcc ccagctatgc atcttga 627

<210> SEQ ID NO 235
<211> LENGTH: 633
<212> TYPE: DNA
<213> ORGANISM: Mus musculus

<400> SEQUENCE: 235
atggaatgga tgagatctag agttgggacc ctgggactgt gggtccgact gctgctggct 60
gtcttcctgc tgggggtcta ccaagcatac cccatccctg actccagccc cctcctccag 120
tttgggggtc aagtccggca gaggtacctc tacacagatg acgaccaaga cactgaagcc 180
cacctggaga tcagggagga tggaacagtg gtaggcgcag cacaccgcag tccagaaagt 240
ctcctggagc tcaaagcctt gaagccaggg gtcattcaaa tcctgggtgt caaagcctct 300
aggtttcttt gccaacagcc agatggagct ctctatggat cgcctcactt tgatcctgag 360
gcctgcagct tcagagaact gctgctggag gacggttaca atgtgtacca gtctgaagcc 420
catggcctgc ccctgcgtct gcctcagaag gactccccaa accaggatgc aacatcctgg 480
ggacctgtgc gcttcctgcc catgccaggc ctgctccacg agccccaaga ccaagcagga 540
ttcctgcccc cagagccccc agatgtgggc tcctctgacc ccctgagcat ggtagagcct 600
ttacagggcc gaagccccag ctatgcgtcc tga 633

<210> SEQ ID NO 236
<211> LENGTH: 324
<212> TYPE: DNA
<213> ORGANISM: Vicugna pacos

<400> SEQUENCE: 236
atggactggg acgaggccaa gttcgagcat cggggactgt gggtcccagt gctcactgtc 60
cttctgctgg gagcctgcca ggcacgcccc attcctgact ccagcccccct cctccaattc 120 gggggccaag tccggcagcg gtacctctac acggatgacg cccaggagac agaagcccac 180

```
ctggagatca gggctgatgg cacagtggtg ggggtggccc gccagcccga aggaattcct    240

cccgagcctc ctgacgtggg ctcctcagac cccctgagca tggtggggcc ttcatacagc    300

agaagcccca gctacacttc ctga                                           324
```

<210> SEQ ID NO 237
<211> LENGTH: 633
<212> TYPE: DNA
<213> ORGANISM: Anolis carolinensis

<400> SEQUENCE: 237

```
tgtaaaagca agggaggagg gaagggggga gagaggatgt gggtagacct agttttctgg     60

gctgccttgc tccgcacagc tcctgctctt cccttgcgga attccaaccc catctaccaa    120

tttgatgggc aggtccggct tcggcacctc tacacagcag atgaacagac gcacctccac    180

ttggagatct tgccagacgg taccgtgggt ggatccaggt ttcagaatcc cttcagtttg    240

atggagatca aagctgtgaa gccaggagtc attcgcatgc aggccaagaa gacctctaga    300

tttctctgta tgaaacccaa tggacgactg tatggctcgc tgttctactc tgaggaggca    360

tgcaacttcc atgagaaggt tctcagcgat ggctacaacc tctactattc tgaaaactac    420

aacatacctg tcagcctcag ctcggcaggg aacctgggtc agagccgtca gttgcctccc    480

ttctcccaat tcctgccgtt agtcaacaaa attcctcttg agcctgtgct tgaagacttt    540

gacttctatg gacatcaatt ggatgttgaa tcagctgatc ctttgagcat tttaggacaa    600

aaccctggtt tcatgagtcc gagctatgtc ttc                                 633
```

<210> SEQ ID NO 238
<211> LENGTH: 564
<212> TYPE: DNA
<213> ORGANISM: Gadus morrhua

<400> SEQUENCE: 238

```
ctcctcctcg ccaccctcct ccacatcggc ctctccttct acgtccccga ctccggcccc     60

ctgctgtggc tgggcgacca ggtcagggag agacacctct acacagcaga gagccaccgg    120

agggggctgt tcctggagat gagcccggac ggtcaggtga caggaagtgc tgctcagacg    180

ccgctcagtg ttctggagct gaggtcggtc agagcaggag atacggtcat cagagcgcgc    240

ctctcctctc tctacctgtg tgtggacagg gcaggtcacc tgacaggaca gagacagtac    300

acagagtccg actgcacctt cagagaggtc atccttgagg acggctacac ccacttcctg    360

tccgtgcacc acggacttcc tatttcgctg gcgccgagac actccccagg gagacagggg    420

ctgcgcttca gcaggttcct cccgctgagg agcagtctgt cagaggatag ggtcgccgag    480

cccccagaca gcccactgaa cctggactct gaagaccccc tggggatggg tctgggttcg    540

ctcctcagcc cggccttctc catg                                           564
```

<210> SEQ ID NO 239
<211> LENGTH: 648
<212> TYPE: DNA
<213> ORGANISM: Latimeria chalumnae

<400> SEQUENCE: 239

```
atgttatgcc agagttttgt gatattaagt cagaaattca tttttgggct ctttttgact     60

ggattggggc taacaggatt ggcttggaca aggcccttcc aggattccaa tcccatcctg    120

cagtattccg attccatccg gctccgacat ctgtacactg ccagtgagag tcggcacctt    180

cacctacaaa tcaactcgga tggacaggtg ggagggacaa ccaagcaaag cccttacagt    240
```

ctgttggaga tgaaggcggt gaagacaggt tttgtggtca tcaggggcaa gaaaagcgcc 300
cgttacctct gtatggaacg tagtggacgg ctctatggat cgctgcagta tacagaaaaa 360
gactgcacct tcaaagaggt tgtgttggca gatggataca acctgtatgt ctcagaggaa 420
caccaggcca cagtgacgct gagccccatg agggcgagga tagcgcaagg gaaaaagatc 480 ccacccttt cccatttcct tccaatggtg aacaaggtgc ctgtggagga tgttgccgct 540
gagatggagt ttgtccaggt gctgcgggaa atgacggccg acgtggactc tccggatccc 600
tttggaatga cctgggaaga atcggttcac agtccgagct tttttgcc 648

<210> SEQ ID NO 240
<211> LENGTH: 579
<212> TYPE: DNA
<213> ORGANISM: Tursiops truncatus

<400> SEQUENCE: 240
atgggctggg acaagaccaa actcgagcac ctgggactgt gggtccctgt gctagctgtc 60
ctgctgggac cctgccaggc acatcccatt cctgactcca gccccctcct ccaatttggg 120
ggccaagtcc gccagcgata cctctacacg gatgacgccc aggagacgga ggcccacctg 180
gagatcaggg ctgatggcac agtggtgggg acggcccgcc ggagccccga aggagttaaa 240
acatccaggt tcctgtgcca ggggccagag gggaggctgt atggatcgct ccacttcaac 300
ccccaggcct gcagcttccg ggagctgctt cttgaggatg gatacaacgt ttaccagtct 360
gaggctcttg gcattcccct ccgcctgccc ccgcaccgct cctccaactg ggacctggcc 420
ccccggggac ctgctcgctt cctgccgctg ccaggcttcc tcccgccacc cctggagcct 480
ccagggatct tggcccccga gcctcccaac gtaggttcct cggacccctt gagcatggtg 540
ggaccttcac atggccgaag ccccagctac acttcctga 579

<210> SEQ ID NO 241
<211> LENGTH: 630
<212> TYPE: DNA
<213> ORGANISM: Mustela putorius furo

<400> SEQUENCE: 241
atgggctggg aagaggccag gtccgagcac ctggggctgt gggtccctgt gctggcggtc 60
cttttgctgg gagcctgcca ggcataccct attcctgact ccagccccct cctccaattt 120
ggaggccaag ttcgacagcg gtacctctac acagacgacg ctcaggagac ggaggcccac 180
ctagagatca gggctgatgg cacggtggtg ggggctgccc gccggagccc cgaaagtctc 240
ttggagctga aagccctgaa gccaggggtc attcagatct tgggagtgaa aacatccagg 300
ttcctgtgcc agggcccgaa tgggacactg tacggatcgt tccacttcga ccccgtagcc 360
tgcagcttcc gggaagtgct tctggaagat ggatacaaca tctaccactc tgagaccctg 420
ggcctcccac tgcgcctgcc cccccacaac tccccacaca gggacctggc gccccggggg 480
cctgcccgct tcctgcccct gccaggcctg cttccggcca ccccggagtc ccgggggatc 540
ccagcccccg agcctcccaa cgtgggctcc tcagaccccc tgagcatggt ggggcctttg 600
cagggtcaaa gtcccagcta cacttcctga 630

<210> SEQ ID NO 242
<211> LENGTH: 597
<212> TYPE: DNA
<213> ORGANISM: Takifugu rubripes

<400> SEQUENCE: 242
tttatttatt tatttattca aactgcactt ttttcccctt ccaaatggtt caacttttat 60
ctccctgact ccaacccgct cttatccttt gacagtcatg gcagaggcat ccacctctac 120
acagataatc aaaggcgagg gatgtatctg cagatgagca cagatggaag cgtttccggg 180
agtgatgtcc agacggcgaa cagtgtgctg gaactgaagt cagtcagaaa cggccacgtc 240
gtcatccgag gaaaatcgtc ttctctgttt ctctgtatgg acagcagagg ccgtttatgg 300
gggcagaggc accccactga ggccgactgc actttcaggg aagtgttgct ggcagatgga 360
tacactcgct tcctgtccct gcacaacgga actcctgtgt ctctggcacc taaacaatct 420
ccagaccagc acacagtccc cttcactcgt ttcctgccgc tcaggaatac actggcagag 480
gagagcatgt ctgaaccacc atcaaaccaa cagagatatt ttaacattga ctctgatgat 540
cttcttggaa tggatttaaa tgcgatggtc agtcctcagt tttcagggga caagtga 597

<210> SEQ ID NO 243
<211> LENGTH: 612
<212> TYPE: DNA
<213> ORGANISM: Dipodomys ordii

<400> SEQUENCE: 243
atggaccagg caaagaccag ggttggggcc cgggggctgg ggggccttgt gctggctgtc 60
ataattctgg gagcatgcaa ggcacggcct atccctgact ccagcccccct cctccaattt 120 gggggtcaag ttcggcttcg gcacctctac acagatgaca ctcaggagac ggaagcccat 180
ctggagatca gggcagatgg cacggtagtg gggactgccc accggagccc tgaaagtctc 240
ttggagctga aagccttgaa gccaggagtc attcaaatct tagggatcaa gacatccaga 300
ttcttatgcc agagaccaga cgggacactg tatggatcac tccactttga ccctgaggtt 360
tgcagcttcc aggagctgct tctggaagat ggatacaaca tttaccgttc tgaagccctg 420
ggtctccccc tgcgcctgtc cccagatcca gcaccctggg ggccagcccg cttcctgccc 480
ctgcctggtg tgccccccgc accgccggag ccccccggga tcctggctcc cgaacccccct 540 gatgtcggct cctccgaccc tctgagtatg gtgggactgt tgcagggccg aagccccagc 600
tatgcatcct ga 612

<210> SEQ ID NO 244
<211> LENGTH: 555
<212> TYPE: DNA
<213> ORGANISM: Echinops telfairi

<400> SEQUENCE: 244
atgggttgca ccaaatctgg gtggaagtcc ccgggactgt gggtccctgt gctggccagc 60
cttctgctgg gaggctgcgg agcacacccc atccctgact ccagcccccct cctccaattc 120 gggggccaag tccggcagcg atacctctat acggatgacg cccagaccac cgaggcccac 180
ctggagatca gagcggatgg cacagtgggg ggcgtcgccc accagagccc agagaagttc 240
ctgagtcaat ggcgtgaaaa gcccctgaga tcactccatt tcgacccagc cgcctgcagc 300
ttccgggaga agcttctaga agacggatac aacttgtacc actctgagac ccacggcctc 360
cccctccgcc tcccaccccg tgggggcgac ccctcttctc agcctggggc ccgcttccca 420
ccgctgccgg gccagctccc acaactccaa gagacgccag ggtcctcgc ccccgaaccc 480 cccgacgtgg gctcttcaga ccccctgagc atggtggggc cttggcgagg gcaaagtccc 540
agttatgcct cctga 555

<210> SEQ ID NO 245
<211> LENGTH: 633
<212> TYPE: DNA
<213> ORGANISM: Macaca mulatta

<400> SEQUENCE: 245
atggactcgg acgagaccgg gttcgagcac tcaggactgt gggttcctgt gctggctggt 60
cttctgctgg gagcctgcca ggcacacccc atccctgact ccagtcctct cctgcaattc 120
gggggccaag tccggcaacg gtacctctac acagatgatg cccagcagac agaagcccac 180
ctggagatca gggaggatgg gacagtgggg ggcgctgctc accagagccc cgaaagtgag 240
tgtgggccag agcctgggtc tgagggagga ggggctgtgg gaggtgctga gggacctgga 300
ctcctgggtc tgagggaggc agggctgggg cctggatcct ggctccactt tgaccctgag 360
gcctgcagct tccgggagct gcttcttgag aacggataca atgtttacca gtccgaggcc 420
cacggcctcc cactgcacct gccgggaaac aagtccccac accgggaccc tgcatcccaa 480
ggaccagctc gcttcctgcc actaccaggc ctgccccccg cacccccgga gccgccagga 540
atcctcgccc cccagccccc cgatgtgggc tcctcggacc ctctgagcat ggtgggacct 600
tcccaggccc gaagccccag ctatgcttcc tga 633

<210> SEQ ID NO 246
<211> LENGTH: 582
<212> TYPE: DNA
<213> ORGANISM: Microcebus marinus

<400> SEQUENCE: 246
atgggctggg acgaggccgg cgccgggttc gagcacccag gactgtggtt tcccatgctg 60
ggtgtcctgc tgctgggagc ctgccaggcg taccccatcc ctgactccag ccccctcctc 120
caatttggcg gccaagtccg gcagcggcac ctctacacag acgatatcca ggagacagaa 180
gcccacctgg agatcagggc ggacggcaca gtggtggggg ccgccccgaca gagccctgag 240 ttggagctga aagccttaaa gccaggggtc attcaaatct tgggagtcaa gacctccagg 300
ttcctgtgcc agaggccaga cggggccctg tacggatcgc tccactttga ccccgagtgc 360
agcttccggg agctgcttct tgaggatgga tacaacgtct actgtcccta cctcccgctg 420
cacctgtccc cacgcatcga actggccgga tcacgctctg cgctgccact gcccccagca 480
cctgaacgca ggattttggc cccggagccc ccggatggct cctcggaccc tctgagcatg 540
gtggggcctt cgcagggccg aagtcccagc tatgcttcct ga 582

<210> SEQ ID NO 247
<211> LENGTH: 615
<212> TYPE: DNA
<213> ORGANISM: Ochotona princeps

<400> SEQUENCE: 247
aaagacatgg acgggctcca gcctccgggg ctgcgggttc ctgtgctggc tgccctgctt 60
ttgggagttg gccaggcacg ccccatccct gattctagcc ctctcctcca attcgggggc 120
caggtccggc agaggcacct ctacacggat gacgcccagg aatcggaagt acacctggag 180
atccgggcag acggcaccgt ggcagggact gcccgccgga gccctgaaag tctcttagaa 240
atgaaagcgt tgaagccagg cgtcattcag atcctggggg tccacacatc caggttcctg 300
tgccagagac cagacgggac gctgtacggc tcgctccact tcgaccacaa ggcctgcagc 360

```
ttccgggagc agctgctgga ggatgggtac aacgtgtacc actcagagac acacggcctc    420

ccgctgcgcc tgtctccaga ccgagccccc cggggcccag cccgcttcct gccactgcca    480

ggccctcctc ctgacctcct ggtgccaccc ctgccaccgg acgtcctagc ccctgagccc    540

cccgacgtgg actccccaga ccccctgagc atggtggggc ccttgcaggg ccaaagcccc    600

agctacactt cctga                                                     615


<210> SEQ ID NO 248
<211> LENGTH: 546
<212> TYPE: DNA
<213> ORGANISM: Xiphophorus maculatus

<400> SEQUENCE: 248

tgcccgttcc ccttcctttt cttaatcctc tctcttccct ttttctcttc ctcgttttac     60

atcccagaat ccaacccaat ctttgccttc aggaatcagc tcagagaggt gcatctctac    120

acagaaaatc acagacgggg tttgtatgtg gagatacatc tggatgggag agtgactgga    180

agtgatgctc agagtcctta tagtgtgttg cagataaagt ctgttaaacc gggtcatgtg    240

gtcataaagg gacagacatc gtccctgttc ctctgcatgg acgactccgg gaatctaaga    300

ggacagacaa cctatgacga ggctgactgc tccttcaggg aactgctgct ggccgatggc    360

tacacccgtt tcctgaactc acaacatggc gttcctttat cactggcatc cagaaactct    420

ccagatcgac actccgttcc tttcacaaga tttttacctc tcaggaatac tttaacggtt    480

tcagaagaat caacaaaaac tcagagggac ttcaacctgg actcggacga ccttctcggg    540

atggga                                                               546


<210> SEQ ID NO 249
<211> LENGTH: 576
<212> TYPE: DNA
<213> ORGANISM: Gasterosteus aculeatus

<400> SEQUENCE: 249

tctctcctcc tcatggtccc acttcctttc tgttcatcct tttatctcac tgactccagc     60

ccacttctac ccttcaataa tcaagtcaaa gaggtgcacc tctacacagc agagaatcac    120

agaagagcga tgtacctgca gatcgctctg gacgggagcg tgtcgggaag cgacgctcgg    180

tccacttaca gtgtgctgca gctgaaatct atccagccgg gccacgtggt catcagaggg    240

aaggcctcct ccatgttcct ctgcgtggac agcgggggcc gtttgagagg acaggggccg    300

tactcagagg ccgactgcag cttcagggag ctgctgctgg gggatggcta cacccggttc    360

ctgtcctcgc agcacgggtc cccgctgtct ctggcgtcga ggccttcccc ggatcccaac    420

tcggtgccct tcactcgatt cctacccatc cggaccgccc ccgaggctga gagcgtgatc    480

gaagagccac cgagcaatca gagatacgtc aacgtggact ccgaggatct tcttggaatg    540

ggcctgaaca ctgtggtcag tcctcagttc tcggcg                              576


<210> SEQ ID NO 250
<211> LENGTH: 495
<212> TYPE: DNA
<213> ORGANISM: Sarcophilus harrisii

<400> SEQUENCE: 250

gtgtctgcca tgggcctgag ggagcgagct cccaggtacc tggccccgct gctgtccttg     60

ctcttggcct gcagggcctc gggtcacccc ctcccggatt ccagccccat gctcctgttt    120

ggggggcagg tccgcctccg gcacctctac acggatgtgg gccaggaggc cgaggcccac    180
```

```
gtggaactgg cgtccgacgg cacagtccgg gcggcagcgc ggaggagtcc caacagtctc    240

ctggagctga aggctgtgaa gccgggcatc gtccgaatcc tggccgtcca cagctctcgg    300

tttctgtgta tgaggcccaa cggggagctg tacggagcga tacactacga cccttccgcc    360

tgcaactttc gggagcgcct gctgggggac ggctacaacg tgtacgagtc cgaggctcac    420

gggaggaccc tccgcctgcc ccccaaggcc gcaccgggac ccgccggacc ttctcgcttc    480

ctgccgctcc ccggc                                                     495


<210> SEQ ID NO 251
<211> LENGTH: 627
<212> TYPE: DNA
<213> ORGANISM: Macropus eugenii

<400> SEQUENCE: 251

acagaggagc cttctactgg gtccaggcac ctgggacaat gggctcccgg gctgcctggt     60

cctctgctgt ccttgctcct ggcctacagg ggctggggct cccccatccc tgattccagc    120

cccatgctcc tgtttggtgg ccaggtccgc ctccgacacc tgtacacaga tgatggccag    180

gacacggagg cccatgtgga gctggggcca gatggagtgg ttcgagctgt ggctgagagg    240

agccccaaca gtcttctgga actgaaggcg gtgaagcctg gagtcatccg aatcctcgct    300

gtccagagct ctcggtttct gtgtatgagg cccaacgggg aactgtatgg agcggtacac    360

tatgaccctt ctgcctgcaa ctttcgggaa catctgctgg gggatggtta taatgtgtat    420

gaatcagaga ctcacagaag gaccctccgt ctgtccccat ccctgggtca ggctggcccc    480

tctcgcttcc tgccacttcc aggcgactgg ctgcccggcc ctgatccacc ttgggcacag    540

ggccctgagc cccagacgt gggctctgca gaccccctga gcatggtggg ggccgtgcag    600

ggcctcagcc ccagctactc ctcctga                                        627


<210> SEQ ID NO 252
<211> LENGTH: 480
<212> TYPE: DNA
<213> ORGANISM: Xenopus tropicalis

<400> SEQUENCE: 252

agagggggta ggaccaaaaa aaagacgtta ctcaggaaat ggctttgcct tttagccatt     60

atgttgagta ggtcaaggtt ttctttagca aatcctatcc agaattcgaa cccaatctta    120

tccaacgaca accaagtacg gactcagtat ttatacacag ataacaataa catgcacctg    180

tatcttcaga tcacccacaa tggagtagta actggtaccg aagaaaagaa tgactatggt    240

gtgctggaaa taaaggcagt aaaagctggg gttgtagtta taaaaggaat tcgaagcaat    300

ctctacctat gcatggattc tagacaccaa ttgtatgcgt cggcatatga taaagatgac    360

tgccatttcc atgaaaagat cacaccagat aattacaaca tgtatagctc agagaagcat    420

tcagaatacg tgtccttagc tccattaaaa ggaagccaga tggctcgttt tctacctata    480


<210> SEQ ID NO 253
<211> LENGTH: 585
<212> TYPE: DNA
<213> ORGANISM: Danio rerio

<400> SEQUENCE: 253

atgcttcttg cctgcttttt tatatttttt gctctttttc ctcatcttcg gtggtgtatg     60

tatgttcctg cacagaacgt gcttctgcag tttggcacac aagtcaggga acgcctgctt    120
```

```
tacacagatg ggttgtttct tgaaatgaat ccagatggct ccgtcaaagg ctctcctgaa    180

aagaatctaa attgtgtgct ggagctgcgt tcagtcaaag cgggtgaaac cgtcatccag    240

agtgcagcta catctctcta cctctgcgtc gatgatcaag acaagctgaa aggacagcat    300

cattactctg cactagactg cacctttcag gaattgctac tggatggata ttcgtttttc    360

ctttctccac acactaatct tcccgtatcg ctcctctcga aacgtcagaa acacggcaat    420

cctctttctc gcttcctccc tgttagcaga gcagaggaca gccggacaca ggaggtgaaa    480

cagtatattc aggatataaa cctggactct gacgacccac taggaatggg acatcggtca    540

cacttacaga ccgtcttcag tcccagtctg catactaaaa aatga                    585
```

```
<210> SEQ ID NO 254
<211> LENGTH: 215
<212> TYPE: PRT
<213> ORGANISM: Artificial
<220> FEATURE:
<223> OTHER INFORMATION: Chimeric protein

<400> SEQUENCE: 254

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile His Phe Asn Thr Pro Glu Glu Pro Glu
                165                 170                 175

Asp Leu Arg Gly His Leu Glu Ser Asp Met Phe Ser Ser Pro Leu Glu
            180                 185                 190

Thr Asp Ser Met Asp Pro Phe Gly Leu Val Thr Gly Leu Glu Ala Val
        195                 200                 205

Arg Ser Pro Ser Phe Glu Lys
    210                 215


<210> SEQ ID NO 255
<211> LENGTH: 210
<212> TYPE: PRT
<213> ORGANISM: Artificial
<220> FEATURE:
<223> OTHER INFORMATION: Chimeric protein

<400> SEQUENCE: 255

Met Leu Gly Ala Arg Leu Arg Leu Trp Val Cys Ala Leu Cys Ser Val
```

```
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160

Arg Asn Leu Pro Met Val Pro Glu Glu Pro Glu Asp Leu Arg Gly His
                165                 170                 175

Leu Glu Ser Asp Met Phe Ser Ser Pro Leu Glu Thr Asp Ser Met Asp
            180                 185                 190

Pro Phe Gly Leu Val Thr Gly Leu Glu Ala Val Arg Ser Pro Ser Phe
        195                 200                 205

Glu Lys
    210


<210> SEQ ID NO 256
<211> LENGTH: 215
<212> TYPE: PRT
<213> ORGANISM: Artificial
<220> FEATURE:
<223> OTHER INFORMATION: Chimeric protein

<400> SEQUENCE: 256

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
```

```
145                 150                 155                 160

Arg Asn Glu Ile Pro Leu Ile His Phe Asn Thr Pro Glu Glu Pro Glu
                165                 170                 175

Asp Leu Arg Gly His Leu Glu Ser Asp Met Phe Ser Ser Pro Leu Glu
            180                 185                 190

Thr Asp Ser Met Asp Pro Phe Gly Leu Val Thr Gly Leu Glu Ala Val
        195                 200                 205

Arg Ser Pro Ser Phe Glu Lys
    210                 215


<210> SEQ ID NO 257
<211> LENGTH: 215
<212> TYPE: PRT
<213> ORGANISM: Artificial
<220> FEATURE:
<223> OTHER INFORMATION: Chimeric protein

<400> SEQUENCE: 257

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile His Phe Asn Thr Pro Glu Glu Pro Glu
                165                 170                 175

Asp Leu Arg Gly His Leu Glu Ser Asp Met Phe Ser Ser Pro Leu Glu
            180                 185                 190

Thr Asp Ser Met Asp Pro Phe Gly Leu Val Thr Gly Leu Glu Ala Val
        195                 200                 205

Arg Ser Pro Ser Phe Glu Lys
    210                 215


<210> SEQ ID NO 258
<211> LENGTH: 214
<212> TYPE: PRT
<213> ORGANISM: Artificial
<220> FEATURE:
<223> OTHER INFORMATION: Chimeric protein

<400> SEQUENCE: 258

Met Leu Gly Ala Arg Leu Arg Leu Trp Val Cys Ala Leu Cys Ser Val
1               5                   10                  15
```

```
Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val His Leu Pro Gly Asn Lys Ser Pro
    130                 135                 140

His Arg Asp Pro Ala Pro Arg Gly Pro Ala Arg Phe Leu Ser Arg Arg
145                 150                 155                 160

Asn Glu Ile Pro Leu Ile His Phe Asn Thr Pro Glu Glu Pro Glu Asp
                165                 170                 175

Leu Arg Gly His Leu Glu Ser Asp Met Phe Ser Ser Pro Leu Glu Thr
            180                 185                 190

Asp Ser Met Asp Pro Phe Gly Leu Val Thr Gly Leu Glu Ala Val Arg
        195                 200                 205

Ser Pro Ser Phe Glu Lys
    210
```

<210> SEQ ID NO 259
<211> LENGTH: 210
<212> TYPE: PRT
<213> ORGANISM: Artificial
<220> FEATURE:
<223> OTHER INFORMATION: Chimeric protein

<400> SEQUENCE: 259

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160
```

```
Arg Asn Leu Pro Met Val Pro Glu Glu Pro Glu Asp Leu Arg Gly His
                165                 170                 175

Leu Glu Ser Asp Met Phe Ser Ser Pro Leu Glu Thr Asp Ser Met Asp
            180                 185                 190

Pro Phe Gly Leu Val Thr Gly Leu Glu Ala Val Arg Ser Pro Ser Phe
        195                 200                 205

Glu Lys
    210


<210> SEQ ID NO 260
<211> LENGTH: 210
<212> TYPE: PRT
<213> ORGANISM: Artificial
<220> FEATURE:
<223> OTHER INFORMATION: Chimeric protein

<400> SEQUENCE: 260

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160

Arg Asn Leu Pro Met Val Pro Glu Glu Pro Glu Asp Leu Arg Gly His
                165                 170                 175

Leu Glu Ser Asp Met Phe Ser Ser Pro Leu Glu Thr Asp Ser Met Asp
            180                 185                 190

Pro Phe Gly Leu Val Thr Gly Leu Glu Ala Val Arg Ser Pro Ser Phe
        195                 200                 205

Glu Lys
    210


<210> SEQ ID NO 261
<211> LENGTH: 209
<212> TYPE: PRT
<213> ORGANISM: Artificial
<220> FEATURE:
<223> OTHER INFORMATION: Chimeric protein

<400> SEQUENCE: 261

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30
```

```
Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val His Leu Pro Gly Asn Lys Ser Pro
    130                 135                 140

His Arg Asp Pro Ala Pro Arg Gly Pro Ala Arg Phe Leu Ser Arg Arg
145                 150                 155                 160

Asn Leu Pro Met Val Pro Glu Glu Pro Glu Asp Leu Arg Gly His Leu
                165                 170                 175

Glu Ser Asp Met Phe Ser Ser Pro Leu Glu Thr Asp Ser Met Asp Pro
            180                 185                 190

Phe Gly Leu Val Thr Gly Leu Glu Ala Val Arg Ser Pro Ser Phe Glu
        195                 200                 205

Lys
```

<210> SEQ ID NO 262
<211> LENGTH: 573
<212> TYPE: DNA
<213> ORGANISM: Artificial
<220> FEATURE:
<223> OTHER INFORMATION: Nucleic acid sequence encoding chimeric protein

<400> SEQUENCE: 262

```
tatcccaatg cctccccact gctcggctcc agctggggtg gcctgatcca cctgtacaca     60

gccacagcca ggaacagcta ccacctgcag atccacaaga atggccatgt ggatggcgca    120

ccccatcaga ccatctacag tgccctgatg atcagatcag aggatgctgg ctttgtggtg    180

attacaggtg tgatgagcag aagatacctc tgcatggatt tcagaggcaa catttttgga    240

tcacactatt tcgacccgga gaactgcagg ttccaacacc agacgctgga aaacgggtac    300

gacgtctacc actctcctca gtatcacttc ctggtcagtc tgggccgggc gaagagagcc    360

ttcctgccag gcatgaaccc acccccgtac tcccagttcc tgtcccggag gaacgagatc    420

cccctaattc acttcaacac ccccgaggag cctgaggacc tcaggggcca cttggaatct    480

gacatgttct cttcgcccct ggagaccgac agcatggacc catttgggct tgtcaccgga    540

ctggaggccg tgaggagtcc cagctttgag aag                                 573
```

<210> SEQ ID NO 263
<211> LENGTH: 558
<212> TYPE: DNA
<213> ORGANISM: Artificial
<220> FEATURE:
<223> OTHER INFORMATION: Nucleic acid sequence encoding chimeric protein

<400> SEQUENCE: 263

```
tatcccaatg cctccccact gctcggctcc agctggggtg gcctgatcca cctgtacaca     60

gccacagcca ggaacagcta ccacctgcag atccacaaga atggccatgt ggatggcgca    120
```

ccccatcaga ccatctacag tgccctgatg atcagatcag aggatgctgg ctttgtggtg 180
attacaggtg tgatgagcag aagatacctc tgcatggatt tcagaggcaa catttttgga 240
tcacactatt tcgacccgga gaactgcagg ttccaacacc agacgctgga aaacgggtac 300
gacgtctacc actctcctca gtatcacttc ctggtcagtc tgggccgggc gaagagagcc 360
ttcctgccag gcatgaaccc acccccgtac tcccagttcc tgtcccggag gaacctgccc 420
atggtcccag aggagcctga ggacctcagg ggccacttgg aatctgacat gttctcttcg 480
cccctggaga ccgacagcat ggacccattt gggcttgtca ccggactgga ggccgtgagg 540
agtcccagct ttgagaag 558

<210> SEQ ID NO 264
<211> LENGTH: 571
<212> TYPE: DNA
<213> ORGANISM: Artificial
<220> FEATURE:
<223> OTHER INFORMATION: Nucleic acid sequence encoding chimeric protein

<400> SEQUENCE: 264
tatcccaatg cctccccact gctcggctcc agctggggtg gcctgatcca cctgtacaca 60
gccacagcca ggaacagcta ccacctgcag atccacaaga atggccatgt ggatggcgca 120
ccccatcaga ccatctacag tgccctgatg atcagatcag aggatgctgg ctttgtggtg 180
attacaggtg tgatgagcag aagatacctc tgcatggatt tcagaggcaa catttttgga 240
tcacactatt tcgacccgga gaactgcagg ttccaacacc agacgctgga aaacgggtac 300
gacgtctacc actctcctca gtatcacttc ctggtcagtc tgggcgcggc gaaggcagcc 360
ttcctgccag gcatgaaccc acccccgtac tcccagttcc tgtcccggag gaacgagatc 420
cccctaattc acttcaacac ccgaggagcc tgaggacctc aggggccact tggaatctga 480
catgttctct tcgcccctgg agaccgacag catggaccca tttgggcttg tcaccggact 540
ggaggccgtg aggagtccca gctttgagaa g 571

<210> SEQ ID NO 265
<211> LENGTH: 571
<212> TYPE: DNA
<213> ORGANISM: Artificial
<220> FEATURE:
<223> OTHER INFORMATION: Nucleic acid sequence encoding chimeric protein

<400> SEQUENCE: 265
tatcccaatg cctccccact gctcggctcc agctggggtg gcctgatcca cctgtacaca 60
gccacagccg cggccagcta ccacctgcag atccacaaga atggccatgt ggatggcgca 120
ccccatcaga ccatctacag tgccctgatg atcagatcag aggatgctgg ctttgtggtg 180
attacaggtg tgatgagcag aagatacctc tgcatggatt tcagaggcaa catttttgga 240
tcacactatt tcgacccgga gaactgcagg ttccaacacc agacgctgga aaacgggtac 300
gacgtctacc actctcctca gtatcacttc ctggtcagtc tgggccgggc gaagagagcc 360
ttcctgccag gcatgaaccc acccccgtac tcccagttcc tgtcccggag gaacgagatc 420
cccctaattc acttcaacac ccgaggagcc tgaggacctc aggggccact tggaatctga 480
catgttctct tcgcccctgg agaccgacag catggaccca tttgggcttg tcaccggact 540
ggaggccgtg aggagtccca gctttgagaa g 571

<210> SEQ ID NO 266

<211> LENGTH: 570
<212> TYPE: DNA
<213> ORGANISM: Artificial
<220> FEATURE:
<223> OTHER INFORMATION: Nucleic acid sequence encoding chimeric protein

<400> SEQUENCE: 266

```
tatcccaatg cctccccact gctcggctcc agctggggtg gcctgatcca cctgtacaca     60

gccacagcca ggaacagcta ccacctgcag atccacaaga atggccatgt ggatggcgca    120

ccccatcaga ccatctacag tgccctgatg atcagatcag aggatgctgg ctttgtggtg    180

attacaggtg tgatgagcag aagatacctc tgcatggatt tcagaggcaa catttttgga    240

tcacactatt tcgacccgga gaactgcagg ttccaacacc agacgctgga aaacgggtac    300

gacgtctacc actctcctca gtatcacttc ctggtccacc tgccagggaa caagtcccca    360

caccgggacc ctgcaccccg aggaccagct cgcttcctgt cccggaggaa cgagatcccc    420

ctaattcact tcaacacccc cgaggagcct gaggacctca ggggccactt ggaatctgac    480

atgttctctt cgcccctgga gaccgacagc atggacccat ttgggcttgt caccggactg    540

gaggccgtga ggagtcccag ctttgagaag                                     570
```

<210> SEQ ID NO 267
<211> LENGTH: 586
<212> TYPE: DNA
<213> ORGANISM: Artificial
<220> FEATURE:
<223> OTHER INFORMATION: Nucleic acid sequence encoding chimeric protein

<400> SEQUENCE: 267

```
tatcccaatg cctccccact gctcggctcc agctggggtg gcctgatcca cctgtacaca     60

gccacagcca ggaacagcta ccacctgcag atccacaaga atggccatgt ggatggcgca    120

ccccatcaga ccatctacag tgccctgatg atcagatcag aggatgctgg ctttgtggtg    180

attacaggtg tgatgagcag aagatacctc tgcatggatt tcagaggcaa catttttgga    240

tcacactatt tcgacccgga gaactgcagg ttccaacacc agacgctgga aaacgggtac    300

gacgtctacc actctcctca gtatcacttc ctggtcagtc tgggcgcggc gaaggcagcc    360

ttcctgccag gcatgaaccc acccccgtac tcccagttcc tgtcccggag gaacgagatc    420

cccctaattc acttcaacac ccctgcccat ggtcccagag gagcctgagg acctcagggg    480

ccacttggaa tctgacatgt tctcttcgcc cctggagacc gacagcatgg acccatttgg    540

gcttgtcacc ggactggagg ccgtgaggag tcccagcttt gagaag                   586
```

<210> SEQ ID NO 268
<211> LENGTH: 586
<212> TYPE: DNA
<213> ORGANISM: Artificial
<220> FEATURE:
<223> OTHER INFORMATION: Nucleic acid sequence encoding chimeric protein

<400> SEQUENCE: 268

```
tatcccaatg cctccccact gctcggctcc agctggggtg gcctgatcca cctgtacaca     60

gccacagccg cggccagcta ccacctgcag atccacaaga atggccatgt ggatggcgca    120

ccccatcaga ccatctacag tgccctgatg atcagatcag aggatgctgg ctttgtggtg    180

attacaggtg tgatgagcag aagatacctc tgcatggatt tcagaggcaa catttttgga    240

tcacactatt tcgacccgga gaactgcagg ttccaacacc agacgctgga aaacgggtac    300

gacgtctacc actctcctca gtatcacttc ctggtcagtc tgggccgggc gaagagagcc    360
```

-continued

```
ttcctgccag gcatgaaccc acccccgtac tcccagttcc tgtcccggag gaacgagatc    420

cccctaattc acttcaacac ccctgcccat ggtcccagag gagcctgagg acctcagggg    480

ccacttggaa tctgacatgt tctcttcgcc cctggagacc gacagcatgg acccatttgg    540

gcttgtcacc ggactggagg ccgtgaggag tcccagcttt gagaag                   586


<210> SEQ ID NO 269
<211> LENGTH: 585
<212> TYPE: DNA
<213> ORGANISM: Artificial
<220> FEATURE:
<223> OTHER INFORMATION: Nucleic acid sequence encoding chimeric protein

<400> SEQUENCE: 269

tatcccaatg cctccccact gctcggctcc agctggggtg gcctgatcca cctgtacaca     60

gccacagcca ggaacagcta ccacctgcag atccacaaga atggccatgt ggatggcgca    120

ccccatcaga ccatctacag tgccctgatg atcagatcag aggatgctgg ctttgtggtg    180

attacaggtg tgatgagcag aagatacctc tgcatggatt tcagaggcaa catttttgga    240

tcacactatt tcgacccgga gaactgcagg ttccaacacc agacgctgga aaacgggtac    300

gacgtctacc actctcctca gtatcacttc ctggtccacc tgccagggaa caagtcccca    360

caccgggacc ctgcaccccg aggaccagct cgcttcctgt cccggaggaa cgagatcccc    420

ctaattcact tcaacacccc cctgcccatg gtcccagagg agcctgagga cctcaggggc    480

cacttggaat ctgacatgtt ctcttcgccc ctggagaccg acagcatgga cccatttggg    540

cttgtcaccg gactggaggc cgtgaggagt cccagctttg agaag                    585
```